(12) United States Patent
Chuprakov et al.

(10) Patent No.: US 11,564,989 B2
(45) Date of Patent: Jan. 31, 2023

(54) CAMPTOTHECINE ANTIBODY-DRUG CONJUGATES AND METHODS OF USE THEREOF

(71) Applicant: R.P. Scherer Technologies, LLC, Carson City, NV (US)

(72) Inventors: Stepan Chuprakov, Walnut Creek, CA (US); Ayodele O. Ogunkoya, Berkeley, CA (US); Penelope M. Drake, Castro Valley, CA (US)

(73) Assignee: R.P. Scherer Technologies, LLC, Carson City, NV (US)

( * ) Notice: Subject to any disclaimer, the term of this patent is extended or adjusted under 35 U.S.C. 154(b) by 0 days.

(21) Appl. No.: 17/575,481

(22) Filed: Jan. 13, 2022

(65) Prior Publication Data

US 2022/0241423 A1 Aug. 4, 2022

Related U.S. Application Data

(60) Provisional application No. 63/237,355, filed on Aug. 26, 2021, provisional application No. 63/214,525, filed on Jun. 24, 2021, provisional application No. 63/186,489, filed on May 10, 2021, provisional application No. 63/138,182, filed on Jan. 15, 2021.

(51) Int. Cl.
| | |
|---|---|
| C07D 471/14 | (2006.01) |
| C07D 491/22 | (2006.01) |
| A61K 47/64 | (2017.01) |
| A61K 47/54 | (2017.01) |
| C07K 5/062 | (2006.01) |

(52) U.S. Cl.
CPC ............ *A61K 47/545* (2017.08); *A61K 47/64* (2017.08); *C07D 471/14* (2013.01); *C07D 491/22* (2013.01); *C07K 5/06026* (2013.01)

(58) Field of Classification Search
CPC ................ C07D 471/14; C07D 491/22; C07K 5/06026; A61K 47/545; A61K 47/64
See application file for complete search history.

(56) References Cited

U.S. PATENT DOCUMENTS

| | | |
|---|---|---|
| 7,985,783 B2 | 7/2011 | Carrico et al. |
| 8,097,701 B2 | 1/2012 | Carrico et al. |
| 8,349,910 B2 | 1/2013 | Carrico et al. |
| 8,846,866 B2 | 9/2014 | Carrico et al. |
| 9,310,374 B2 | 4/2016 | Kudirka et al. |
| 9,447,390 B2 | 9/2016 | Carrico et al. |
| 9,493,413 B2 | 11/2016 | Rabuka et al. |
| 9,833,515 B2 | 12/2017 | Kudirka et al. |
| 10,150,806 B2 | 12/2018 | Carrico et al. |
| 10,314,919 B2 | 6/2019 | Kudirka et al. |
| 10,464,894 B2 | 11/2019 | Rabuka et al. |
| 10,604,483 B2 | 3/2020 | Rabuka et al. |
| 10,745,464 B2 | 8/2020 | Carrico et al. |
| 10,888,623 B2 | 1/2021 | Kudirka et al. |
| 11,180,451 B2 | 11/2021 | Rabuka et al. |
| 2021/0024614 A1 | 1/2021 | Carrico et al. |
| 2021/0162054 A1 | 6/2021 | Kudirka et al. |

FOREIGN PATENT DOCUMENTS

WO 2020154437 7/2020

*Primary Examiner* — Brenda L Coleman
(74) *Attorney, Agent, or Firm* — Rudy J. Ng; Bozicevic, Field & Francis LLP

(57) ABSTRACT

The present disclosure provides antibody-drug conjugate (ADC) structures, which include a camptothecine or a camptothecine derivative linked to a polypeptide (e.g., an antibody) through a linker. The disclosure also encompasses compounds and methods for production of such conjugates, as well as methods of using the conjugates.

17 Claims, 74 Drawing Sheets

CAMPTOTHECINE ANTIBODY-DRUG CONJUGATES AND METHODS OF USE THEREOF

CROSS-REFERENCE TO RELATED APPLICATIONS

This application claims the benefit of U.S. Provisional Application No. 63/237,355, filed Aug. 26, 2021, U.S. Provisional Application No. 63/214,525, filed Jun. 24, 2021, U.S. Provisional Application No. 63/186,489, filed May 10, 2021, and U.S. Provisional Application No. 63/138,182, filed Jan. 15, 2021, the disclosures of which are incorporated herein by reference.

INTRODUCTION

The field of protein-small molecule therapeutic conjugates has advanced greatly, providing a number of clinically beneficial drugs with the promise of providing more in the years to come. Protein-conjugate therapeutics can provide several advantages, due to, for example, specificity, multiplicity of functions and relatively low off-target activity, resulting in fewer side effects.

SUMMARY

Camptothecines are a family of antitumor agents sharing common structural core i (FIG. 1, panel A). Due to their ability to inhibit the activity of DNA Topoisomerase I, an intracellular enzyme essential for cell replication, several synthetic and semi-synthetic camptothecines have been used as small-molecule cancer chemotherapies (e.g. topotecan and irinotecan). In contrast, more potent analogs, such as SN-38 (1) and Exatecan (3) (FIG. 1, panel B), show significant off-target toxicities that prevent using them directly to treat cancers. Targeted delivery of highly potent camptothecines to tumor tissue may circumvent the toxicity problem and offer a more well-tolerated therapy. The present disclosure describes the preparation of antibody-drug conjugates (ADCs) containing camptothecines of general structure i (FIG. 1, panel A). In each conjugate, the cytotoxin of choice is connected to the antibody (e.g., mAb) through a cleavable linker attached to either the common C20 alcohol, or through various chemical handles specific to particular camptothecine analogs (FIG. 1).

The present disclosure provides antibody-drug conjugate (ADC) structures, which include a camptothecine or a camptothecine derivative linked to a polypeptide (e.g., an antibody) through a linker. The disclosure also encompasses compounds and methods for production of such conjugates, as well as methods of using the conjugates.

Aspects of the present disclosure include a conjugate of formula (I):

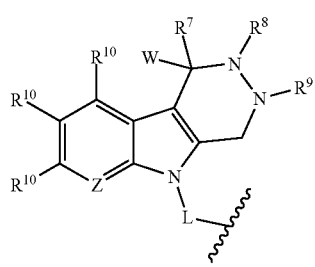

(I)

wherein:

Z is $CR^{10}$ or N, $R^7$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^8$ and $R^9$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^8$ and $R^9$ are optionally cyclically linked to form a 5 or 6-membered heterocyclyl;

each $R^{10}$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

W is a polypeptide;

L is a linker attached to a compound of formula (II) at $R^1$, $R^2$, $R^3$, $R^4$, $R^5$ or $R^6$:

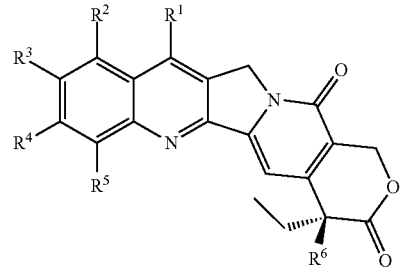

(II)

$R^1$ and $R^2$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^1$ and $R^2$ are optionally cyclically linked to form a 5 or 6-membered cycloalkyl or heterocyclyl ring;

$R^3$ and $R^4$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^3$ and $R^4$ are optionally cyclically linked to form a 5 or 6-membered cycloalkyl or heterocyclyl ring;

$R^5$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl;

$R^6$ is selected from OH and $OC(O)R^{11}$; and $R^{11}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl, wherein at least one $R^{10}$ is optionally linked to a second compound of formula (II).

In some embodiments, the compound of formula (II) has the structure of formula (IIa):

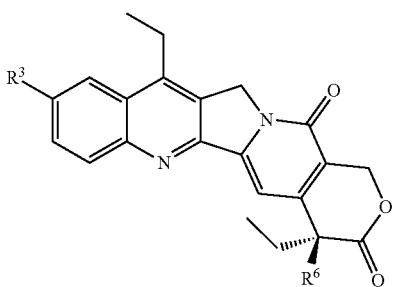

(IIa)

wherein $R^3$ is OH and L is attached at $R^6$; or L is attached at $R^3$ and $R^6$ is OH; or wherein the compound of formula (II) has the structure of formula (IIb):

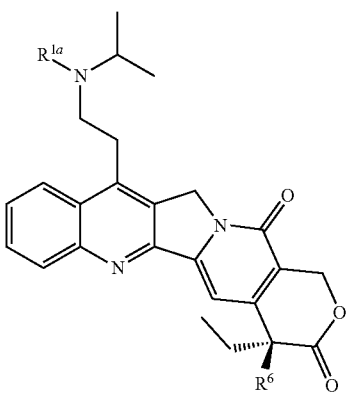

(IIb)

wherein $R^{1a}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$; or L is attached at $R^{1a}$ and $R^6$ is OH; or wherein the compound of formula (II) has the structure of formula (IIc):

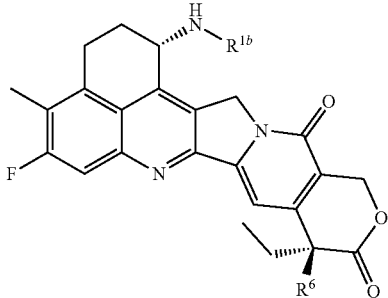

(IIc)

wherein $R^{1b}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$; or L is attached at $R^{1b}$ and $R^6$ is OH; or wherein the compound of formula (II) has the structure of formula (IId):

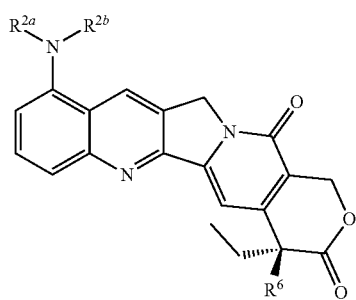

(IId)

wherein $R^{2a}$ and $R^{2b}$ are each independently selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$; or L is attached at $R^{2a}$ or $R^{2b}$ and $R^6$ is OH; or wherein the compound of formula (II) has the structure of formula (IIe):

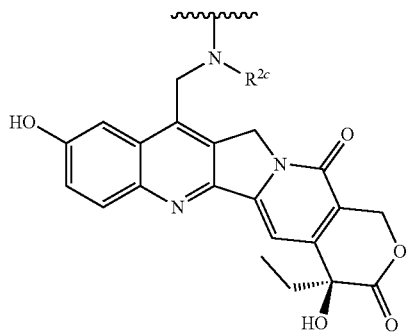

(IIb)

wherein $R^{2c}$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and attachment to L is indicated by the wavy line.

In some embodiments, L comprises:

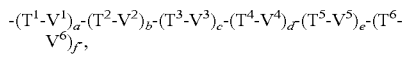

wherein a, b, c, d, e and f are each independently 0 or 1;

$T^1$, $T^2$, $T^3$, $T^4$, $T^5$ and $T^6$ are each independently selected from a covalent bond, ($C_1$-$C_{12}$)alkyl, substituted ($C_1$-$C_{12}$) alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;

$V^1$, $V^2$, $V^3$, $V^4$, $V^5$ and $V^6$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;

each $R^{13}$ is independently selected from hydrogen, alkyl, substituted alkyl, aryl, and substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, L is a linker wherein:
$T^1$ is selected from a $(C_1\text{-}C_{12})$alkyl and a substituted $(C_1\text{-}C_{12})$alkyl;

$T^2$, $T^3$, $T^4$, $T^5$ and $T^6$ are each independently selected from a covalent bond, $(C_1\text{-}C_{12})$alkyl, substituted $(C_1\text{-}C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), MABO, MABC, PABO, PABC, PAB, PABA, PAP, PHP, an acetal group, a hydrazine, and an ester; and $V^1$, $V^2$, $V^3$, $V^4$, $V^5$ and $V^6$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$—, and —P(O)OH—;

wherein:

$(PEG)_n$ is

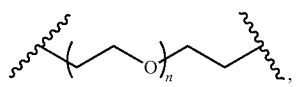

where n is an integer from 1 to 30;

EDA is an ethylene diamine moiety having the following structure:

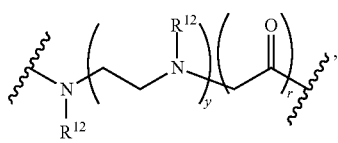

where y is an integer from 1 to 6 and r is 0 or 1;

4-amino-piperidine (4AP) is

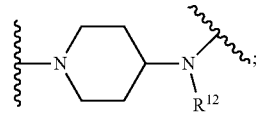

and each $R^{12}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring.

In some embodiments, $T^1$, $T^2$, $T^3$, $T^4$, $T^5$ and $T^6$ are each optionally substituted with a glycoside. In some embodiments, MABO, MABC, PABO, PABC, PAB, PABA, PAP and PHP are each optionally substituted with a glycoside. In some embodiments, the glycoside is selected from a glucuronide, a galactoside, a glucoside, a mannoside, a fucoside, O-GlcNAc, and O-GalNAc.

In some embodiments, L is a linker wherein:
$T^1$ is $(C_1\text{-}C_{12})$alkyl and $V^1$ is —CO—;
$T^2$ is an amino acid analog and $V^2$ is —NH—;
$T^3$ is $(PEG)n$ and $V^3$ is —CO—;
$T^4$ is AA and $V^4$ is absent;
$T^5$ is PABC and $V^5$ is absent; and
$T^6$ is EDA and $V^6$ is —CO—; or
wherein:
$T^1$ is $(C_1\text{-}C_{12})$alkyl and $V^1$ is —CO—;
$T^2$ is an amino acid analog and $V^2$ is —NH—;
$T^3$ is $(PEG)_n$ and $V^3$ is —CO—;
$T^4$ is AA and $V^4$ is absent;
$T^5$ is absent and $V^5$ is —$NR^{15}(C_6H_4)$—; and
$T^6$ is absent and $V^6$ is —CO—; or
wherein:
$T^1$ is $(C_1\text{-}C_{12})$alkyl and $V^1$ is —CO—;
$T^2$ is an amino acid analog and $V^2$ is —NH—;
$T^3$ is $(PEG)_n$ and $V^3$ is —CO—;
$T^4$ is AA and $V^4$ is absent;
$T^5$ is PABC and $V^5$ is —$NR^{15}$—; and
$T^6$ is $(C_1\text{-}C_{12})$alkyl and $V^6$ is —CO—; or
wherein:
$T^1$ is $(C_1\text{-}C_{12})$alkyl and $V^1$ is —CO—;
$T^2$ is AA and $V^2$ is absent;
$T^3$ is PABC and $V^3$ is absent;
$T^4$ is EDA and $V^4$ is —CO—; and
e and f are each 0; or
wherein:
$T^1$ is $(C_1\text{-}C_{12})$alkyl and $V^1$ is —CO—;
$T^2$ is an amino acid analog and $V^2$ is —NH—;
$T^3$ is $(PEG)_n$ and $V^3$ is —CO—;
$T^4$ is AA and $V^4$ is absent;
$T^5$ is PABC and $V^5$ is absent; and
f is 0; or
wherein:
$T^1$ is $(C_1\text{-}C_{12})$alkyl and $V^1$ is —CO—;
$T^2$ is AA and $V^2$ is absent;
$T^3$ is PABC and $V^3$ is absent; and
d, e and f are each 0; or
wherein:
$T^1$ is $(C_1\text{-}C_{12})$alkyl and $V^1$ is —CO—;
$T^2$ is an amino acid analog and $V^2$ is —NH—;
$T^3$ is $(PEG)_n$ and $V^3$ is —CO—;
$T^4$ is AA and $V^4$ is absent;
$T^5$ is PABA and $V^5$ is —CO—; and
$T^6$ is $(C_1\text{-}C_{12})$alkyl and $V^6$ is —$SO_2$—; or wherein:
  $T^1$ is $(C_1-C_{12})$alkyl and $V^1$ is —CONH—;
  $T^2$ is $(PEG)_n$ and $V^2$ is —CO—;
  $T^3$ is AA and $V^3$ is absent;
  $T^4$ is PABC and $V^4$ is absent;
  e and f are each 0; or
wherein:
  $T^1$ is $(C_1-C_{12})$alkyl and $V^1$ is —CONH—;
  $T^2$ is substituted $(C_1-C_{12})$alkyl and $V^2$ is —CO—;
  $T^3$ is AA and $V^3$ is absent;
  $T^4$ is PABC and $V^4$ is absent;
  e and f are each 0; or
wherein:
  $T^1$ is $(C_1-C_{12})$alkyl and $V^1$ is —CONH—;
  $T^2$ is $(PEG)_n$ and $V^2$ is —CO—;
  $T^3$ is AA and $V^3$ is absent;
  $T^4$ is PABC and $V^4$ is absent;
  $T^5$ is $(C_1-C_{12})$alkyl and $V^5$ is absent;
  f is 0; or
wherein:
  $T^1$ is $(C_1-C_{12})$alkyl and $V^1$ is —CO—;
  $T^2$ is 4AP and $V^2$ is —CO—;
  $T^3$ is $(C_1-C_{12})$alkyl and $V^3$ is —CO—;
  $T^4$ is AA and $V^4$ is absent;
  $T^5$ is PABC and $V^5$ is absent;
  f is 0; or
wherein:
  $T^1$ is $(C_1-C_{12})$alkyl and $V^1$ is —CO—;
  $T^2$ is 4AP and $V^2$ is —CO—;
  $T^3$ is $(C_1-C_{12})$alkyl and $V^3$ is —O—;
  $T^4$ is $(C_1-C_{12})$alkyl and $V^4$ is —CO—;
  $T^5$ is AA and $V^5$ is absent;
  $T^6$ is PABC and $V^6$ is absent; or
wherein:
  $T^1$ is $(C_1-C_{12})$alkyl and $V^1$ is —CO—;
  $T^2$ is an amino acid analog and $V^2$ is absent;
  $T^3$ is AA and $V^3$ is absent;
  $T^4$ is PABC and $V^4$ is absent;
  e and f are each 0; or
wherein:
  $T^1$ is $(C_1-C_{12})$alkyl and $V^1$ is —CONH—;
  $T^2$ is $(PEG)_n$ and $V^2$ is —CONH—;
  $T^3$ is substituted $(C_1-C_{12})$alkyl and $V^3$ is —CO—;
  $T^4$ is AA and $V^4$ is absent;
  $T^5$ is PABC and $V^5$ is absent;
  f is 0; or
wherein:
  $T^1$ is $(C_1-C_{12})$alkyl and $V^1$ is —CO—;
  $T^2$ is AA and $V^2$ is —NH—;
  $T^3$ is $(PEG)_n$ and $V^3$ is —CO—;
  $T^4$ is AA and $V^4$ is absent;
  $T^5$ is PABC and $V^5$ is absent;
  f is 0; or
wherein:
  $T^1$ is $(C_1-C_{12})$alkyl and $V^1$ is —CO—;
  $T^2$ is an amino acid analog and $V^2$ is —NH—;
  $T^3$ is $(PEG)_n$ and $V^3$ is —CO—;
  $T^4$ is AA and $V^4$ is absent;
  $T^5$ is PABO and $V^5$ is absent; and
  f is 0; or
wherein:
  $T^1$ is $(C_1-C_{12})$alkyl and $V^1$ is —CO—;
  $T^2$ is an amino acid analog and $V^2$ is —NH—;
  $T^3$ is $(PEG)_n$ and $V^3$ is —CO—;
  $T^4$ is AA and $V^4$ is absent;
  $T^5$ is PAP and $V^5$ is —COO—; and
  f is 0; or wherein:
  $T^1$ is $(C_1-C_{12})$alkyl and $V^1$ is —CONH—;
  $T^2$ is $(PEG)_n$ and $V^2$ is —CO—;
  $T^3$ is AA and $V^3$ is absent;
  $T^4$ is PAP and $V^4$ is —COO—; and
  e and f are each 0.

In some embodiments, one $R^{10}$ is linked via a second linker, $L^B$, to a second compound of formula (II).

In some embodiments, $L^B$ comprises:

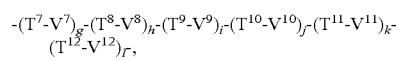

wherein
  g, h, i, j, k and l are each independently 0 or 1;
  $T^7$, $T^8$, $T^9$, $T^{10}$, $T^{11}$ and $T^{12}$ are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;
  $V^7$, $V^8$, $V^9$, $V^{10}$, $V^{11}$ and $V^{12}$ are each independently selected from the group consisting of a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, wherein each q is an integer from 1 to 6;
  each $R^{13}$ is independently selected from hydrogen, alkyl, substituted alkyl, aryl, and substituted aryl; and
  each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, wherein $T^7$, $T^8$, $T^9$, $T^{10}$, $T^{11}$ and $T^{12}$ are each optionally substituted with a glycoside. In some embodiments, MABO, MABC, PABO, PABC, PAB, PABA, PAP and PHP are each optionally substituted with a glycoside. In some embodiments, the glycoside is selected from a glucuronide, a galactoside, a glucoside, a mannoside, a fucoside, O-GlcNAc, and O-GalNAc.

In some embodiments, $L^B$ is a linker wherein:
  $T^7$ is absent and $V^7$ is —$NR^{15}CO$—;
  $T^8$ is $(C_1-C_{12})$alkyl and $V^8$ is —CO—;
  $T^9$ is AA and $V^9$ is absent;
  $T^{10}$ is PABC and $V^{10}$ is absent;
  $T^{11}$ is EDA and $V^{11}$ is —CO—; and
  l is 0; or
wherein:
  $T^7$ is absent and $V^7$ is —$NR^{15}CO$—;
  $T^8$ is $(C_1-C_{12})$alkyl and $V^8$ is —CO—;
  $T^9$ is AA and $V^9$ is absent;
  $T^{10}$ is PABC and $V^{10}$ is absent; and
  k and l are each 0; or wherein:
- $T^7$ is absent and $V^7$ is —NHCO—;
- $T^8$ is $(C_1-C_{12})$alkyl and $V^8$ is —CO—;
- $T^9$ is an amino acid analog and $V^9$ is —NH—;
- $T^{10}$ is $(PEG)_n$ and $V^{10}$ is —CO—;
- $T^{11}$ is AA and $V^{11}$ is absent; and
- $T^{12}$ is PABC and $V^{12}$ is absent; or wherein:
- $T^7$ is absent and $V^7$ is —NHCO—;
- $T^8$ is $(C_1-C_{12})$alkyl and $V^8$ is —CONH—;
- $T^9$ is $(PEG)_n$ and $V^9$ is —CO—;
- $T^{10}$ is AA and $V^{10}$ is absent;
- $T^{11}$ is PABC and $V^{11}$ is absent; and
- l is 0; or wherein:
- $T^7$ is $(C_1-C_{12})$alkyl and $V^7$ is —CONH—;
- $T^8$ is substituted $(C_1-C_{12})$alkyl and $V^8$ is —CO—;
- $T^9$ is AA and $V^9$ is absent;
- $T^{10}$ is PABC and $V^{10}$ is absent;
- k and l are each 0; or wherein:
- $T^7$ is $(C_1-C_{12})$alkyl and $V^7$ is —CONH—;
- $T^8$ is $(PEG)_n$ and $V^8$ is —CO—;
- $T^9$ is AA and $V^9$ is absent;
- $T^{10}$ is PABC and $V^{10}$ is absent;
- $T^{11}$ is $(C_1-C_{12})$alkyl and $V^{11}$ is absent;
- l is 0; or wherein:
- $T^7$ is $(C_1-C_{12})$alkyl and $V^7$ is —CO—;
- $T^8$ is 4AP and $V^8$ is —CO—;
- $T^9$ is $(C_1-C_{12})$alkyl and $V^9$ is —CO—;
- $T^{10}$ is AA and $V^{10}$ is absent;
- $T^{11}$ is PABC and $V^{11}$ is absent;
- l is 0; or wherein:
- $T^7$ is $(C_1-C_{12})$alkyl and $V^7$ is —CO—;
- $T^8$ is 4AP and $V^8$ is —CO—;
- $T^9$ is $(C_1-C_{12})$alkyl and $V^9$ is —O—;
- $T^{10}$ is $(C_1-C_{12})$alkyl and $V^{10}$ is —CO—;
- $T^{11}$ is AA and $V^{11}$ is absent;
- $T^{12}$ is PABC and $V^{12}$ is absent; or wherein:
- $T^7$ is $(C_1-C_{12})$alkyl and $V^7$ is —CO—;
- $T^8$ is an amino acid analog and $V^8$ is absent;
- $T^9$ is AA and $V^9$ is absent;
- $T^{10}$ is PABC and $V^{10}$ is absent;
- k and l are each 0; or wherein:
- $T^7$ is $(C_1-C_{12})$alkyl and $V^7$ is —CONH—;
- $T^8$ is $(PEG)_n$ and $V^8$ is —CONH—;
- $T^9$ is substituted $(C_1-C_{12})$alkyl and $V^9$ is —CO—;
- $T^{10}$ is AA and $V^{10}$ is absent;
- $T^{11}$ is PABC and $V^{11}$ is absent;
- l is 0; or wherein:
- $T^7$ is $(C_1-C_{12})$alkyl and $V^7$ is —CO—;
- $T^8$ is AA and $V^8$ is —NH—;
- $T^9$ is $(PEG)_n$ and $V^9$ is —CO—;
- $T^{10}$ is AA and $V^{10}$ is absent;
- $T^{11}$ is PABC and $V^{11}$ is absent;
- l is 0; or wherein:
- $T^7$ is $(C_1-C_{12})$alkyl and $V^7$ is —CONH—;
- $T^8$ is $(PEG)_n$ and $V^8$ is —CO—;
- $T^9$ is AA and $V^9$ is absent;
- $T^{10}$ is PAP and $V^{10}$ is —COO—; and
- k and l are each 0.

In some embodiments, the conjugate is selected from:

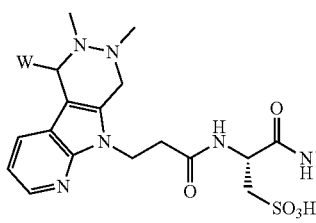
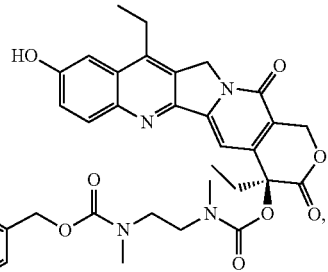
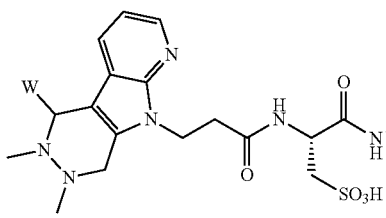
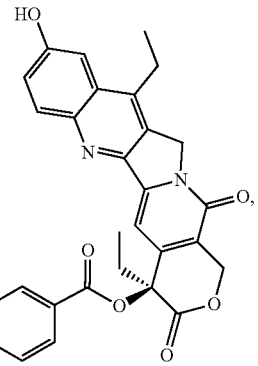

-continued
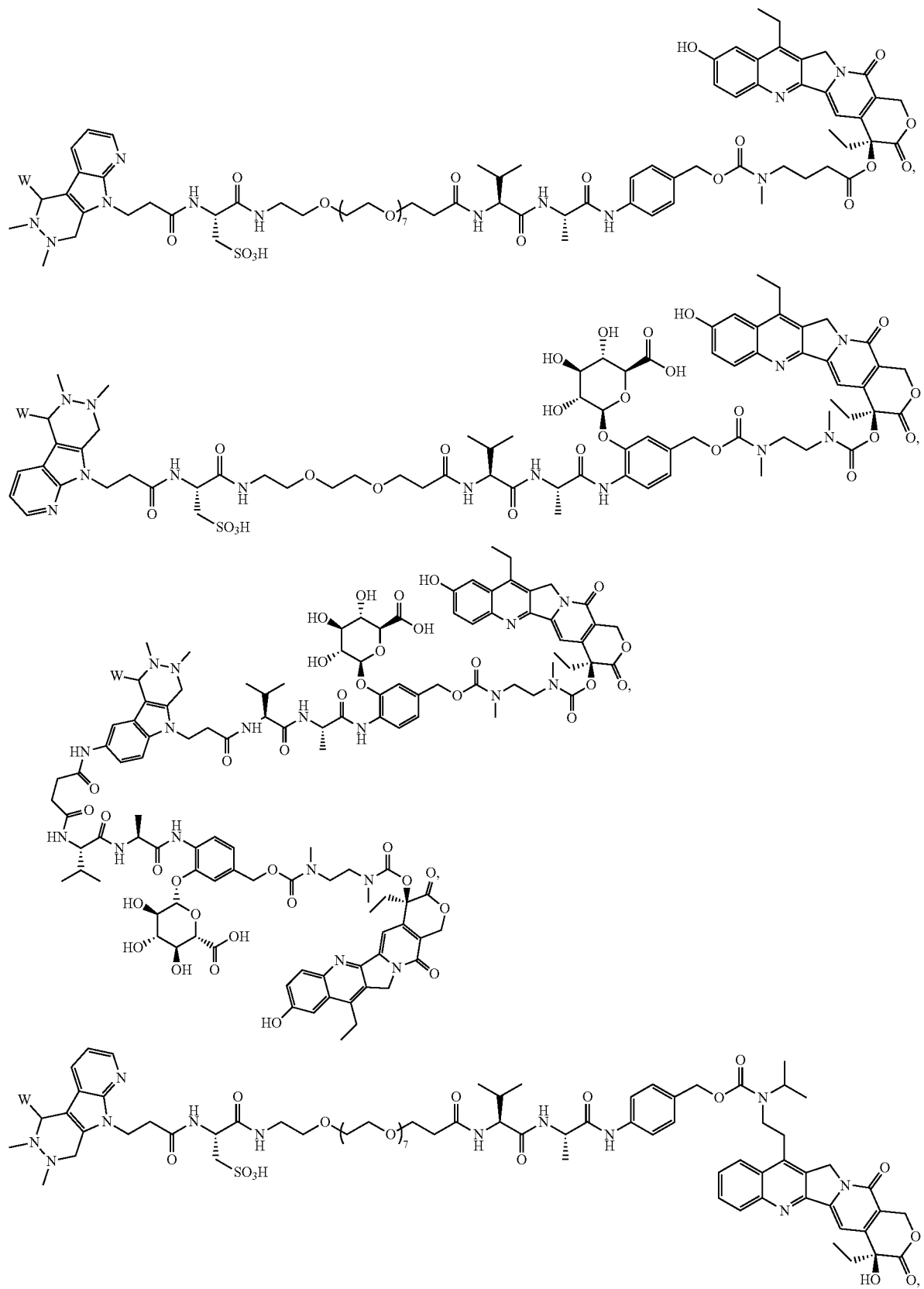

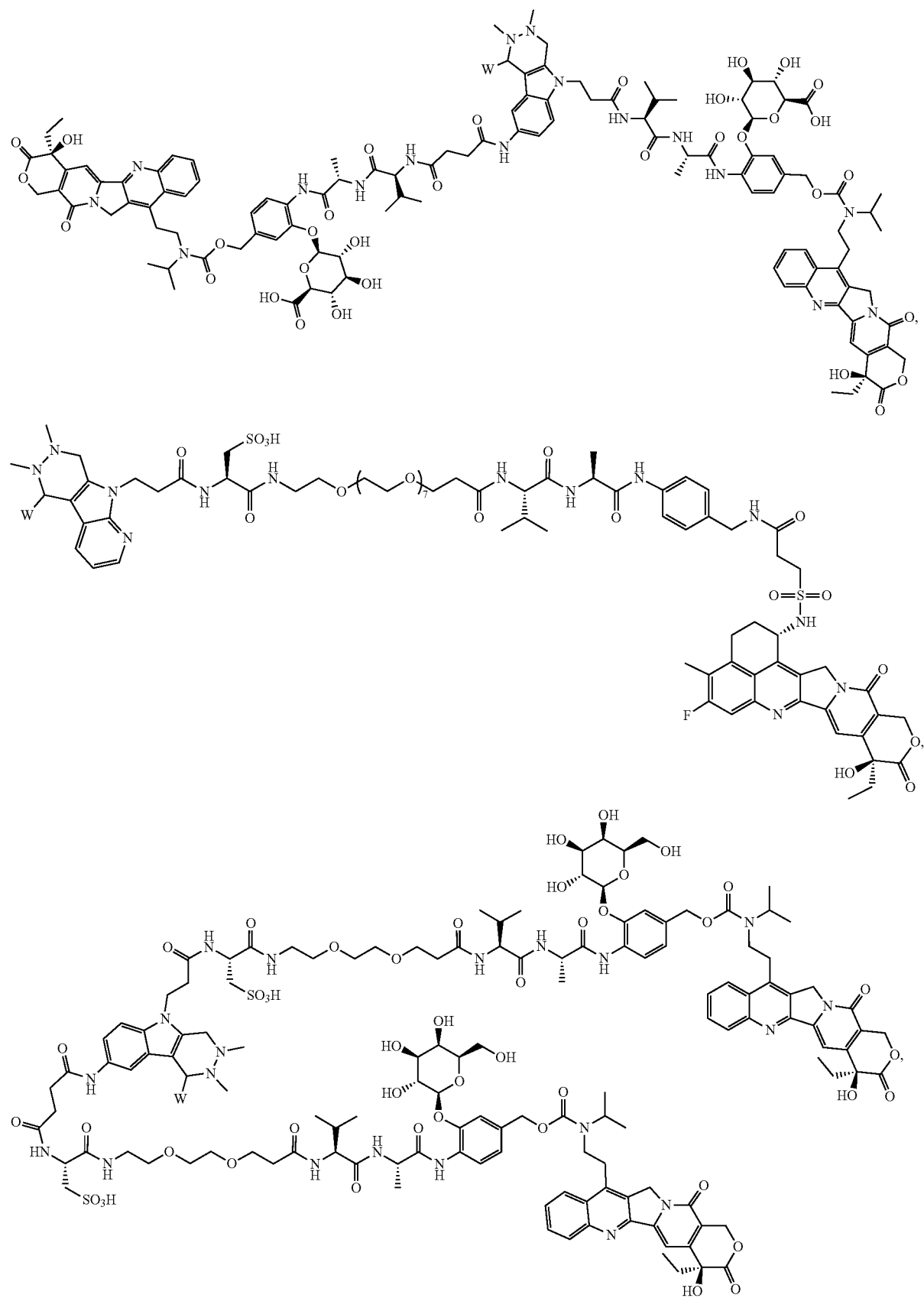

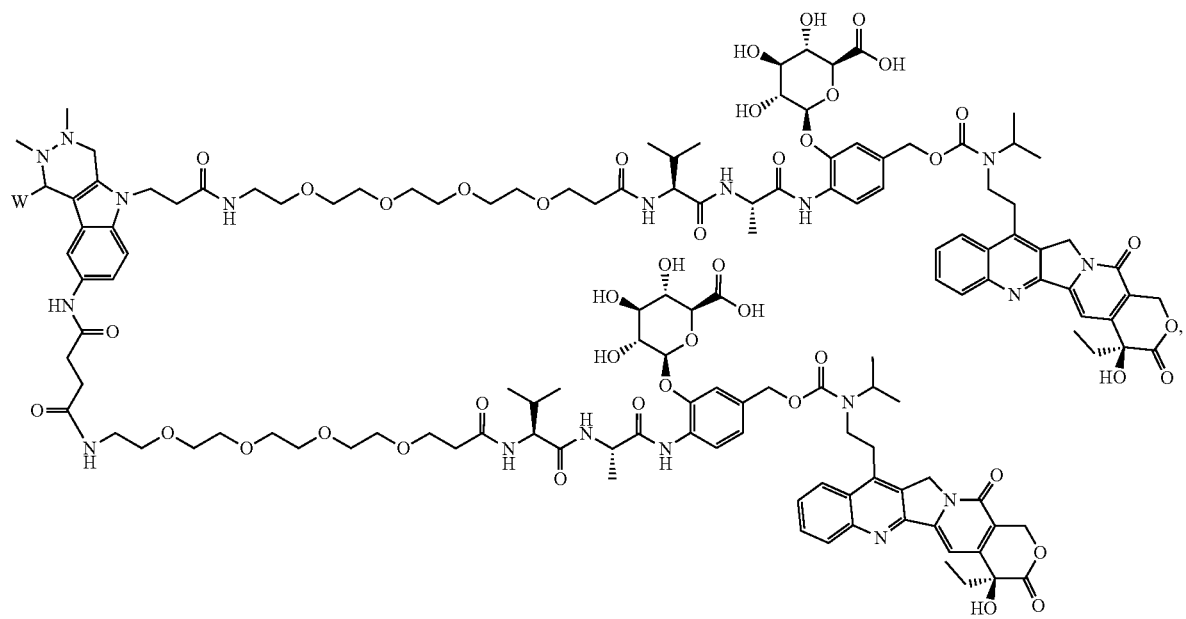
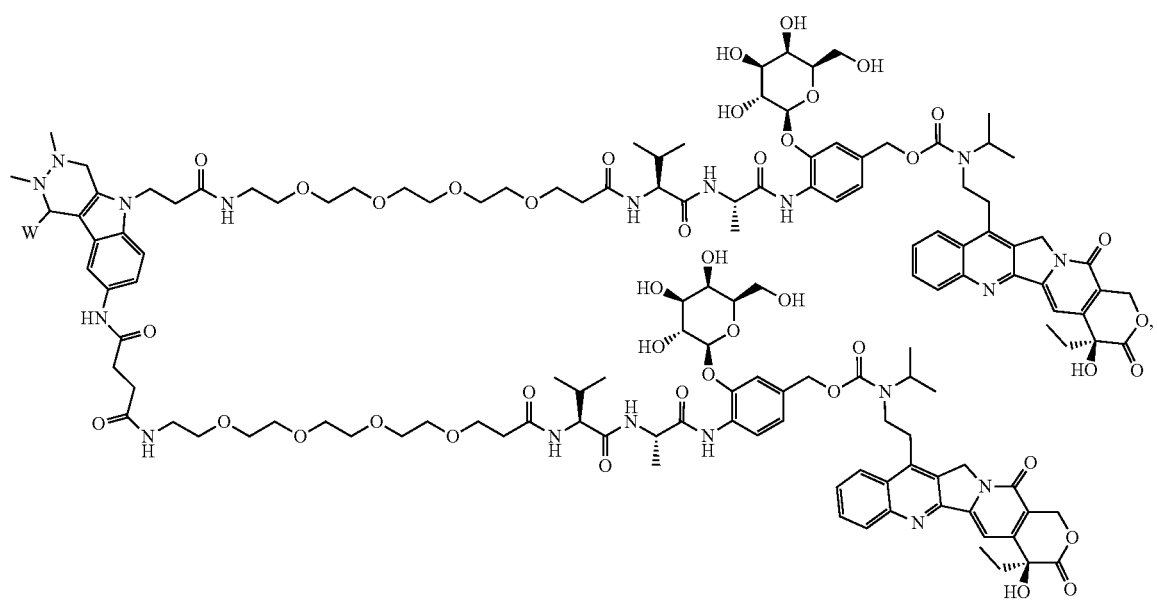

-continued
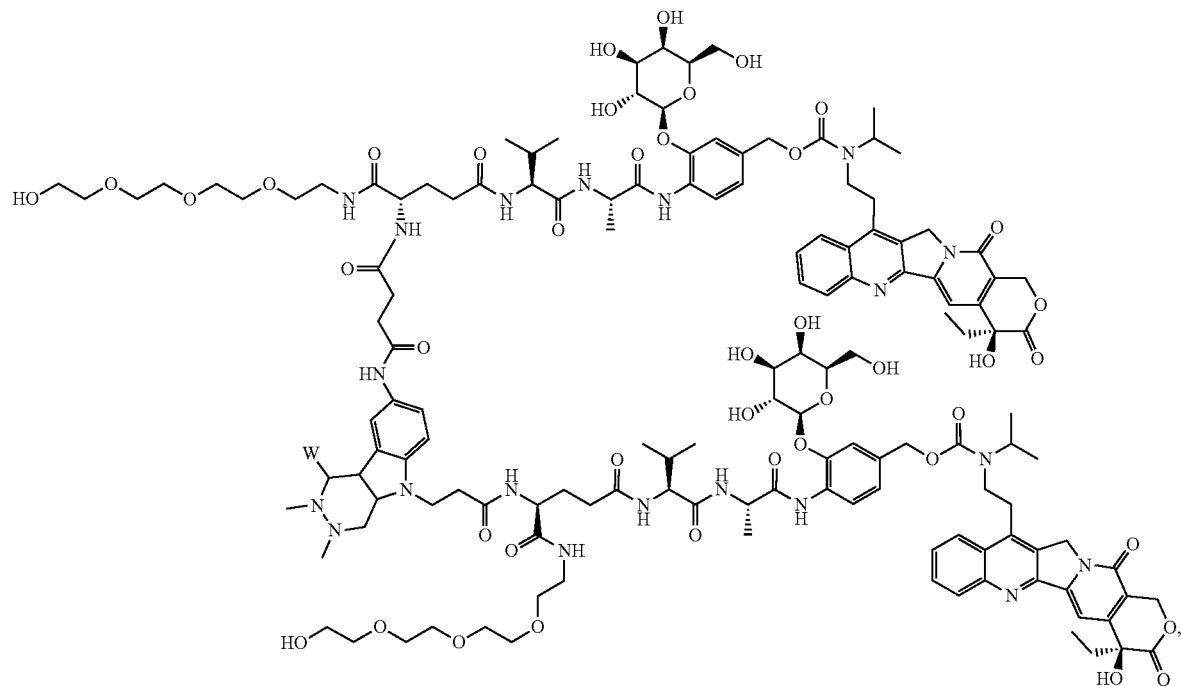
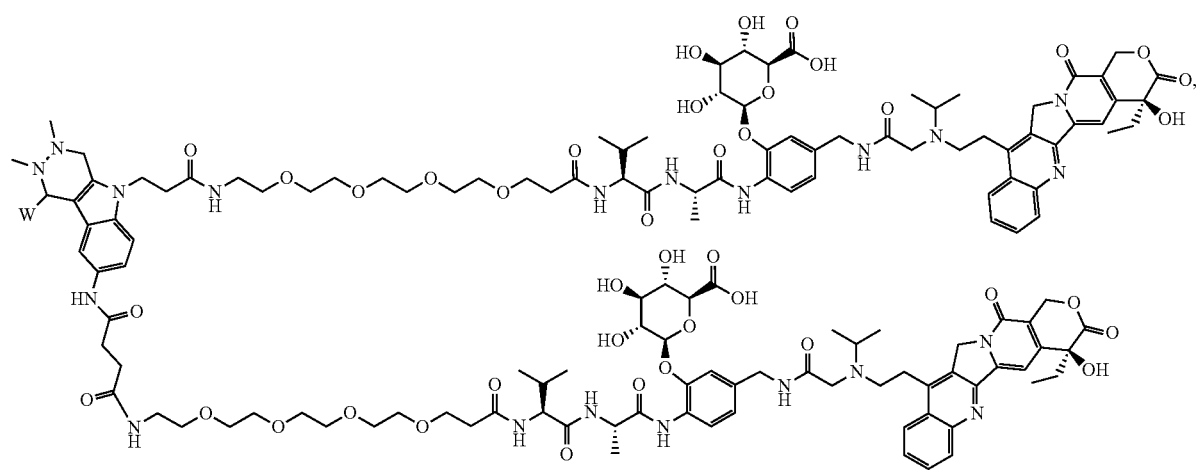

-continued
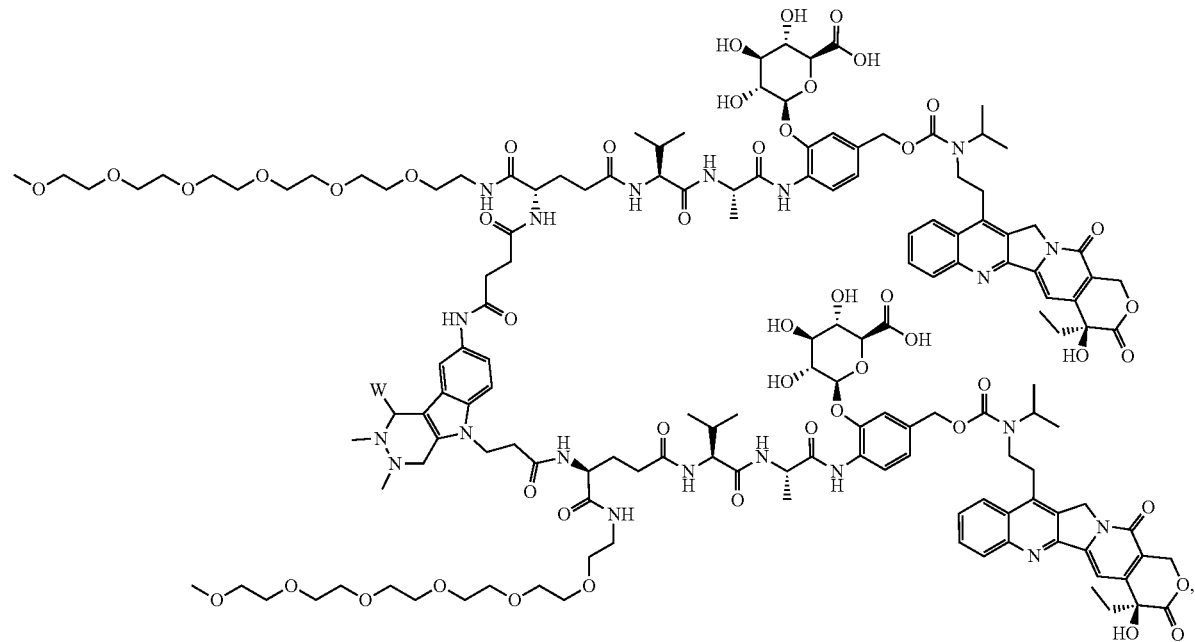 [SMILES: CC[C@@]1(O)C(=O)OCc2c1cc1n(c2=O)Cc2c-1nc1ccccc1c2CCN(C(=O)OCc1ccc(NC(=O)[C@H](C)NC(=O)[C@@H](NC(=O)CC[C@H](NC(=O)CCC(=O)Nc2ccc3c(c2)cc(CN(C)NC)n3CCC(=O)N[C@@H](CCC(=O)N[C@H](C(=O)N[C@@H](C)C(=O)Nc2ccc(COC(=O)N(CCc3c4c(nc5ccccc35)-c3cc5c(c(=O)n3C4)COC(=O)[C@]5(O)CC)C(C)C)cc2O[C@@H]2O[C@H](C(=O)O)[C@@H](O)[C@H](O)[C@H]2O)C(C)C)C(=O)NCCOCCOCCOCCOCCOCCOC)C(=O)NCCOCCOCCOCCOCCOCCOC)C(C)C)c(O[C@@H]2O[C@H](C(=O)O)[C@@H](O)[C@H](O)[C@H]2O)c1)C(C)C]
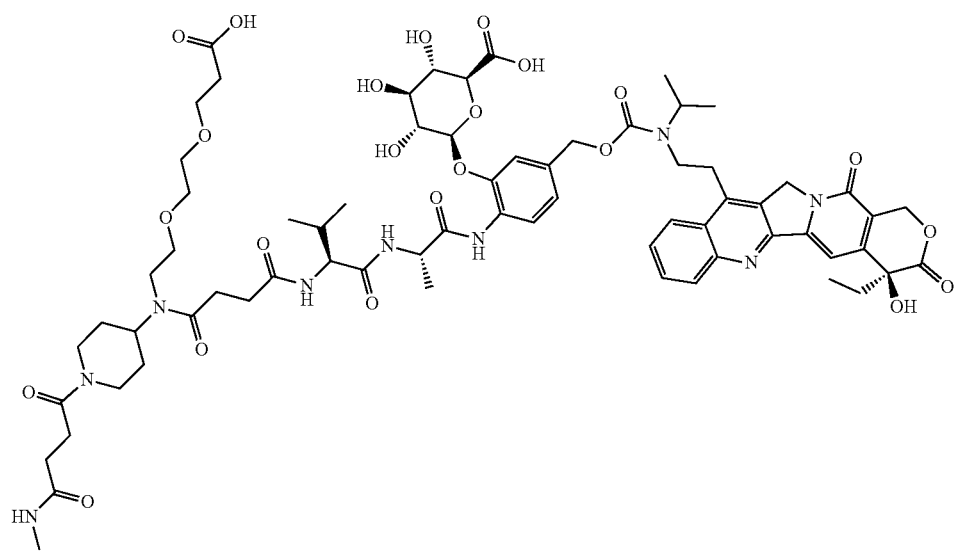

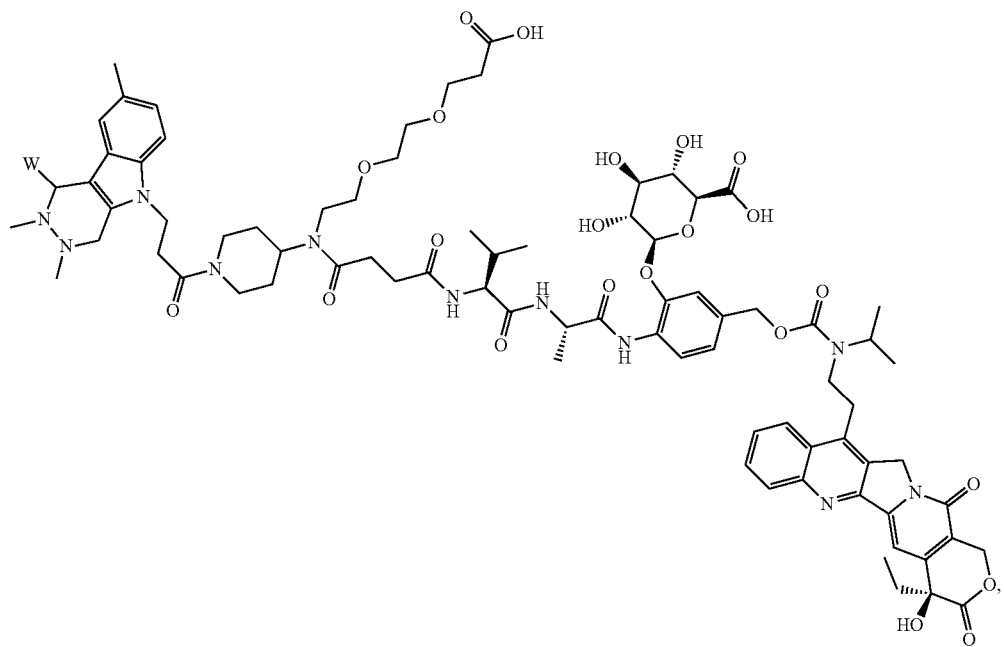
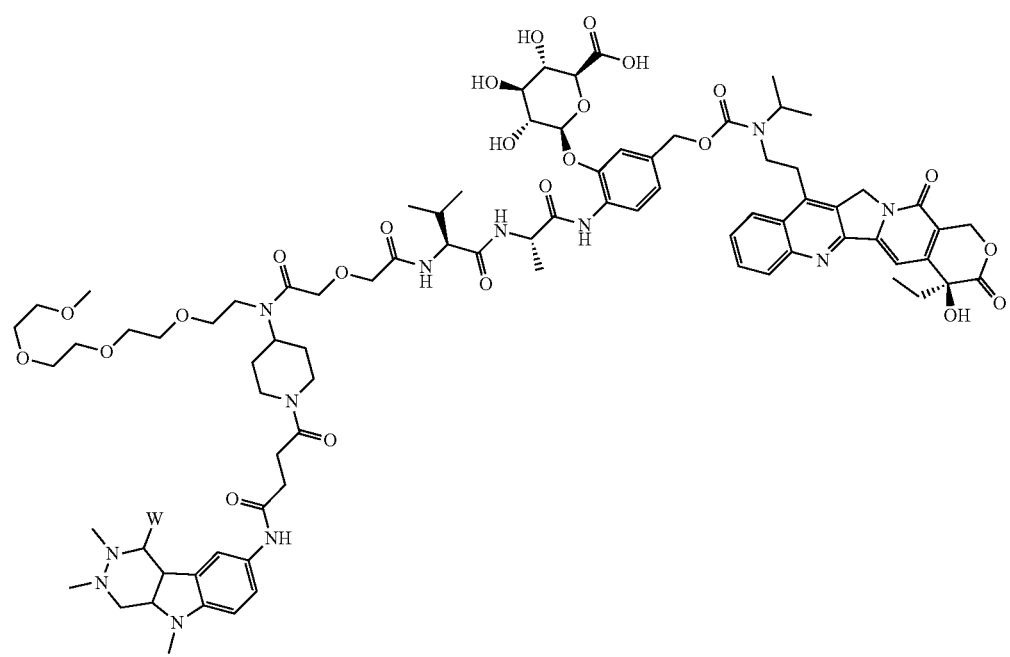

-continued
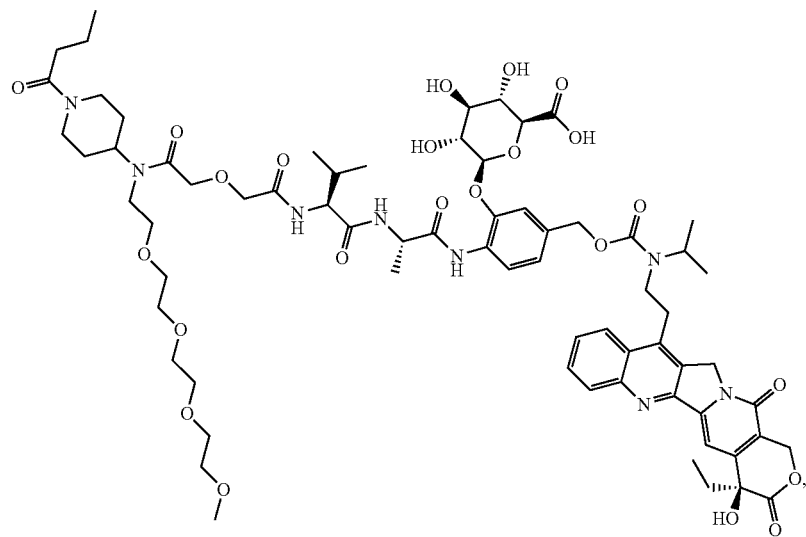
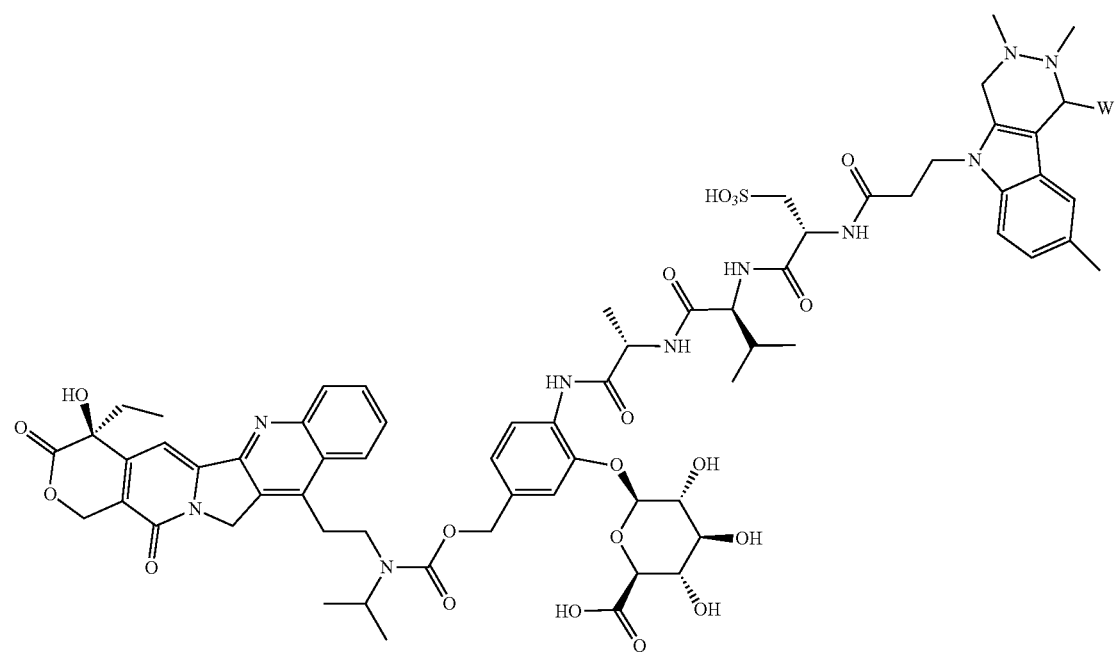

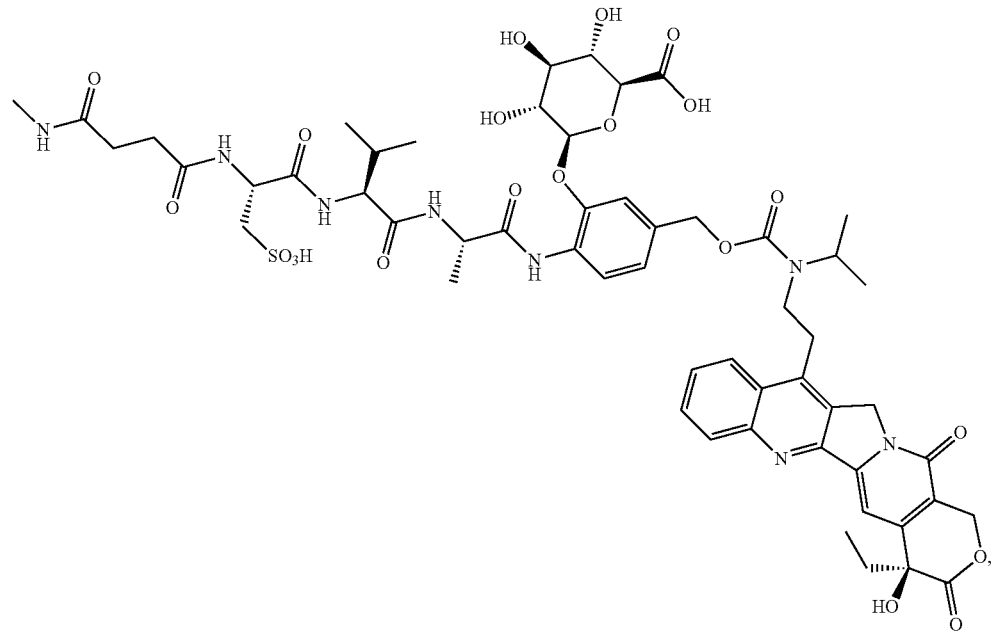
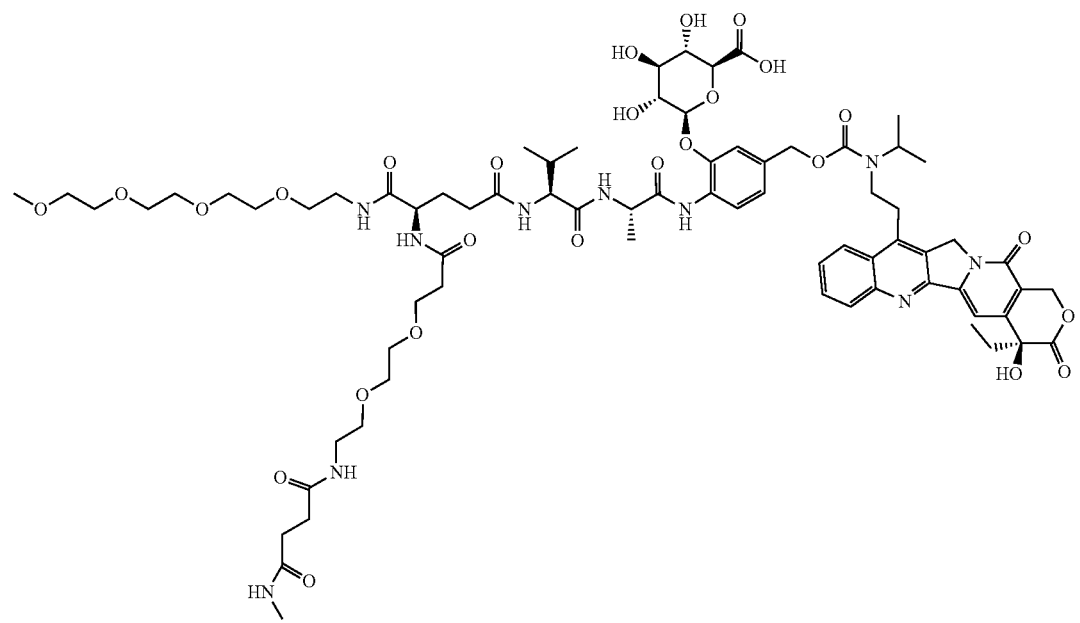

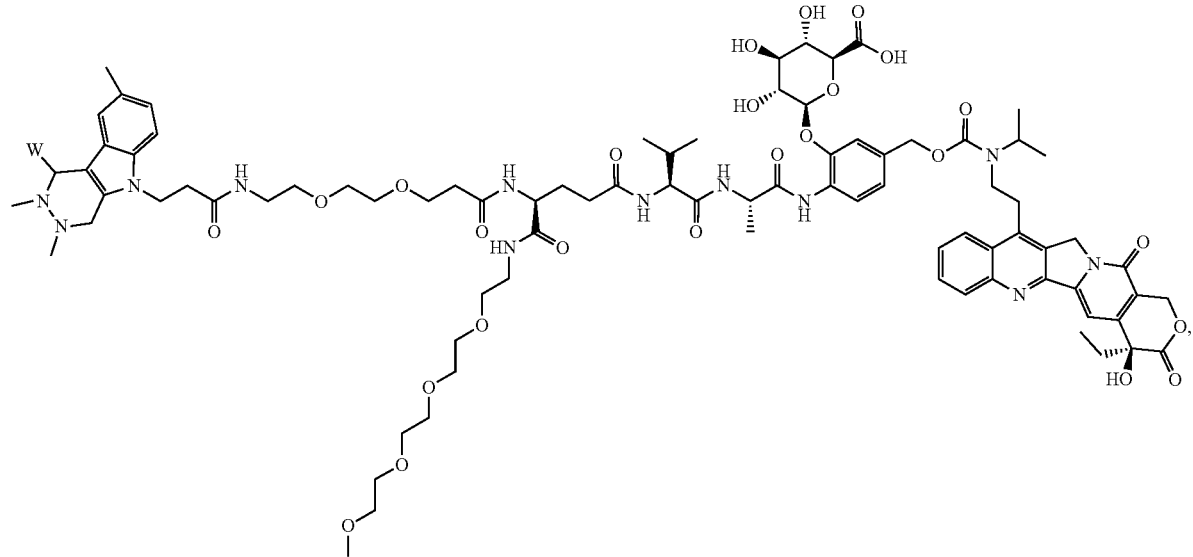
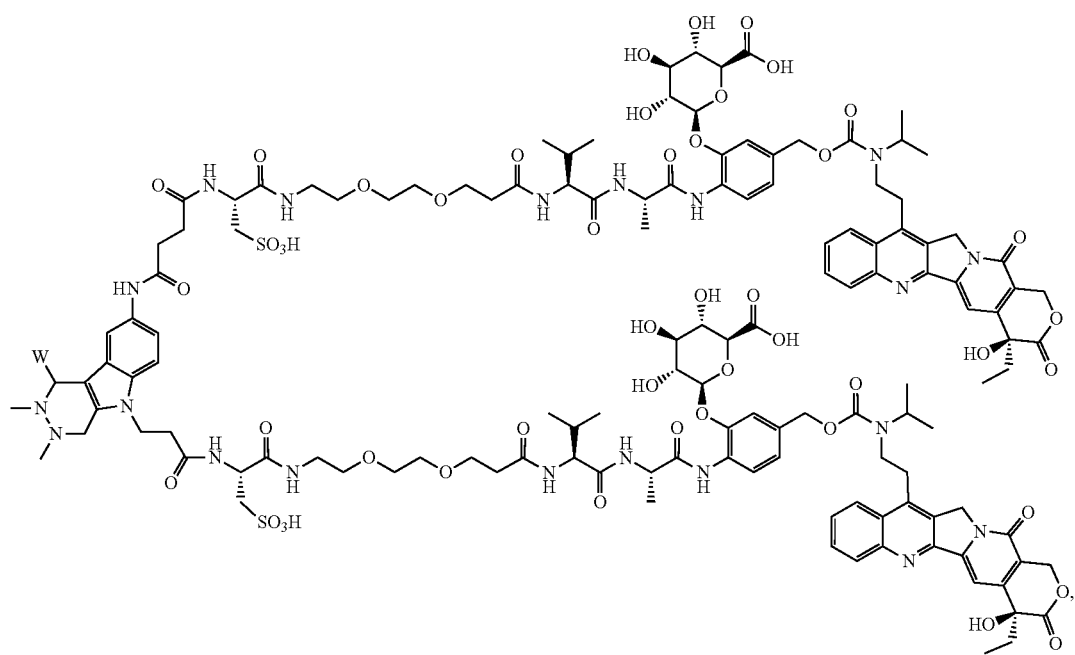

-continued
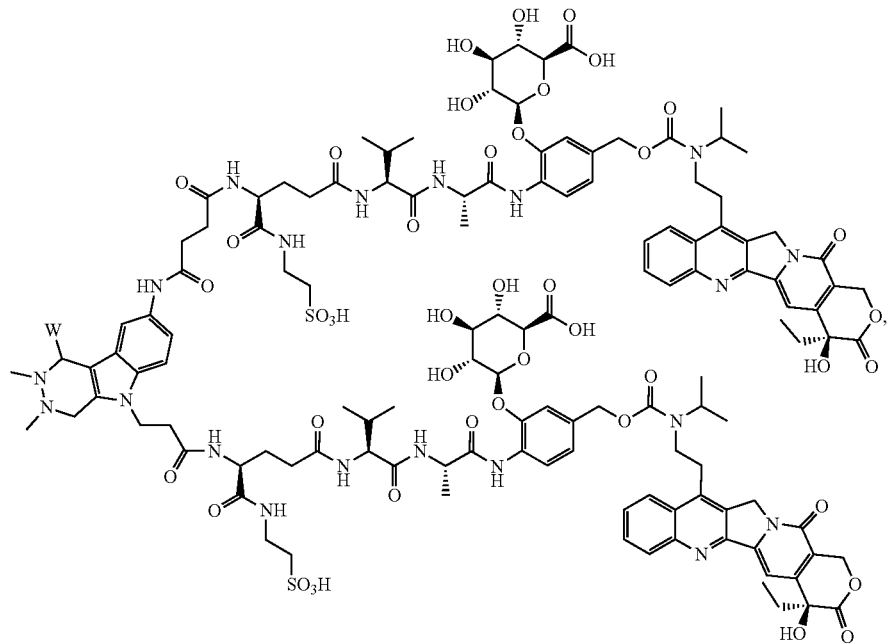
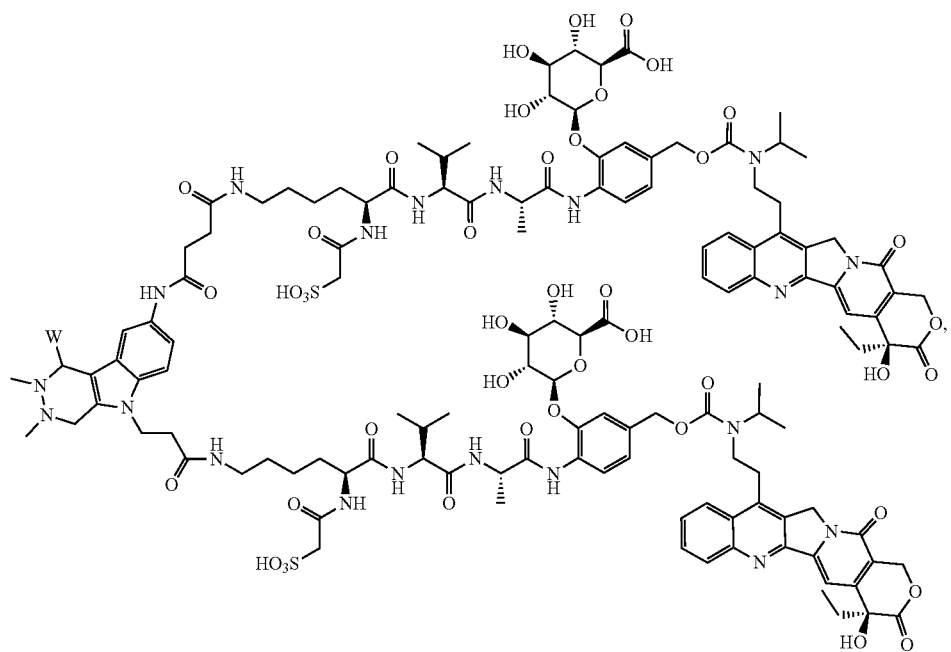

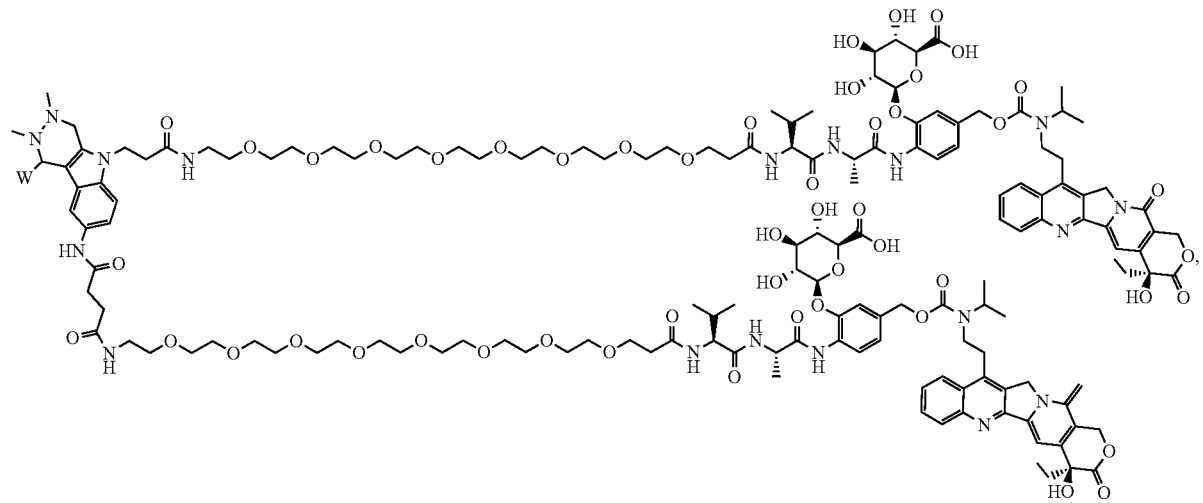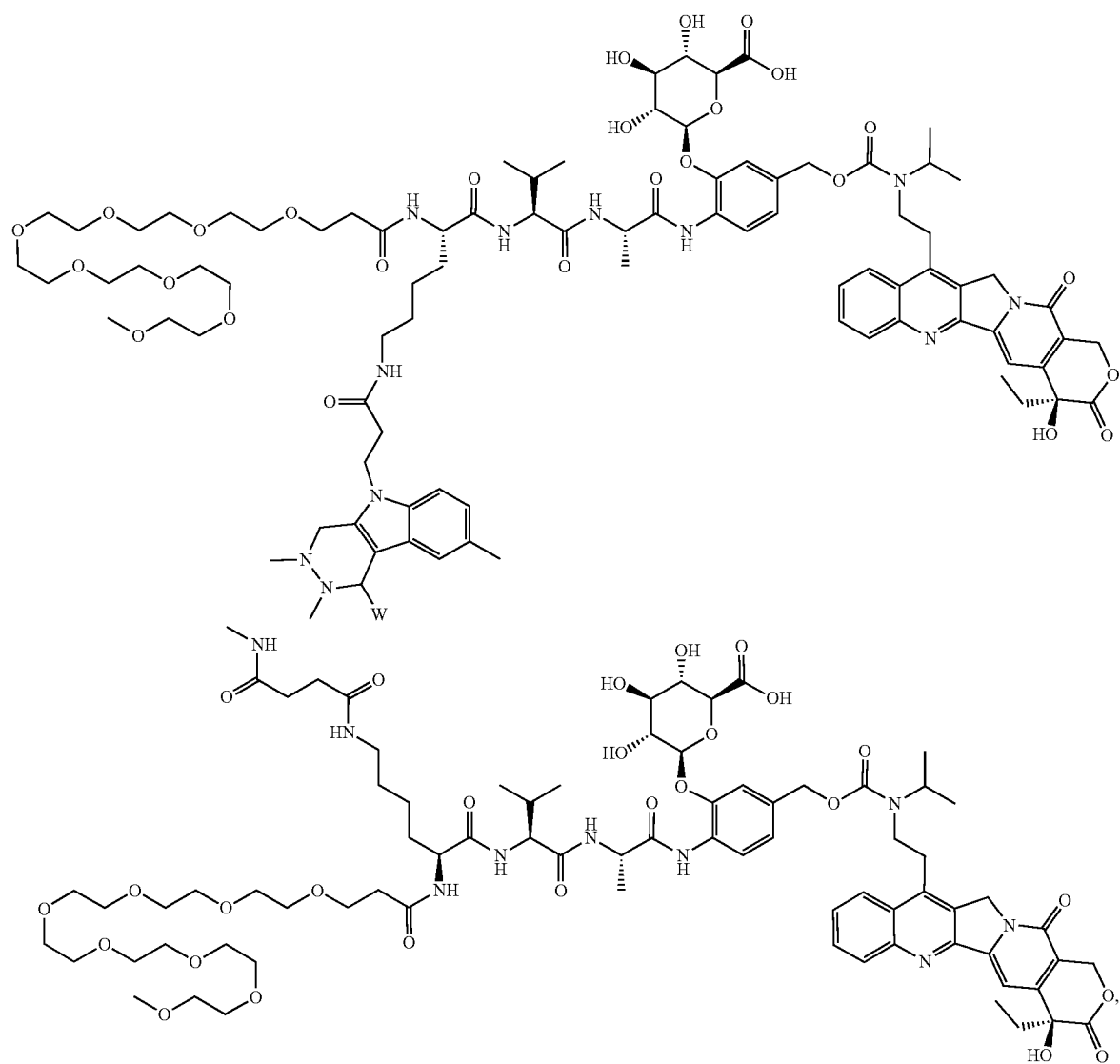

-continued
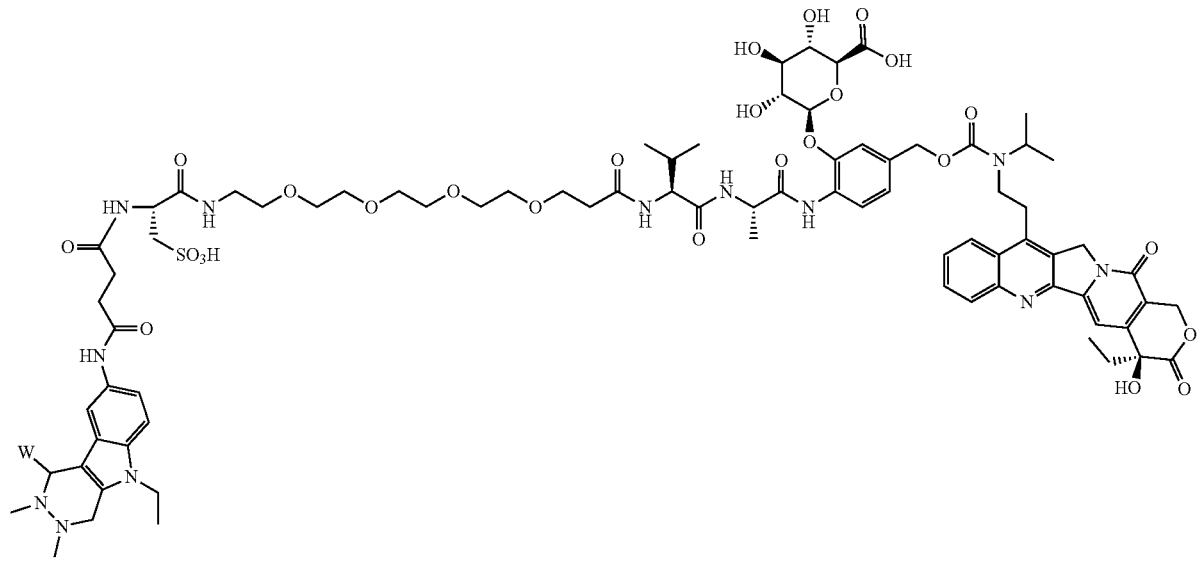
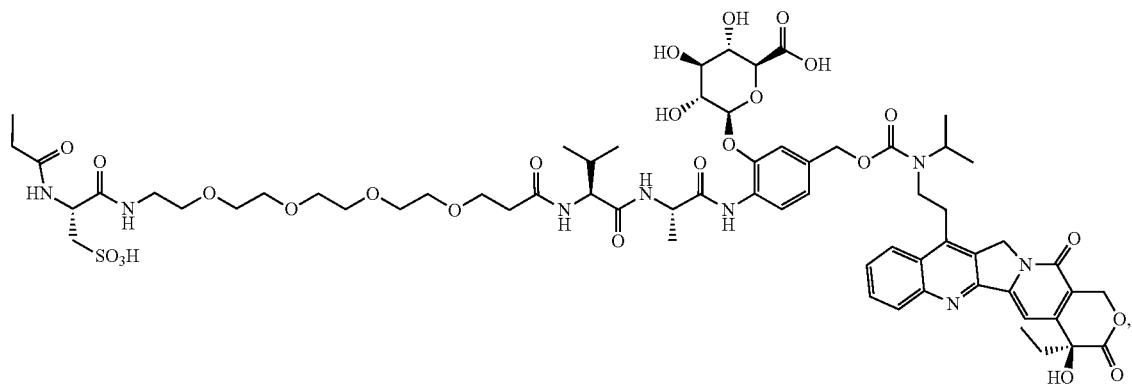
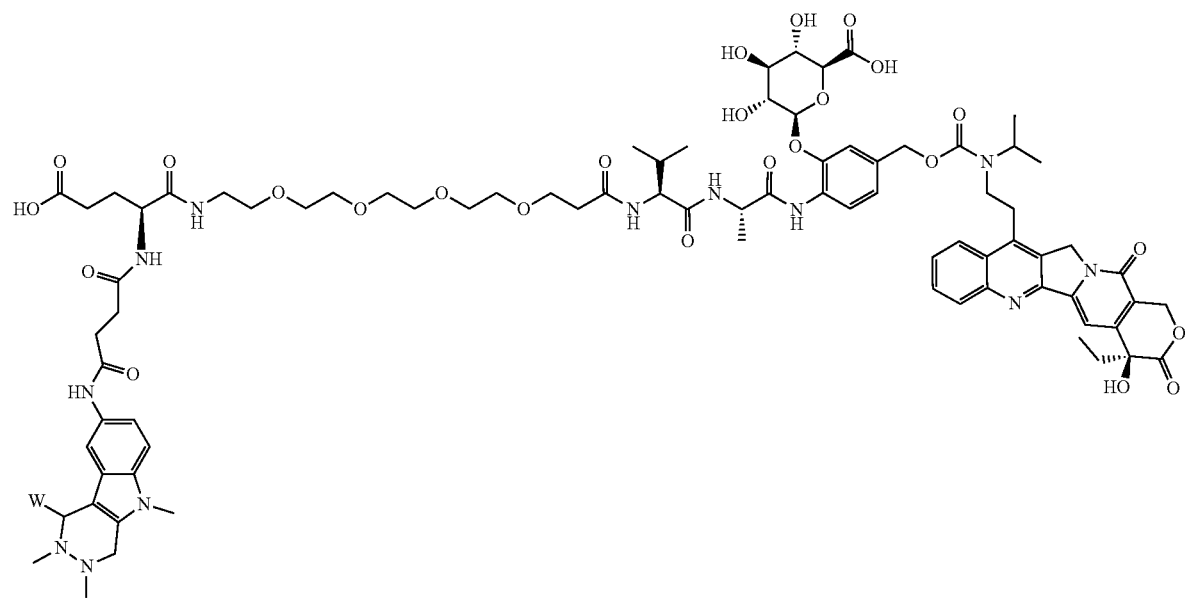

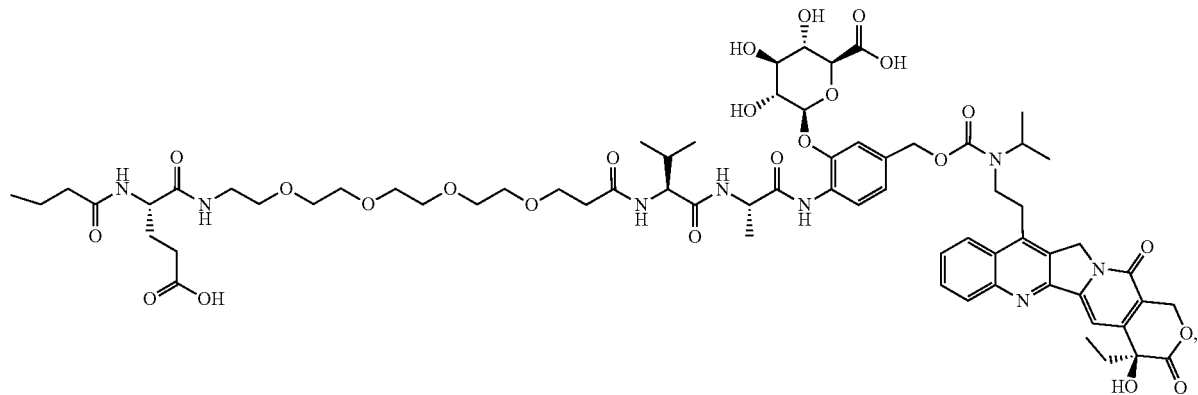
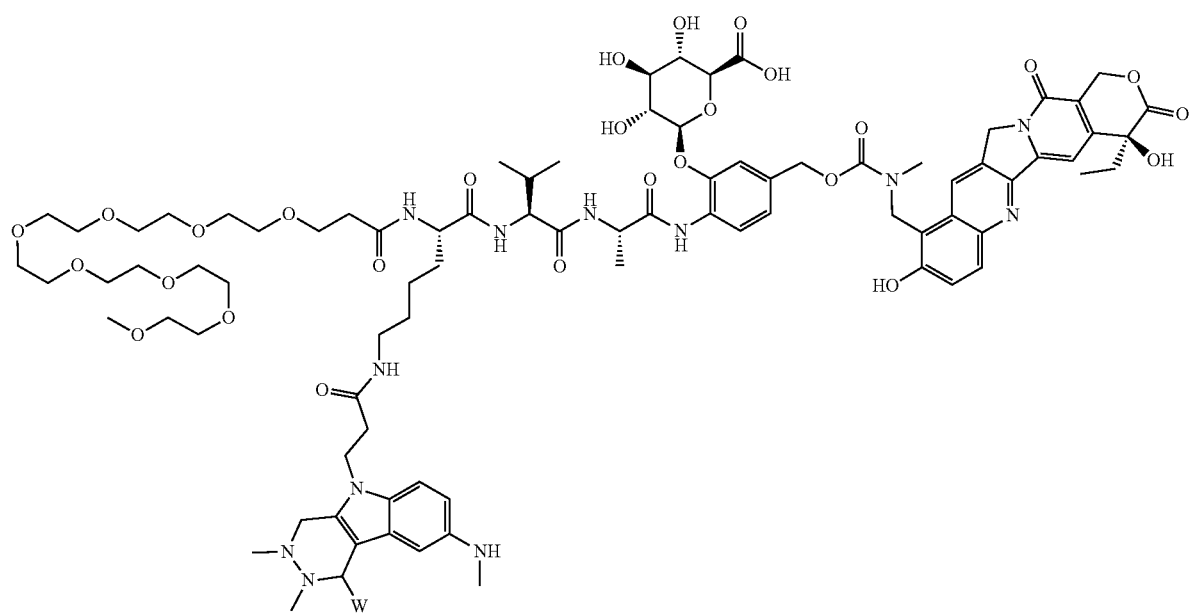
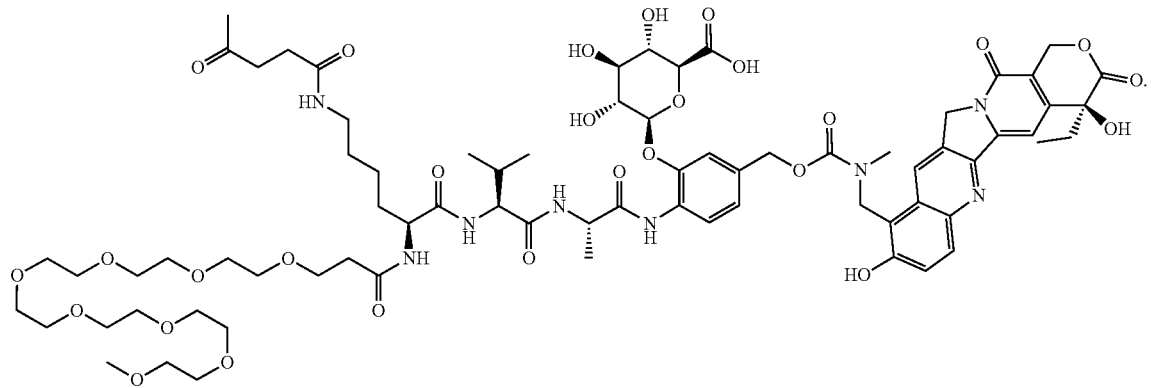

-continued
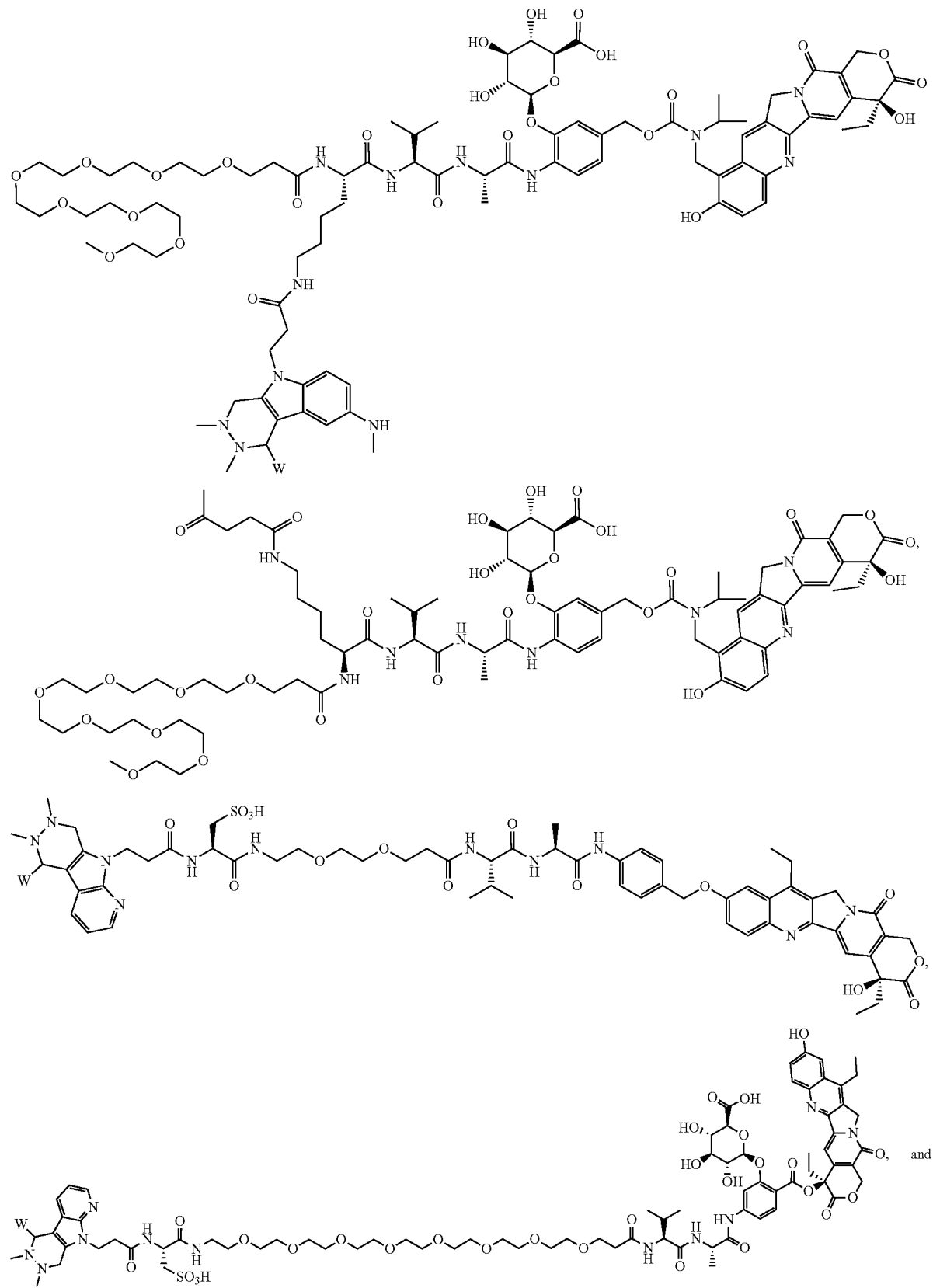

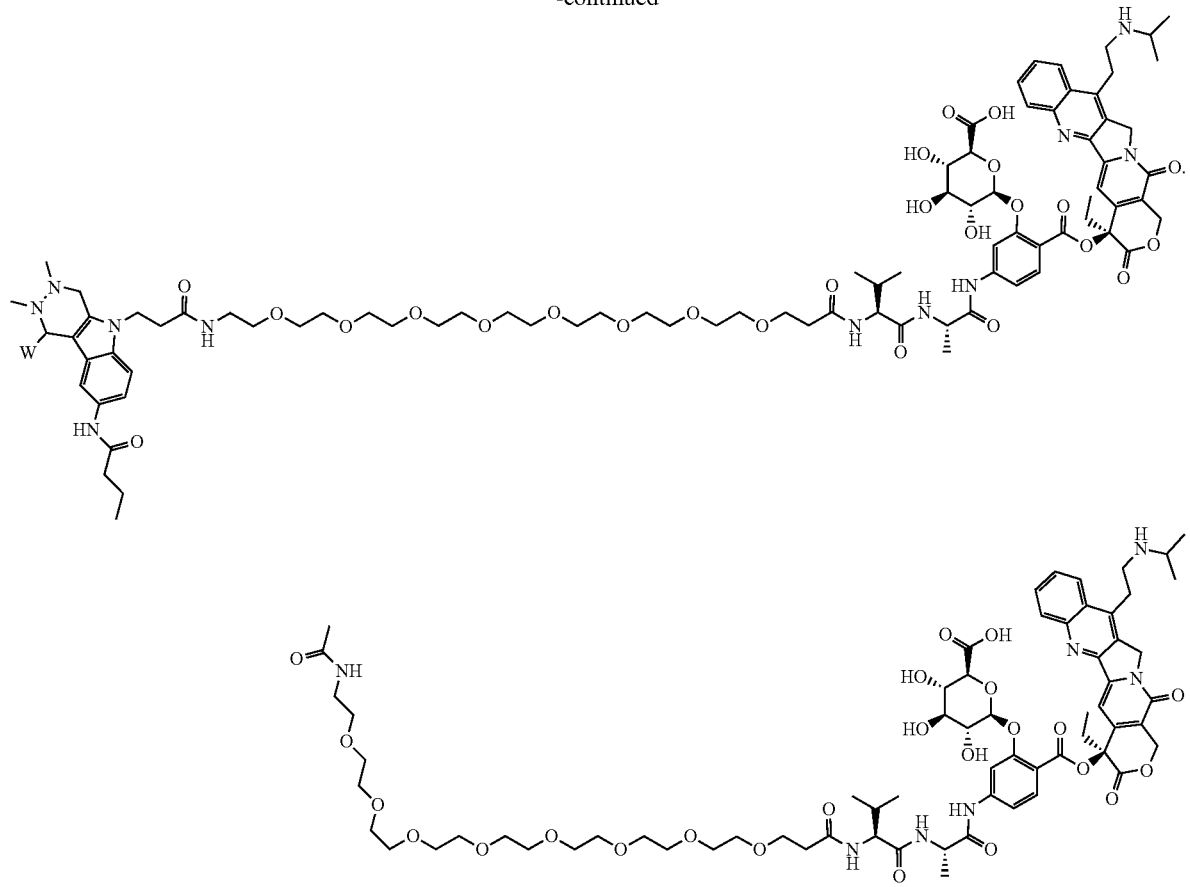

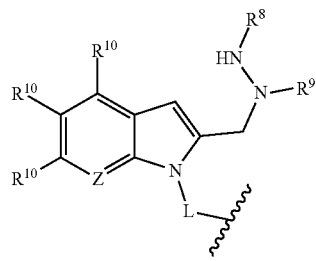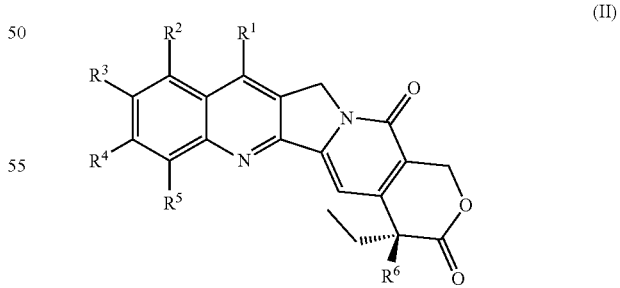

Aspects of the present disclosure include a compound of formula (III):

(III)

wherein:

Z is $CR^{10}$ or N, $R^8$ and $R^9$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^8$ and $R^9$ are optionally cyclically linked to form a 5 or 6-membered heterocyclyl;

each $R^{10}$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

L is a linker attached to a compound of formula (II) at $R^1$, $R^2$, $R^3$, $R^4$, $R^5$ or $R^6$:

(II)

$R^1$ and $R^2$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^1$ and R² are optionally cyclically linked to form a 5 or 6-membered cycloalkyl or heterocyclyl ring;

R³ and R⁴ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or R³ and R⁴ are optionally cyclically linked to form a 5 or 6-membered cycloalkyl or heterocyclyl ring;

R⁵ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl;

R⁶ is selected from OH and OC(O)R¹¹; and

R¹¹ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl, wherein at least one R¹⁰ is optionally linked to a second compound of formula (II).

In some embodiments, the compound of formula (II) has the structure of formula (IIa):

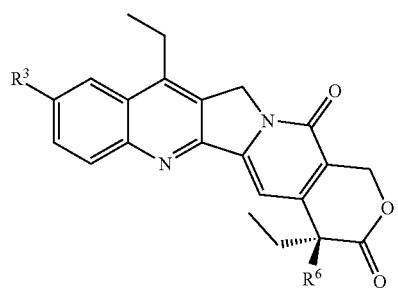

(IIa)

wherein R³ is OH and L is attached at R⁶; or L is attached at R³ and R⁶ is OH; or wherein the compound of formula (II) has the structure of formula (IIb):

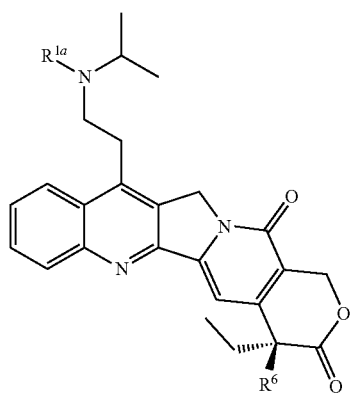

(IIb)

wherein R¹ᵃ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at R⁶; or L is attached at R¹ᵃ and R⁶ is OH; or wherein the compound of formula (II) has the structure of formula (IIc):

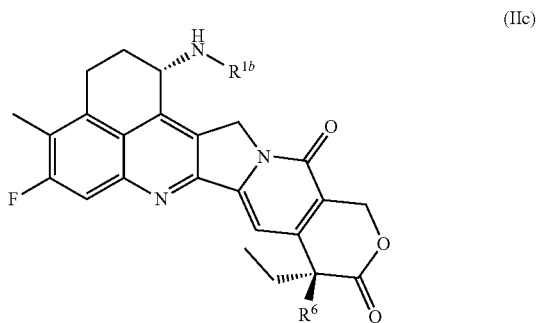

(IIc)

wherein R¹ᵇ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at R⁶; or L is attached at R¹ᵇ and R⁶ is OH; or wherein the compound of formula (II) has the structure of formula (IId):

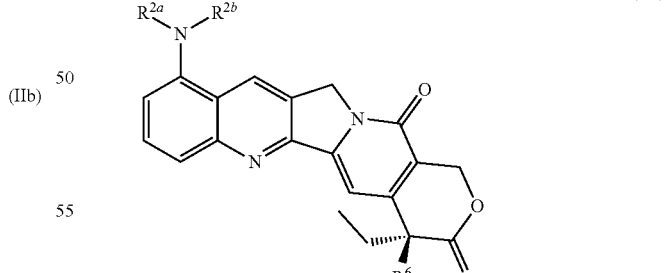

(IId)

wherein R²ᵃ and R²ᵇ are each independently selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at R⁶; or L is attached at R²ᵃ or R²ᵇ and R⁶ is OH; or wherein the compound of formula (II) has the structure of formula (IIe):

(IIe)

wherein $R^{2c}$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and attachment to L is indicated by the wavy line.

In some embodiments, L comprises:

-(T$^1$-V$^1$)$_a$-(T$^2$-V$^2$)$_b$-(T$^3$-V$^3$)$_c$-(T$^4$-V$^4$)$_d$-(T$^5$-V$^5$)$_e$-(T$^6$-V$^6$)$_f$, wherein a, b, c, d, e and f are each independently 0 or 1;

$T^1$, $T^2$, $T^3$, $T^4$, $T^5$ and $T^6$ are each independently selected from a covalent bond, $(C_1$-$C_{12})$alkyl, substituted $(C_1$-$C_{12})$alkyl, aryl, substituted aryl, heteroaryl, substituted heteroaryl, cycloalkyl, substituted cycloalkyl, heterocyclyl, and substituted heterocyclyl, (EDA)$_w$, (PEG)$_n$, (AA)$_p$, —(CR$^{13}$OH)$_m$—, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;

$V^1$, $V^2$, $V^3$, $V^4$, $V^5$ and $V^6$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein each q is an integer from 1 to 6;

each $R^{13}$ is independently selected from hydrogen, alkyl, substituted alkyl, aryl, and substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, L is a linker wherein:

$T^1$ is selected from a $(C_1$-$C_{12})$alkyl and a substituted $(C_1$-$C_{12})$alkyl;

$T^2$, $T^3$, $T^4$, $T^5$ and $T^6$ are each independently selected from a covalent bond, $(C_1$-$C_{12})$alkyl, substituted $(C_1$-$C_{12})$alkyl, aryl, substituted aryl, heteroaryl, substituted heteroaryl, cycloalkyl, substituted cycloalkyl, heterocyclyl, and substituted heterocyclyl, (EDA)$_w$, (PEG)$_n$, (AA)$_p$, —(CR$^{13}$OH)$_m$—, 4-amino-piperidine (4AP), MABO, MABC, PABO, PABC, PAB, PABA, PAP, PHP, an acetal group, a hydrazine, and an ester; and $V^1$, $V^2$, $V^3$, $V^4$, $V^5$ and $V^6$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$—, and —P(O)OH—;

wherein:

(PEG)$_n$ is where n is an integer from 1 to 30;

EDA is an ethylene diamine moiety having the following structure:

where y is an integer from 1 to 6 and r is 0 or 1;

4-amino-piperidine (4AP) is and each $R^{12}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring.

In some embodiments, $T^1$, $T^2$, $T^3$, $T^4$, $T^5$ and $T^6$ are each optionally substituted with a glycoside. In some embodiments, MABO, MABC, PABO, PABC, PAB, PABA, PAP and PHP are each optionally substituted with a glycoside. In some embodiments, the glycoside is selected from a glucuronide, a galactoside, a glucoside, a mannoside, a fucoside, O-GlcNAc, and O-GalNAc.

In some embodiments, L is a linker wherein:

$T^1$ is $(C_1$-$C_{12})$alkyl and $V^1$ is —CO—;
$T^2$ is an amino acid analog and $V^2$ is —NH—;
$T^3$ is (PEG)$_n$ and $V^3$ is —CO—;
$T^4$ is AA and $V^4$ is absent;
$T^5$ is PABC and $V^5$ is absent; and
$T^6$ is EDA and $V^6$ is —CO—; or wherein:

$T^1$ is $(C_1$-$C_{12})$alkyl and $V^1$ is —CO—;
$T^2$ is an amino acid analog and $V^2$ is —NH—;
$T^3$ is (PEG)$_n$ and $V^3$ is —CO—;
$T^4$ is AA and $V^4$ is absent;
$T^5$ is absent and $V^5$ is —NR$^{15}$(C$_6$H$_4$)—; and
$T^6$ is absent and $V^6$ is —CO—; or wherein:
T¹ is $(C_1-C_{12})$alkyl and V¹ is —CO—;
T² is an amino acid analog and V² is —NH—;
T³ is $(PEG)_n$ and V³ is —CO—;
T⁴ is AA and V⁴ is absent;
T⁵ is PABC and V⁵ is —NR¹⁵—; and
T⁶ is $(C_1-C_{12})$alkyl and V⁶ is —CO—; or
wherein:
T¹ is $(C_1-C_{12})$alkyl and V¹ is —CO—;
T² is AA and V² is absent;
T³ is PABC and V³ is absent;
T⁴ is EDA and V⁴ is —CO—; and
e and f are each 0; or
wherein:
T¹ is $(C_1-C_{12})$alkyl and V¹ is —CO—;
T² is an amino acid analog and V² is —NH—;
T³ is $(PEG)_n$ and V³ is —CO—;
T⁴ is AA and V⁴ is absent;
T⁵ is PABC and V⁵ is absent; and
f is 0; or
wherein:
T¹ is $(C_1-C_{12})$alkyl and V¹ is —CO—;
T² is AA and V² is absent;
T³ is PABC and V³ is absent; and
d, e and f are each 0; or
wherein:
T¹ is $(C_1-C_{12})$alkyl and V¹ is —CO—;
T² is an amino acid analog and V² is —NH—;
T³ is $(PEG)_n$ and V³ is —CO—;
T⁴ is AA and V⁴ is absent;
T⁵ is PABA and V⁵ is —CO—; and
T⁶ is $(C_1-C_{12})$alkyl and V⁶ is —SO₂—; or
wherein:
T¹ is $(C_1-C_{12})$alkyl and V¹ is —CONH—;
T² is $(PEG)_n$ and V² is —CO—;
T³ is AA and V³ is absent;
T⁴ is PABC and V⁴ is absent;
T⁵ is PABC and V⁵ is absent; and
e and f are each 0; or
wherein:
T¹ is $(C_1-C_{12})$alkyl and V¹ is —CO—;
T² is an amino acid analog and V² is —NH—;
T³ is $(PEG)_n$ and V³ is —CO—;
T⁴ is AA and V⁴ is absent;
T⁵ is PABA and V⁵ is —CO—; and
T⁶ is $(C_1-C_{12})$alkyl and V⁶ is —SO₂—; or
wherein:
T¹ is $(C_1-C_{12})$alkyl and V¹ is —CONH—;
T² is $(PEG)_n$ and V² is —CO—;
T³ is AA and V³ is absent;
T⁴ is PABC and V⁴ is absent;
e and f are each 0; or
wherein:
T¹ is $(C_1-C_{12})$alkyl and V¹ is —CONH—;
T² is substituted $(C_1-C_{12})$alkyl and V² is —CO—;
T³ is AA and V³ is absent;
T⁴ is PABC and V⁴ is absent;
e and f are each 0; or
wherein:
T¹ is $(C_1-C_{12})$alkyl and V¹ is —CONH—;
T² is $(PEG)_n$ and V² is —CO—;
T³ is AA and V³ is absent;
T⁴ is PABC and V⁴ is absent;
T⁵ is $(C_1-C_{12})$alkyl and V⁵ is absent;
f is 0; or
wherein:
T¹ is $(C_1-C_{12})$alkyl and V¹ is —CO—;
T² is 4AP and V² is —CO—;
T³ is $(C_1-C_{12})$alkyl and V³ is —CO—;
T⁴ is AA and V⁴ is absent;
T⁵ is PABC and V⁵ is absent;
f is 0; or
wherein:
T¹ is $(C_1-C_{12})$alkyl and V¹ is —CO—;
T² is 4AP and V² is —CO—;
T³ is $(C_1-C_{12})$alkyl and V³ is —O—;
T⁴ is $(C_1-C_{12})$alkyl and V⁴ is —CO—;
T⁵ is AA and V⁵ is absent;
T⁶ is PABC and V⁶ is absent; or
wherein:
T¹ is $(C_1-C_{12})$alkyl and V¹ is —CO—;
T² is an amino acid analog and V² is absent;
T³ is AA and V³ is absent;
T⁴ is PABC and V⁴ is absent;
e and f are each 0; or
wherein:
T¹ is $(C_1-C_{12})$alkyl and V¹ is —CONH—;
T² is $(PEG)_n$ and V² is —CONH—;
T³ is substituted $(C_1-C_{12})$alkyl and V³ is —CO—;
T⁴ is AA and V⁴ is absent;
T⁵ is PABC and V⁵ is absent;
f is 0; or
wherein:
T¹ is $(C_1-C_{12})$alkyl and V¹ is —CO—;
T² is AA and V² is —NH—;
T³ is $(PEG)_n$ and V³ is —CO—;
T⁴ is AA and V⁴ is absent;
T⁵ is PABC and V⁵ is absent;
f is 0; or
wherein:
T¹ is $(C_1-C_{12})$alkyl and V¹ is —CO—;
T² is an amino acid analog and V² is —NH—;
T³ is $(PEG)_n$ and V³ is —CO—;
T⁴ is AA and V⁴ is absent;
T⁵ is PABO and V⁵ is absent; and
f is 0; or
wherein:
T¹ is $(C_1-C_{12})$alkyl and V¹ is —CO—;
T² is an amino acid analog and V² is —NH—;
T³ is $(PEG)_n$ and V³ is —CO—;
T⁴ is AA and V⁴ is absent;
T⁵ is PAP and V⁵ is —COO—; and
f is 0; or
wherein:
T¹ is $(C_1-C_{12})$alkyl and V¹ is —CONH—;
T² is $(PEG)_n$ and V² is —CO—;
T³ is AA and V³ is absent;
T⁴ is PAP and V⁴ is —COO—; and
e and f are each 0.

In some embodiments, one R¹⁰ is linked via a second linker, $L^B$, to a second compound of formula (II).

In some embodiments, $L^B$ comprises:

$$-(T^7-V^7)_g-(T^8-V^8)_h-(T^9-V^9)_i-(T^{10}-V^{10})_j-(T^{11}-V^{11})_k-(T^{12}-V^{12})_l-$$

wherein
g, h, i, j, k and l are each independently 0 or 1;
T⁷, T⁸, T⁹, T¹⁰, T¹¹ and T¹² are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;

$V^7$, $V^8$, $V^9$, $V^{10}$, $V^{11}$ and $V^{12}$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein each q is an integer from 1 to 6;

each $R^{13}$ is independently selected from hydrogen, alkyl, substituted alkyl, aryl, and substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In some embodiments, $T^7$, $T^8$, $T^9$, $T^{10}$, $T^{11}$ and $T^{12}$ are each optionally substituted with a glycoside. In some embodiments, MABO, MABC, PABO, PABC, PAB, PABA, PAP and PHP are each optionally substituted with a glycoside. In some embodiments, the glycoside is selected from a glucuronide, a galactoside, a glucoside, a mannoside, a fucoside, O-GlcNAc, and O-GalNAc.

In some embodiments, $L^B$ is a linker wherein:
$T^7$ is absent and $V^7$ is —NR$^{15}$CO—;
$T^8$ is (C$_1$-C$_{12}$)alkyl and $V^8$ is —CO—;
$T^9$ is AA and $V^9$ is absent;
$T^{10}$ is PABC and $V^{10}$ is absent;
$T^{11}$ is EDA and $V^{11}$ is —CO—; and
l is 0; or
wherein:
$T^7$ is absent and $V^7$ is —NR$^{15}$CO—;
$T^8$ is (C$_1$-C$_{12}$)alkyl and $V^8$ is —CO—;
$T^9$ is AA and $V^9$ is absent;
$T^{10}$ is PABC and $V^{10}$ is absent; and
k and l are each 0; or
wherein:
$T^7$ is absent and $V^7$ is —NHCO—;
$T^8$ is (C$_1$-C$_{12}$)alkyl and $V^8$ is —CO—;
$T^9$ is an amino acid analog and $V^9$ is —NH—;
$T^{10}$ is (PEG)$_n$ and $V^{10}$ is —CO—;
$T^{11}$ is AA and $V^{11}$ is absent; and
$T^{12}$ is PABC and $V^{12}$ is absent; or
wherein:
$T^7$ is absent and $V^7$ is —NHCO—;
$T^8$ is (C$_1$-C$_{12}$)alkyl and $V^8$ is —CONH—;
$T^9$ is (PEG)$_n$ and $V^9$ is —CO—;
$T^{10}$ is AA and $V^{10}$ is absent;
$T^{11}$ is PABC and $V^{11}$ is absent; and
l is 0; or
wherein:
$T^7$ is (C$_1$-C$_{12}$)alkyl and $V^7$ is —CONH—;
$T^8$ is substituted (C$_1$-C$_{12}$)alkyl and $V^8$ is —CO—;
$T^9$ is AA and $V^9$ is absent;
$T^{10}$ is PABC and $V^{10}$ is absent;
k and l are each 0; or
wherein:
$T^7$ is (C$_1$-C$_{12}$)alkyl and $V^7$ is —CONH—;
$T^8$ is (PEG)$_n$ and $V^8$ is —CO—;
$T^9$ is AA and $V^9$ is absent;
$T^{10}$ is PABC and $V^{10}$ is absent;
$T^{11}$ is (C$_1$-C$_{12}$)alkyl and $V^{11}$ is absent;
l is 0; or
wherein:
$T^7$ is (C$_1$-C$_{12}$)alkyl and $V^7$ is —CO—;
$T^8$ is 4AP and $V^8$ is —CO—;
$T^9$ is (C$_1$-C$_{12}$)alkyl and $V^9$ is —CO—;
$T^{10}$ is AA and $V^{10}$ is absent;
$T^{11}$ is PABC and $V^{11}$ is absent;
l is 0; or
wherein:
$T^7$ is (C$_1$-C$_{12}$)alkyl and $V^7$ is —CO—;
$T^8$ is 4AP and $V^8$ is —CO—;
$T^9$ is (C$_1$-C$_{12}$)alkyl and $V^9$ is —O—;
$T^{10}$ is (C$_1$-C$_{12}$)alkyl and $V^{10}$ is —CO—;
$T^{11}$ is AA and $V^{11}$ is absent;
$T^{12}$ is PABC and $V^{12}$ is absent; or
wherein:
$T^7$ is (C$_1$-C$_{12}$)alkyl and $V^7$ is —CO—;
$T^8$ is an amino acid analog and $V^8$ is absent;
$T^9$ is AA and $V^9$ is absent;
$T^{10}$ is PABC and $V^{10}$ is absent;
k and l are each 0; or
wherein:
$T^7$ is (C$_1$-C$_{12}$)alkyl and $V^7$ is —CONH—;
$T^8$ is (PEG)$_n$ and $V^8$ is —CONH—;
$T^9$ is substituted (C$_1$-C$_{12}$)alkyl and $V^9$ is —CO—;
$T^{10}$ is AA and $V^{10}$ is absent;
$T^{11}$ is PABC and $V^{11}$ is absent;
l is 0; or
wherein:
$T^7$ is (C$_1$-C$_{12}$)alkyl and $V^7$ is —CO—;
$T^8$ is AA and $V^8$ is —NH—;
$T^9$ is (PEG)$_n$ and $V^9$ is —CO—;
$T^{10}$ is AA and $V^{10}$ is absent;
$T^{11}$ is PABC and $V^{11}$ is absent;
l is 0; or
wherein:
$T^7$ is (C$_1$-C$_{12}$)alkyl and $V^7$ is —CONH—;
$T^8$ is (PEG)$_n$ and $V^8$ is —CO—;
$T^9$ is AA and $V^9$ is absent;
$T^{10}$ is PAP and $V^{10}$ is —COO—; and
k and l are each 0.

In some embodiments, the compound is selected from:
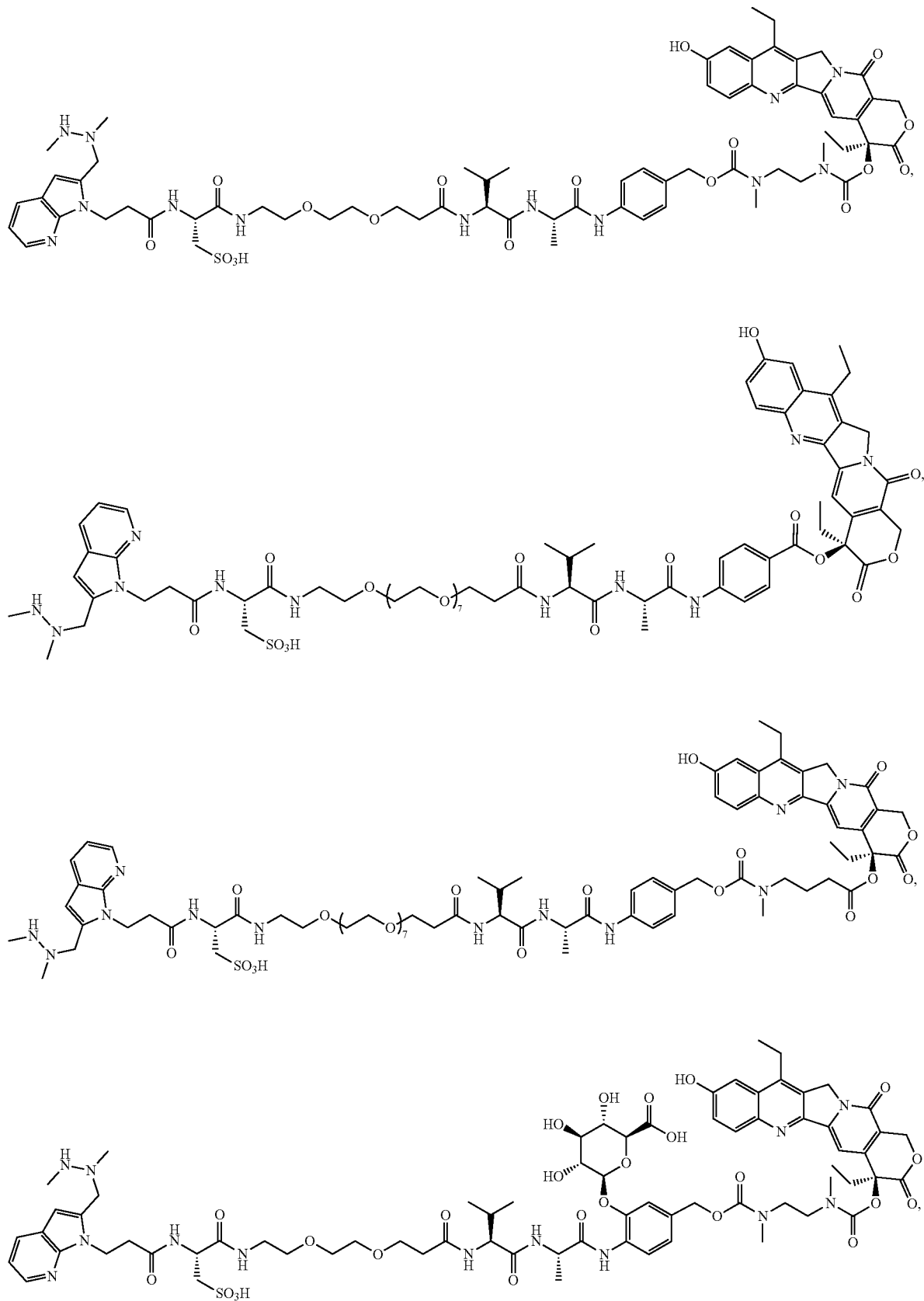

-continued
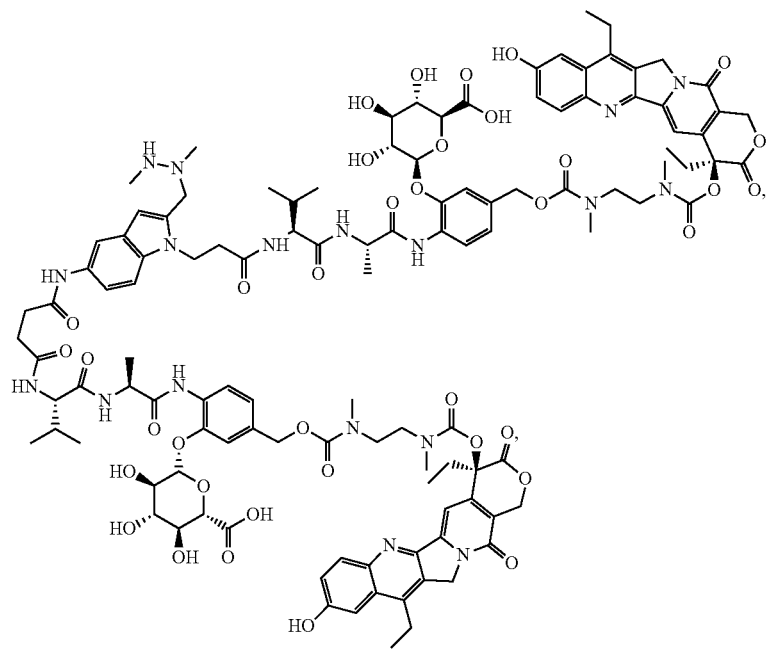
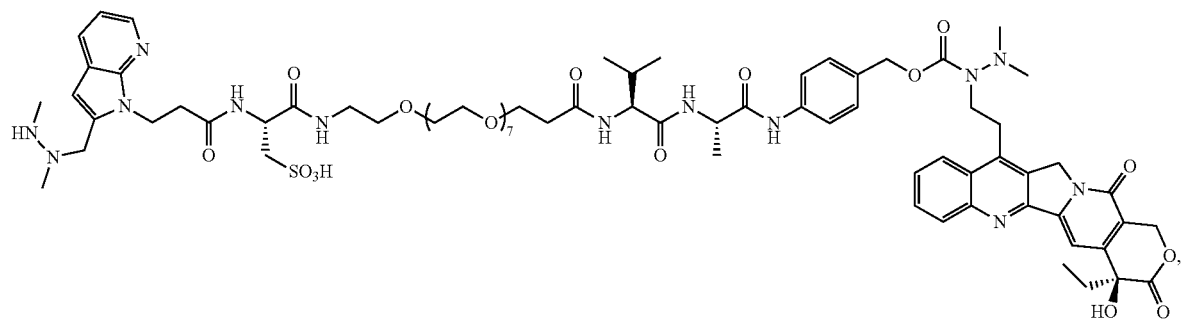
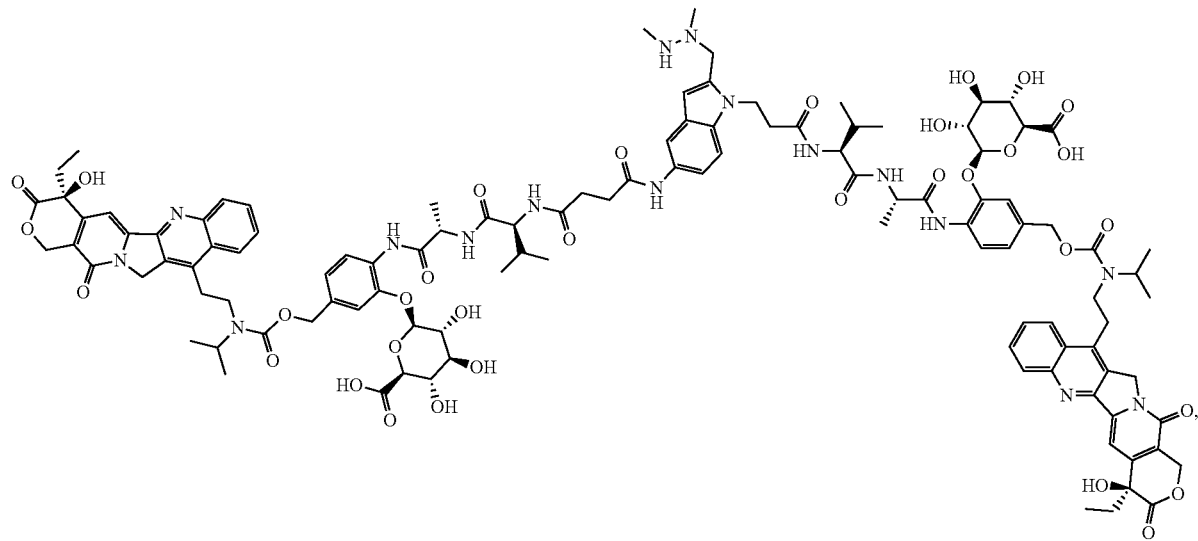

-continued
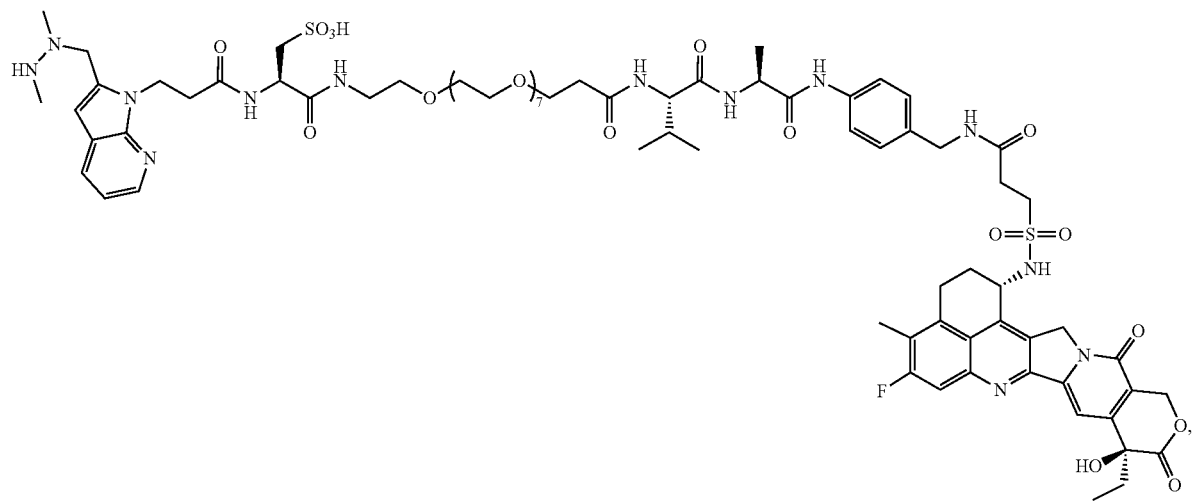
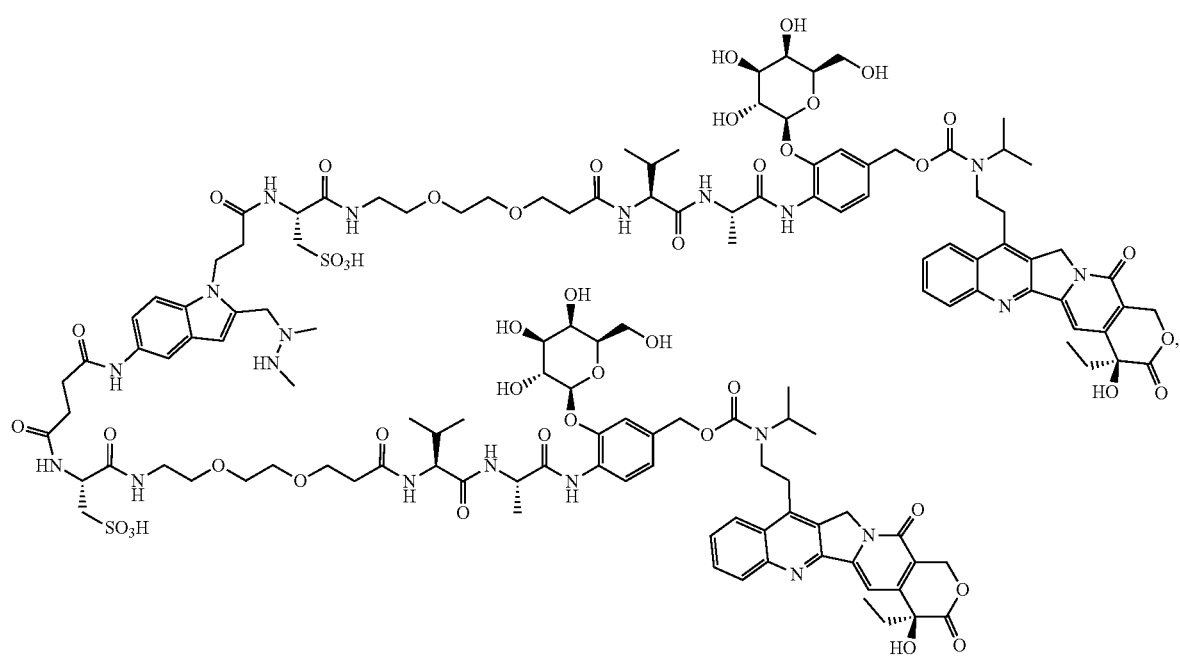

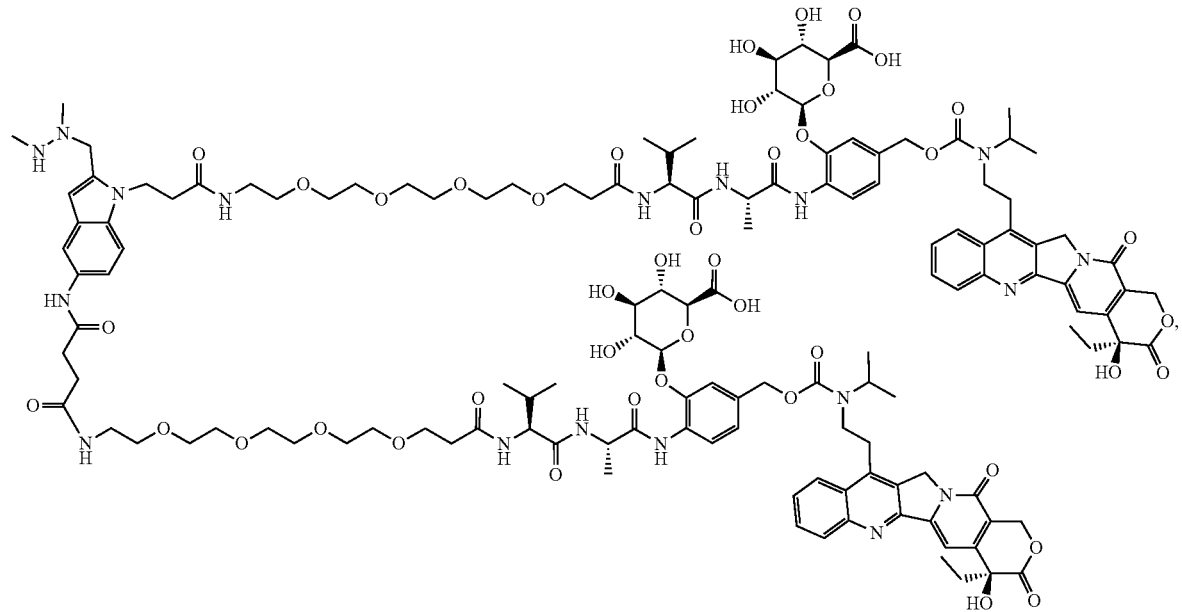
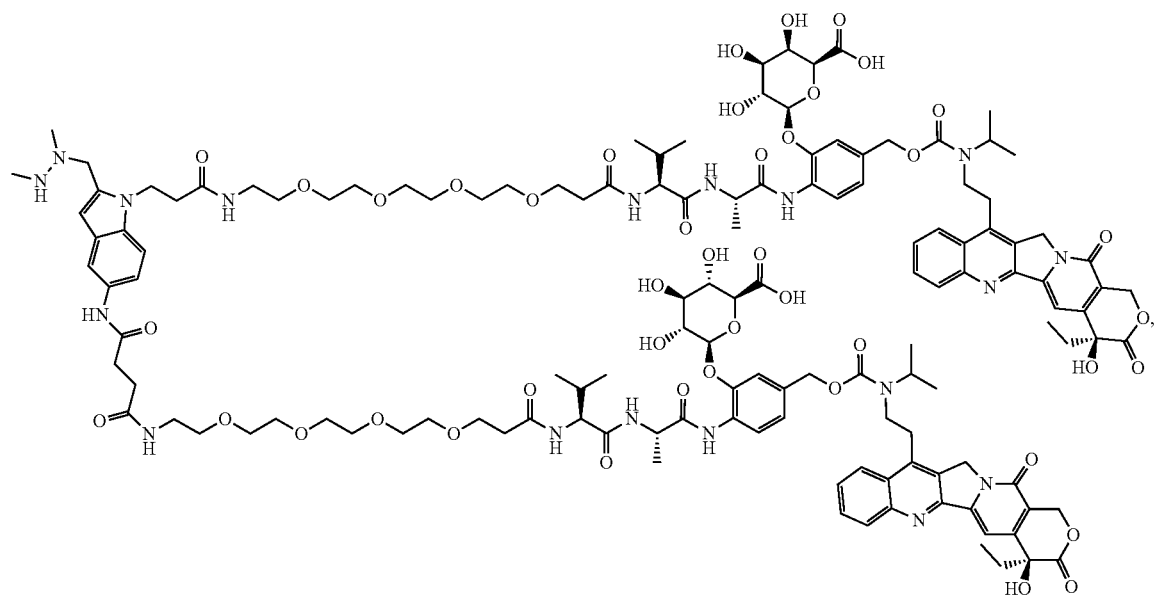

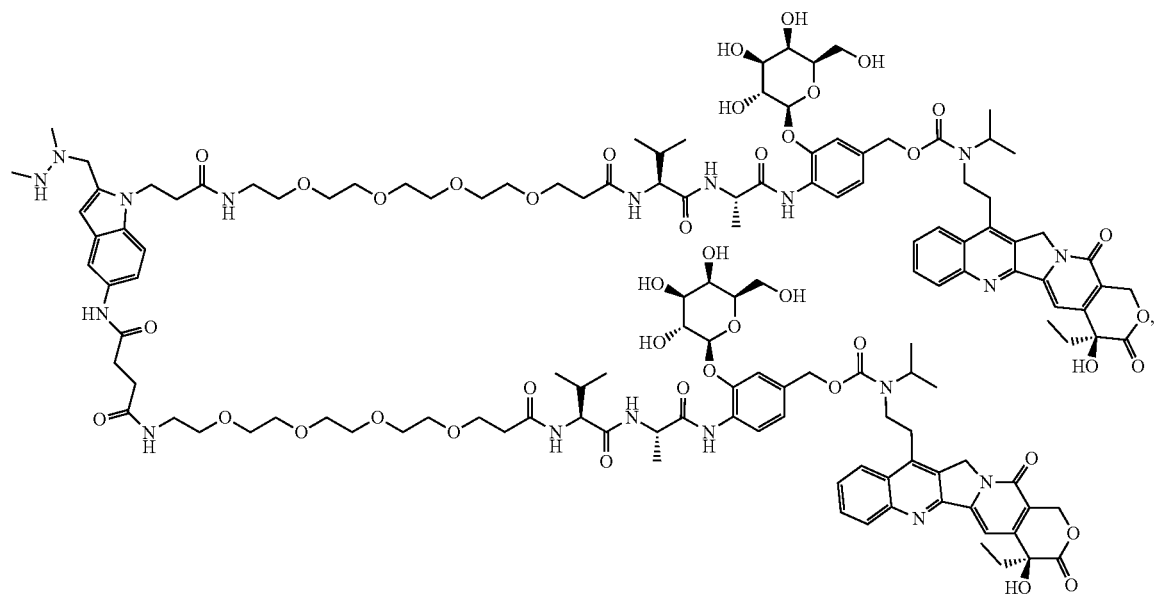
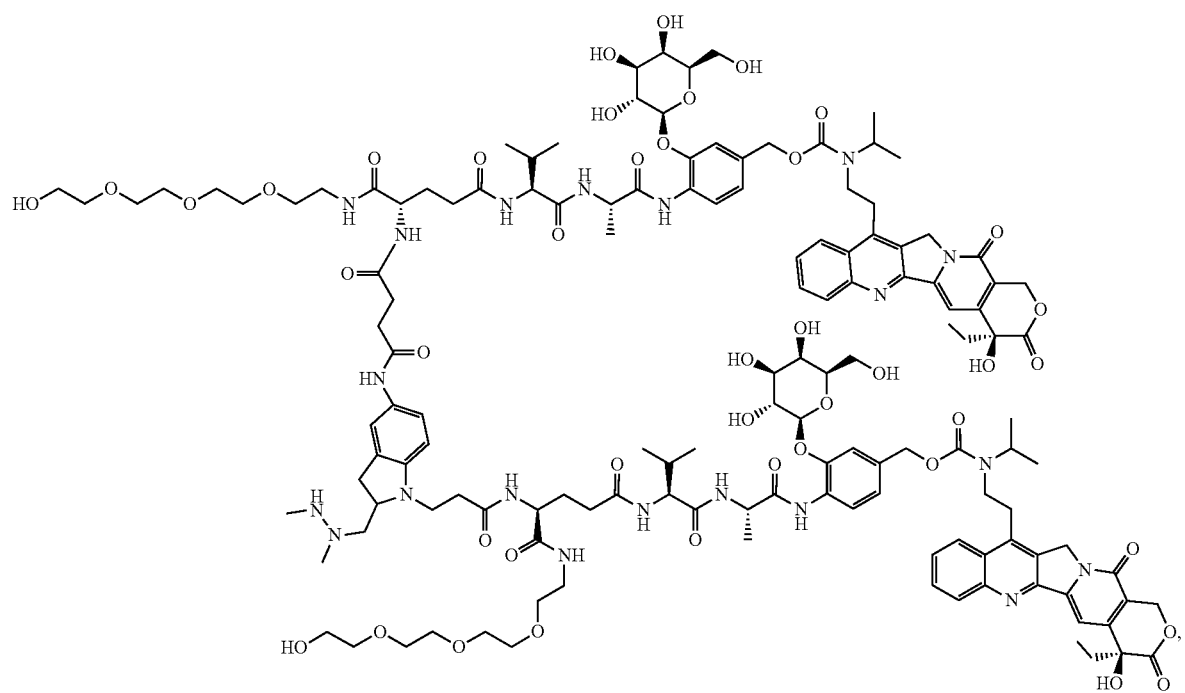

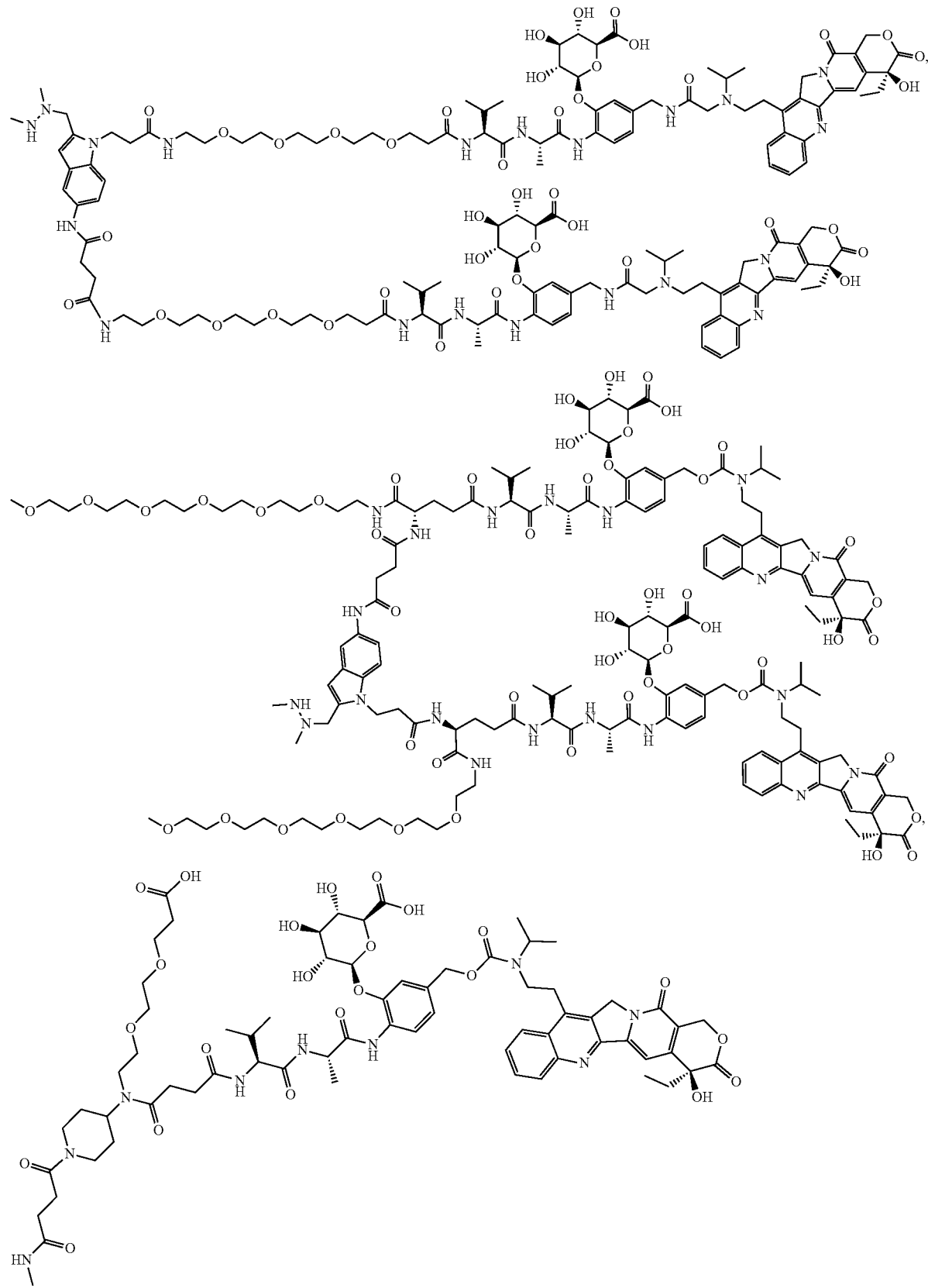

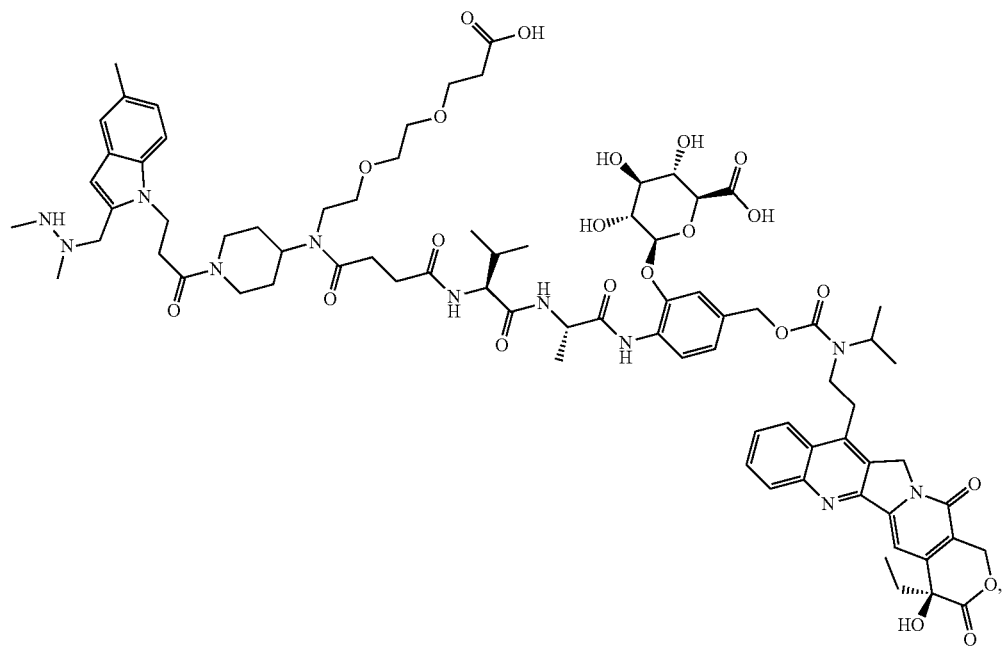
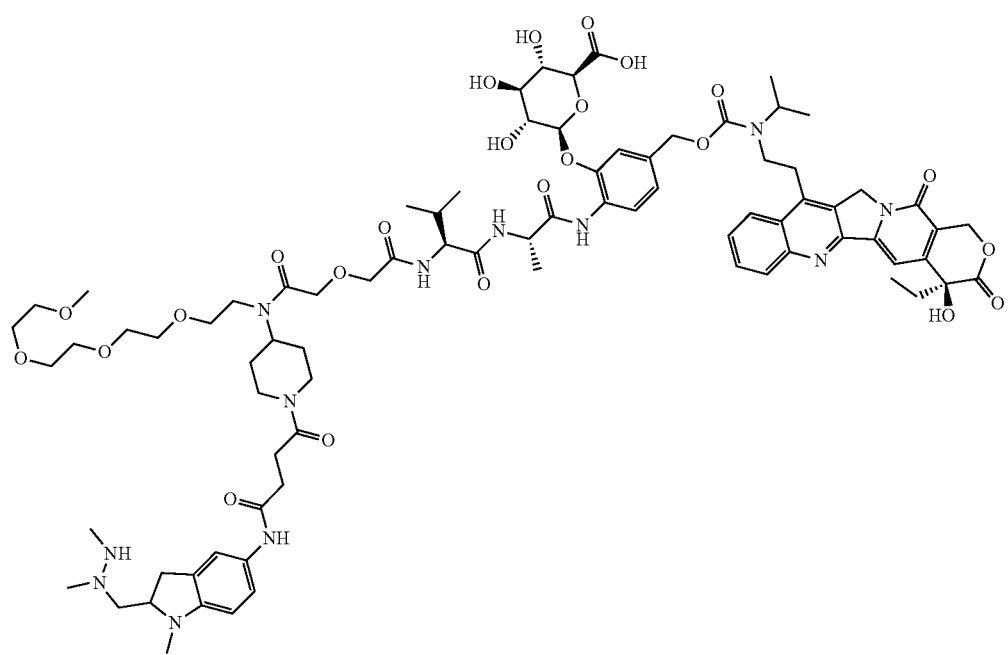

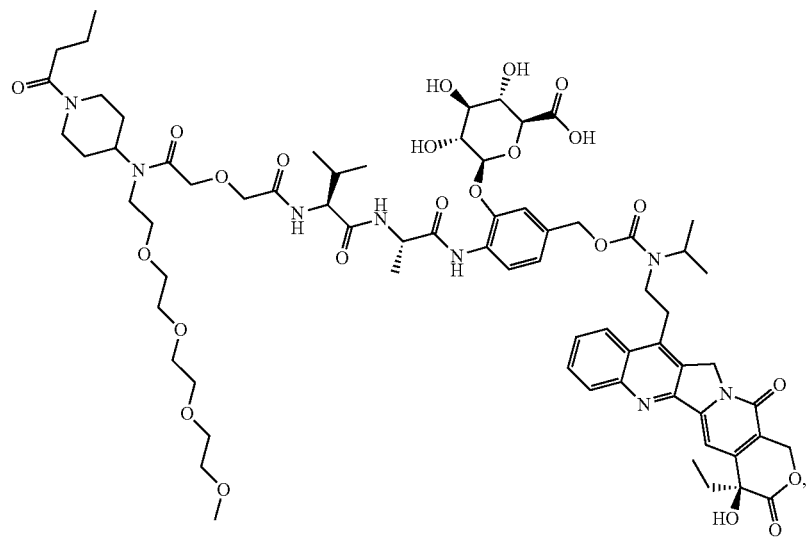
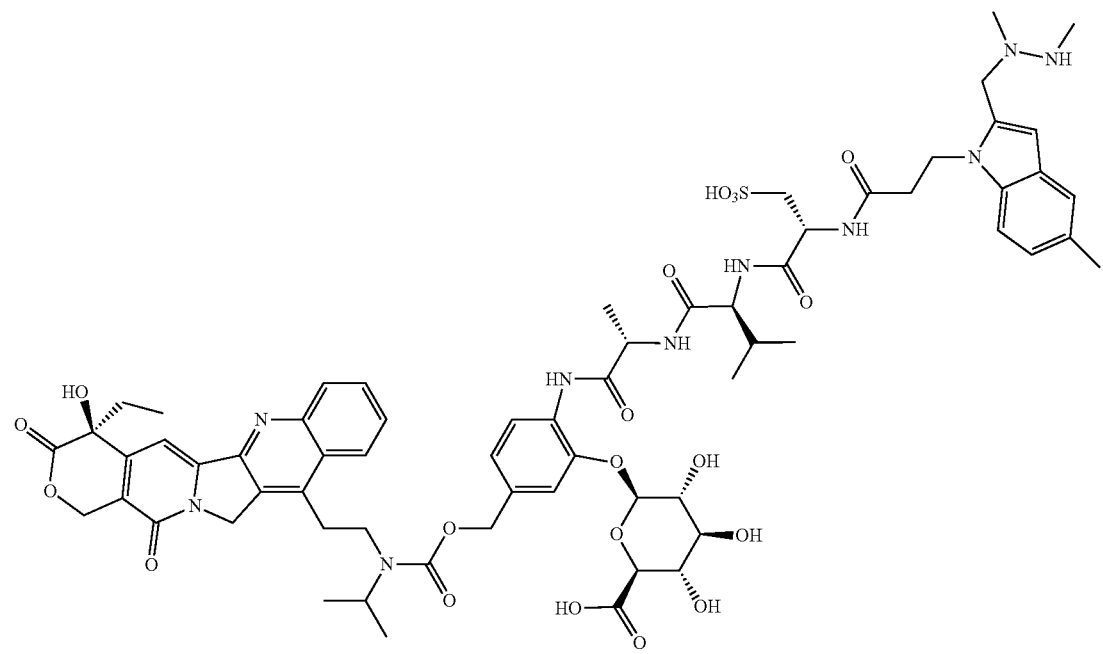

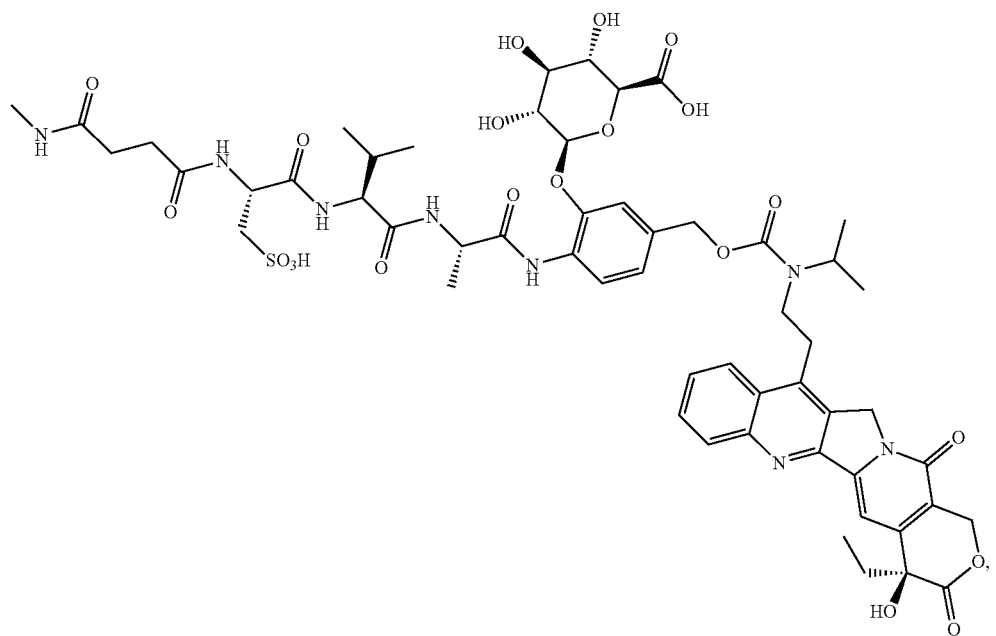
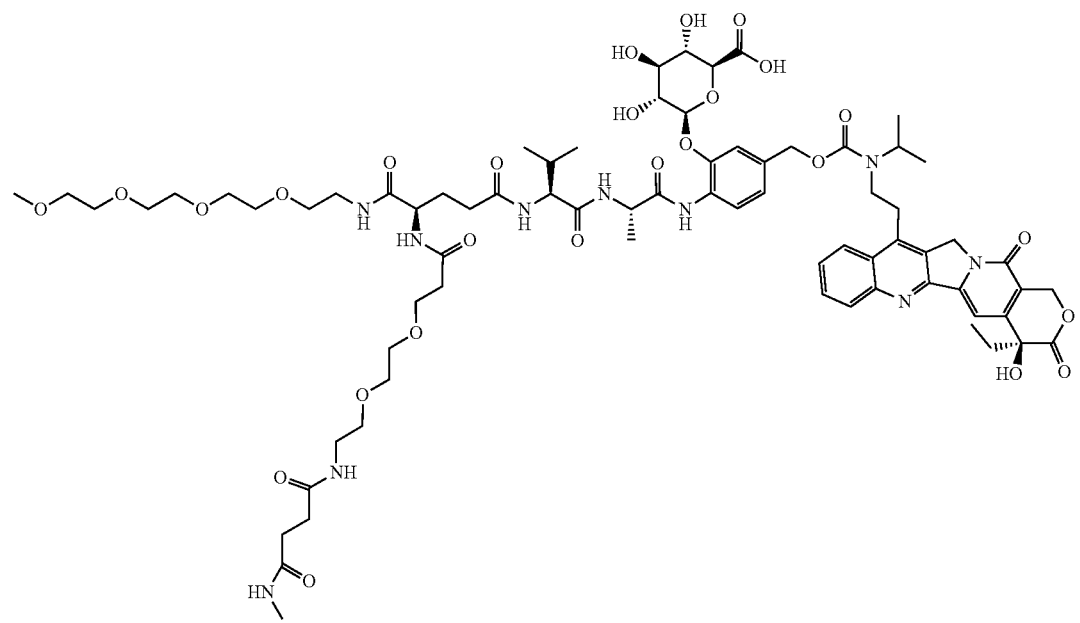

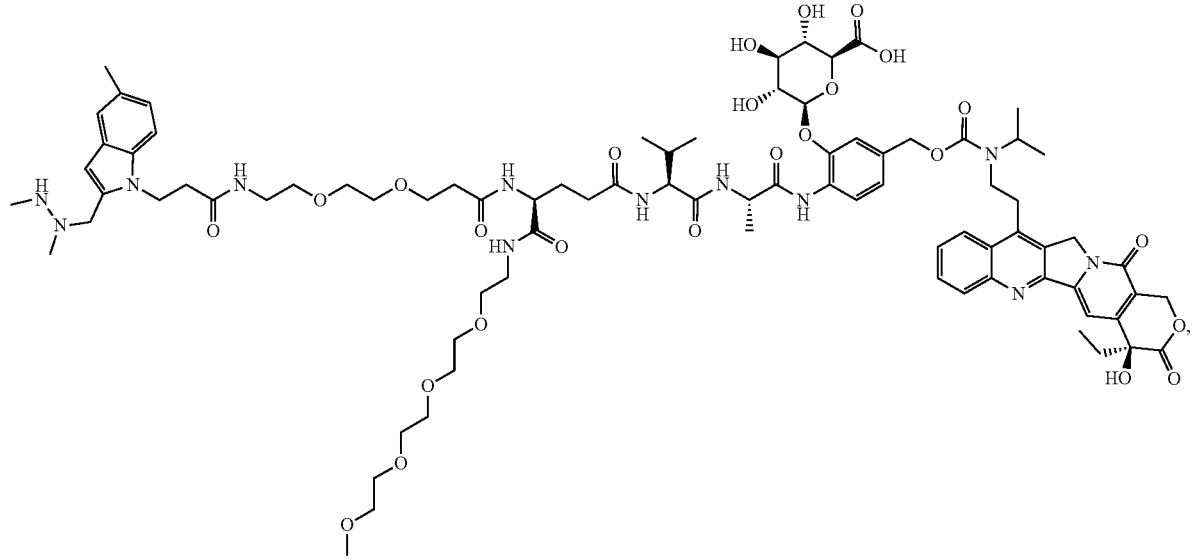
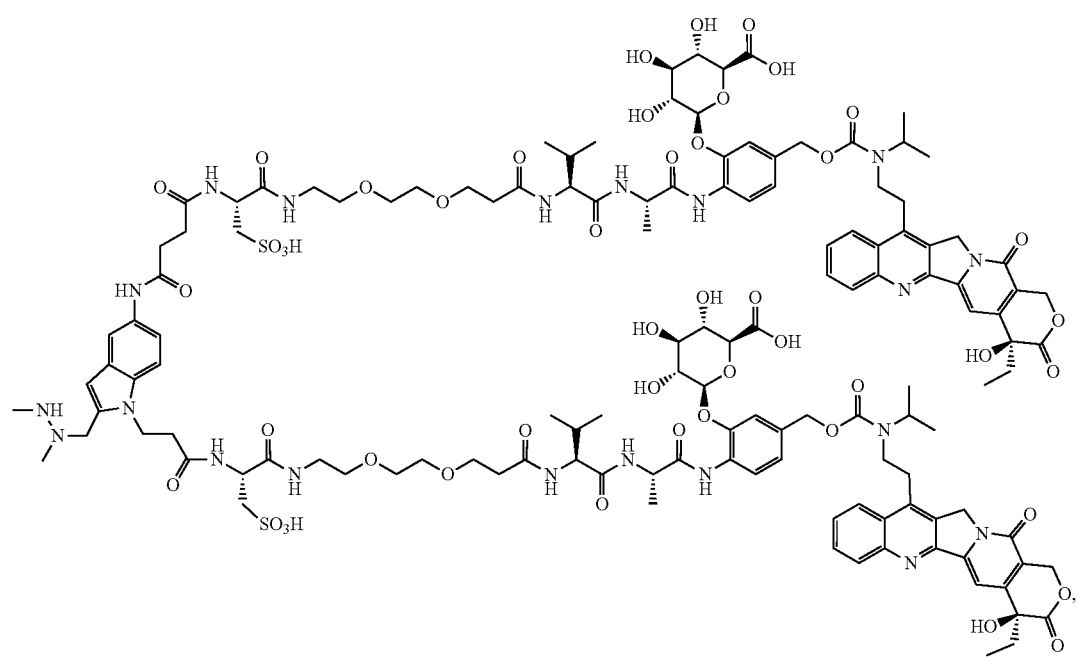

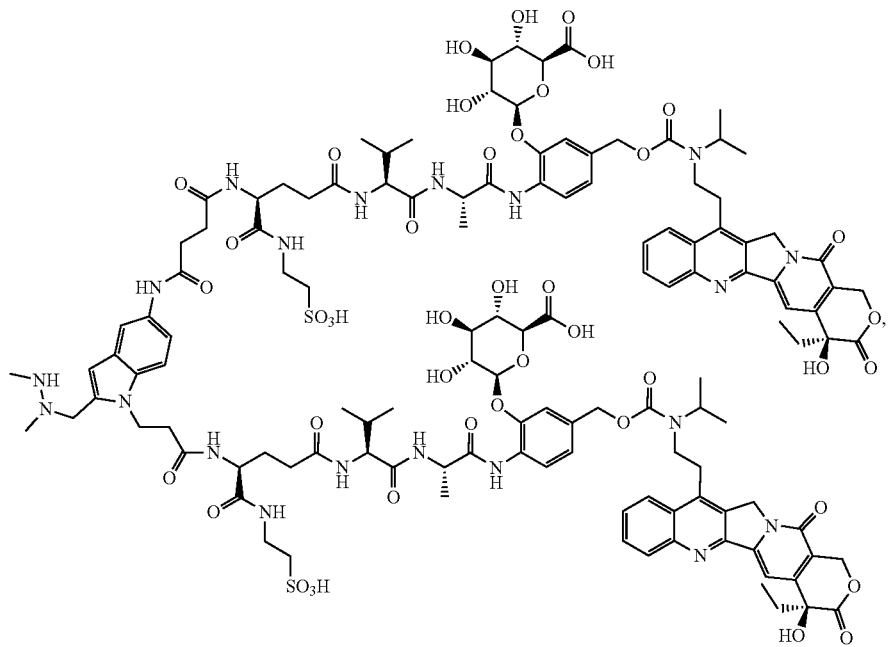
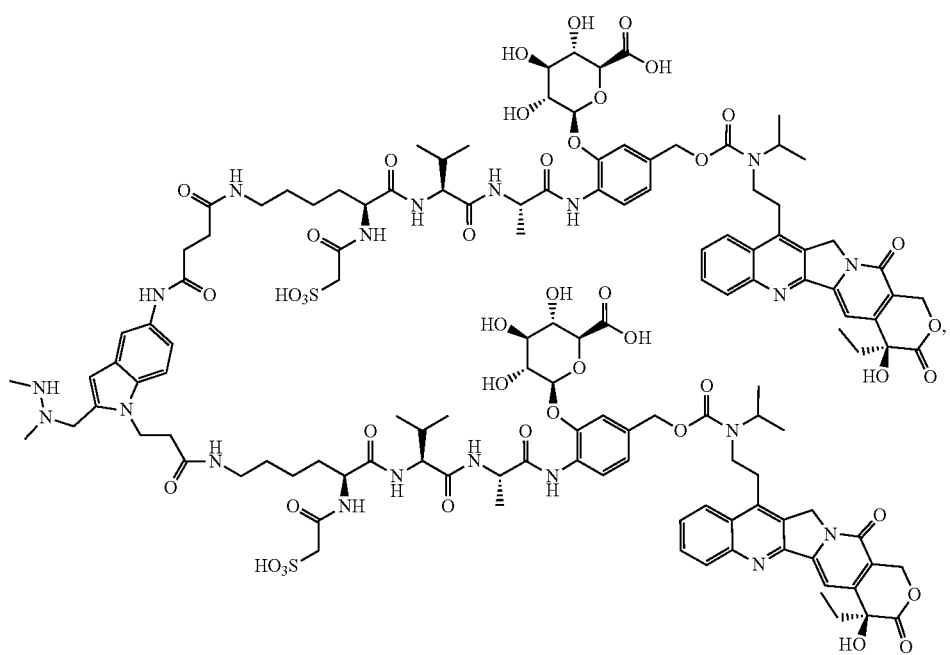

-continued
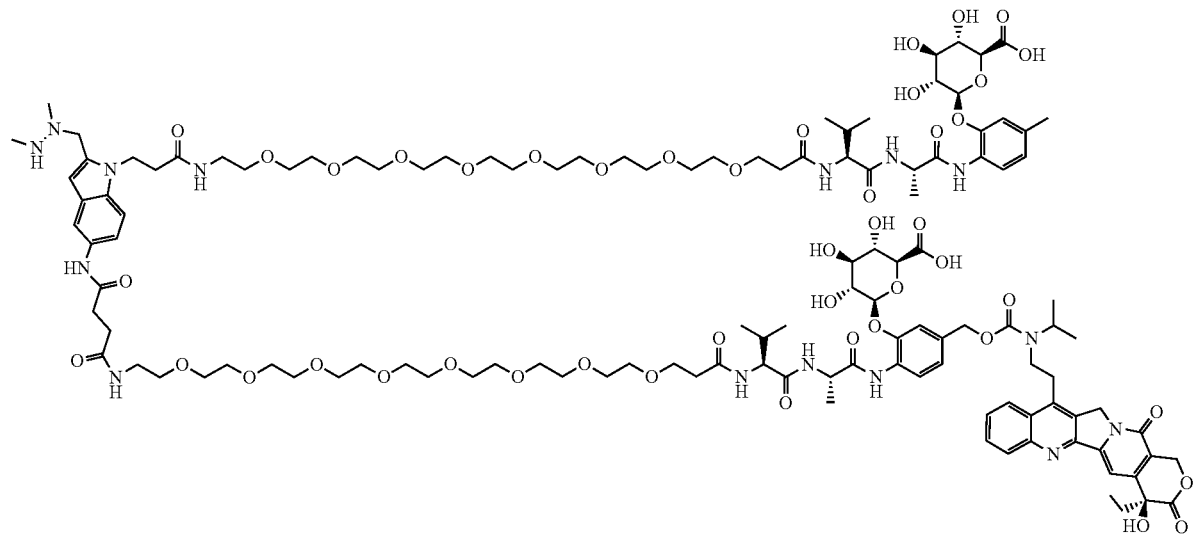
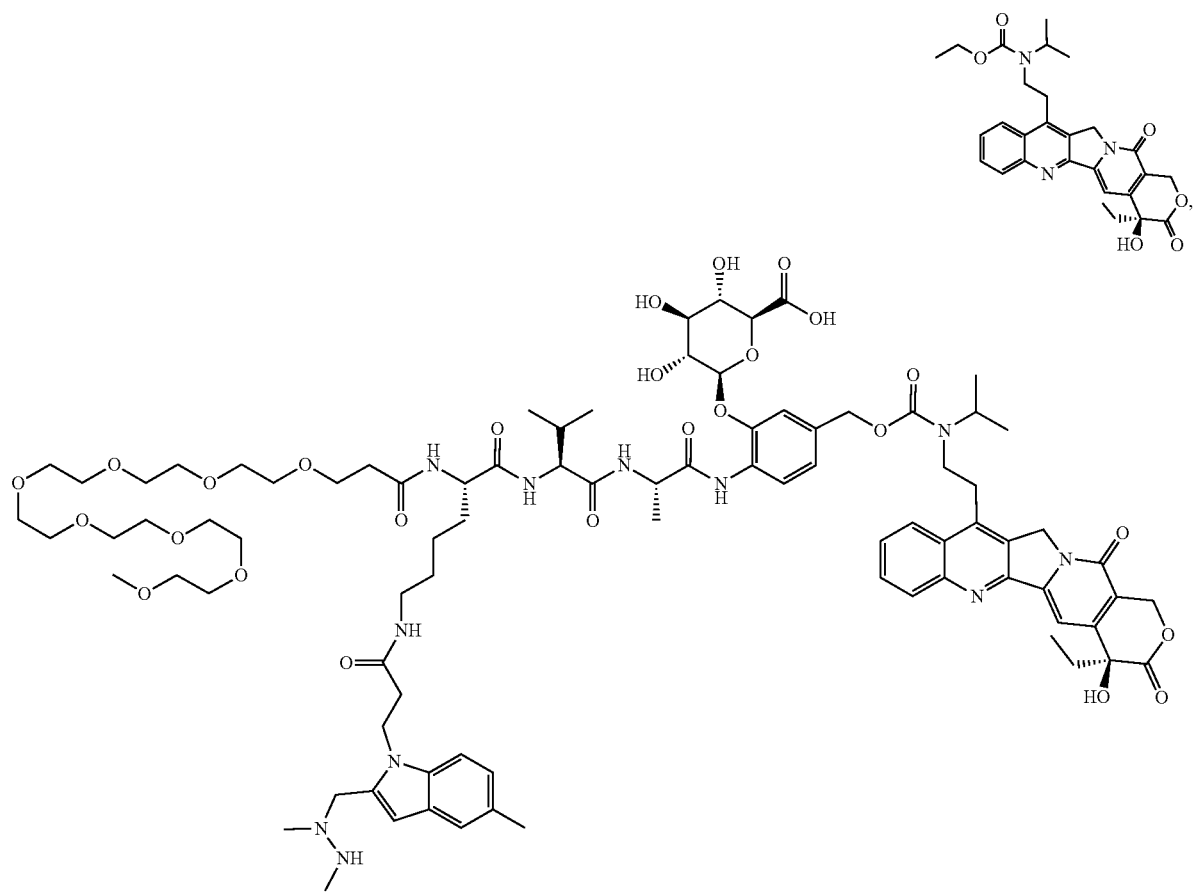

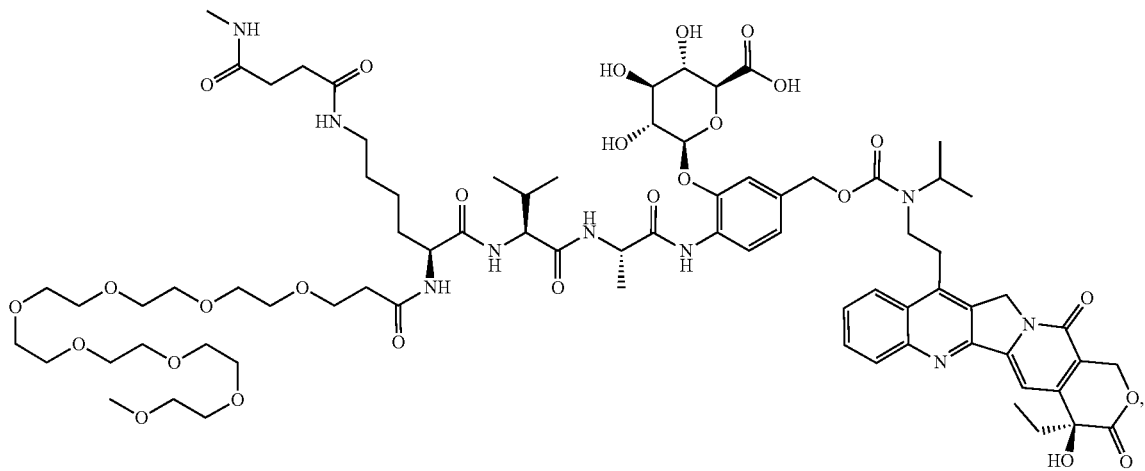
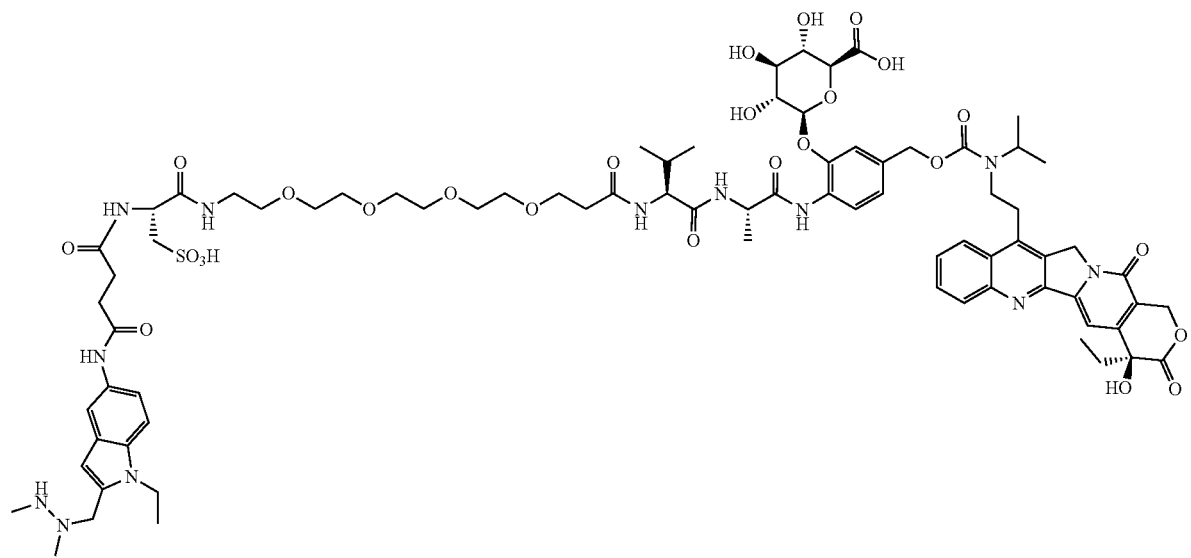
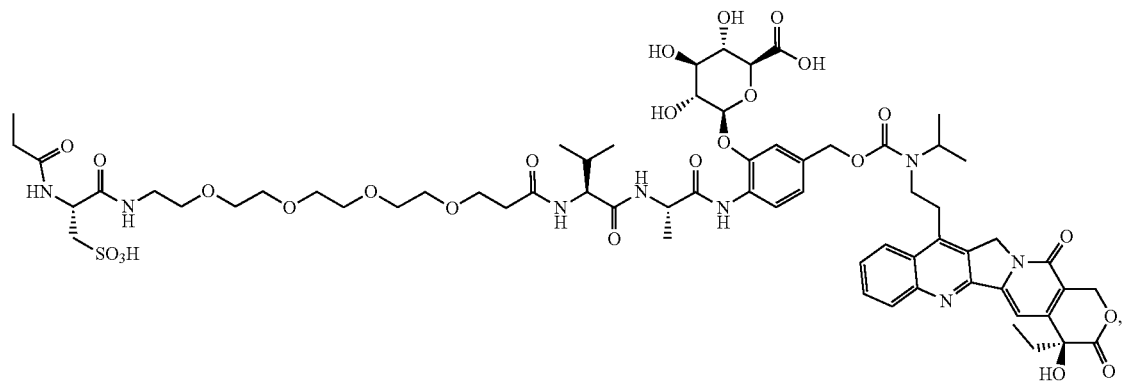

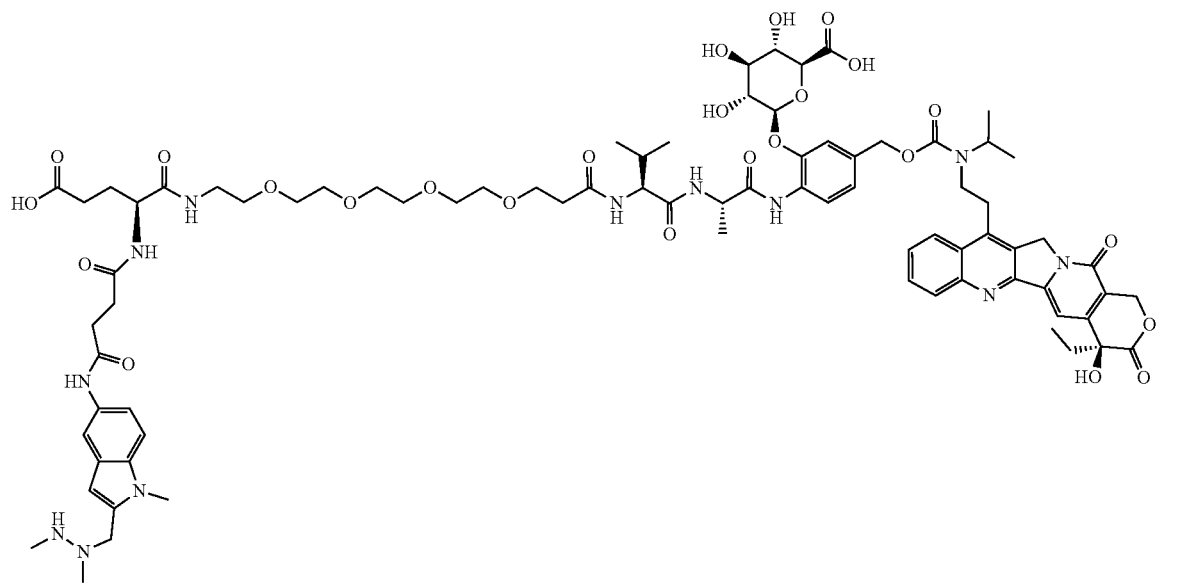
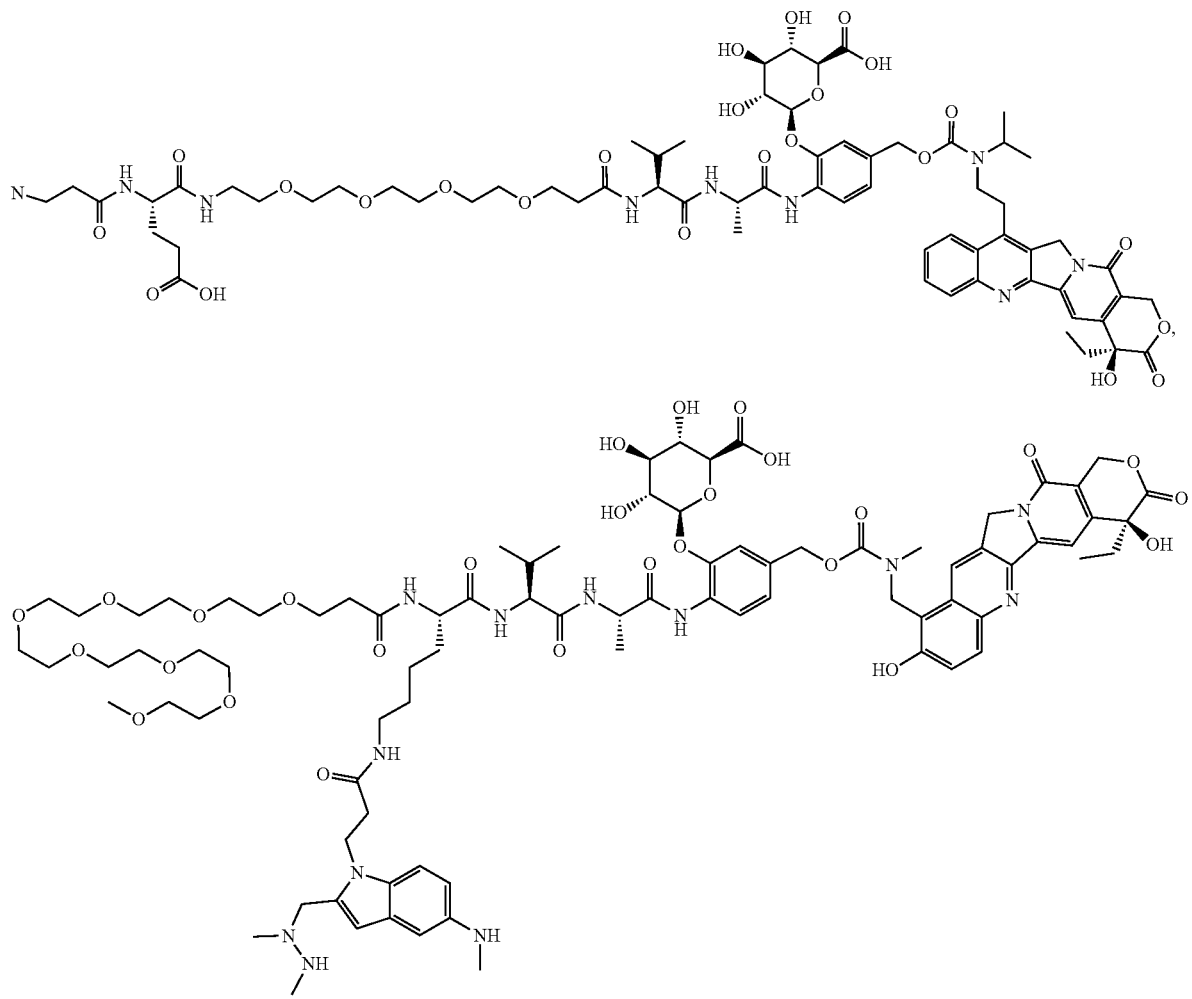

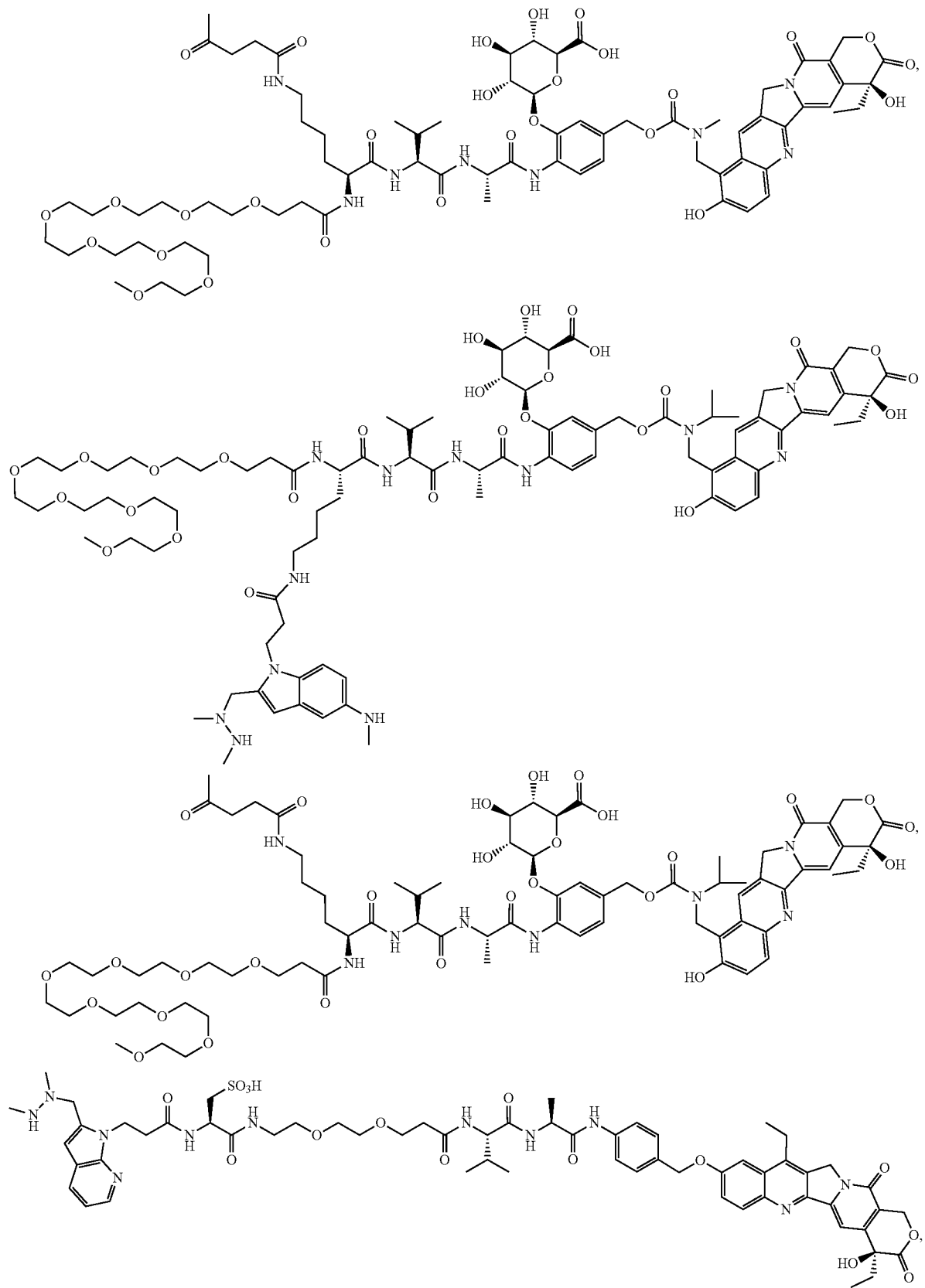

-continued

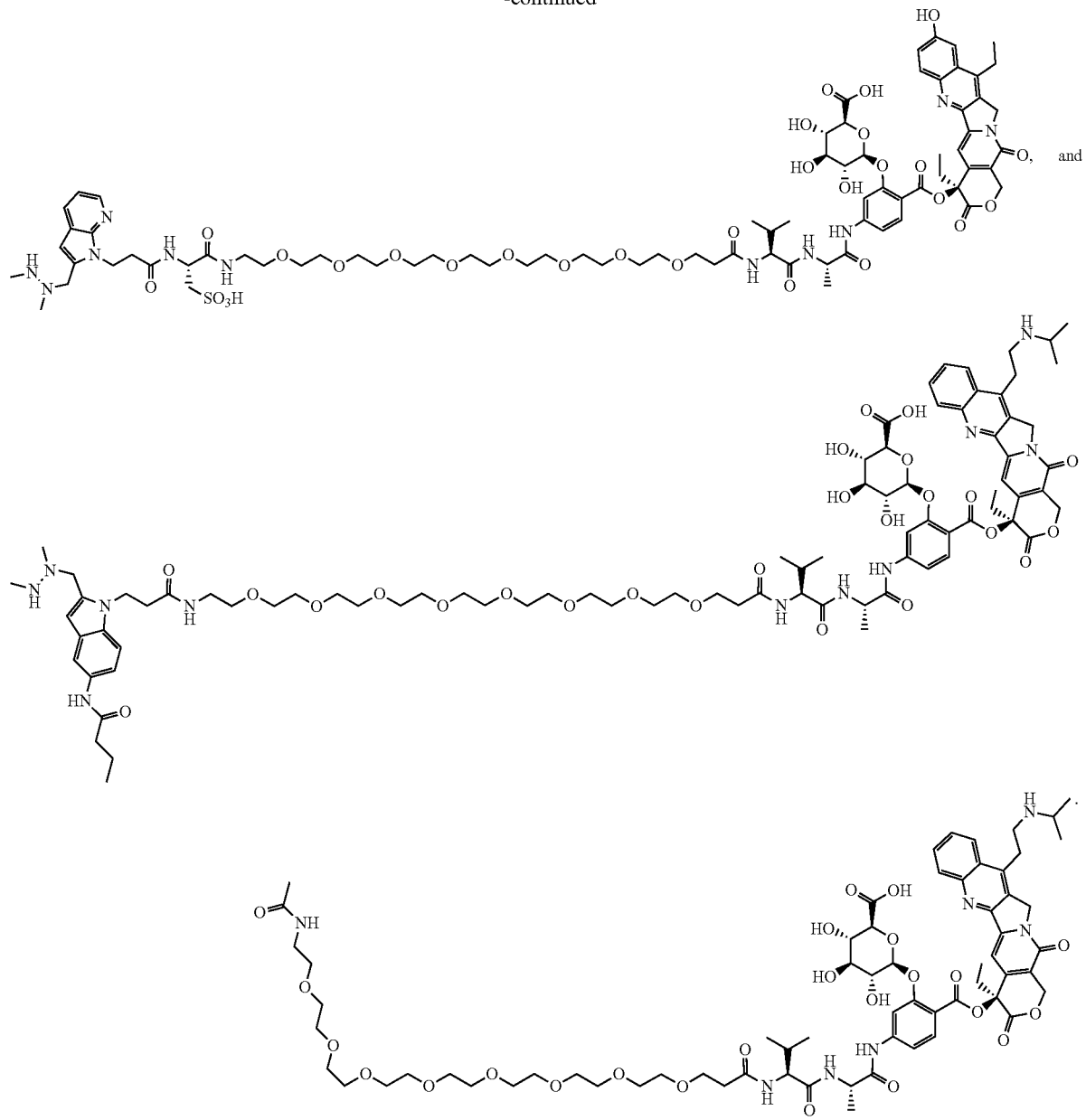

Aspects of the present disclosure include a pharmaceutical composition comprising a conjugate according to the present disclosure, and a pharmaceutically-acceptable excipient.

Aspects of the present disclosure include a method comprising administering to a subject an effective amount of a conjugate according to the present disclosure.

Aspects of the present disclosure include a method of treating cancer in a subject by administering to the subject a therapeutically effective amount of a pharmaceutical composition comprising a conjugate according to the present disclosure, where the administering is effective to treat cancer in the subject.

BRIEF DESCRIPTION OF THE DRAWINGS

(FIG. 1, panel A) General structure of camptothecines. (FIG. 1, panel B) Representative examples of camptothecines to be used as payloads for antibody-drug conjugates (arrows indicate modification sites for linker attachment).

FIG. 120 shows a graph of Compound 92 CH1-3/CT-tagged anti-FITC conjugate yields a DAR of 1.58 as determined by PLRP.

FIG. 121 shows a graph of Compound 92 CH1-3/CT-tagged anti-FITC conjugate is 96.1% monomeric as determined by analytical SEC.

FIG. 122 shows a graph of Compound 99 CH1-3/CT-tagged anti-FITC conjugate yields a DAR of 3.07 as determined by PLRP.

FIG. 123 shows a graph of Compound 99 CH1-3/CT-tagged anti-FITC conjugate is 97.9% monomeric as determined by analytical SEC.

FIG. 124 shows a graph of Compound 103 CH1-3/CT-tagged trastuzumab conjugate yields a DAR of 6.56 as determined by PLRP.

FIG. 125 shows a graph of Compound 103 CH1-3/CT-tagged trastuzumab conjugate is 97.3% monomeric as determined by analytical SEC.

FIG. 126 shows a graph of Compound 110 CH1-3/CT-tagged anti-FITC conjugate yields a DAR of 5.66 as determined by PLRP.

FIG. 127 shows a graph of Compound 110 CH1-3/CT-tagged anti-FITC conjugate is 98.5% monomeric as determined by analytical SEC.

FIG. 128 shows a graph of Compound 113 CH1-3/CT-tagged sacituzumab conjugate yields a DAR of 6.41 as determined by PLRP.

FIG. 129 shows a graph of Compound 113 CH1-3/CT-tagged sacituzumab conjugate is 97.4% monomeric as determined by analytical SEC.

FIG. 130 shows a graph of Compound 123 CH1-3/CT-tagged anti-FITC conjugate yields a DAR of 5.56 as determined by PLRP.

FIG. 131 shows a graph of Compound 123 CH1-3/CT-tagged anti-FITC conjugate is 95.5% monomeric as determined by analytical SEC.

Figure 132:
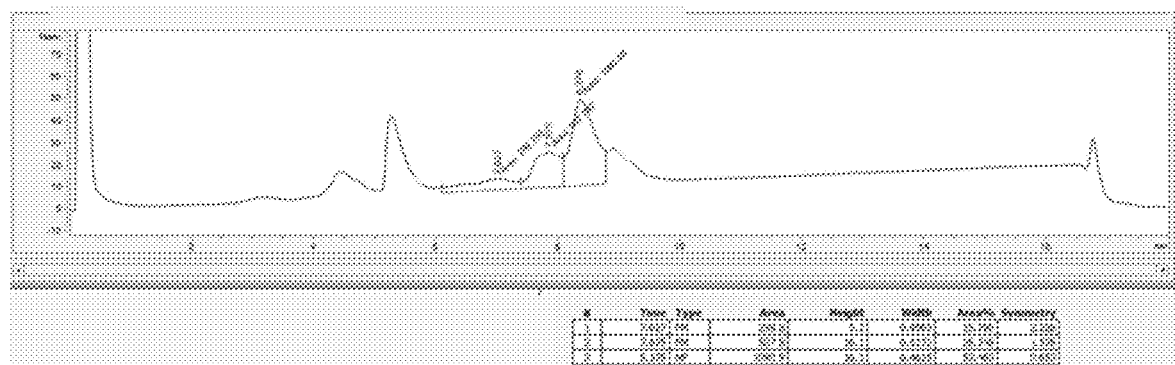

FIG. 132 shows a graph of Compound 151 CH1-3/CT-tagged anti-FITC conjugate yields a DAR of 5.67 as determined by PLRP.

Figure 133:
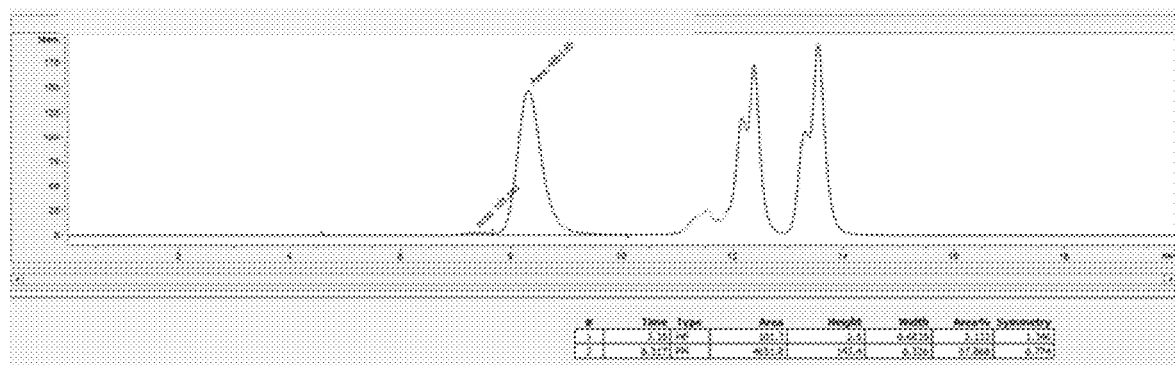

FIG. 133 shows a graph of Compound 151 CH1-3/CT-tagged anti-FITC conjugate is 97.8% monomeric as determined by analytical SEC.

Figure 134:
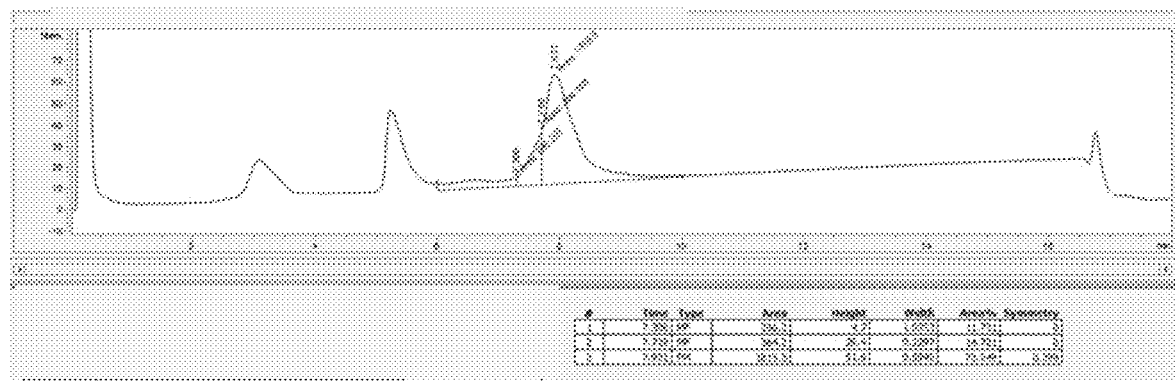

FIG. 134 shows a graph of Compound 147 CH1-3/CT-tagged anti-FITC conjugate yields a DAR of 6.47 as determined by PLRP.

Figure 135:
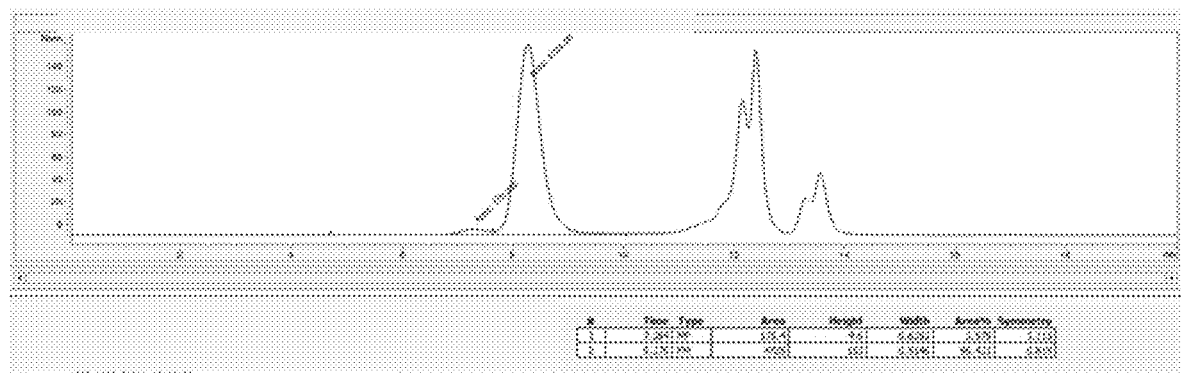

FIG. 135 shows a graph of Compound 147 CH1-3/CT-tagged anti-FITC conjugate is 96.4% monomeric as determined by analytical SEC.

Figure 136:
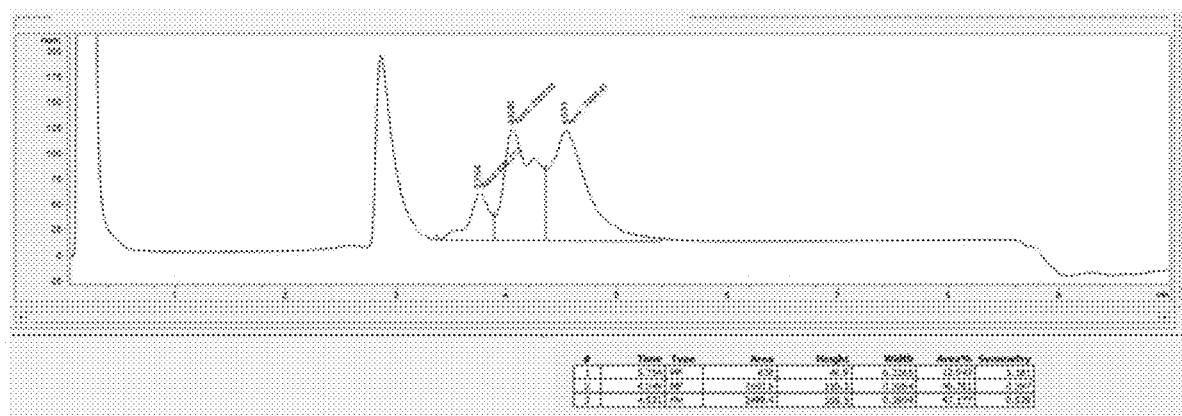

FIG. 136 shows a graph of Compound 73 CH1-3/CT-tagged trastuzumab conjugate yields a DAR of 5.41 as determined by PLRP.

Figure 137:
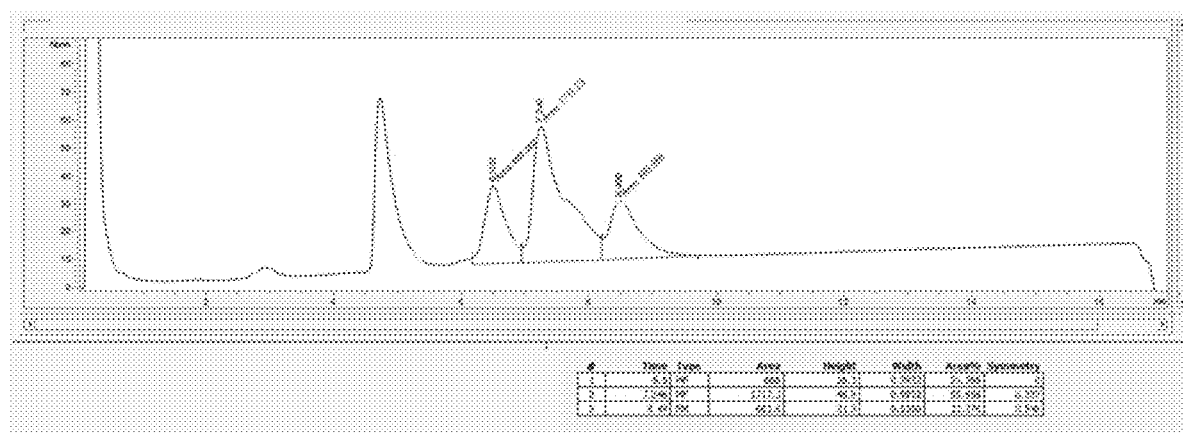

FIG. 137 shows a graph of Compound 67 CH1-3/CT-tagged trastuzumab conjugate yields a DAR of 4.02 as determined by PLRP.

Figure 138:
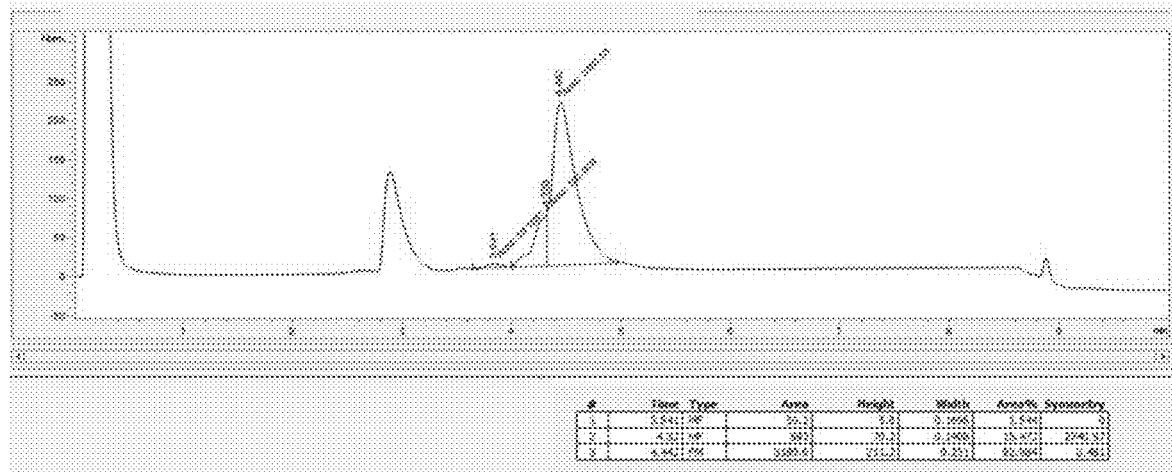

FIG. 138 shows a graph of Compound 136 CH1-3/CT-tagged trastuzumab conjugate yields a DAR of 7.26 as determined by PLRP.

Figure 139:
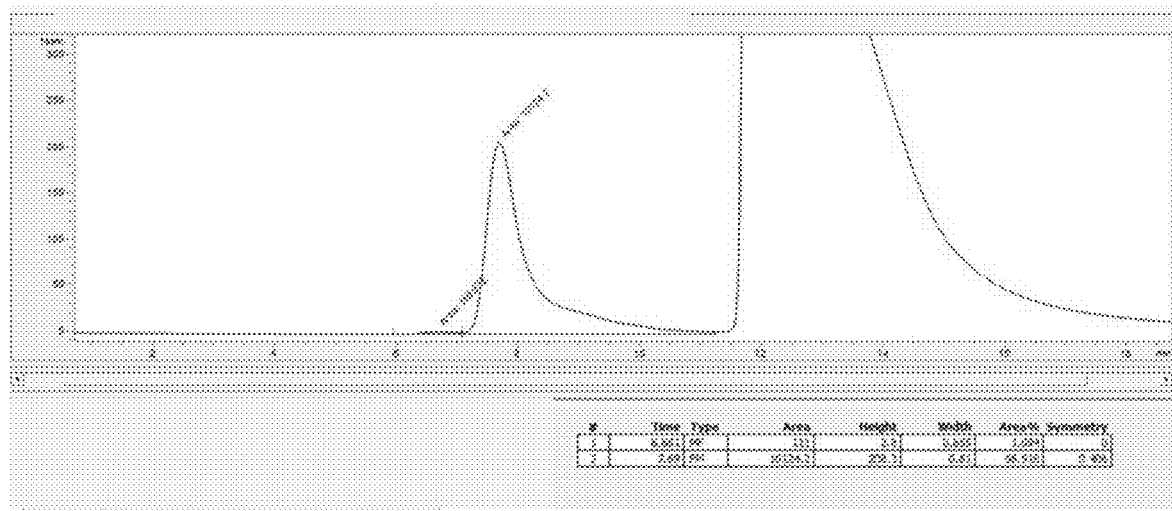

FIG. 139 shows a graph of Compound 136 CH1-3/CT-tagged trastuzumab conjugate is 98.9% monomeric as determined by analytical SEC.

Figure 140:
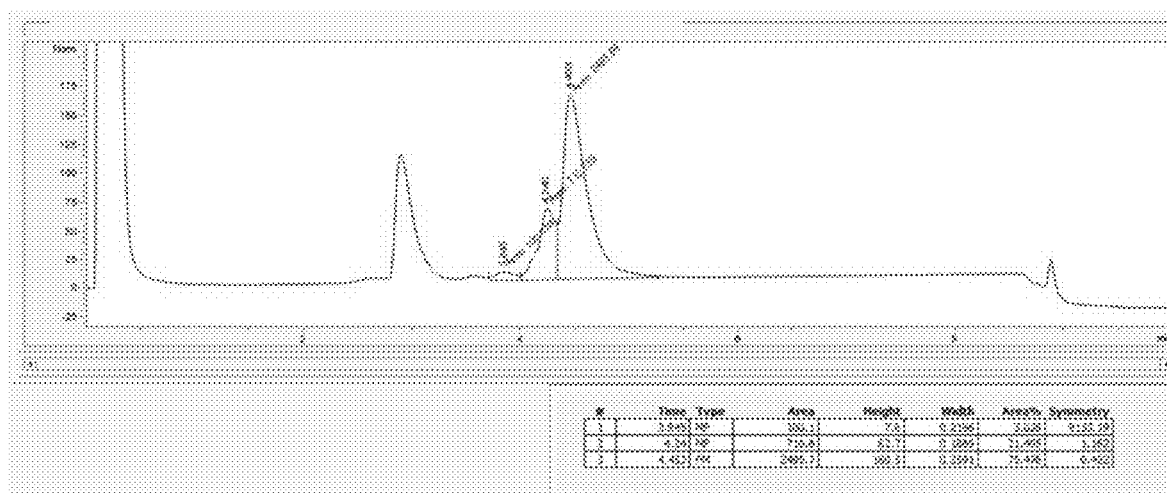

FIG. 140 shows a graph of Compound 142 CH1-3/CT-tagged trastuzumab conjugate yields a DAR of 6.9 as determined by PLRP.

Figure 141:
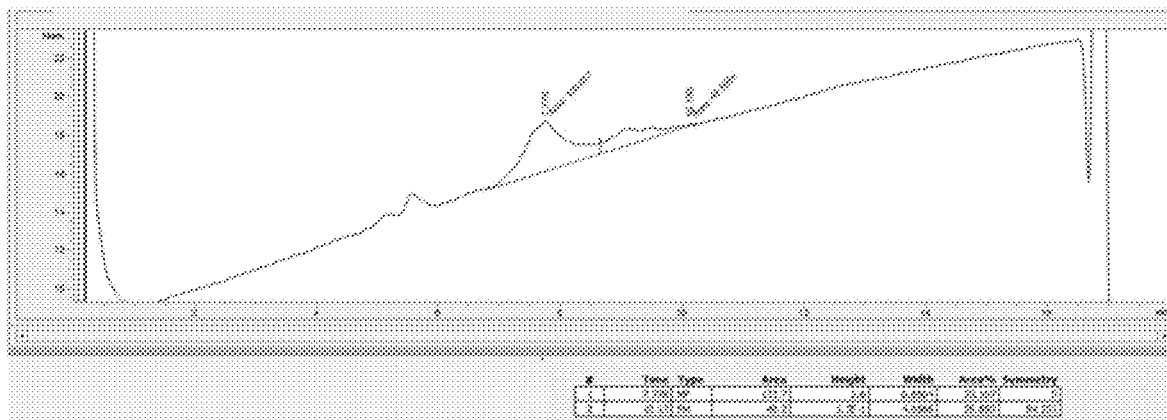

FIG. 141 shows a graph of Compound 175 CH1-3/CT-tagged anti-FITC conjugate yields a DAR of 5.08 as determined by PLRP.

Figure 142:
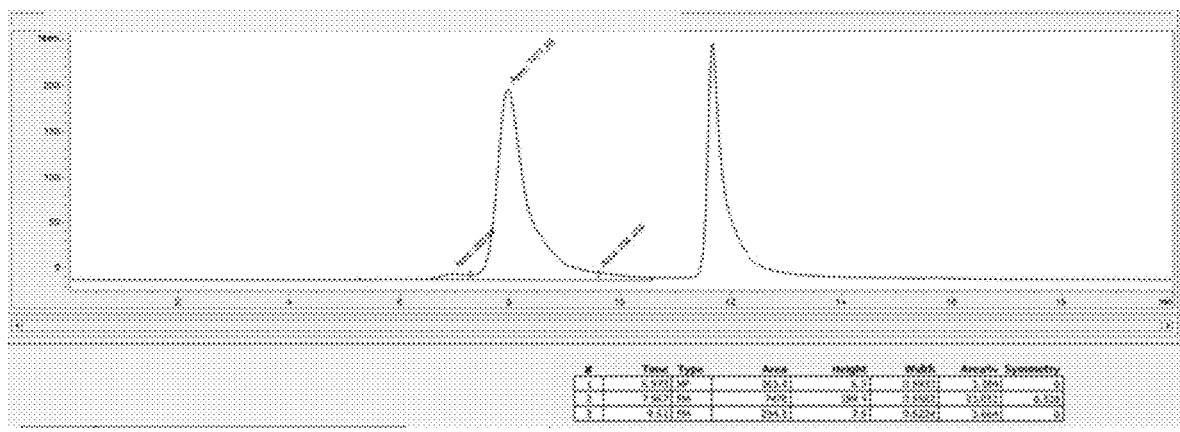

FIG. 142 shows a graph of Compound 175 CH1-3/CT-tagged anti-FITC conjugate is 93.0% monomeric as determined by analytical SEC.

Figure 143:
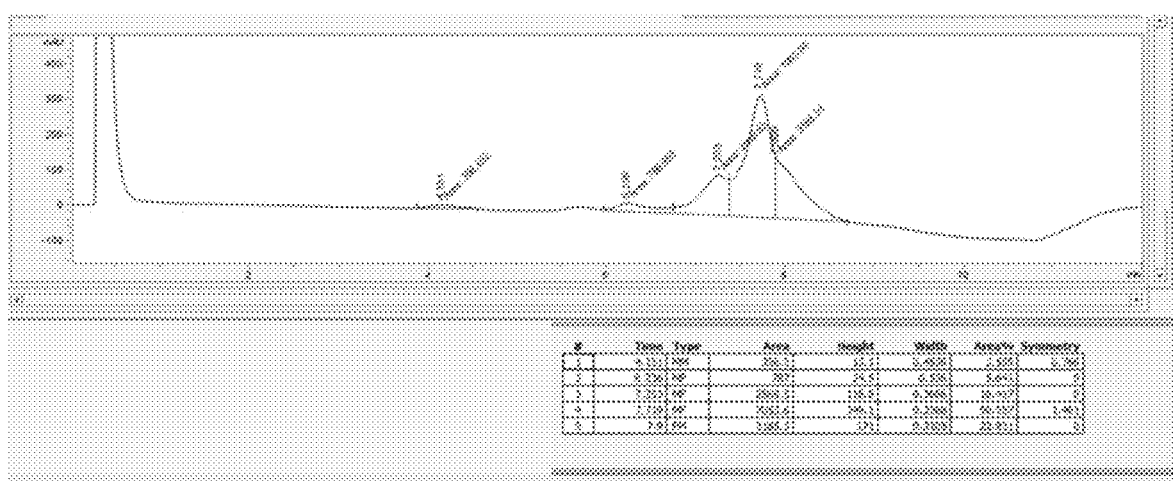

FIG. 143 shows a graph of Compound 155 CH1-3/CT-tagged trastuzumab conjugate yields a DAR of 2.82 as determined by HIC.

Figure 144:
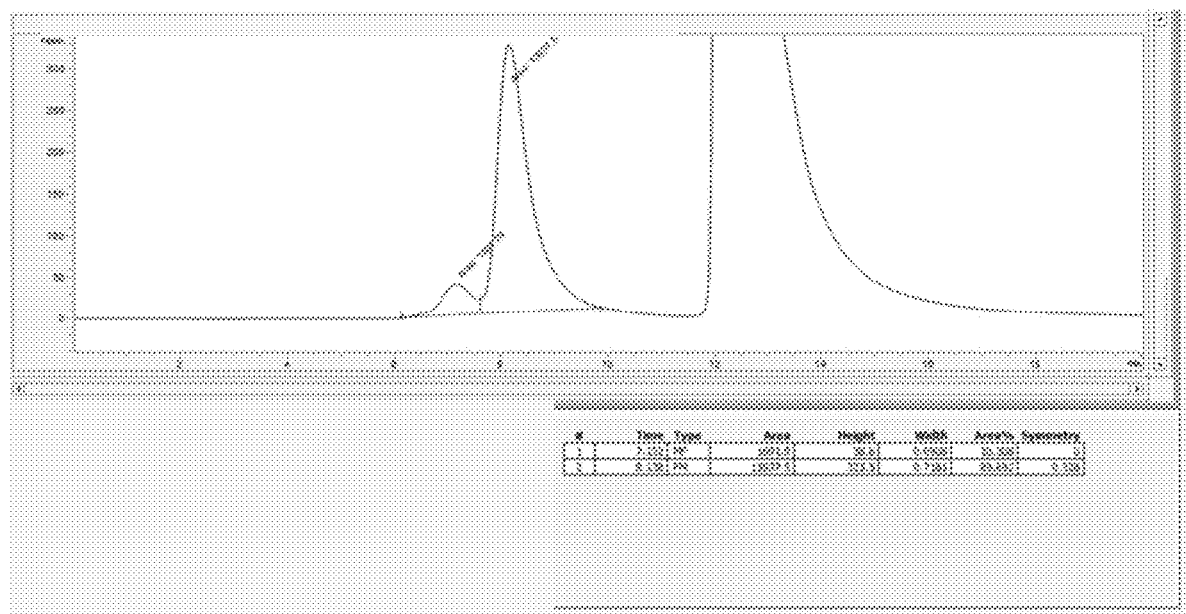

FIG. 144 shows a graph of Compound 155 CH1-3/CT-tagged anti-FITC conjugate is 89.7% monomeric as determined by analytical SEC.

DEFINITIONS

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O-, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O)substituted alkyl, NR$^{20}$C(O)cycloalkyl, —NR$^{20}$C(O)substituted cycloalkyl, —NR$^{20}$C(O)cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C(O)heteroaryl, —NR$^{20}$C(O)substituted heteroaryl, —NR$^{20}$C(O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O— alkynyl, —O—C(O)O-substituted alkynyl, —O—C(O)O-aryl, —O—C(O)O-substituted aryl, —O—C(O)O—cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic. To satisfy valence requirements, any heteroatoms in such heteroaryl rings may or may not be bonded to H or a substituent group, e.g., an alkyl group or other substituent as described herein. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from nitrogen, sulfur, or oxygen, where, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties. To satisfy valence requirements, any heteroatoms in such heterocyclic rings may or may not be bonded to one or more H or one or more substituent group(s), e.g., an alkyl group or other substituent as described herein.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group —O-heterocyclyl.

The term "heterocyclylthio" refers to the group heterocyclic-S-.

The term "heterocyclene" refers to the diradical group formed from a heterocycle, as defined herein.

The term "hydroxyamino" refers to the group —NHOH.

"Nitro" refers to the group —NO$_2$.

"Oxo" refers to the atom (=O).

"Sulfonyl" refers to the group —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-cycloalkenyl, —SO$_2$-substituted cylcoalkenyl, —SO$_2$-aryl, —SO$_2$-substituted aryl, —SO$_2$-heteroaryl, —SO$_2$-substituted heteroaryl, —SO$_2$-heterocyclic, and —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group —OSO$_2$-alkyl, —OSO$_2$-substituted alkyl, —OSO$_2$-alkenyl, —OSO$_2$-substituted alkenyl, —OSO$_2$-cycloalkyl, —OSO$_2$-substituted cycloalkyl, —OSO$_2$-cycloalkenyl, —OSO$_2$-substituted cylcoalkenyl, —OSO$_2$-aryl, —OSO$_2$-substituted aryl, —OSO$_2$-heteroaryl, —OSO$_2$-substituted heteroaryl, —OSO$_2$-heterocyclic, and —OSO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Sulfate" or "sulfate ester" refers the group —O—SO$_2$—OH, —O—SO$_2$—O-alkyl, —O—SO$_2$—O-substituted alkyl, —O—SO$_2$—O-alkenyl, —O—SO$_2$—O-substituted alkenyl, —O—SO$_2$—O-cycloalkyl, —O—SO$_2$—O-substituted cycloalkyl, —O—SO$_2$—O-cycloalkenyl, —O—SO$_2$—O-substituted cylcoalkenyl, —O—SO$_2$—O-aryl, —O—SO$_2$—O-substituted aryl, —O—SO$_2$—O-heteroaryl, —O—SO$_2$—O-substituted heteroaryl, —O—SO$_2$—O-heterocyclic, and —O—SO$_2$—O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant host cell); immunologically tagged proteins; and the like. In certain embodiments, a polypeptide is an antibody.

"Native amino acid sequence" or "parent amino acid sequence" are used interchangeably herein to refer to the amino acid sequence of a polypeptide prior to modification to include at least one modified amino acid residue.

The terms "amino acid analog," "unnatural amino acid," and the like may be used interchangeably, and include amino acid-like compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like. Examples of amino acid analogs include, but are not limited to, sulfoalanine, and the like.

The terms "amino acid side chain" or "side chain of an amino acid" and the like may be used to refer to the substituent attached to the α-carbon of an amino acid residue, including natural amino acids, unnatural amino acids, and amino acid analogs. An amino acid side chain can also include an amino acid side chain as described in the context of the modified amino acids and/or conjugates described herein.

The term "carbohydrate" and the like may be used to refer to monomers units and/or polymers of monosaccharides, disaccharides, oligosaccharides, and polysaccharides. The term sugar may be used to refer to the smaller carbohydrates, such as monosaccharides, disaccharides. The term "carbohydrate derivative" includes compounds where one or more functional groups of a carbohydrate of interest are substituted (replaced by any convenient substituent), modified (converted to another group using any convenient chemistry) or absent (e.g., eliminated or replaced by H). A variety of carbohydrates and carbohydrate derivatives are available and may be adapted for use in the subject compounds and conjugates.

The term "glycoside" or "glycosyl" refers to a sugar molecule or group bound to a moiety via a glycosidic bond. For example, the moiety that the glycoside is bound to can be a cleavable linker as described herein. A glycosidic bond can link the glycoside to the other moiety through various types of bonds, such as, but not limited to, an O-glycosidic bond (an O-glycoside), an N-glycosidic bond (a glycosylamine), an S-glycosidic bond (a thioglycoside), or C-glycosidic bond (a C-glycoside or C-glycosyl). In some cases, glycosides can be cleaved from the moiety they are attached to, such as by chemically-mediated hydrolysis or enzymatically-mediated hydrolysis.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

An immunoglobulin polypeptide immunoglobulin light or heavy chain variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of a sulfatase motif and Formylglycine Generating Enzyme (FGE), which react to form a reaction product of a converted aldehyde tag containing a formylglycine (fGly) in lieu of cysteine or serine in the motif. Other exemplary reactive partners include an aldehyde of an fGly residue of a converted aldehyde tag (e.g., a reactive aldehyde group) and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a the fGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides antibody-drug conjugate (ADC) structures, which include a camptothecine or a camptothecine derivative linked to a polypeptide (e.g., an antibody) through a linker. The disclosure also encompasses compounds and methods for production of such conjugates, as well as methods of using the conjugates.

Antibody-Drug Conjugates

The present disclosure provides a conjugate, e.g., an antibody-drug conjugate (ADC). By "conjugate" is meant a polypeptide (e.g., an antibody) is covalently attached to one or more other moieties (e.g., drugs or active agents). For example, an antibody-drug conjugate according to the present disclosure includes one or more drugs or active agents covalently attached to an antibody. In certain embodiments, the polypeptide (e.g., antibody) and the one or more drugs or active agents are bound to each other through one or more functional groups and covalent bonds. For example, the one or more functional groups and covalent bonds can include a cleavable linker as described herein.

In certain embodiments, the conjugate is a polypeptide conjugate, which includes a polypeptide (e.g., an antibody) conjugated to one or more other moieties. In certain embodiments, the one or more moieties conjugated to the polypeptide can each independently be any of a variety of moieties of interest such as, but not limited to, a drug, an active agent, a detectable label, a water-soluble polymer, or a moiety for immobilization of the polypeptide to a membrane or a surface. In certain embodiments, the conjugate is a drug conjugate, where a polypeptide is an antibody, thus providing an antibody-drug conjugate. For instance, the conjugate can be a drug conjugate, where a polypeptide is conjugated to one or more drugs or active agents. In certain embodiments the drug or active agent is a camptothecine or a camptothecine derivative. Various types of camptothecine or camptothecine derivatives may be used in the conjugates and are described in more detail below.

The one or more drugs or active agents can be conjugated to the polypeptide (e.g., antibody) at any desired site of the polypeptide. Thus, the present disclosure provides, for example, a polypeptide having a drug or active agent conjugated at a site at or near the C-terminus of the polypeptide. Other examples include a polypeptide having a drug or active agent conjugated at a position at or near the N-terminus of the polypeptide. Examples also include a polypeptide having a drug or active agent conjugated at a position between the C-terminus and the N-terminus of the polypeptide (e.g., at an internal site of the polypeptide). Combinations of the above are also possible where the polypeptide is conjugated to two or more drugs or active agents.

In certain embodiments, a conjugate of the present disclosure includes one or more drugs or active agents conjugated to an amino acid residue of a polypeptide at the α-carbon of an amino acid residue. Stated another way, a conjugate includes a polypeptide where the side chain of one or more amino acid residues in the polypeptide has been modified and attached to one or more drugs or active agents (e.g., attached to one or more drugs or active agents through a linker as described herein). For example, a conjugate includes a polypeptide where the α-carbon of one or more amino acid residues in the polypeptide has been modified and attached to one or more drugs or active agents (e.g., attached to one or more drugs or active agents through a linker as described herein).

Embodiments of the present disclosure include conjugates where a polypeptide is conjugated to one or more moieties, such as 2 moieties, 3 moieties, 4 moieties, 5 moieties, 6 moieties, 7 moieties, 8 moieties, 9 moieties, or 10 or more moieties. The moieties may be conjugated to the polypeptide at one or more sites in the polypeptide. For example, one or more moieties may be conjugated to a single amino acid residue of the polypeptide. In some cases, one moiety is conjugated to an amino acid residue of the polypeptide. In other embodiments, two moieties may be conjugated to the same amino acid residue of the polypeptide. In other embodiments, a first moiety is conjugated to a first amino acid residue of the polypeptide and a second moiety is conjugated to a second amino acid residue of the polypeptide. Combinations of the above are also possible, for example where a polypeptide is conjugated to a first moiety at a first amino acid residue and conjugated to two other moieties at a second amino acid residue. Other combinations are also possible, such as, but not limited to, a polypeptide conjugated to first and second moieties at a first amino acid residue and conjugated to third and fourth moieties at a second amino acid residue, etc. In some cases, two or more amino acid residues in the polypeptide are each conjugated to a pair of moieties (i.e., two moieties), where each pair of moieties is conjugated to the polypeptide through a branched linker as described herein. In some cases, 1 amino acid residue in the polypeptide is conjugated to a pair of moieties through a branched linker as described herein.

The one or more amino acid residues of the polypeptide that are conjugated to the one or more moieties may be naturally occurring amino acids, unnatural amino acids, or combinations thereof. For instance, the conjugate may include one or more drugs or active agents conjugated to a naturally occurring amino acid residue of the polypeptide. In other instances, the conjugate may include one or more drugs or active agents conjugated to an unnatural amino acid residue of the polypeptide. One or more drugs or active agents may be conjugated to the polypeptide at a single natural or unnatural amino acid residue as described above. One or more natural or unnatural amino acid residues in the polypeptide may be conjugated to the moiety or moieties as described herein. For example, two (or more) amino acid residues (e.g., natural or unnatural amino acid residues) in the polypeptide may each be conjugated to one or two moieties, such that multiple sites in the polypeptide are conjugated to the moieties of interest.

In certain embodiments, the polypeptide (e.g., antibody) and the moiety of interest (e.g., drug or active agent) are conjugated through a conjugation moiety. For example, the polypeptide and the moiety of interest may each be bound (e.g., covalently bonded) to the conjugation moiety, thus indirectly binding the polypeptide and the moiety of interest together through the conjugation moiety. In some cases, the conjugation moiety includes a hydrazinyl-indolyl or a hydrazinyl-pyrrolo-pyridinyl compound, or a derivative of a hydrazinyl-indolyl or a hydrazinyl-pyrrolo-pyridinyl compound. For instance, a general scheme for coupling a moiety of interest to a polypeptide through a hydrazinyl-indolyl or a hydrazinyl-pyrrolo-pyridinyl conjugation moiety is shown in the general reaction scheme below. Hydrazinyl-indolyl and hydrazinyl-pyrrolo-pyridinyl conjugation moiety are also referred to herein as a hydrazino-iso-Pictet-Spengler (HIPS) conjugation moiety and an aza-hydrazino-iso-Pictet-Spengler (azaHIPS) conjugation moiety, respectively.

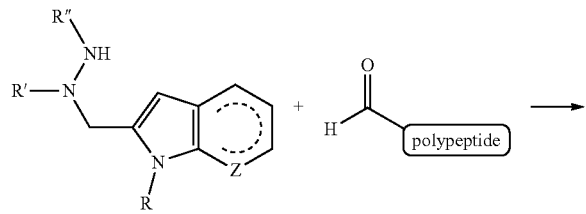

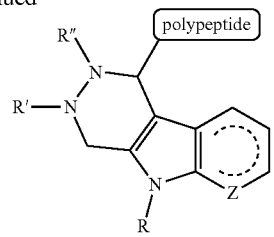

In the reaction scheme above, R includes the moiety of interest (e.g., a drug or active agent) that is conjugated to the polypeptide (e.g., conjugated to the polypeptide through a cleavable linker as described herein). As shown in the reaction scheme above, a polypeptide that includes a 2-formylglycine residue (fGly) is reacted with a drug or active agent that has been modified to include a conjugation moiety (e.g., a hydrazinyl-indolyl or a hydrazinyl-pyrrolo-pyridinyl conjugation moiety) to produce a polypeptide conjugate attached to the conjugation moiety, thus attaching the drug or active agent to the polypeptide through the conjugation moiety.

As described herein, the moiety can be any of a variety of moieties such as, but not limited to, chemical entities, such as detectable labels, or drugs or active agents. R' and R" may each independently be any desired substituent, such as, but not limited to, hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. Z may be $CR^{21}$, $NR^{22}$, N, O or S, where $R^{21}$ and $R^{22}$ are each independently selected from any of the substituents described for R' and R" above.

Other hydrazinyl-indolyl or hydrazinyl-pyrrolo-pyridinyl coupling moieties are also possible, as shown in the conjugates and compounds described herein. For example, the hydrazinyl-indolyl or hydrazinyl-pyrrolo-pyridinyl coupling moieties may be attached (e.g., covalently attached) to a linker. As such, embodiments of the present disclosure include a hydrazinyl-indolyl or hydrazinyl-pyrrolo-pyridinyl conjugation moiety attached to a drug or active agent through a linker. Various embodiments of the linker that may couple the hydrazinyl-indolyl or hydrazinyl-pyrrolo-pyridinyl conjugation moiety to the drug or active agent are described in detail herein. For example, in some instances, the linker is a cleavable linker, such as a cleavable linker as described herein.

In some instances, the hydrazinyl-indolyl or hydrazinyl-pyrrolo-pyridinyl conjugation moieties may be attached (e.g., covalently attached) to two or more linkers. As such, embodiments of the present disclosure include a hydrazinyl-indolyl or hydrazinyl-pyrrolo-pyridinyl conjugation moiety attached to two or more drugs or active agents each through a corresponding linker. Thus, conjugates of the present disclosure may include two or more linkers, where each linker attaches a corresponding drug or active agent to the hydrazinyl-indolyl or hydrazinyl-pyrrolo-pyridinyl conjugation moiety. Accordingly, the hydrazinyl-indolyl or hydrazinyl-pyrrolo-pyridinyl conjugation moiety and two or more linkers may be viewed overall as a "branched linker", where the hydrazinyl-indolyl or hydrazinyl-pyrrolo-pyridinyl conjugation moiety is attached to two of more "branches", where each branch includes a linker attached to a drug or active agent.

In certain embodiments, the polypeptide may be conjugated to one or more moieties of interest, where one or more amino acid residues of the polypeptide are modified before conjugation to the moiety of interest. Modification of one or more amino acid residues of the polypeptide may produce a polypeptide that contains one or more reactive groups suitable for conjugation to the moiety of interest. In some cases, the polypeptide may be include one or more modified amino acid residues to provide one or more reactive groups suitable for conjugation to the moiety of interest (e.g., one or more moieties that includes a conjugation moiety, such as a hydrazinyl-indolyl or a hydrazinyl-pyrrolo-pyridinyl conjugation moiety as described above). For example, an amino acid of the polypeptide may be modified to include a reactive aldehyde group (e.g., a reactive aldehyde). A reactive aldehyde may be included in an "aldehyde tag" or "ald-tag", which as used herein refers to an amino acid sequence derived from a sulfatase motif (e.g., L(C/S)TPSR) that has been converted by action of a formylglycine generating enzyme (FGE) to contain a 2-formylglycine residue (referred to herein as "fGly"). The fGly residue generated by an FGE may also be referred to as a "formylglycine". Stated differently, the term "aldehyde tag" is used herein to refer to an amino acid sequence that includes a "converted" sulfatase motif (i.e., a sulfatase motif in which a cysteine or serine residue has been converted to fGly by action of an FGE, e.g., L(fGly)TPSR). A converted sulfatase motif may be produced from an amino acid sequence that includes an "unconverted" sulfatase motif (i.e., a sulfatase motif in which the cysteine or serine residue has not been converted to fGly by an FGE, but is capable of being converted, e.g., an unconverted sulfatase motif with the sequence: L(C/S)TPSR). By "conversion" as used in the context of action of a formylglycine generating enzyme (FGE) on a sulfatase motif refers to biochemical modification of a cysteine or serine residue in a sulfatase motif to a formylglycine (fGly) residue (e.g., Cys to fGly, or Ser to fGly). Additional aspects of aldehyde tags and uses thereof in site-specific protein modification are described in U.S. Pat. Nos. 7,985,783 and 8,729,232, the disclosures of each of which are incorporated herein by reference.

In some cases, to produce the conjugate, the polypeptide containing the fGly residue may be conjugated to the moiety of interest by reaction of the fGly with a compound (e.g., a compound containing a hydrazinyl-indolyl or a hydrazinyl-pyrrolo-pyridinyl conjugation moiety, as described above). For example, an fGly-containing polypeptide may be contacted with a reactive partner-containing drug under conditions suitable to provide for conjugation of the drug to the polypeptide. In some instances, the reactive partner-containing drug may include a hydrazinyl-indolyl or a hydrazinyl-pyrrolo-pyridinyl conjugation moiety as described above. For example, a drug or active agent may be modified to include a hydrazinyl-indolyl or a hydrazinyl-pyrrolo-pyridinyl conjugation moiety. In some cases, the drug or active agent is attached to a hydrazinyl-indolyl or a hydrazinyl-pyrrolo-pyridinyl, such as covalently attached to a hydrazinyl-indolyl or a hydrazinyl-pyrrolo-pyridinyl through a linker, such as a linker as described in detail herein.

In certain embodiments, a conjugate of the present disclosure includes a polypeptide (e.g., an antibody) having at least one amino acid residue that has been attached to one or more moieties of interest (e.g., drugs or active agents). In order to make the conjugate, an amino acid residue of the polypeptide may be modified and then coupled to one or more drugs or active agents attached to a hydrazinyl-indolyl or a hydrazinyl-pyrrolo-pyridinyl conjugation moiety as described above. In certain embodiments, an amino acid residue of the polypeptide (e.g., antibody) is a cysteine or serine residue that is modified to an fGly residue, as described above. In certain embodiments, the modified amino acid residue (e.g. fGly residue) is conjugated to a drug or active agent containing a hydrazinyl-indolyl or a hydrazinyl-pyrrolo-pyridinyl conjugation moiety as described above to provide a conjugate of the present disclosure where the one or more drugs or active agents are conjugated to the polypeptide through the hydrazinyl-indolyl or hydrazinyl-pyrrolo-pyridinyl conjugation moiety. As used herein, the term fGly' refers to the modified amino acid residue of the polypeptide (e.g., antibody) that is coupled to the moiety of interest (e.g., a drug or active agent).

In certain embodiments, the conjugate includes a polypeptide (e.g. an antibody) having at least one amino acid residue attached to a linker as described herein, which in turn is attached to one or more drugs or active agents. For instance, the conjugate may include a polypeptide (e.g., an antibody) having at least one amino acid residue (fGly') that is conjugated to the one or more moieties of interest (e.g., one or more drugs or active agents) as described above.

Aspects of the present disclosure include a conjugate of formula (I):

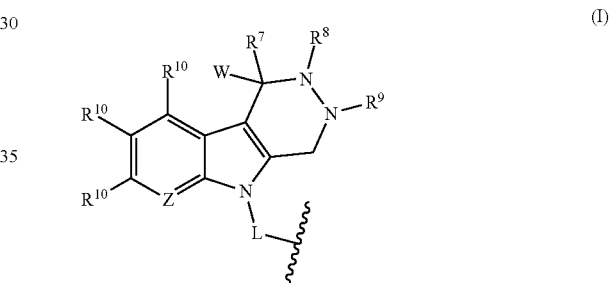

wherein
Z is $CR^{10}$ or N,
$R^7$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl;

$R^8$ and $R^9$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^8$ and $R^9$ are optionally cyclically linked to form a 5 or 6-membered heterocyclyl;

each $R^{10}$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

W is a polypeptide;

L is a linker attached to a compound of formula (II) at $R^1$, $R^2$, $R^3$, $R^4$, $R^5$ or $R^6$:

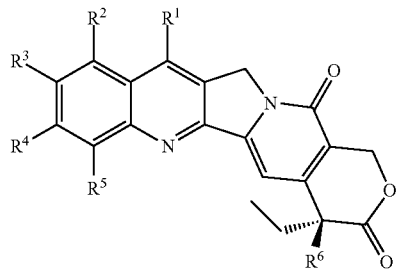

(II)

$R^1$ and $R^2$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^1$ and $R^2$ are optionally cyclically linked to form a 5 or 6-membered cycloalkyl or heterocyclyl ring;

$R^3$ and $R^4$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^3$ and $R^4$ are optionally cyclically linked to form a 5 or 6-membered cycloalkyl or heterocyclyl ring;

$R^5$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl;

$R^6$ is selected from OH and $OC(O)R^{11}$; and $R^{11}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl, wherein at least one $R^{10}$ is optionally linked to a second compound of formula (II).

The substituents related to conjugates of formula (I) are described in more detail below.

In certain embodiments, Z is $CR^{10}$ or N. In certain embodiments, Z is $CR^{10}$. In certain embodiments, Z is N.

In certain embodiments, $R^7$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^7$ is hydrogen. In certain embodiments, $R^7$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^7$ is methyl. In certain embodiments, $R^7$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^7$ is alkynyl or substituted alkynyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^7$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^7$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^7$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^7$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^8$ and $R^9$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^8$ and $R^9$ are optionally cyclically linked to form a 5 or 6-membered heterocyclyl.

In certain embodiments, $R^8$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^8$ is hydrogen. In certain embodiments, $R^8$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^8$ is methyl. In certain embodiments, $R^8$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^8$ is alkynyl or substituted alkynyl. In certain embodiments, $R^8$ is alkoxy or substituted alkoxy. In certain embodiments, $R^8$ is amino or substituted amino. In certain embodiments, $R^8$ is carboxyl or carboxyl ester. In certain embodiments, $R^8$ is acyl or acyloxy. In certain embodiments, $R^8$ is acyl amino or amino acyl. In certain embodiments, $R^8$ is alkylamide or substituted alkylamide. In certain embodiments, $R^8$ is sulfonyl. In certain embodiments, $R^8$ is thioalkoxy or substituted thioalkoxy. In certain embodiments, $R^8$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^8$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^8$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^8$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^9$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^9$ is hydrogen. In certain embodiments, $R^9$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^9$ is methyl. In certain embodiments, $R^9$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^9$ is alkynyl or substituted alkynyl. In certain embodiments, $R^9$ is alkoxy or substituted alkoxy. In certain embodiments, $R^9$ is amino or substituted amino. In certain embodiments, $R^9$ is carboxyl or carboxyl ester. In certain embodiments, $R^9$ is acyl or acyloxy. In certain embodiments, $R^9$ is acyl amino or amino acyl. In certain embodiments, $R^9$ is alkylamide or substituted alkylamide. In certain embodiments, $R^9$ is sulfonyl. In certain embodiments, $R^9$ is thioalkoxy or substituted thioalkoxy. In certain embodiments, $R^9$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^9$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^9$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^9$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^8$ and $R^9$ are optionally cyclically linked to form a 5 or 6-membered heterocyclyl. In certain embodiments, $R^8$ and $R^9$ are cyclically linked to form a 5 or 6-membered heterocyclyl. In certain embodiments, $R^8$ and $R^9$ are cyclically linked to form a 5-membered heterocyclyl. In certain embodiments, $R^8$ and $R^9$ are cyclically linked to form a 6-membered heterocyclyl.

In certain embodiments, each $R^{10}$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

The various possibilities for each $R^{10}$ are described in more detail as follows. In certain embodiments, $R^{10}$ is hydrogen. In certain embodiments, each $R^{10}$ is hydrogen. In certain embodiments, $R^{10}$ is halogen, such as F, Cl, Br or I. In certain embodiments, $R^{10}$ is F. In certain embodiments, $R^{10}$ is Cl. In certain embodiments, $R^{10}$ is Br. In certain embodiments, $R^{10}$ is I. In certain embodiments, $R^{10}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{10}$ is methyl. In certain embodiments, $R^{10}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ substituted alkenyl. In certain embodiments, $R^{10}$ is alkynyl or substituted alkynyl. In certain embodiments, $R^{10}$ is alkoxy or substituted alkoxy. In certain embodiments, $R^{10}$ is amino or substituted amino. In certain embodiments, $R^{10}$ is carboxyl or carboxyl ester. In certain embodiments, $R^{10}$ is acyl or acyloxy. In certain embodiments, $R^{10}$ is acyl amino or amino acyl. In certain embodiments, $R^{10}$ is alkylamide or substituted alkylamide. In certain embodiments, $R^{10}$ is sulfonyl. In certain embodiments, $R^{10}$ is thioalkoxy or substituted thioalkoxy. In certain embodiments, $R^{10}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl (e.g., phenyl or substituted phenyl). In certain embodiments, $R^{10}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{10}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{10}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, W is a polypeptide. For example, W can be an antibody. In certain embodiments, W comprises one or more fGly' residues as described herein. In certain embodiments, the polypeptide is attached to the rest of the conjugate through an fGly' residue as described herein. Further description of polypeptides and antibodies that find use in the subject conjugates is found in the disclosure herein.

In certain embodiments, L is a linker attached to a compound of formula (II) at $R^1$, $R^2$, $R^3$, $R^4$, $R^5$ or $R^6$. Linkers suitable for L are described in more detail below.

In certain embodiments, the conjugate of formula (I) includes a linker, L. The linker may be utilized to bind one or more moieties of interest (e.g., drug or active agent) to one or more polypeptides through a conjugation moiety. The linker may be bound (e.g., covalently bonded) to the conjugation moiety (e.g., as described herein) at any convenient position. For example, the linker may attach a hydrazinyl-indolyl or a hydrazinyl-pyrrolo-pyridinyl conjugation moiety to a drug (e.g., a camptothecine or camptothecine derivative). The hydrazinyl-indolyl or hydrazinyl-pyrrolo-pyridinyl conjugation moiety may be used to conjugate the linker (and thus the drug) to a polypeptide, such as an antibody. For example, the conjugation moiety may be used to conjugate the linker (and thus the drug) to a modified amino acid residue of the polypeptide, such as an fGly reside of an antibody, as described herein.

For example, as shown in formula (I) above, L is attached to W through a conjugation moiety, and thus W is indirectly bonded to the linker L through the conjugation moiety. As described above, W is a polypeptide (e.g., an antibody), and thus L is attached through the conjugation moiety to the polypeptide (antibody), e.g., the linker L is indirectly bonded to the polypeptide (antibody) through the conjugation moiety (e.g., through a hydrazinyl-indolyl or hydrazinyl-pyrrolo-pyridinyl conjugation moiety as described herein).

Any convenient linker may be utilized for the linker L in the subject conjugates and compounds. In certain embodiments, the linker L may include a group selected from alkyl, substituted alkyl, alkenyl, substituted alkenyl, alkynyl, substituted alkynyl, alkoxy, substituted alkoxy, amino, substituted amino, carboxyl, carboxyl ester, acyl amino, alkylamide, substituted alkylamide, aryl, substituted aryl, heteroaryl, substituted heteroaryl, cycloalkyl, substituted cycloalkyl, heterocyclyl, and substituted heterocyclyl. In certain embodiments, the linker L may include an alkyl or substituted alkyl group. In certain embodiments, the linker L may include an alkenyl or substituted alkenyl group. In certain embodiments, the linker L may include an alkynyl or substituted alkynyl group. In certain embodiments, the linker L may include an alkoxy or substituted alkoxy group. In certain embodiments, the linker L may include an amino or substituted amino group. In certain embodiments, the linker L may include a carboxyl or carboxyl ester group. In certain embodiments, the linker L may include an acyl amino group. In certain embodiments, the linker L may include an alkylamide or substituted alkylamide group. In certain embodiments, the linker L may include an aryl or substituted aryl group. In certain embodiments, the linker L may include a heteroaryl or substituted heteroaryl group. In certain embodiments, the linker L may include a cycloalkyl or substituted cycloalkyl group. In certain embodiments, the linker L may include a heterocyclyl or substituted heterocyclyl group.

In certain embodiments, the linker L may include a polymer. For example, the polymer may include a polyalkylene glycol and derivatives thereof, including polyethylene glycol, methoxypolyethylene glycol, polyethylene glycol homopolymers, polypropylene glycol homopolymers, copolymers of ethylene glycol with propylene glycol (e.g., where the homopolymers and copolymers are unsubstituted or substituted at one end with an alkyl group), polyvinyl alcohol, polyvinyl ethyl ethers, polyvinylpyrrolidone, combinations thereof, and the like. In certain embodiments, the polymer is a polyalkylene glycol. In certain embodiments, the polymer is a polyethylene glycol. Other linkers are also possible, as shown in the conjugates and compounds described in more detail below.

In some embodiments, L is a linker (e.g., a first linker) described by the formula:

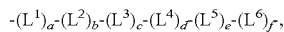

-(L$^1$)$_a$-(L$^2$)$_b$-(L$^3$)$_c$-(L$^4$)$_d$-(L$^5$)$_e$-(L$^6$)$_f$, wherein L$^1$, L$^2$, L$^3$, L$^4$, L$^5$ and L$^6$ are each independently a linker subunit, and a, b, c, d, e and f are each independently 0 or 1, wherein the sum of a, b, c, d, e and f is 1 to 6.

In certain embodiments, the sum of a, b, c, d, e and f is 1. In certain embodiments, the sum of a, b, c, d, e and f is 2. In certain embodiments, the sum of a, b, c, d, e and f is 3. In certain embodiments, the sum of a, b, c, d, e and f is 4. In certain embodiments, the sum of a, b, c, d, e and f is 5. In certain embodiments, the sum of a, b, c, d, e and f is 6. In certain embodiments, a, b, c, d, e and f are each 1. In certain embodiments, a, b, c, d and e are each 1 and f is 0. In certain embodiments, a, b, c and d are each 1 and e and f are each 0. In certain embodiments, a, b, and c are each 1 and d, e and f are each 0. In certain embodiments, a and b are each 1 and c, d, e and f are each 0. In certain embodiments, a is 1 and b, c, d, e and f are each 0.

In certain embodiments, the linker subunit L$^1$ is attached to the hydrazinyl-indolyl or the hydrazinyl-pyrrolo-pyridinyl conjugation moiety (e.g., as shown in formula (I) above). In certain embodiments, the linker subunit L$^2$, if present, is attached to the camptothecine or camptothecine derivative. In certain embodiments, the linker subunit L$^3$, if present, is attached to the camptothecine or camptothecine derivative. In certain embodiments, the linker subunit L$^4$, if present, is attached to the camptothecine or camptothecine derivative. In certain embodiments, the linker subunit L$^5$, if present, is attached to the camptothecine or camptothecine derivative. In certain embodiments, the linker subunit L$^6$, if present, is attached to the camptothecine or camptothecine derivative.

Any convenient linker subunits may be utilized in the linker L. Linker subunits of interest include, but are not limited to, units of polymers such as polyethylene glycols, polyethylenes and polyacrylates, amino acid residue(s), carbohydrate-based polymers or carbohydrate residues and derivatives thereof, polynucleotides, alkyl groups, aryl groups, heterocyclic groups, combinations thereof, and substituted versions thereof. In some embodiments, each of L$^1$, L$^2$, L$^3$, L$^4$, L$^5$ and L$^6$ (if present) comprise one or more groups independently selected from a polyethylene glycol, a modified polyethylene glycol, an amino acid residue, an alkyl group, a substituted alkyl, an aryl group, a substituted aryl group, and a diamine (e.g., a linking group that includes an alkylene diamine).

In some embodiments, L$^1$ (if present) comprises a polyethylene glycol, a modified polyethylene glycol, an amino acid residue, an alkyl group, a substituted alkyl, an aryl group, a substituted aryl group, or a diamine. In some embodiments, L$^1$ comprises a polyethylene glycol. In some embodiments, L$^1$ comprises a modified polyethylene glycol. In some embodiments, L$^1$ comprises an amino acid residue. In some embodiments, L$^1$ comprises an alkyl group or a substituted alkyl. In some embodiments, L$^1$ comprises an aryl group or a substituted aryl group. In some embodiments, L$^1$ comprises a diamine (e.g., a linking group comprising an alkylene diamine).

In some embodiments, L$^2$ (if present) comprises a polyethylene glycol, a modified polyethylene glycol, an amino acid residue, an alkyl group, a substituted alkyl, an aryl group, a substituted aryl group, or a diamine. In some embodiments, L$^2$ comprises a polyethylene glycol. In some embodiments, L$^2$ comprises a modified polyethylene glycol. In some embodiments, L$^2$ comprises an amino acid residue. In some embodiments, L$^2$ comprises an alkyl group or a substituted alkyl. In some embodiments, L$^2$ comprises an aryl group or a substituted aryl group. In some embodiments, L$^2$ comprises a diamine (e.g., a linking group comprising an alkylene diamine).

In some embodiments, L$^3$ (if present) comprises a polyethylene glycol, a modified polyethylene glycol, an amino acid residue, an alkyl group, a substituted alkyl, an aryl group, a substituted aryl group, or a diamine. In some embodiments, L$^3$ comprises a polyethylene glycol. In some embodiments, L$^3$ comprises a modified polyethylene glycol. In some embodiments, L$^3$ comprises an amino acid residue. In some embodiments, L$^3$ comprises an alkyl group or a substituted alkyl. In some embodiments, L$^3$ comprises an aryl group or a substituted aryl group. In some embodiments, L$^3$ comprises a diamine (e.g., a linking group comprising an alkylene diamine).

In some embodiments, L$^4$ (if present) comprises a polyethylene glycol, a modified polyethylene glycol, an amino acid residue, an alkyl group, a substituted alkyl, an aryl group, a substituted aryl group, or a diamine. In some embodiments, L$^4$ comprises a polyethylene glycol. In some embodiments, L$^4$ comprises a modified polyethylene glycol. In some embodiments, L$^4$ comprises an amino acid residue. In some embodiments, L$^4$ comprises an alkyl group or a substituted alkyl. In some embodiments, L$^4$ comprises an aryl group or a substituted aryl group. In some embodiments, L$^4$ comprises a diamine (e.g., a linking group comprising an alkylene diamine).

In some embodiments, L$^5$ (if present) comprises a polyethylene glycol, a modified polyethylene glycol, an amino acid residue, an alkyl group, a substituted alkyl, an aryl group, a substituted aryl group, or a diamine. In some embodiments, $L^5$ comprises a polyethylene glycol. In some embodiments, $L^5$ comprises a modified polyethylene glycol. In some embodiments, $L^5$ comprises an amino acid residue. In some embodiments, $L^5$ comprises an alkyl group or a substituted alkyl. In some embodiments, $L^5$ comprises an aryl group or a substituted aryl group. In some embodiments, $L^5$ comprises a diamine (e.g., a linking group comprising an alkylene diamine).

In some embodiments, $L^6$ (if present) comprises a polyethylene glycol, a modified polyethylene glycol, an amino acid residue, an alkyl group, a substituted alkyl, an aryl group, a substituted aryl group, or a diamine. In some embodiments, $L^6$ comprises a polyethylene glycol. In some embodiments, $L^6$ comprises a modified polyethylene glycol. In some embodiments, $L^6$ comprises an amino acid residue. In some embodiments, $L^6$ comprises an alkyl group or a substituted alkyl. In some embodiments, $L^6$ comprises an aryl group or a substituted aryl group. In some embodiments, $L^6$ comprises a diamine (e.g., a linking group comprising an alkylene diamine).

In some embodiments, L is a linker comprising $-(L^1)_a-(L^2)_b-(L^3)_c-(L^4)_d-(L^5)_e-(L^6)_f-$, where:
 $-(L^1)_a-$ is $-(T^1-V^1)_a-$;
 $-(L^2)_b-$ is $-(T^2-V^2)_b-$;
 $-(L^3)_c-$ is $-(T^3-V^3)_c-$;
 $-(L^4)_d-$ is $-(T^4-V^4)_d-$;
 $-(L^5)_e-$ is $-(T^5-V^5)_e-$; and
 $-(L^6)_f-$ is $-(T^6-V^6)_f-$,
 wherein $T^1$, $T^2$, $T^3$, $T^4$, $T^5$ and $T^6$, if present, are tether groups;
 $V^1$, $V^2$, $V^3$, $V^4$, $V^5$ and $V^6$, if present, are covalent bonds or linking functional groups; and
 a, b, c, d, e and f are each independently 0 or 1, wherein the sum of a, b, c, d, e and f is 1 to 6.

As described above, in certain embodiments, $L^1$ is attached to the hydrazinyl-indolyl or the hydrazinyl-pyrrolopyridinyl conjugation moiety (e.g., as shown in formula (I) above). As such, in certain embodiments, $T^1$ is attached to the hydrazinyl-indolyl or the hydrazinyl-pyrrolo-pyridinyl conjugation moiety (e.g., as shown in formula (I) above). In certain embodiments, $V^1$ is attached to the camptothecine or camptothecine derivative. In certain embodiments, $L^2$, if present, is attached to the camptothecine or camptothecine derivative. As such, in certain embodiments, $T^2$, if present, is attached to the camptothecine or camptothecine derivative, or $V^2$, if present, is attached to the camptothecine or camptothecine derivative. In certain embodiments, $L^3$, if present, is attached to the camptothecine or camptothecine derivative. As such, in certain embodiments, $T^3$, if present, is attached to the camptothecine or camptothecine derivative, or $V^3$, if present, is attached to the camptothecine or camptothecine derivative. In certain embodiments, $L^4$, if present, is attached to the camptothecine or camptothecine derivative. As such, in certain embodiments, $T^4$, if present, is attached to the camptothecine or camptothecine derivative, or $V^4$, if present, is attached to the camptothecine or camptothecine derivative. In certain embodiments, $L^5$, if present, is attached to the camptothecine or camptothecine derivative. As such, in certain embodiments, $T^5$, if present, is attached to the camptothecine or camptothecine derivative, or $V^5$, if present, is attached to the camptothecine or camptothecine derivative. In certain embodiments, $L^6$, if present, is attached to the camptothecine or camptothecine derivative. As such, in certain embodiments, $T^6$, if present, is attached to the camptothecine or camptothecine derivative, or $V^6$, if present, is attached to the camptothecine or camptothecine derivative.

Regarding the tether groups, $T^1$, $T^2$, $T^3$, $T^4$, $T^5$ and $T^6$, any convenient tether groups may be utilized in the subject linkers. In some embodiments, $T^1$, $T^2$, $T^3$, $T^4$, $T^5$ and $T^6$ each comprise one or more groups independently selected from a covalent bond, a $(C_1-C_{12})$alkyl, a substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, where each w is an integer from 1 to 20, each n is an integer from 1 to 30, each p is an integer from 1 to 20, and each m is an integer from 1 to 12.

In certain embodiments, the tether group (e.g., $T^1$, $T^2$, $T^3$, $T^4$, $T^5$ and/or $T^6$) includes a $(C_1-C_{12})$alkyl or a substituted $(C_1-C_{12})$alkyl. In certain embodiments, $(C_1-C_{12})$alkyl is a straight chain or branched alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, $(C_1-C_{12})$alkyl may be an alkyl or substituted alkyl, such as $C_1-C_{12}$ alkyl, or $C_1-C_{10}$ alkyl, or $C_1-C_6$ alkyl, or $C_1-C_3$ alkyl. In some instances, $(C_1-C_{12})$alkyl is a $C_2$-alkyl. For example, $(C_1-C_{12})$alkyl may be an alkylene or substituted alkylene, such as $C_1-C_{12}$ alkylene, or $C_1-C_{10}$ alkylene, or $C_1-C_6$ alkylene, or $C_1-C_3$ alkylene. In some instances, $(C_1-C_{12})$alkyl is a $C_2$-alkylene (e.g., $CH_2CH_2$). In some instances, $(C_1-C_{12})$alkyl is a $C_3$-alkylene (e.g., $CH_2CH_2CH_2$).

In certain embodiments, substituted $(C_1-C_{12})$alkyl is a straight chain or branched substituted alkyl group that includes from 1 to 12 carbon atoms, such as 1 to 10 carbon atoms, or 1 to 8 carbon atoms, or 1 to 6 carbon atoms, or 1 to 5 carbon atoms, or 1 to 4 carbon atoms, or 1 to 3 carbon atoms. In some instances, substituted $(C_1-C_{12})$alkyl may be a substituted alkyl, such as substituted $C_1-C_{12}$ alkyl, or substituted $C_1-C_{10}$ alkyl, or substituted $C_1-C_6$ alkyl, or substituted $C_1-C_3$ alkyl. In some instances, substituted $(C_1-C_{12})$alkyl is a substituted $C_2$-alkyl. For example, substituted $(C_1-C_{12})$alkyl may be a substituted alkylene, such as substituted $C_1-C_{12}$ alkylene, or substituted $C_1-C_{10}$ alkylene, or substituted $C_1-C_6$ alkylene, or substituted $C_1-C_3$ alkylene. In some instances, substituted $(C_1-C_{12})$alkyl is a substituted $C_2$-alkylene. In some instances, substituted $(C_1-C_{12})$alkyl is a substituted $C_3$-alkylene. For example, substituted $(C_1-C_{12})$ alkyl may include $C_1-C_{12}$ alkylene (e.g., $C_3$-alkylene or $C_5$-alkylene) substituted with a $(PEG)_n$ group as described herein (e.g., —$CONH(PEG)_3$ or —$NHCO(PEG)_7$), or may include $C_1-C_{12}$ alkylene (e.g., $C_3$-alkylene) substituted with a —$CONHCH_2CH_2SO_3H$ group, or may include $C_1-C_{12}$ alkylene (e.g., $C_5$-alkylene) substituted with a —$NHCOCH_2SO_3H$ group.

In certain embodiments, the tether group (e.g., $T^1$, $T^2$, $T^3$, $T^4$, $T^5$ and/or $T^6$) includes an aryl, substituted aryl, heteroaryl, substituted heteroaryl, cycloalkyl, substituted cycloalkyl, heterocyclyl, or substituted heterocyclyl. In some instances, the tether group (e.g., $T^1$, $T^2$, $T^3$, $T^4$, $T^5$ and $T^6$) includes an aryl or substituted aryl. For example, the aryl can be phenyl. In some cases, the substituted aryl is a substituted phenyl. The substituted phenyl can be substituted with one or more substituents selected from (C$_1$-C$_{12}$)alkyl, a substituted (C$_1$-C$_{12}$)alkyl, aryl, substituted aryl, heteroaryl, substituted heteroaryl, cycloalkyl, substituted cycloalkyl, heterocyclyl, and substituted heterocyclyl. In some instances, the substituted aryl is a substituted phenyl, where the substituent includes a cleavable moiety as described herein (e.g., an enzymatically cleavable moiety, such as a glycoside or glycoside derivative).

In some instances, the tether group (e.g., T$^1$, T$^2$, T$^3$, T$^4$, T$^5$ and/or T$^6$) includes a heteroaryl or substituted heteroaryl. In some instances, the tether group (e.g., T$^1$, T$^2$, T$^3$, T$^4$, T$^5$ and T$^6$) includes a cycloalkyl or substituted cycloalkyl. In some instances, the tether group (e.g., T$^1$, T$^2$, T$^3$, T$^4$, T$^5$ and T$^6$) includes a heterocyclyl or substituted heterocyclyl. In some instances, the substituent on the substituted heteroaryl, substituted cycloalkyl or substituted heterocyclyl includes a cleavable moiety as described herein (e.g., an enzymatically cleavable moiety, such as a glycoside or glycoside derivative).

In certain embodiments, the tether group (e.g., T$^1$, T$^2$, T$^3$, T$^4$, T$^5$ and/or T$^6$) includes an ethylene diamine (EDA) moiety, e.g., an EDA containing tether group. In certain embodiments, (EDA)$_w$ includes one or more EDA moieties, such as where w is an integer from 1 to 50, such as from 1 to 40, from 1 to 30, from 1 to 20, from 1 to 12 or from 1 to 6, such as 1, 2, 3, 4, 5 or 6). The linked ethylene diamine (EDA) moieties may optionally be substituted at one or more convenient positions with any convenient substituents, e.g., with an alkyl, a substituted alkyl, an acyl, a substituted acyl, an aryl or a substituted aryl. In certain embodiments, the EDA moiety is described by the structure:

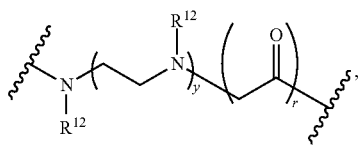

where y is an integer from 1 to 6, or is 0 or 1, and each R$^{12}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, y is 1, 2, 3, 4, 5 or 6. In certain embodiments, y is 1 and r is 0. In certain embodiments, y is 1 and r is 1. In certain embodiments, y is 2 and r is 0. In certain embodiments, y is 2 and r is 1. In certain embodiments, each R$^{12}$ is independently selected from hydrogen, an alkyl, a substituted alkyl, an aryl and a substituted aryl. In certain embodiments, any two adjacent R$^{12}$ groups of the EDA may be cyclically linked, e.g., to form a piperazinyl ring. In certain embodiments, y is 1 and the two adjacent R$^{12}$ groups are an alkyl group, cyclically linked to form a piperazinyl ring. In certain embodiments, y is 1 and the adjacent R$^{12}$ groups are selected from hydrogen, an alkyl (e.g., methyl) and a substituted alkyl (e.g., lower alkyl-OH, such as ethyl-OH or propyl-OH).

In certain embodiments, the tether group (e.g., T$^1$, T$^2$, T$^3$, T$^4$, T$^5$ and/or T$^6$) includes a 4-amino-piperidine (4AP) moiety (also referred to herein as piperidin-4-amino, P4A). The 4AP moiety may optionally be substituted at one or more convenient positions with any convenient substituents, e.g., with an alkyl, a substituted alkyl, a polyethylene glycol moiety, an acyl, a substituted acyl, an aryl or a substituted aryl. In certain embodiments, the 4AP moiety is described by the structure:

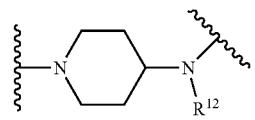

where R$^{12}$ is selected from hydrogen, alkyl, substituted alkyl, a polyethylene glycol moiety (e.g., a polyethylene glycol or a modified polyethylene glycol), alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, R$^{12}$ is a polyethylene glycol moiety. In certain embodiments, R$^{12}$ is a carboxy modified polyethylene glycol.

In certain embodiments, R$^{12}$ includes a polyethylene glycol moiety described by the formula: (PEG)$_k$, which may be represented by the structure:

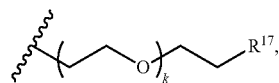

where k is an integer from 1 to 20, such as from 1 to 18, or from 1 to 16, or from 1 to 14, or from 1 to 12, or from 1 to 10, or from 1 to 8, or from 1 to 6, or from 1 to 4, or 1 or 2, such as 1, 2, 3, 4, 5, 6, 7, 8, 9, 10, 11, 12, 13, 14, 15, 16, 17, 18, 19 or 20. In some instances, k is 2. In certain embodiments, R$^{17}$ is selected from OH, OR, COOH, or COOR, where R is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, R$^{17}$ is COOH. In certain embodiments, R$^{17}$ is OH. In certain embodiments, R$^{17}$ is OR, such as OCH$_3$.

In certain embodiments, a tether group (e.g., T$^1$, T$^2$, T$^3$, T$^4$, T$^5$ and/or T$^6$) includes (PEG)$_n$, where (PEG)$_n$ is a polyethylene glycol or a modified polyethylene glycol linking unit. In certain embodiments, (PEG)$_n$ is described by the structure:

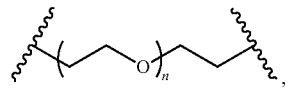

where n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In some instances, n is 2. In some instances, n is 3. In some instances, n is 6. In some instances, n is 12.

In certain embodiments, a tether group (e.g., T$^1$, T$^2$, T$^3$, T$^4$, T$^5$ and/or T$^6$) includes (AA)$_p$, where AA is an amino acid residue. Any convenient amino acids may be utilized. Amino acids of interest include but are not limited to, L- and D-amino acids, naturally occurring amino acids such as any of the 20 primary alpha-amino acids and beta-alanine, non-naturally occurring amino acids (e.g., amino acid analogs), such as a non-naturally occurring alpha-amino acid or a non-naturally occurring beta-amino acid, etc. In certain embodiments, p is an integer from 1 to 50, such as from 1 to 40, from 1 to 30, from 1 to 20, from 1 to 12 or from 1 to 6, such as 1, 2, 3, 4, 5, 6, 7, 8, 9, 10, 11, 12, 13, 14, 15, 16, 17, 18, 19 or 20. In certain embodiments, p is 1. In certain embodiments, p is 2.

In certain embodiments, a tether group (e.g., $T^1$, $T^2$, $T^3$, $T^4$, $T^5$ and/or $T^6$) includes an amino acid analog. Amino acid analogs include compounds that are similar in structure and/or overall shape to one or more amino acids commonly found in naturally occurring proteins (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid analogs also include natural amino acids with modified side chains or backbones. Amino acid analogs also include amino acid analogs with the same stereochemistry as in the naturally occurring D-form, as well as the L-form of amino acid analogs. In some instances, the amino acid analogs share backbone structures, and/or the side chain structures of one or more natural amino acids, with difference(s) being one or more modified groups in the molecule. Such modification may include, but is not limited to, substitution of an atom (such as N) for a related atom (such as S), addition of a group (such as methyl, or hydroxyl, etc.) or an atom (such as Cl or Br, etc.), deletion of a group, substitution of a covalent bond (single bond for double bond, etc.), or combinations thereof. For example, amino acid analogs may include α-hydroxy acids, and α-amino acids, and the like. Examples of amino acid analogs include, but are not limited to, sulfoalanine, and the like.

In certain embodiments, a tether group (e.g., $T^1$, $T^2$, $T^3$, $T^4$, $T^5$ and/or $T^6$) includes a moiety described by the formula $-(CR^{13}OH)_m-$, where m is 0 or n is an integer from 1 to 50, such as from 1 to 40, from 1 to 30, from 1 to 20, from 1 to 12 or from 1 to 6, such as 1, 2, 3, 4, 5, 6, 7, 8, 9, 10, 11 or 12. In certain embodiments, m is 1. In certain embodiments, m is 2. In certain embodiments, $R^{13}$ is selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl. In certain embodiments, $R^{13}$ is hydrogen. In certain embodiments, $R^{13}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{13}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{13}$ is alkynyl or substituted alkynyl. In certain embodiments, $R^{13}$ is alkoxy or substituted alkoxy. In certain embodiments, $R^{13}$ is amino or substituted amino. In certain embodiments, $R^{13}$ is carboxyl or carboxyl ester. In certain embodiments, $R^{13}$ is acyl or acyloxy. In certain embodiments, $R^{13}$ is acyl amino or amino acyl. In certain embodiments, $R^{13}$ is alkylamide or substituted alkylamide. In certain embodiments, $R^{13}$ is sulfonyl. In certain embodiments, $R^{13}$ is thioalkoxy or substituted thioalkoxy. In certain embodiments, $R^{13}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{13}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{13}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{13}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^{13}$ is selected from hydrogen, alkyl, substituted alkyl, aryl, and substituted aryl. In these embodiments, alkyl, substituted alkyl, aryl, and substituted aryl are as described above for $R^{13}$.

In certain embodiments, a tether group (e.g., $T^1$, $T^2$, $T^3$, $T^4$, $T^5$ and/or $T^6$) includes a meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), or para-hydroxy-phenyl (PHP).

In some embodiments, a tether includes a MABO group described by the following structure:

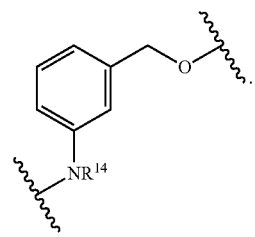

In some embodiments, a tether includes a MABC group described by the following structure:

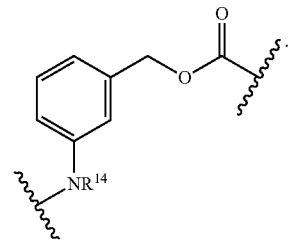

In some embodiments, a tether includes a PABO group described by the following structure:

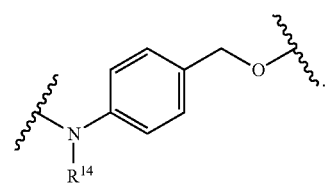

In some embodiments, a tether includes a PABC group described by the following structure:

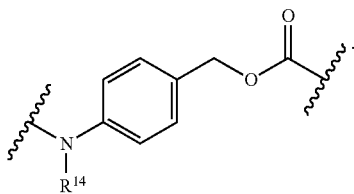

In some embodiments, a tether includes a PAB group described by the following structure:

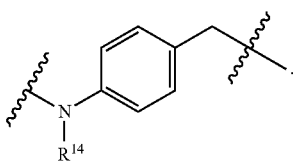

In some embodiments, a tether includes a PABA group described by the following structure:

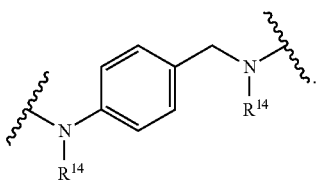

In some embodiments, a tether includes a PAP group described by the following structure:

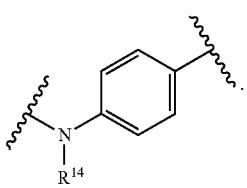

In some embodiments, a tether includes a PHP group described by the following structure:

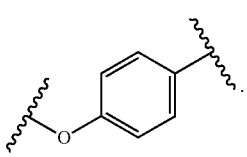 [SMILES: *Oc1ccc(*)cc1]

In certain embodiments, each $R^{14}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In certain embodiments, $R^{14}$ is hydrogen. In certain embodiments, each $R^{14}$ is hydrogen. In certain embodiments, $R^{14}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{14}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{14}$ is alkynyl or substituted alkynyl. In certain embodiments, $R^{14}$ is alkoxy or substituted alkoxy. In certain embodiments, $R^{14}$ is amino or substituted amino. In certain embodiments, $R^{14}$ is carboxyl or carboxyl ester. In certain embodiments, $R^{14}$ is acyl or acyloxy. In certain embodiments, $R^{14}$ is acyl amino or amino acyl. In certain embodiments, $R^{14}$ is alkylamide or substituted alkylamide. In certain embodiments, $R^{14}$ is sulfonyl. In certain embodiments, $R^{14}$ is thioalkoxy or substituted thioalkoxy. In certain embodiments, $R^{14}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{14}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{14}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{14}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In some embodiments of the MABO, MABC, PABO, PABC, PAB, PABA, PAP, and PHP tether structures shown above, the phenyl ring may be substituted with one or more additional groups selected from halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In certain embodiments of the linker L, one or more of the tether groups $T^1$, $T^2$, $T^3$, $T^4$, $T^5$ or $T^6$ is each optionally substituted with a glycoside or glycoside derivative. In certain embodiments, the glycoside or glycoside derivative is selected from a glucuronide, a galactoside, a glucoside, a mannoside, a fucoside, O-GlcNAc, and O-GalNAc.

In certain embodiments, the MABO, MABC, PABO, PABC, PAB, PABA, PAP, and PHP tether structures shown above may be substituted with an one or more additional groups selected from a glycoside and a glycoside derivative. For example, in some embodiments of the MABO, MABC, PABO, PABC, PAB, PABA, PAP, and PHP tether structures shown above, the phenyl ring may be substituted with one or more additional groups selected from a glycoside and a glycoside derivative. In certain embodiments, the glycoside or glycoside derivative is selected from a glucuronide, a galactoside, a glucoside, a mannoside, a fucoside, O-GlcNAc, and 0-GalNAc.

For example, in some embodiments, the glycoside or glycoside derivative can be selected from the following structures:

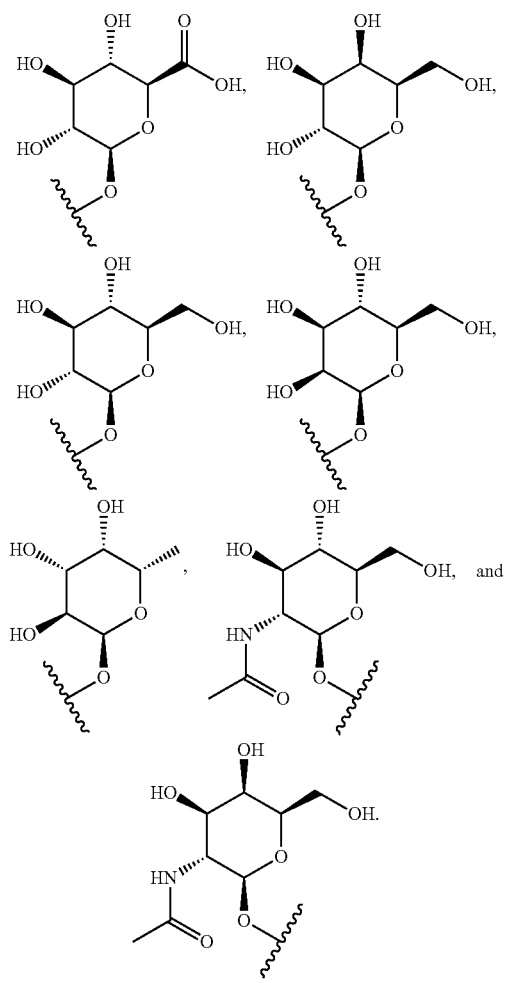

Regarding the linking functional groups, $V^1$, $V^2$, $V^3$, $V^4$, $V^5$ and $V^6$, any convenient linking functional groups may be utilized in the linker L. Linking functional groups of interest include, but are not limited to, amino, carbonyl, amido, oxycarbonyl, carboxy, sulfonyl, sulfoxide, sulfonylamino, aminosulfonyl, thio, oxy, phospho, phosphoramidate, thiophosphoraidate, and the like. In some embodiments, $V^1$, $V^2$, $V^3$, $V^4$, $V^5$ and $V^6$ are each independently selected from a covalent bond, —CO—, —$NR^{15}$—, —$NR^{15}(CH_2)_q$—, —$NR^{15}(C_6H_4)$—, —$CONR^{15}$—, —$NR^{15}CO$—, —C(O)O—, —OC(O)—, —O—, —S—, —S(O)—, —$SO_2$—, —$SO_2NR^{15}$—, —$NR^{15}SO_2$— and —P(O)OH—, where q is an integer from 1 to 6. In certain embodiments, q is an integer from 1 to 6 (e.g., 1, 2, 3, 4, 5 or 6). In certain embodiments, q is 1. In certain embodiments, q is 2. In certain embodiments, q is 3. In certain embodiments, q is 4. In certain embodiments, q is 5. In certain embodiments, q is 6.

In some embodiments, each $R^{15}$ is independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl.

In certain embodiments, $R^{15}$ is hydrogen. In certain embodiments, each $R^{15}$ is hydrogen. In certain embodiments, $R^{15}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{15}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{15}$ is alkynyl or substituted alkynyl. In certain embodiments, $R^{15}$ is alkoxy or substituted alkoxy. In certain embodiments, $R^{15}$ is amino or substituted amino. In certain embodiments, $R^{15}$ is carboxyl or carboxyl ester. In certain embodiments, $R^{15}$ is acyl or acyloxy. In certain embodiments, $R^{15}$ is acyl amino or amino acyl. In certain embodiments, $R^{15}$ is alkylamide or substituted alkylamide. In certain embodiments, $R^{15}$ is sulfonyl. In certain embodiments, $R^{15}$ is thioalkoxy or substituted thioalkoxy. In certain embodiments, $R^{15}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{15}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{15}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{15}$ is heterocyclyl or substituted heterocyclyl, such as $C_{3-8}$ heterocyclyl or $C_{3-8}$ substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl are as described above for $R^{15}$.

In certain embodiments, the tether group includes an acetal group, a disulfide, a hydrazine, or an ester. In some embodiments, the tether group includes an acetal group. In some embodiments, the tether group includes a hydrazine. In some embodiments, the tether group includes a disulfide. In some embodiments, the tether group includes an ester.

As described above, in some embodiments, L is a linker comprising -$(T^1$-$V^1)_a$-$(T^2$-$V^2)_b$-$(T^3$-$V^3)_c$-$(T^4$-$V^4)_d$-$(T^5$-$V^5)_e$-$(T^6$-$V^6)_f$-, where a, b, c, d, e and f are each independently 0 or 1, where the sum of a, b, c, d, e and f is 1 to 6.

In some embodiments, in the linker L:

$T^1$ is selected from a $(C_1$-$C_{12})$alkyl and a substituted $(C_1$-$C_{12})$alkyl;

$T^2$, $T^3$, $T^4$, $T^5$ and $T^6$ are each independently selected from $(C_1$-$C_{12})$alkyl, substituted $(C_1$-$C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, —$(CR^{13}OH)_m$—, 4-amino-piperidine (4AP), MABO, MABC, PABO, PABC, PAB, PABA, PAP, PHP, an acetal group, a disulfide, a hydrazine, and an ester; and $V^1$, $V^2$, $V^3$, $V^4$, $V^5$ and $V^6$ are each independently selected from a covalent bond, —CO—, —$NR^{15}$—, —$NR^{15}$ $-(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, wherein q is an integer from 1 to 6;

wherein:

$(PEG)_n$ is

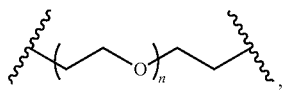

where n is an integer from 1 to 30;

EDA is an ethylene diamine moiety having the following structure:

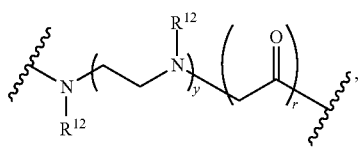

where y is an integer from 1 to 6 and r is 0 or 1;

4-amino-piperidine (4AP) is

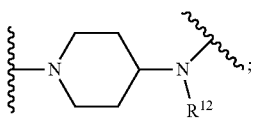

AA is an amino acid residue, where p is an integer from 1 to 20; and each $R^{12}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring;

each $R^{13}$ is independently selected from hydrogen, alkyl, substituted alkyl, aryl, and substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

In certain embodiments, $T^1$, $T^2$, $T^3$, $T^4$, $T^5$ and $T^6$ and $V^1$, $V^2$, $V^3$, $V^4$, $V^5$ and $V^6$ are selected from the following:

wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is PABC and $V^5$ is absent; and
$T^6$ is EDA and $V^6$ is $-CO-$; or wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is absent and $V^5$ is $-NR^{15}(C_6H_4)-$; and
$T^6$ is absent and $V^6$ is $-CO-$; or wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is PABC and $V^5$ is $-NR^{15}-$; and
$T^6$ is $(C_1-C_{12})$alkyl and $V^6$ is $-CO-$; or wherein:
$T^1$ is $(C_1-C_{12})$alkyl and $V^1$ is $-CO-$;
$T^2$ is AA and $V^2$ is absent;
$T^3$ is PABC and $V^3$ is absent;
$T^4$ is EDA and $V^4$ is $-CO-$; and
e and f are each 0; or wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is PABC and $V^5$ is absent; and
f is 0; or wherein:
$T^1$ is $(C_1-C_{12})$alkyl and $V^1$ is $-CO-$;
$T^2$ is AA and $V^2$ is absent;
$T^3$ is PABC and $V^3$ is absent; and
d, e and f are each 0; or wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is PABA and $V^5$ is $-CO-$; and
$T^6$ is $(C_1-C_{12})$alkyl and $V^6$ is $-SO_2-$; or wherein:
$T^1$ is $(C_1-C_{12})$alkyl and $V^1$ is $-CONH-$;
$T^2$ is $(PEG)_n$ and $V^2$ is $-CO-$;
$T^3$ is AA and $V^3$ is absent;
$T^4$ is PABC and $V^4$ is absent;
e and f are each 0; or wherein:
$T^1$ is $(C_1-C_{12})$alkyl and $V^1$ is $-CONH-$;
$T^2$ is substituted $(C_1-C_{12})$alkyl and $V^2$ is $-CO-$;
$T^3$ is AA and $V^3$ is absent;
$T^4$ is PABC and $V^4$ is absent;
e and f are each 0; or wherein:
$T^1$ is $(C_1-C_{12})$alkyl and $V^1$ is $-CONH-$;
$T^2$ is $(PEG)_n$ and $V^2$ is $-CO-$;
$T^3$ is AA and $V^3$ is absent;
$T^4$ is PABC and $V^4$ is absent;
$T^5$ is $(C_1-C_{12})$alkyl and $V^5$ is absent;
f is 0; or wherein:
$T^1$ is $(C_1-C_{12})$alkyl and $V^1$ is $-CO-$;
$T^2$ is 4AP and $V^2$ is $-CO-$;
$T^3$ is $(C_1-C_{12})$alkyl and $V^3$ is $-CO-$;
$T^4$ is AA and $V^4$ is absent;
$T^5$ is PABC and $V^5$ is absent;
f is 0; or wherein:
$T^1$ is $(C_1-C_{12})$alkyl and $V^1$ is $-CO-$;
$T^2$ is 4AP and $V^2$ is $-CO-$;
$T^3$ is $(C_1-C_{12})$alkyl and $V^3$ is $-O-$;
$T^4$ is $(C_1-C_{12})$alkyl and $V^4$ is $-CO-$;
$T^5$ is AA and $V^5$ is absent;
$T^6$ is PABC and $V^6$ is absent; or wherein:
$T^1$ is $(C_1-C_{12})$alkyl and $V^1$ is $-CO-$;
$T^2$ is an amino acid analog and $V^2$ is absent;
$T^3$ is AA and $V^3$ is absent;

T⁴ is PABC and V⁴ is absent;
e and f are each 0; or
wherein:
T¹ is (C₁-C₁₂)alkyl and V¹ is —CONH—;
T² is (PEG)ₙ and V² is —CONH—;
T³ is substituted (C₁-C₁₂)alkyl and V³ is —CO—;
T⁴ is AA and V⁴ is absent;
T⁵ is PABC and V⁵ is absent;
f is 0; or
wherein:
T¹ is (C₁-C₁₂)alkyl and V¹ is —CO—;
T² is AA and V² is —NH—;
T³ is (PEG)ₙ and V³ is —CO—;
T⁴ is AA and V⁴ is absent;
T⁵ is PABC and V⁵ is absent;
f is 0; or
wherein:
T¹ is (C₁-C₁₂)alkyl and V¹ is —CO—;
T² is an amino acid analog and V² is —NH—;
T³ is (PEG)ₙ and V³ is —CO—;
T⁴ is AA and V⁴ is absent;
T⁵ is PABO and V⁵ is absent; and
f is 0; or
wherein:
T¹ is (C₁-C₁₂)alkyl and V¹ is —CO—;
T² is an amino acid analog and V² is —NH—;
T³ is (PEG)ₙ and V³ is —CO—;
T⁴ is AA and V⁴ is absent;
T⁵ is PAP and V⁵ is —COO—; and
f is 0; or
wherein:
T¹ is (C₁-C₁₂)alkyl and V¹ is —CONH—;
T² is (PEG)ₙ and V² is —CO—;
T³ is AA and V³ is absent;
T⁴ is PAP and V⁴ is —COO—; and
e and f are each 0.

In certain embodiments, the left-hand side of the linker structure is attached to the hydrazinyl-indolyl or the hydrazinyl-pyrrolo-pyridinyl conjugation moiety, and the right-hand side of the linker structure is attached to the camptothecine or a camptothecine derivative.

In certain embodiments of the conjugate of formula (I), the linker L is attached to a camptothecine or a camptothecine derivative. In some instances, the linker L is attached to a compound of formula (II) at $R^1$, $R^2$, $R^3$, $R^4$, $R^5$ or $R^6$:

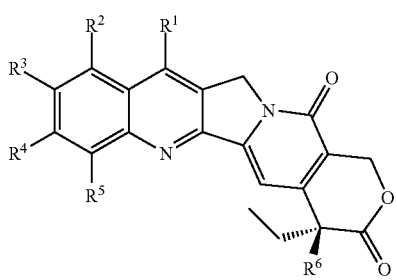

wherein:
$R^1$ and $R^2$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^1$ and $R^2$ are optionally cyclically linked to form a 5 or 6-membered cycloalkyl or heterocyclyl ring;

$R^3$ and $R^4$ are each independently selected from hydrogen, halo, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^3$ and $R^4$ are optionally cyclically linked to form a 5 or 6-membered cycloalkyl or heterocyclyl ring;

$R^5$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl;

$R^6$ is selected from OH and OC(O)$R^{11}$; and $R^{11}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl, wherein at least one $R^{10}$ is optionally linked to a second compound of formula (II).

In certain embodiments, $R^1$ and $R^2$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^1$ and $R^2$ are optionally cyclically linked to form a 5 or 6-membered cycloalkyl or heterocyclyl ring.

In certain embodiments, $R^1$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl. In certain embodiments, $R^1$ is hydrogen. In certain embodiments, $R^1$ is halogen (e.g., F, Cl, Br, I). In certain embodiments, $R^1$ is hydroxy. In certain embodiments, $R^1$ is amino or substituted amino. In certain embodiments, $R^1$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^1$ is methyl. In certain embodiments, $R^1$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^1$ is alkynyl or substituted alkynyl. In certain embodiments, $R^1$ is alkoxy or substituted alkoxy. In certain embodiments, $R^1$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^1$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^1$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^1$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^2$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl. In certain embodiments, $R^2$ is hydrogen. In certain embodiments, $R^2$ is halogen (e.g., F, Cl, Br, I). In certain embodiments, $R^2$ is hydroxy. In certain embodiments, $R^2$ is amino or substituted amino. In certain embodiments, $R^2$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^2$ is methyl. In certain embodiments, $R^2$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^2$ is alkynyl or substituted alkynyl. In certain embodiments, $R^2$ is alkoxy or substituted alkoxy. In certain embodiments, $R^2$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^2$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^2$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^2$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^1$ and $R^2$ are optionally cyclically linked to form a 5 or 6-membered cycloalkyl or heterocyclyl ring. In certain embodiments, $R^1$ and $R^2$ are cyclically linked to form a 5 or 6-membered cycloalkyl. In certain embodiments, $R^1$ and $R^2$ are cyclically linked to form a 5 or 6-membered heterocyclyl. In certain embodiments, $R^1$ and $R^2$ are cyclically linked to form a 5-membered cycloalkyl. In certain embodiments, $R^1$ and $R^2$ are cyclically linked to form a 6-membered cycloalkyl. In certain embodiments, $R^1$ and $R^2$ are cyclically linked to form a 5-membered heterocyclyl. In certain embodiments, $R^1$ and $R^2$ are cyclically linked to form a 6-membered heterocyclyl.

In certain embodiments, $R^3$ and $R^4$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^3$ and $R^4$ are optionally cyclically linked to form a 5 or 6-membered cycloalkyl or heterocyclyl ring.

In certain embodiments, $R^3$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl. In certain embodiments, $R^3$ is hydrogen. In certain embodiments, $R^3$ is halogen (e.g., F, Cl, Br, I). In certain embodiments, $R^3$ is hydroxy. In certain embodiments, $R^3$ is amino or substituted amino. In certain embodiments, $R^3$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^3$ is methyl. In certain embodiments, $R^3$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^3$ is alkynyl or substituted alkynyl. In certain embodiments, $R^3$ is alkoxy or substituted alkoxy. In certain embodiments, $R^3$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^3$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^3$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^3$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^4$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl. In certain embodiments, $R^4$ is hydrogen. In certain embodiments, $R^4$ is halogen (e.g., F, Cl, Br, I). In certain embodiments, $R^4$ is hydroxy. In certain embodiments, $R^4$ is amino or substituted amino. In certain embodiments, $R^4$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^4$ is methyl. In certain embodiments, $R^4$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^4$ is alkynyl or substituted alkynyl. In certain embodiments, $R^4$ is alkoxy or substituted alkoxy. In certain embodiments, $R^4$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^4$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^4$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-8}$ substituted cycloalkyl. In certain embodiments, $R^4$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^3$ and $R^4$ are optionally cyclically linked to form a 5 or 6-membered cycloalkyl or heterocyclyl ring. In certain embodiments, $R^3$ and $R^4$ are cyclically linked to form a 5 or 6-membered cycloalkyl. In certain embodiments, $R^3$ and $R^4$ are cyclically linked to form a 5 or 6-membered heterocyclyl. In certain embodiments, $R^3$ and $R^4$ are cyclically linked to form a 5-membered cycloalkyl. In certain embodiments, $R^3$ and $R^4$ are cyclically linked to form a 6-membered cycloalkyl. In certain embodiments, $R^3$ and $R^4$ are cyclically linked to form a 5-membered heterocyclyl. In certain embodiments, $R^3$ and $R^4$ are cyclically linked to form a 6-membered heterocyclyl.

In certain embodiments, $R^5$ is selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl. In certain embodiments, $R^5$ is hydrogen. In certain embodiments, $R^5$ is halogen (e.g., F, Cl, Br, I). In certain embodiments, $R^5$ is hydroxy. In certain embodiments, $R^5$ is amino or substituted amino. In certain embodiments, $R^5$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^5$ is methyl. In certain embodiments, $R^5$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^5$ is alkynyl or substituted alkynyl. In certain embodiments, $R^5$ is alkoxy or substituted alkoxy. In certain embodiments, $R^5$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^5$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^5$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^5$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, $R^6$ is selected from OH and $OC(O)R^{11}$. In certain embodiments, $R^6$ is OH. In certain embodiments, $R^6$ is $OC(O)R^{11}$.

In certain embodiments, $R^{11}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl. In certain embodiments, $R^{11}$ is hydrogen. In certain embodiments, $R^{11}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{11}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{11}$ is alkynyl or substituted alkynyl. In certain embodiments, $R^{11}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{11}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{11}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{11}$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl.

In certain embodiments, the compound of formula (II) has the structure of formula (IIa):

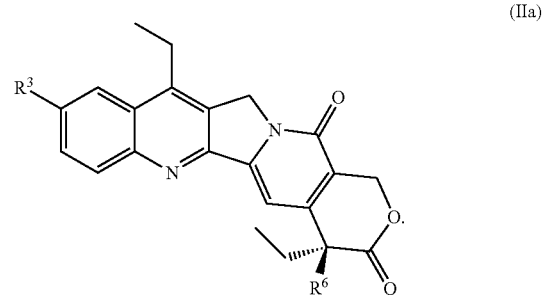

(IIa)

In certain embodiments of the compound of formula (IIa), $R^3$ is as described above.

In certain embodiments of the compound of formula (IIa), $R^6$ is as described above.

In certain embodiments of the compound of formula (IIa), $R^3$ is OH and L is attached at $R^6$. In certain embodiments of the compound of formula (IIa), L is attached at $R^3$ and $R^6$ is OH.

In certain embodiments, the compound of formula (II) has the structure of formula (IIb):

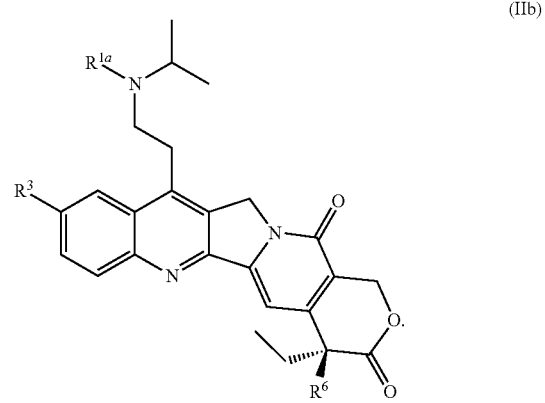

(IIb)

In certain embodiments of the compound of formula (IIb), $R^{1a}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl. In certain embodiments, $R^{1a}$ is hydrogen. In certain embodiments, $R^{1a}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{1a}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{1a}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{1a}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{1a}$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl. In certain embodiments, $R^{1a}$ is carboxyl. In certain embodiments, $R^{1a}$ is carboxyl ester. In certain embodiments, $R^{1a}$ is acyl. In certain embodiments, $R^{1a}$ is sulfonyl.

In certain embodiments of the compound of formula (IIb), $R^6$ is as described above.

In certain embodiments of the compound of formula (IIb), $R^{1a}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$. In certain embodiments of the compound of formula (IIb), L is attached at $R^{1a}$ and $R^6$ is OH.

In certain embodiments, the compound of formula (II) has the structure of formula (IIc):

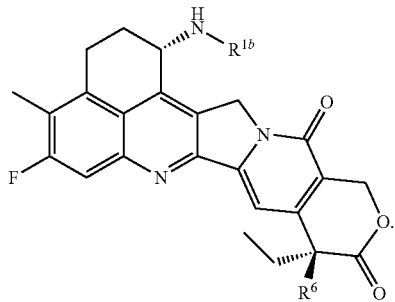

(IIc)

In certain embodiments of the compound of formula (IIc), $R^{1b}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl. In certain embodiments, $R^{1b}$ is hydrogen. In certain embodiments, $R^{1b}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{1b}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{1b}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{1b}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{1b}$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl. In certain embodiments, $R^{1b}$ is carboxyl. In certain embodiments, $R^{1b}$ is carboxyl ester. In certain embodiments, $R^{1b}$ is acyl. In certain embodiments, $R^{1b}$ is sulfonyl.

In certain embodiments of the compound of formula (IIc), $R^6$ is as described above.

In certain embodiments of the compound of formula (IIc), $R^{1b}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$. In certain embodiments of the compound of formula (IIc), L is attached at $R^{1b}$ and $R^6$ is OH.

In certain embodiments, the compound of formula (II) has the structure of formula (IId):

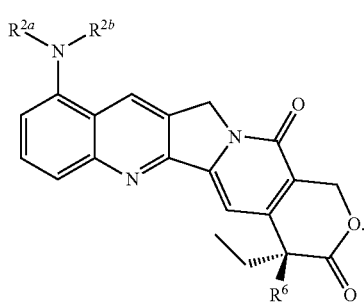

(IId)

In certain embodiments of the compound of formula (IId), $R^{2a}$ and $R^{2b}$ are each independently selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl.

In certain embodiments of the compound of formula (IId), $R^{2a}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl. In certain embodiments, $R^{2a}$ is hydrogen. In certain embodiments, $R^{2a}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{2a}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{2a}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{2a}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{2a}$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl. In certain embodiments, $R^{2a}$ is carboxyl. In certain embodiments, $R^{2a}$ is carboxyl ester. In certain embodiments, $R^{2a}$ is acyl. In certain embodiments, $R^{2a}$ is sulfonyl.

In certain embodiments of the compound of formula (IId), $R^{2b}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl. In certain embodiments, $R^{2b}$ is hydrogen. In certain embodiments, $R^{2b}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{2b}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{2b}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{2b}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{2b}$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl. In certain embodiments, $R^{2b}$ is carboxyl. In certain embodiments, $R^{2b}$ is carboxyl ester. In certain embodiments, $R^{2b}$ is acyl. In certain embodiments, $R^{2b}$ is sulfonyl.

In certain embodiments of the compound of formula (IId), $R^6$ is as described above.

In certain embodiments of the compound of formula (IId), $R^{2a}$ and $R^{2b}$ are each independently selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$. In certain embodiments of the compound of formula (IId), L is attached at $R^{2a}$ or $R^{2b}$ and $R^6$ is OH. In certain embodiments of the compound of formula (IId), L is attached at $R^{2a}$ and $R^6$ is OH. In certain embodiments of the compound of formula (IId), L is attached at $R^{2b}$ and $R^6$ is OH.

In certain embodiments, the compound of formula (II) has the structure of formula (IIe):

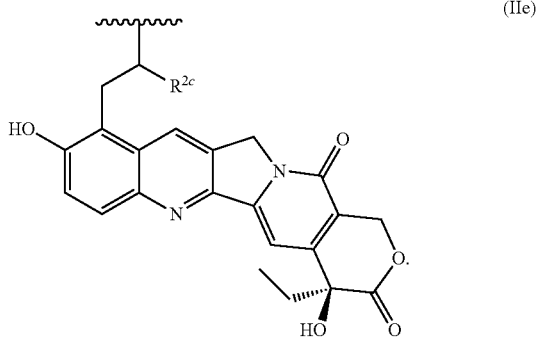

(IIe)

In certain embodiments of the compound of formula (IIe), $R^{2c}$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and attachment to L is indicated by the wavy line.

In certain embodiments, $R^{2c}$ is alkyl or substituted alkyl, such as $C_{1-6}$ alkyl or $C_{1-6}$ substituted alkyl, or $C_{1-4}$ alkyl or $C_{1-4}$ substituted alkyl, or $C_{1-3}$ alkyl or $C_{1-3}$ substituted alkyl. In certain embodiments, $R^{2c}$ is alkenyl or substituted alkenyl, such as $C_{2-6}$ alkenyl or $C_{2-6}$ substituted alkenyl, or $C_{2-4}$ alkenyl or $C_{2-4}$ substituted alkenyl, or $C_{2-3}$ alkenyl or $C_{2-3}$ substituted alkenyl. In certain embodiments, $R^{2c}$ is alkynyl or substituted alkynyl, such as $C_{2-6}$ alkynyl or $C_{2-6}$ substituted alkynyl, or $C_{2-4}$ alkynyl or $C_{2-4}$ substituted alkynyl, or $C_{2-3}$ alkynyl or $C_{2-3}$ substituted alkynyl. In certain embodiments, $R^{2c}$ is aryl or substituted aryl, such as $C_{5-8}$ aryl or $C_{5-8}$ substituted aryl, such as a $C_5$ aryl or $C_5$ substituted aryl, or a $C_6$ aryl or $C_6$ substituted aryl. In certain embodiments, $R^{2c}$ is heteroaryl or substituted heteroaryl, such as $C_{5-8}$ heteroaryl or $C_{5-8}$ substituted heteroaryl, such as a $C_5$ heteroaryl or $C_5$ substituted heteroaryl, or a $C_6$ heteroaryl or $C_6$ substituted heteroaryl. In certain embodiments, $R^{2c}$ is cycloalkyl or substituted cycloalkyl, such as $C_{3-8}$ cycloalkyl or $C_{3-8}$ substituted cycloalkyl, such as a $C_{3-6}$ cycloalkyl or $C_{3-6}$ substituted cycloalkyl, or a $C_{3-5}$ cycloalkyl or $C_{3-5}$ substituted cycloalkyl. In certain embodiments, $R^{2c}$ is heterocyclyl or substituted heterocyclyl, such as a $C_{3-6}$ heterocyclyl or $C_{3-6}$ substituted heterocyclyl, or a $C_{3-5}$ heterocyclyl or $C_{3-5}$ substituted heterocyclyl. In certain embodiments, $R^{2c}$ is carboxyl. In certain embodiments, $R^{2c}$ is carboxyl ester. In certain embodiments, $R^{2c}$ is acyl. In certain embodiments, $R^{2c}$ is sulfonyl.

In certain embodiments of the compound of formula (IIe), attachment to L is indicated by the wavy line. Stated another way, the bond with the wavy line indicates the bond that attaches the compound of formula (IIe) to the linker.

In certain embodiments of the conjugate of formula (I), the polypeptide (e.g., antibody) can be linked to one drug or active agent through the conjugation moiety. In some instances, the polypeptide (e.g., antibody) can be linked to more than one drug or active agent through the conjugation moiety. For example, the conjugation moiety can be linked to two or more drugs or active agents. Each drug or active agent can be linked via a corresponding linker to the same conjugation moiety, which in turn can be attached to a polypeptide (e.g., antibody) as described herein, thus linking the polypeptide (e.g., antibody) to two or more drugs or active agents.

For example, in certain embodiments of the conjugate of formula (I), one or more $R^{10}$ is optionally linked to a second compound of formula (II). In some cases, one or more $R^{10}$ is linked to a second compound of formula (II). In other cases, $R^{10}$ is not linked to a second compound of formula (II). For example, at least one $R^{10}$ is optionally linked to a second compound of formula (II). In some instances, one $R^{10}$ is linked to a second compound of formula (II).

In certain embodiments, one $R^{10}$ is linked via a second linker, $L^2$, to a second compound of formula (II). In certain embodiments, the second linker $L^2$ is a linker (e.g., a second linker) described by the formula:

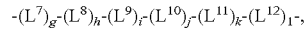

wherein $L^7$, $L^8$, $L^9$, $L^{10}$, $L^{11}$ and $L^{12}$ are each independently a linker subunit, and g, h, i, j, k and l are each independently 0 or 1, wherein the sum of g, h, i, j, k and l is 1 to 6.

In certain embodiments, the sum of g, h, i, j, k and l is 1. In certain embodiments, the sum of g, h, i, j, k and l is 2. In certain embodiments, the sum of g, h, i, j, k and l is 3. In certain embodiments, the sum of g, h, i, j, k and l is 4. In certain embodiments, the sum of g, h, i, j, k and l is 5. In certain embodiments, the sum of g, h, i, j, k and l is 6. In certain embodiments, g, h, i, j, k and l are each 1. In certain embodiments, g, h, i, j and k are each 1 and l is 0. In certain embodiments, g, h, i and j are each 1 and k and l are each 0. In certain embodiments, g, h, and i are each 1 and j, k and l are each 0. In certain embodiments, g and h are each 1 and i, j, k and l are each 0. In certain embodiments, g is 1 and h, i, j, k and l are each 0.

In certain embodiments, the linker subunit $L^7$ is attached to the hydrazinyl-indolyl or the hydrazinyl-pyrrolo-pyridinyl conjugation moiety (e.g., as shown in formula (I) above). In certain embodiments, the linker subunit $L^8$, if present, is attached to the camptothecine or camptothecine derivative. In certain embodiments, the linker subunit $L^9$, if present, is attached to the camptothecine or camptothecine derivative. In certain embodiments, the linker subunit $L^{10}$, if present, is attached to the camptothecine or camptothecine derivative. In certain embodiments, the linker subunit $L^{11}$, if present, is attached to the camptothecine or camptothecine derivative.

In certain embodiments, the linker subunit $L^{12}$, if present, is attached to the camptothecine or camptothecine derivative.

Any convenient linker subunits may be utilized in the second linker $L^B$. For example, any of the linker subunits described above in relation to $L^1$, $L^2$, $L^3$, $L^4$, $L^5$ and $L^6$ may be used for the linker subunits $L^7$, $L^8$, $L^9$, $L^{10}$, $L^{11}$ and $L^{12}$.

In certain embodiments, the second linker $L^B$ is a linker comprising -($L^7$)$_g$-($L^8$)$_h$-($L^9$)$_i$-($L^{10}$)$_j$-($L^{11}$)$_k$-($L^{12}$)$_l$-, where:
-($L^7$)$_g$- is -($T^7$-$V^7$)$_g$-;
-($L^8$)$_h$- is -($T^8$-$V^8$)$_h$-;
-($L^9$)$_i$- is -($T^9$-$V^9$)$_i$-;
-($L^{10}$)$_j$- is -($T^{10}$-$V^{10}$)$_j$-;
-($L^{11}$)$_k$- is -($T^{11}$-$V^{11}$)$_k$-; and
-($L^{12}$)$_l$- is -($T^{12}$-$V^{12}$)$_l$-,
wherein $T^7$, $T^8$, $T^9$, $T^{10}$, $T^{11}$ and $T^{12}$, if present, are tether groups;

$V^7$, $V^8$, $V^9$, $V^{10}$, $V^{11}$ and $V^{12}$, if present, are covalent bonds or linking functional groups; and g, h, i, j, k and l are each independently 0 or 1, wherein the sum of g, h, i, j, k and l is 1 to 6.

Accordingly, in certain embodiments, the second linker $L^B$ comprises:

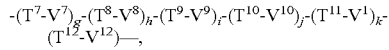

wherein
g, h, i, j, k and l are each independently 0 or 1;
$T^7$, $T^8$, $T^9$, $T^{10}$, $T^{11}$ and $T^{12}$ are each independently selected from a covalent bond, $(C_1$-$C_{12})$alkyl, substituted $(C_1$-$C_{12})$alkyl, aryl, substituted aryl, heteroaryl, substituted heteroaryl, cycloalkyl, substituted cycloalkyl, heterocyclyl, and substituted heterocyclyl, (EDA)$_w$, (PEG)$_n$, (AA)$_p$, —(CR$^{13}$OH)$_m$—, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;

$V^7$, $V^8$, $V^9$, $V^{10}$, $V^{11}$ and $V^{12}$ are each independently selected from the group consisting of a covalent bond, —CO—, —NR$^{15}$—, —NR$^{15}$(CH2)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein each q is an integer from 1 to 6;

each $R^{13}$ is independently selected from hydrogen, alkyl, substituted alkyl, aryl, and substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

Any convenient tether groups may be utilized for $T^7$, $T^8$, $T^9$, $T^{10}$, $T^{11}$ and $T^{12}$. For example, any of the tether groups described above in relation to $T^1$, $T^2$, $T^3$, $T^4$, $T^5$ and $T^6$ may be used for the tether groups $T^7$, $T^8$, $T^9$, $T^{10}$, $T^{11}$ and $T^{12}$.

Any convenient linking functional groups may be utilized for $V^7$, $V^8$, $V^9$, $V^{10}$, $V^{11}$ and $V^{12}$. For example, any of the linking functional groups described above in relation to $V^1$, $V^2$, $V^3$, $V^4$, $V^5$ and $V^6$ may be used for the linking functional groups $V^7$, $V^8$, $V^9$, $V^{10}$, $V^{11}$ and $V^{12}$.

In certain embodiments, each $R^{13}$ is independently selected from hydrogen, alkyl, substituted alkyl, aryl, and substituted aryl. In these embodiments, alkyl, substituted alkyl, aryl, and substituted aryl are as described above for $R^{13}$.

In certain embodiments, each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl. In these embodiments, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl are as described above for $R^{15}$. In these embodiments, various possible substituents are as described above for $R^{15}$.

In certain embodiments of the second linker $L^B$, one or more of the tether groups $T^7$, $T^8$, $T^9$, $T^{10}$, $T^{11}$ and $T^{12}$ is each optionally substituted with a glycoside or glycoside derivative. In certain embodiments, the glycoside or glycoside derivative is selected from a glucuronide, a galactoside, a glucoside, a mannoside, a fucoside, O-GlcNAc, and O-GalNAc.

In certain embodiments of the second linker $L^B$, the MABO, MABC, PABO, PABC, PAB, PABA, PAP, and PHP tether structures shown above may be substituted with an one or more additional groups selected from a glycoside and a glycoside derivative. For example, in some embodiments of the MABO, MABC, PABO, PABC, PAB, PABA, PAP, and PHP tether structures shown above, the phenyl ring may be substituted with one or more additional groups selected from a glycoside and a glycoside derivative. In certain embodiments, the glycoside or glycoside derivative is selected from a glucuronide, a galactoside, a glucoside, a mannoside, a fucoside, O-GlcNAc, and O-GalNAc.

In certain embodiments, $T^7$, $T^8$, $T^9$, $T^{10}$, $T^{11}$ and $T^{12}$ and $V^7$, $V^8$, $V^9$, $V^{10}$, $V^{11}$ and $V^{12}$ are selected from the following:
wherein:
$T^7$ is absent and $V^7$ is —NR$^{15}$CO—;
$T^8$ is $(C_1$-$C_{12})$alkyl and $V^8$ is —CO—;
$T^9$ is AA and $V^9$ is absent;
$T^{10}$ is PABC and $V^{10}$ is absent;
$T^{11}$ is EDA and $V^{11}$ is —CO—; and
l is 0; or
wherein:
$T^7$ is absent and $V^7$ is —NR$^{15}$CO—;
$T^8$ is $(C_1$-$C_{12})$alkyl and $V^8$ is —CO—;
$T^9$ is AA and $V^9$ is absent;
$T^{10}$ is PABC and $V^{10}$ is absent; and
k and l are each 0; or
wherein:
$T^7$ is absent and $V^7$ is —NHCO—;
$T^8$ is $(C_1$-$C_{12})$alkyl and $V^8$ is —CO—;
$T^9$ is an amino acid analog and $V^9$ is —NH—;
$T^{10}$ is (PEG)$_n$ and $V^{10}$ is —CO—;
$T^{11}$ is AA and $V^{11}$ is absent; and
$T^{12}$ is PABC and $V^{12}$ is absent; or
wherein:
$T^7$ is absent and $V^7$ is —NHCO—;
$T^8$ is $(C_1$-$C_{12})$alkyl and $V^8$ is —CONH—;
$T^9$ is (PEG)$_n$ and $V^9$ is —CO—;
$T^{10}$ is AA and $V^{10}$ is absent;

$T^{11}$ is PABC and $V^{11}$ is absent; and
l is 0; or
wherein:
$T^7$ is $(C_1$-$C_{12})$alkyl and $V^7$ is —CONH—;
$T^8$ is substituted $(C_1$-$C_{12})$alkyl and $V^8$ is —CO—;
$T^9$ is AA and $V^9$ is absent;
$T^{10}$ is PABC and $V^{10}$ is absent;
k and l are each 0; or
wherein:
$T^7$ is $(C_1$-$C_{12})$alkyl and $V^7$ is —CONH—;
$T^8$ is $(PEG)_n$ and $V^8$ is —CO—;
$T^9$ is AA and $V^9$ is absent;
$T^{10}$ is PABC and $V^{10}$ is absent;
$T^{11}$ is $(C_1$-$C_{12})$alkyl and $V^{11}$ is absent;
l is 0; or
wherein:
$T^7$ is $(C_1$-$C_{12})$alkyl and $V^7$ is —CO—;
$T^8$ is 4AP and $V^8$ is —CO—;
$T^9$ is $(C_1$-$C_{12})$alkyl and $V^9$ is —CO—;
$T^{10}$ is AA and $V^{10}$ is absent;
$T^{11}$ is PABC and $V^{11}$ is absent;
l is 0; or
wherein:
$T^7$ is $(C_1$-$C_{12})$alkyl and $V^7$ is —CO—;
$T^8$ is 4AP and $V^8$ is —CO—;
$T^9$ is $(C_1$-$C_{12})$alkyl and $V^9$ is —O—;
$T^{10}$ is $(C_1$-$C_{12})$alkyl and $V^{10}$ is —CO—;
$T^{11}$ is AA and $V^{11}$ is absent;
$T^{12}$ is PABC and $V^{12}$ is absent; or
wherein:
$T^7$ is $(C_1$-$C_{12})$alkyl and $V^7$ is —CO—;
$T^8$ is an amino acid analog and $V^8$ is absent;
$T^9$ is AA and $V^9$ is absent;
$T^{10}$ is PABC and $V^{10}$ is absent;
k and l are each 0; or
wherein:
$T^7$ is $(C_1$-$C_{12})$alkyl and $V^7$ is —CONH—;
$T^8$ is $(PEG)_n$ and $V^8$ is —CONH—;
$T^9$ is substituted $(C_1$-$C_{12})$alkyl and $V^9$ is —CO—;
$T^{10}$ is AA and $V^{10}$ is absent;
$T^{11}$ is PABC and $V^{11}$ is absent;
l is 0; or
wherein:
$T^7$ is $(C_1$-$C_{12})$alkyl and $V^7$ is —CO—;
$T^8$ is AA and $V^8$ is —NH—;
$T^9$ is $(PEG)_n$ and $V^9$ is —CO—;
$T^{10}$ is AA and $V^{10}$ is absent;
$T^{11}$ is PABC and $V^{11}$ is absent;
l is 0; or
wherein:
$T^7$ is $(C_1$-$C_{12})$alkyl and $V^7$ is —CONH—;
$T^8$ is $(PEG)_n$ and $V^8$ is —CO—;
$T^9$ is AA and $V^9$ is absent;
$T^{10}$ is PAP and $V^{10}$ is —COO—; and
k and l are each 0.

In certain embodiments of the second linker $L^B$, the left-hand side of the linker structure is attached to the hydrazinyl-indolyl or the hydrazinyl-pyrrolo-pyridinyl conjugation moiety, and the right-hand side of the linker structure is attached to the camptothecine or a camptothecine derivative. In certain embodiments of the second linker $L^B$, the left-hand side of the linker structure is attached to the hydrazinyl-indolyl or the hydrazinyl-pyrrolo-pyridinyl conjugation moiety through a linking functional group, such as —NHCO—.

In certain embodiments, the conjugate is an antibody-drug conjugate where the antibody and the drug are linked together by a linker (e.g., L or $L^B$), as described above. In some instances, the linker is a cleavable linker. A cleavable linker is a linker that includes one or more cleavable moieties, where the cleavable moiety includes one or more bonds that can dissociate under certain conditions, thus separating the cleavable linker into two or more separatable portions. For example, the cleavable moiety may include one or more covalent bonds, which under certain conditions, can dissociate or break apart to separate the cleavable linker into two or more portions. As such a cleavable linker can be included in an antibody-drug conjugate, such that under appropriate conditions, the cleavable linker is cleaved to separate or release the drug from the antibody at a desired target site of action for the drug.

In some instances, the cleavable linker includes two cleavable moieties, such as a first cleavable moiety and a second cleavable moiety. The cleavable moieties can be configured such that cleavage of both cleavable moieties is needed in order to separate or release the drug from the antibody at a desired target site of action for the drug. For example, cleavage of the cleavable linker can be achieved by initially cleaving one of the two cleavable moieties and then cleaving the other of the two cleavable moieties. In certain embodiments, the cleavable linker includes a first cleavable moiety and a second cleavable moiety that hinders cleavage of the first cleavable moiety. By "hinders cleavage" is meant that the presence of an uncleaved second cleavable moiety reduces the likelihood or substantially inhibits the cleavage of the first cleavable moiety, thus substantially reducing the amount or preventing the cleavage of the cleavable linker. For instance, the presence of uncleaved second cleavable moiety can hinder cleavage of the first cleavable moiety. The hinderance of cleavage of the first cleavable moiety by the presence of the second cleavable moiety, in turn, substantially reduces the amount or prevents the release of the drug from the antibody. For example, the premature release of the drug from the antibody can be substantially reduced or prevented until the antibody-drug conjugate is at or near the desired target site of action for the drug.

In some cases, since the second cleavable moiety hinders cleavage of the first cleavable moiety, cleavage of the cleavable linker can be achieved by initially cleaving the second cleavable moiety and then cleaving the first cleavable moiety. Cleavage of the second cleavable moiety can reduce or eliminate the hinderance on the cleavage of the first cleavable moiety, thus allowing the first cleavable moiety to be cleaved. Cleavage of the first cleavable moiety can result in the cleavable linker dissociating or separating into two or more portions as described above to release the drug from the antibody-drug conjugate. In some instances, cleavage of the first cleavable moiety does not substantially occur in the presence of an uncleaved second cleavable moiety. By substantially is meant that about 10% or less cleavage of the first cleavable moiety occurs in the presence of an uncleaved second cleavable moiety, such as about 9% or less, or about 8% or less, or about 7% or less, or about 6% or less, or about 5% or less, or about 4% or less, or about 3% or less, or about 2% or less, or about 1% or less, or about 0.5% or less, or about 0.1% or less cleavage of the first cleavable moiety occurs in the presence of an uncleaved second cleavable moiety.

Stated another way, the second cleavable moiety can protect the first cleavable moiety from cleavage. For instance, the presence of uncleaved second cleavable moiety can protect the first cleavable moiety from cleavage, and thus substantially reduce or prevent premature release of the drug from the antibody until the antibody-drug conjugate is at or near the desired target site of action for the drug. As such, cleavage of the second cleavable moiety exposes the first cleavable moiety (e.g., deprotects the first cleavable moiety), thus allowing the first cleavable moiety to be cleaved, which results in cleavage of the cleavable linker, which, in turn, separates or releases the drug from the antibody at a desired target site of action for the drug as described above. In certain instances, cleavage of the second cleavable moiety exposes the first cleavable moiety to subsequent cleavage, but cleavage of the second cleavable moiety does not in and of itself result in cleavage of the cleavable linker (i.e., cleavage of the first cleavable moiety is still needed in order to cleave the cleavable linker).

The cleavable moieties included in the cleavable linker may each be an enzymatically cleavable moiety. For example, the first cleavable moiety can be a first enzymatically cleavable moiety and the second cleavable moiety can be a second enzymatically cleavable moiety. An enzymatically cleavable moiety is a cleavable moiety that can be separated into two or more portions as described above through the enzymatic action of an enzyme. The enzymatically cleavable moiety can be any cleavable moiety that can be cleaved through the enzymatic action of an enzyme, such as, but not limited to, a peptide, a glycoside, and the like. In some instances, the enzyme that cleaves the enzymatically cleavable moiety is present at a desired target site of action, such as the desired target site of action of the drug that is to be released from the antibody-drug conjugate. In some cases, the enzyme that cleaves the enzymatically cleavable moiety is not present in a significant amount in other areas, such as in whole blood, plasma or serum. As such, the cleavage of an enzymatically cleavable moiety can be controlled such that substantial cleavage occurs at the desired site of action, whereas cleavage does not significantly occur in other areas or before the antibody-drug conjugate reaches the desired site of action.

For example, as described herein, antibody-drug conjugates of the present disclosure can be used for the treatment of cancer, such as for the delivery of a cancer therapeutic drug to a desired site of action where the cancer cells are present. In some cases, enzymes, such as the protease enzyme cathepsin B, can be a biomarker for cancer that is overexpressed in cancer cells. The overexpression, and thus localization, of certain enzymes in cancer can be used in the context of the enzymatically cleavable moieties included in the cleavable linkers of the antibody-drug conjugates of the present disclosure to specifically release the drug at the desired site of action (i.e., the site of the cancer (and overexpressed enzyme)). Thus, in some embodiments, the enzymatically cleavable moiety is a cleavable moiety (e.g., a peptide) that can be cleaved by an enzyme that is overexpressed in cancer cells. For instance, the enzyme can be the protease enzyme cathepsin B. As such, in some instances, the enzymatically cleavable moiety is a cleavable moiety (e.g., a peptide) that can be cleaved by a protease enzyme, such as cathepsin B.

In certain embodiments, the enzymatically cleavable moiety is a peptide. The peptide can be any peptide suitable for use in the cleavable linker and that can be cleaved through the enzymatic action of an enzyme. Non-limiting examples of peptides that can be used as an enzymatically cleavable moiety include, for example, Val-Ala, Phe-Lys, and the like. For example, the first cleavable moiety described above (i.e., the cleavable moiety protected from premature cleavage by the second cleavable moiety) can include a peptide. The presence of uncleaved second cleavable moiety can protect the first cleavable moiety (peptide) from cleavage by a protease enzyme (e.g., cathepsin B), and thus substantially reduce or prevent premature release of the drug from the antibody until the antibody-drug conjugate is at or near the desired target site of action for the drug. In some instances, one of the amino acid residues of the peptide that comprises the first cleavable moiety is linked to or includes a substituent, where the substituent comprises the second cleavable moiety. In some instances, the second cleavable moiety includes a glycoside.

In some embodiments, the enzymatically cleavable moiety is sugar moiety, such as a glycoside (or glyosyl). In some cases, the glycoside can facilitate an increase in the hydrophilicity of the cleavable linker as compared to a cleavable linker that does not include the glycoside. The glycoside can be any glycoside or glycoside derivative suitable for use in the cleavable linker and that can be cleaved through the enzymatic action of an enzyme. For example, the second cleavable moiety (i.e., the cleavable moiety that protects the first cleavable moiety from premature cleavage) can be a glycoside. For instance, in some embodiments, the first cleavable moiety includes a peptide and the second cleavable moiety includes a glycoside. In certain embodiments, the second cleavable moiety is a glycoside or glycoside derivative selected from a glucuronide, a galactoside, a glucoside, a mannoside, a fucoside, O-GlcNAc, and O-GalNAc. In some instances, the second cleavable moiety is a glucuronide. In some instances, the second cleavable moiety is a galactoside. In some instances, the second cleavable moiety is a glucoside. In some instances, the second cleavable moiety is a mannoside. In some instances, the second cleavable moiety is a fucoside. In some instances, the second cleavable moiety is O-GlcNAc. In some instances, the second cleavable moiety is O-GalNAc.

The glycoside can be attached (covalently bonded) to the cleavable linker through a glycosidic bond. The glycosidic bond can link the glycoside to the cleavable linker through various types of bonds, such as, but not limited to, an O-glycosidic bond (an O-glycoside), an N-glycosidic bond (a glycosylamine), an S-glycosidic bond (a thioglycoside), or C-glycosidic bond (a C-glycoside or C-glycosyl). In some instances, the glycosidic bond is an O-glycosidic bond (an 0-glycoside). In some cases, the glycoside can be cleaved from the cleavable linker it is attached to by an enzyme (e.g., through enzymatically-mediated hydrolysis of the glycosidic bond). A glycoside can be removed or cleaved from the cleavable linker by any convenient enzyme that is able to carry out the cleavage (hydrolysis) of the glycosidic bond that attaches the glycoside to the cleavable linker. An example of an enzyme that can be used to mediate the cleavage (hydrolysis) of the glycosidic bond that attaches the glycoside to the cleavable linker is a glucuronidase, a glycosidase, such as a galactosidase, a glucosidase, a mannosidase, a fucosidase, and the like. Other suitable enzymes may also be used to mediate the cleavage (hydrolysis) of the glycosidic bond that attaches the glycoside to the cleavable linker. In some cases, the enzyme used to mediate the cleavage (hydrolysis) of the glycosidic bond that attaches the glycoside to the cleavable linker is found at or near the desired site of action for the drug of the antibody-drug conjugate. For instance, the enzyme can be a lysosomal enzyme, such as a lysosomal glycosidase, found in cells at or near the desired site of action for the drug of the antibody-drug conjugate. In some cases, the enzyme is an enzyme found at or near the target site where the enzyme that mediates cleavage of the first cleavable moiety is found.

In certain embodiments, the conjugate of formula (I) has a structure selected from the following:

141 142
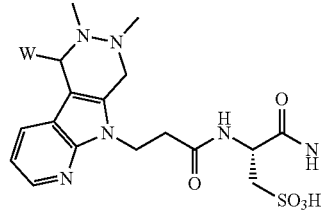
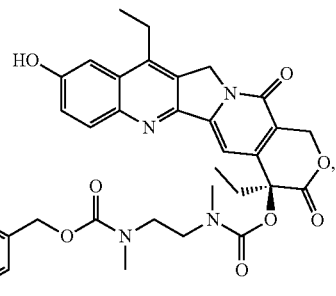
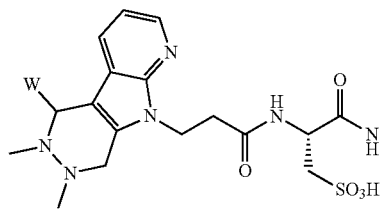
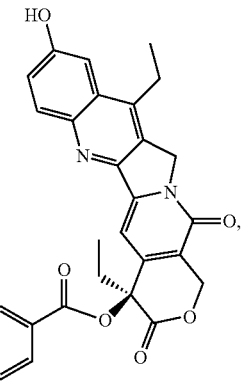
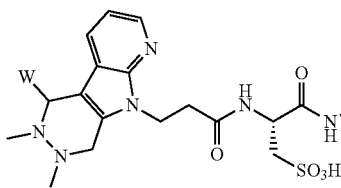
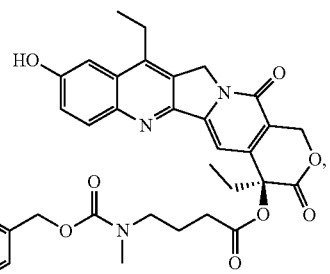
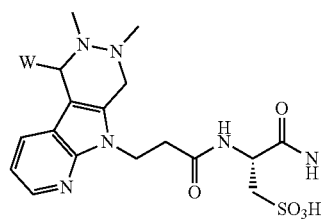
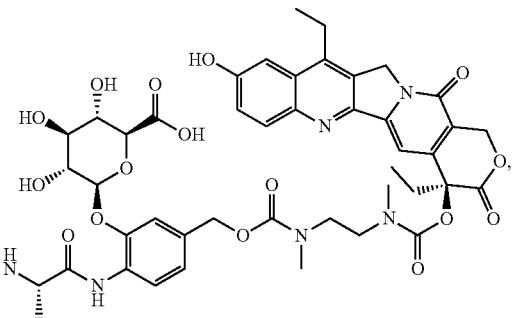

-continued
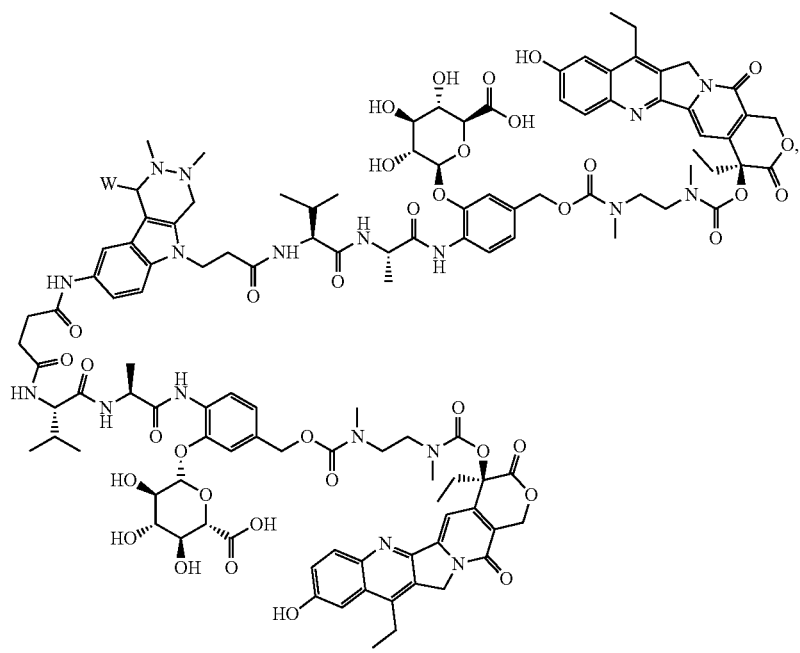
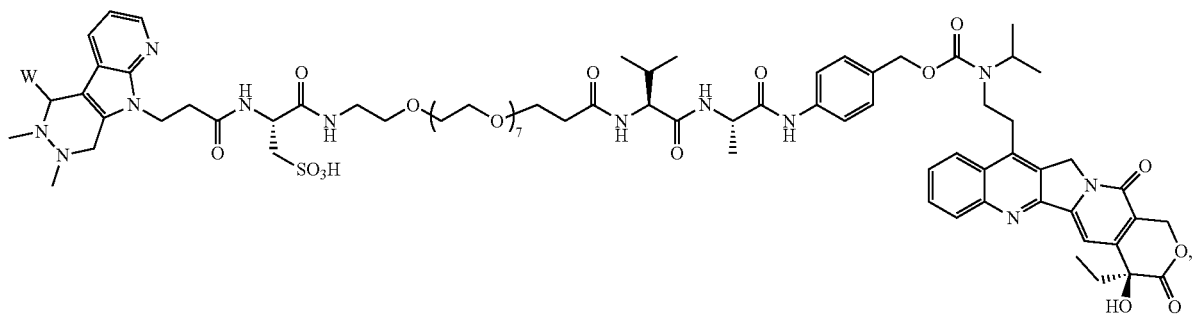
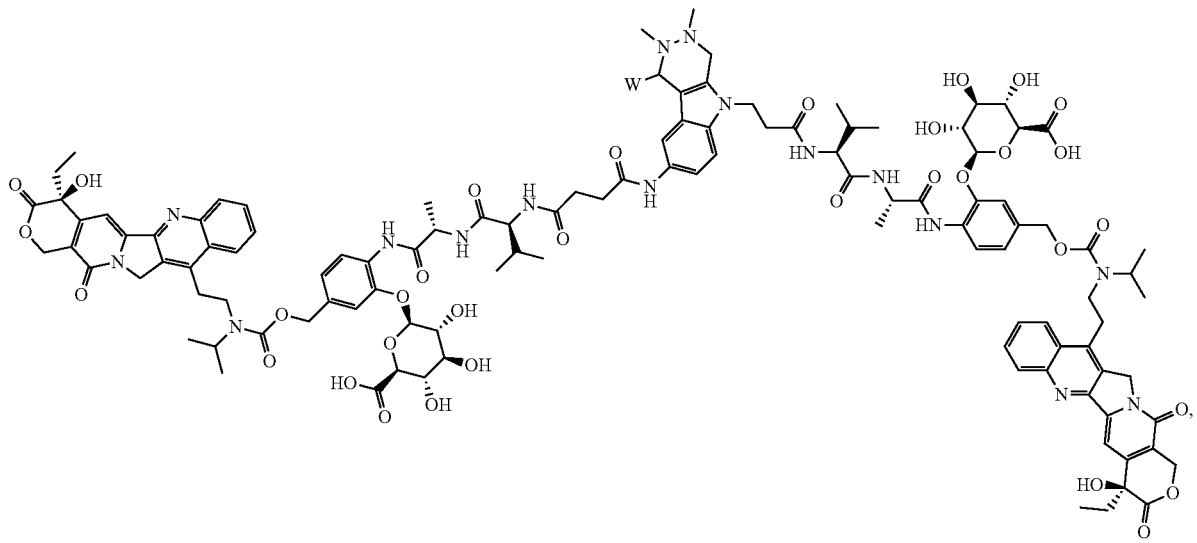

-continued
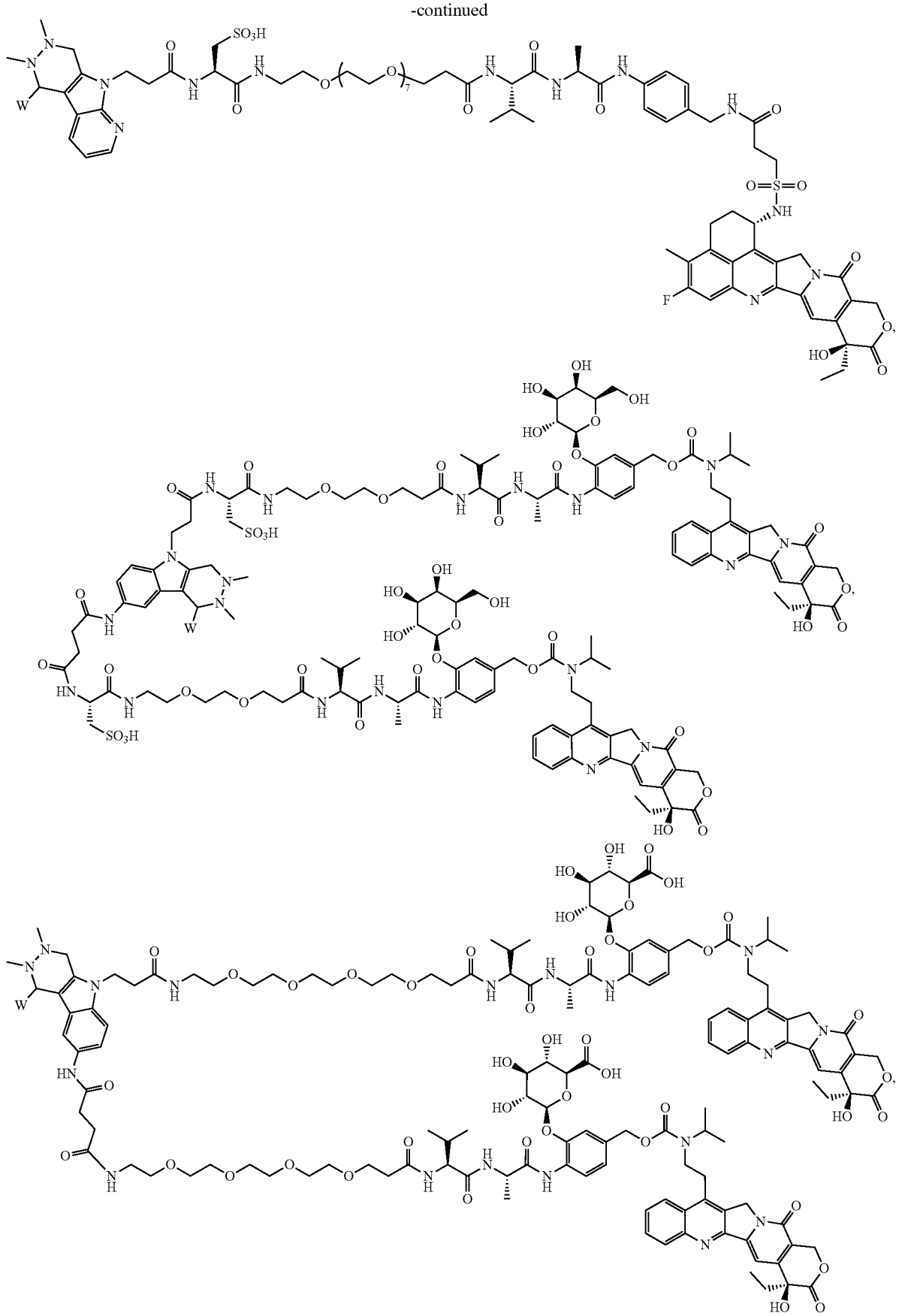

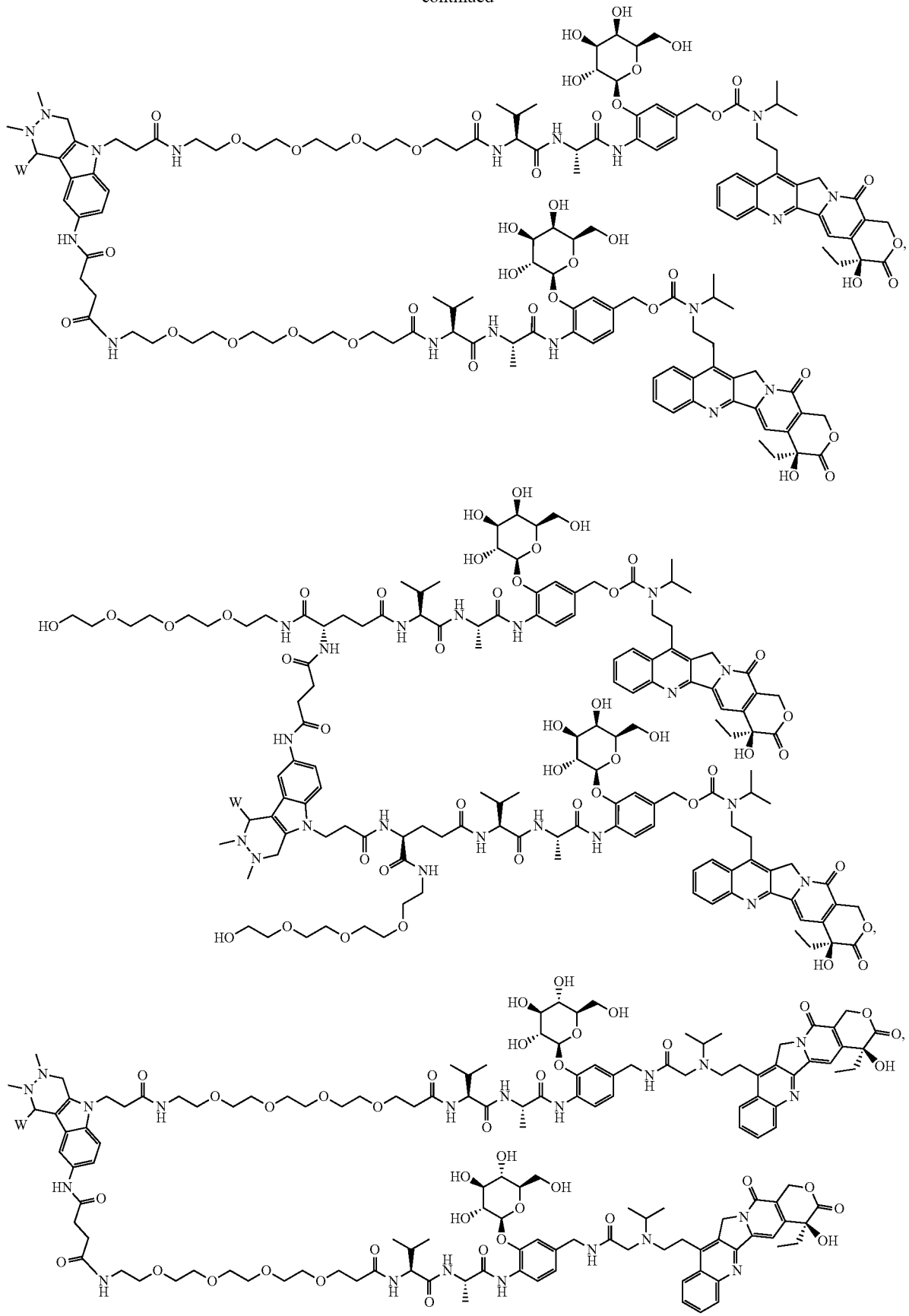

-continued
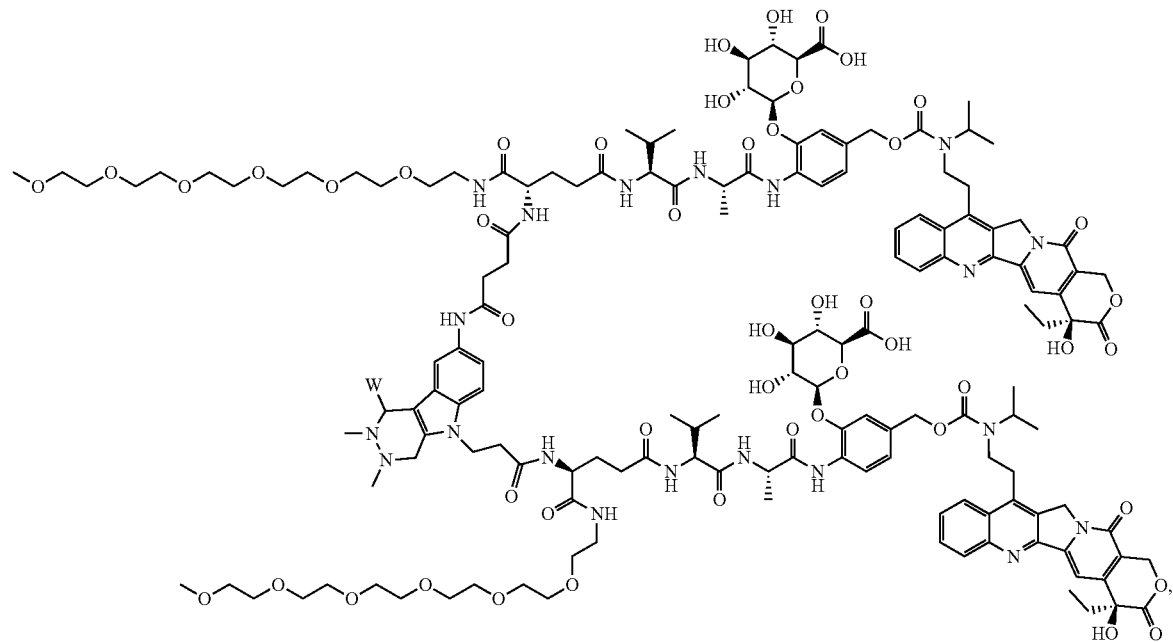
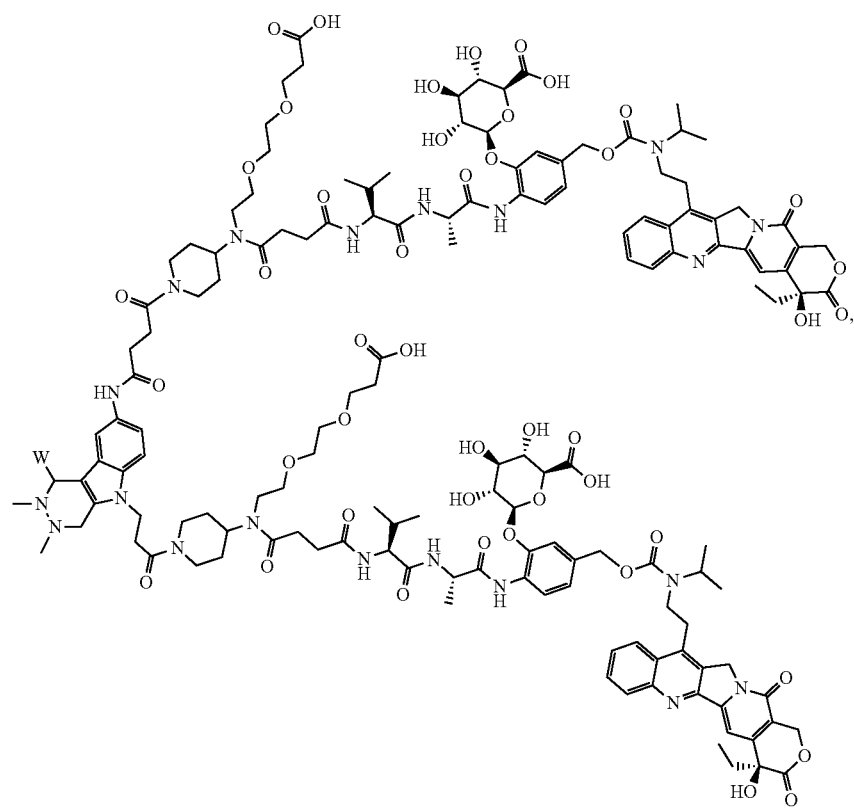

-continued
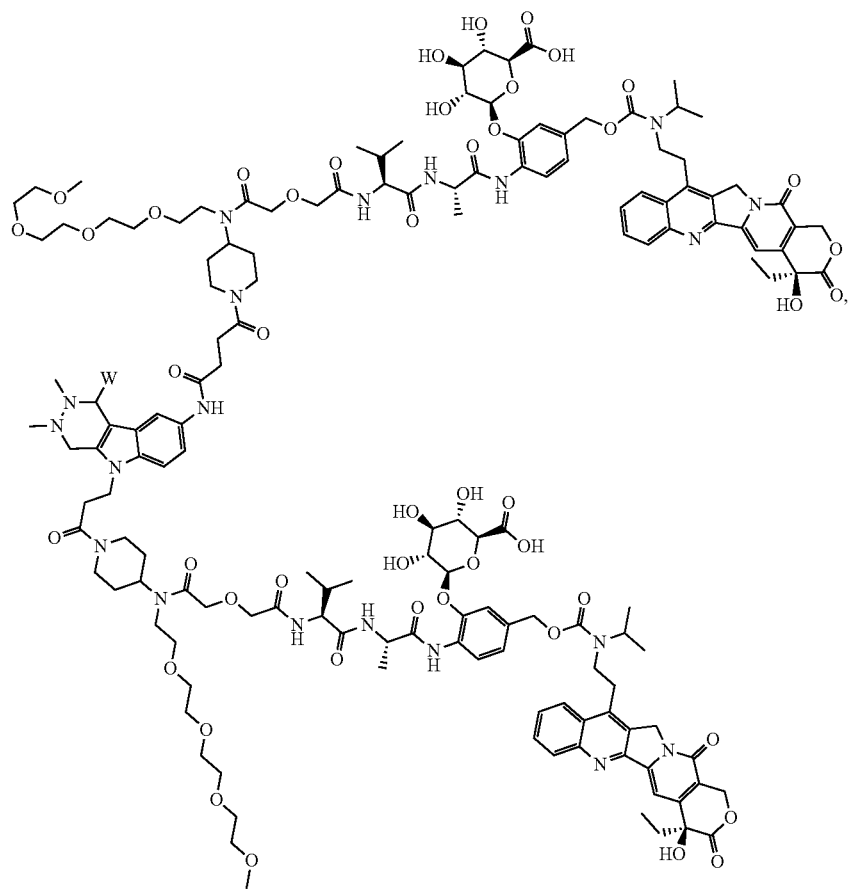
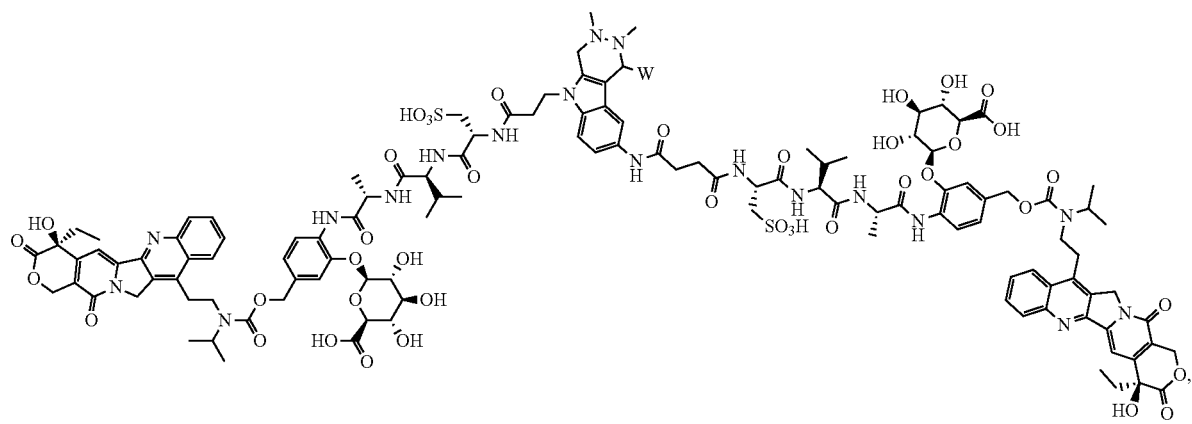

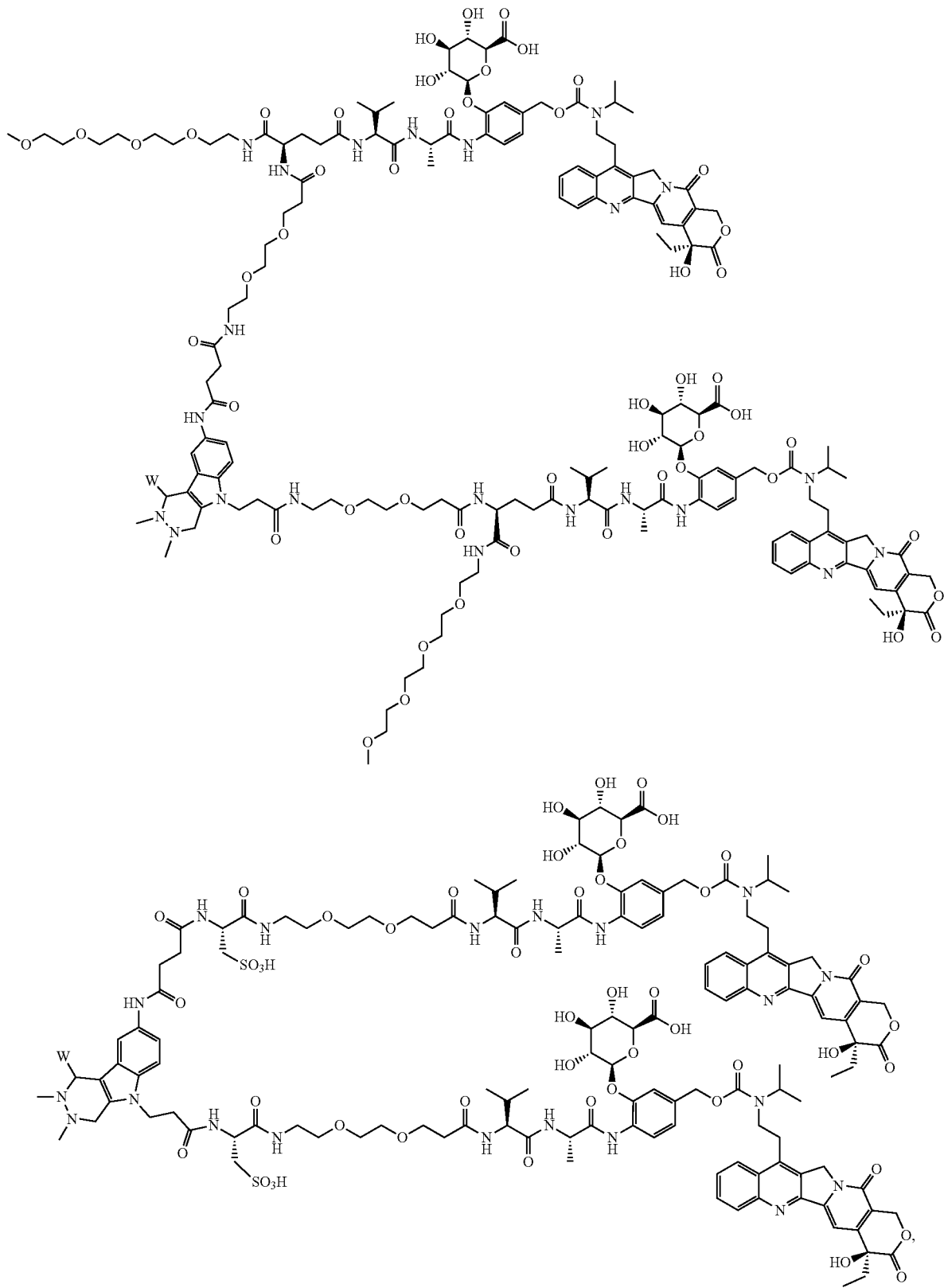

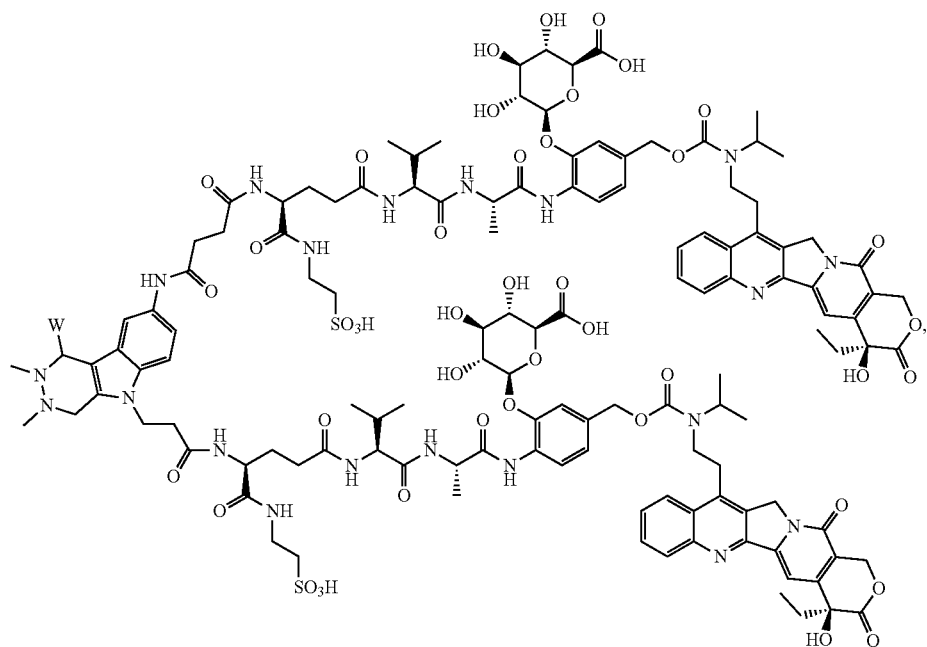
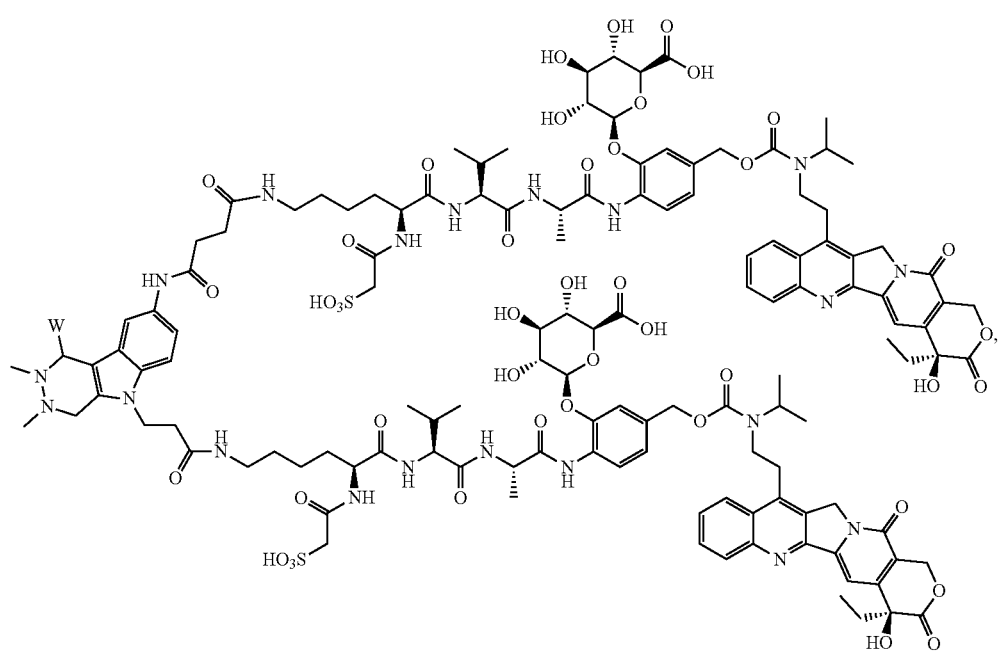

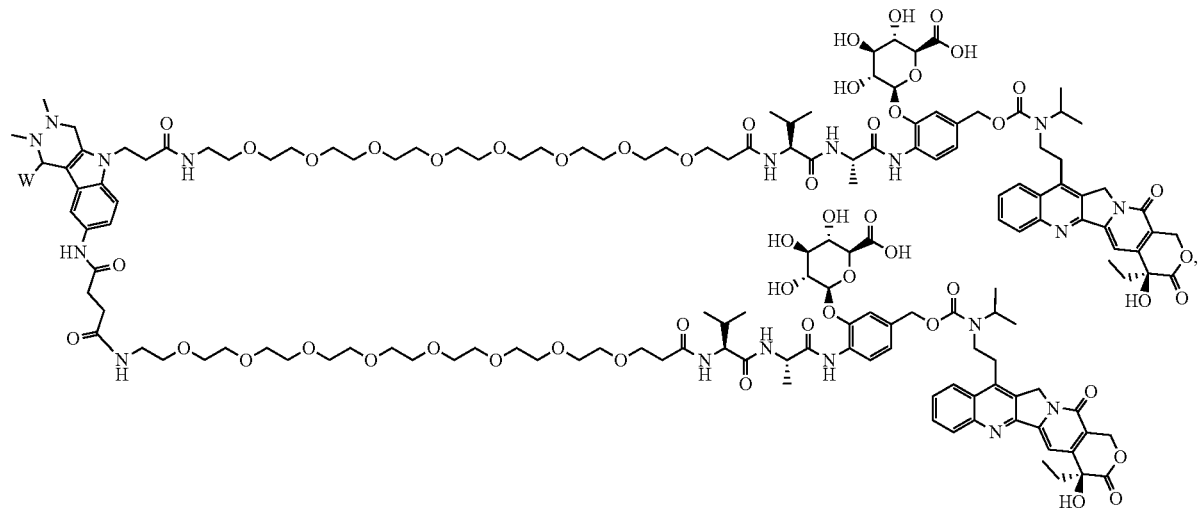
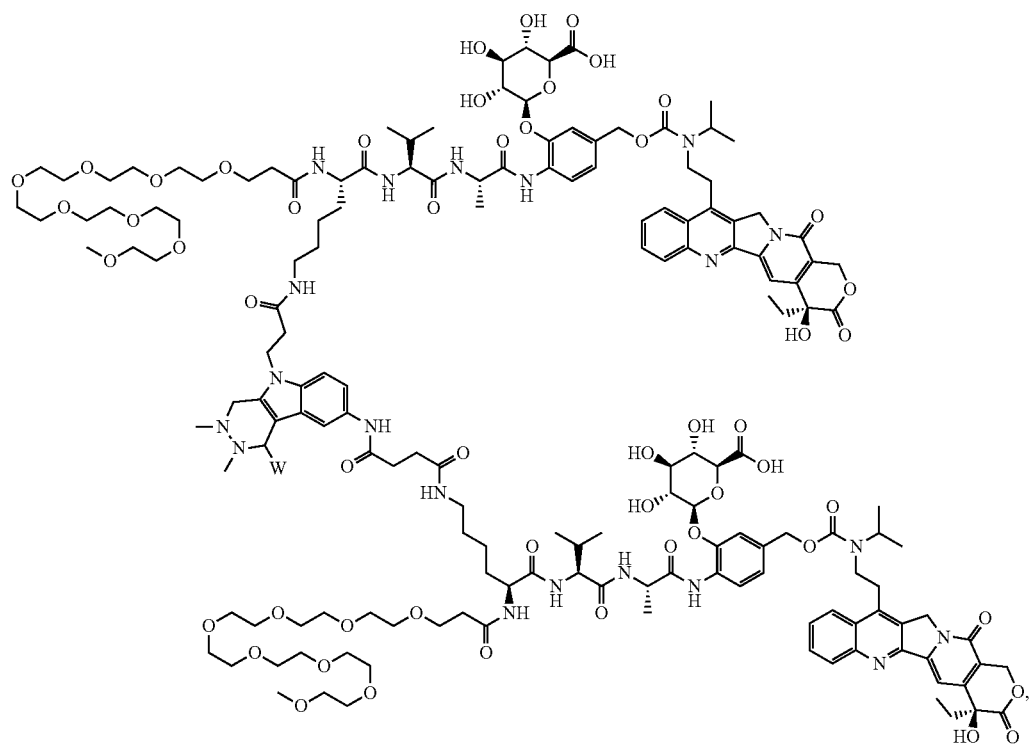

-continued
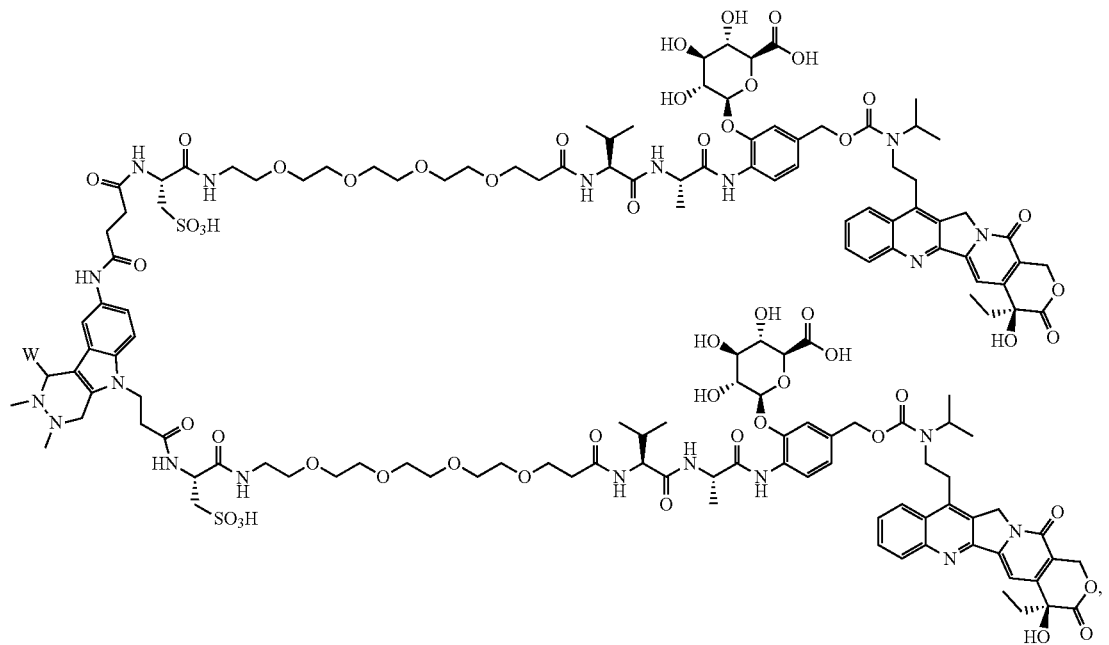
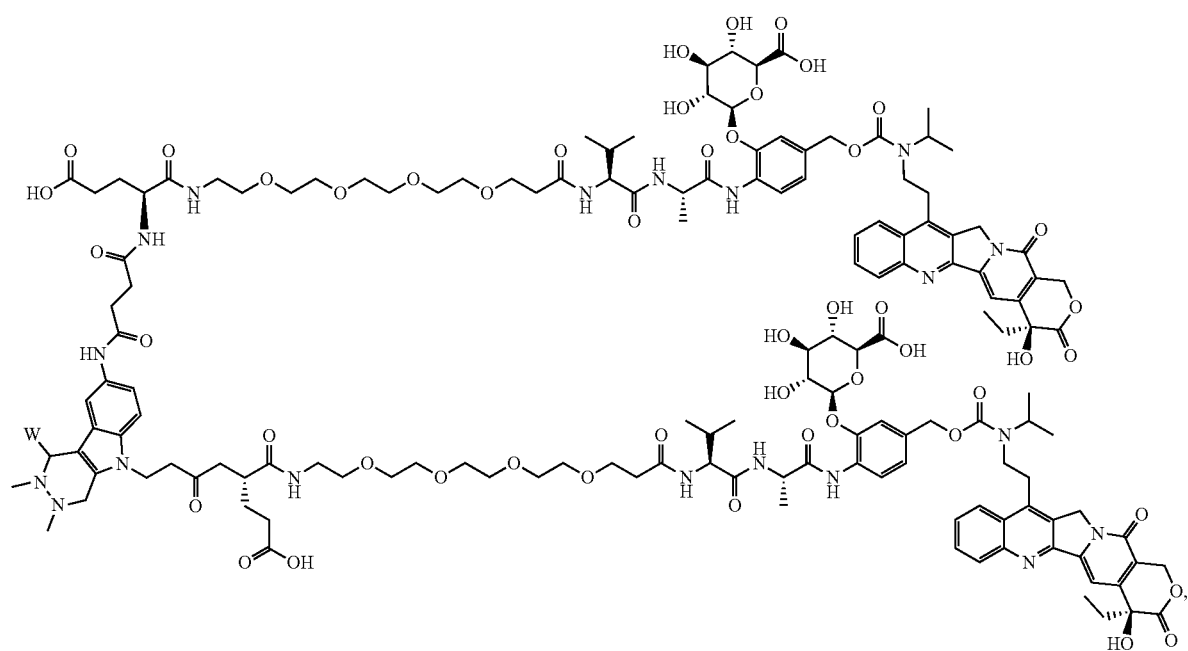

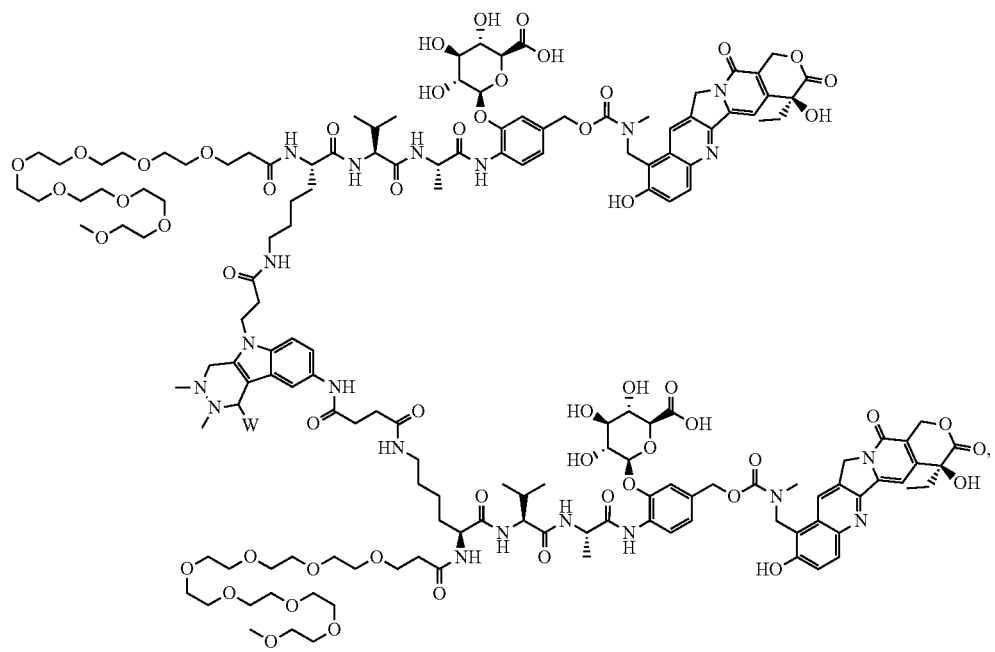
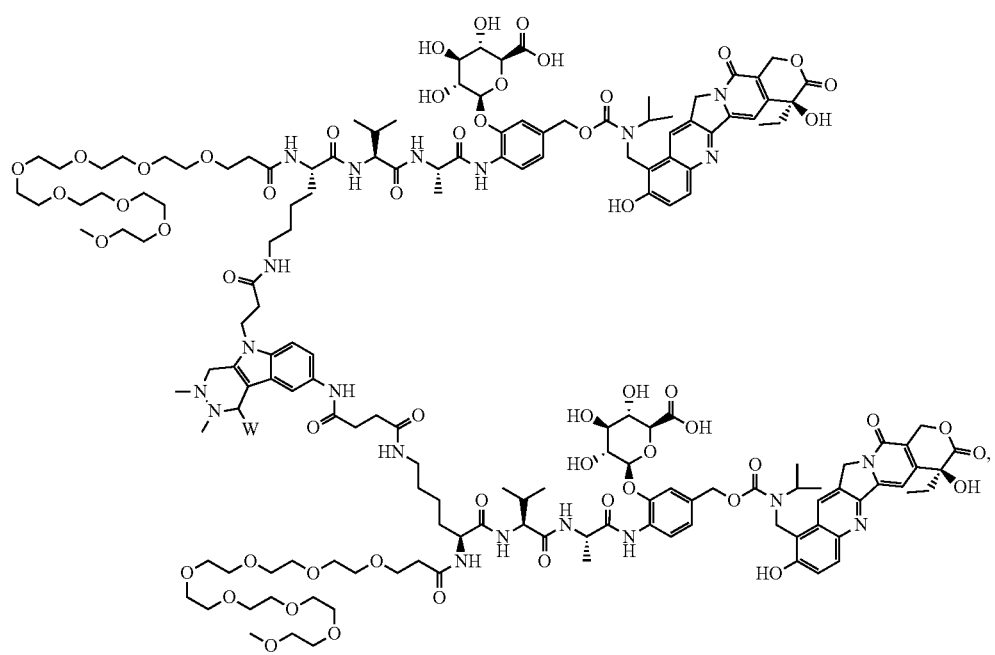

-continued

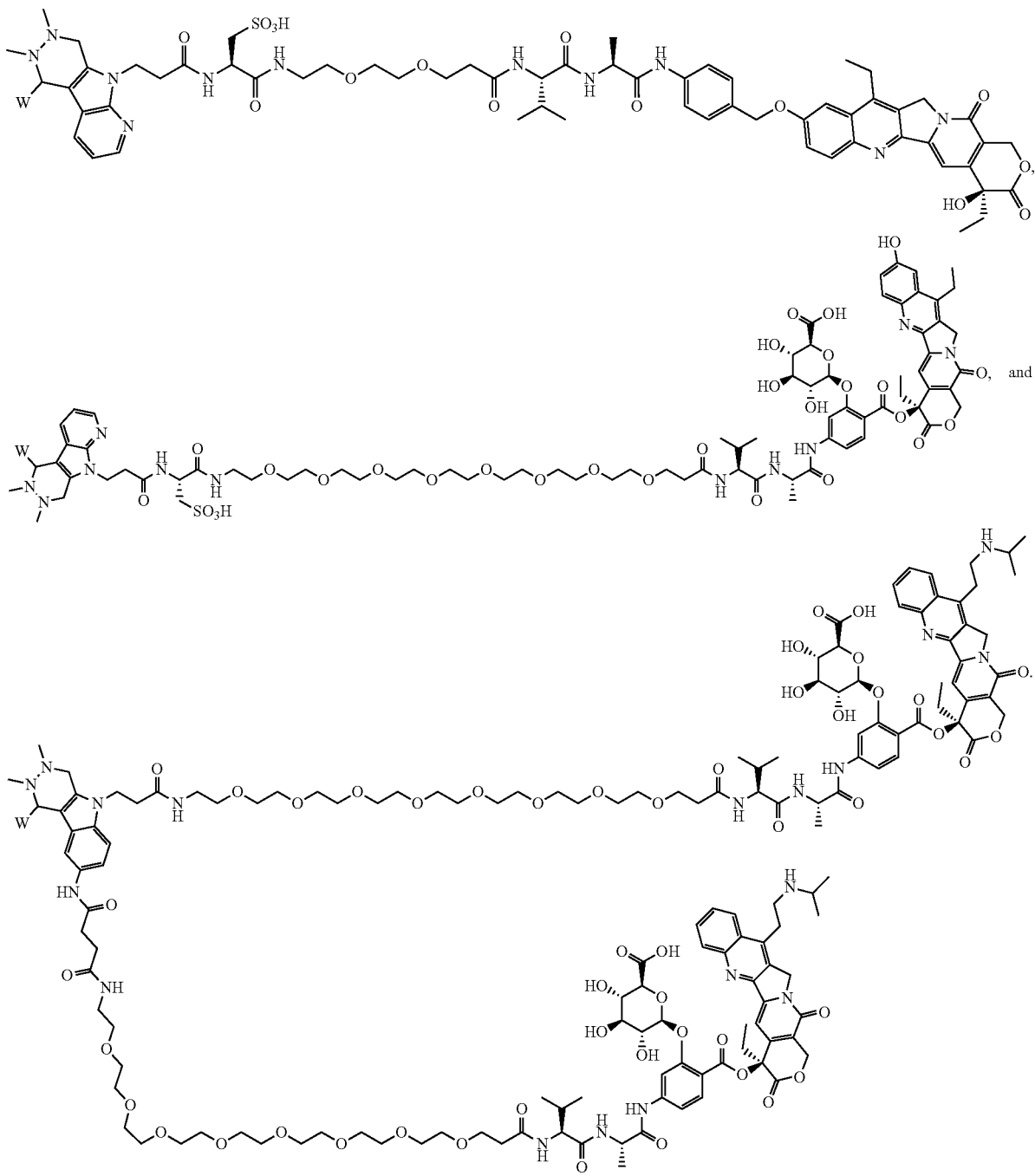

Any of the chemical entities, linkers and coupling moieties set forth in the structures above may be adapted for use in the subject compounds and conjugates.

Additional disclosure related to hydrazinyl-indolyl and hydrazinyl-pyrrolo-pyridinyl compounds and methods for producing a conjugate is found in U.S. Pat. Nos. 9,310,374 and 9,493,413, the disclosures of each of which are incorporated herein by reference. Additional disclosure related to cleavable linkers is found in U.S. Provisional Application No. 63/116,632, filed Nov. 20, 2020, the disclosure of which is incorporated herein by reference.

Compounds Useful for Producing Conjugates

The present disclosure provides hydrazinyl-indolyl and hydrazinyl-pyrrolo-pyridinyl compounds useful for producing the conjugates described herein. In certain embodiments, the hydrazinyl-indolyl or hydrazinyl-pyrrolo-pyridinyl compound may be a conjugation moiety useful for conjugation of a polypeptide (e.g., an antibody) and a drug or active agent (e.g., a camptothecine or a camptothecine derivative). For example, the hydrazinyl-indolyl or hydrazinyl-pyrrolo-pyridinyl compound may be bound to the polypeptide (antibody) and also bound to the drug or active agent, thus indirectly binding the polypeptide (antibody) and the drug together.

In certain embodiments, the compound is a compound of formula (III):

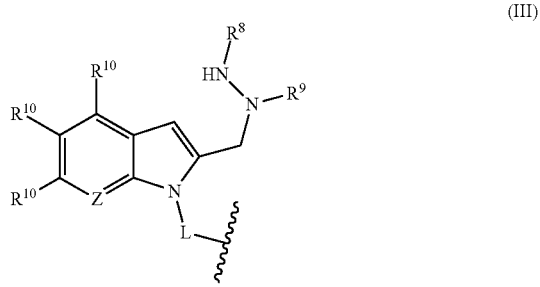

(III)

wherein

Z is $CR^4$ or N;

$R^8$ and $R^9$ are each independently selected from hydrogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl, or $R^8$ and $R^9$ are optionally cyclically linked to form a 5 or 6-membered heterocyclyl;

each $R^{10}$ is independently selected from hydrogen, halogen, alkyl, substituted alkyl, alkenyl, substituted alkenyl, alkynyl, substituted alkynyl, alkoxy, substituted alkoxy, amino, substituted amino, carboxyl, carboxyl ester, acyl, acyloxy, acyl amino, amino acyl, alkylamide, substituted alkylamide, sulfonyl, thioalkoxy, substituted thioalkoxy, aryl, substituted aryl, heteroaryl, substituted heteroaryl, cycloalkyl, substituted cycloalkyl, heterocyclyl, and substituted heterocyclyl;

L is a linker attached to a compound of formula (II) at $R^1$, $R^2$, $R^3$, $R^4$, $R^5$ or $R^6$:

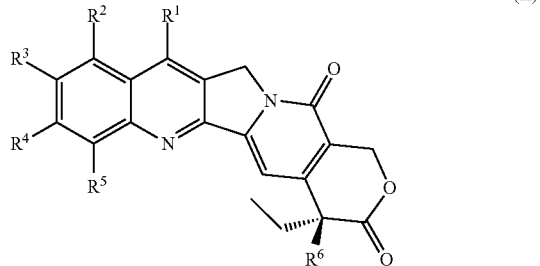

(II)

$R^1$ and $R^2$ are each independently selected from hydrogen, halogen, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^1$ and $R^2$ are optionally cyclically linked to form a 5 or 6-membered cycloalkyl or heterocyclyl ring;

$R^3$ and $R^4$ are each independently selected from hydrogen, halo, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl, or $R^3$ and $R^4$ are optionally cyclically linked to form a 5 or 6-membered cycloalkyl or heterocyclyl ring;

$R^5$ is selected from hydrogen, halo, hydroxy, amino, substituted amino, alkyl, substituted alkyl, alkenyl, substituted alkenyl, alkynyl, substituted alkynyl, alkoxy, substituted alkoxy, aryl, substituted aryl, heteroaryl, substituted heteroaryl, cycloalkyl, substituted cycloalkyl, heterocyclyl, and substituted heterocyclyl;

$R^6$ is selected from OH and $OC(O)R^{11}$; and $R^{11}$ is selected from hydrogen, alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, and substituted heterocyclyl, wherein at least one $R^{10}$ is optionally linked to a second compound of formula (II).

In some instances, the compound of formula (II) has the structure of formula (IIa):

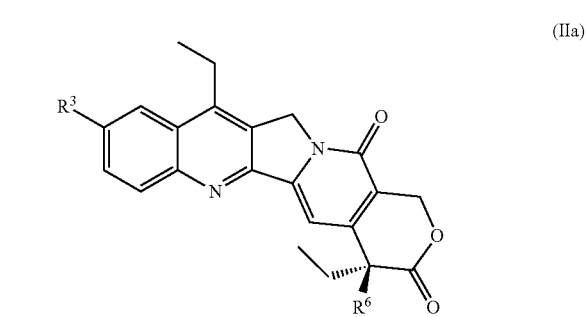

(IIa)

wherein $R^3$ is OH and L is attached at $R^6$; or L is attached at $R^3$ and $R^6$ is OH In some instances, the compound of formula (II) has the structure of formula (IIb):

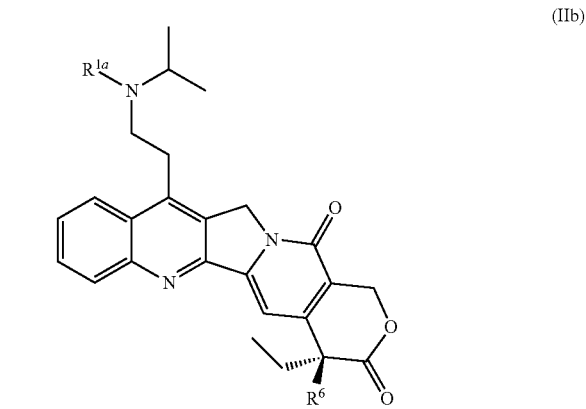

(IIb)

wherein $R^{1a}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$; or L is attached at $R^{1a}$ and $R^6$ is OH.

In some instances, the compound of formula (II) has the structure of formula (IIc):

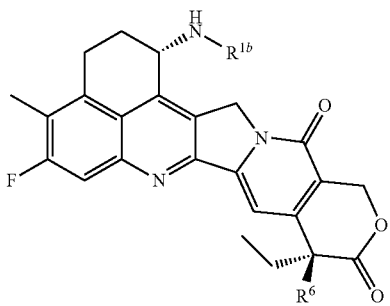
(IIc)

wherein $R^{1b}$ is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$; or L is attached at $R^{1b}$ and $R^6$ is OH.

In some instances, the compound of formula (II) has the structure of formula (IId):

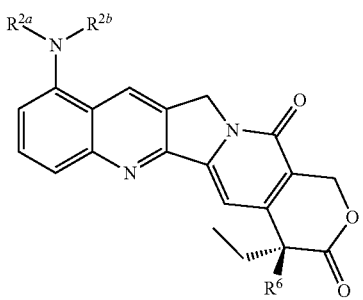
(IId)

wherein $R^{2a}$ and $R^{2b}$ are each independently selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at $R^6$; or L is attached at $R^{2a}$ or $R^{2b}$ and $R^6$ is OH.

In some instances, the compound of formula (II) has the structure of formula (IIe):

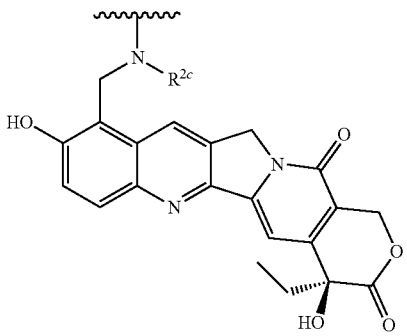
(IIe)

wherein $R^{2c}$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and attachment to L is indicated by the wavy line.

The substituents related to compounds of formula (II), (IIa), (IIb), (IIc), (IId) and (IIe) are described above. References to formula (II) are intended to also encompass formulae (IIa), (IIb), (IIc), (IId) and (IIe).

Regarding compounds of formula (III), the substituents Z, $R^8$, $R^9$, $R^{10}$, L, $L^B$, and W are as described above in relation to the conjugates of formula (I). Similarly, regarding the first linker L and the second linker $L^B$ of formula (III), the $T^1$, $T^2$, $T^3$, $T^4$, $T^5$, $T^6$, $V^1$, $V^2$, $V^3$, $V^4$, $V^5$ and $V^6$, and $T^7$, $T^8$, $T^9$, $T^{10}$, $T^{11}$, $T^{12}$, $V^7$, $V^8$, $V^9$, $V^{10}$, $V^{11}$ and $V^{12}$ substituents are as described above in relation to the conjugates of formula (I).

For example, in some instances, $T^1$, $T^2$, $T^3$, $T^4$, $T^5$ and $T^6$ and $V^1$, $V^2$, $V^3$, $V^4$, $V^5$ and $V^6$ are selected from the following:
wherein:
 $T^1$ is ($C_1$-$C_{12}$)alkyl and $V^1$ is —CO—;
 $T^2$ is an amino acid analog and $V^2$ is —NH—;
 $T^3$ is (PEG)$_n$ and $V^3$ is —CO—;
 $T^4$ is AA and $V^4$ is absent;
 $T^5$ is PABC and $V^5$ is absent; and
 $T^6$ is EDA and $V^6$ is —CO—; or
wherein:
 $T^1$ is ($C_1$-$C_{12}$)alkyl and $V^1$ is —CO—;
 $T^2$ is an amino acid analog and $V^2$ is —NH—;
 $T^3$ is (PEG)$_n$ and $V^3$ is —CO—;
 $T^4$ is AA and $V^4$ is absent;
 $T^5$ is absent and $V^5$ is —$NR^{15}(C_6H_4)$—; and
 $T^6$ is absent and $V^6$ is —CO—; or
wherein:
 $T^1$ is ($C_1$-$C_{12}$)alkyl and $V^1$ is —CO—;
 $T^2$ is an amino acid analog and $V^2$ is —NH—;
 $T^3$ is (PEG)$_n$ and $V^3$ is —CO—;
 $T^4$ is AA and $V^4$ is absent;
 $T^5$ is PABC and $V^5$ is —$NR^{15}$—; and
 $T^6$ is ($C_1$-$C_{12}$)alkyl and $V^6$ is —CO—; or
wherein:
 $T^1$ is ($C_1$-$C_{12}$)alkyl and $V^1$ is —CO—;
 $T^2$ is AA and $V^2$ is absent;
 $T^3$ is PABC and $V^3$ is absent;
 $T^4$ is EDA and $V^4$ is —CO—; and
 e and f are each 0; or
wherein:
 $T^1$ is ($C_1$-$C_{12}$)alkyl and $V^1$ is —CO—;
 $T^2$ is an amino acid analog and $V^2$ is —NH—;
 $T^3$ is (PEG)$_n$ and $V^3$ is —CO—;
 $T^4$ is AA and $V^4$ is absent;
 $T^5$ is PABC and $V^5$ is absent; and
 f is 0; or
wherein:
 $T^1$ is ($C_1$-$C_{12}$)alkyl and $V^1$ is —CO—;
 $T^2$ is AA and $V^2$ is absent;
 $T^3$ is PABC and $V^3$ is absent; and
 d, e and f are each 0; or
wherein:
 $T^1$ is ($C_1$-$C_{12}$)alkyl and $V^1$ is —CO—;
 $T^2$ is an amino acid analog and $V^2$ is —NH—;
 $T^3$ is (PEG)$_n$ and $V^3$ is —CO—;
 $T^4$ is AA and $V^4$ is absent;
 $T^5$ is PABA and $V^5$ is —CO—; and
 $T^6$ is ($C_1$-$C_{12}$)alkyl and $V^6$ is —$SO_2$—; or
wherein:
 $T^1$ is ($C_1$-$C_{12}$)alkyl and $V^1$ is —CONH—;
 $T^2$ is (PEG)$_n$ and $V^2$ is —CO—;
 $T^3$ is AA and $V^3$ is absent;
 $T^4$ is PABC and $V^4$ is absent;
 e and f are each 0; or wherein:
T$^1$ is (C$_1$-C$_{12}$)alkyl and V$^1$ is —CONH—;
T$^2$ is substituted (C$_1$-C$_{12}$)alkyl and V$^2$ is —CO—;
T$^3$ is AA and V$^3$ is absent;
T$^4$ is PABC and V$^4$ is absent;
e and f are each 0; or
wherein:
T$^1$ is (C$_1$-C$_{12}$)alkyl and V$^1$ is —CONH—;
T$^2$ is (PEG)$_n$ and V$^2$ is —CO—;
T$^3$ is AA and V$^3$ is absent;
T$^4$ is PABC and V$^4$ is absent;
T$^5$ is (C$_1$-C$_{12}$)alkyl and V$^5$ is absent;
f is 0; or
wherein:
T$^1$ is (C$_1$-C$_{12}$)alkyl and V$^1$ is —CO—;
T$^2$ is 4AP and V$^2$ is —CO—;
T$^3$ is (C$_1$-C$_{12}$)alkyl and V$^3$ is —CO—;
T$^4$ is AA and V$^4$ is absent;
T$^5$ is PABC and V$^5$ is absent;
f is 0; or
wherein:
T$^1$ is (C$_1$-C$_{12}$)alkyl and V$^1$ is —CO—;
T$^2$ is 4AP and V$^2$ is —CO—;
T$^3$ is (C$_1$-C$_{12}$)alkyl and V$^3$ is —O—;
T$^4$ is (C$_1$-C$_{12}$)alkyl and V$^4$ is —CO—;
T$^5$ is AA and V$^5$ is absent;
T$^6$ is PABC and V$^6$ is absent; or
wherein:
T$^1$ is (C$_1$-C$_{12}$)alkyl and V$^1$ is —CO—;
T$^2$ is an amino acid analog and V$^2$ is absent;
T$^3$ is AA and V$^3$ is absent;
T$^4$ is PABC and V$^4$ is absent;
e and f are each 0; or
wherein:
T$^1$ is (C$_1$-C$_{12}$)alkyl and V$^1$ is —CONH—;
T$^2$ is (PEG)$_n$ and V$^2$ is —CONH—;
T$^3$ is substituted (C$_1$-C$_{12}$)alkyl and V$^3$ is —CO—;
T$^4$ is AA and V$^4$ is absent;
T$^5$ is PABC and V$^5$ is absent;
f is 0; or
wherein:
T$^1$ is (C$_1$-C$_{12}$)alkyl and V$^1$ is —CO—;
T$^2$ is AA and V$^2$ is —NH—;
T$^3$ is (PEG)$_n$ and V$^3$ is —CO—;
T$^4$ is AA and V$^4$ is absent;
T$^5$ is PABC and V$^5$ is absent;
f is 0; or
wherein:
T$^1$ is (C$_1$-C$_{12}$)alkyl and V$^1$ is —CO—;
T$^2$ is an amino acid analog and V$^2$ is —NH—;
T$^3$ is (PEG)$_n$ and V$^3$ is —CO—;
T$^4$ is AA and V$^4$ is absent;
T$^5$ is PABO and V$^5$ is absent; and
f is 0; or
wherein:
T$^1$ is (C$_1$-C$_{12}$)alkyl and V$^1$ is —CO—;
T$^2$ is an amino acid analog and V$^2$ is —NH—;
T$^3$ is (PEG)$_n$ and V$^3$ is —CO—;
T$^4$ is AA and V$^4$ is absent;
T$^5$ is PAP and V$^5$ is —COO—; and
f is 0; or
wherein:
T$^1$ is (C$_1$-C$_{12}$)alkyl and V$^1$ is —CONH—;
T$^2$ is (PEG)$_n$ and V$^2$ is —CO—;
T$^3$ is AA and V$^3$ is absent;
T$^4$ is PAP and V$^4$ is —COO—; and
e and f are each 0.

For example, in some instances, T$^7$, T$^8$, T$^9$, T$^{10}$, T$^{11}$ and T$^{12}$ and V$^7$, V$^8$, V$^9$, V$^{10}$, V$^{11}$ and V$^{12}$ are selected from the following:
wherein:
T$^7$ is absent and V$^7$ is —NHCO—;
T$^8$ is (C$_1$-C$_{12}$)alkyl and V$^8$ is —CO—;
T$^9$ is AA and V$^9$ is absent;
T$^{10}$ is PABC and V$^{10}$ is absent;
T$^{11}$ is EDA and V$^{11}$ is —CO—; and
l is 0; or
wherein:
T$^7$ is absent and V$^7$ is —NHCO—;
T$^8$ is (C$_1$-C$_{12}$)alkyl and V$^8$ is —CO—;
T$^9$ is AA and V$^9$ is absent;
T$^{10}$ is PABC and V$^{10}$ is absent; and
k and l are each 0; or
wherein:
T$^7$ is absent and V$^7$ is —NHCO—;
T$^8$ is (C$_1$-C$_{12}$)alkyl and V$^8$ is —CO—;
T$^9$ is an amino acid analog and V$^9$ is —NH—;
T$^{10}$ is (PEG)$_n$ and V$^{10}$ is —CO—;
T$^{11}$ is AA and V$^{11}$ is absent; and
T$^{12}$ is PABC and V$^{12}$ is absent; or
wherein:
T$^7$ is absent and V$^7$ is —NHCO—;
T$^8$ is (C$_1$-C$_{12}$)alkyl and V$^8$ is —CONH—;
T$^9$ is (PEG)$_n$ and V$^9$ is —CO—;
T$^{10}$ is AA and V$^{10}$ is absent;
T$^{11}$ is PABC and V$^{11}$ is absent; and
l is 0; or
wherein:
T$^7$ is (C$_1$-C$_{12}$)alkyl and V$^7$ is —CONH—;
T$^8$ is substituted (C$_1$-C$_{12}$)alkyl and V$^8$ is —CO—;
T$^9$ is AA and V$^9$ is absent;
T$^{10}$ is PABC and V$^{10}$ is absent;
k and l are each 0; or
wherein:
T$^7$ is (C$_1$-C$_{12}$)alkyl and V$^7$ is —CONH—;
T$^8$ is (PEG)$_n$ and V$^8$ is —CO—;
T$^9$ is AA and V$^9$ is absent;
T$^{10}$ is PABC and V$^{10}$ is absent;
T$^{11}$ is (C$_1$-C$_{12}$)alkyl and V$^{11}$ is absent;
l is 0; or
wherein:
T$^7$ is (C$_1$-C$_{12}$)alkyl and V$^7$ is —CO—;
T$^8$ is 4AP and V$^8$ is —CO—;
T$^9$ is (C$_1$-C$_{12}$)alkyl and V$^9$ is —CO—;
T$^{10}$ is AA and V$^{10}$ is absent;
T$^{11}$ is PABC and V$^{11}$ is absent;
l is 0; or
wherein:
T$^7$ is (C$_1$-C$_{12}$)alkyl and V$^7$ is —CO—;
T$^8$ is 4AP and V$^8$ is —CO—;
T$^9$ is (C$_1$-C$_{12}$)alkyl and V$^9$ is —O—;
T$^{10}$ is (C$_1$-C$_{12}$)alkyl and V$^{10}$ is —CO—;
T$^{11}$ is AA and V$^{11}$ is absent;
T$^{12}$ is PABC and V$^{12}$ is absent; or
wherein:
T$^7$ is (C$_1$-C$_{12}$)alkyl and V$^7$ is —CO—;
T$^8$ is an amino acid analog and V$^8$ is absent;
T$^9$ is AA and V$^9$ is absent;
T$^{10}$ is PABC and V$^{10}$ is absent;
k and l are each 0; or
wherein:
T$^7$ is (C$_1$-C$_{12}$)alkyl and V$^7$ is —CONH—;
T$^8$ is (PEG)$_n$ and V$^8$ is —CONH—;
T$^9$ is substituted (C$_1$-C$_{12}$)alkyl and V$^9$ is —CO—;

$T^{10}$ is AA and $V^{10}$ is absent;
$T^{11}$ is PABC and $V^{11}$ is absent;
l is 0; or wherein:
$T^7$ is (C$_1$-C$_{12}$)alkyl and $V^7$ is —CO—;
$T^8$ is AA and $V^8$ is —NH—;
$T^9$ is (PEG)$_n$ and $V^9$ is —CO—;
$T^{10}$ is AA and $V^{10}$ is absent;
$T^{11}$ is PABC and $V^{11}$ is absent;
l is 0; or wherein:
$T^7$ is (C$_1$-C$_{12}$)alkyl and $V^7$ is —CONH—;
$T^8$ is (PEG)$_n$ and $V^8$ is —CO—;

$T^9$ is AA and $V^9$ is absent;
$T^{10}$ is PAP and $V^{10}$ is —COO—; and
k and l are each 0.

Compounds of formula (III) can be used in conjugation reactions described herein, where a drug or active agent attached to a hydrazinyl-indolyl or a hydrazinyl-pyrrolo-pyridinyl conjugation moiety is conjugated to a polypeptide (e.g., antibody) to form an antibody-drug conjugate.

In certain embodiments, the compound of formula (III) has the following structure:

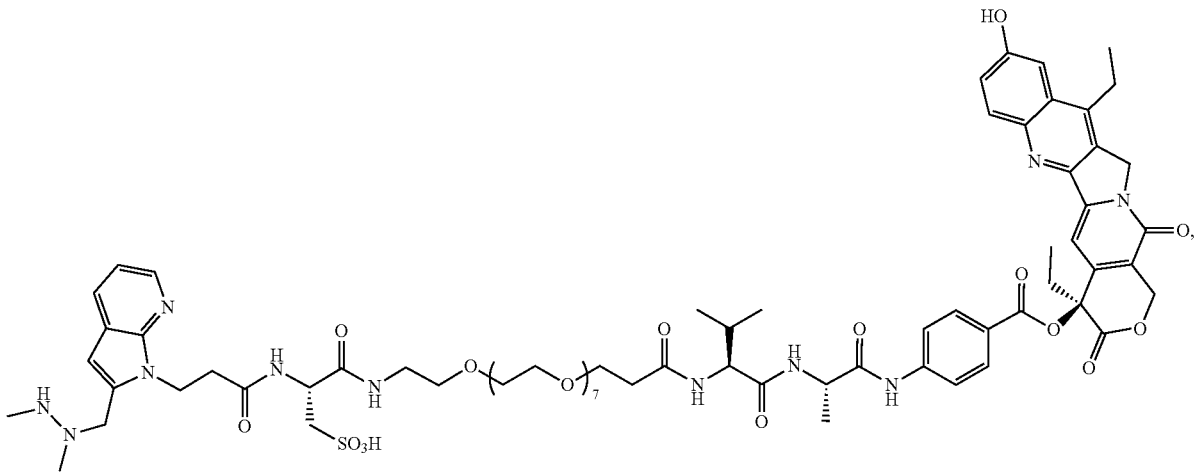

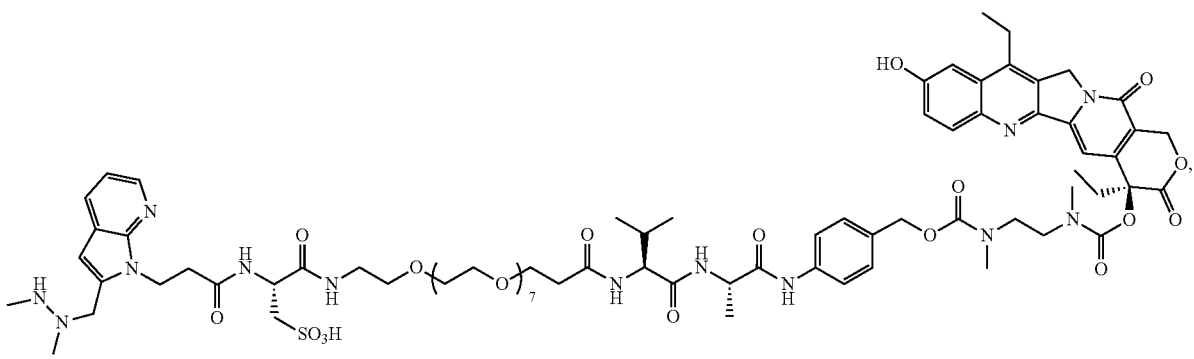

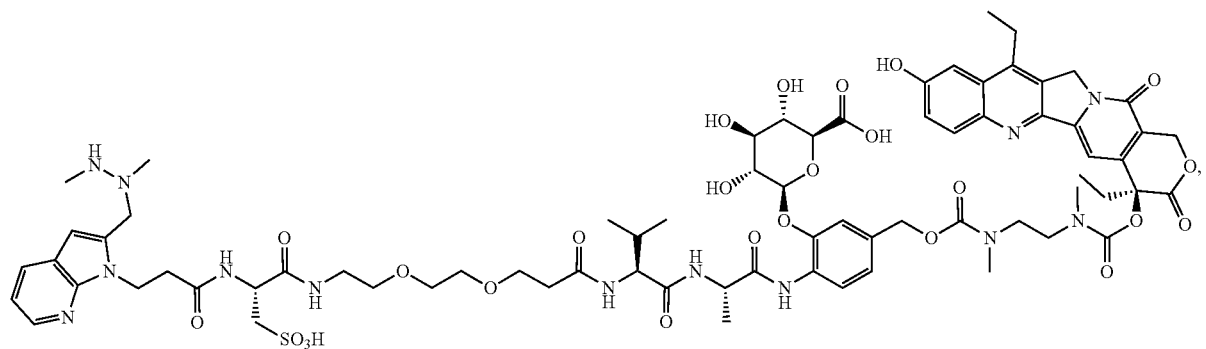
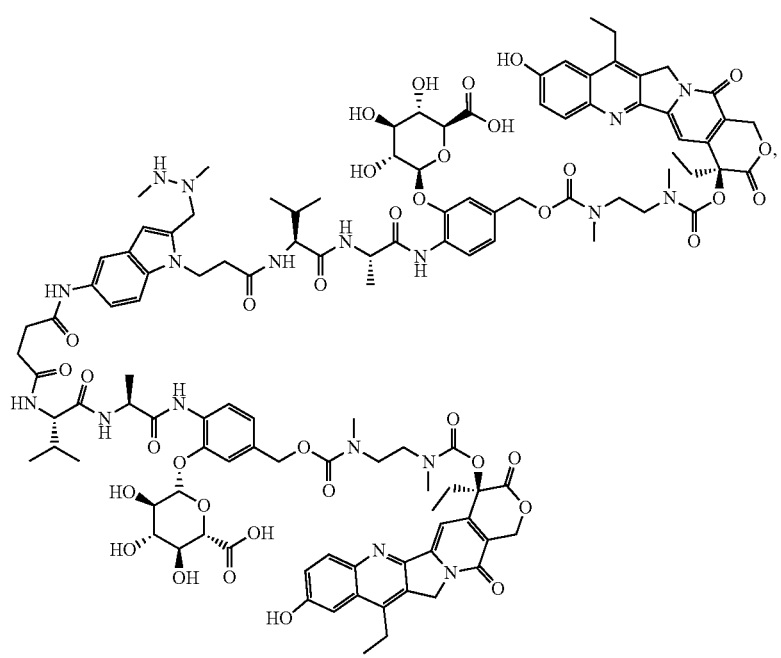
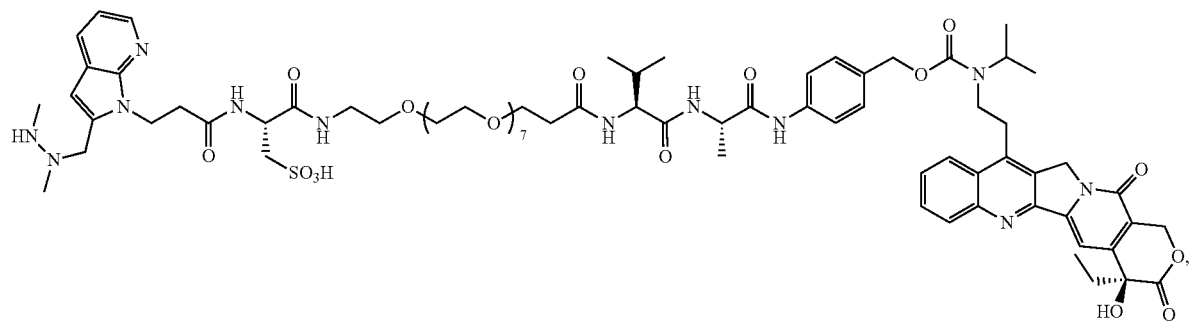

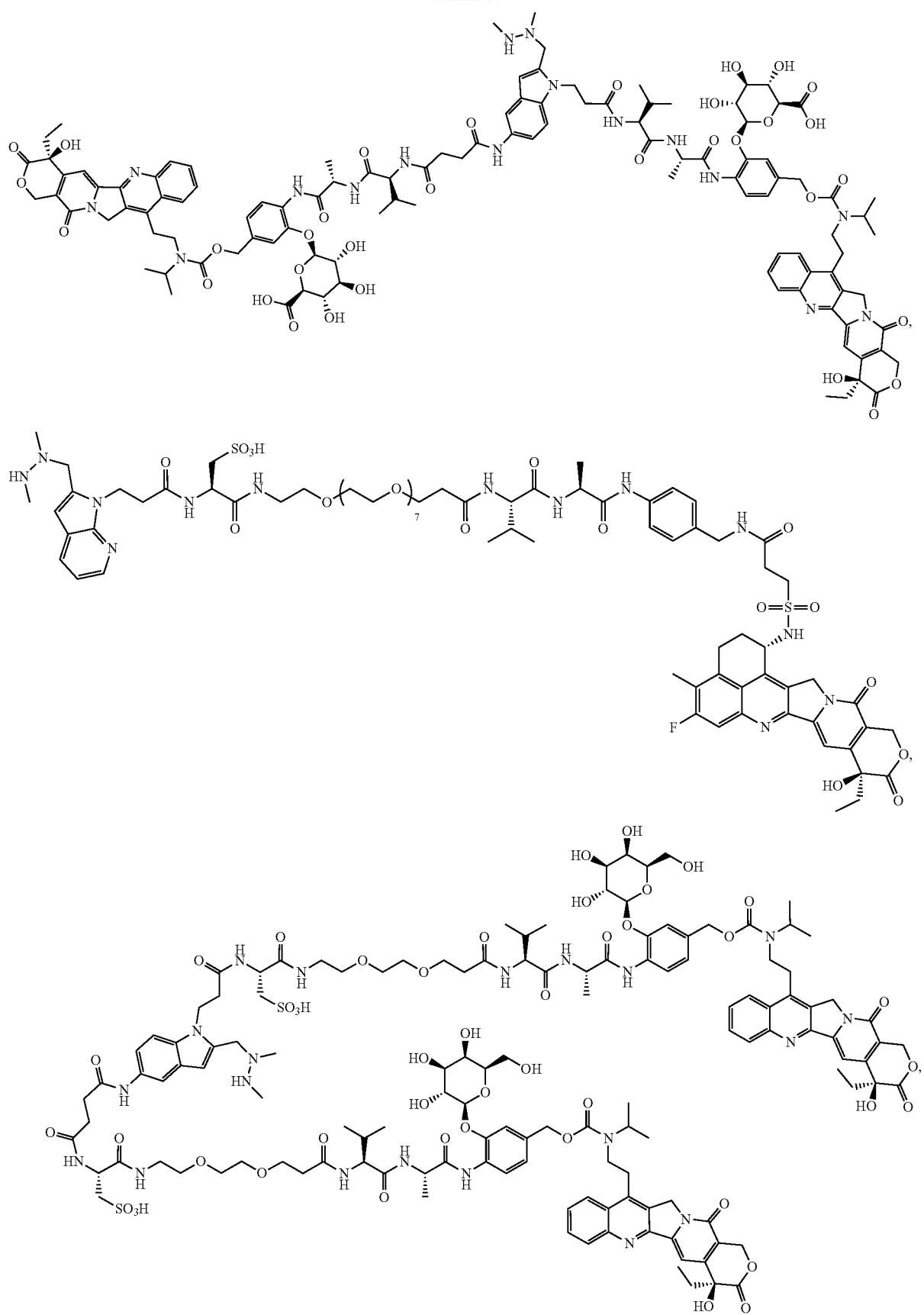

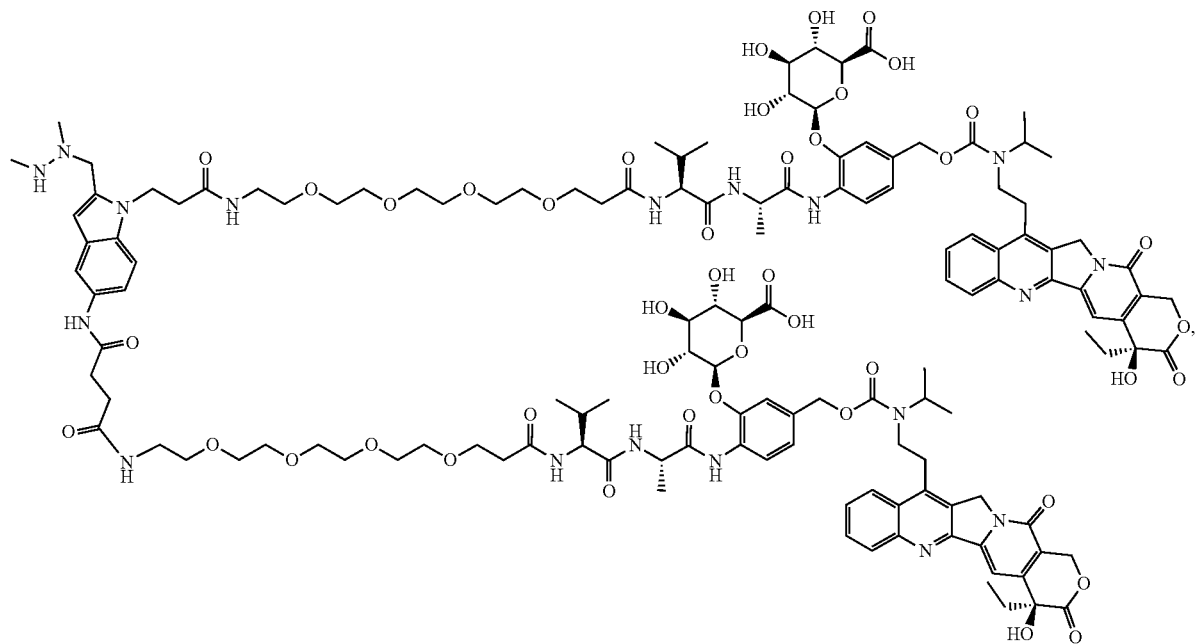
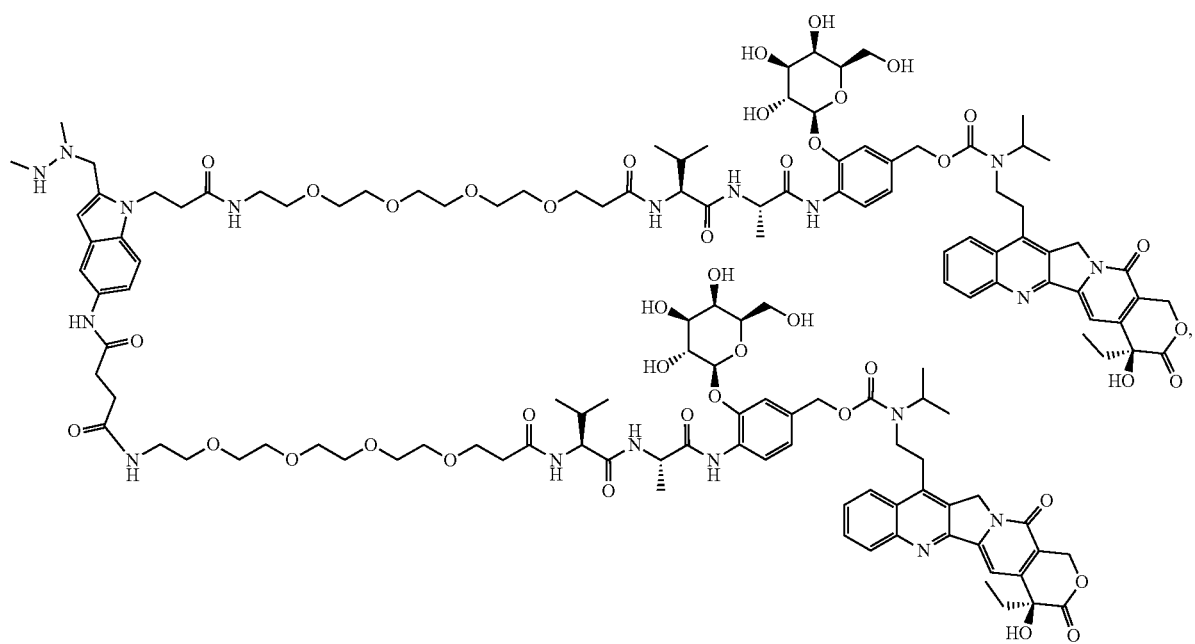

-continued
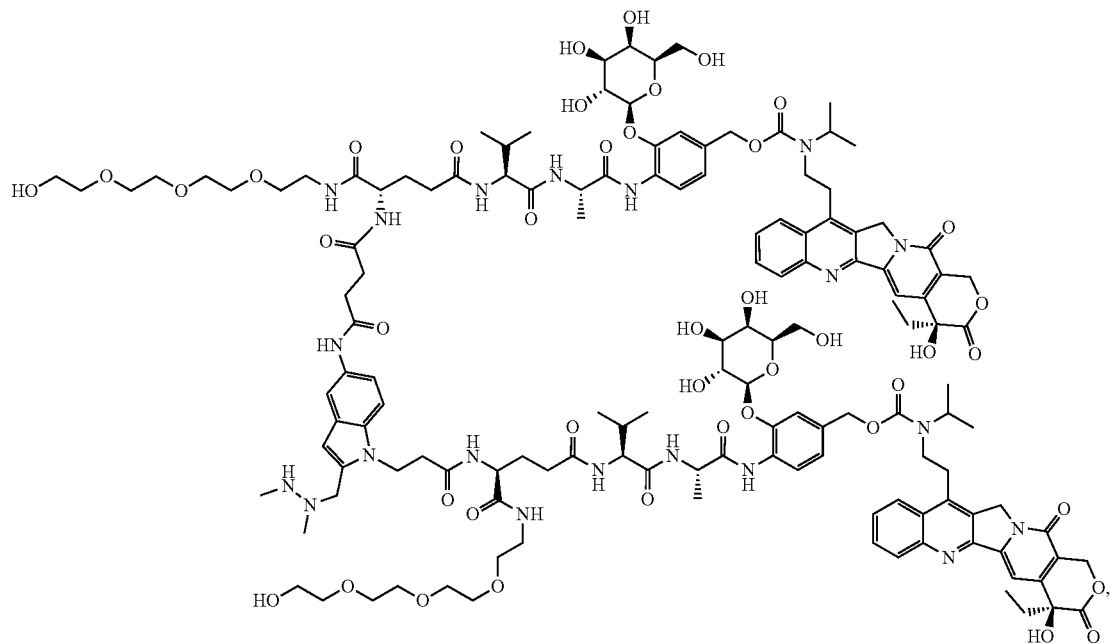
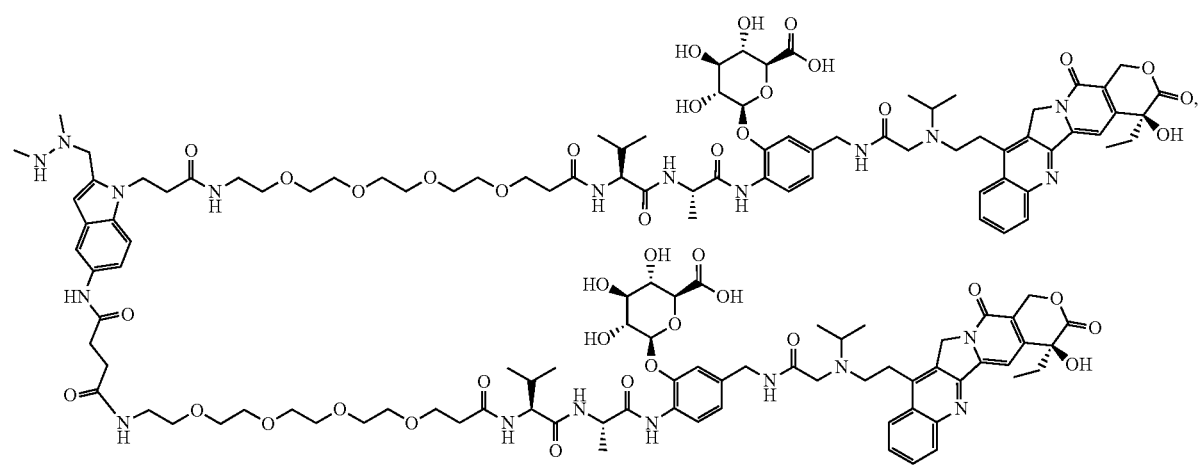

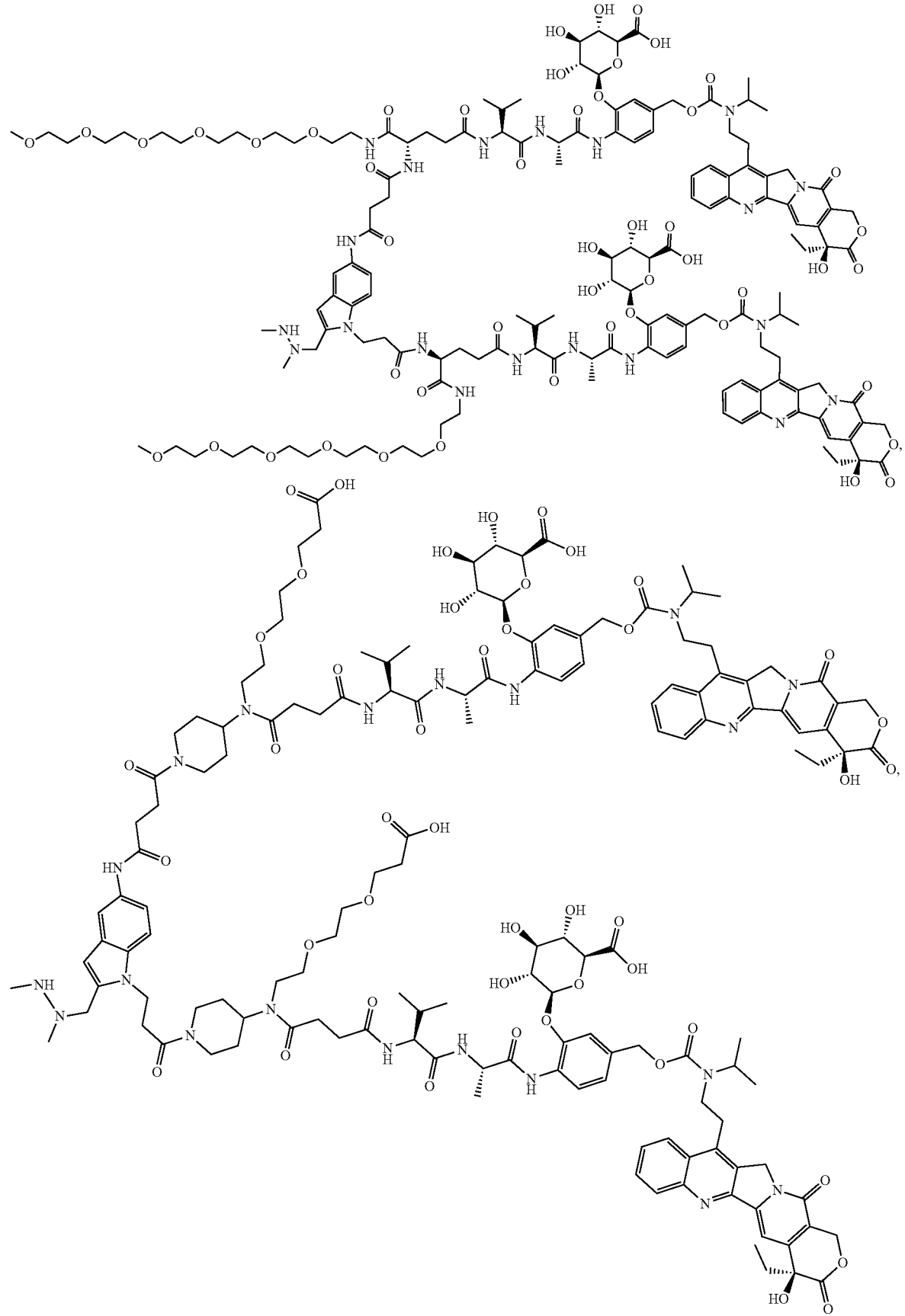

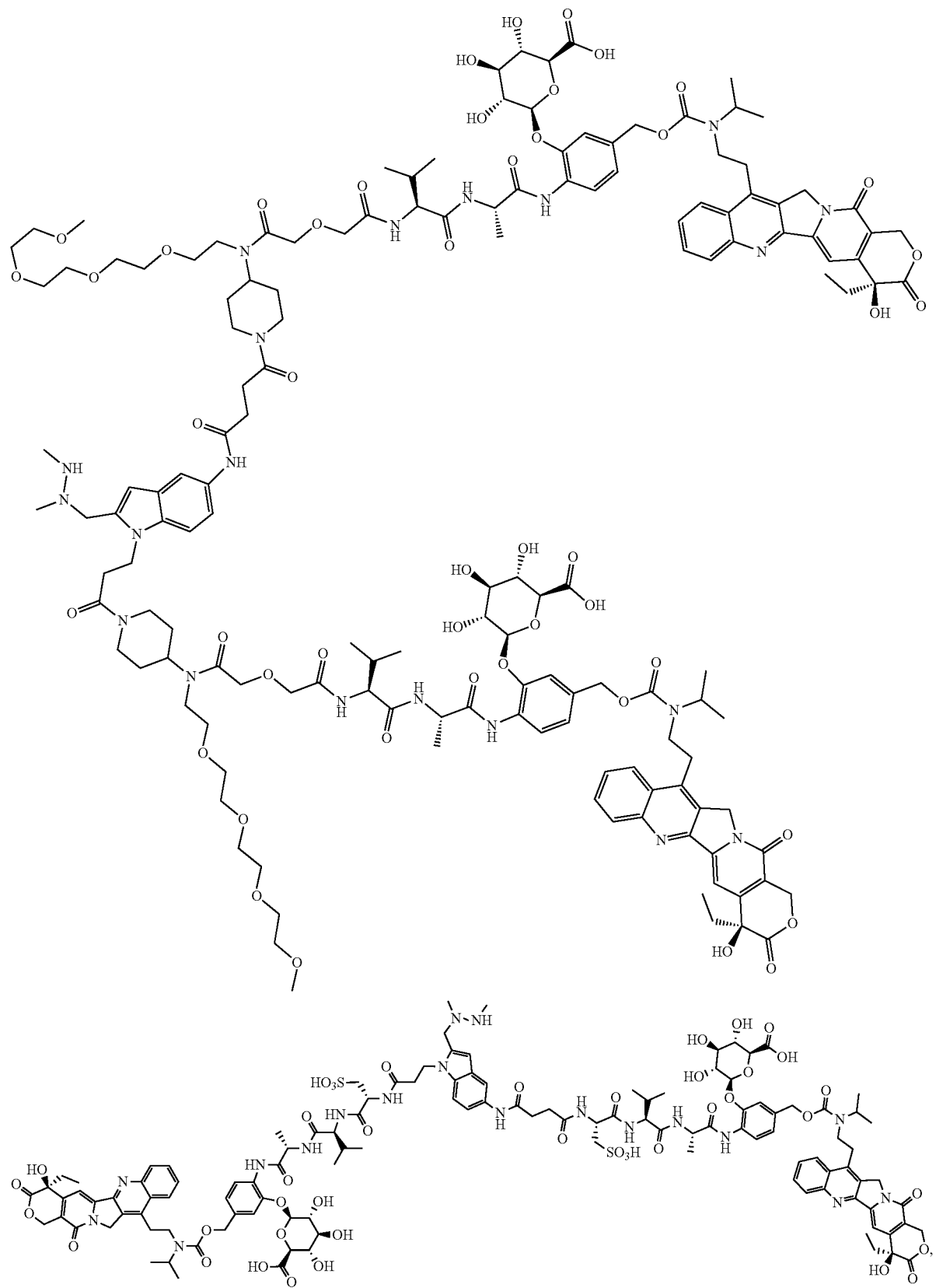

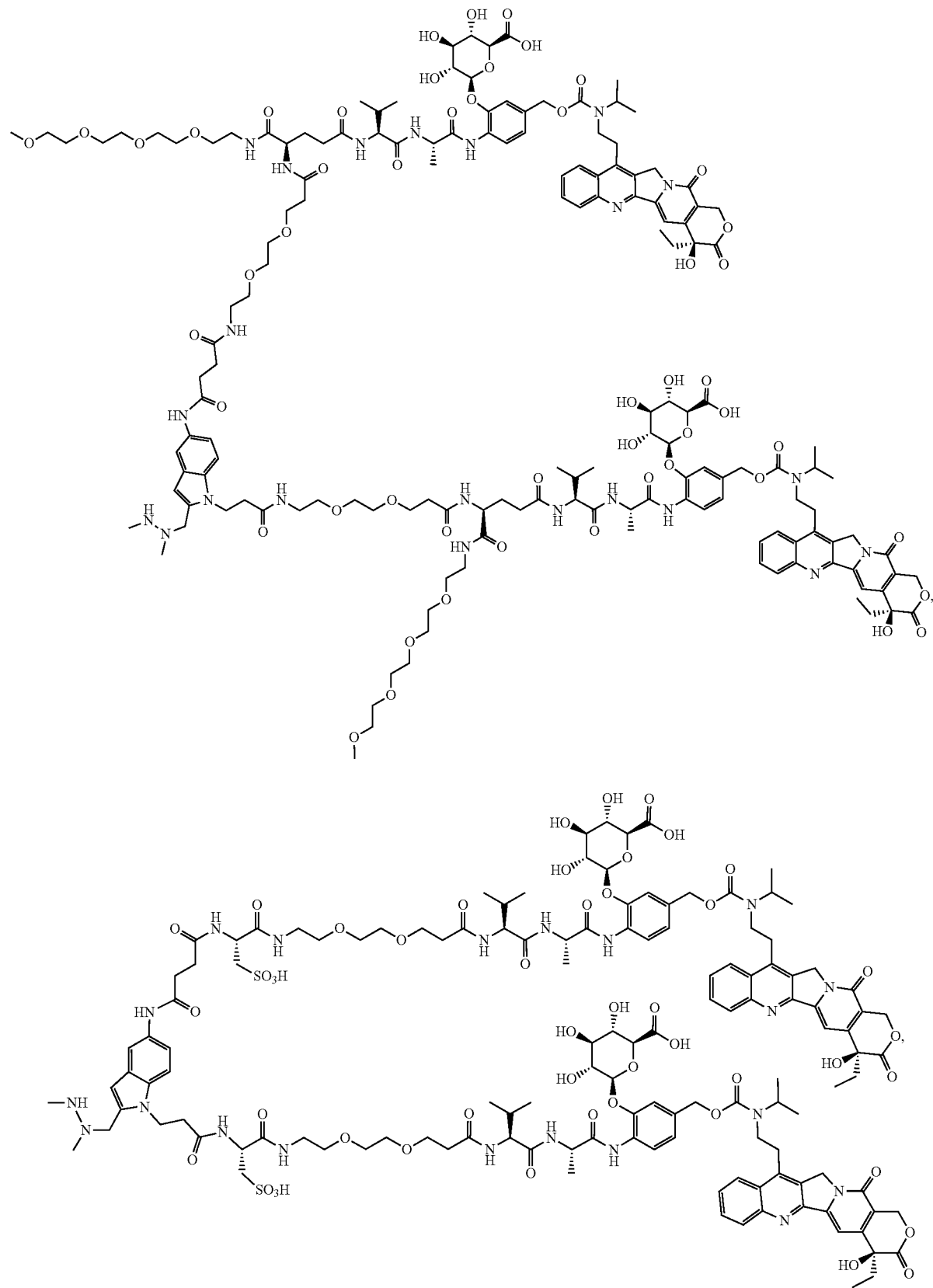

-continued
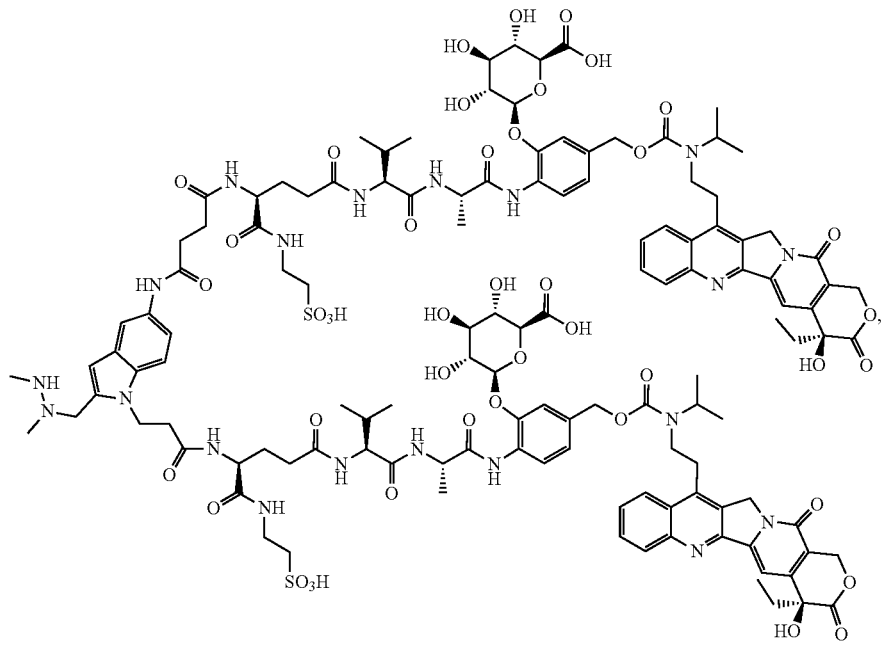
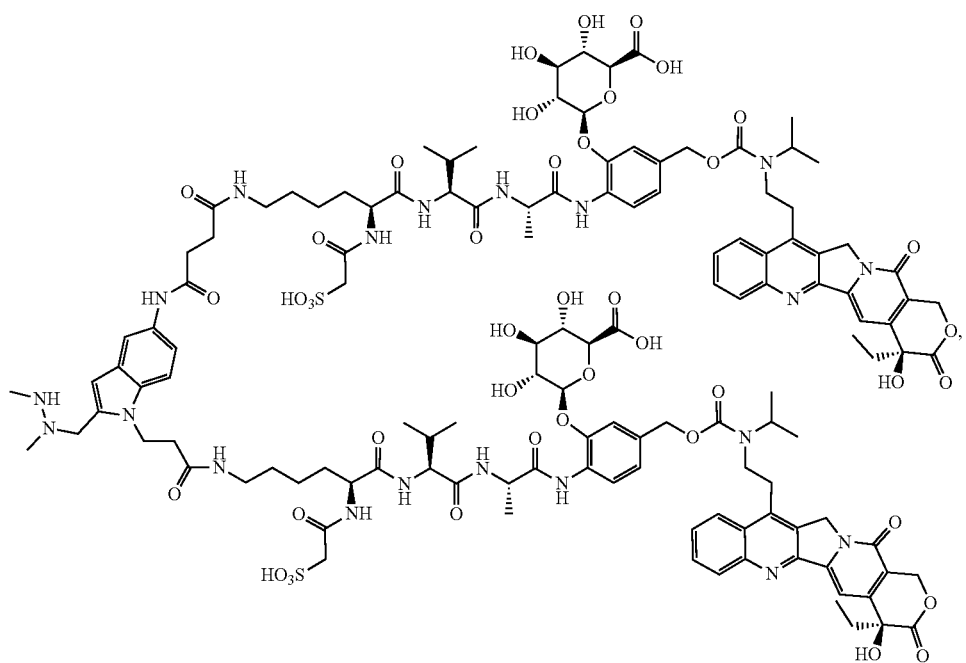

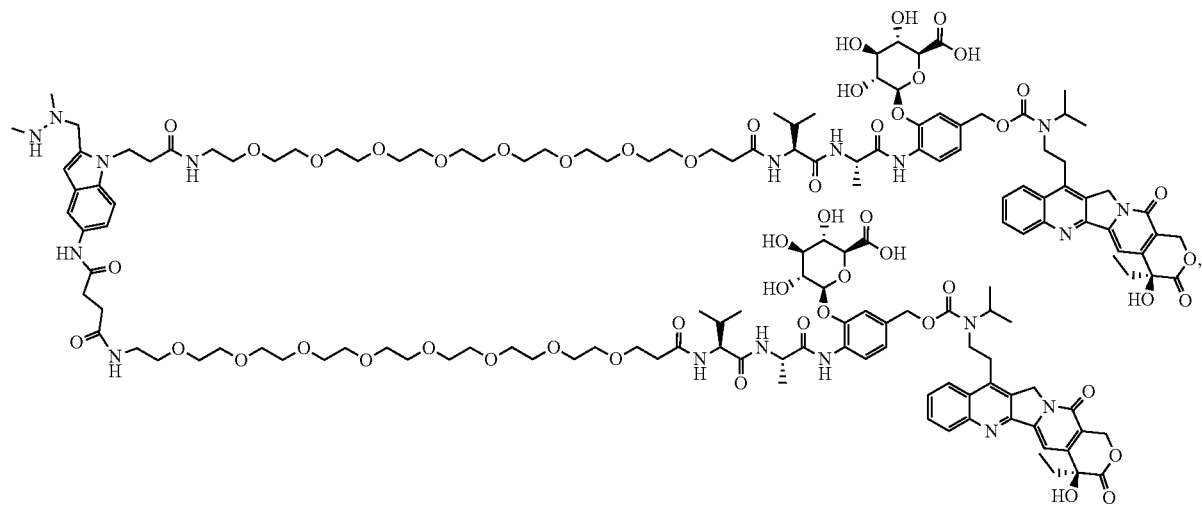
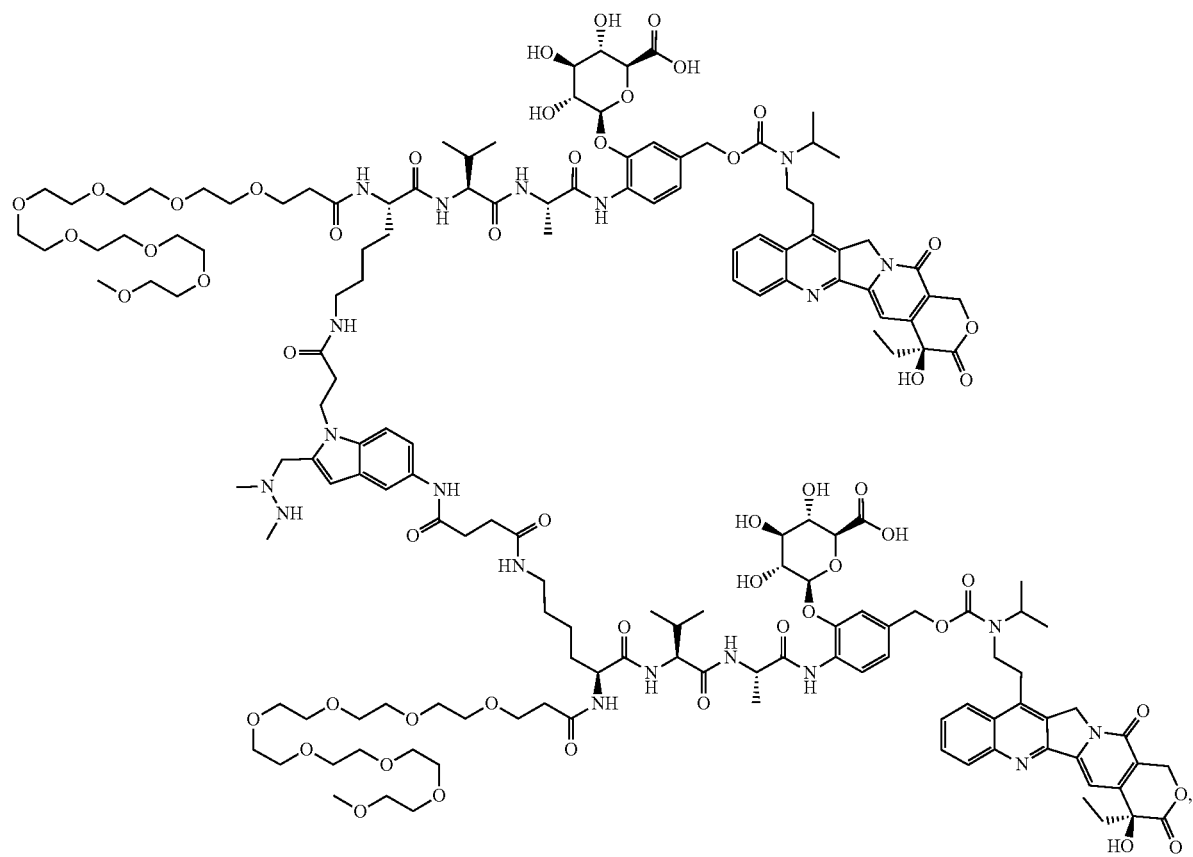

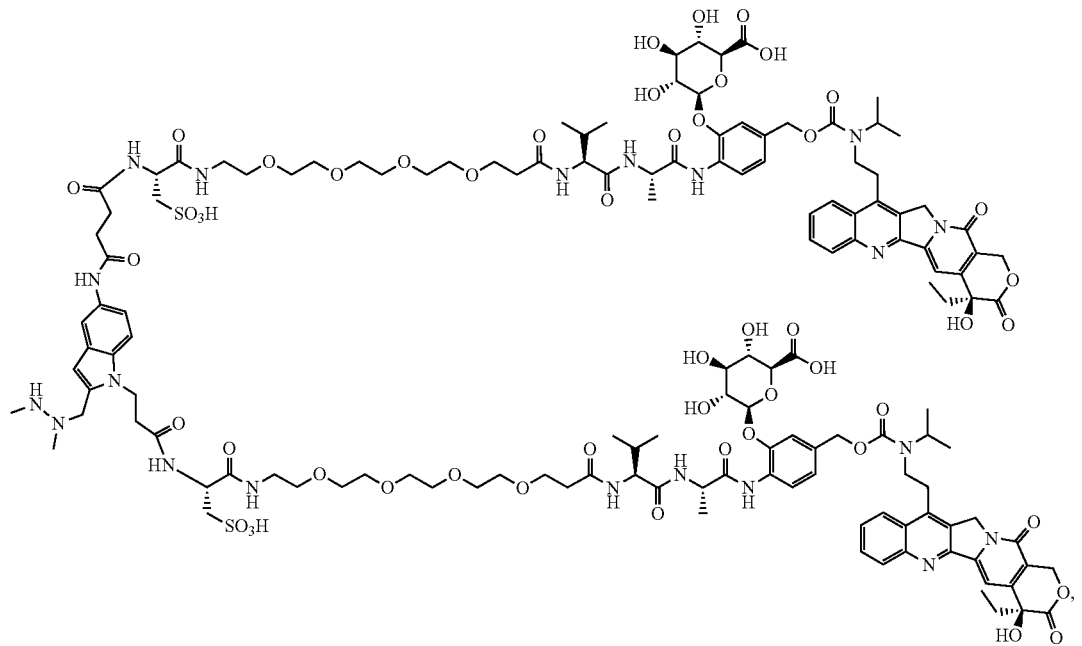
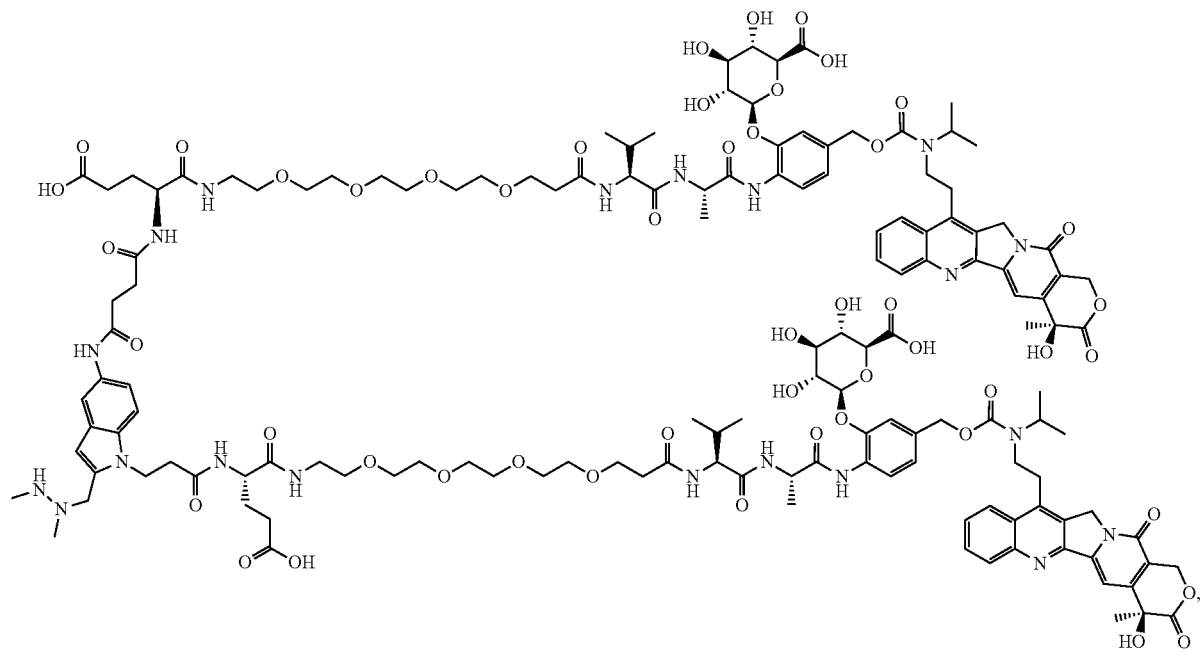

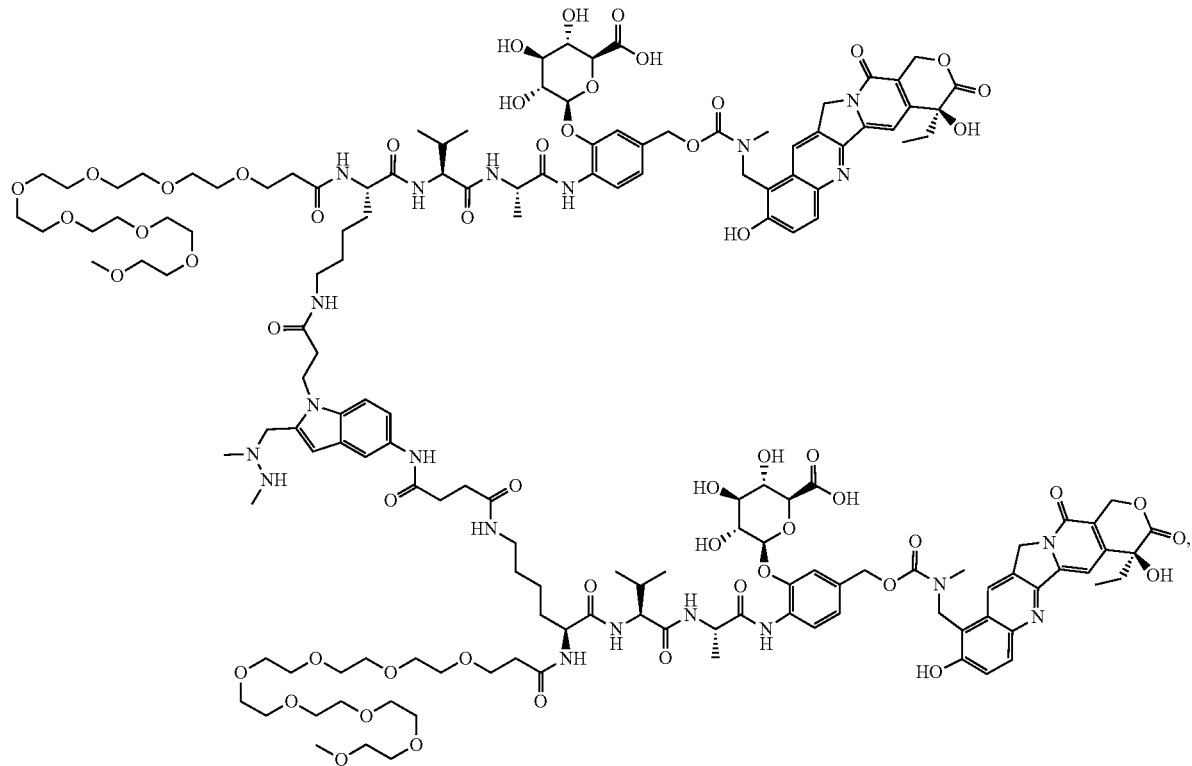
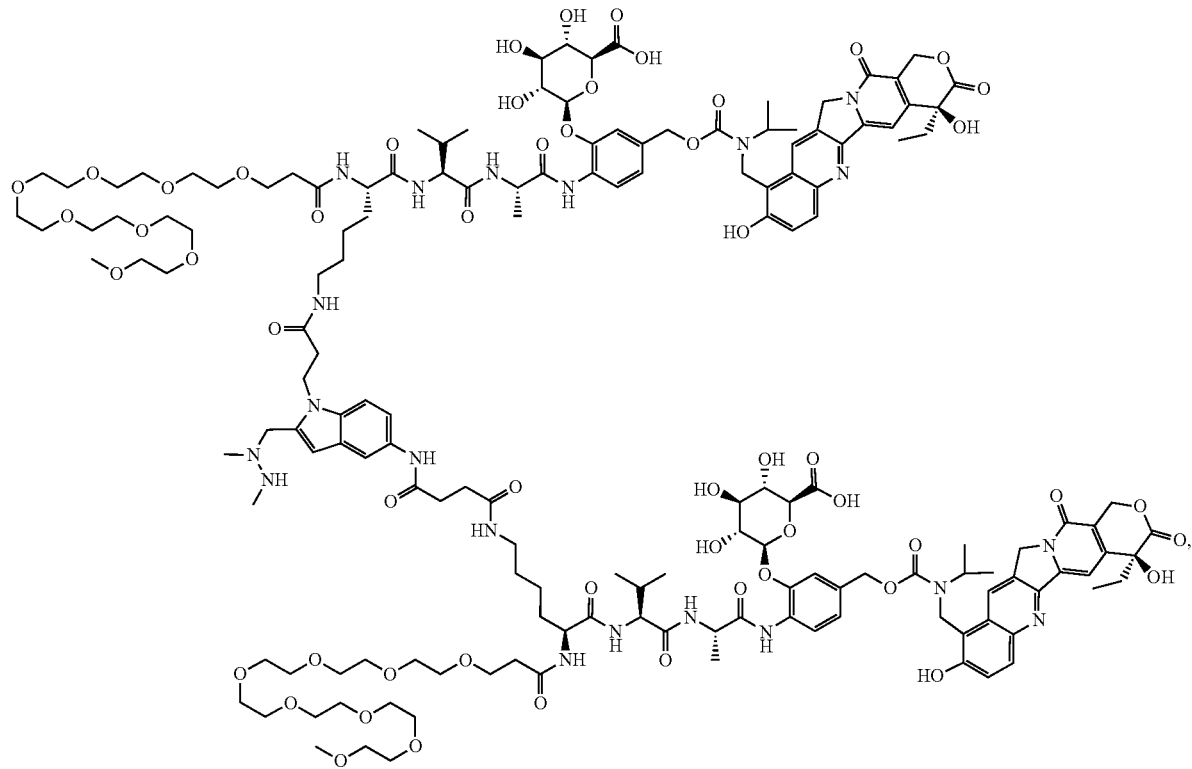

-continued

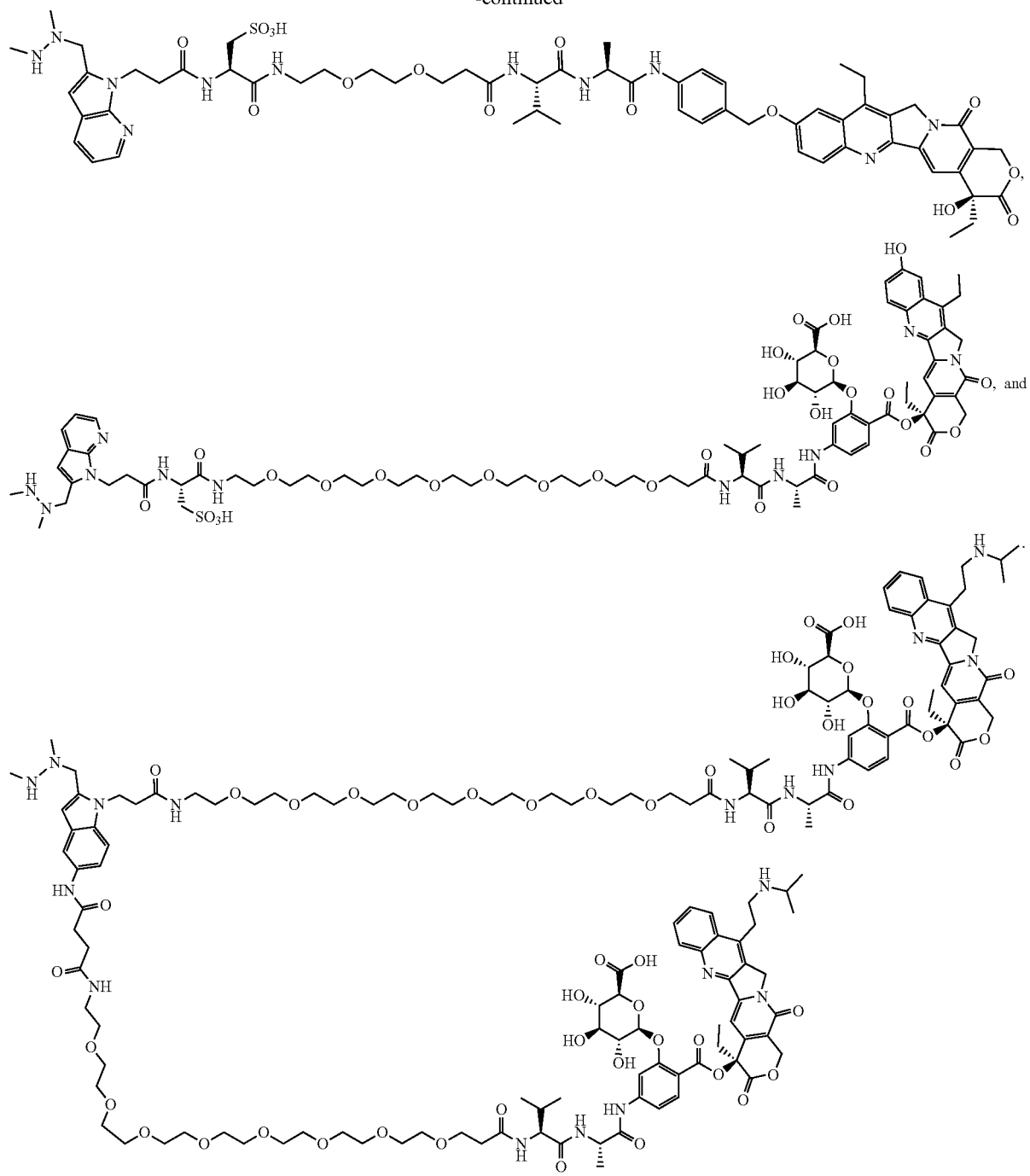

Any of the chemical entities, linkers and conjugation moieties set forth in the structures above may be adapted for use in the subject compounds and conjugates.

Polypeptides and Antibodies

As noted above, a subject conjugate can comprise as substituent W a polypeptide (e.g., an antibody). The amino acid sequence of the polypeptide (antibody) has been modified to include a 2-formylglycine (fGly) residue. As used herein, amino acids may be referred to by their standard name, their standard three letter abbreviation and/or their standard one letter abbreviation, such as: Alanine or Ala or A; Cysteine or Cys or C; Aspartic acid or Asp or D; Glutamic acid or Glu or E; Phenylalanine or Phe or F; Glycine or Gly or G; Histidine or His or H; Isoleucine or Ile or I; Lysine or Lys or K; Leucine or Leu or L; Methionine or Met or M; Asparagine or Asn or N; Proline or Pro or P; Glutamine or Gln or Q; Arginine or Arg or R; Serine or Ser or S; Threonine or Thr or T; Valine or Val or V; Tryptophan or Trp or W; and Tyrosine or Tyr or Y.

In certain embodiments, the amino acid sequence of the polypeptide (antibody) is modified to include a sulfatase motif that contains a serine or cysteine residue that is capable of being converted (oxidized) to a 2-formylglycine (fGly) residue by action of a formylglycine generating enzyme (FGE) either in vivo (e.g., at the time of translation of an aldehyde tag-containing protein in a cell) or in vitro (e.g., by contacting an aldehyde tag-containing protein with an FGE in a cell-free system). Such sulfatase motifs may also be referred to herein as an FGE-modification site.

Sulfatase Motifs

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8, 7 or 6 amino acid residues in length.

In certain embodiments, polypeptides of interest include those where one or more amino acid residues, such as 2 or more, or 3 or more, or 4 or more, or 5 or more, or 6 or more, or 7 or more, or 8 or more, or 9 or more, or 10 or more, or 11 or more, or 12 or more, or 13 or more, or 14 or more, or 15 or more, or 16 or more, or 17 or more, or 18 or more, or 19 or more, or 20 or more amino acid residues have been inserted, deleted, substituted (replaced) relative to the native amino acid sequence to provide for a sequence of a sulfatase motif in the polypeptide. In certain embodiments, the polypeptide includes a modification (insertion, addition, deletion, and/or substitution/replacement) of less than 20, 19, 18, 17, 16, 15, 14, 13, 12, 11, 10, 9, 8, 7, 6, 5, 4, 3 or 2 amino acid residues of the amino acid sequence relative to the native amino acid sequence of the polypeptide. Where an amino acid sequence native to the polypeptide (e.g., antibody) contains one or more residues of the desired sulfatase motif, the total number of modifications of residues can be reduced, e.g., by site-specification modification (insertion, addition, deletion, substitution/replacement) of amino acid residues flanking the native amino acid residues to provide a sequence of the desired sulfatase motif. In certain embodiments, the extent of modification of the native amino acid sequence of the target antibody is minimized, so as to minimize the number of amino acid residues that are inserted, deleted, substituted (replaced), or added (e.g., to the N- or C-terminus). Minimizing the extent of amino acid sequence modification of the target antibody may minimize the impact such modifications may have upon antibody function and/or structure.

It should be noted that while aldehyde tags of particular interest are those comprising at least a minimal sulfatase motif (also referred to a "consensus sulfatase motif"), it will be readily appreciated that longer aldehyde tags are both contemplated and encompassed by the present disclosure and can find use in the compositions and methods of the present disclosure. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

An aldehyde tag can be present at or near the C-terminus of an Ig heavy chain; e.g., an aldehyde tag can be present within 1, 2, 3, 4, 5, 6, 7, 8, 9, or 10 amino acids of the C-terminus of a native, wild-type Ig heavy chain. An aldehyde tag can be present within a CH1 domain of an Ig heavy chain. An aldehyde tag can be present within a CH2 domain of an Ig heavy chain. An aldehyde tag can be present within a CH3 domain of an Ig heavy chain. An aldehyde tag can be present in an Ig light chain constant region, e.g., in a kappa light chain constant region or a lambda light chain constant region.

In certain embodiments, the sulfatase motif used may be described by the formula:

$$X^1Z^{10}X^2Z^{20}X^3Z^{30} \quad (I')$$

where $Z^{10}$ is cysteine or serine (which can also be represented by (C/S));

$Z^{20}$ is either a proline or alanine residue (which can also be represented by (P/A));

$Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I;

$X^1$ is present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M, S or V, with the proviso that when the sulfatase motif is at the N-terminus of the target polypeptide, XV is present; and $X^2$ and $X^3$ independently can be any amino acid, though usually an aliphatic amino acid, a polar, uncharged amino acid, or a sulfur containing amino acid (i.e., other than an aromatic amino acid or a charged amino acid), e.g., S, T, A, V, G or C, e.g., S, T, A, V or G.

The amino acid sequence of an antibody heavy and/or light chain can be modified to provide a sequence of at least 5 amino acids of the formula $X^1Z^{10}X^2Z^{20}X^3Z^{30}$, where $Z^{10}$ is cysteine or serine;

$Z^{20}$ is a proline or alanine residue;

$Z^{30}$ is an aliphatic amino acid or a basic amino acid;

$X^1$ is present or absent and, when present, is any amino acid, with the proviso that when the heterologous sulfatase motif is at an N-terminus of the polypeptide, $X^1$ is present;

$X^2$ and $X^3$ are each independently any amino acid.

The sulfatase motif is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

For example, where the FGE is a eukaryotic FGE (e.g., a mammalian FGE, including a human FGE), the sulfatase motif can be of the formula:

$$X^1CX^2PX^3Z^{30} \quad (I'')$$

where $X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, S or V, with the proviso that when the sulfatase motif is at the N-terminus of the target polypeptide, $X^1$ is present;

$X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G, or C, e.g., S, T, A, V or G; and $Z^{30}$ is a basic amino acid (e.g., arginine (R), and may be lysine (K) or histidine (H), e.g., lysine), or an aliphatic amino acid (alanine (A), glycine (G), leucine (L), valine (V), isoleucine (I), or proline (P), e.g., A, G, L, V, or I.

Specific examples of sulfatase motifs include LCTPSR (SEQ ID NO://), MCTPSR (SEQ ID NO://), VCTPSR (SEQ ID NO://), LCSPSR (SEQ ID NO://), LCAPSR (SEQ ID NO://), LCVPSR (SEQ ID NO://), LCGPSR (SEQ ID NO://), ICTPAR (SEQ ID NO://), LCTPSK (SEQ ID NO://), MCTPSK (SEQ ID NO://), VCTPSK (SEQ ID NO://), LCSPSK (SEQ ID NO://), LCAPSK (SEQ ID NO://), LCVPSK (SEQ ID NO://), LCGPSK (SEQ ID NO://), LCTPSA (SEQ ID NO://), ICTPAA (SEQ ID NO://), MCTPSA (SEQ ID NO://), VCTPSA (SEQ ID NO://), LCSPSA (SEQ ID NO://), LCAPSA (SEQ ID NO://), LCVPSA (SEQ ID NO://), and LCGPSA (SEQ ID NO://).

fGly-Containing Sequences

Upon action of FGE on the antibody heavy and/or light chain, the serine or the cysteine in the sulfatase motif is modified to fGly. Thus, the fGly-containing sulfatase motif can be of the formula:

$$X^1(fGly)X^2Z^{20}X^3Z^{30} \qquad (I''')$$

where fGly is the formylglycine residue;

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, $X^1$ is present; and $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

As described above, to produce the conjugate, the polypeptide containing the fGly residue may be conjugated to a drug or active agent by reaction of the fGly with a reactive moiety (e.g., a hydrazinyl-indolyl or a hydrazinyl-pyrrolopyridinyl conjugation moiety, as described above) of a linker attached to the drug or active agent to produce an fGly'-containing sulfatase motif. As used herein, the term fGly' refers to the amino acid residue of the sulfatase motif that is coupled to the drug or active agent through a linker, as described herein. Thus, the fGly'-containing sulfatase motif can be of the formula:

$$X^1(fGly')X^2Z^{20}X^3Z^{30} \qquad (II)$$

where fGly' is the amino acid residue coupled to the drug or active agent through a linker as described herein;

$Z^{20}$ is either a proline or alanine residue (which can also be represented by (P/A));

$Z^{30}$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), e.g., A, G, L, V, or I;

$X^1$ may be present or absent and, when present, can be any amino acid, e.g., an aliphatic amino acid, a sulfur-containing amino acid, or a polar, uncharged amino acid, (i.e., other than an aromatic amino acid or a charged amino acid), e.g., L, M, V, S or T, e.g., L, M or V, with the proviso that when the sulfatase motif is at the N-terminus of the target polypeptide, XV is present; and $X^2$ and $X^3$ independently can be any amino acid, e.g., an aliphatic amino acid, a sulfur-containing amino acid, or a polar, uncharged amino acid, (i.e., other than an aromatic amino acid or a charged amino acid), e.g., S, T, A, V, G or C, e.g., S, T, A, V or G.

Site of Modification

As noted above, the amino acid sequence of the polypeptide (antibody) is modified to include a sulfatase motif that contains a serine or cysteine residue that is capable of being converted (oxidized) to an fGly residue by action of an FGE either in vivo (e.g., at the time of translation of an aldehyde tag-containing protein in a cell) or in vitro (e.g., by contacting an aldehyde tag-containing protein with an FGE in a cell-free system). The antibody used to generate a conjugate of the present disclosure include at least an Ig constant region, e.g., an Ig heavy chain constant region (e.g., at least a CH1 domain; at least a CH1 and a CH2 domain; a CH1, a CH2, and a CH3 domain; or a CH1, a CH2, a CH3, and a CH4 domain), or an Ig light chain constant region. Such Ig polypeptides are referred to herein as "target Ig polypeptides" or "target antibodies".

The site in an antibody into which a sulfatase motif is introduced can be any convenient site. As noted above, in some instances, the extent of modification of the native amino acid sequence of the target polypeptide is minimized, so as to minimize the number of amino acid residues that are inserted, deleted, substituted (replaced), and/or added (e.g., to the N- or C-terminus). Minimizing the extent of amino acid sequence modification of the target antibody may minimize the impact such modifications may have upon antibody function and/or structure.

An antibody heavy chain constant region can include Ig constant regions of any heavy chain isotype, non-naturally occurring Ig heavy chain constant regions (including consensus Ig heavy chain constant regions). An Ig constant region amino acid sequence can be modified to include an aldehyde tag, where the aldehyde tag is present in or adjacent a solvent-accessible loop region of the Ig constant region. An Ig constant region amino acid sequence can be modified by insertion and/or substitution of 1, 2, 3, 4, 5, 6, 7, 8, 9, 10, 11, 12, 13, 14, 15, or 16 amino acids, or more than 16 amino acids, to provide an amino acid sequence of a sulfatase motif as described above.

In some cases, an aldehyde-tagged antibody comprises an aldehyde-tagged Ig heavy chain constant region (e.g., at least a CH1 domain; at least a CH1 and a CH2 domain; a CH1, a CH2, and a CH3 domain; or a CH1, a CH2, a CH3, and a CH4 domain). The aldehyde-tagged Ig heavy chain constant region can include heavy chain constant region sequences of an IgA, IgM, IgD, IgE, IgG1, IgG2, IgG3, or IgG4 isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc., modified to include at least one sulfatase motif that can be modified by an FGE to generate an fGly-modified Ig polypeptide. Allotypic variants of Ig heavy chains are known in the art. See, e.g., Jefferis and Lefranc (2009) MAbs 1:4.

In some cases, an aldehyde-tagged antibody comprises an aldehyde-tagged Ig light chain constant region. The aldehyde-tagged Ig light chain constant region can include constant region sequences of a kappa light chain, a lambda light chain, e.g., human kappa or lambda light chain constant regions, a hybrid light chain constant region, a synthetic light chain constant region, or a consensus light chain constant region sequence, etc., that includes at least one sulfatase motif that can be modified by an FGE to generate an fGly-modified antibody. Exemplary constant regions include human gamma 1 and gamma 3 regions. With the exception of the sulfatase motif, a modified constant region may have a wild-type amino acid sequence, or it may have an amino acid sequence that is at least 70% identical (e.g., at least 80%, at least 90% or at least 95% identical) to a wild type amino acid sequence.

In some embodiments the sulfatase motif is at a position other than, or in addition to, the C-terminus of the Ig polypeptide heavy chain. As noted above, an isolated aldehyde-tagged antibody can comprise a heavy chain constant region amino acid sequence modified to include a sulfatase motif as described above, where the sulfatase motif is in or adjacent a surface-accessible loop region of the antibody heavy chain constant region.

A sulfatase motif can be provided within or adjacent one or more of these amino acid sequences of such modification sites of an Ig heavy chain. For example, an Ig heavy chain polypeptide amino acid sequence can be modified (e.g., where the modification includes one or more amino acid residue insertions, deletions, and/or substitutions) at one or more of these amino acid sequences to provide a sulfatase motif adjacent and N-terminal and/or adjacent and C-terminal to these modification sites. Alternatively or in addition, an Ig heavy chain polypeptide amino acid sequence can be modified (e.g., where the modification includes one or more amino acid residue insertions, deletions, and/or substitutions) at one or more of these amino acid sequences to provide a sulfatase motif between any two residues of the Ig heavy chain modifications sites. In some embodiments, an Ig heavy chain polypeptide amino acid sequence may be modified to include two motifs, which may be adjacent to one another, or which may be separated by one, two, three, four or more (e.g., from about 1 to about 25, from about 25 to about 50, or from about 50 to about 100, or more, amino acids. Alternatively or in addition, where a native amino acid sequence provides for one or more amino acid residues of a sulfatase motif sequence, selected amino acid residues of the modification sites of an Ig heavy chain polypeptide amino acid sequence can be modified (e.g., where the modification includes one or more amino acid residue insertions, deletions, and/or substitutions) so as to provide a sulfatase motif at the modification site.

An antibody used in an antibody-drug conjugate of the present disclosure can have any of a variety of antigen-binding specificities, including but not limited to, e.g., an antigen present on a cancer cell; an antigen present on an autoimmune cell; an antigen present on a pathogenic microorganism; an antigen present on a virus-infected cell (e.g., a human immunodeficiency virus-infected cell); an antigen present on a diseased cell; and the like. For example, an antibody conjugate can bind an antigen, where the antigen is present on the surface of the cell. An antibody conjugate of the present disclosure can bind antigen with a suitable binding affinity, e.g., from $5\times10^{-6}$ M to $10^{-7}$ M, from $10^{-7}$ M to $5\times10^{-7}$ M, from $5\times10^{-7}$ M to $10^{-8}$ M, from $10^{-8}$ M to $5\times10^{-8}$ M, from $5\times10^{-8}$ M to $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the conjugated moiety can be a drug, such as a cytotoxic compound (e.g., a cytotoxic small molecule, a cytotoxic synthetic peptide, etc.). For example, a subject antibody conjugate can be specific for an antigen on a cancer cell, where the conjugated moiety is a drug, such as a cytotoxic compound (e.g., a cytotoxic small molecule, a cytotoxic synthetic peptide, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the conjugated moiety can be a drug, such as a viral fusion inhibitor. For example, a subject antibody conjugate can bind an antigen present on a cell infected with a virus, and the conjugated moiety can be a drug, such as a viral fusion inhibitor.

Drugs for Conjugation to a Polypeptide

The present disclosure provides drug-polypeptide conjugates (e.g., antibody-drug conjugates). Drugs suitable for use, or that can be modified to be rendered suitable for use, as a reactive partner to conjugate to a polypeptide (e.g., an antibody) as described herein include a camptothecine or a camptothecine derivative. For example, camptothecine and camptothecine derivatives suitable for use in the conjugates and compounds described herein include, by are not limited to compounds of formula (II), (IIa), (IIb), (IIc) and (IId), as described above.

Embodiments of the present disclosure include conjugates where a polypeptide (e.g., an antibody) is conjugated to one or more drug moieties, such as 2 drug moieties, 3 drug moieties, 4 drug moieties, 5 drug moieties, 6 drug moieties, 7 drug moieties, 8 drug moieties, 9 drug moieties, or 10 or more drug moieties. The drug moieties may be conjugated to the antibody at one or more sites in the polypeptide (antibody), as described herein. In certain embodiments, the conjugates have an average drug-to-antibody ratio (DAR) (molar ratio) in the range of from 0.1 to 10, or from 0.5 to 10, or from 1 to 10, such as from 1 to 9, or from 1 to 8, or from 1 to 7, or from 1 to 6, or from 1 to 5, or from 1 to 4, or from 1 to 3, or from 1 to 2. In certain embodiments, the conjugates have an average DAR from 1 to 3, such as 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3. In certain embodiments, the conjugates have an average DAR of 1 to 2. In certain embodiments, the conjugates have an average DAR of 2 to 3. By average is meant the arithmetic mean.

Formulations

The conjugates of the present disclosure can be formulated in a variety of different ways. In general, where the conjugate is an antibody-drug conjugate, the conjugate is formulated in a manner compatible with the drug, the antibody, the condition to be treated, and the route of administration to be used.

In some embodiments, provided is a pharmaceutical composition that includes any of the conjugates of the present disclosure and a pharmaceutically-acceptable excipient.

The conjugate (e.g., antibody-drug conjugate) can be provided in any suitable form, e.g., in the form of a pharmaceutically acceptable salt, and can be formulated for any suitable route of administration, e.g., oral, topical or parenteral administration. Where the conjugate is provided as a liquid injectable (such as in those embodiments where they are administered intravenously or directly into a tissue), the conjugate can be provided as a ready-to-use dosage form, or as a reconstitutable storage-stable powder or liquid composed of pharmaceutically acceptable carriers and excipients.

Methods for formulating conjugates can be adapted from those readily available. For example, conjugates can be provided in a pharmaceutical composition comprising a therapeutically effective amount of a conjugate and a pharmaceutically acceptable carrier (e.g., saline). The pharmaceutical composition may optionally include other additives (e.g., buffers, stabilizers, preservatives, and the like). In some embodiments, the formulations are suitable for administration to a mammal, such as those that are suitable for administration to a human.

Methods of Treatment

The antibody-drug conjugates of the present disclosure find use in treatment of a condition or disease in a subject that is amenable to treatment by administration of the parent drug (i.e., the camptothecine or camptothecine derivative prior to conjugation to the antibody).

In some embodiments, provided are methods that include administering to a subject an effective amount (e.g., a therapeutically effective amount) of any of the conjugates of the present disclosure.

In certain aspects, provided are methods of delivering a drug to a target site in a subject, the method including administering to the subject a pharmaceutical composition including any of the conjugates of the present disclosure, where the administering is effective to release a therapeutically effective amount of the drug (e.g., a camptothecine or a camptothecine derivative) from the conjugate at the target site in the subject. For example, as described herein, antibody-drug conjugates of the present disclosure can include a cleavable linker, such as an enzymatically cleavable linker that includes a first enzymatically cleavable moiety and a second enzymatically cleavable moiety. In some instances, the cleavable linker can be cleaved under appropriate conditions to separate or release the drug from the antibody at a desired target site of action for the drug. For example, the second cleavable moiety, which protects the first cleavable moiety from cleavage, may be cleaved in order to allow the first cleavable moiety to be cleaved, which results in cleavage of the cleavable linker into two or more portions, thus releasing the drug from the antibody-drug conjugate at a desired site of action.

In certain embodiments, the first cleavable moiety can be an enzymatically cleavable moiety. In some instances, the enzyme that facilitates cleavage of the first cleavable moiety is an enzyme that is administered to the subject to be treated (i.e., exogenous to the subject to be treated). For example, a first enzyme can be administered before, concurrently with, or after administration of an antibody-drug conjugate described herein.

In certain embodiments, the second cleavable moiety can be an enzymatically cleavable moiety. In some instances, the enzyme that facilitates cleavage of the second cleavable moiety is an enzyme that is administered to the subject to be treated (i.e., exogenous to the subject to be treated). For example, a second enzyme can be administered before, concurrently with, or after administration of an antibody-drug conjugate described herein. In certain embodiments, the first enzyme and the second enzyme are different enzymes.

In other instances, the first enzyme that facilitates cleavage of the first cleavable moiety is an enzyme that is present in the subject to be treated (i.e., endogenous to the subject to be treated). For instance, the first enzyme may be present at the desired site of action for the drug of the antibody-drug conjugate. The antibody of the antibody-drug conjugate may be specifically targeted to a desired site of action (e.g., may specifically bind to an antigen present at a desired site of action), where the desired site of action also includes the presence of the first enzyme. In some instances, the first enzyme is present in an overabundance at the desired site of action as compared to other areas in the body of the subject to be treated. For example, the first enzyme may be overexpressed at the desired site of action as compared to other areas in the body of the subject to be treated. In some instances, the first enzyme is present in an overabundance at the desired site of action due to localization of the first enzyme at a particular area or location. For instance, the first enzyme may be associated with a certain structure within the desired site of action, such as lysosomes. In some cases, the first enzyme is present in an overabundance in lysosomes as compared to other areas in the body of the subject. In some embodiments, the lysosomes that include the first enzyme, are found at a desired site of action for the drug of the antibody-drug conjugate, such as the site of a cancer or tumor that is to be treated with the drug. In certain embodiments, the first enzyme is a protease, such as a human protease enzyme (e.g., cathepsin B).

In certain embodiments, the second enzyme that facilitates cleavage of the second cleavable moiety is an enzyme that is present in the subject to be treated (i.e., endogenous to the subject to be treated). For instance, the second enzyme may be present at the desired site of action for the drug of the antibody-drug conjugate. The antibody of the antibody-drug conjugate may be specifically targeted to a desired site of action (e.g., may specifically bind to an antigen present at a desired site of action), where the desired site of action also includes the presence of the second enzyme. In some instances, the second enzyme is present in an overabundance at the desired site of action as compared to other areas in the body of the subject to be treated. For example, the second enzyme may be overexpressed at the desired site of action as compared to other areas in the body of the subject to be treated. In some instances, the second enzyme is present in an overabundance at the desired site of action due to localization of the second enzyme at a particular area or location. For instance, the second enzyme may be associated with a certain structure within the desired site of action, such as lysosomes. In some cases, the second enzyme is present in an overabundance in lysosomes as compared to other areas in the body of the subject. In some embodiments, the lysosomes that include the second enzyme, are found at a desired site of action for the drug of the antibody-drug conjugate, such as the site of a cancer or tumor that is to be treated with the drug. In certain embodiments, the second enzyme is a glycosidase, such as a galactosidase, a glucosidase, or a mannosidase.

Any suitable enzymes can be used for cleavage of the first cleavable moiety and the second cleavable moiety of the antibody-drug conjugates described herein. Other enzymes may also be suitable for use in cleavage of the first cleavable moiety and the second cleavable moiety of the antibody-drug conjugates described herein, such as but not limited to, enzymes from other vertebrates (e.g., primates, mice, rats, cats, pigs, quails, goats, dogs, rabbits, etc.).

In certain embodiments, the antibody-drug conjugate is substantially stable under standard conditions. By substantially stable is meant that the cleavable linker of the antibody-drug conjugate does not undergo a significant amount of cleavage in the absence of a first enzyme and a second enzyme as described above. For example, as described above, the second cleavable moiety can protect the first cleavable moiety from being cleaved, and as such the cleavable linker of the antibody-drug conjugate does not undergo a significant amount of cleavage in the absence of a second enzyme as described above. For instance, the cleavable linker of the antibody-drug conjugate may be substantially stable such that 25% or less of the antibody-drug conjugate is cleaved in the absence of the first enzyme and/or second enzyme, such as 20% or less, or 15% or less, or 10% or less, or 5% or less, or 4% or less, or 3% or less, or 2% or less, or 1% or less. In some cases, the antibody-drug conjugate is substantially stable such that the cleavable linker of the antibody-drug conjugate does not undergo a significant amount of cleavage in the absence of the first enzyme and/or second enzyme, but can be cleaved when in the presence of the first enzyme and the second enzyme. For example, the antibody-drug conjugate can be substantially stable after administration to a subject. In some cases, the antibody-drug conjugate is substantially stable after administration to a subject, and then, when the antibody-drug conjugate is in the presence of the second enzyme at a desired site of action, the second cleavable moiety can be cleaved from the cleavable linker, thus exposing the first cleavable moiety to subsequent cleavage by the first enzyme, which in turn releases the drug at the desired site of action. In certain embodiments, after administration to a subject the antibody-drug conjugate is stable for an extended period of time in the absence of the first enzyme and/or second enzyme, such as 1 hr or more, or 2 hrs or more, or 3 hrs or more, or 4 hrs or more, or 5 hrs or more, or 6 hrs or more, or 7 hrs or more, or 8 hrs or more, or 9 hrs or more, or 10 hrs or more, or 15 hrs or more, or 20 hrs or more, or 24 hrs (1 day) or more, or 2 days or more, or 3 days or more, or 4 days or more, or 5 days or more, or 6 days or more, or 7 days (1 week) or more. In certain embodiments, the antibody-drug conjugate is stable at a range pH values for an extended period of time in the absence of the first enzyme and/or second enzyme, such as at a pH ranging from 2 to 10, or from 3 to 9, or from 4 to 8, or from 5 to 8, or from 6 to 8, or from 7 to 8.

As described above, the antibody-drug conjugates of the present disclosure find use in treatment of a condition or disease in a subject that is amenable to treatment by administration of the parent drug. By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The subject to be treated can be one that is in need of therapy, where the subject to be treated is one amenable to treatment using the parent drug. Accordingly, a variety of subjects may be amenable to treatment using the antibody-drug conjugates disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees and monkeys).

The amount of antibody-drug conjugate administered can be initially determined based on guidance of a dose and/or dosage regimen of the parent drug. In general, the antibody-drug conjugates can provide for targeted delivery and/or enhanced serum half-life of the bound drug, thus providing for at least one of reduced dose or reduced administrations in a dosage regimen. Thus, the antibody-drug conjugates can provide for reduced dose and/or reduced administration in a dosage regimen relative to the parent drug prior to being conjugated in an antibody-drug conjugate of the present disclosure.

Furthermore, as noted above, because the antibody-drug conjugates can provide for controlled stoichiometry of drug delivery, dosages of antibody-drug conjugates can be calculated based on the number of drug molecules provided on a per antibody-drug conjugate basis.

In some embodiments, multiple doses of an antibody-drug conjugate are administered. The frequency of administration of an antibody-drug conjugate can vary depending on any of a variety of factors, e.g., severity of the symptoms, condition of the subject, etc. For example, in some embodiments, an antibody-drug conjugate is administered once per month, twice per month, three times per month, every other week, once per week (qwk), twice per week, three times per week, four times per week, five times per week, six times per week, every other day, daily (qd/od), twice a day (bds/bid), or three times a day (tds/tid), etc.

Methods of Treating Cancer

The present disclosure provides methods that include delivering a conjugate of the present disclosure to an individual having a cancer. The methods are useful for treating a wide variety of cancers, including, but not limited to breast, ovarian, colon, lung, stomach, and pancreatic cancer. In the context of cancer, the term "treating" includes one or more (e.g., each) of: reducing growth of a solid tumor, inhibiting replication of cancer cells, reducing overall tumor burden, and ameliorating one or more symptoms associated with a cancer.

Carcinomas that can be treated using a subject method include, but are not limited to, colon carcinoma, colorectal carcinoma, gastric carcinoma, lung carcinoma, including small cell carcinoma and non-small cell carcinoma of the lung, pancreatic carcinoma, breast carcinoma, ovarian carcinoma, prostate carcinoma, adenocarcinoma, cystadenocarcinoma, medullary carcinoma, renal cell carcinoma, ductal carcinoma in situ or bile duct carcinoma, choriocarcinoma, seminoma, embryonal carcinoma, cervical carcinoma, uterine carcinoma, testicular carcinoma, and epithelial carcinoma, etc.

In certain aspects, provided are methods of treating cancer in a subject, such methods including administering to the subject a therapeutically effective amount of a pharmaceutical composition including any of the conjugates of the present disclosure, where the administering is effective to treat cancer in the subject.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. By "average" is meant the arithmetic mean. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4' edition, Vol. 15/l, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. A variety of examples of synthetic routes that can be used to synthesize the compounds disclosed herein are described in the schemes below.

Example 1

Materials and Methods
General

Synthetic reagents were purchased from Sigma-Aldrich, Acros, AK Scientific, or other commercial sources and were used without purification. Anhydrous solvents were obtained from commercial sources in sealed bottles. Compounds 7, 13, 21, 28, 74, and 152, as well as HIPS linkers 10, 18, and 36 were obtained commercially from Shanghai Medicilon and used without purification. Compounds 156, 157, 169, and 171 were purchased from other commercial sources; synthesis of compounds 87 and 93 was previously reported. In all cases, solvent was removed under reduced pressure with a Buchi Rotovapor R-114 equipped with a Buchi V-700 vacuum pump. Column chromatography was performed with a Biotage Isolera chromatography system. Preparative HPLC purifications were performed using a Waters preparative HPLC unit equipped with a Phenomenex Kinetex 5 μm EVO C18 150×21.2 mm column. HPLC analyses were conducted on an Agilent 1100 Series Analytical HPLC equipped with a Model G1322A Degasser, Model G1311A Quarternary Pump, Model G1329A Autosampler, Model G1314 Variable Wavelength Detector, Agilent Poroshell 120 SB C18, 4.6 mm×50 mm column at room temperature using a 10-100% gradient of water and acetonitrile containing 0.1% formic acid. HPLCs were monitored at 254 or 205 nm.

Synthesis of HIPS Constructs Bearing Camptothecines

Scheme 1. Synthesis of intermediate 6.

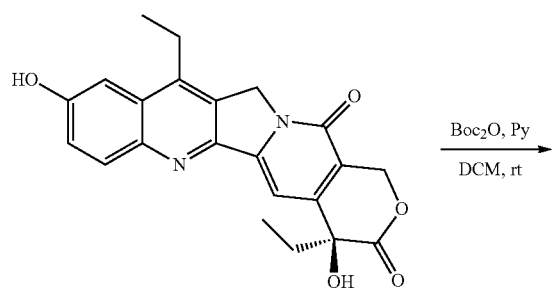

1

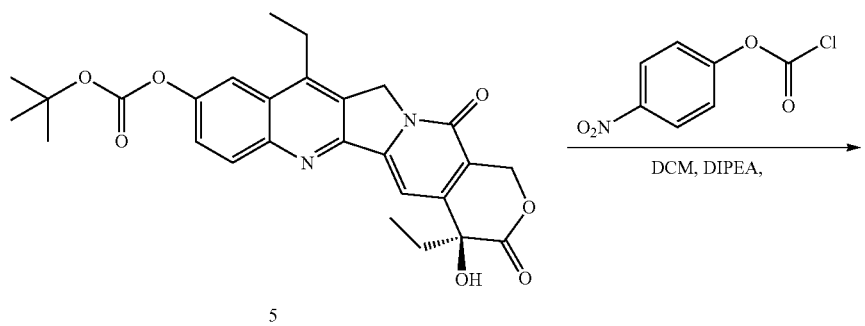

5

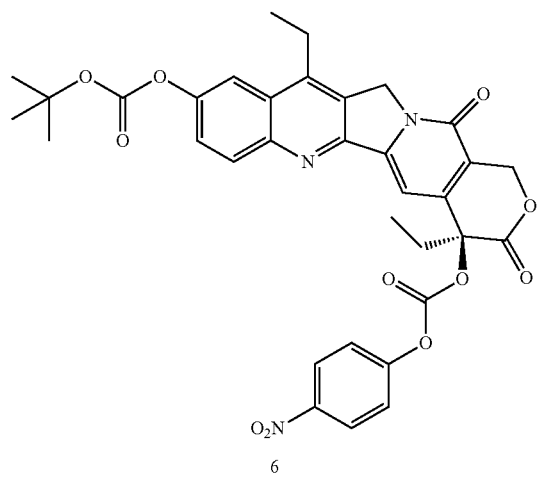

6

Preparation of (S)-tert-butyl (4,11-diethyl-4-hydroxy-3,14-dioxo-3,4,12,14-tetrahydro-1H-pyrano[3',4':6,7]indolizino[1,2-b]quinolin-9-yl) carbonate (5)

To a solution of SN-38 1 (158 mg, 0.402 mmol) and Boc$_2$O (114 mg, 1.3 mmol) in dichloromethane (16 mL) was added pyridine (0.980 mL, 12.2 mmol) at 0° C. After one hour the solution was allowed to warm up to room temperature and stirred for two hours. The reaction mixture was then concentrated under vacuum, and the residue was purified on silica gel (hexane/EtOAc, 100:0 to 0:100 v/v) to yield 5 (160 mg, 80%) as an off-white solid. LRMS (ESI): m/z 493.2 [M+H]+, Calcd for C$_{27}$H$_{29}$N$_2$O$_7$ m/z 493.2.

Preparation of (S)-tert-butyl (4,11-diethyl-3,14-dioxo-3,4,12,14-tetrahydro-1H-pyrano[3',4':6,7]indolizino[1,2-b]quinoline-4,9-diyl) (4-nitrophenyl) bis(carbonate) (6)

To a solution of 5 (15 mg, 0.030 mmol) in dichloromethane (1 mL) was added nitrophenyl chloroformate (6 mg, 0.030 mmol) and DIPEA (11 mg, 0.060 mmol) at 0° C. The solution was allowed to warm to room temperature and stirred for 3 hours. The reaction mixture was then concentrated and used in the next step without further purification. LRMS (ESI): m/z 658.2 [M+H]+, Calcd for C$_{34}$H$_{32}$N$_3$O$_{11}$ m/z 652.2.

Scheme 2. Synthesis of construct 12.

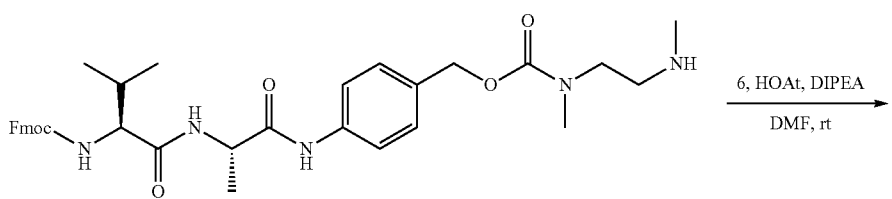

7

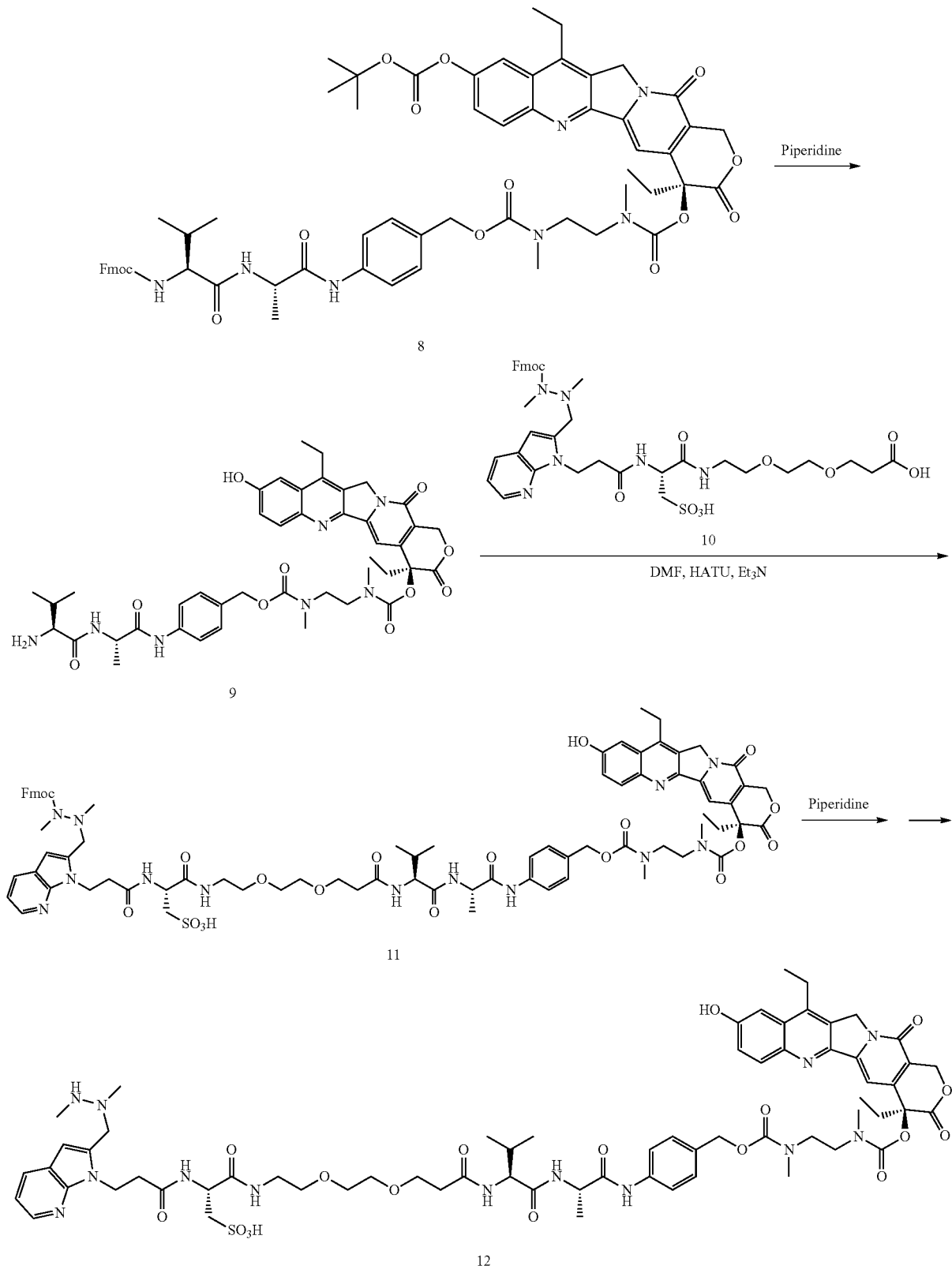

Preparation of 4-((S)-2-((S)-2-((((9H-fluoren-9-yl)methoxy)carbonyl)amino)-3-methylbutanamido)propanamido)benzyl ((S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)ethane-1,2-diylbis(methylcarbamate) (8)

To a solution of PNP carbonate 6 (20 mg, 0.030 mmol) and amine 7 (46 mg, 0.076 mmol) in DMF (1 mL) was added DIPEA (26 uL, 0.15 mmol). The reaction mixture was stirred overnight at room temperature and used further in synthesis without purification. LRMS (ESI): m/z 1148.4 [M+H]$^+$, Calcd for $C_{63}H_{70}N_7O_{14}$ m/z 1148.5.

Preparation of 4-((S)-2-((S)-2-amino-3-methylbutanamido)propanamido)benzyl ((S)-4,11-diethyl-9-hydroxy-3,14-dioxo-3,4,12,14-tetrahydro-1H-pyrano[3',4':6,7]indolizino[1,2-b]quinolin-4-yl) ethane-1,2-diylbis(methylcarbamate) (9)

To a solution of compound 8 (35 mg, 30 µmol) in DMF (1 mL) was added piperidine (100 µL) at room temperature. After 30 minutes, the mixture was purified by reversed-phase chromatography on C18 column (H$_2$O/CH$_3$CN with 0.05% TFA, 9:1 to 35:65 v/v). The fractions containing the desired compound were pooled and concentrated under vacuum to yield compound 9 (2.0 mg, 8% yield) as an off-white solid. LRMS (ESI): m/z 826.3 [M+H]$^+$, Calcd for $C_{43}H_{52}N_7O_{10}$ m/z 826.4.

Preparation of (2S,5S,36R)-36-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-1-((4-((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)phenyl)amino)-5-isopropyl-2-methyl-1,4,7,35-tetraoxo-10,13,16,19,22,25,28,31-octaoxa-3,6,34-triazaheptatriacontane-37-sulfonic Acid (11)

To a solution of amine 9 (2 mg, 2.4 µmol) and carboxylic acid 10 (2 mg, 2.5 µmol) in DMF (0.5 mL) was added HATU (1.3 mg, 3.3 µmol) and DIPEA (1.3 µL, 7 µmol). The reaction was complete after 30 minutes and the crude solution of 11 was taken to the next step without further purification. LRMS (ESI): m/z 1603.2 [M+H]$^+$, Calcd for $C_{81}H_{96}N_{13}O_{20}S$ m/z 1602.7.

Preparation of (2S,5S,36R)-1-((4-((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)phenyl)amino)-36-(3-(2-((1,2-dimethylhydrazinyl)methyl)-1H-pyrrolo[2,3-b]pyridin-1-yl)propanamido)-5-isopropyl-2-methyl-1,4,7,35-tetraoxo-10,13,16,19,22,25,28,31-octaoxa-3,6,34-triazaheptatriacontane-37-sulfonic Acid (12)

To a crude solution of 11 (~2.4 µmol) in DMF (0.5 mL) was added piperidine (50 µL). After stirring for 15 minutes at room temperature, the reaction mixture was directly purified by reversed phase HPLC using C18 column (H$_2$O/CH$_3$CN with 0.05% TFA, 100:0 to 40:60 v/v). Product 12 was obtained as a white solid (0.8 mg, 20% yield). LRMS (ESI): m/z 690.9 [M+2H]$^{++}$, Calcd for $C_{66}H_{87}N_{13}O_{18}S$ m/z 690.6.

Scheme 3. Synthesis of SN-38 construct 20.

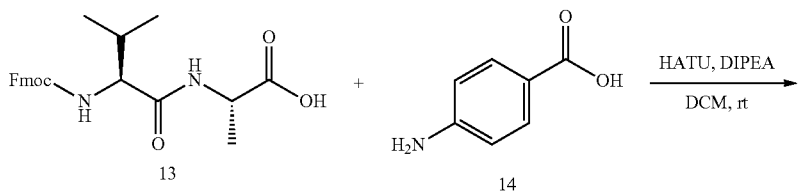

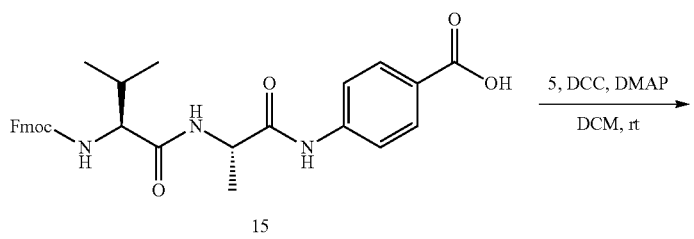

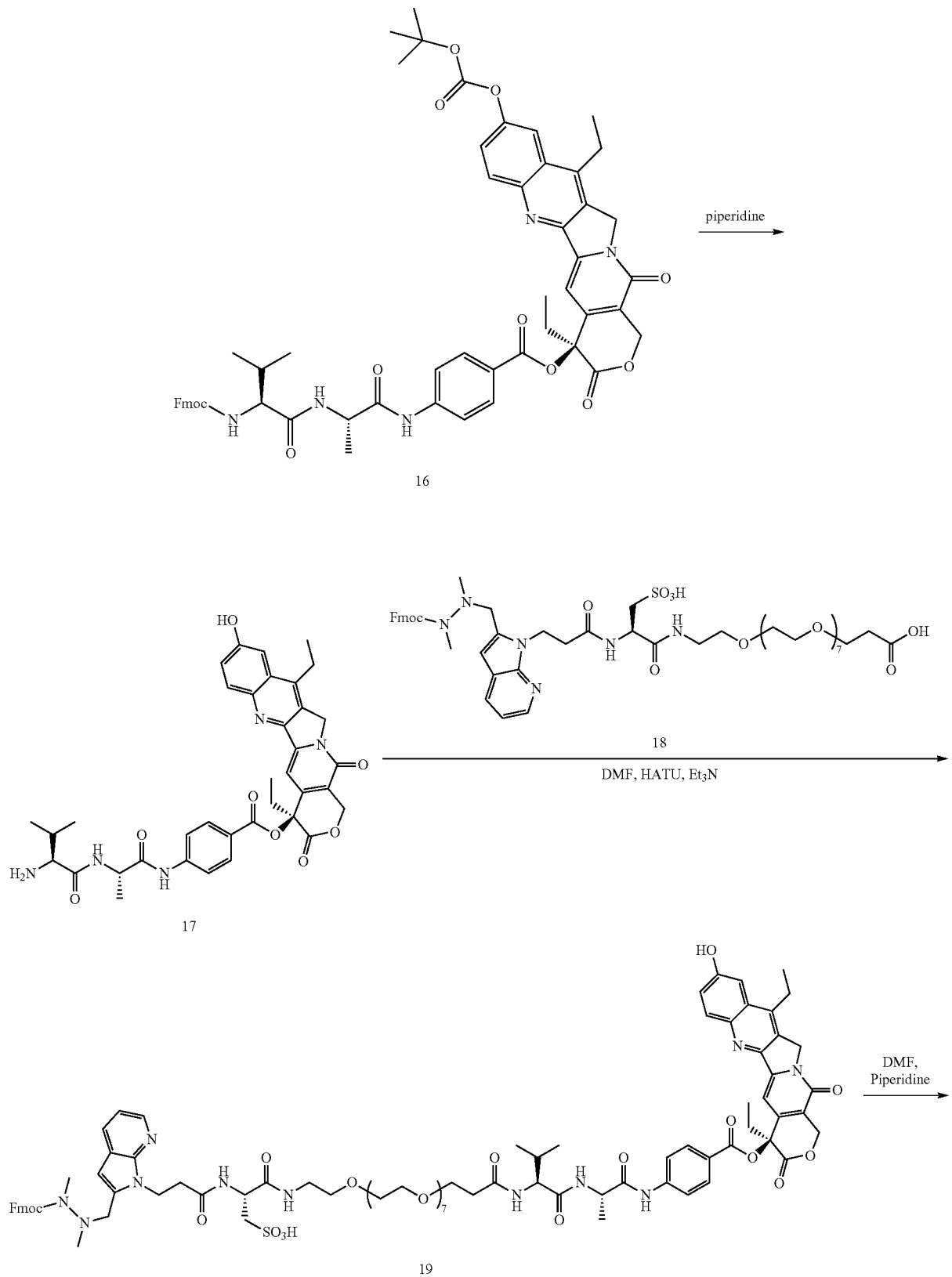

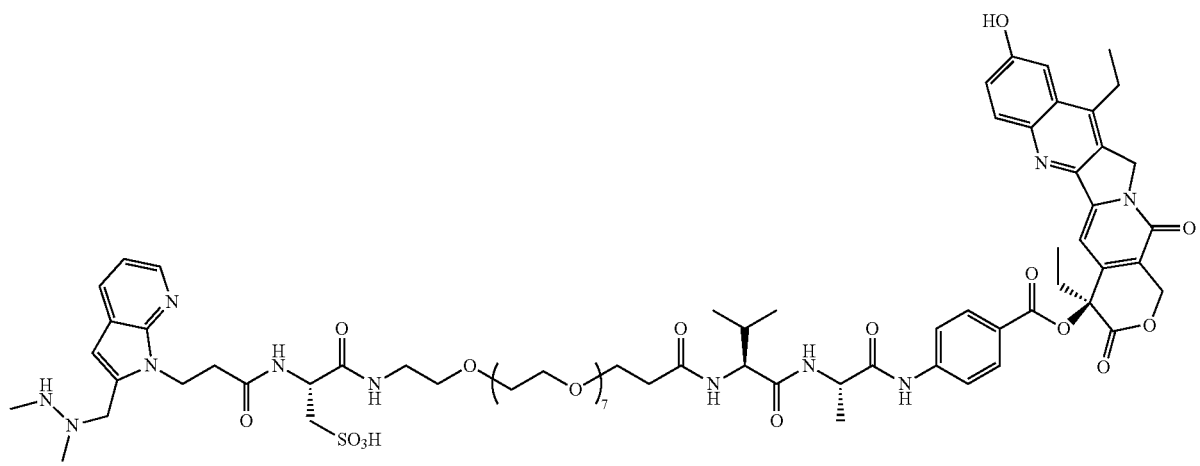

20

Preparation of 4-((S)-2-((S)-2-((((9H-fluoren-9-yl)methoxy)carbonyl)amino)-3-methylbutanamido)propanamido)benzoic Acid (15)

To a solution of Fmoc-Val-Ala-OH 13 (38 mg, 93 µmol) and HATU (35 mg, 93 µmol) in DMF (1 mL) was added DIPEA (32 uL, 196 µmol). The solution was stirred for 30 minutes at room temperature, afterwards, 4-amino benzoic acid 14 was added (51 mg, 372 µmol). After stirring for 15 minutes, the reaction mixture was purified by reversed phase chromatography on C18 column (H$_2$O/CH$_3$CN with 0.05% TFA, 90:10 to 30:70 v/v) to remove excess 4-aminobenzoic acid and used in the next step without further purification. LRMS (ESI): m/z 530.2 [M+H]$^+$, Calcd for C$_{30}$H$_{32}$N$_3$O$_6$ m/z 530.2.

Preparation of (S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl 4-((S)-2-((S)-2-((((9H-fluoren-9-yl)methoxy)carbonyl)amino)-3-methylbutanamido)propanamido)benzoate (16)

To the crude carboxylic acid 15 in dichloromethane (2 mL) and DMF (0.5 mL) was added Boc-protected SN-38 5 (10 mg, 20 µmol), followed by DCC (38 mg, 180 µmol) and DMAP (16 mg, 130 µmol) at 0° C. After 1 h, the reaction was allowed to warm to room temperature and stirred overnight. The mixture was concentrated under vacuum and used without further purification. LRMS (ESI): m/z 1004.5 [M+H]$^+$, Calcd for C$_{57}$H$_{58}$N$_5$O$_{12}$ m/z 1004.4.

Preparation of (S)-4,11-diethyl-9-hydroxy-3,14-dioxo-3,4,12,14-tetrahydro-1H-pyrano[3',4':6,7]indolizino[1,2-b]quinolin-4-yl 4-((S)-2-((S)-2-amino-3-methylbutanamido)propanamido)benzoate (2S,5S,36R)-36-(3-(2-((2-(((9H-fluoren-9-yl)methoxy)carbonyl)-1,2-dimethylhydrazineyl)methyl)-1H-pyrrolo[2,3-b]pyridin-1-yl)propanamido)-1-((4-((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)phenyl)amino)-5-isopropyl-2-methyl-1,4,7,35-tetraoxo-10,13,16,19,22,25,28,31-octaoxa-3,6,34-triazaheptatriacontane-37-sulfonate (R)-1-(2-((2-(((9H-fluoren-9-yl)methoxy)carbonyl)-1,2-dimethylhydrazineyl)methyl)-1H-pyrrolo[2,3-b]pyridin-1-yl)-3,6-dioxo-5-(sulfomethyl)-10,13,16,19,22,25,28,31-octaoxa-4,7-diazatetratriacontan-34-oate (17)

To the crude compound 16 were added DMF (1 mL) followed by piperidine (50 µL) at room temperature. The mixture was stirred for 15 minutes and purified directly by reversed phased HPLC using C18 column (H$_2$O/CH$_3$CN with 0.05% TFA, 100:0 to 30:70 v/v). Fractions containing the desired compound were pooled and concentrated under vacuum to yield 17 (3 mg, 27% over 2 steps) as an off-white solid. LRMS (ESI): m/z 682.3 [M+H]$^+$, Calcd for C$_{37}$H$_{40}$N$_5$O$_8$ m/z 682.3.

Preparation of (S)-4,11-diethyl-9-hydroxy-3,14-dioxo-3,4,12,14-tetrahydro-1H-pyrano[3',4':6,7]indolizino[1,2-b]quinolin-4-yl 4-((S)-2-((S)-2-amino-3-methylbutanamido)propanamido)benzoate (2S,5S,36R)-36-(3-(2-((2-(((9H-fluoren-9-yl)methoxy)carbonyl)-1,2-dimethylhydrazineyl)methyl)-1H-pyrrolo[2,3-b]pyridin-1-yl)propanamido)-1-((4-((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)phenyl)amino)-5-isopropyl-2-methyl-1,4,7,35-tetraoxo-10,13,16,19,22,25,28,31-octaoxa-3,6,34-triazaheptatriacontane-37-sulfonate (R)-1-(2-((2-(((9H-fluoren-9-yl)methoxy)carbonyl)-1,2-dimethylhydrazineyl)methyl)-1H-pyrrolo[2,3-b]pyridin-1-yl)-3,6-dioxo-5-(sulfomethyl)-10,13,16,19,22,25,28,31-octaoxa-4,7-diazatetratriacontan-34-oate (19)

To a solution of amine 17 (3 mg, 4.4 µmol) and carboxylic acid 18 (7 mg, 6.6 µmol) in DMF (0.5 mL) was added HATU (2.5 mg, 6.6 µmol) and DIPEA (3.4 µL, 20 µmol). The reaction was complete after 30 minutes, and product 19 was used crude without further purification. LRMS (ESI): m/z 1722.5 [M+H]$^+$, Calcd for $C_{87}H_{108}N_{11}O_{24}S$ m/z 1722.7.

Preparation of (2S,5S,36R)-36-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-1-((4-(((4-(((S)-4,11-diethyl-9-hydroxy-3,14-dioxo-3,4,12,14-tetrahydro-1H-pyrano[3',4':6,7]indolizino[1,2-b]quinolin-4-yl)oxy)-4-oxobutyl)(methyl)carbamoyl)oxy)methyl)phenyl)amino)-5-isopropyl-2-methyl-1,4,7,35-tetraoxo-10,13,16,19,22,25,28,31-octaoxa-3,6,34-triazaheptatriacontane-37-sulfonic Acid (20)

To a crude solution of 19 (4.4 µmol) in DMF (0.5 mL) was added piperidine (50 µL). After stirring 15 minutes, the solution was purified by reversed phase chromatography using C18 column ($H_2O/CH_3CN$ with 0.05% TFA, 100:0 to 40:60 v/v). Product 20 was obtained as a white solid (1.5 mg, 21% yield). LRMS (ESI): m/z 1722.5 [M+2H]$^{++}$, Calcd for $C_{72}H_{99}N_{11}O_{22}S$ m/z 750.8.

Scheme 3. Synthesis of SN-38 construct 27.

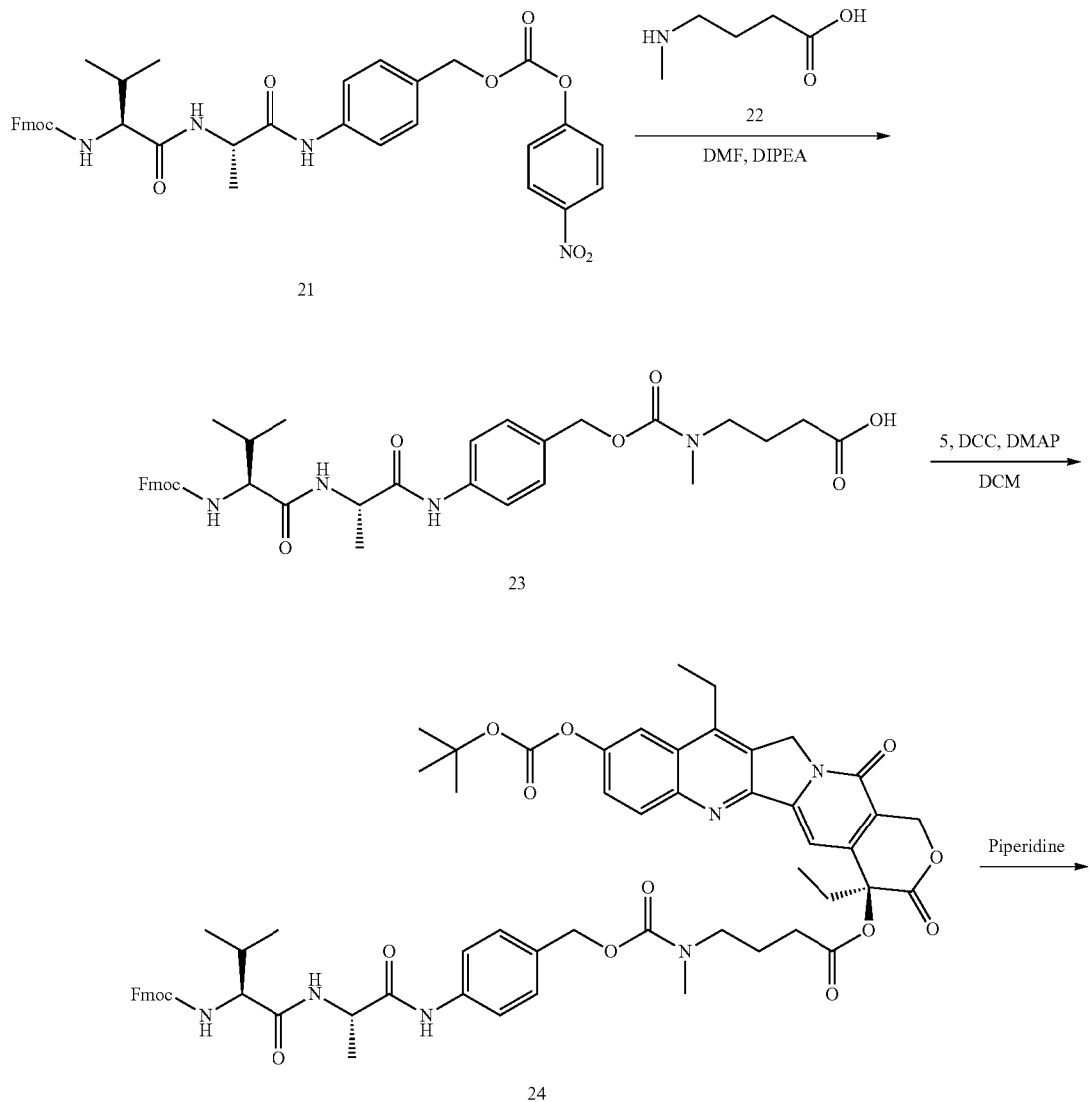

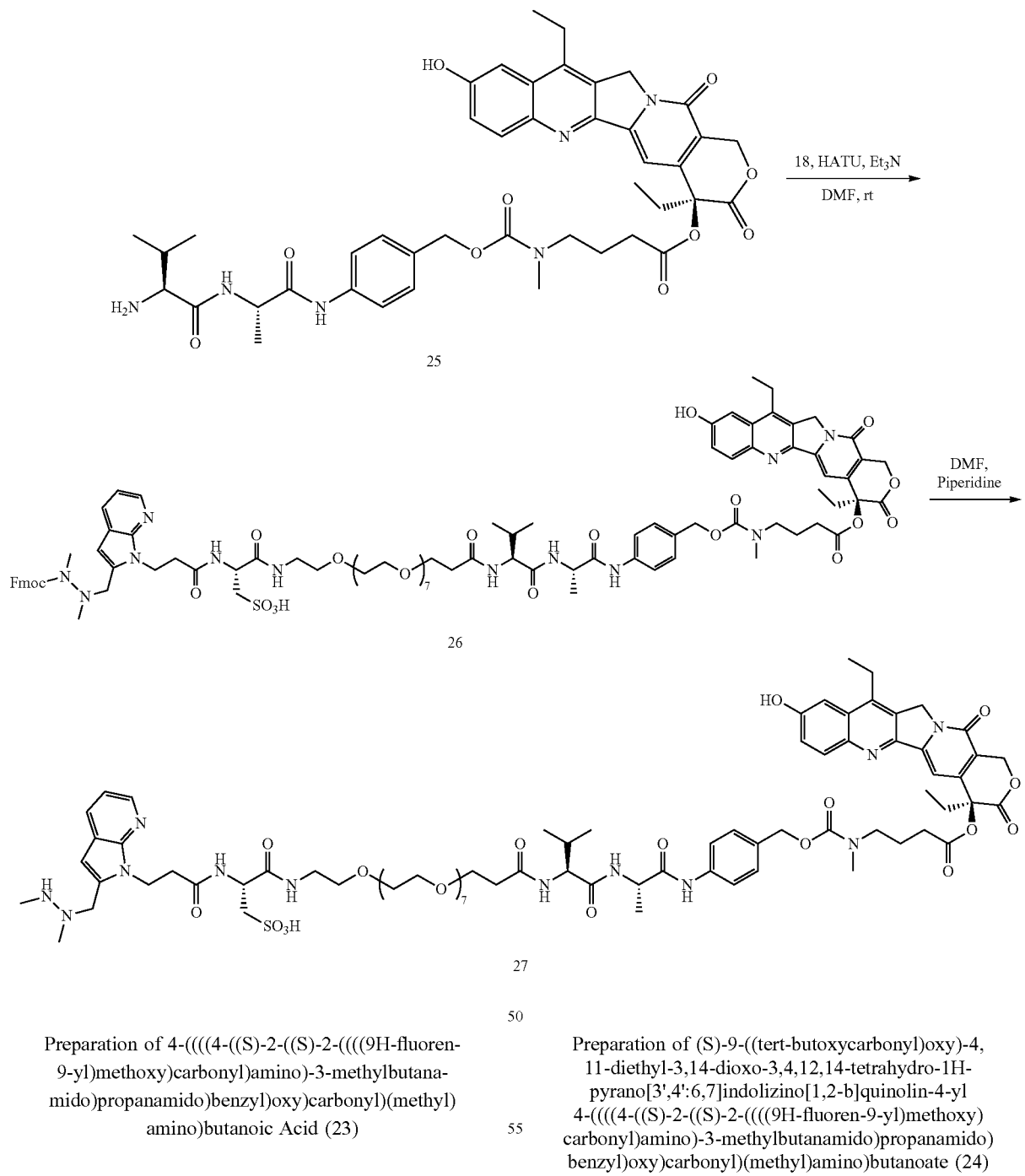

Preparation of 4-(((((4-((S)-2-((S)-2-((((9H-fluoren-9-yl)methoxy)carbonyl)amino)-3-methylbutanamido)propanamido)benzyl)oxy)carbonyl)(methyl)amino)butanoic Acid (23)

To a solution of PNP carbonate 21 (100 mg, 0.15 mmol) and 4-(methylamino)butyric acid 22 (27 mg, 0.18 mmol) in DCM (1 mL) were added DIPEA (72 uL, 0.36 mmol). The reaction was stirred overnight and then purified by reversed phase chromatography on C18 column ($H_2O/CH_3CN$ with 0.05% TFA, 100:0 to 0:100 v/v). Product 23 was obtained as a white solid (60 mg, 63% yield). LRMS (ESI): m/z 681.3 [M+Na]$^-$, Calcd for $C_{36}H_{42}N_{4Na}O_8$ m/z 681.3.

Preparation of (S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl 4-(((((4-((S)-2-((S)-2-((((9H-fluoren-9-yl)methoxy)carbonyl)amino)-3-methylbutanamido)propanamido)benzyl)oxy)carbonyl)(methyl)amino)butanoate (24)

To a solution of carboxylic acid 23 (60 mg, 92 μmol) in dichloromethane (1 mL) and DMF (0.25 mL) was added Boc-protected SN-38 5 (15 mg, 30 μmol), followed by DCC (21 mg, 90 μmol), and DMAP (12 mg, 99 μmol) at 0° C. After 1 h, the reaction was allowed to warm up to room temperature and stirred overnight. Reaction mixture was concentrated under vacuum, and crude product 24 was used without further purification. LRMS (ESI): m/z 1133.4 [M+H]$^+$, Calcd for $C_{63}H_{69}N_6O_{14}$ m/z 1133.5.

Preparation of (S)-4,11-diethyl-9-hydroxy-3,14-dioxo-3,4,12,14-tetrahydro-1H-pyrano[3',4':6,7]indolizino[1,2-b]quinolin-4-yl 4-((((4-((S)-2-((S)-2-amino-3-methylbutanamido)propanamido)benzyl)oxy)carbonyl)(methyl)amino)butanoate (25)

To the crude compound 24 was added DMF (1 mL) followed by piperidine (50 μL). The mixture was stirred for 15 minutes and purified by reversed phased HPLC using C18 column (H$_2$O/CH$_3$CN with 0.05% TFA, 100:0 to 40:60 v/v). The fractions containing the desired compound were pooled and concentrated under vacuum to yield 25 (14 mg, 57% over 2 steps) as an off-white solid. LRMS (ESI): m/z 811.3 [M+H]$^+$, Calcd for C$_{43}$H$_{51}$N$_6$O$_{10}$ m/z 811.4.

Preparation of (2S,5S,36R)-36-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-1-((4-((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)phenyl)amino)-5-isopropyl-2-methyl-1,4,7,35-tetraoxo-10,13,16,19,22,25,28,31-octaoxa-3,6,34-triazaheptatriacontane-37-sulfonic Acid (26)

To a mixture of amine 25 (4 mg, 4.9 μmol) and carboxylic acid 18 (7.8 mg, 7.4 μmol) in DMF (0.5 mL) were added HATU (2.8 mg, 7.4 μmol) and DIPEA (3.8 μL, 22 μmol) at room temperature. After 30 minutes, reaction mixture was concentrated under vacuum, and crude compound 26 was taken to the next step without further purification. LRMS (ESI): m/z 926.6 [M+2H]$^{++}$, Calcd for C$_{93}$H$_{120}$N$_{12}$O$_{26}$S m/z 926.9.

Preparation of (2S,5S,36R)-36-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-1-((4-(((((S)-4,11-diethyl-9-hydroxy-3,14-dioxo-3,4,12,14-tetrahydro-1H-pyrano[3',4':6,7]indolizino[1,2-b]quinolin-4-yl)oxy)-4-oxobutyl)(methyl)carbamoyl)oxy)methyl)phenyl)amino)-5-isopropyl-2-methyl-1,4,7,35-tetraoxo-10,13,16,19,22,25,28,31-octaoxa-3,6,34-triazaheptatriacontane-37-sulfonic Acid (27)

To a crude solution of 26 (4.9 μmol) in DMF (0.5 mL) was added piperidine (45 μL). After stirring for 15 minutes at room temperature, the reaction mixture was directly purified by reversed phase HPLC on C18 column (H$_2$O/CH$_3$CN with 0.05% TFA, 100:0 to 40:60 v/v). Product 27 was obtained as a white solid (3.4 mg, 42% yield). LRMS (ESI): m/z 815.5 [M+2H]$^{++}$, Calcd for C$_{78}$H$_{109}$N$_{12}$O$_{24}$S m/z 814.9.

Scheme 4. Synthesis of SN-38 construct 34.

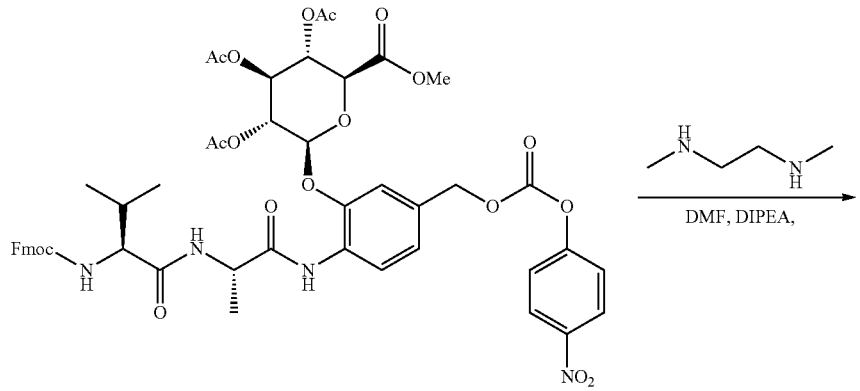

28

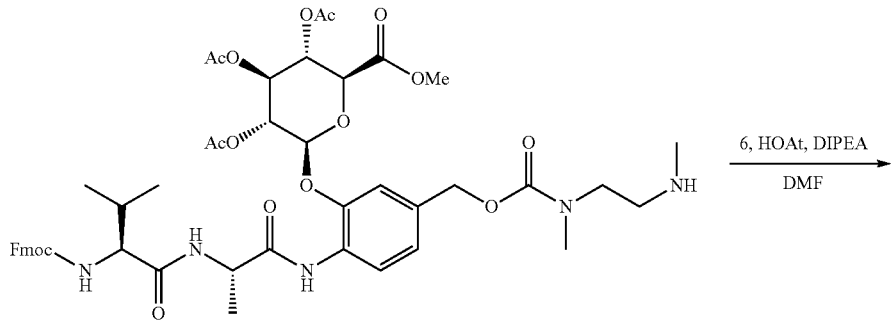

29

-continued
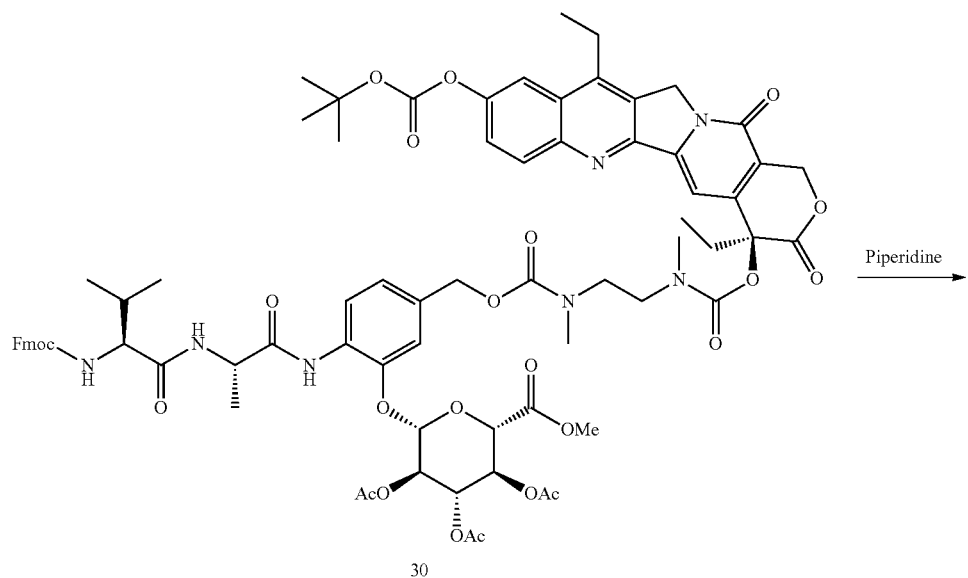
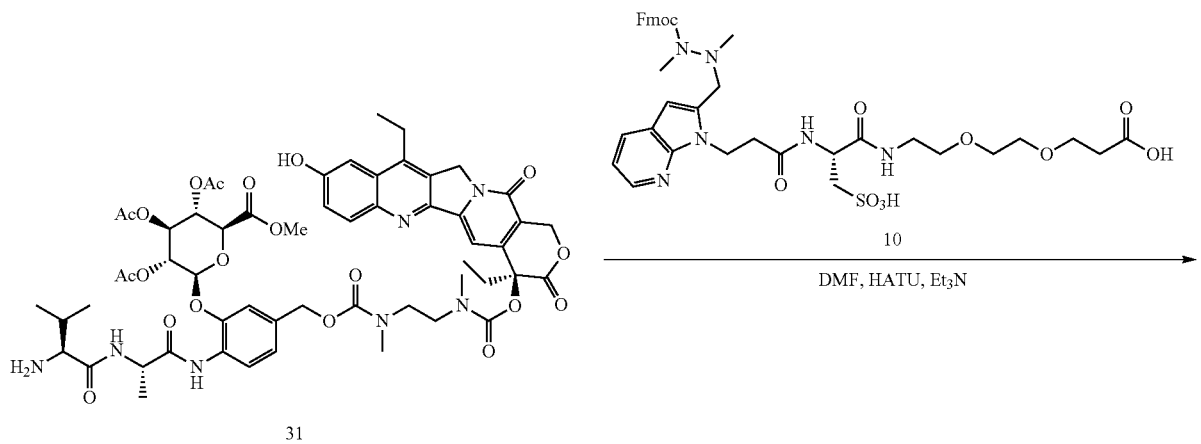
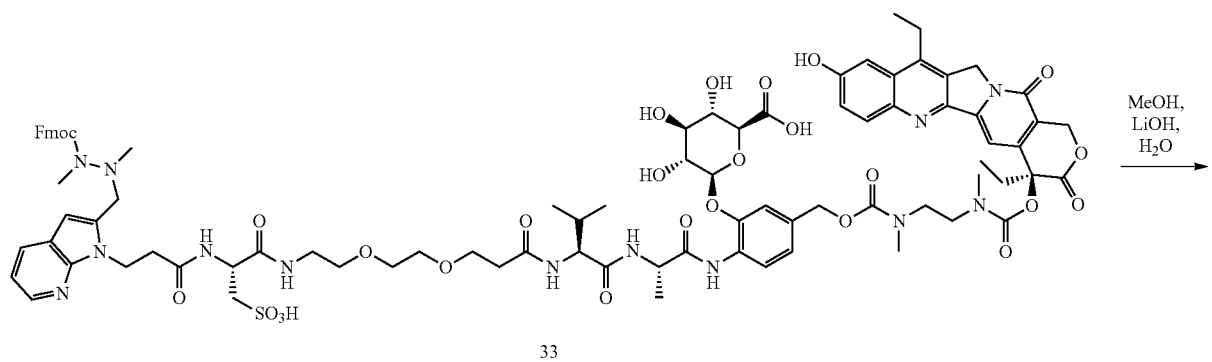

-continued

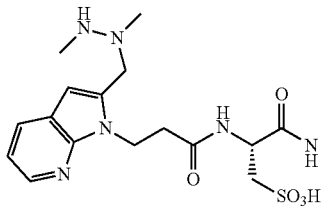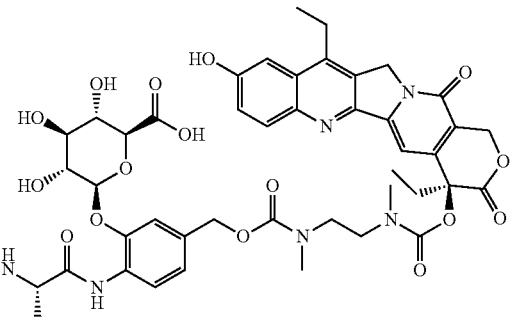

34

Preparation of (2S,3R,4S,5S,6S)-2-(2-((S)-2-((S)-2-((((9H-fluoren-9-yl)methoxy)carbonyl)amino)-3-methylbutanamido)propanamido)-5-(((methyl(2-(methylamino)ethyl)carbamoyl)oxy)methyl)phenoxy)-6-(methoxycarbonyl)tetrahydro-2H-pyran-3,4,5-triyl Triacetate (29)

To a mixture of PNP carbonate 28 (20 mg, 0.020 mmol), $N^1,N^2$-dimethylethane-1,2-diamine (3.3 mg, 0.038 mmol), and HOAT (2.7 mg, 0.020 mmol) in DMF (1 mL) were added DIPEA (6.9 uL, 0.040 mmol) at room temperature. After stirring the resulting mixture for 2 hours, the solution was purified by reversed phase HPLC on C18 column ($H_2O/CH_3CN$ with 0.05% TFA, 9:1 to 25:75 v/v) and semi-pure product 29 was used in the next step. LRMS (ESI): m/z 962.3 $[M+H]^+$, Calcd for $C_{48}H_{60}N_5O_{16}$ m/z 962.4.

Preparation of (2S,3R,4S,5S,6S)-2-(2-((S)-2-((S)-2-((((9H-fluoren-9-yl)methoxy)carbonyl)amino)-3-methylbutanamido)propanamido)-5-(((((2-(((((S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)phenoxy)-6-(methoxycarbonyl)tetrahydro-2H-pyran-3,4,5-triyl Triacetate (30)

To a mixture of PNP carbonate 6 (13 mg, 0.020 mmol), crude compound 29, and HOAT (5.4 mg, 0.040 mmol) in DMF (1 mL) were added DIPEA (6.9 uL, 0.040 mmol). The reaction was stirred for 1 hour and used without further purification. LRMS (ESI): m/z 1480.5 $[M+H]^+$, Calcd for $C_{76}H_{86}N_7O_{24}$ m/z 1480.6.

Preparation of (2S,3R,4S,5S,6S)-2-(2-((S)-2-((S)-2-amino-3-methylbutanamido)propanamido)-5-(((((2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)phenoxy)-6-(methoxycarbonyl)tetrahydro-2H-pyran-3,4,5-triyl Triacetate (31)

To a crude solution of 30 in DMF (0.5 mL) was added piperidine (30 μL) at 0° C. After stirring for 2 hours, the reaction mixture was directly purified by reversed phase HPLC on C18 column ($H_2O/CH_3CN$ with 0.05% TFA, 100:0 to 40:60 v/v). Product 31 was obtained as a white solid (5 mg, 22% yield over 3 steps). LRMS (ESI): m/z 1158.4 $[M+H]^+$, Calcd for $C_{56}H_{68}N_7O_{20}$ m/z 1158.5.

Preparation of (2S,5S,18R)-18-(3-(2-((2-(((9H-fluoren-9-yl)methoxy)carbonyl)-1,2-dimethylhydrazineyl)methyl)-1H-pyrrolo[2,3-b]pyridin-1-yl)propanamido)-1-((4-((((2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)-2-(((2S,3R,4S,5S,6S)-3,4,5-triacetoxy-6-(methoxycarbonyl)tetrahydro-2H-pyran-2-yl)oxy)phenyl)amino)-5-isopropyl-2-methyl-1,4,7,17-tetraoxo-10,13-dioxa-3,6,16-triazanonadecane-19-sulfonic Acid (33)

To a solution of amine 31 (2 mg, 2.6 μmol) and carboxylic acid 10 (2 mg, 2.6 μmol) in DMF (0.5 mL) were added HATU (1 mg, 2.6 μmol) and DIPEA (1.3 μL, 7.8 μmol). The reaction was complete after 30 minutes, and crude compound 33 was used without further purification. LRMS (ESI): m/z 1017.1 $[M+2H]^{++}$, Calcd for $C_{94}H_{111}N_{13}O_{30}S$ m/z 967.9.

Preparation of (2S,3S,4S,5R,6S)-6-(5-((((2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)-2-((2S,5S,18R)-22-(2-((1,2-dimethylhydrazinyl)methyl)-1H-pyrrolo[2,3-b]pyridin-1-yl)-5-isopropyl-2-methyl-4,7,17,20-tetraoxo-18-(sulfomethyl)-10,13-dioxa-3,6,16,19-tetraazadocosanamido)phenoxy)-3,4,5-trihydroxytetrahydro-2H-pyran-2-carboxylic Acid (34)

To the crude compound 33 in MeOH (0.6 mL) at 0° C. were added a solution of LiOH (22 mg) in water (0.9 mL). After stirring reaction mixture for 2 h, the mixture was purified by reversed phased HPLC on C18 column ($H_2O/CH_3CN$ with 0.05% TFA, 100:0 to 35:65 v/v). Fractions containing the desired compound were pooled and concentrated under vacuum to yield compound 34 (0.6 mg, 20% over 2 steps) as a white solid. LRMS (ESI): m/z 1572.5 $[M+H]^+$, Calcd for $C_{72}H_{94}N_{13}O_{25}S$ m/z 1572.6.

Scheme 5. Synthesis of intermediate 40.
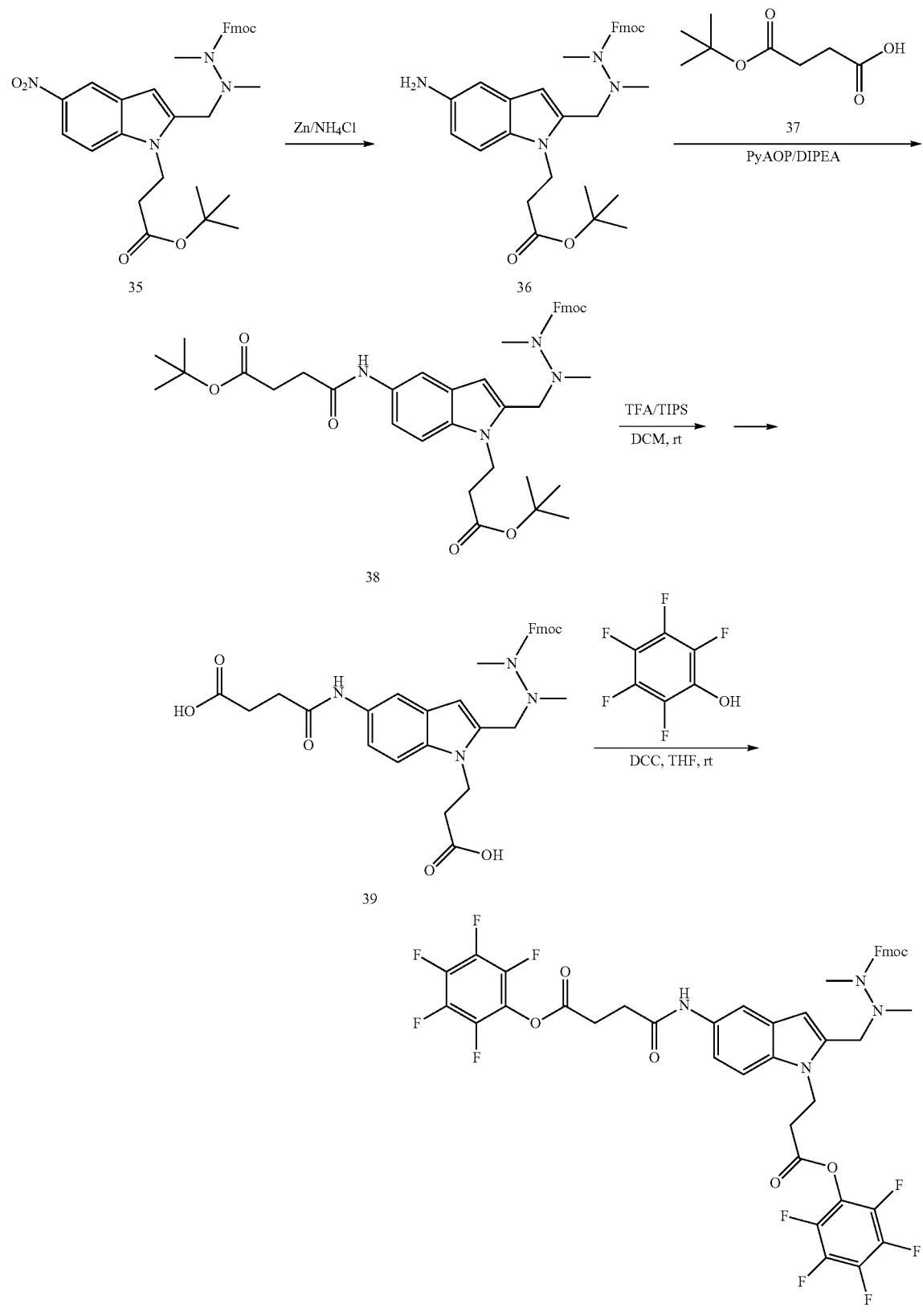

Preparation of (9H-fluoren-9-yl)methyl 2-((5-amino-1-(3-(tert-butoxy)-3-oxopropyl)-1H-indol-2-yl)methyl)-1,2-dimethylhydrazine-1-carboxylate (36)

Nitro compound 35 (116 mg, 0.20 mmol) was dissolved in 1 mL of THF and combined with a solution of ammonium chloride (85 mg, 1.6 mmol) in 0.5 mL of water and 1 mL of methanol. The resulting mixture was vigorously stirred at room temperature and treated with zinc powder (104 mg, 1.6 mmol) in small portions over 5 minutes. Reaction mixture was stirred for 2 hours, solids were filtered off, filtrate was diluted with 20 mL of saturated aqueous ammonium chloride solution, and extracted with ethyl acetate (2×25 mL). Organic extracts were dried over sodium sulfate, solvents removed under vacuum to give crude product 36 which was taken to the next step without purification. LRMS (ESI): m/z 555.3 [M+H]$^+$, Calcd for $C_{33}H_{38}N_4O_4$ m/z 555.3.

Preparation of (9H-fluoren-9-yl)methyl 2-((1-(3-(tert-butoxy)-3-oxopropyl)-5-(4-(tert-butoxy)-4-oxobutanamido)-1H-indol-2-yl)methyl)-1,2-dimethylhydrazine-1-carboxylate (38)

Crude compound 36 (~0.20 mmol) was combined with 4-(tert-butoxy)-4-oxobutanoic acid 37 (40 mg, 0.23 mmol) in 2 mL of DMF. To this mixture were added DIPEA (0.12 mL, 0.6 mmol), followed by PyAOP (110 mg, 0.21 mmol) in one portion at room temperature. After 30 minutes, reaction was quenched by pouring into saturated aqueous ammonium chloride, extracted with ethyl acetate, washed with brine, dried over sodium sulfate. Solvent was removed under vacuum to give 120 mg (0.17 mmol, 85% yield over 2 steps) of product 38 as a dark oil which was used further without additional purification. LRMS (ESI): m/z 733.4 [M+Na]$^+$, Calcd for $C_{41}H_{50}N_4O_7$ m/z 733.4.

Preparation of 4-((2-((2-(((9H-fluoren-9-yl)methoxy)carbonyl)-1,2-dimethylhydrazinyl)methyl)-1-(2-carboxyethyl)-1H-indol-5-yl)amino)-4-oxobutanoic Acid (39)

Bis-tert-butyl ester compound 38 (120 mg, 0.17 mmol) was dissolved in a mixture of 2 mL of anhydrous DCM, 2 mL of TFA, and 0.5 mL of trisopropylsilane. The resulting mixture was allowed to stand at room temperature for 4 hours. Solvents were removed under vacuum, and the residue was purified by reversed phase chromatography (C18 column, 0-70% v/v gradient of $CH_3CN/H_2O$ with 0.05% TFA) to obtain 53 mg (0.09 mmol, 53% yield) of diacid product 39. LRMS (ESI): m/z 599.3 [M+H]$^+$, Calcd for $C_{33}H_{34}N_4O_7$ m/z 599.2.

Preparation of (9H-fluoren-9-yl)methyl 1,2-dimethyl-2-((1-(3-oxo-3-(perfluorophenoxy)propyl)-5-(4-oxo-4-(perfluorophenoxy)butanamido)-1H-indol-2-yl)methyl)hydrazine-1-carboxylate (40)

To a mixture of diacid 39 (50 mg, 0.084 mmol) and pentafluorophenol (46 mg, 0.25 mmol) in 2 mL of anhydrous THF were added DCC (51 mg, 0.25 mmol) in one portion at room temperature. The resulting mixture was stirred for 16 hours, solids were filtered off, filtrate concentrated, and purified by reversed phased chromatography (C18 column, 0-100% v/v gradient of $CH_3CN/H_2O$ with 0.05% TFA). Fractions containing product were concentrated to about 20 mL, poured into 50 mL of 10% aqueous citric acid, and extracted with ethyl acetate (2×20 mL), dried over sodium sulfate. Solvents were removed under vacuum to give 67 mg (0.072 mmol, 86% yield) of bis-pfp ester product 40 as a dark viscous oil. LRMS (ESI): m/z 953.1 [M+Na]$^+$, Calcd for $C_{45}H_{32}F_{10}N_4O_7$ m/z 953.2.

Scheme 6. Synthesis of SN-38 construct 42.

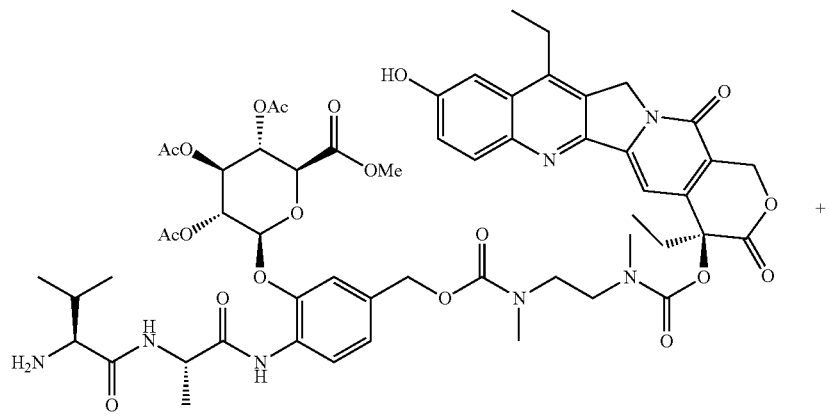

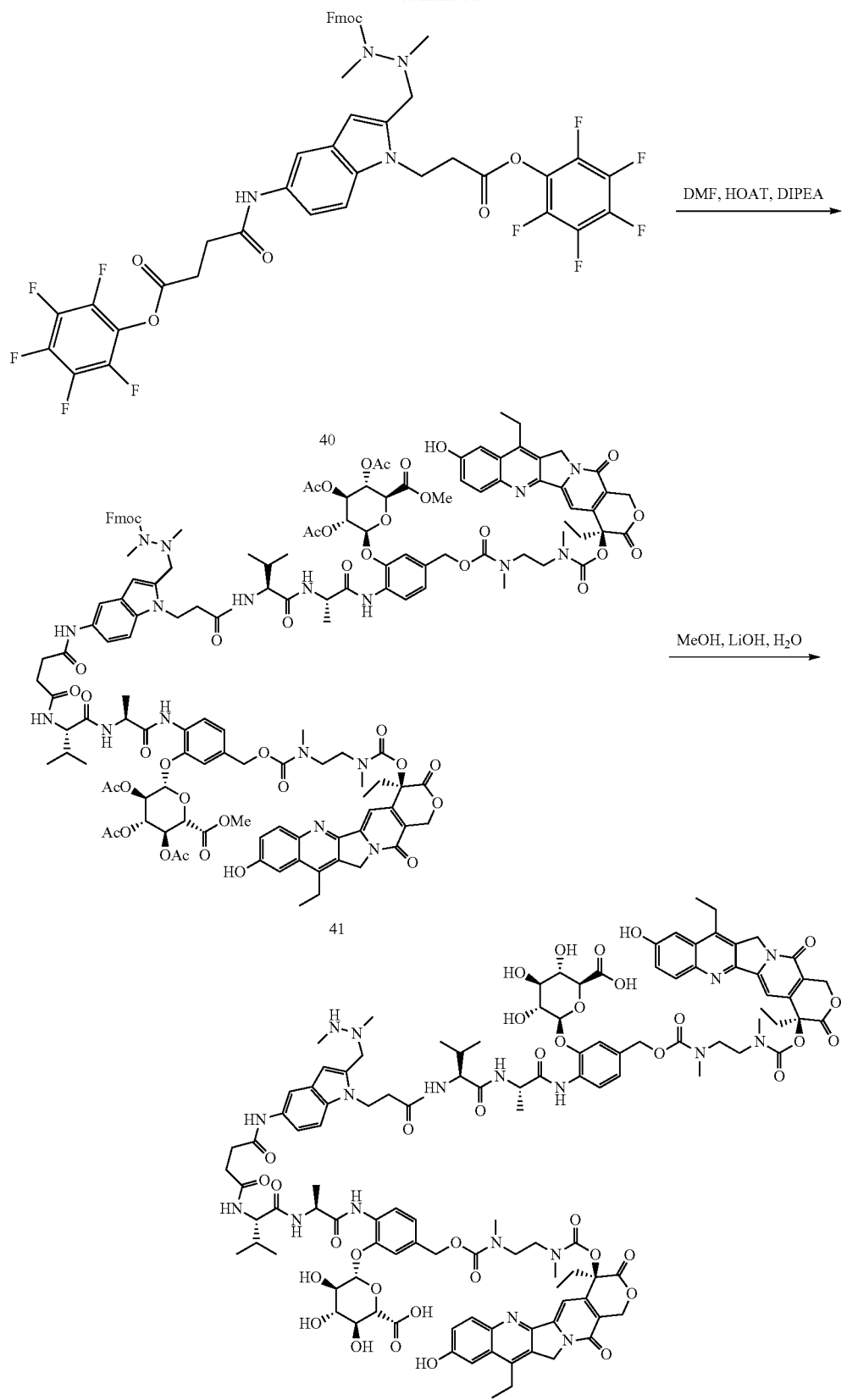

Preparation of (2S,3R,4S,5S,6S)-2-(2-((S)-2-((S)-2-(4-((2-((2-(((9H-fluoren-9-yl)methoxy)carbonyl)-1,2-dimethylhydrazineyl)methyl)-1-(3-(((S)-1-(((S)-1-((4-((((2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)-2-(((2S,3R,4S,5S,6S)-3,4,5-triacetoxy-6-(methoxycarbonyl)tetrahydro-2H-pyran-2-yl)oxy)phenyl)amino)-1-oxopropan-2-yl)amino)-3-methyl-1-oxobutan-2-yl)amino)-3-oxopropyl)-1H-indol-5-yl)amino)-4-oxobutanamido)-3-methylbutanamido)propanamido)-5-((((2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)phenoxy)-6-(methoxycarbonyl)tetrahydro-2H-pyran-3,4,5-triyl Triacetate (41)

To a mixture of bis-PFP ester 40 (1.2 mg, 1.3 μmol), amine 31 (3 mg, 2.6 μmol), and HOAT (0.45 mg, 3.3 μmol) in DMF (0.5 mL) were added DIPEA (1.1 uL, 6.5 μmol). The reaction was stirred for 1 hour at room temperature. After removing solvent under vacuum, crude intermediate 41 was taken to the next step without further purification. LRMS (ESI): m/z 1439.9 [M+2H]$^{++}$, Calcd for $C_{145}H_{166}N_{18}O_{45}$ m/z 1439.6.

Preparation of (2S,3S,4S,5R,6S)-6-(2-((S)-2-((S)-2-(4-((1-(3-(((S)-1-(((S)-1-((2-(((2S,3R,4S,5S,6S)-6-carboxy-3,4,5-trihydroxytetrahydro-2H-pyran-2-yl)oxy)-4-((((2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)phenyl)amino)-1-oxopropan-2-yl)amino)-3-methyl-1-oxobutan-2-yl)amino)-3-oxopropyl)-2-((1,2-dimethylhydrazineyl)methyl)-1H-indol-5-yl)amino)-4-oxobutanamido)-3-methylbutanamido)propanamido)-5-((((2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)(methyl)amino)ethyl)(methyl)carbamoyl)oxy)methyl)phenoxy)-3,4,5-trihydroxytetrahydro-2H-pyran-2-carboxylic Acid (42)

To the crude compound 41 in MeOH (0.6 mL) at 0° C. was added a solution of LiOH (22 mg) in water (0.9 mL). After stirring for 2 h, the mixture was purified by reversed C18 column chromatography ($H_2O$/$CH_3CN$ with 0.05% TFA, 100:0 to 35:65 v/v). The fractions containing the desired compound were pooled and concentrated under vacuum to yield 42 (0.3 mg, 8% over 2 steps) as a white solid. LRMS (ESI): m/z 1188.6 [M+2H]$^{++}$, Calcd for $C_{116}H_{140}N_{18}O_{37}$ m/z 1188.5

Scheme 7. Synthesis of belotecan construct 45

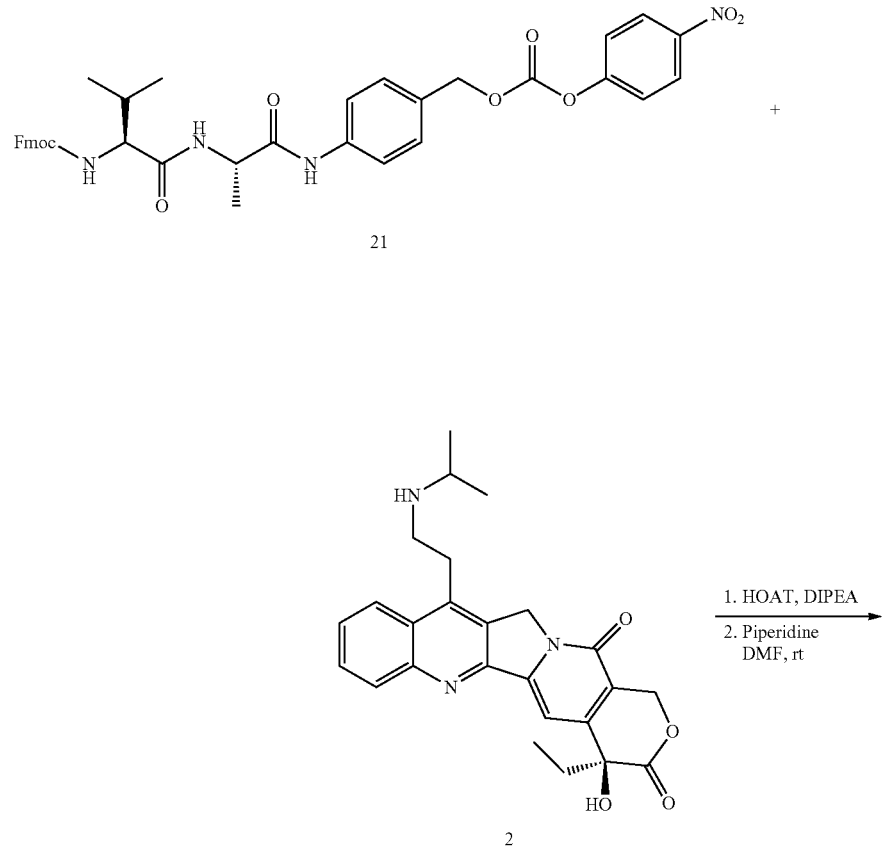

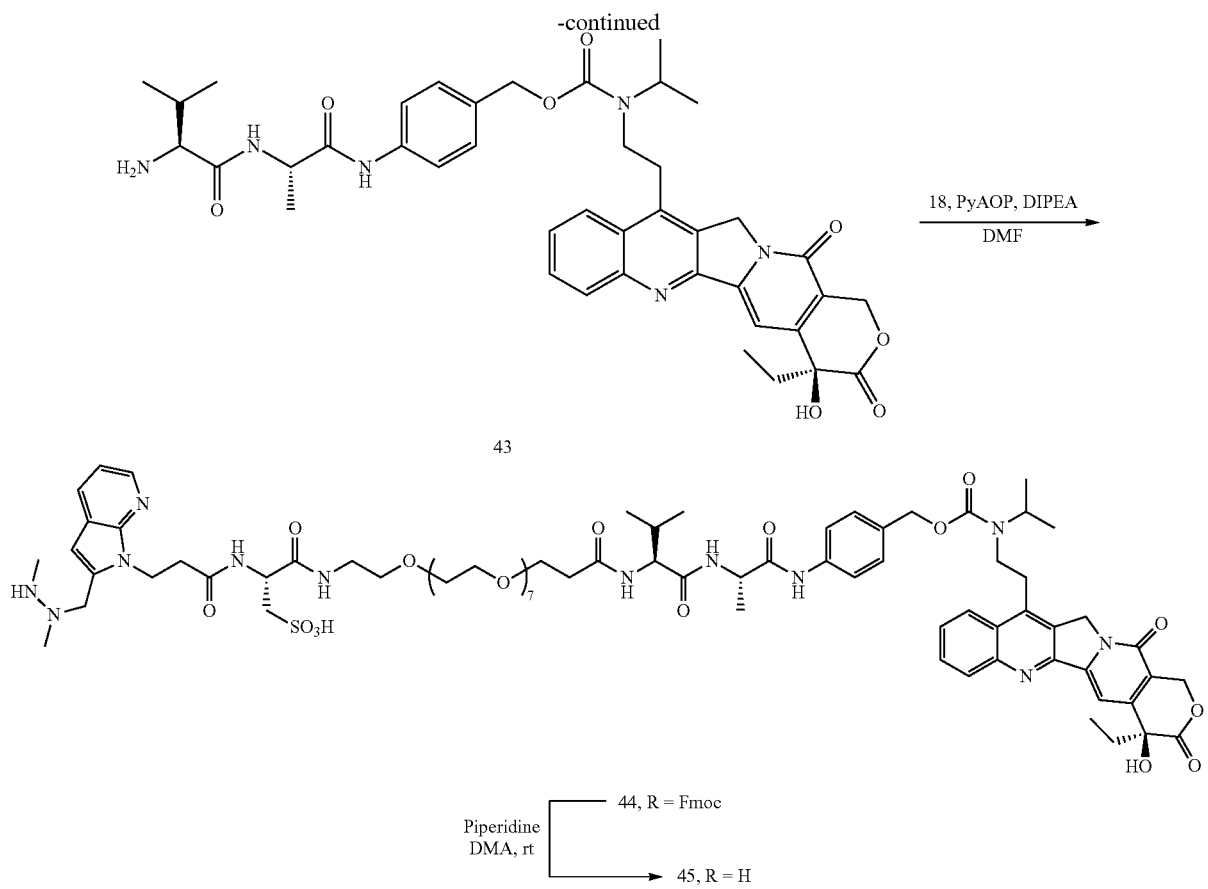

Preparation of 4-((S)-2-((S)-2-amino-3-methylbutanamido)propanamido)benzyl (2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamate (43)

To a mixture of belotecan hydrochloride (9.4 mg, 20 μmol), HOAT (2.8 mg, 20 μmol), and 7 μL of DIPEA (40 μmol) in 1 mL of DMF were added PNP carbonate 18 (13.6 mg, 20 μmol) in one portion at room temperature. After one hour, 40 μL (0.40 mmol) of piperidine was directly added to the reaction mixture. After 20 minutes, reaction mixture was purified by reversed phase HPLC (C18 column, 0-50% v/v gradient of $CH_3CN/H_2O$ with 0.05% TFA) to give 10.8 mg (14.3 μmol, 72% yield) of compound 43 as a yellow solid. LRMS (ESI): m/z 753.4 [M+H]$^+$, Calcd for $C_{41}H_{48}N_6O_8$ m/z 753.4.

Preparation of (2S,5S,36R)-36-(3-(2-((1-(((9H-fluoren-9-yl)methoxy)carbonyl)-2,2-dimethylhydrazineyl)methyl)-1H-pyrrolo[2,3-b]pyridin-1-yl)propanamido)-1-((4-(((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,35-tetraoxo-10,13,16,19,22,25,28,31-octaoxa-3,6,34-triazaheptatriacontane-37-sulfonic Acid (44)

To a mixture of compound 43 (10.8 mg, 14.3 μmol) and carboxylic acid 18 (15.2 mg, 14.3 μmol) in 2 mL of DMF were added 8 μL of DIPEA (46 μmol), followed by PyAOP (7.5 mg, 14.3 μmol). After 30 minutes at room temperature, reaction mixture was directly purified by reversed phase HPLC (C18 column, 5-95% v/v gradient of $CH_3CN/H_2O$ with 0.05% TFA). Fractions were lyophilized to give 16.5 mg (9.2 μmol, 64% yield) of compound 44 as a yellowish powder. LRMS (ESI): m/z 1794.8 [M+H]$^+$, Calcd for $C_{91}H_{116}N_{12}O_{24}S$ m/z 1794.8.

Preparation of (2S,5S,36R)-36-(3-(2-((1,2-dimethylhydrazineyl)methyl)-1H-pyrrolo[2,3-b]pyridin-1-yl)propanamido)-1-((4-(((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,35-tetraoxo-10,13,16,19,22,25,28,31-octaoxa-3,6,34-triazaheptatriacontane-37-sulfonic Acid (45)

To a solution of compound 44 (16.5 mg, 9.2 μmol) in 2 mL of DMA were added piperidine (18 μL, 0.18 mmol) at room temperature. After 30 minutes, reaction mixture was purified on reversed phase HPLC (C18 column, 0-50% v/v gradient of $CH_3CN/H_2O$ with 0.05% TFA). Pure fractions were lyophilized to give 11.2 mg (7.1 μmol, 77% yield) of compound 45 as a yellow powder. LRMS (ESI): m/z 1572.7 [M+H]$^+$, Calcd for $C_{76}H_{106}N_{12}O_{22}S$ m/z 1572.8.

Scheme 8. Synthesis of branched belotecan construct 47
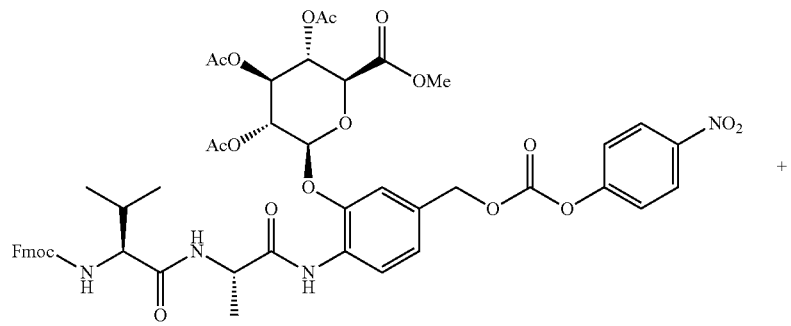
28
+
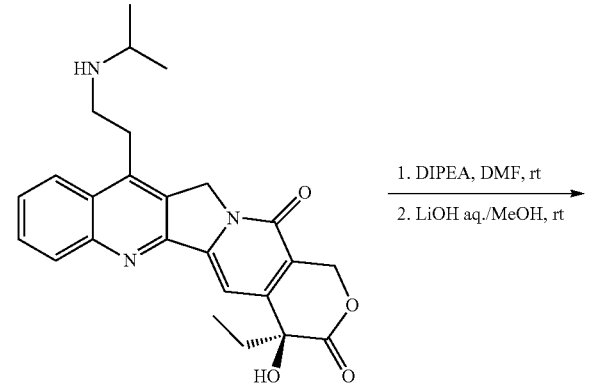
2
1. DIPEA, DMF, rt
2. LiOH aq./MeOH, rt
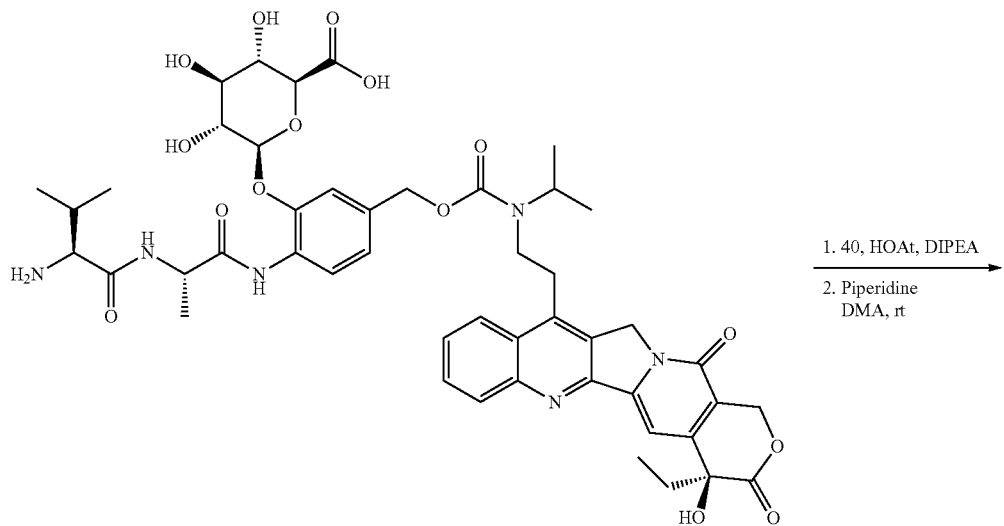
46
1. 40, HOAt, DIPEA
2. Piperidine DMA, rt

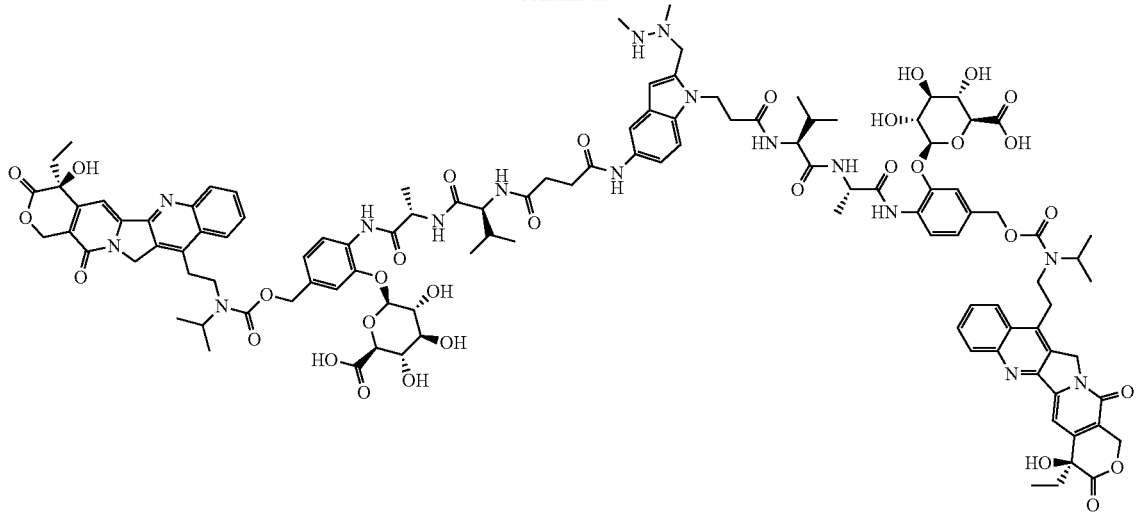

47

Preparation of (2S,3S,4S,5R,6S)-6-(2-((S)-2-((S)-2-amino-3-methylbutanamido)propanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (46)

To a solution of belotecan hydrochloride (20 mg, 43 μmol) in 2 mL DMF were added 15 uL of DIPEA (86 μmol) and 6 mg of HOAt (43 μmol). The resulting mixture was combined with PNP carbonate 28 (43 mg, 43 μmol) at room temperature and stirred for one hour, then DMF was removed under vacuum. The residue was dissolved in 1 mL of MeOH and treated with 1 mL of 1M aqueous LiOH. After 10 minutes, 1 mL of 1M aqueous HCl was added to the mixture, followed by 1 mL of 0.5M pH 4.7 acetate buffer. The resulting mixture was stirred for 30 minutes at room temperature and directly purified by reversed phase HPLC (C18 column, 0-50% v/v gradient of $CH_3CN/H_2O$ with 0.05% TFA). Solvent was removed under vacuum to give 17 mg (18 μmol, 43% yield) of compound 46 as a glassy yellow solid. LRMS (ESI): m/z 945.4 [M+H]$^+$, Calcd for $C_{47}H_{56}N_6O_{15}$ m/z 945.4.

Preparation of (2S,3S,4S,5R,6S)-6-(2-((S)-2-((S)-2-(4-((1-(3-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-1-oxopropan-2-yl)amino)-3-methyl-1-oxobutan-2-yl)amino)-3-oxopropyl)-2-((1,2-dimethylhydrazineyl)methyl)-1H-indol-5-yl)amino)-4-oxobutanamido)-3-methylbutanamido)propanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (47)

Compound 46 (17 mg, 18 μmol) was combined with bis-PFP ester 40 (8.3 mg, 9 μmol), 2.5 mg of HOAt (18 μmol), and 10 μL of DIPEA (54 μmol) in 2 mL of DMA at room temperature. After one hour, piperidine (35 μL, 0.36 mmol) was added to the reaction mixture. After 30 minutes, reaction mixture was directly purified by reversed phase HPLC (C18 column, 0-50% v/v gradient of $CH_3CN/H_2O$ with 0.05% TFA). Lyophilization of pure fractions gave 5.0 mg of compound 47 (2.2 μmol, 24% yield) as a yellowish powder. LRMS (ESI): m/z 1116.1 [M+2H]$^{++}$, Calcd for $C_{112}H_{132}N_{16}O_{33}$ m/z 1116.0.

Scheme 8. Synthesis of intermediate 50

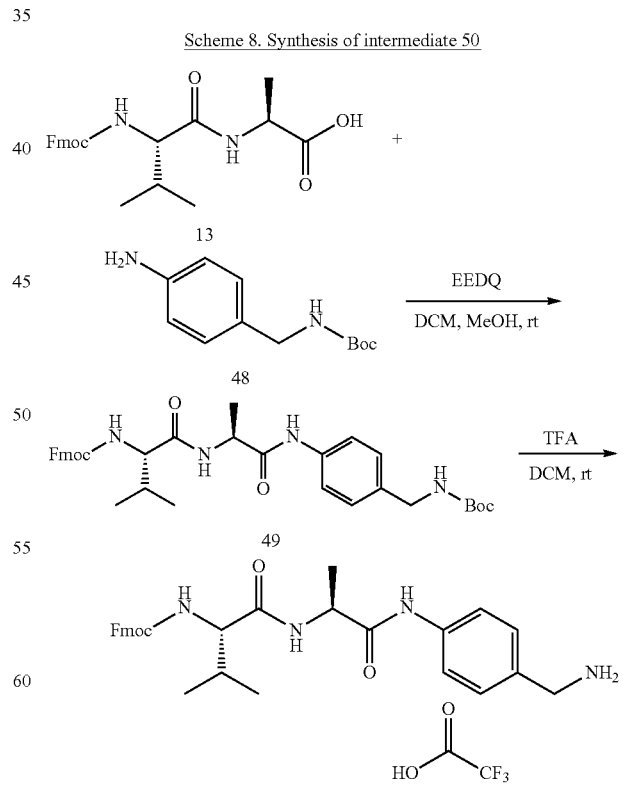

245

Preparation of (9H-fluoren-9-yl)methyl ((S)-1-(((S)-1-((4-(((tert-butoxycarbonyl)amino)methyl)phenyl)amino)-1-oxopropan-2-yl)amino)-3-methyl-1-oxobutan-2-yl)carbamate (49)

To a stirred mixture of Fmoc-Val-Ala-OH 13 (410 mg, 1.0 mmol) and tert-butyl (4-aminobenzyl)carbamate 48 (267 mg, 1.2 mmol) in 5 mL of DCM and 0.5 mL of MeOH were added EEDQ (495 mg, 2.0 mmol) in one portion at room temperature. The resulting mixture was stirred in the dark overnight, precipitate was collected by filtration, washed with MTBE, and dried on air to give 520 mg of product 49 (0.85 mmol, 85% yield) as a tan powder. LRMS (ESI): m/z 637.3 [M+Na]$^+$, Calcd for $C_{35}H_{42}N_4O_6$ m/z 637.3.

246

Preparation of (9H-fluoren-9-yl)methyl ((S)-1-(((S)-1-((4-(aminomethyl)phenyl)amino)-1-oxopropan-2-yl)amino)-3-methyl-1-oxobutan-2-yl)carbamate 2,2,2-trifluoroacetate (50)

Boc-protected compound 49 (520 mg, 0.85 mmol) was dissolved in 5 mL of DCM-TFA mixture (1:1) at room temperature. The reaction mixture was stirred for 15 minutes, then solvents were removed under vacuum. The residue was triturated with 20 mL of MTBE, and the resulting precipitate was collected by filtration, washed with MTBE, and dried on air to give 525 mg of product 50 (0.84 mmol, 99% yield) as a tan powder (TFA salt). LRMS (ESI): m/z 515.3 [M+H]$^+$, Calcd for $C_{30}H_{34}N_4O_4$ m/z 515.3.

Scheme 9. Synthesis of exatecan construct 56

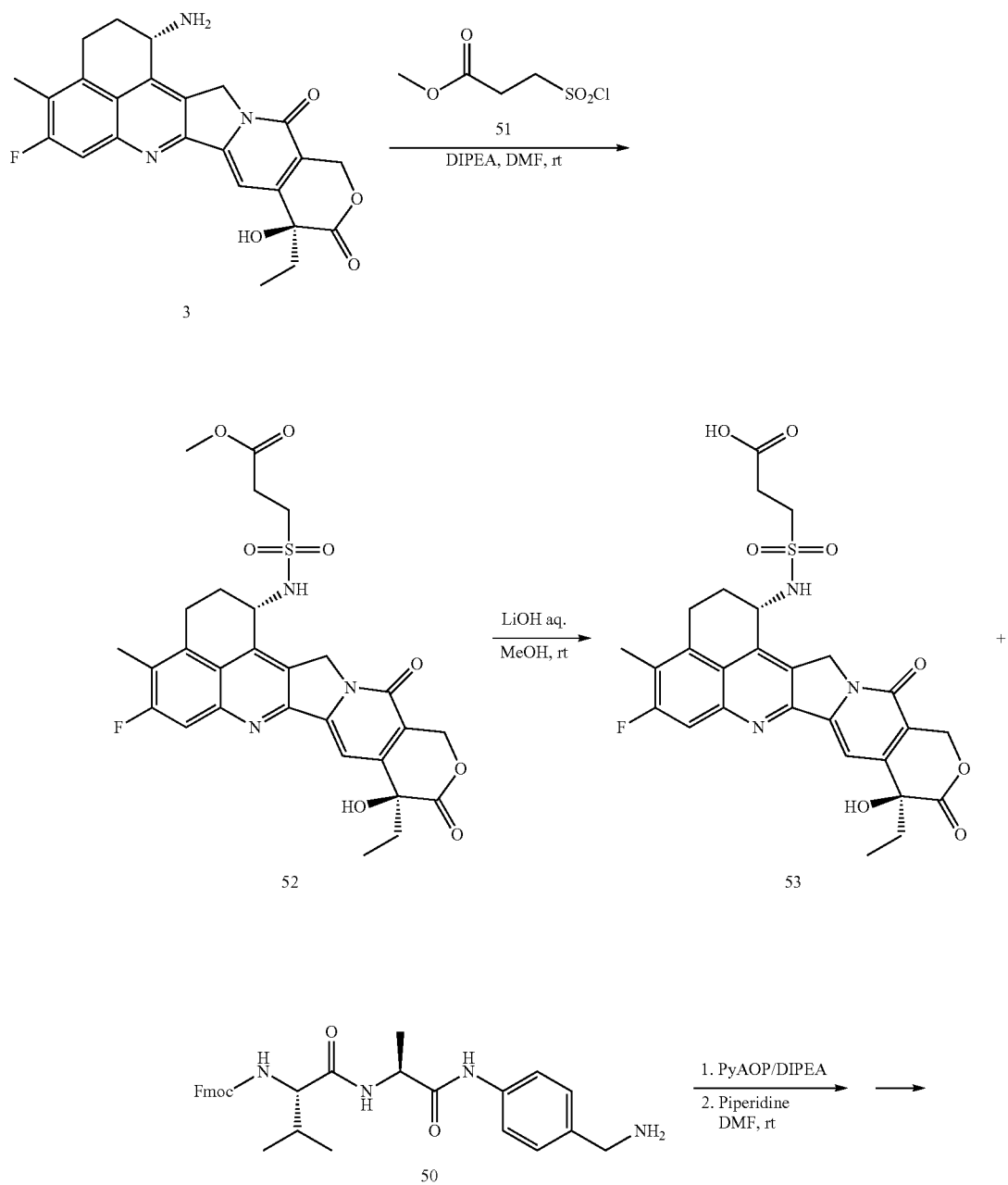

-continued

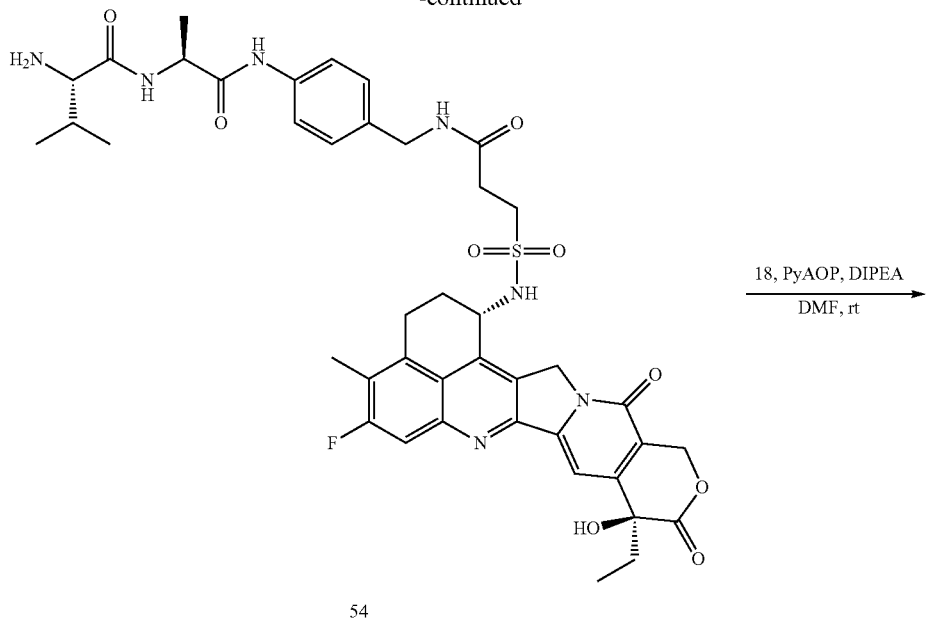

54

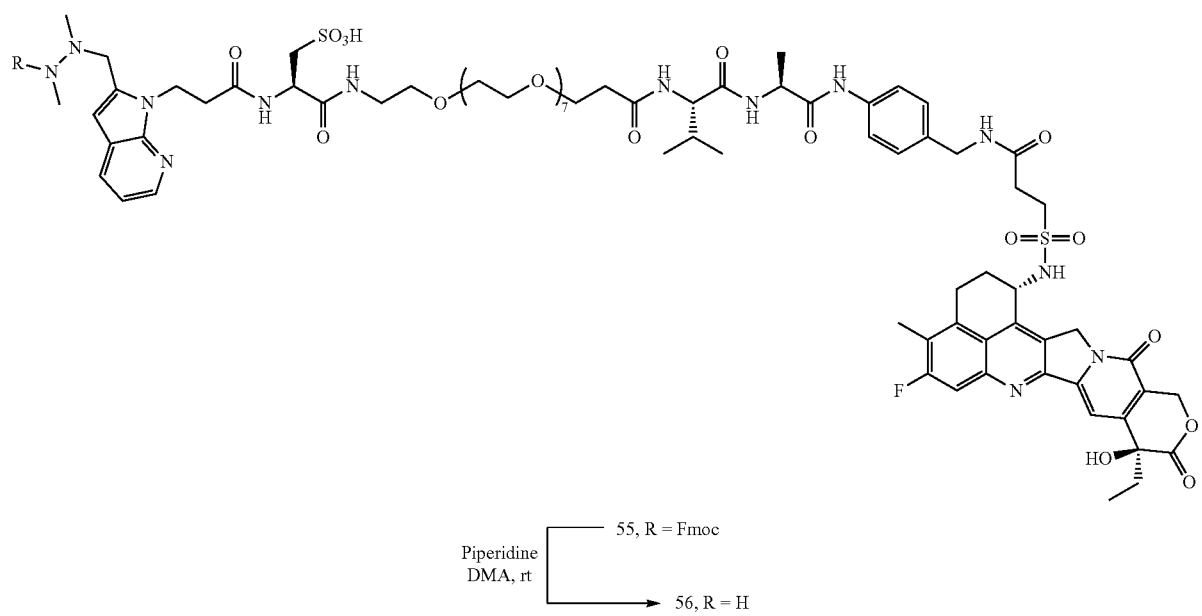

55, R = Fmoc

Piperidine
DMA, rt

56, R = H

Preparation of methyl 3-(N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)sulfamoyl)propanoate (5)

To a solution of exatecan mesylate (10 mg, 19 μmole) in 1 mL of anhydrous DMF were added 10 μL of DIPEA (56 μmole), followed by 4 μL of sulfonyl chloride 51 (21 μmole) at room temperature. After one hour, reaction mixture was directly purified on reversed phase HPLC (C18 column, 0-75% v/v gradient of $CH_3CN/H_2O$ with 0.05% TFA) to give 5 mg (9 μmole, 47% yield) of product as a yellow solid. LRMS (ESI): m/z 586.2 [M+H]+, Calcd for $C_{28}H_{28}FN_3O_8S$ m/z 586.2.

Preparation of 3-(N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)sulfamoyl)propanoic Acid (53)

Methyl ester 52 (5 mg, 8.5 μmole) was dissolved in 2 mL of methanol and treated with 1 mL of 1M aqueous LiOH at room temperature. The resulting mixture was stirred for one hour, quenched with 1 mL of 1M aqueous HCl, followed by 1 mL of 0.5M pH 4.7 acetate buffer. After 10 minutes, reaction mixture was concentrated under vacuum and purified by reversed phase HPLC (C18 column, 0-75% v/v gradient of $CH_3CN/H_2O$ with 0.05% TFA) to give 5.0 mg of carboxylic acid product 53 (8.7 mole, quant.) as a bright yellow solid. LRMS (ESI): m/z 572.2 [M+H]+, Calcd for $C_{28}H_{28}FN_3O_8S$ m/z 572.6

Preparation of (S)-2-amino-N—((S)-1-((4-((3-(N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)sulfamoyl)propanamido)methyl)phenyl)amino)-1-oxopropan-2-yl)-3-methylbutanamide (54)

To a mixture of carboxylic acid 53 (5.0 mg, 8.7 mole) and amine 50 (5.5 mg, 8.7 mole) in 1 mL of DMF were added DIPEA (4.6 µL, 26 mole), followed by PyAOP (4.6 mg, 8.7 mole) in one portion at room temperature. After 30 minutes, reaction mixture was treated with piperidine (17 µL, 0.17 mmol), stirred for 15 minutes at room temperature, and purified by reversed phase HPLC (C18 column, 0-50% v/v gradient of CH$_3$CN/H$_2$O with 0.05% TFA). Solvents were removed under vacuum to obtain 5.0 mg (5.7 mole, 66% yield) of compound 54 as a dark yellow oil. LRMS (ESI): m/z 846.4 [M+H]$^+$, Calcd for C$_{42}$H$_{48}$FN$_7$O$_9$S m/z 846.3.

Preparation of (2S,5S,36R)-36-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-1-((4-((3-(N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)sulfamoyl)propanamido)methyl)phenyl)amino)-5-isopropyl-2-methyl-1,4,7,35-tetraoxo-10,13,16,19,22,25,28,31-octaoxa-3,6,34-triazaheptatriacontane-37-sulfonic Acid (55)

To a mixture of compound 54 (5.0 mg, 4.7 mole) and carboxylic acid 18 (6.3 mg, 4.7 mole) in 1 mL of DMF were added DIPEA (3 µL, 14 mole), followed by PyAOP (3.1 mg, 4.7 mole) in one portion at room temperature. After 30 minutes, reaction mixture was directly purified by reversed phase HPLC (C18 column, 0-75% v/v gradient of CH$_3$CN/H$_2$O with 0.05% TFA) to give 6.0 mg (2.6 mole, 55% yield) of compound 55 as a yellow powder. LRMS (ESI): m/z 1887.8 [M+H]$^+$, Calcd for C$_{92}$H$_{116}$FN$_{13}$O$_{25}$S$_2$ m/z 1886.8.

Preparation of (2S,5S,36R)-36-(3-(2-((1,2-dimethylhydrazinyl)methyl)-1H-pyrrolo[2,3-b]pyridin-1-yl)propanamido)-1-((4-((3-(N-((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl)sulfamoyl)propanamido)methyl)phenyl)amino)-5-isopropyl-2-methyl-1,4,7,35-tetraoxo-10,13,16,19,22,25,28,31-octaoxa-3,6,34-triazaheptatriacontane-37-sulfonic acid (56)

To a solution of compound 55 (6.0 mg, 3.2 mole) in 1 mL of DMA were added piperidine (6.3 µL, 63 mole) at room temperature. After 30 minutes, reaction mixture was directly purified by reversed phase HPLC (C18 column, 0-50% v/v gradient of CH$_3$CN/H$_2$O with 0.05% TFA). Fractions containing product were lyophilized to obtain 3.0 mg of compound 56 (1.8 mole, 56% yield) as a yellow powder. LRMS (ESI): m/z 1665.7 [M+H]$^+$, Calcd for C$_{77}$H$_{106}$FN$_{13}$O$_{23}$S$_2$ m/z 1664.7.

Scheme 10. Synthesis of branched belotecan construct 61

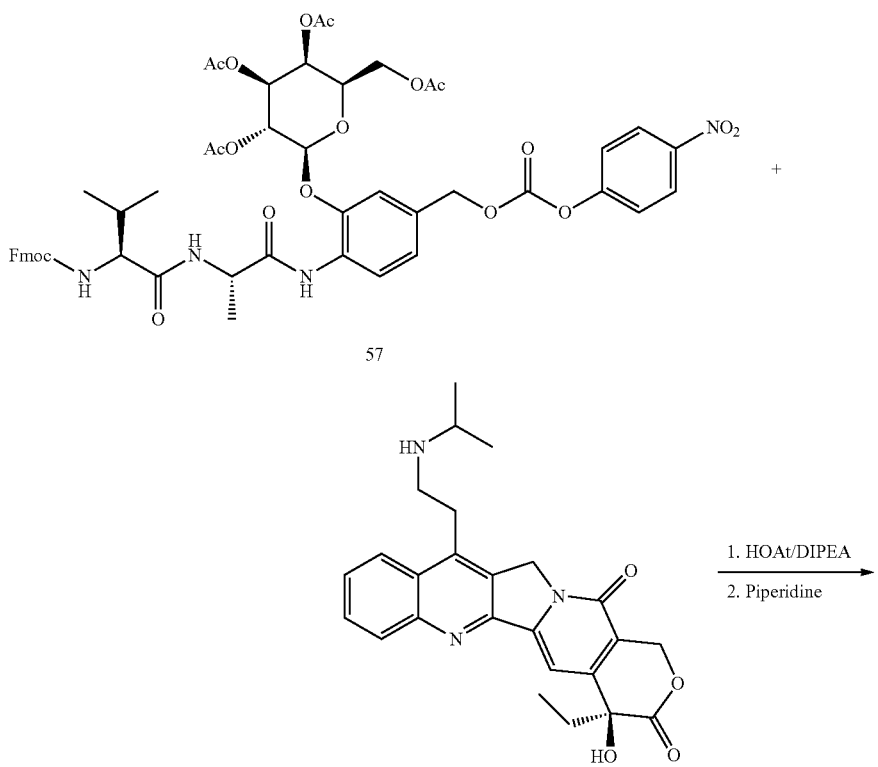

-continued
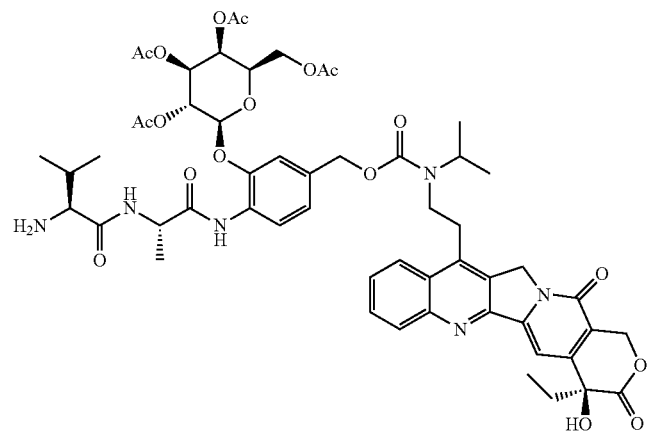
58
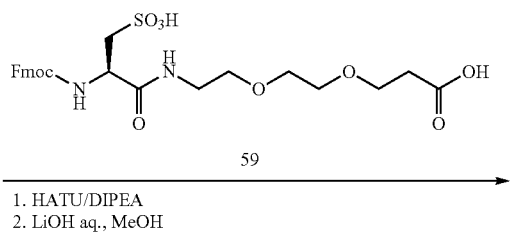
59
1. HATU/DIPEA
2. LiOH aq., MeOH
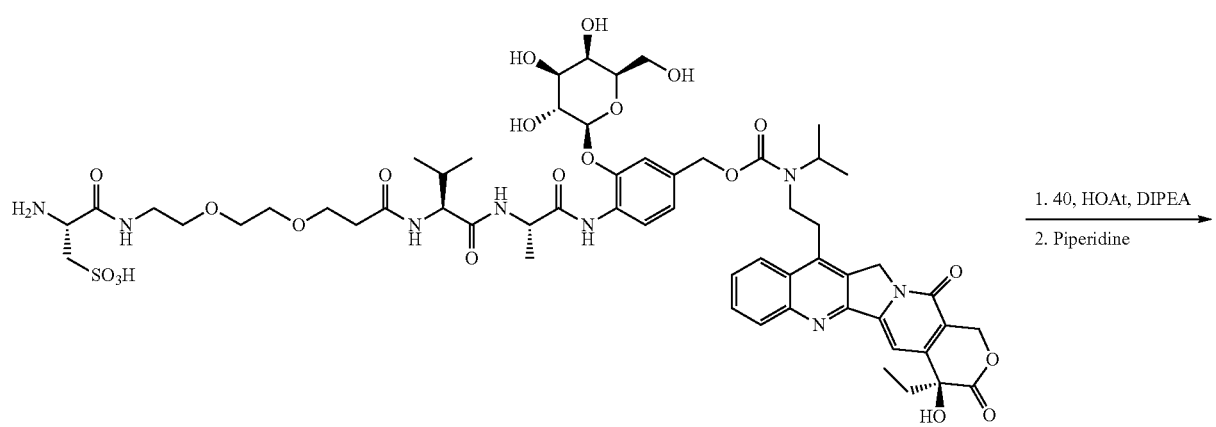
60
1. 40, HOAt, DIPEA
2. Piperidine
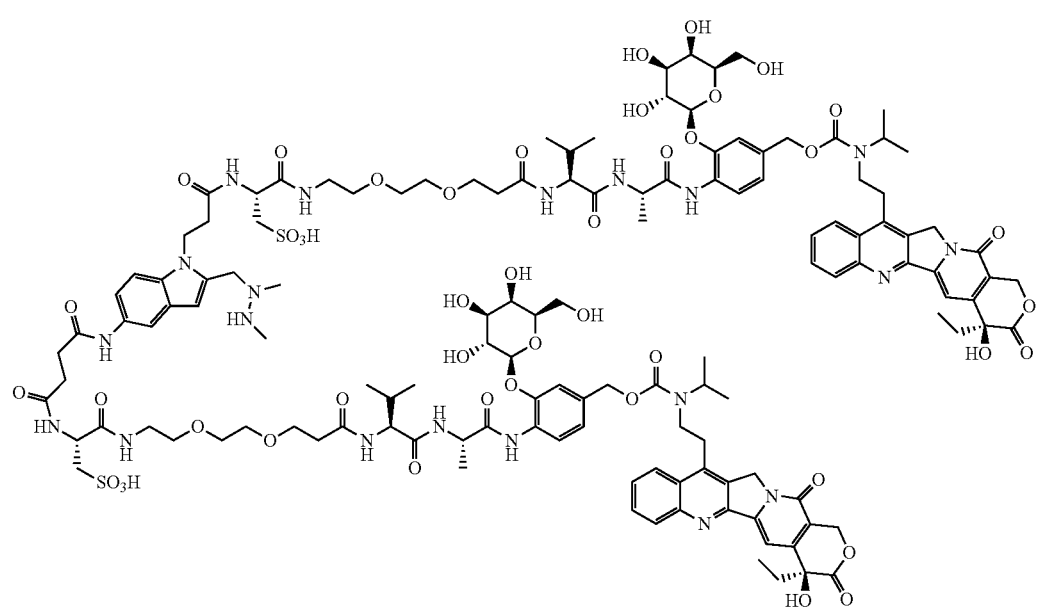
61

Preparation of (2R,3S,4S,5R,6S)-2-(acetoxymethyl)-6-(2-((S)-2-((S)-2-amino-3-methylbutanamido)propanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)tetrahydro-2H-pyran-3,4,5-triyl triacetate (58)

To an oven-dried 20 mL scintillation vial were added Belotecan HCl (2, 48 mg, 102 mol) and 1.6 mL of anhydrous DMF, followed by 47 μL of DIPEA (269 μmol) and 13 mg of HOAt (96 μmol). The resulting mixture was treated with PNP carbonate 57 (104 mg, 101 mmol) as a solid in one portion at room temperature, stirred overnight. After starting material was consumed, 200 μL piperidine (2 mmol) was added. The mixture was stirred for 30 minutes and was monitored by LC-MS. The reaction mixture was purified by reversed-phase Biotage® (C18, 0-100% v/v $CH_3CN$—$H_2O$ with 0.05% TFA). Lyophilized pure fractions gave 100 mg of compound 58 (91 μmol, 90% yield) as a yellow powder. LRMS (ESI): m/z 1099.4 [M+H]$^+$, Calcd for $C_{55}H_{67}N_6O_{18}$ m/z 1099.5.

Preparation of (2S,5S,18R)-18-amino-1-((4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)-2-(((2S,3R,4S,5R,6R)-3,4,5-trihydroxy-6-(hydroxymethyl)tetrahydro-2H-pyran-2-yl)oxy)phenyl)amino)-5-isopropyl-2-methyl-1,4,7,17-tetraoxo-10,13-dioxa-3,6,16-triazanonadecane-19-sulfonic Acid (60)

To an oven-dried 20 mL scintillation vial were added amine (58, 50 mg, 46 μmol), cysteic acid linker (59, 27 mg, 49 μmol), and 0.5 mL of anhydrous DMF, followed by 24 μL of DIPEA (138 μmol) and 18 mg of HATU (46 μmol). The resulting mixture was stirred at room temperature and was monitored by LCMS. After starting material was consumed, the solution was concentrated under vacuum to remove DMF. The residue was dissolved in 1 mL of methanol and slowly treated with 1.5 mL of 1M aqueous LiOH solution at 0° C. Reaction mixture was stirred for 15 minutes, then warmed up to room temperature and stirring continued for 1 hours, until hydrolysis was judged complete by LCMS analysis. Reaction mixture was quenched by addition of 1 mL of 1M HCl, followed by 1 mL of 0.5M pH 4.7 acetate buffer, concentrated under vacuum, and purified by reversed-phase HPLC (C18, 0-75% v/v $CH_3CN$—$H_2O$ with 0.05% TFA). Lyophilized pure fractions gave 39 mg of compound 60 (31 μmol, 68% yield) as a yellow powder. LRMS (ESI): m/z 1241.5 [M+H]$^+$, Calcd for $C_{57}H_{77}N_8O_{21}S$ m/z 1241.5.

Preparation of (2S,5S,18R)-18-(4-((2-((1,2-dimethylhydrazineyl)methyl)-1-((2S,5S,18R)-1-((4-((((2-((S)-4-ethyl-4-hydroxy-3,14-dioxo-3,4,12,14-tetrahydro-1H-pyrano[3',4':6,7]indolizino[1,2-b]quinolin-1-yl)ethyl)(isopropyl)carbamoyl)oxy)methyl)-2-(((2S,3R,4S,5R,6R)-3,4,5-trihydroxy-6-(hydroxymethyl)tetrahydro-2H-pyran-2-yl)oxy)phenyl)amino)-5-isopropyl-2-methyl-1,4,7,17,20-pentaoxo-18-(sulfomethyl)-10,13-dioxa-3,6,16,19-tetraazadocosan-22-yl)-1H-indol-5-yl)amino)-4-oxobutanamido)-1-((4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)-2-(((2S,3R,4S,5R,6R)-3,4,5-trihydroxy-6-(hydroxymethyl)tetrahydro-2H-pyran-2-yl)oxy)phenyl)amino)-5-isopropyl-2-methyl-1,4,7,17-tetraoxo-10,13-dioxa-3,6,16-triazanonadecane-19-sulfonic Acid (61)

Compound 60 (39 mg, 31 μmol) was combined with bis-PFP ester 40 (14.7 mg, 15.5 μmol), 5 mg of HOAt (31 μmol), and 17 μL of DIPEA (93 μmol) in 1 mL of DMF at room temperature. After one hour, piperidine 61 μL (0.62 mmol) was added to the reaction mixture. After 30 minutes, reaction mixture was directly purified by reversed phase HPLC (C18 column, 0-75% v/v gradient of $CH_3CN/H_2O$ with 0.05% TFA). Lyophilization of pure fractions gave 29 mg of compound 61 (10.3 μmol, 66% yield) as a yellowish powder. LRMS (ESI): m/z 1412.1 [M+2H]$^{++}$, Calcd for $C_{132}H_{174}N_{20}O_{45}S_2$ m/z 1412.1.

Scheme 11. Synthesis of branched belotecan construct 65

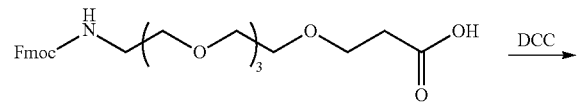

62

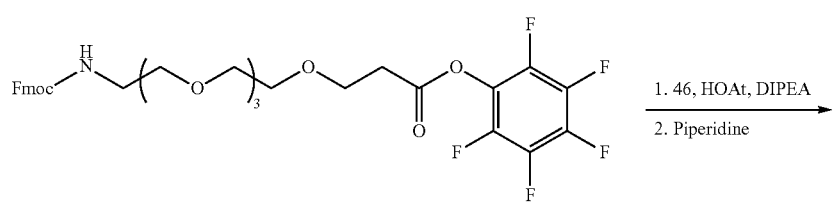

63

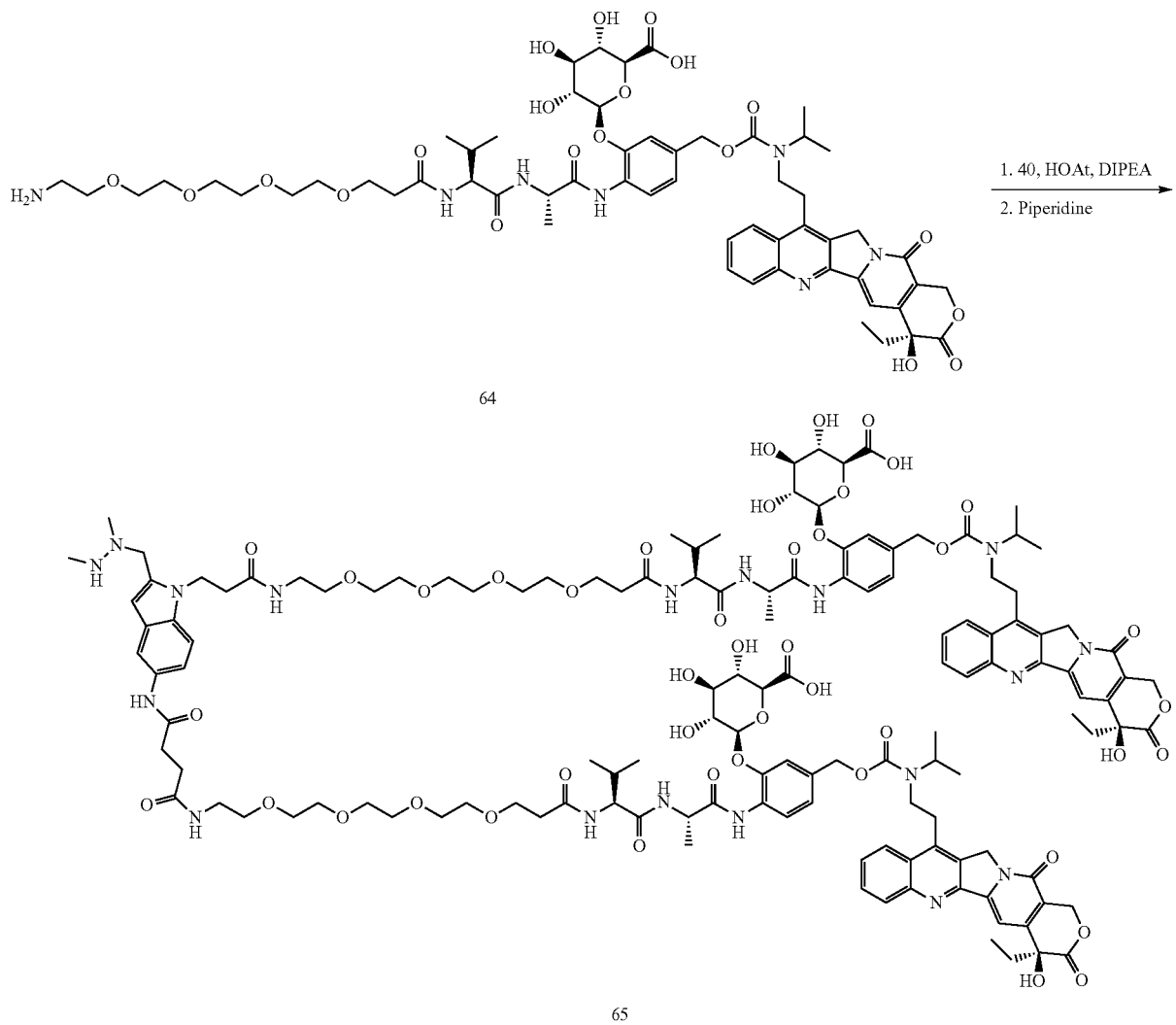

Preparation of perfluorophenyl 1-(9H-fluoren-9-yl)-3-oxo-2,7,10,13,16-pentaoxa-4-azanonadecan-19-oate (63)

In an oven-dried scintillation vial were combined 1-(9H-fluoren-9-yl)-3-oxo-2,7,10,13,16-pentaoxa-4-azanonadecan-19-oic acid (62, 487 mg, 1 mmol) and pentafluorophenol (368 mg, 2 mmol) in 5 mL of anhydrous THF. The resulting mixture was treated with DCC (247 mg, 1.2 mmol) in one portion at room temperature, and reaction mixture was stirred overnight. Precipitated solids were filtered off, solvents removed under vacuum, and the residue was purified by reversed-phase chromatography (C18 column, 10-100% v/v gradient of $CH_3CN/H_2O$ with 0.05% TFA) to give 670 mg of PFP ester 63 (570 mg, 0.87 mmol, 87% yield) as a colorless oil. LRMS (ESI): m/z 654.2 [M+H]$^+$, Calcd for $C_{32}H_{32}F_5NO_8$ m/z 654.2.

Preparation of (2S,3S,4S,5R,6S)-6-(2-((17S,20S)-1-amino-17-isopropyl-20-methyl-15,18-dioxo-3,6,9,12-tetraoxa-16,19-diazahenicosan-21-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (64)

Compound 46 (262 mg, 0.22 mmol) was dissolved in 4 mL of DMF. To this solution were added DIPEA (105 µL, 0.66 mmol) and PFP ester 63 (181 mg, 0.22 mmol) as a solution in 0.5 mL of DMF, followed by HOAt (38 mg, 0.22 mmol). The resulting mixture was allowed to stand at room temperature for one hour, then treated directly with 4 mL of triethylamine. Reaction mixture was stirred for 5 hours, until Fmoc-deprotection was complete as judged by LCMS analysis. Reaction mixture was concentrated under vacuum and purified by reversed-phase chromatography (C18 column, 0-50% v/v gradient of $CH_3CN/H_2O$ with 0.05% TFA) to give 185 mg (0.16 mmol, 73% yield) of compound 64 as a yellow powder. LRMS (ESI): m/z 1192.5 [M+H]⁺, Calcd for $C_{58}H_{77}N_7O_2$ m/z 1192.5.

Preparation of (2S,3S,4S,5R,6S)-6-(2-((2S,5S)-25-(5-((2S,5S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,23-tetraoxo-10,13,16,19-tetraoxa-3,6,22-triazahexacosan-26-amido)-2-((1,2-dimethylhydrazinyl)methyl)-1H-indol-1-yl)-5-isopropyl-2-methyl-4,7,23-trioxo-10,13,16,19-tetraoxa-3,6,22-triazapentacosanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (65)

Compound 64 (23 mg, 19 μmol) was dissolved in 2 mL of anhydrous DMA. To this solution were added DIPEA (10 μL, 57 μmol) and bis-PFP ester 40 (8 mg, 8.6 μmol) as solid in one portion at room temperature, followed by HOAt (2.6 mg, 19 μmol). The resulting mixture was allowed to stand at room temperature for one hour, then treated directly with 17 μL of piperidine (172 μmol). After 20 minutes, reaction mixture was purified by reversed-phase chromatography HPLC (C18 column, 0-50% v/v gradient of $CH_3CN/H_2O$ with 0.05% TFA). Pure fractions were lyophilized to give 5.8 mg (2.1 μmol, 24% yield) of compound 65 as a yellow powder. LRMS (ESI): m/z 1363.1 [M+2H]⁺⁺, Calcd for $C_{134}H_{174}N_{18}O_{43}$ m/z 1362.6.

Scheme 12. Synthesis of branched belotecan construct 67

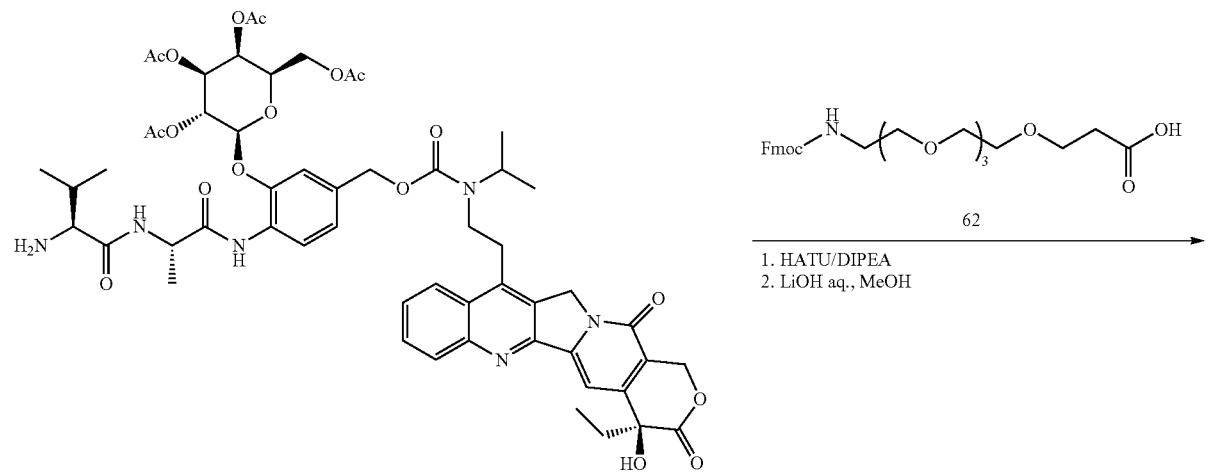

58

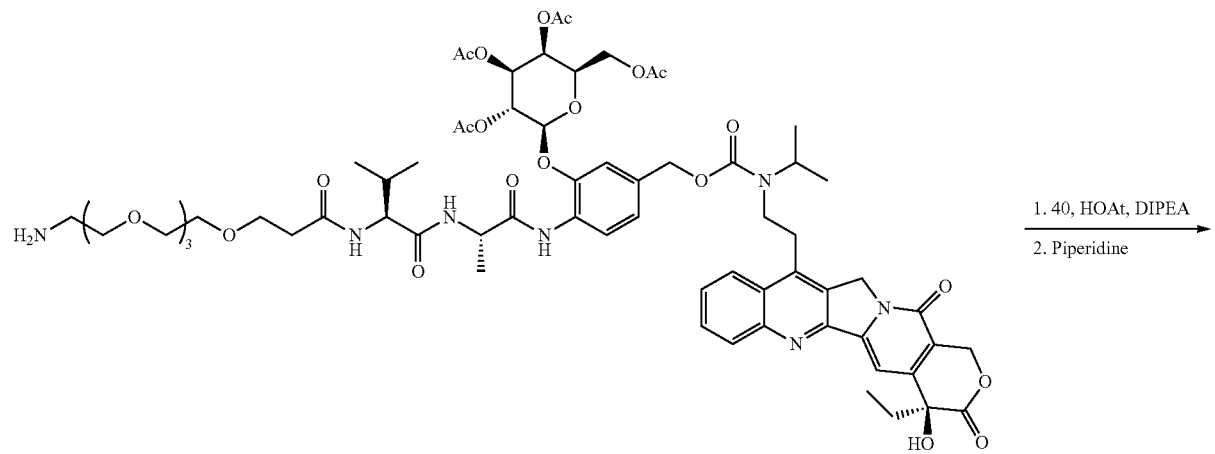

66

-continued

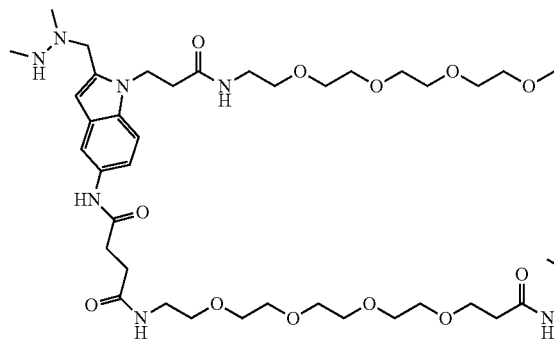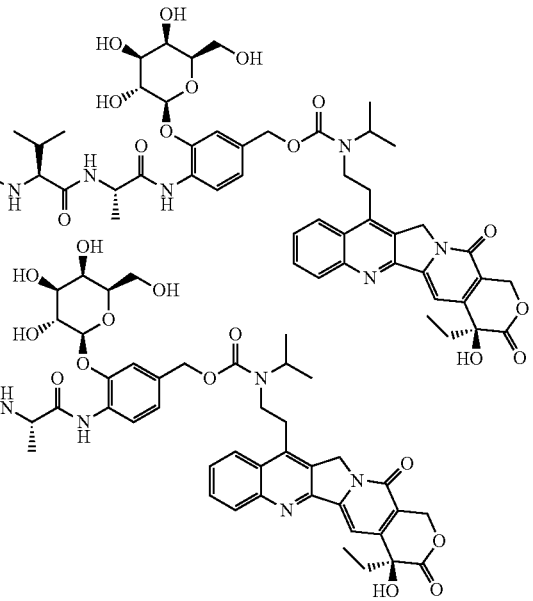

67

Preparation of 4-((17S,20S)-1-amino-17-isopropyl-20-methyl-15,18-dioxo-3,6,9,12-tetraoxa-16,19-diazahenicosan-21-amido)-3-(((2S,3R,4S,5R,6R)-3,4,5-trihydroxy-6-(hydroxymethyl)tetrahydro-2H-pyran-2-yl)oxy)benzyl (2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamate (66)

To a mixture of compounds 58 (30 mg, 27 μmol) and 62 (17 mg, 35 μmol) in DMF (0.5 mL) were added HATU (12 mg, 32 mol), followed by DIPEA (14 μL, 82 mol) at room temperature, and the resulting solution was stirred for 1 h. Solvent was removed under reduced pressure, and the residue was dissolved in MeOH (1 mL). To this solution was then added 1 M aqueous LiOH solution (1 mL) at 0° C., and the reaction mixture was allowed to slowly warm up to room temperature. After hydrolysis was judged complete by LCMS analysis, reaction mixture was quenched with pH 4.7 acetate buffer (1 mL). Solids were filtered off, filtrate was purified by reversed-phase prep HPLC (C18 column, 0-75% acetonitrile-water with 0.05% TFA). Pure fractions were collected and lyophilized to give product 66 as a yellow solid (19 mg, 16 μmol, 59% yield). LRMS (ESI): m/z 1178.5 [M+H]$^+$, Calcd for $C_{58}H_{79}N_7O_{19}$ m/z: 1178.5.

Preparation of 4-((2S,5S)-25-(2-((1,2-dimethylhydrazinyl)methyl)-5-((2S,5S)-1-((4-(((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)-2-(((2S,3R,4S,5R,6R)-3,4,5-trihydroxy-6-(hydroxymethyl)tetrahydro-2H-pyran-2-yl)oxy)phenyl)amino)-5-isopropyl-2-methyl-1,4,7,23-tetraoxo-10,13,16,19-tetraoxa-3,6,22-triazahexacosan-26-amido)-1H-indol-1-yl)-5-isopropyl-2-methyl-4,7,23-trioxo-10,13,16,19-tetraoxa-3,6,22-triazapentacosanamido)-3-(((2S,3R,4S,5R,6R)-3,4,5-trihydroxy-6-(hydroxymethyl)tetrahydro-2H-pyran-2-yl)oxy)benzyl (2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamate (67)

To a solution of compound 66 (19 mg, 16 μmol) in DMF (0.5 mL) were added DIPEA (9 μL, 48 μmol and HOAt (3 mg, 21 μmol), followed by bis-PFP ester 40 (7.4 mg, 8 μmol) at room temperature. The resulting mixture was stirred for 1 h, until coupling was judged complete by LCMS analysis. Piperidine (32 μL, 0.32 mmol) was then added directly to the reaction mixture at rt, and stirring continued for 15 minutes. Reaction mixture was then purified by reversed-phase prep HPLC (C18 column, 0-70% acetonitrile-water with 0.05% TFA). Pure fractions were collected and lyophilized to obtain product 67 as a yellow solid (13 mg, 4.8 μmol, 60% yield). LRMS (ESI): m/z 1349.0 [M+2H]$^{2+}$, Calcd for $C_{134}H_{178}N_{18}O_{41}$ m/z: 1349.1.

Scheme 13. Synthesis of branched belotecan construct 73

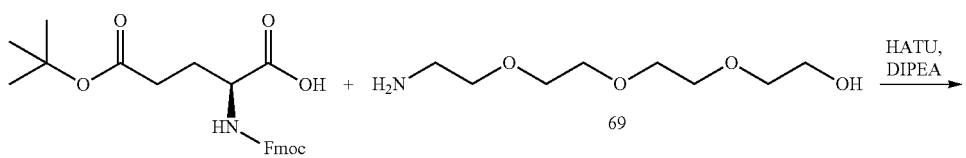

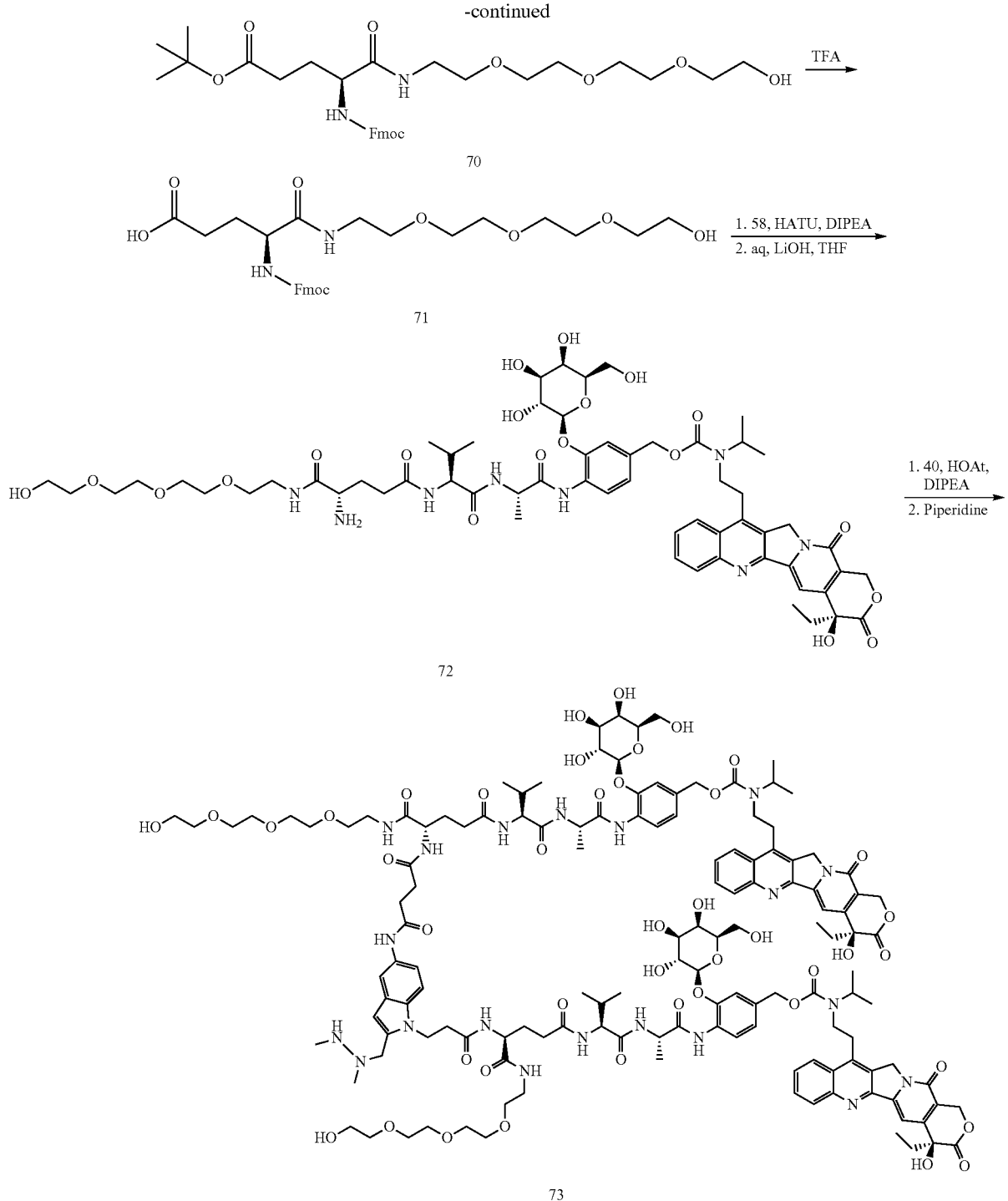

Preparation of tert-butyl (S)-14-((((9H-fluoren-9-yl)methoxy)carbonyl)amino)-1-hydroxy-13-oxo-3,6,9-trioxa-12-azaheptadecan-17-oate (70)

To a mixture of Fmoc-Glu(OtBu)-OH (68, 42 mg, 0.1 mmol) and amino-PEG4-OH (69, 19 mg, 0.1 mmol) in DMF (1 mL) were added HATU (38 mg, 0.1 mmol) and DIPEA (52 μL, 0.3 mmol) at room temperature. Reaction mixture was stirred for 1 h and directly purified by reversed-phase chromatography (C18 column, 0-70% acetonitrile-water with 0.05% TFA). Pure fractions were lyophilized to give compound 70 as a white solid (50 mg, 0.83 mmol, 83% yield). LRMS (ESI): m/z 601.3 [M+H]$^+$, Calcd for $C_{32}H_{44}N_2O_9$ m/z: 601.3.

Preparation of (S)-14-((((9H-fluoren-9-yl)methoxy)carbonyl)amino)-1-hydroxy-13-oxo-3,6,9-trioxa-12-azaheptadecan-17-oic Acid (71)

Compound 70 (50 mg, 83 μmol) was dissolved in TFA (2 mL) and stirred for 1 minute at room temperature. Solvent was removed under reduced pressure and the residue was purified by reversed-phase chromatography (C18 column, 0-75% acetonitrile-water with 0.05% TFA). Pure fractions were collected and lyophilized to obtain compound 71 as a white solid (35 mg, 83 µmol, 77% yield). LRMS (ESI): m/z 545.3 [M+H]$^+$, Calcd for $C_{28}H_{36}N_2O_9$ m/z: 545.2.

Preparation of 4-((14S,19S,22S)-14-amino-1-hydroxy-19-isopropyl-22-methyl-13,17,20-trioxo-3,6,9-trioxa-12,18,21-triazatricosan-23-amido)-3-(((2S,3R,4S,5R,6R)-3,4,5-trihydroxy-6-(hydroxymethyl)tetrahydro-2H-pyran-2-yl)oxy)benzyl (2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamate (72)

To a mixture of amine 58 (30 mg, 27 µmol) and carboxylic acid 71 (15 mg, 28 µmol) in DMF (0.5 mL) were added HATU (10 mg, 27 µmol), followed by DIPEA (14 µL, 82 µmol) at room temperature. Reaction mixture was stirred for 1 h until coupling was found complete by LCMS analysis. Solvent was removed under reduced pressure; the residue was dissolved in MeOH (1 mL) and treated with 1M aqueous LiOH solution (1 mL) at 0° C. Reaction mixture was allowed to slowly warm up to room temperature, stirred for additional 1 h, and quenched with pH 4.7 acetate buffer (1 mL). Solids were filtered off, and the clear filtrate was purified by reversed-phase prep HPLC (C18 column, 0-75% acetonitrile-water with 0.05% TFA). Pure fractions were combined and lyophilized to give 30 mg (24 µmol, 89% yield) of compound 72 as a yellow solid. LRMS (ESI): m/z 1235.5 [M+H]$^+$, Calcd for $C_{60}H_{82}N_8O_{21}$ m/z: 1235.6.

Preparation of 4-((14S,19S,22S)-14-(4-((2-((1,2-dimethylhydrazinyl)methyl)-1-((S)-14-(3-(((S)-1-(((S)-1-((4-((((2-((S)-4-ethyl-4-hydroxy-3,14-dioxo-3,4,12,14-tetrahydro-1H-pyrano[3',4':6,7]indolizino[1,2-b]quinolin-1-yl)ethyl)(isopropyl)carbamoyl)oxy)methyl)-2-(((2S,3R,4S,5R,6R)-3,4,5-trihydroxy-6-(hydroxymethyl)tetrahydro-2H-pyran-2-yl)oxy)phenyl)amino)-1-oxopropan-2-yl)amino)-3-methyl-1-oxobutan-2-yl)amino)-3-oxopropyl)-1-hydroxy-13,16-dioxo-3,6,9-trioxa-12,15-diazaoctadecan-18-yl)-1H-indol-5-yl)amino)-4-oxobutanamido)-1-hydroxy-19-isopropyl-22-methyl-13,17,20-trioxo-3,6,9-trioxa-12,18,21-triazatricosan-23-amido)-3-(((2S,3R,4S,5R,6R)-3,4,5-trihydroxy-6-(hydroxymethyl)tetrahydro-2H-pyran-2-yl)oxy)benzyl (2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamate (73)

To a solution of compound 72 (30 mg, 24 µmol) in DMF (1.0 mL) were added DIPEA (13 µL, 73 µmol) and HOAt (4.2 mg, 32 µmol), followed by bis-PFP ester 40 (11 mg, 12 µmol) in one portion at room temperature. Reaction mixture was allowed to stand for 1 h until reaction was judged complete by LCMS analysis, and treated with piperidine (49 µL, 0.49 mmol) at room temperature. Reaction mixture was directly purified by reversed-phase prep HPLC (C18 column, 0-70% acetonitrile-water with 0.05% TFA). Pure fractions were collected and lyophilized to give 24 mg of compound 73 as a yellow solid (8.5 µmol, 70% yield). LRMS (ESI): m/z 1406.3 [M+2H]$^{2+}$, Calcd for $C_{138}H_{184}N_{20}O_{43}$ m/z: 1406.2.

Scheme 14. Synthesis of branched belotecan construct 80

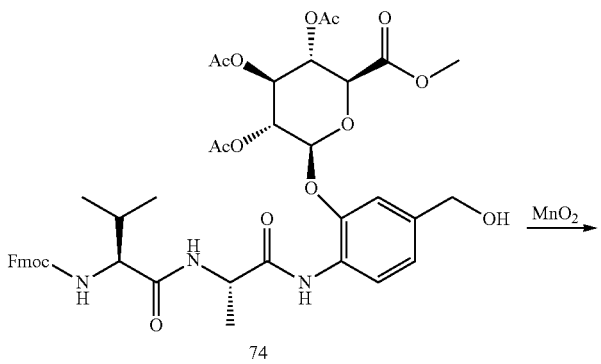

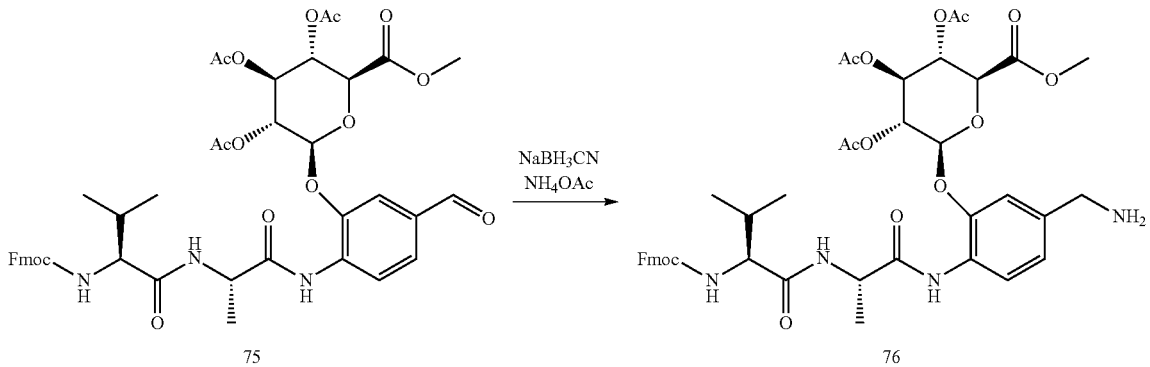

-continued
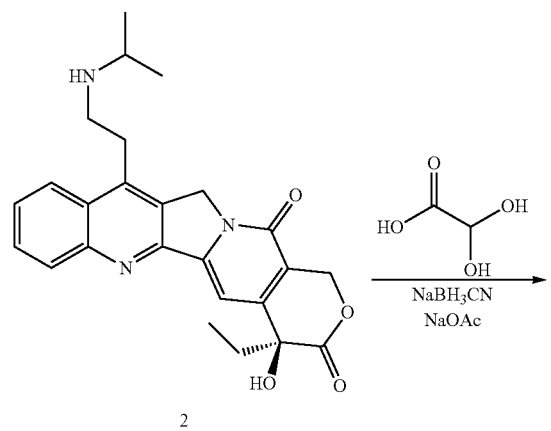
2
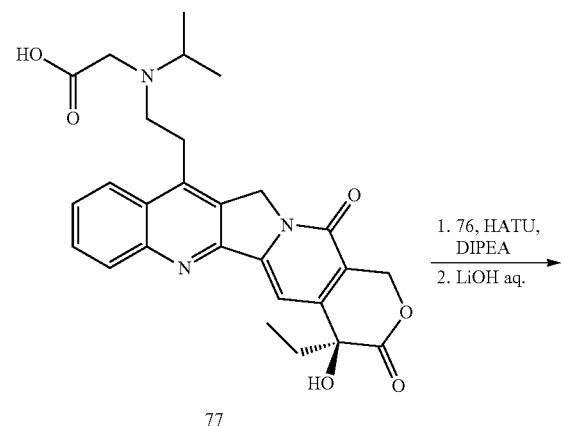
77
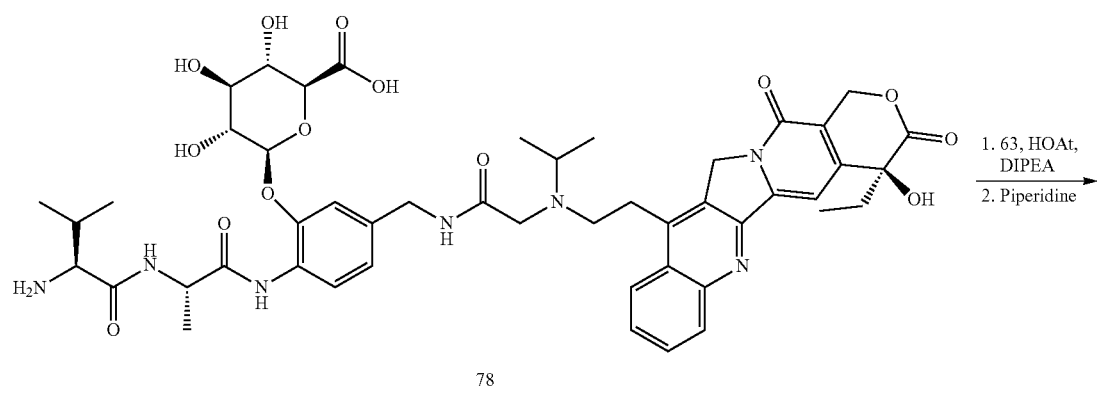
78
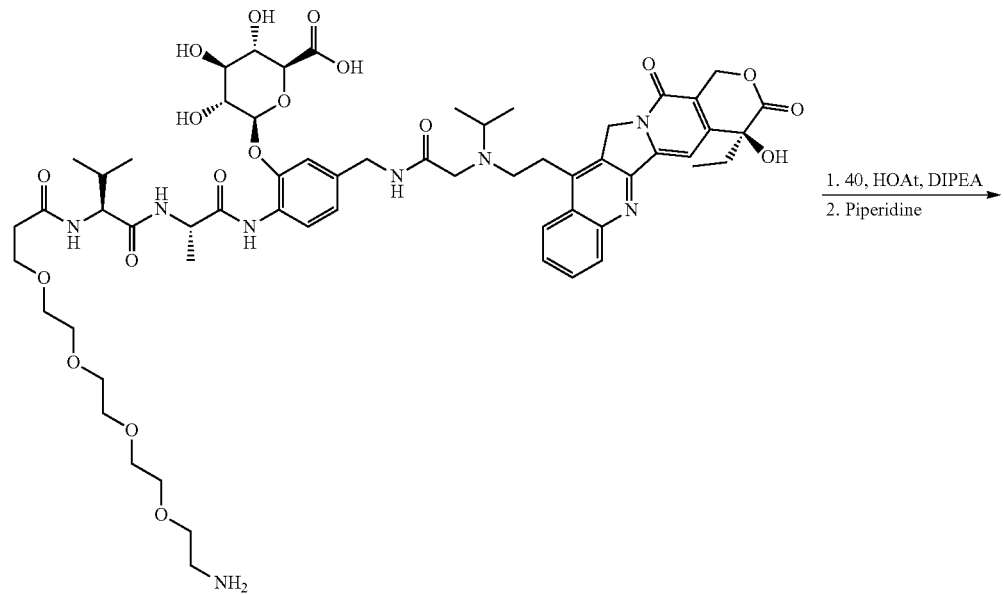
79

-continued

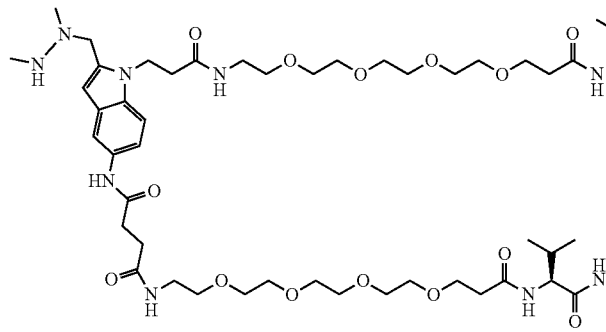
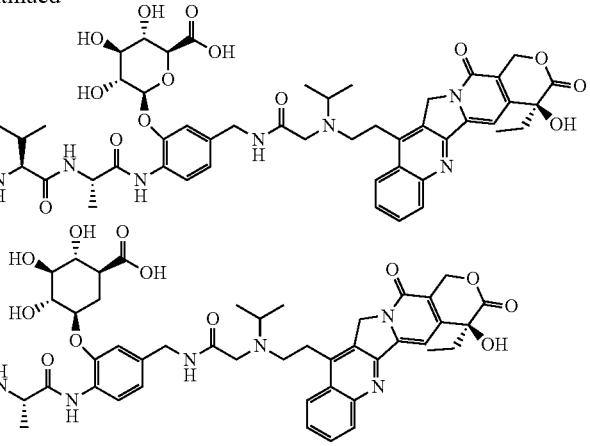

80

Preparation of (2S,3R,4S,5S,6S)-2-(2-((S)-2-((S)-2-((((9H-fluoren-9-yl)methoxy)carbonyl)amino)-3-methylbutanamido)propanamido)-5-formylphenoxy)-6-(methoxycarbonyl)tetrahydro-2H-pyran-3,4,5-triyl Triacetate (75)

To a round-bottom flask with a stir bar were added alcohol 74 (0.075 g, 0.088 mmol) and anhydrous DCM (15 mL), followed by MnO$_2$ at ambient temperature in one portion (0.400 g, 4.6 mmol, activated by heating overnight in an oven @ 130° C.). Reaction mixture was allowed to stir for 90 minutes, until starting material was completely consumed as judged by TLC analysis. Reaction mixture was filtered through a pad of celite, eluted with DCM. Combined filtrates were concentrated and purified by silica gel chromatography (0-50% gradient of EtOAc-hexane) to give aldehyde 75 as a white solid (0.057 g, 0.068 mmol, 77% yield). LRMS (ESI): m/z 846.5 [M+H]$^+$, Calcd for $C_{43}H_{47}N_3O_{15}$ m/z: 846.3.

Preparation of (2S,3R,4S,5S,6S)-2-(2-((S)-2-((S)-2-((((9H-fluoren-9-yl)methoxy)carbonyl)amino)-3-methylbutanamido)propanamido)-5-(aminomethyl)phenoxy)-6-(methoxycarbonyl)tetrahydro-2H-pyran-3,4,5-triyl Triacetate (76)

To an oven dried vial with a stir bar were added aldehyde 75 (0.100 g; 0.118 mmol) and anhydrous MeOH (10 mL), followed by oven-dried 4A molecular sieves (~1 g). The resulting mixture was allowed to stir for 10 min at room temperature. Anhydrous ammonium acetate (0.911 g; 11.8 mmol) was then added to the mixture and stirring continued for 1 h before the addition of sodium cyanoborohydride (0.038 g; 0.591 mmol) in one portion at room temperature. After stirring for additional 1 h, reaction mixture was filtered, concentrated under reduced pressure, and purified by silica gel chromatography (0-10% MeOH in DCM gradient) to give 0.043 g of amine product 76 (0.051 mmol, 43% yield). LRMS (ESI): m/z 847.4 [M+H]$^+$, Calcd for $C_{43}H_{50}N_4O_{14}$ m/z: 847.3.

Preparation of (S)—N-(2-(4-ethyl-4-hydroxy-3,14-dioxo-3,4,12,14-tetrahydro-1H-pyrano[3',4':6,7]indolizino[1,2-b]quinolin-11-yl)ethyl)-N-isopropylglycine (77)

Belotecan-HCl (2, 0.025 g; 0.057 mmol) was dissolved in DMF (0.25 mL) and diluted with MeOH (3.0 mL). The resulting solution was combined with glyoxylic acid (0.011 g; 0.115 mmol) and sodium acetate (0.033 g; 0.40 mmol) and stirred for 1 h at room temperature. Reaction mixture was then treated with sodium cyanoborohydride (0.025 g; 0.40 mmol), stirred overnight at room temperature, and quenched with 1 mL of 0.05% aqueous TFA. Solvents were removed in vacuum to leave crude oil, which was purified by reversed-phase prep HPLC (C18 column, 5-55% acetonitrile-water/0.05% TFA). Fractions containing the desired product were collected and lyophilized to give 0.027 g (0.055 mmol, 96% yield) of compound 77 as a pale-yellow solid. LRMS (ESI): m/z 492.2 [M+H]$^+$, Calcd for $C_{27}H_{29}N_3O_6$ m/z: 492.2.

Preparation of (2S,3S,4S,5R,6S)-6-(2-((S)-2-((S)-2-amino-3-methylbutanamido)propanamido)-5-((2-((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)amino)acetamido)methyl)phenoxy)-3,4,5-trihydroxytetrahydro-2H-pyran-2-carboxylic Acid (78)

To an oven-dried scintillation vial with a stir bar were added carboxylic acid 77 (0.018 g; 0.037 mmol) and anhydrous DMF (2 mL), followed by HATU (0.013 g; 0.034 mmol) and DIPEA (30 µL) at room temperature. The mixture was allowed to stir for 45 min and then combined with a mixture amine 76 (0.026 g; 0.030 mmol) and DIPEA (30 µL) in 2 mL of DMF. Reaction mixture was stirred for 1 h, quenched by addition of aqueous 1% TFA solution (15 mL), transferred to a separatory funnel, and extracted with EtOAc. Organic layer was washed with water and brine, and dried over Na$_2$SO$_4$. Removal of solvents under vacuum gave a crude yellow oily solid (0.048 g), which was dissolved in 5 mL of THF. This solution was cooled to 0° C. in an ice bath and slowly treated with chilled aqueous LiOH (1M, 2.0 mL). Reaction mixture was allowed to stir at 0° C. for 1 h, slowly warmed to room temperature, and quenched by adding aqueous HCl (1.0 M) to pH 4. The mixture was purified by reversed-phase prep HPLC (C18 column, 0-50% acetonitrile-water/0.05% TFA) to give 0.020 g of compound 78 (0.021 mmol, 70% yield) as an off-white solid. LRMS (ESI): m/z 959.1 [M+H]$^+$, Calcd for $C_{48}H_{59}N_7O_{14}$ m/z: 958.4

(2S,3S,4S,5R,6S)-6-(2-((17S,20S)-1-amino-17-isopropyl-20-methyl-15,18-dioxo-3,6,9,12-tetraoxa-16,19-diazahenicosan-21-amido)-5-((2-((2-((S)-4-ethyl-4-hydroxy-3,14-dioxo-3,4,12,14-tetrahydro-1H-pyrano[3′,4′:6,7]indolizino[1,2-b]quinolin-11-yl)ethyl)(isopropyl)amino)acetamido)methyl)phenyl)-3,4,5-trihydroxytetrahydro-2H-pyran-2-carboxylic Acid (79)

To a solution of amine 78 (0.020 g, 0.021 mmol) in anhydrous DMF (2 mL) were added PFP ester 63 (0.020 g, 0.031 mmol), HOAt (0.004 g; 0.031 mmol), and DIPEA (11 µL) at room temperature. Reaction mixture was allowed to stir for 45 min, then treated with piperidine (50 µL) and stirred for additional 20 min. The mixture was purified by reversed-phase prep HPLC (C18 column, 0-50% acetonitrile-water/0.05% TFA). Pure fractions were combined and lyophilized to obtain amine product 79 as a pale-yellow solid (0.015 g, 0.012 mmol, 57% yield). LRMS (ESI): m/z 1205.5 [M+H]$^+$, Calcd for $C_{59}H_{80}N_8O_{19}$ m/z: 1205.6.

(2S,3S,4S,5R,6S)-6-(2-((2S,5S)-25-(5-((2S,5S)-1-((2-(((2S,3R,4S,5S,6S)-6-carboxy-3,4,5-trihydroxytetrahydro-2H-pyran-2-yl)oxy)-4-((2-((S)-4-ethyl-4-hydroxy-3,14-dioxo-3,4,12,14-tetrahydro-1H-pyrano[3′,4′:6,7]indolizino[1,2-b]quinolin-11-yl)ethyl)(isopropyl)amino)acetamido)methyl)phenyl)amino)-5-isopropyl-2-methyl-1,4,7,23-tetraoxo-10,13,16,19-tetraoxa-3,6,22-triazahexacosan-26-amido)-2-((1,2-dimethylhydrazinyl)methyl)-1H-indol-1-yl)-5-isopropyl-2-methyl-4,7,23-trioxo-10,13,16,19-tetraoxa-3,6,22-triazapentacosanamido)-5-((2-((2-((S)-4-ethyl-4-hydroxy-3,14-dioxo-3,4,12,14-tetrahydro-1H-pyrano[3′,4′:6,7]indolizino[1,2-b]quinolin-11-yl)ethyl)(isopropyl)amino)acetamido)methyl)phenoxy)-3,4,5-trihydroxytetrahydro-2H-pyran-2-carboxylic Acid (80)

To a solution of amine 79 (15 mg; 12 µmol) in anhydrous DMF (2 mL) were added bis-PFP ester 40 (5.5 mg; 6 µmol), followed by HOAt (3.4 mg; 2.5 µmol) and DIPEA (22 µL) at room temperature. The resulting mixture was allowed to stir for 30 min, then 50 µL of piperidine was added, and stirring continued for 20 min. Reaction mixture was diluted with 0.05% TFA (1 mL) and purified by reversed-phase prep HPLC (C18 column, 0-50% acetonitrile-water/0.05% TFA). Pure fractions were collected and immediately subjected to lyophilization to give 5.2 mg of compound 80 as a yellow solid (1.9 µmol, 32% yield). LRMS (ESI): m/z 1376.2 [M+2H]$^{2+}$, Calcd for $C_{136}H_{180}N_{20}O_{41}$ m/z: 1376.1.

Scheme 15. Synthesis of branched belotecan construct 86

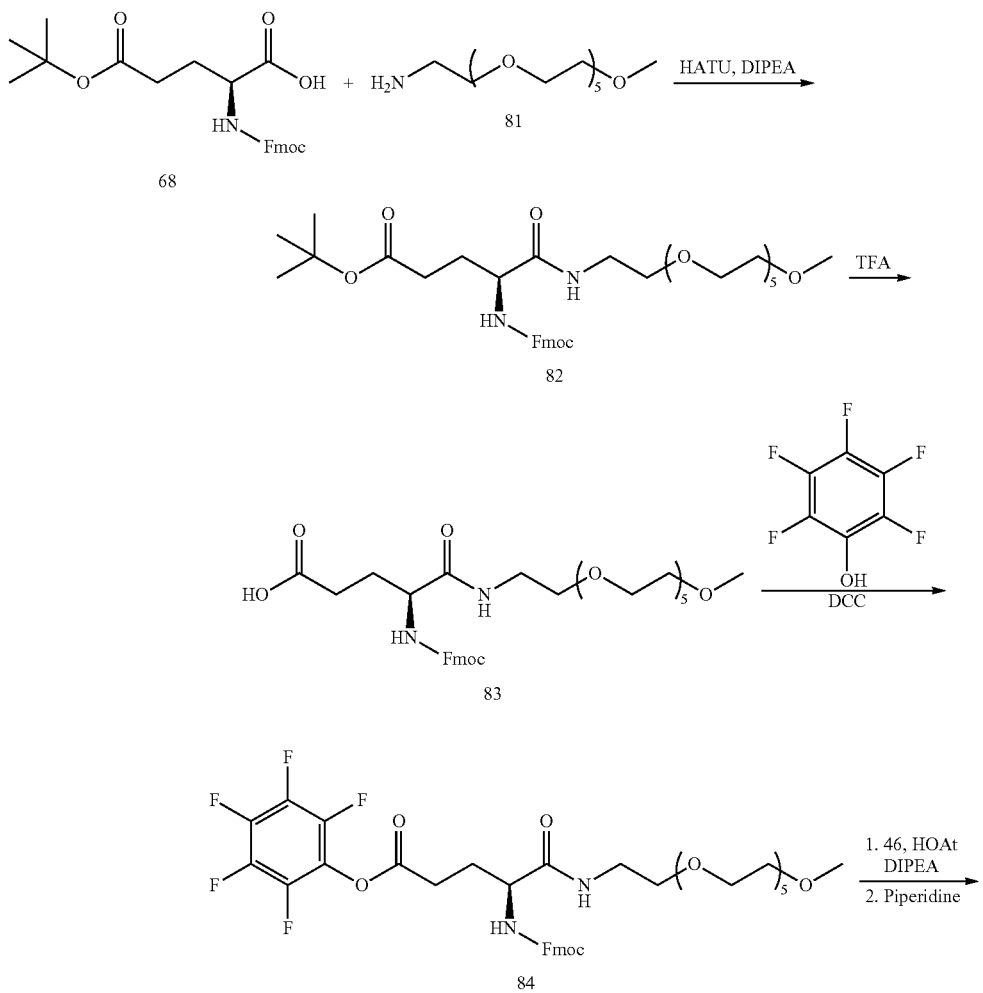

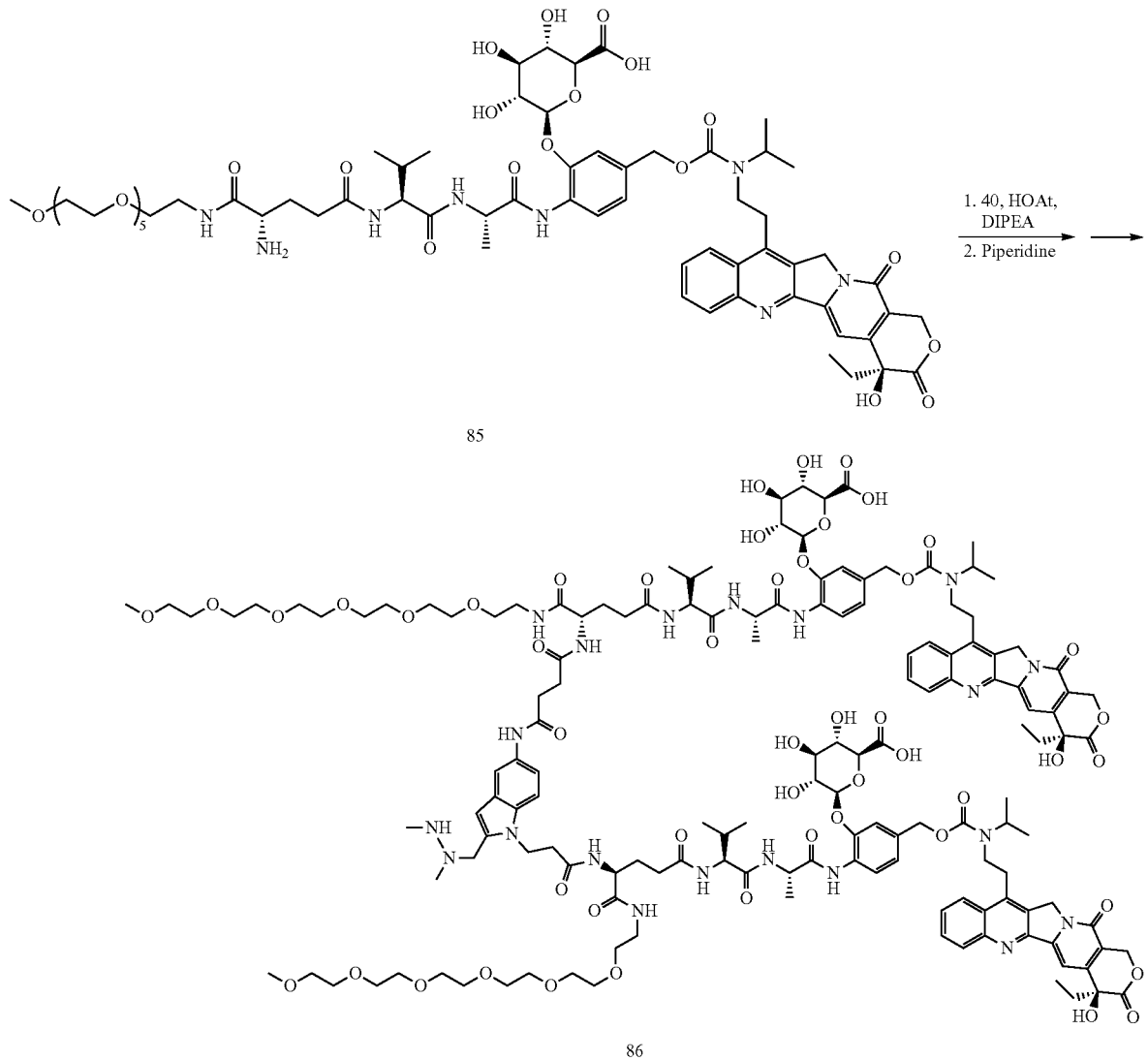

85

86

Preparation of tert-butyl (S)-22-((((9H-fluoren-9-yl)methoxy)carbonyl)amino)-21-oxo-2,5,8,11,14,17-hexaoxa-20-azapentacosan-25-oate (82)

To a round bottom flask with a stir bar were added Fmoc-Glu(OtBu)-OH 68 (0.259 g; 0.609 mmol) and DMF (15 mL), followed by HATU (0.215 g; 0.558 mmol) and DIPEA (440 μL; 2.54 mmol) at room temperature. The resulting mixture was allowed to stir for 30 min, and combined with mPEG6-amine 81 (0.150 g; 0.507 mmol). After 1 h, reaction mixture was transferred to a separatory funnel, diluted with water (30 mL), and extracted with EtOAc (2×30 mL). Organic layer was washed with water and brine, dried over sodium sulfate. Solvents were removed in vacuum to give 0.50 g of crude product 82 as a colorless oil, which was used further without purification. LRMS (ESI): m/z 703.4 [M+H]$^+$, Calcd for $C_{37}H_{54}N_2O_{11}$ m/z: 703.4.

Preparation of (S)-22-((((9H-fluoren-9-yl)methoxy)carbonyl)amino)-21-oxo-2,5,8,11,14,17-hexaoxa-20-azapentacosan-25-oic Acid (83)

Crude compound 82 (0.50 g) was dissolved in anhydrous DCM (5 mL) and treated with TFA (2 mL) at room temperature. Reaction mixture was allowed to stir for 2 h, then solvents were removed under reduced pressure, and the residue was dried under high vacuum overnight to give 0.50 g of crude carboxylic acid 83 as a colorless oil, which was used further without purification. LRMS (ESI): m/z 647.7 [M+H]$^+$, Calcd for $C_{33}H_{46}N_2O_{11}$ m/z: 647.3.

Preparation of perfluorophenyl (S)-22-((((9H-fluoren-9-yl)methoxy)carbonyl)amino)-21-oxo-2,5,8,11,14,17-hexaoxa-20-azapentacosan-25-oate (84)

To a stirred solution of crude carboxylic acid 83 (0.50 g) in anhydrous THF (20 mL) were added pentafluorophenol (1.42 g; 7.73 mmol), followed by DCC (0.32 g; 1.55 mmol)

in one portion at room temperature. Reaction mixture was stirred overnight at room temperature, filtered, and concentrated under vacuum. The residue was then purified by silica gel chromatography (0-10% MeOH in DCM gradient) to give PFP-ester 84 as a colorless solid (0.43 g, 0.53 mmol, 87% yield over 3 steps). LRMS (ESI): m/z 813.7 [M+H]$^+$, Calcd for $C_{39}H_{45}F_5N_2O_{11}$ m/z: 813.3.

Preparation of (2S,3S,4S,5R,6S)-6-(2-((22S,27S,30S)-22-amino-27-isopropyl-30-methyl-21,25,28-trioxo-2,5,8,11,14,17-hexaoxa-20,26,29-triazahentriacontan-31-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (85)

To a solution of compound 46 (30 mg, 31 μmol) in anhydrous DMF (3 mL) were added PFP-ester 84 (31 mg, 38 μmol), followed by HOAt (1.5 mg, 47 μmol) and DIPEA (10 μL) at room temperature. Reaction mixture was stirred for 45 min, then directly treated with piperidine (50 μL). After 30 min, reaction mixture was quenched with aqueous 0.05% TFA (1 mL) and purified by reversed-phase prep HPLC (C18 column, 0-50% acetonitrile-water/0.05% TFA). Fractions containing the desired product were combined and lyophilized to yield 38 mg of amine 85 as a pale-yellow solid (28 μmol, 90% yield). LRMS (ESI): m/z 1351.6 [M+H]$^+$, Calcd for $C_{65}H_{90}N_8O_{23}$ m/z: 1351.6.

(2S,3S,4S,5R,6S)-6-(2-((22S,27S,30S)-22-(3-(5-((S)-22-(3-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-1-oxopropan-2-yl)amino)-3-methyl-1-oxobutan-2-yl)amino)-3-oxopropyl)-21,24-dioxo-2,5,8,11,14,17-hexaoxa-20,23-diazaheptacosan-27-amido)-2-((1,2-dimethylhydrazinyl)methyl)-1H-indol-1-yl)propanamido)-27-isopropyl-30-methyl-21,25,28-trioxo-2,5,8,11,14,17-hexaoxa-20,26,29-triazahentriacontan-31-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (86)

To a stirred solution of amine 85 (20 mg; 15 μmol) in 3 mL of anhydrous DMF were added bis-PFP ester 40 (6.8 mg; 7.3 μmol), followed by HOAt (2.5 mg; 18 μmol) and DIPEA (13 μL) at room temperature. Reaction mixture was stirred for 30 min and then treated directly with piperidine (50 μL). After 20 min, reaction mixture was purified by reversed-phase prep HPLC (C18 column, 0-50% acetonitrile-water/ 0.05% TFA). Pure fractions containing product were combined and lyophilized to yield 15 mg of compound 86 (5 μmol, 69% yield) as a pale-yellow solid. LRMS (ESI): m/z 1522.2 [M+2H]$^{2+}$, Calcd for $C_{148}H_{200}N_{20}O_{49}$ m/z: 1522.2.

Scheme 16. Synthesis of branched belotecan construct 92

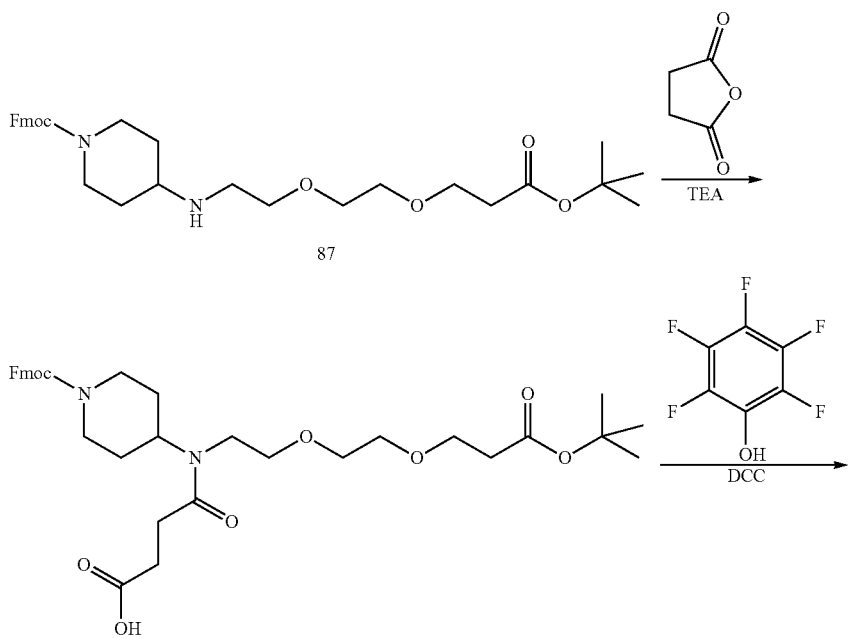

-continued
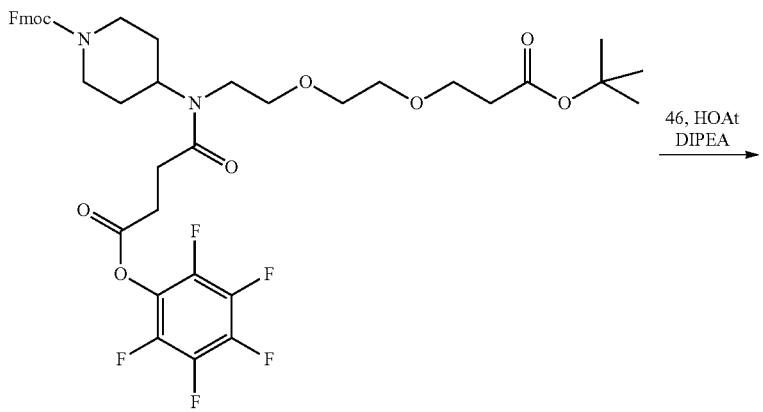
89
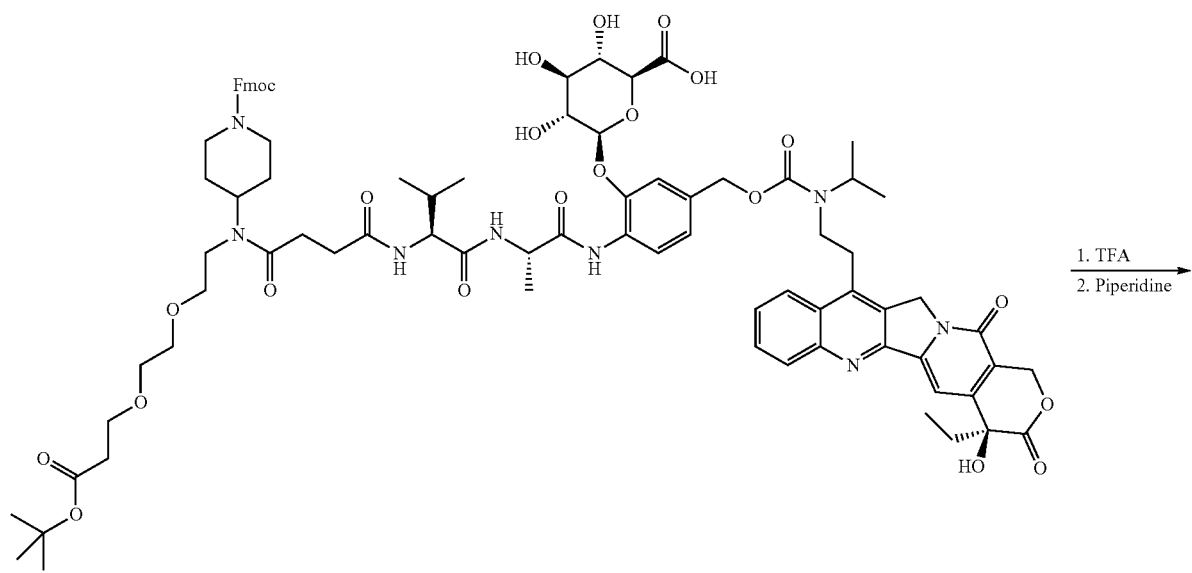
90
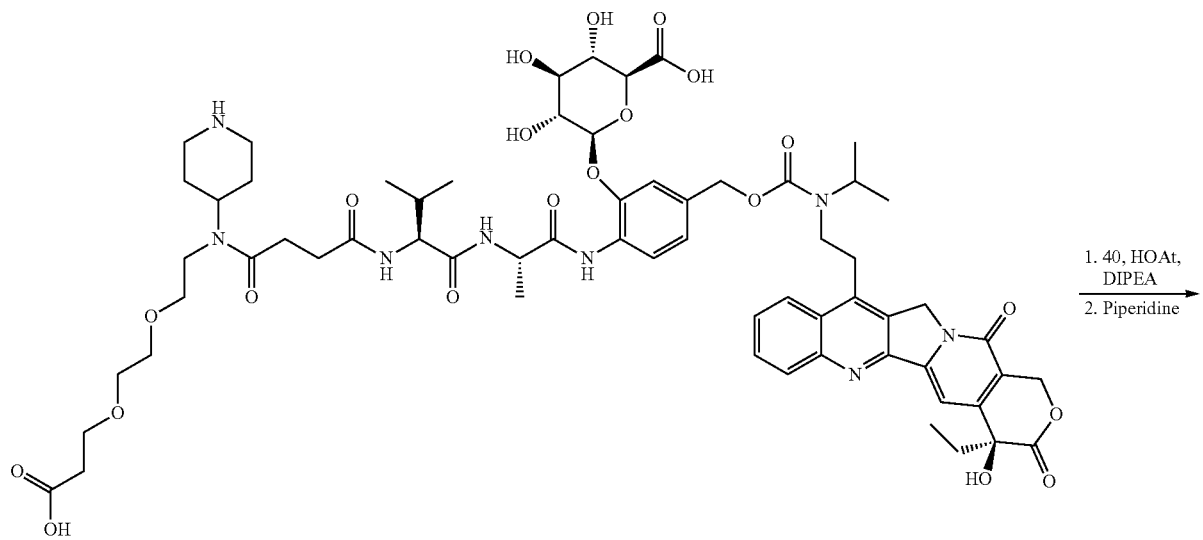
91

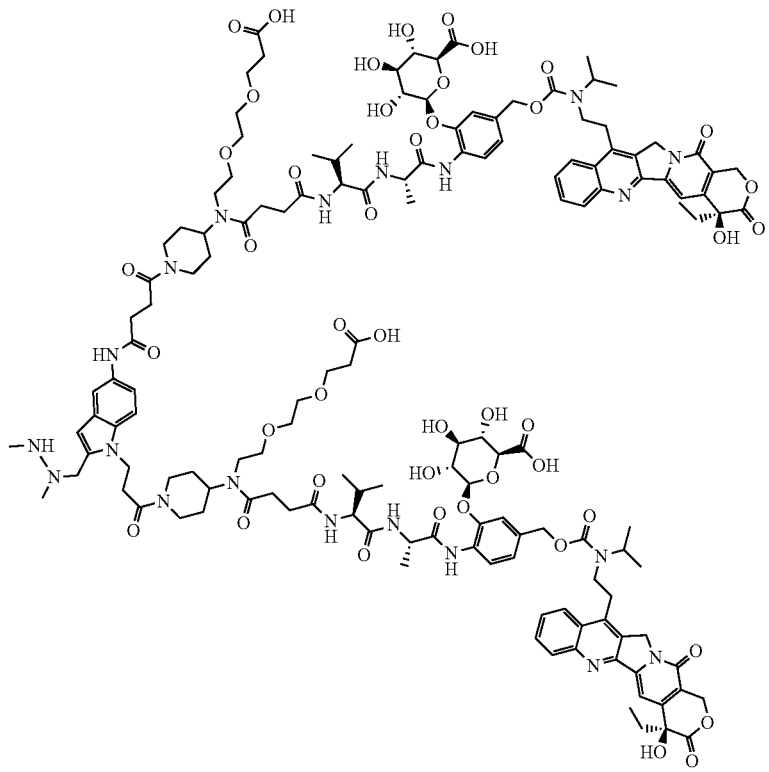

92

Preparation of 13-(1-(((9H-fluoren-9-yl)methoxy) carbonyl)piperidin-4-yl)-2,2-dimethyl-4,14-dioxo-3,7,10-trioxa-13-azaheptadecan-17-oic Acid (88)

To a stirred solution of compound 87 (100 mg, 186 µmol) in MeCN (2 mL) were added succinic anhydride (93 mg, 928 µmol) and triethylamine (129 µL, 928 µmol) at ambient temperature. Reaction mixture was stirred for 10 min and then directly purified by reversed-phase chromatography (C18 column, 0-50% acetonitrile-water/0.05% TFA). Pure fractions were collected and lyophilized to obtain compound 88 as a colorless oil (90 mg, 141 µmol, 76% yield).

Preparation of (9H-fluoren-9-yl)methyl 4-(N-(2-(2-(3-(tert-butoxy)-3-oxopropoxy)ethoxy)ethyl)-4-oxo-4-(perfluorophenoxy)butanamido)piperidine-1-carboxylate (89)

To a mixture of carboxylic acid 88 (90 mg, 141 µmol) and pentafluorophenol (91 mg, 493 µmol) in 2 mL of anhydrous THF were added DCC (101 mg, 493 µmol) at room temperature. Reaction mixture was stirred overnight, solids were filtered off, solvent was removed under reduced pressure, and the residue was purified by silica gel chromatography (EtOAc-hexane, 0-50% gradient) to yield 42 mg of PFP-ester 89 (52 µmol, 37% yield) as an off-white solid.

Preparation of (2S,3S,4S,5R,6S)-6-(2-((2S,5S)-11-(1-(((9H-fluoren-9-yl)methoxy)carbonyl)piperidin-4-yl)-5-isopropyl-2,22,22-trimethyl-4,7,10,20-tetraoxo-14,17,21-trioxa-3,6,11-triazatricosanamido)-5-(((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (90)

To a solution of compound 46 (25 mg, 26 µmol) in DMF (1.0 mL) were added DIPEA (14 µL, 73 µmol) and HOAt (5 mg, 35 µmol), followed by PFP-ester 89 (21 mg, 26 µmol) at room temperature. Reaction mixture was stirred for 30 min and then directly purified by reversed-phase chromatography (C18, 0-100% v/v MeCN—H$_2$O with 0.05% TFA). Lyophilized pure fractions gave 38 mg of compound 90 (24 µmol, 92% yield) as a yellow powder. LRMS (ESI): m/z 1565.7 [M+H]$^+$, Calcd for $C_{82}H_{100}N_8O_{23}$ m/z: 1565.7.

Preparation of (2S,5S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,10-tetraoxo-11-(piperidin-4-yl)-14,17-dioxa-3,6,11-triazaicosan-20-oic Acid (91)

A solution of compound 90 (38 mg, 24 µmol) in TFA (2 mL) was stirred for one minute, then diluted with 2 mL of water-acetonitrile mixture (1:1 v/v) and lyophilized to give a white solid. The solid was dissolved in DMF (1 mL) and treated with piperidine (49 μL, 0.49 mmol) at room temperature. After 20 minutes, reaction mixture was purified by reversed-phase prep HPLC (C18, 0-70% v/v MeCN—H$_2$O with 0.05% TFA). Lyophilized pure fractions gave 10 mg of compound 91 (7 μmol, 34% yield) as a yellow powder. LRMS (ESI): m/z 1287.5 [M+H]$^+$, Calcd for C$_{63}$H$_{82}$N$_8$O$_{21}$ m/z 1287.6.

Preparation of (2S,3S,4S,5R,6S)-6-(2-((15S,18S)-1-carboxy-9-(1-(3-(5-(4-(4-(4-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-1-oxopropan-2-yl)amino)-3-methyl-1-oxobutan-2-yl)amino)-N-(2-(2-(2-carboxyethoxy)ethoxy)ethyl)-4-oxobutanamido)piperidin-1-yl)-4-oxobutanamido)-2-((1,2-dimethylhydrazinyl)methyl)-1H-indol-1-yl)propanoyl)piperidin-4-yl)-15-isopropyl-18-methyl-10,13,16-trioxo-3,6-dioxa-9,14,17-triazanonadecan-19-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (92)

To a solution of amine 91 (10 mg, 8 μmol) in anhydrous DMF (0.5 mL) were added DIPEA (2 μL, 12 μmol) and HOAt (0.7 mg, 5 μmol), followed by compound 40 (3.5 mg, 4 μmol) in one portion at room temperature. Reaction mixture was stirred for 1 h and then directly treated with piperidine (8 μL, 160 μmol) at room temperature. After 20 minutes, reaction mixture was purified by reversed-phase prep HPLC (C18, 0-70% v/v MeCN—H$_2$O with 0.05% TFA). Lyophilized pure fractions gave 2.8 mg of compound 92 (1 μmol, 26% yield) as a yellow powder. LRMS (ESI): m/z 1458.2 [M+2H]$^{2+}$, Calcd for C$_{144}$H$_{184}$N$_{20}$O$_{45}$ m/z 1458.1.

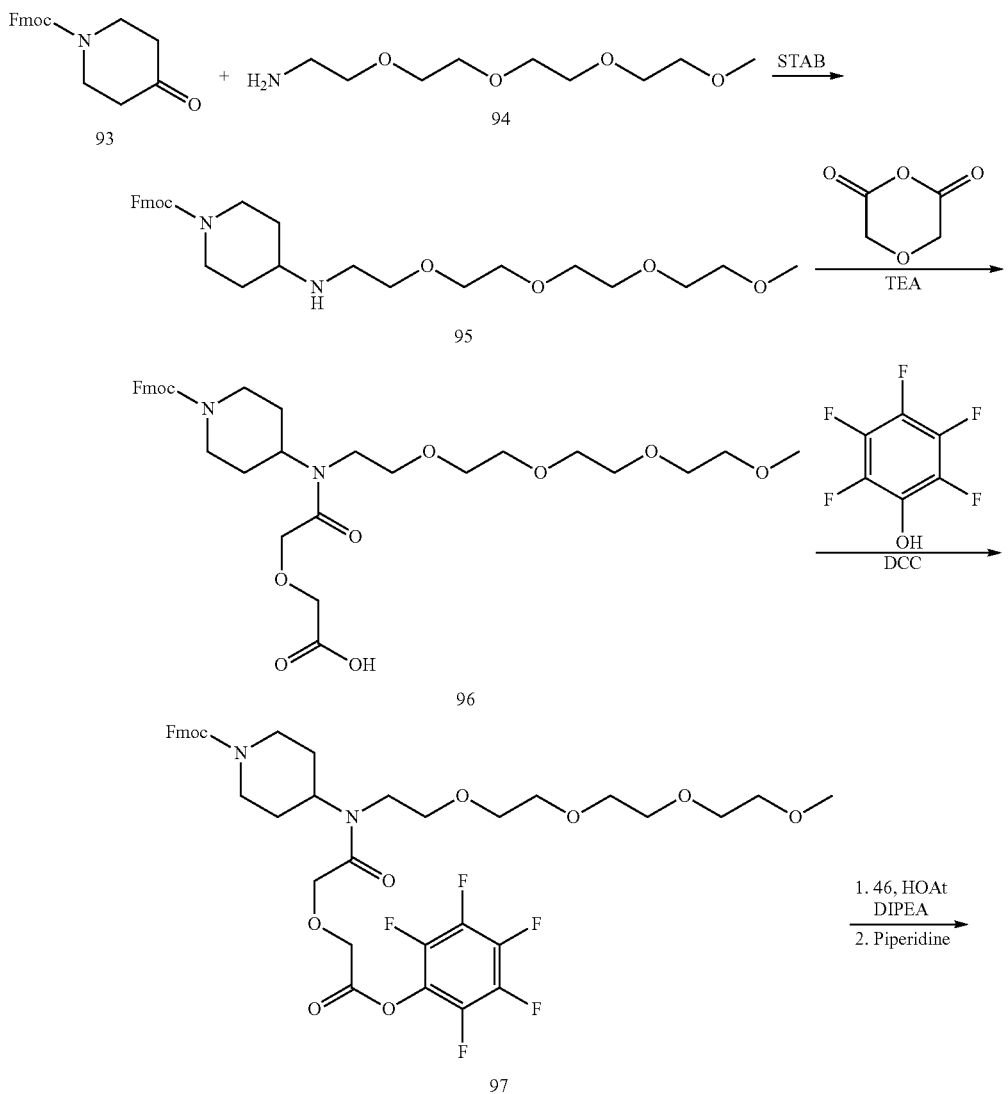

Scheme 17. Synthesis of branched belotecan construct 99

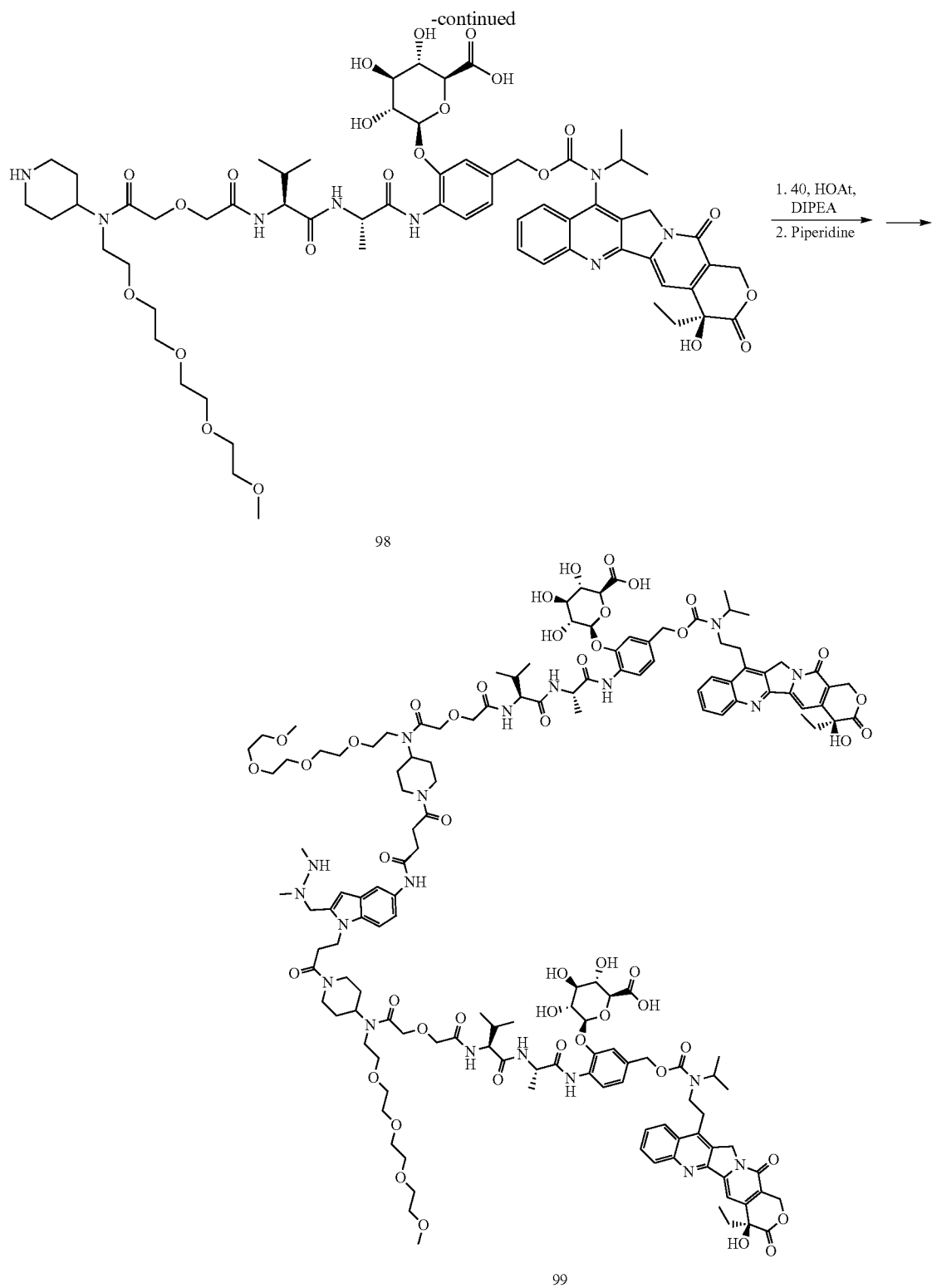

98

99

Preparation of (9H-fluoren-9-yl)methyl 4-((2,5,8,11-tetraoxatridecan-13-yl)amino)piperidine-1-carboxylate (95)

A mixture of N-Fmoc-piperidone (93, 642 mg, 2 mmol) and mPEG4-amine (94, 414 mg, 2 mmol) in DCE (10 mL) was stirred for 30 mins at room temperature, and then treated with STAB (840 mg, 4 mmol) in small portions. The resulting mixture was allowed to stir for 2 h, quenched with sat. sodium bicarbonate solution (5 mL), and extracted with EtOAc (3×15 mL). Combined organic layers were washed with brine and dried over sodium sulfate. Solvents were removed in vacuum to give crude product 95 as colorless oil (900 mg), which was used further without purification.

Preparation of 14-(1-(((9H-fluoren-9-yl)methoxy) carbonyl)piperidin-4-yl)-15-oxo-2,5,8,11,17-pentaoxa-14-azanonadecan-19-oic Acid (96)

To a solution of crude compound 95 (900 mg) in anhydrous MeCN (10 mL) were added 1,4-dioxane-2,6-dione (1.0 g, 0.93 mmol) and triethylamine (0.85 mL, 0.93 mmol) at room temperature. Reaction mixture was stirred for 30 min and then directly purified by reversed-phase chromatography (C18, 0-70% v/v MeCN—$H_2O$ with 0.05% TFA). Pure fractions were collected and lyophilized to obtain compound 96 as a colorless oil (260 mg, 0.45 mmol, 23% yield over 2 steps). LRMS (ESI): m/z 629.3 [M+H]$^+$, Calcd for $C_{33}H_{44}N_2O_{10}$ m/z 629.3.

Preparation of (9H-fluoren-9-yl)methyl 4-(2-(2-oxo-2-(perfluorophenoxy)ethoxy)-N-(2,5,8,11-tetraoxatridecan-13-yl)acetamido)piperidine-1-carboxylate (97)

To a mixture of acid 96 (260 mg, 0.41 mmol) and pentafluorophenol (264 mg, 1.23 mmol) in 2 mL of anhydrous THF were added DCC (253 mg, 1.23 mmol) at room temperature. Reaction mixture was stirred overnight, solids were filtered off, solvent was removed under reduced pressure, and the residue was purified by silica gel chromatography (EtOAc-hexane 0-50% v/v gradient) to give 163 mg of PFP-ester 97 (0.20 mmol, 50% yield) as a colorless oil. LRMS (ESI): m/z 795.3 [M+H]$^+$, Calcd for $C_{39}H_{43}F_5N_2O_{10}$ m/z 795.3.

Preparation of (2S,3S,4S,5R,6S)-6-(5-(((((2-((S)-4-ethyl-4-hydroxy-3,14-dioxo-3,4,12,14-tetrahydro-1H-pyrano[3',4':6,7]indolizino[1,2-b]quinolin-11-yl) ethyl)(isopropyl)carbamoyl)oxy)methyl)-2-((21S,24S)-21-isopropyl-24-methyl-15,19,22-trioxo-14-(piperidin-4-yl)-2,5,8,11,17-pentaoxa-14,20,23-triazapentacosan-25-amido)phenoxy)-3,4,5-trihydroxytetrahydro-2H-pyran-2-carboxylic Acid (98)

To a solution of compound 46 (25 mg, 26 µmol) in anhydrous DMF (1.0 mL) were added DIPEA (14 µL, 73 µmol) and HOAt (4.6 mg, 34 µmol) followed by PFP-ester 97 (21 mg, 26 µmol) at room temperature. Reaction mixture was stirred for 30 min, then piperidine (52 uL, 0.52 mmol) was added, and stirring continued for 20 minutes. Reaction mixture was purified directly by reversed-phase chromatography (C18, 0-100% v/v MeCN—$H_2O$ with 0.05% TFA). Lyophilized pure fractions gave 22 mg of compound 98 (16 µmol, 62% yield) as a yellow powder. LRMS (ESI): m/z 1333.6 [M+H]$^+$, Calcd for $C_{65}H_{88}N_8O_{22}$ m/z 1333.6.

Preparation of (2S,3S,4S,5R,6S)-6-(2-((21S,24S)-14-(1-(4-((1-(3-(4-(2-(2-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7] indolizino[1,2-b]quinolin-11-yl)ethyl)(isopropyl) carbamoyl)oxy)methyl)phenyl)amino)-1-oxopropan-2-yl)amino)-3-methyl-1-oxobutan-2-yl)amino)-2-oxoethoxy)-N-(2,5,8,11-tetraoxatridecan-13-yl) acetamido)piperidin-1-yl)-3-oxopropyl)-2-((1,2-dimethylhydrazinyl)methyl)-1H-indol-5-yl)amino)-4-oxobutanoyl)piperidin-4-yl)-21-isopropyl-24-methyl-15,19,22-trioxo-2,5,8,11,17-pentaoxa-14,20, 23-triazapentacosan-25-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl) ethyl)(isopropyl)carbamoyl)oxy)methyl)phenoxy)-3,4,5-trihydroxytetrahydro-2H-pyran-2-carboxylic Acid (99)

To a solution of compound 98 (22 mg, 16 µmol) in anhydrous DMF (1.0 mL) were added DIPEA (4.3 µL, 24 µmol) and HOAt (1.4 mg, 11 µmol), followed by the addition of compound 40 (7 mg, 8 µmol) at room temperature. After 30 minutes, piperidine (16 µL, 0.16 mmol) was added in one shot at room temperature. Reaction mixture was stirred for 15 minutes and then directly purified by reversed-phase prep HPLC (C18, 0-70% v/v MeCN—$H_2O$ with 0.05% TFA). Lyophilized pure fractions gave 15 mg of 99 (5 µmol, 63% yield) as a yellow powder. LRMS (ESI): m/z 1504.2 [M+2H]$^{2+}$, Calcd for $C_{148}H_{196}N_{20}O_{47}$ m/z 1504.2.

Scheme 18. Synthesis of branched belotecan construct 103

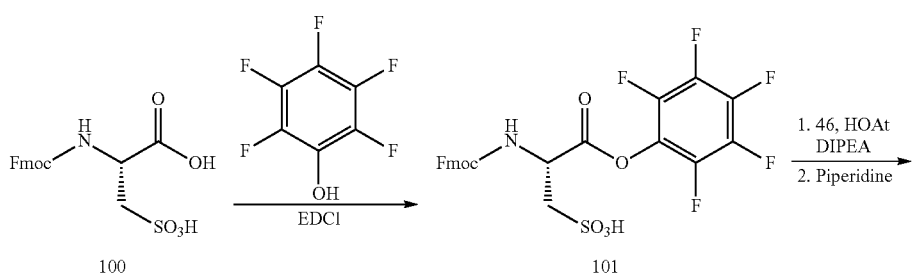

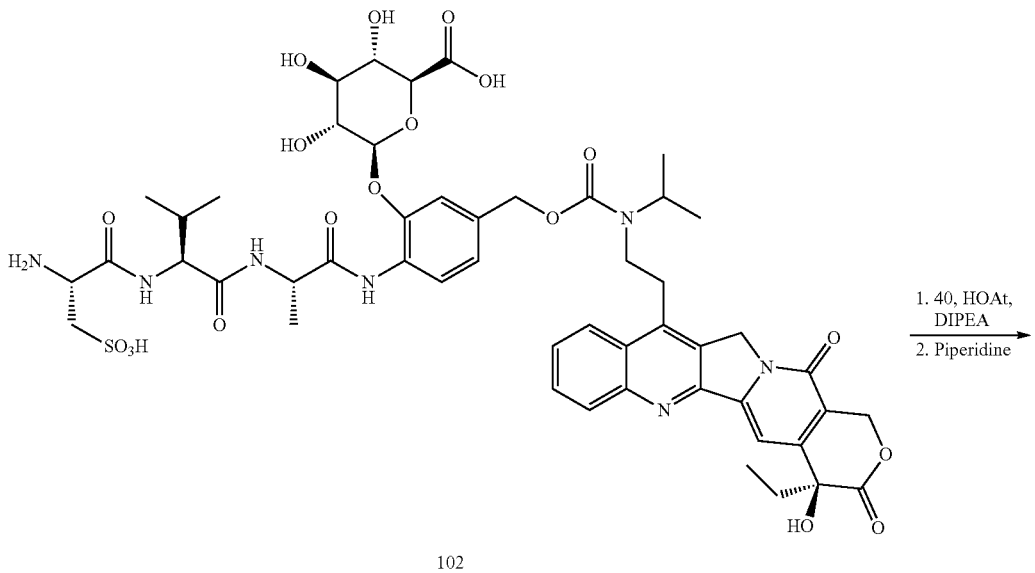

102

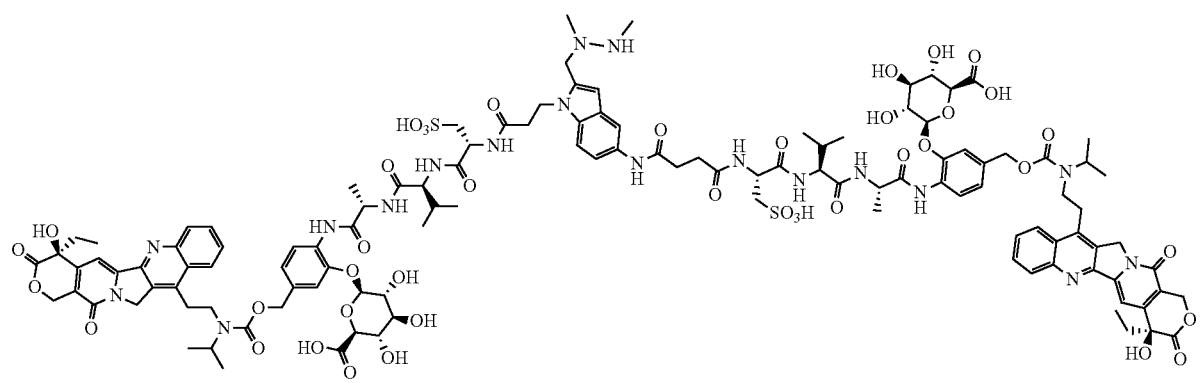

103

Preparation of (R)-2-((((9H-fluoren-9-yl)methoxy)carbonyl)amino)-3-oxo-3-(perfluorophenoxy)propane-1-sulfonic Acid (101)

To a stirred mixture of Fmoc-L-cysteic acid 100 (100 mg, 0.26 mmol) and pentafluorophenol (94 mg, 0.51 mmol) in 2 mL of anhydrous DMF were added EDCI-HCl (98 mg, 0.51 mmol) in one portion at room temperature. The resulting mixture was stirred overnight and then directly purified by reversed-phase chromatography (C18, 0-100% v/v MeCN—$H_2O$ with 0.05% TFA). Pure fractions were concentrated under reduced pressure until solution became murky and lyophilized to give 122 mg of PFP-ester 101 (0.22 mmol, 85% yield) as an off-white solid. LRMS (ESI-): m/z 556.2 [M–H]⁻, Calcd for $C_{24}H_{16}F_5NO_7S$ m/z 556.1.

Preparation of (2S,3S,4S,5R,6S)-6-(2-((S)-2-((S)-2-((R)-2-amino-3-sulfopropanamido)-3-methylbutanamido)propanamido)-5-(((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (102)

To a mixture of compound 46 (30 mg, 32 μmol) and DIPEA (11 μL, 64 μmol) in 2 mL of anhydrous DMF were added PFP-ester 101 (18 mg, 32 μmol) at room temperature, followed by HOAt (4.5 mg, 32 μmol). The resulting mixture was allowed to stand at room temperature for 1 h and then treated with piperidine (63 μL, 0.63 mmol). After 20 minutes, reaction mixture was purified by reversed-phase prep HPLC (C18, 0-50% v/v MeCN—$H_2O$ with 0.05% TFA). Pure fractions containing product were combined and lyophilized to give 12 mg of compound 102 (11 μmol, 34% yield) as a yellow solid.

Preparation of (2S,3S,4S,5R,6S)-6-(2-((S)-2-((S)-2-((R)-2-(4-((1-(3-(((R)-1-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-1-oxopropan-2-yl)amino)-3-methyl-1-oxobutan-2-yl)amino)-1-oxo-3-sulfopropan-2-yl)amino)-3-oxopropyl)-2-((1,2-dimethylhydrazinyl)methyl)-1H-indol-5-yl)amino)-4-oxobutanamido)-3-sulfopropanamido)-3-methylbutanamido)propanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (103)

To a mixture of compound 102 (12 mg, 11 µmol) and DIPEA (4 µL, 22 µmol) in 2 mL of anhydrous DMF were added bis-PFP-ester 40 (4.5 mg, 5 µmol) at room temperature, followed by HOAt (1.5 mg, 11 µmol). The resulting mixture was allowed to stand at room temperature for 1 h and then treated with piperidine (22 µL, 0.22 mmol). After 20 minutes, reaction mixture was purified by reversed-phase prep HPLC (C18, 0-50% v/v MeCN—H$_2$O/10 mM ammonium formate). Pure fractions containing product were combined and lyophilized to give 7 mg of compound 103 (2.8 µmol, 56% yield) as a tan powder. LRMS (ESI): m/z 1266.5 [M+2H]$^{2+}$, Calcd for C$_{118}$H$_{142}$N$_{18}$O$_{41}$S$_2$ m/z 1266.5.

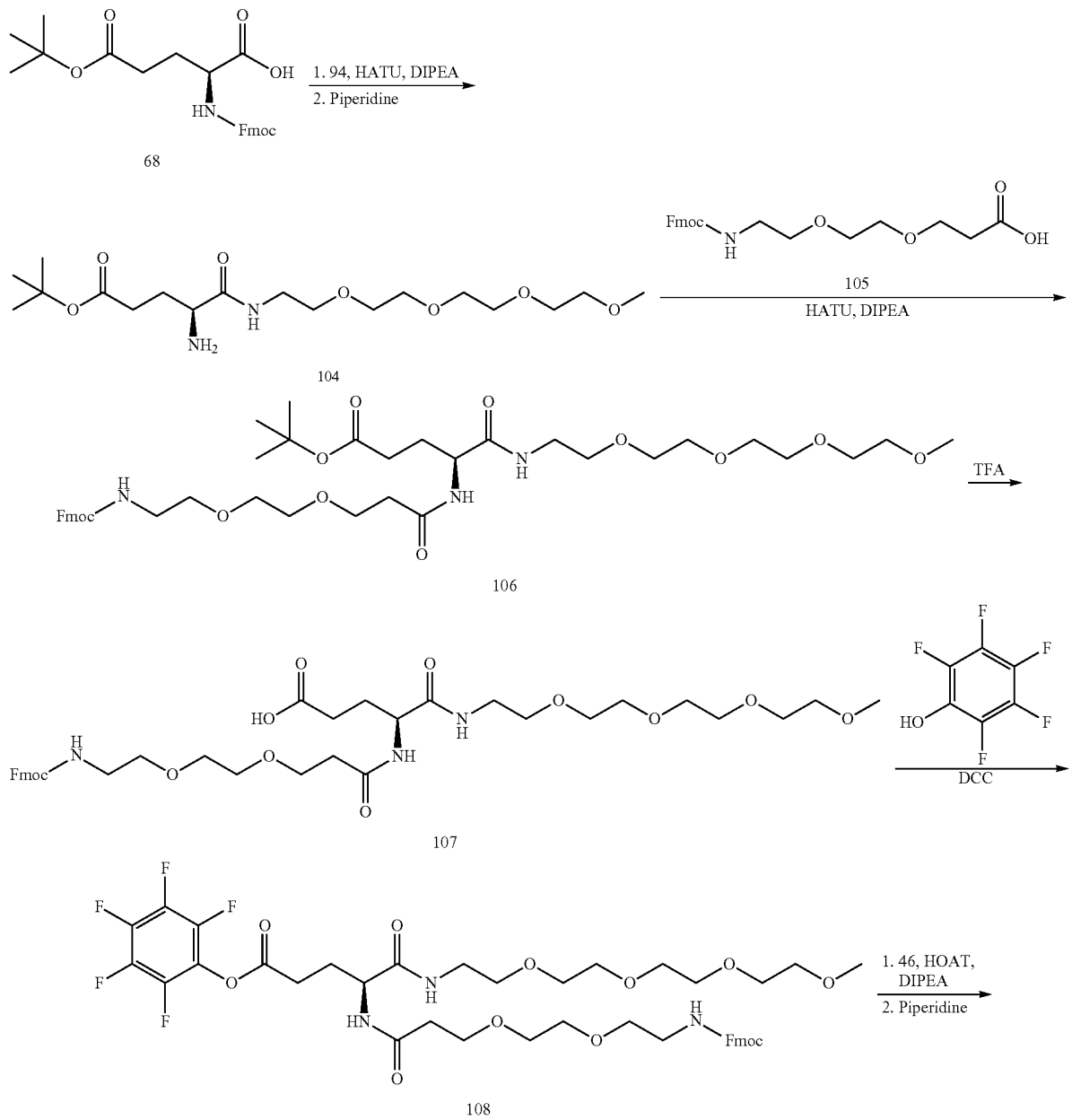

Scheme 19. Synthesis of branched belotecan construct 110

-continued

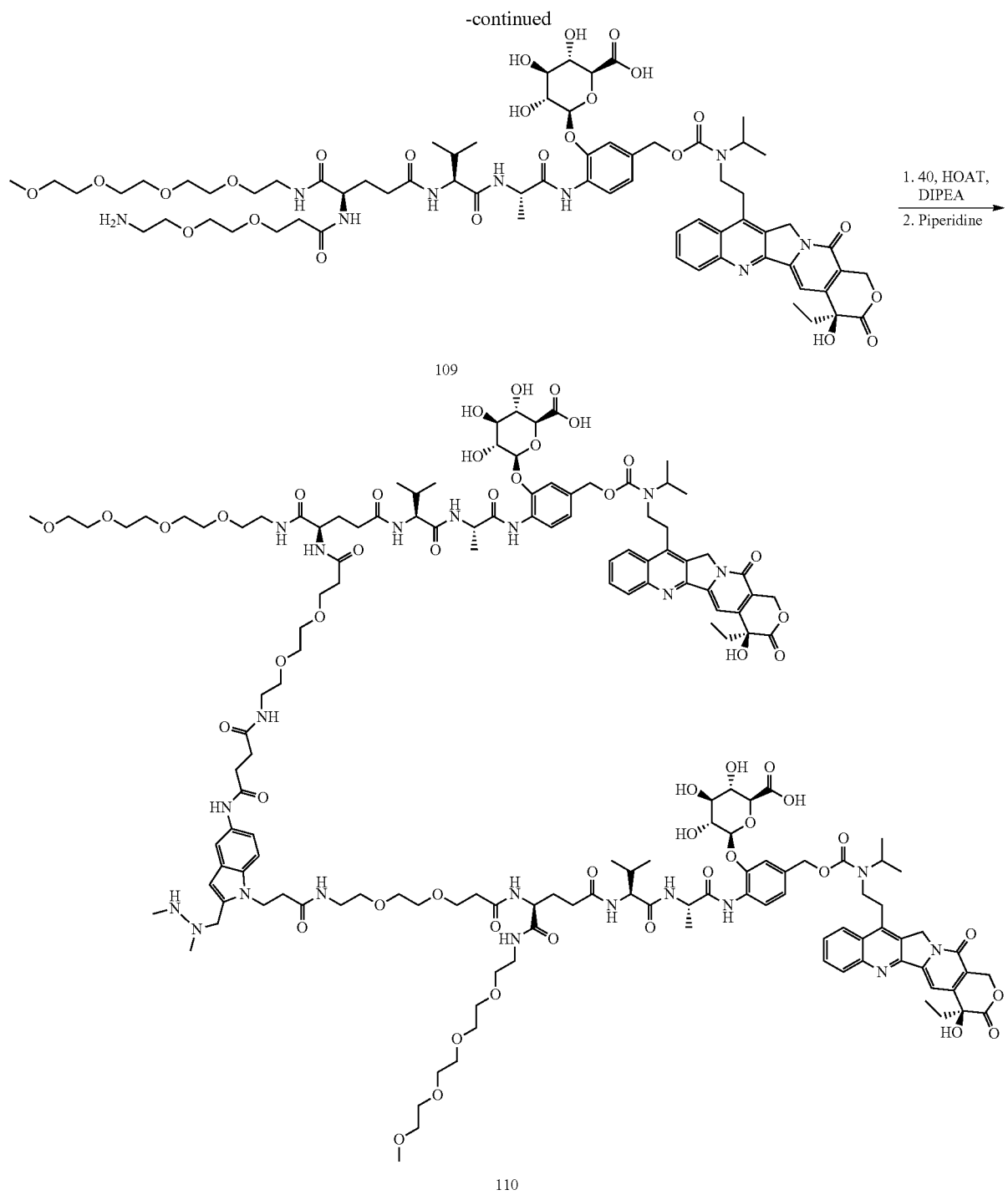

Preparation of tert-butyl (S)-16-amino-15-oxo-2,5,8,11-tetraoxa-14-azanonadecan-19-oate (104)

To a solution of Fmoc-Glu-OtBu 68 (0.49 g, 1.2 mmol) in DMF (15 mL) were added HATU (0.42 g, 1.1 mmol) and DIPEA (1 mL) at room temperature. The resulting mixture was stirred for 45 min, then combined with mPEG4-amine 94 (0.20 g, 0.96 mmol) and stirred for 30 min at room temperature. Reaction was quenched by addition of 0.05% TFA in water (30 mL) and extracted with EtOAc (2×30 mL). Organic layer was washed with water and brine, dried over $Na_2SO_4$, filtered, and concentrated in vacuum to give crude oil. The crude was resuspended in acetonitrile (20 mL) and treated with piperidine (1.0 mL, 1 mmol) at room temperature. After 45 min, solvents were removed in vacuum to give crude oil, which was washed once with hexane (10 mL) and purified by reversed-phase chromatography (C18, 0-50% v/v MeCN—$H_2O$ with 0.05% TFA). Pure fractions were combined and concentrated, followed by lyophilization to give amine 104 (0.23 g, 0.57 mmol, 58% yield) as an oily solid. LRMS (ESI): m/z 393.3 [M+H]$^+$, Calcd for $C_{18}H_{36}N_2O_7$ m/z 393.3.

Preparation of tert-butyl (S)-16-(1-(9H-fluoren-9-yl)-3-oxo-2,7,10-trioxa-4-azatridecan-13-amido)-15-oxo-2,5,8,11-tetraoxa-14-azanonadecan-19-oate (106)

To a solution of amine 104 (0.23 g; 0.57 mmol) in DMF (10 mL) were added carboxylic acid 105 (0.29 g; 0.72 mmol), HATU (0.27 g; 0.69 mmol), and DIPEA (0.50 mL, 2.9 mmol) at room temperature. Reaction mixture was allowed to stir for 2 h, then poured into 0.05% aqueous TFA (15 mL) and extracted with EtOAc (2×25 mL). Organic layer was washed with water and brine, and dried over sodium sulfate. Solvents were removed under vacuum to afford crude compound 106 as an oil (0.50 g), which was use further without purification. LRMS (ESI): m/z 774.9 [M+H]$^+$, Calcd for $C_{40}H_{59}N_3O_{12}$ m/z 774.4.

Preparation of (S)-16-(1-(9H-fluoren-9-yl)-3-oxo-2,7,10-trioxa-4-azatridecan-13-amido)-15-oxo-2,5,8,11-tetraoxa-14-azanonadecan-19-oic acid (107)

To a solution of crude ester 106 (0.25 g, 0.32 mmol) in DCM (10 mL) were added TFA (4.0 mL), and the resulting solution was allowed to stir at room temperature for 6h. Solvents were removed in vacuum to give 0.23 g (0.32 mmol, quant. yield) of crude compound 107 as an oil. LRMS (ESI): m/z 718.4 [M+H]$^+$, Calcd for $C_{36}H_{51}N_3O_{12}$ m/z 718.4.

Preparation of perfluorophenyl (S)-16-(1-(9H-fluoren-9-yl)-3-oxo-2,7,10-trioxa-4-azatridecan-13-amido)-15-oxo-2,5,8,11-tetraoxa-14-azanonadecan-19-oate (108)

To a solution of crude acid 107 (0.23 g; 0.32 mmol) in anhydrous THF (10 mL) were added DCC (0.33 g; 1.57 mmol) and pentafluoro phenol (0.29 g; 1.57 mmol) at room temperature. Reaction mixture was allowed to stir overnight at room temperature, then filtered, and concentrated under vacuum. The residue was purified by silica gel chromatography using 0-10% MeOH in DCM gradient to give 0.23 g of PFP-ester 106 a colorless oil (0.23 g, 0.26 mmol, 81% yield). LRMS (ESI): m/z 884.9 [M+H]$^+$, Calcd for $C_{42}H_{50}F_5N_3O_{12}$ m/z 884.3.

Preparation of (2S,3S,4S,5R,6S)-6-(2-((16R,21S,24S)-16-(3-(2-(2-aminoethoxy)ethoxy)propanamido)-21-isopropyl-24-methyl-15,19,22-trioxo-2,5,8,11-tetraoxa-14,20,23-triazapentacosan-25-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (109)

To a solution of amine 46 (10 mg; 10 μmol) in anhydrous DMF (2 mL) were added PFP-ester 106 (11.5 mg; 13 μmol), followed by HOAt (3 mg, 22 μmol) and DIPEA (10 μL) at room temperature. Reaction mixture was allowed to stir for 1 h, then piperidine (50 μL) was added to directly to the mixture and stirring continued for 30 mins. Reaction mixture was quenched by adding 2 mL of aqueous 0.05% TFA solution and purified by reversed-phase prep HPLC (C18, 0-50% v/v MeCN—$H_2O$ with 0.05% TFA). Pure fractions were lyophilized to give 13 mg of compound 109 (9 μmol, 90% yield) as a pale-yellow solid. LRMS (ESI): m/z 1422.6 [M+H]$^+$, Calcd for $C_{68}H_{95}N_9O_{24}$ m/z 1422.7.

Preparation of (2S,3S,4S,5R,6S)-6-(2-((16S,21S,24S)-16-(3-(2-(2-(3-(5-((R)-16-(3-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-1-oxopropan-2-yl)amino)-3-methyl-1-oxobutan-2-yl)amino)-3-oxopropyl)-15,18,28-trioxo-2,5,8,11,21,24-hexaoxa-14,17,27-triazahentriacontan-31-amido)-2-((1,2-dimethylhydrazinyl)methyl)-1H-indol-1-yl)propanamido)ethoxy)ethoxy)propanamido)-21-isopropyl-24-methyl-15,19,22-trioxo-2,5,8,11-tetraoxa-14,20,23-triazapentacosan-25-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (110)

To a solution of amine 110 (13 mg, 9 μmol) in 2.5 mL of anhydrous DMF were added bis-PFP-ester 40 (4.2 mg, 4.5 μmol), followed by HOAt (2.4 mg, 18 μmol) and DIPEA (5 μL). Reaction mixture was allowed to stir for 30 mins, then piperidine (50 μL) was added directly to the mixture and stirring continued for 30 min. Reaction mixture was purified by reversed-phase prep HPLC (C18, 0-50% v/v MeCN—$H_2O$ with 0.05% TFA). Lyophilization of pure fractions gave 5 mg of compound 110 (1.6 μmol, 36% yield) as a pale-yellow solid. LRMS (ESI): m/z 1593.3 [M+2H]$^{2+}$, Calcd for $C_{154}H_{210}N_{22}O_{51}$ m/z 1593.2.

Scheme 20. Synthesis of branched belotecan construct 113

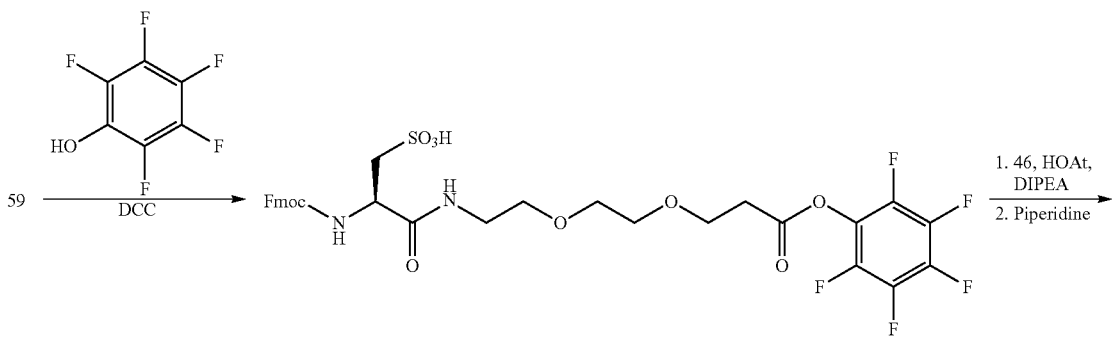

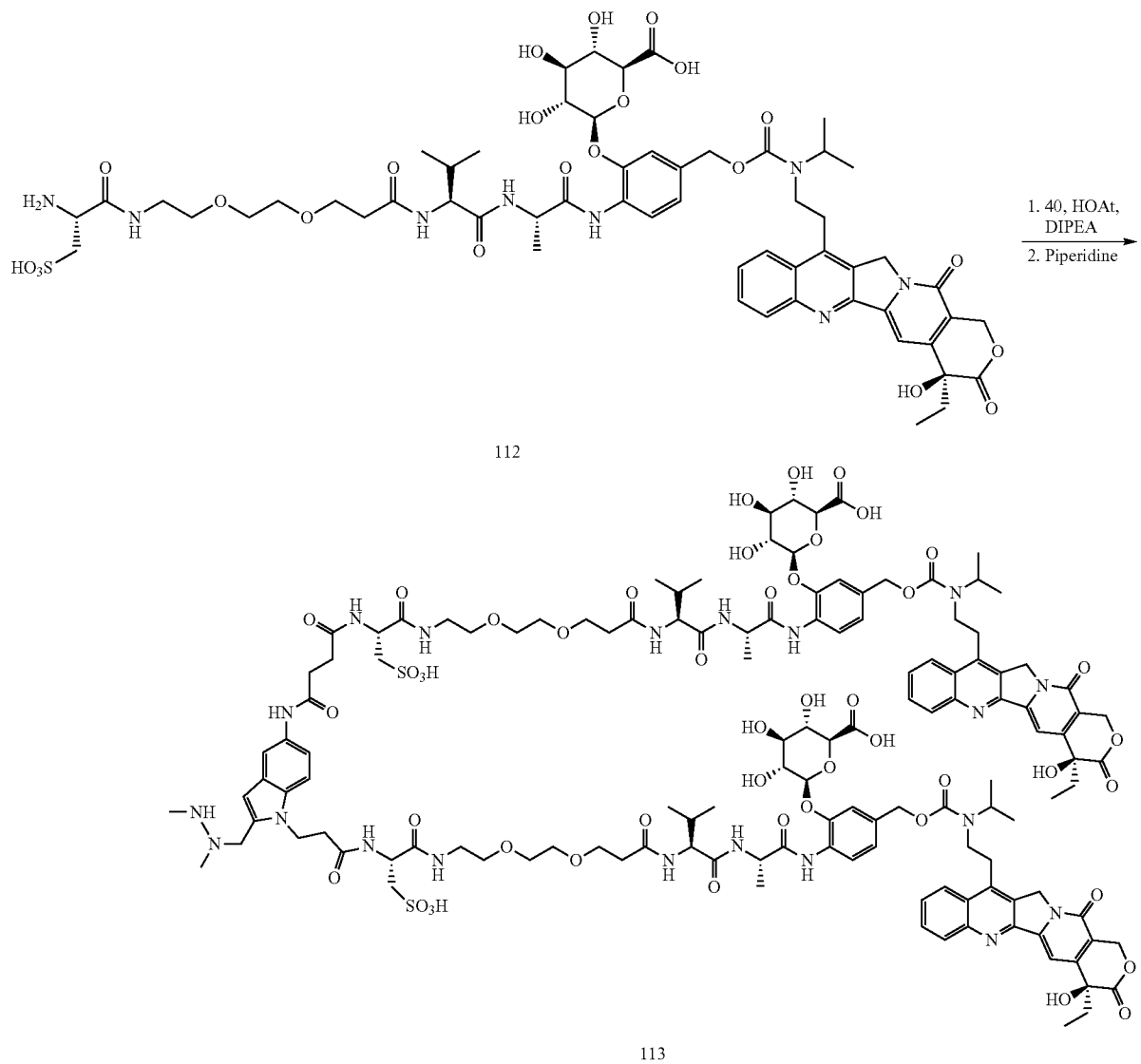

112

113

Preparation of (R)-2-(((((9H-fluoren-9-yl)methoxy)carbonyl)amino)-3-oxo-3-((2-(2-(3-oxo-3-(perfluorophenoxy)propoxy)ethoxy)ethyl)amino)propane-1-sulfonic Acid (111)

To a mixture of compound 59 (136 mg, 0.25 mmol) and pentafluorophenol (136 mg, 0.75 mmol) in 2 mL of anhydrous THF were added DCC (155 mg, 0.75 mmol) at room temperature. Reaction mixture was stirred overnight, solids were filtered off, solvent was removed under reduced pressure, and the residue was purified by silica gel chromatography (EtOAc-hexane, 0-50% v/v gradient) to obtain PFP-ester 111 (27 mg, 38 μmol, 15% yield) as a colorless oil. LRMS (ESI): m/z 717.2 [M+H]$^+$, Calcd for $C_{31}H_{29}F_5N_2O_{10}S$ m/z 717.2.

Preparation of (2S,3S,4S,5R,6S)-6-(2-((2S,5S,18R)-18-amino-5-isopropyl-2-methyl-4,7,17-trioxo-19-sulfo-10,13-dioxa-3,6,16-triazanonadecanamido)-5-(((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (112)

To a stirred solution of compound 46 (25 mg, 26 μmol) in anhydrous DMF (1.0 mL) were added DIPEA (14 μL, 73 μmol) and HOAt (5 mg, 35 μmol), followed by PFP-ester 111 (19 mg, 27 μmol) in one portion at room temperature. Reaction mixture was stirred for 1 h, then purified by reversed-phase chromatography (C18, 0-100% v/v MeCN—H$_2$O with 0.05% TFA). Lyophilized pure fractions gave 9 mg of compound 112 (7 μmol, 26% yield) as a yellow powder. LRMS (ESI): m/z 1255.4 [M+H]$^+$, Calcd for $C_{57}H_{74}N_8O_{22}S$ m/z 1255.5.

Preparation of (2S,3S,4S,5R,6S)-6-(2-((2S,5S,18R)-23-((1-((2S,5S,18R)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,17,20-pentaoxo-18-(sulfomethyl)-10,13-dioxa-3,6,16,19-tetraazadocosan-22-yl)-2-((1,2-dimethylhydrazinyl)methyl)-1H-indol-5-yl)amino)-5-isopropyl-2-methyl-4,7,17,20,23-pentaoxo-18-(sulfomethyl)-10,13-dioxa-3,6,16,19-tetraazatricosanamido)-5-(((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (113)

To a solution of compound 112 (9 mg, 7 µmol) in anhydrous DMF (1.0 mL) were added DIPEA (2 µL, 10 µmol) and HOAt (1.4 mg, 10 µmol), followed by bis-PFP ester 40 (3.0 mg, 3.5 µmol) in one portion at room temperature. Reaction mixture was stirred for 30 min, then treated with piperidine (7 µL, 70 µmol), let stir for 15 minutes, and then directly purified by reversed-phase prep HPLC (C18, 0-70% v/v MeCN—H$_2$O with 0.05% TFA). Lyophilized pure fractions gave 6 mg of compound 113 (2.0 µmol, 57% yield) as a yellow powder. LRMS (ESI): m/z 1426.1 [M+2H]$^{2+}$, Calcd for C$_{132}$H$_{168}$N$_{20}$O$_{47}$S$_2$ m/z 1426.0.

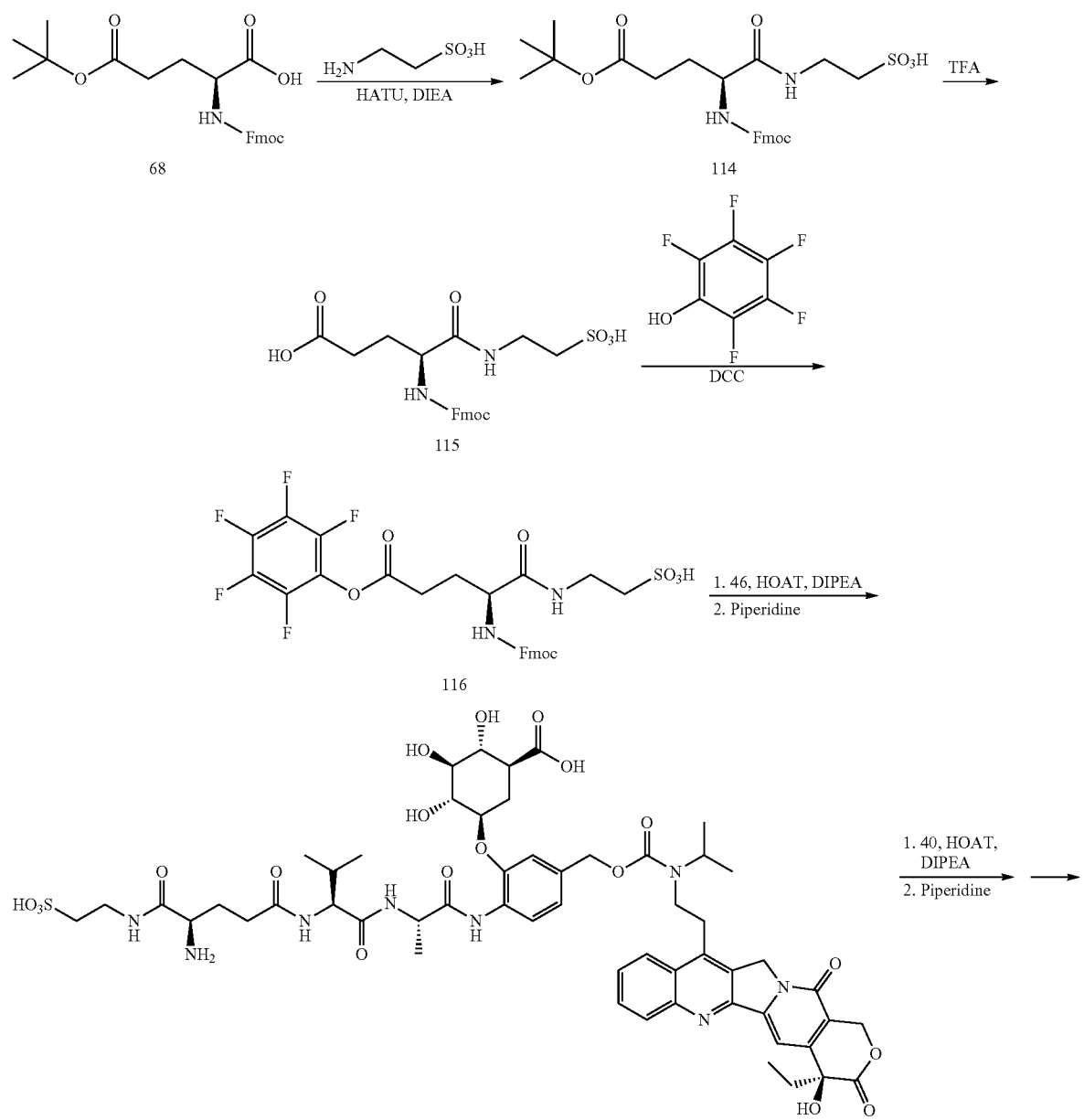

Scheme 21. Synthesis of branched belotecan construct 118

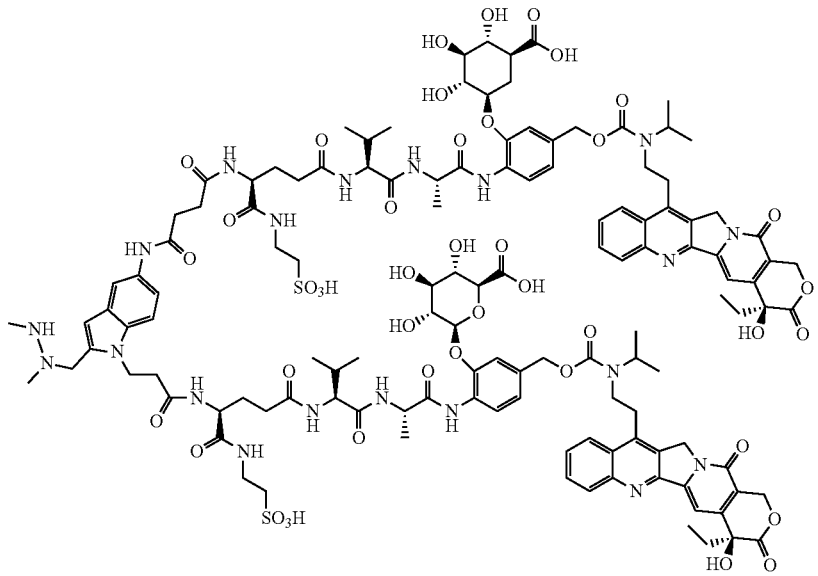

118

Preparation of (S)-2-(2-((((9H-fluoren-9-yl)methoxy)carbonyl)amino)-5-(tert-butoxy)-5-oxopentanamido)ethane-1-sulfonic Acid (114)

To a 100 mL round bottom flask were added Fmoc-Glu(OtBu)-OH 68 (0.750 g, 1.77 mmol) and anhydrous DMF (20 mL), followed by HATU (1.02 g, 2.64 mmol), HOAt (0.250 g, 2.12 mmol), and DIPEA (500 µL) at room temperature. The resulting mixture was stirred for 45 min, then taurine (0.445 g, 3.53 mmol) was added, and the mixture was allowed to stir overnight. Reaction mixture was poured into water and extracted with DCM. Organic layer was washed with water, brine, dried over $Na_2SO_4$. Solvents were removed in vacuum to give crude compound 114 (1.4 g) as a white solid. LRMS (ESI-): m/z 531.2 [M–H]$^-$, Calcd for $C_{26}H_{32}N_2O_8S$ m/z 531.2.

Preparation of (S)-4-((((9H-fluoren-9-yl)methoxy)carbonyl)amino)-5-oxo-5-((2-sulfoethyl)amino)pentanoic Acid (115)

To a solution of crude compound 114 (1.4 g) in DCM (10 mL) were added TFA (5 mL) at room temperature. The reaction mixture was allowed to stir overnight, then solvents were removed in vacuum and the residue was purified by reversed-phase chromatography (C18 column, 0-50% v/v MeCN—$H_2O$ with 0.05% TFA) to give 0.74 g of product 115 as a white solid (1.6 mmol, 88% yield over 2 steps). LRMS (ESI-): m/z 475.1 [M–H]$^-$, Calcd for $C_{22}H_{24}N_2O_8S$ m/z 475.1.

Preparation of (S)-2-(2-((((9H-fluoren-9-yl)methoxy)carbonyl)amino)-5-oxo-5-(perfluorophenoxy)pentanamido)ethane-1-sulfonic Acid (116)

To a 100 mL round bottom flask with anhydrous THF (25 mL) were added carboxylic acid 115 (0.25 g; 0.53 mmol) and pentafluorophenol (0.49 g; 2.6 mmol), followed by DCC (0.83 g; 3.9 mmol) at room temperature. The resulting mixture was allowed to stir overnight at room temperature, then filtered, concentrated under vacuum, and purified by silica gel chromatography (0-10% MeOH in DCM gradient) to yield 0.18 g of PFP-ester 116 as a white solid (0.28 mmol, 53% yield). LRMS (ESI-): m/z 641.1 [M–H]$^-$, Calcd for $C_{28}H_{23}F_5N_2O_8S$ m/z 641.1.

Preparation of (2S,3S,4S,5R,6S)-6-(2-((S)-2-((S)-2-((R)-4-amino-5-oxo-5-((2-sulfoethyl)amino)pentanamido)-3-methylbutanamido)propanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (117)

To a solution of PFP-ester 116 (30 mg, 48 µmol) in anhydrous DMF (3 mL) were added amine 46 (29 mg, 32 µmol), followed by HOAt (7.4 mg, 54 µmol) and DIPEA (30 µL) at room temperature. The resulting mixture was stirred for 45 min, then piperidine (50 µL) was added to the mixture and stirring continued for 30 min. Reaction mixture was purified directly by reversed-phase prep HPLC (C18 column, 0-50% v/v MeCN—$H_2O$ with 0.05% TFA). Fractions containing product were concentrated and lyophilized to give 28 mg (24 µmol, 75% yield) of compound 117 as a bright yellow solid. LRMS (ESI-): m/z 1179.4 [M–H]$^-$, Calcd for $C_{54}H_{68}N_8O_{20}S$ m/z 1179.4.

Preparation of (2S,3S,4S,5R,6S)-6-(2-((S)-2-((S)-2-((S)-4-(4-((1-(3-(((S)-5-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-1-oxopropan-2-yl)amino)-3-methyl-1-oxobutan-2-yl)amino)-1,5-dioxo-1-((2-sulfoethyl)amino)pentan-2-yl)amino)-3-oxopropyl)-2-((1,2-dimethylhydrazinyl)methyl)-1H-indol-5-yl)amino)-4-oxobutanamido)-5-oxo-5-((2-sulfoethyl)amino)pentanamido)-3-methylbutanamido)propanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (118)

To a solution of compound 117 (28 mg, 24 μmol) in 2 mL of anhydrous DMF were added bis-PFP-ester 40 (11 mg, 11.6 μmol), followed by HOAt (39 mg, 28 μmol) and DIPEA (21 μL). The resulting mixture was stirred for 45 min, then treated with piperidine (50 μL), stirred for additional 30 min, and purified by reversed-phase prep HPLC (C18 column, 0-50% v/v MeCN—H$_2$O with 0.05% TFA). Fractions containing the desired product were collected and lyophilized to give 15 mg of compound 118 as a pale-yellow solid (5.5 μmol, 47% yield). LRMS (ESI−): m/z 1350.0 [M-2H]$^{2-}$, Calcd for C$_{126}$H$_{156}$N$_{20}$O$_{43}$S$_2$ m/z 1350.0.

Scheme 22. Synthesis of branched belotecan construct 123

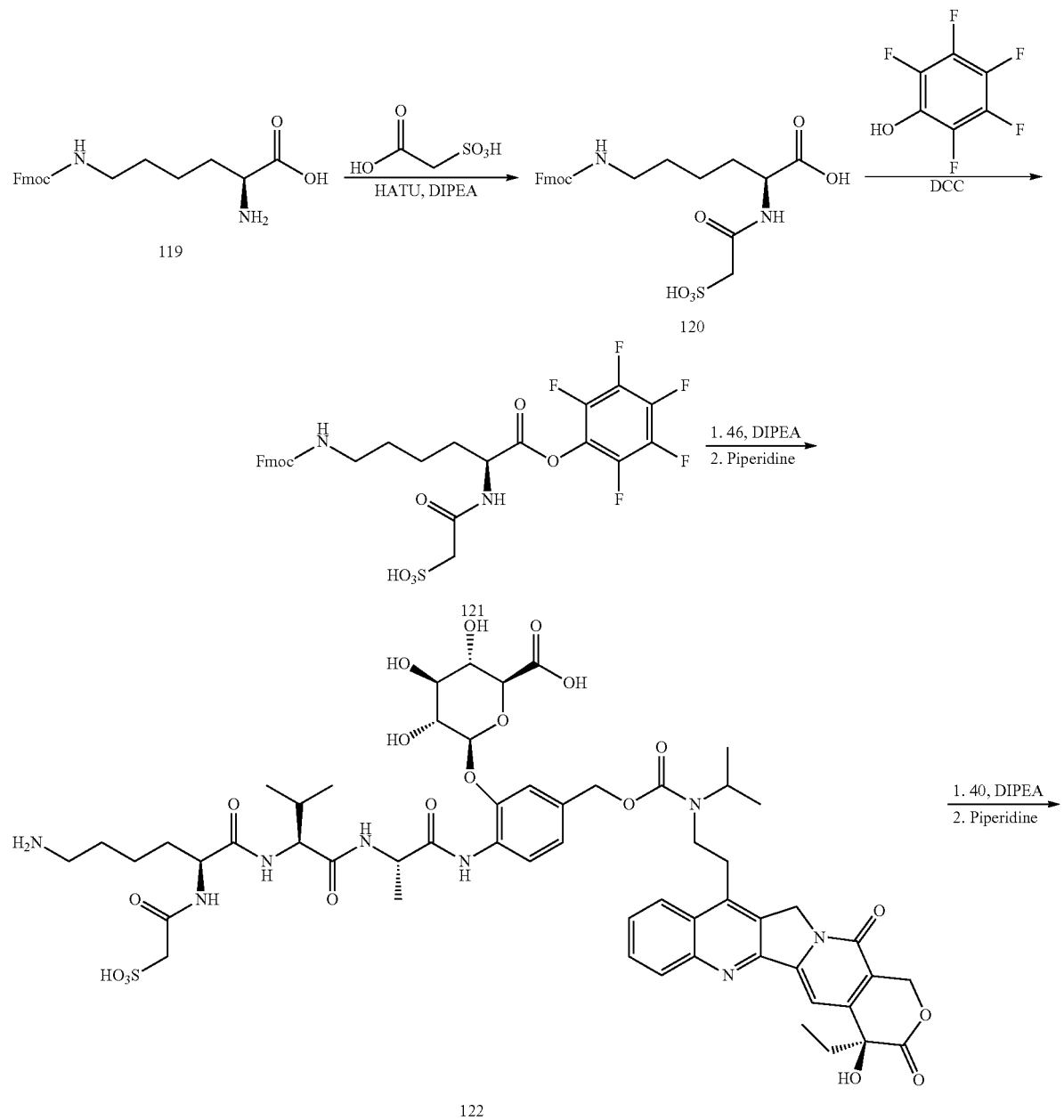

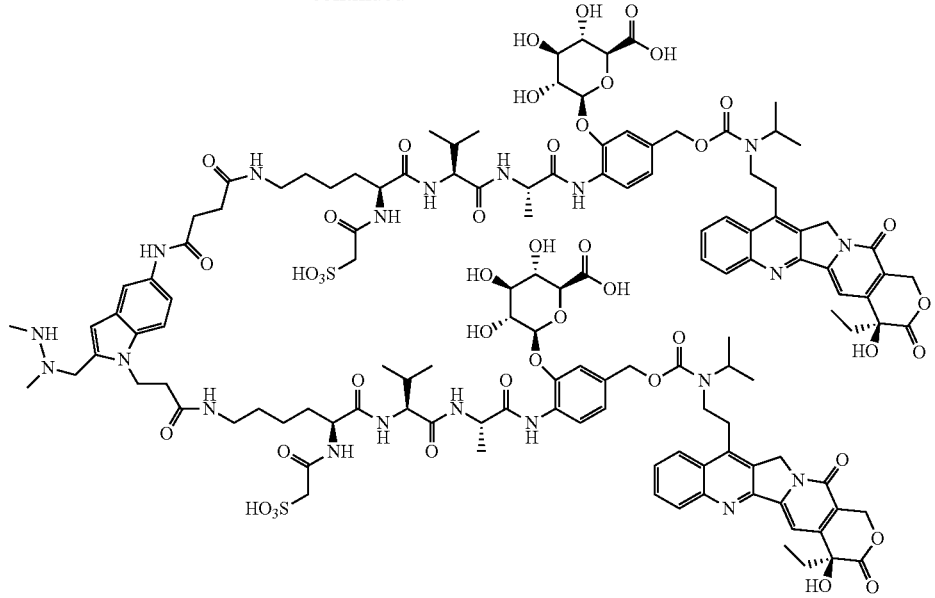

123

Preparation of N⁶-(((9H-fluoren-9-yl)methoxy)carbonyl)-N²-(2-sulfoacetyl)-L-lysine (120)

To a solution of 2-sulfoacetic acid (280 mg, 2.0 mmol) in DMF (3 mL) were added HATU (760 mg, 2.0 mmol) and DIPEA (695 µL, 4.0 mmol) at room temperature. After stirring this mixture for 30 minutes, amino acid 119 (330 mg, 0.90 mmol) was added, and stirring continued for one hour. Reaction mixture was directly purified by reversed phase HPLC using C18 column (H₂O/CH₃CN with 0.05% TFA, 90:10 to 0:100 v/v). Fractions containing the desired compound were pooled and lyophilized to yield compound 1280 mg, 0.57 mmol, 63% yield). LRMS (ESI): m/z 491.2 [M+H]⁺, Calcd for $C_{23}H_{26}N_2O_8S$ m/z 491.1.

Preparation of (S)-2-((6-((((9H-fluoren-9-yl)methoxy)carbonyl)amino)-1-oxo-1-(perfluorophenoxy)hexan-2-yl)amino)-2-oxoethane-1-sulfonic Acid (121)

To a stirred mixture of carboxylic acid 120 (280 mg, 0.76 mmol) and pentafluorophenol (315 mg, 1.7 mmol) in DCM (5 mL) was at DCC (35 mg, 1.7 mmol) at room temperature. After stirring for one hour, reaction mixture was filtered, concentrated, and purified by reversed phased chromatography on C18 column (H₂O/CH₃CN with 0.05% TFA, 90:10 to 0:100 v/v) to afford compound 121 as a white solid (80 mg, 0.12 mmol, 16% yield). LRMS (ESI): m/z 657.1 [M+H]⁺, Calcd for $C_{29}H_{25}F_5N_2O_8S$ m/z 657.1.

Preparation of (2S,3S,4S,5R,6S)-6-(2-((S)-2-((S)-2-((S)-6-amino-2-(2-sulfoacetamido)hexanamido)-3-methylbutanamido)propanamido)-5-((((2-((S)-4-ethyl-4-hydroxy-3,14-dioxo-3,4,12,14-tetrahydro-1H-pyrano[3′,4′:6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (122)

To a mixture of amine 46 (10 mg, 11 µmol) and PFP-ester 121 (15 mg, 23 µmol) in anhydrous DMF (0.5 mL) were added DIPEA (4.4 µL, 26 µmol) at room temperature. After stirring overnight, piperidine (50 µL) was added to the reaction mixture. After stirring for 15 minutes at room temperature, reaction mixture was directly purified by reversed phase prep HPLC using C18 column (H₂O/CH₃CN with 0.05% TFA, 90:10 to 45:55 v/v). Fractions containing the desired compound were pooled and lyophilized to yield compound 122 (7 mg, 5.9 µmol, 54% yield). LRMS (ESI): m/z 1195.5 [M+H]⁺, Calcd for $C_{55}H_{70}N_8O_{20}S$ m/z 1195.4.

Preparation of (2S,3S,4S,5R,6S)-6-(2-((S)-2-((S)-2-((S)-6-(4-((1-(3-(((S)-6-(((S)-1-(((S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3′,4′:6,7]indolizino[1,2-b]quinolin-11-yl)ethyl)(isopropyl)carbamoyl)oxy)methyl)phenyl)amino)-1-oxopropan-2-yl)amino)-3-methyl-1-oxobutan-2-yl)amino)-6-oxo-5-(2-sulfoacetamido)hexyl)amino)-3-oxopropyl)-2-((1,2-dimethylhydrazineyl)methyl)-1H-indol-5-yl)amino)-4-oxobutanamido)-2-(2-sulfoacetamido)hexanamido)-3-methylbutanamido)propanamido)-5-((((2-((S)-4-ethyl-4-hydroxy-3,14-dioxo-3,4,12,14-tetrahydro-1H-pyrano[3′,4′:6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (123)

To a stirred mixture of amine 122 (7 mg, 6 µmol) and bis-PFP-ester 40 (2.6 mg, 2.8 µmol) in DMF (0.5 mL) were added DIPEA (5 µL, 26 µmol) at room temperature. The resulting mixture was stirred for 2 hours, then piperidine (50 µL) was added to the mixture. After stirring for 15 minutes at room temperature, the reaction mixture was directly purified by reversed phase prep HPLC using C18 column (H₂O/CH₃CN with 0.05% TFA, 90:10 to 45:55 v/v). Fractions containing the desired compound were pooled and lyophilized to yield compound 123 (3 mg, 1 µmol, 36% yield). LRMS (ESI): m/z 1365.5 [M+H]²⁺, Calcd for $C_{128}H_{160}N_{20}O_{43}S_2$ m/z 1365.5.

Scheme 23. Synthesis of branched belotecan construct 127
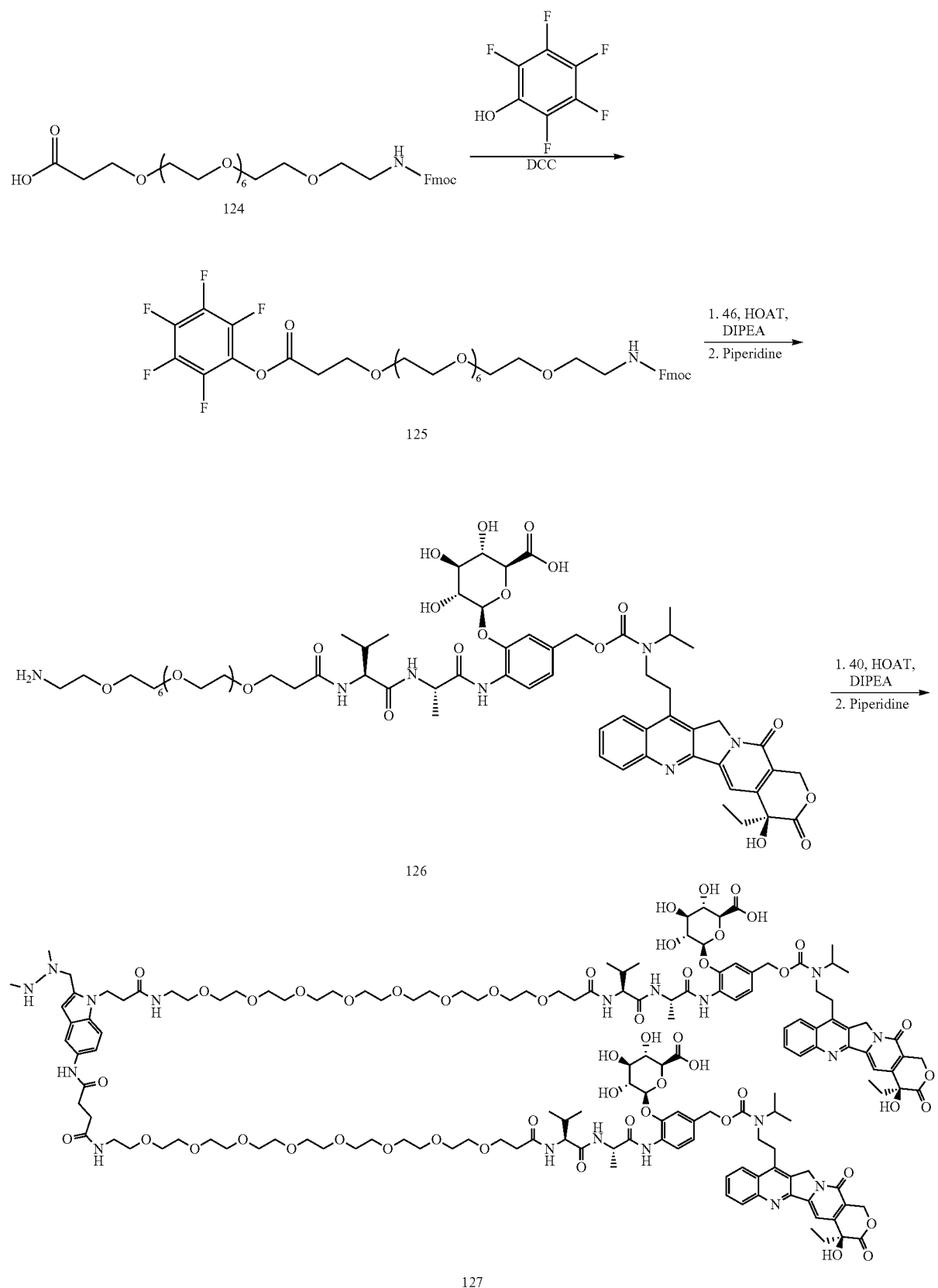

Preparation of perfluorophenyl 1-(9H-fluoren-9-yl)-3-oxo-2,7,10,13,16,19,22,25,28-nonaoxa-4-azahentriacontan-31-oate (125)

To a stirred mixture of carboxylic acid 124 (100 mg, 0.15 mmol) and pentafluorophenol (140 mg, 0.75 mmol) in anhydrous THF (2 mL) were added DCC (37 mg, 0.18 mmol) in one portion at room temperature. The resulting mixture was stirred overnight, filtered, and concentrated under vacuum. The residue was purified by reversed-phase chromatography (C18 column, 0-70% v/v MeCN—H$_2$O with 0.05% TFA) to afford 120 mg of compound 125 (0.14 mmol, 93% yield) as a clear colorless oil. LRMS (ESI): m/z 830.3 [M+H]$^+$, Calcd for C$_{40}$H$_{48}$F$_5$NO$_{12}$ m/z 830.3.

Preparation of (2S,3S,4S,5R,6S)-6-(2-((29S,32S)-1-amino-29-isopropyl-32-methyl-27,30-dioxo-3,6,9,12,15,18,21,24-octaoxa-28,31-diazatritriacontan-33-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (126)

A solution of amine 46 (55 mg, 58 μmol) in 2 mL of anhydrous DMF was treated with DIPEA (20 μL, 0.12 mmol) and HOAt (8 mg, 58 μmol), and then combined with PFP-ester 125 (48 mg, 58 μmol) in DMF (1 mL) at room temperature. The resulting mixture was stirred for 30 minutes, then piperidine (115 μL, 115 μmol) was added to the mixture. After 20 minutes, reaction mixture was purified by reversed-phase prep HPLC (C18 column, 0-50% v/v MeCN—H$_2$O with 0.05% TFA). Pure fractions containing product were combined and lyophilized to give 49 mg of compound 126 as a yellowish solid (36 μmol, 62% yield). LRMS (ESI): m/z 1368.6 [M+H]$^+$, Calcd for C$_{66}$H$_{93}$N$_7$O$_{24}$ m/z 1368.6.

Preparation of (2S,3S,4S,5R,6S)-6-(2-((2S,5S)-38-((1-((2S,5S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,35-tetraoxo-10,13,16,19,22,25,28,31-octaoxa-3,6,34-triazaheptatriacontan-37-yl)-2-((1,2-dimethylhydrazineyl)methyl)-1H-indol-5-yl)amino)-5-isopropyl-2-methyl-4,7,35,38-tetraoxo-10,13,16,19,22,25,28,31-octaoxa-3,6,34-triazaoctatriacontanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (127)

To a mixture of compound 126 (49 mg, 36 μmol) and DIPEA (13 μL, 72 μmol) in 2 mL of DMA were added bis-PFP-ester 40 (14.6 mg, 16 μmol) in one portion at room temperature, followed by HOAt (5 mg, 36 μmol). The resulting mixture was stirred at room temperature for 30 minutes, then piperidine (21 μL), was added, and stirring continued for 20 minutes. Reaction mixture was directly purified by reversed-phase prep HPLC (C18 column, 0-50% v/v MeCN—H$_2$O with 0.05% TFA). Lyophilized fractions gave 32 mg of compound 127 (10 μmol, 63% yield) as a yellow powder. LRMS (ESI): m/z 1539.3 [M+H]$^{2+}$, Calcd for C$_{150}$H$_{206}$N$_{18}$O$_5$ m/z 1538.7.

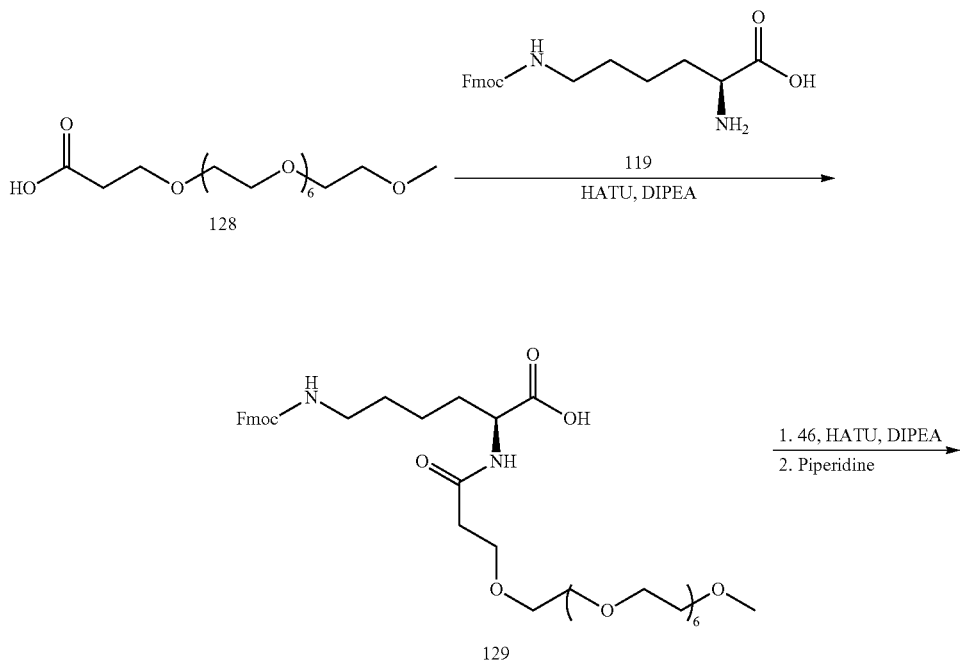

Scheme 24. Synthesis of branched belotecan construct 131

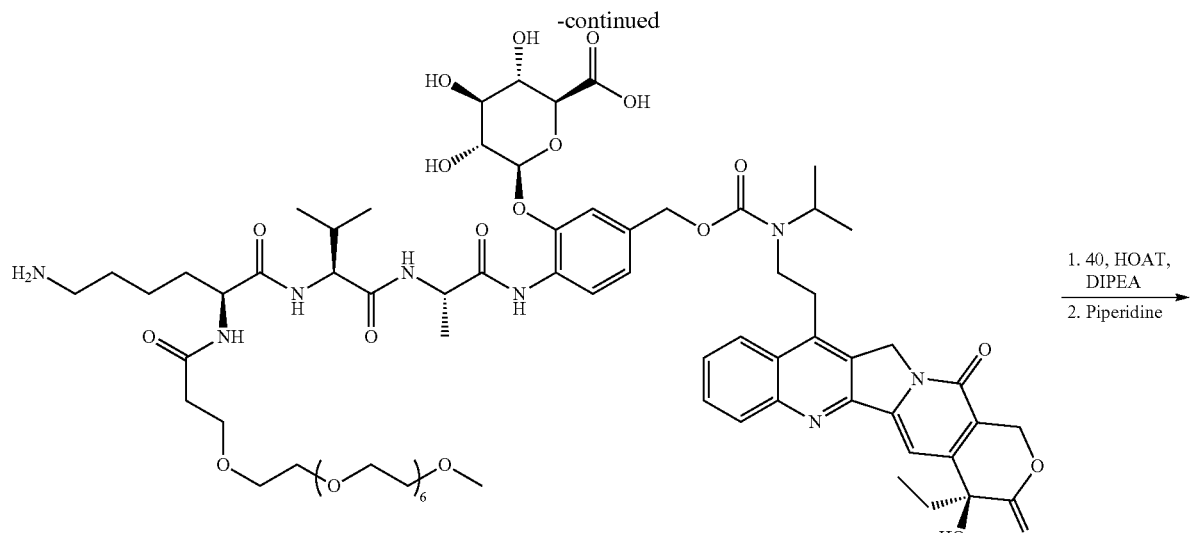

130

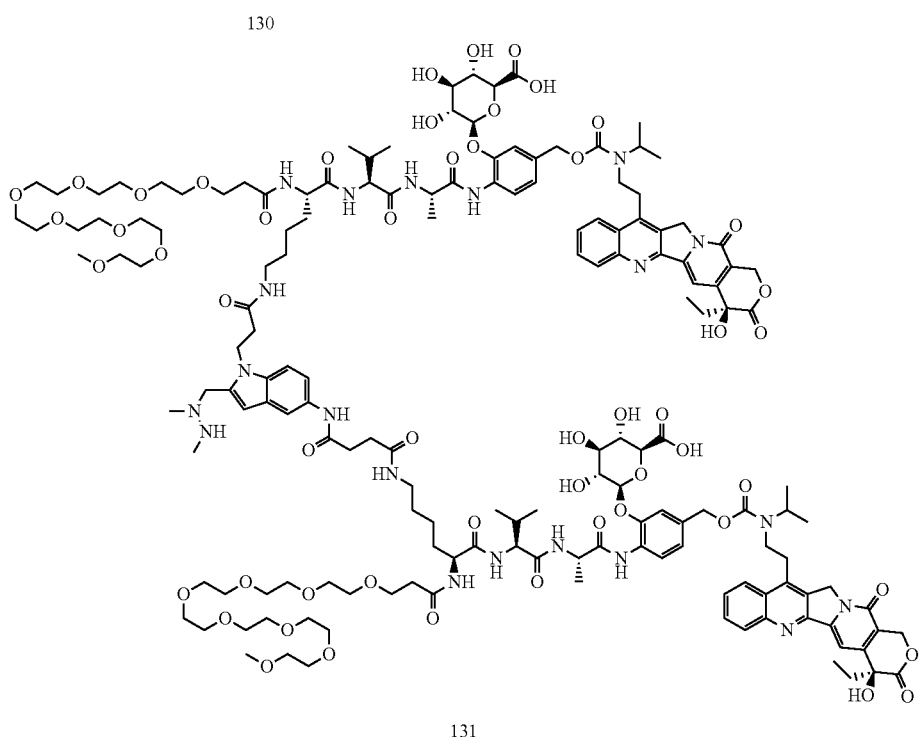

131

Preparation of N[6]-(((9H-fluoren-9-yl)methoxy)carbonyl)-N[2]-(3-(2-(2-methoxyethoxy)ethoxy)propanoyl)-L-lysine (129)

To a solution of mPEG8-acid 128 (100 mg, 0.24 mmol) in 2 mL of anhydrous DMF were added DIPEA (0.13 mL, 0.72 mmol) and HATU (93 mg, 0.24 mmol) at room temperature. The resulting mixture was stirred for one hour, then Lys (Fmoc)-OH 119 (89 mg, 0.24 mmol) was added to the mixture, and stirring continued for one hour. Reaction mixture was directly purified by reversed-phase chromatography HPLC (C18, 0-70% v/v MeCN—H$_2$O with 0.05% TFA) to give 120 mg of compound 129 (0.16 mmol, 67% yield) as a colorless oil. LRMS (ESI): m/z 763.4 [M+H]$^+$, Calcd for C$_{39}$H$_{58}$N$_2$O$_{13}$ m/z 763.4.

Preparation of (2S,3S,4S,5R,6S)-6-(2-((28S,31S,34S)-28-(4-aminobutyl)-31-isopropyl-34-methyl-26,29,32-trioxo-2,5,8,11,14,17,20,23-octaoxa-27,30,33-triazapentatriacontan-35-amido)-5-((((2-((S)-4-ethyl-4-hydroxy-3,14-dioxo-3,4,12,14-tetrahydro-1H-pyrano[3′,4′:6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (130)

To a solution of carboxylic acid 129 (45 mg, 59 μmol) in 3 mL of anhydrous DMF were added DIPEA (21 μL, 120 μmol) and HATU (22 mg, 59 μmol) at room temperature. The resulting mixture was stirred for 20 minutes and combined with amine 46 (55 mg, 58 μmol) in 1 mL of DMF. Reaction mixture was stirred for 30 minutes, then piperidine (115 μL, 1.2 mmol) was added to the mixture at room temperature. After 20 minutes, reaction mixture was directly purified by reversed phase prep HPLC (C18, 0-50% v/v MeCN—H$_2$O with 0.05% TFA). Lyophilization of pure fractions afforded 34 mg (23 μmol, 40% yield) of compound 130 as a yellow powder. LRMS (ESI): m/z 1467.7 [M+H]$^+$, Calcd for C$_{71}$H$_{102}$N$_8$O$_{25}$ m/z 1467.7.

Preparation of (2S,3S,4S,5R,6S)-6-(2-((28S,31S, 34S)-28-(4-(3-(5-((S)-28-(((S)-1-(((S)-1-((2-(((2S, 3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6, 7]indolizino[1,2-b]quinolin-11-yl)ethyl)(isopropyl) carbamoyl)oxy)methyl)phenyl)amino)-1-oxopropan-2-yl)amino)-3-methyl-1-oxobutan-2-yl)carbamoyl)-26,34-dioxo-2,5,8,11,14,17,20,23-octaoxa-27,33-diazaheptatriacontan-37-amido)-2-((1,2-dimethylhydrazineyl)methyl)-1H-indol-1-yl) propanamido)butyl)-31-isopropyl-34-methyl-26,29, 32-trioxo-2,5,8,11,14,17,20,23-octaoxa-27,30,33-triazapentatriacontan-35-amido)-5-((((2-((S)-4-ethyl-4-hydroxy-3,14-dioxo-3,4,12,14-tetrahydro-1H-pyrano[3',4':6,7]indolizino[1,2-b]quinolin-11-yl) ethyl)(isopropyl)carbamoyl)oxy)methyl)phenoxy)-3, 4,5-trihydroxytetrahydro-2H-pyran-2-carboxylic Acid (131)

To a mixture of compound 130 (34 mg, 23 μmol) and DIPEA (8 μL, 46 μmol) in 2 mL of DMA were added bis-PFP ester 40 (9.4 mg, 10.5 μmol), followed by HOAt (3 mg, 23 μmol) at room temperature. The resulting mixture was allowed to stand for 30 minutes at room temperature, then piperidine (21 μL, 0.21 mmol) was added to the mixture at room temperature. After 20 minutes, reaction mixture was directly purified by reversed phase prep HPLC (C18, 0-50% v/v MeCN—H$_2$O with 0.05% TFA). Pure fractions were combined and lyophilized to afford compound 131 as a yellow solid (23 mg, 7 μmol, 67% yield). LRMS (ESI): m/z 1638.3 [M+H]$^{2+}$, Calcd for C$_{160}$H$_{224}$N$_{20}$O$_{53}$ m/z 1638.8.

Scheme 25. Synthesis of branched belotecan construct 136

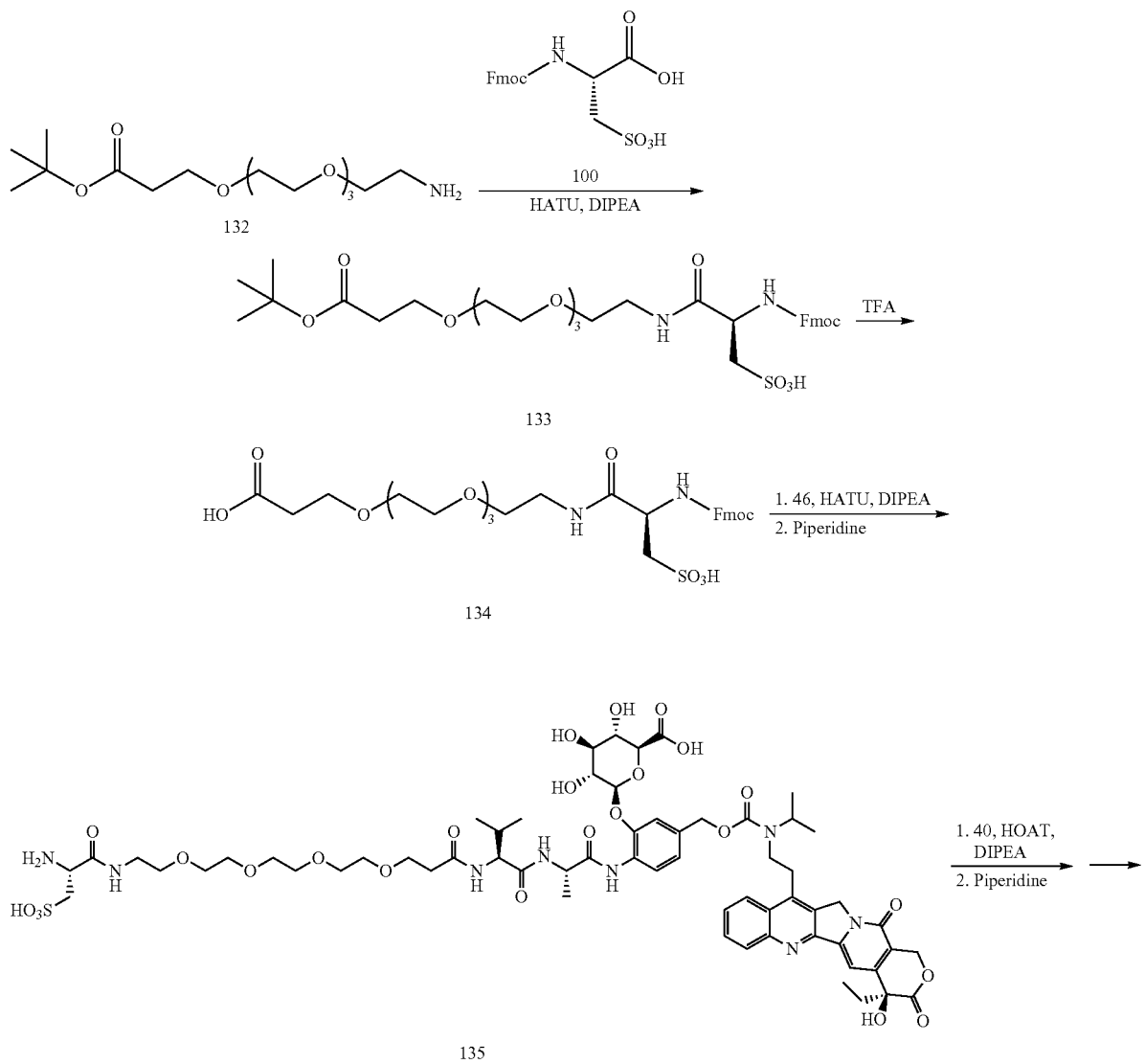

-continued

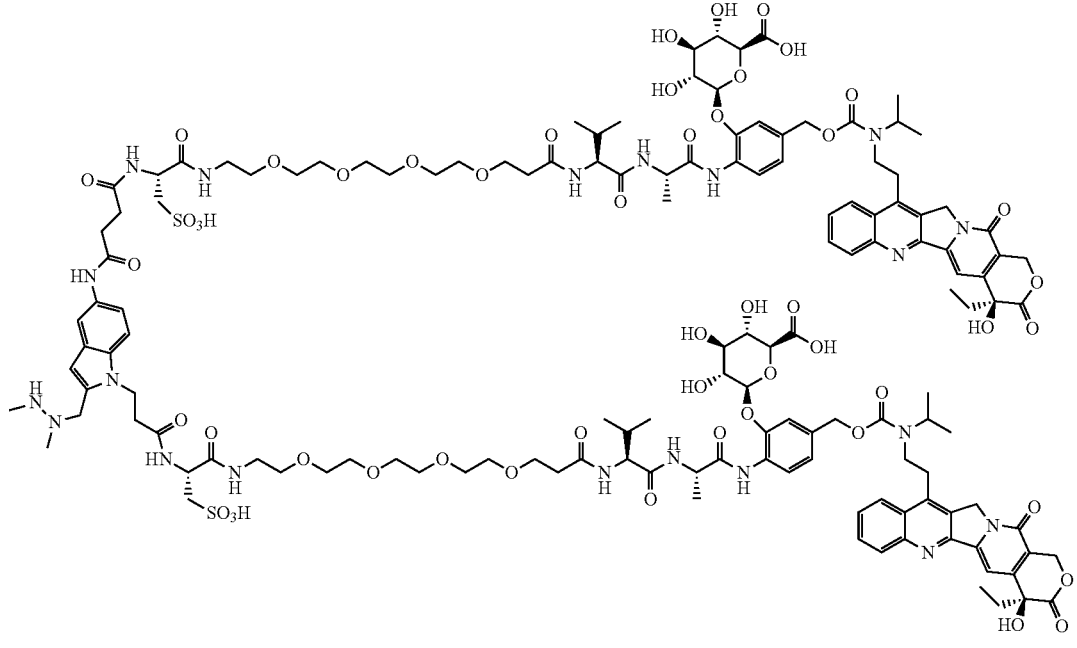

136

Preparation of (R)-21-((((9H-fluoren-9-yl)methoxy)carbonyl)amino)-2,2-dimethyl-4,20-dioxo-3,7,10,13,16-pentaoxa-19-azadocosane-22-sulfonic Acid (133)

To a mixture of Fmoc-L-cysteic acid 100 (391 mg, 1.0 mmol) and amine 132 (321 mg, 1.0 mmol) in anhydrous DMF (2 mL) were added HATU (400 mg, 1.05 mmol) and DIPEA (0.52 mL, 3 mmol). Reaction mixture was stirred for one hour, and then directly purified by reversed phase chromatography (C18, 0-50% v/v MeCN—H$_2$O with 0.05% TFA) to obtain compound 133 as a colorless oil (500 mg, 0.72 mmol, 72% yield). LRMS (ESI-): m/z 693.3 [M−H]$^-$, Calcd for C$_{33}$H$_{46}$N$_2$O$_{12}$S m/z 693.3.

Preparation of (R)-1-(9H-fluoren-9-yl)-3,6-dioxo-5-(sulfomethyl)-2,10,13,16,19-pentaoxa-4,7-diazadocosan-22-oic Acid (134)

To a solution of compound 133 (100 mg, 0.14 mmol) in DCM (2 mL) were added TFA (2 mL) at ambient temperature. Reaction mixture was stirred for 10 minutes, then solvents were removed under vacuum, and the residue was purified by reversed phase chromatography (C18, 0-75% v/v MeCN—H$_2$O with 0.05% TFA) to give compound 134 as a colorless oil (80 mg, 0.12 mmol, 86% yield). LRMS (ESI-): m/z 637.2 [M−H]$^-$, Calcd for C$_{29}$H$_{38}$N$_2$O$_{12}$S m/z 637.2.

Preparation of (2S,3S,4S,5R,6S)-6-(2-((2S,5S,24R)-24-amino-5-isopropyl-2-methyl-4,7,23-trioxo-25-sulfo-10,13,16,19-tetraoxa-3,6,22-triazapentacosanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (135)

To a solution of compound 134 (9 mg, 14 µmol) in anhydrous DMF (1.0 mL) were added DIPEA (7.4 µL, 42 µmol) and HATU (5 mg, 13 µmol) at room temperature. The resulting mixture was stirred for 30 minutes, and then combined with compound 46 (14 mg, 15 µmol) at room temperature. After one hour, piperidine (30 µL) was added to the reaction mixture, and stirring continued for 20 minutes. Reaction mixture was purified by reversed-phase prep HPLC (C18, 0-70% v/v MeCN—H$_2$O with 0.05% TFA). Lyophilized pure fractions gave 13 mg of compound 135 (10 µmol, 68% yield) as a yellow powder. LRMS (ESI): m/z 1343.5 [M+H]$^+$, Calcd for C$_{61}$H$_{82}$N$_8$O$_{24}$S m/z 1343.5.

Preparation of (2S,3S,4S,5R,6S)-6-(2-((2S,5S,24R)-28-(5-((2S,5S,24R)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,23,26-pentaoxo-24-(sulfomethyl)-10,13,16,19-tetraoxa-3,6,22,25-tetraazanonacosan-29-amido)-2-((1,2-dimethylhydrazinyl)methyl)-1H-indol-1-yl)-5-isopropyl-2-methyl-4,7,23,26-tetraoxo-24-(sulfomethyl)-10,13,16,19-tetraoxa-3,6,22,25-tetraazaoctacosanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (136)

To a solution of compound 135 (13 mg, 10 µmol) in anhydrous DMF (0.5 mL) were added DIPEA (5 µL, 15 µmol) and HOAt (2 mg, 15 µmol), followed by bis-PFP ester 40 (4.3 mg, 5 µmol) at room temperature. After 30 minutes, reaction was judged complete by LCMS analysis, and piperidine (10 µL, 97 µmol) was added directly to the mixture in one shot at room temperature. After 15 minutes, reaction mixture was purified by reversed phase prep HPLC (C18, 0-70% v/v MeCN—H$_2$O with 0.05% TFA). Lyophilized pure fractions gave 7.4 mg of compound 136 (2.4 μmol, 57% yield) as a yellow powder. LRMS (ESI): m/z 1514.2.1 [M+2H]$^{2+}$, Calcd for C$_{140}$H$_{184}$N$_{20}$O$_{51}$S$_2$ m/z 1514.1.
Scheme 26. Synthesis of branched belotecan construct 142
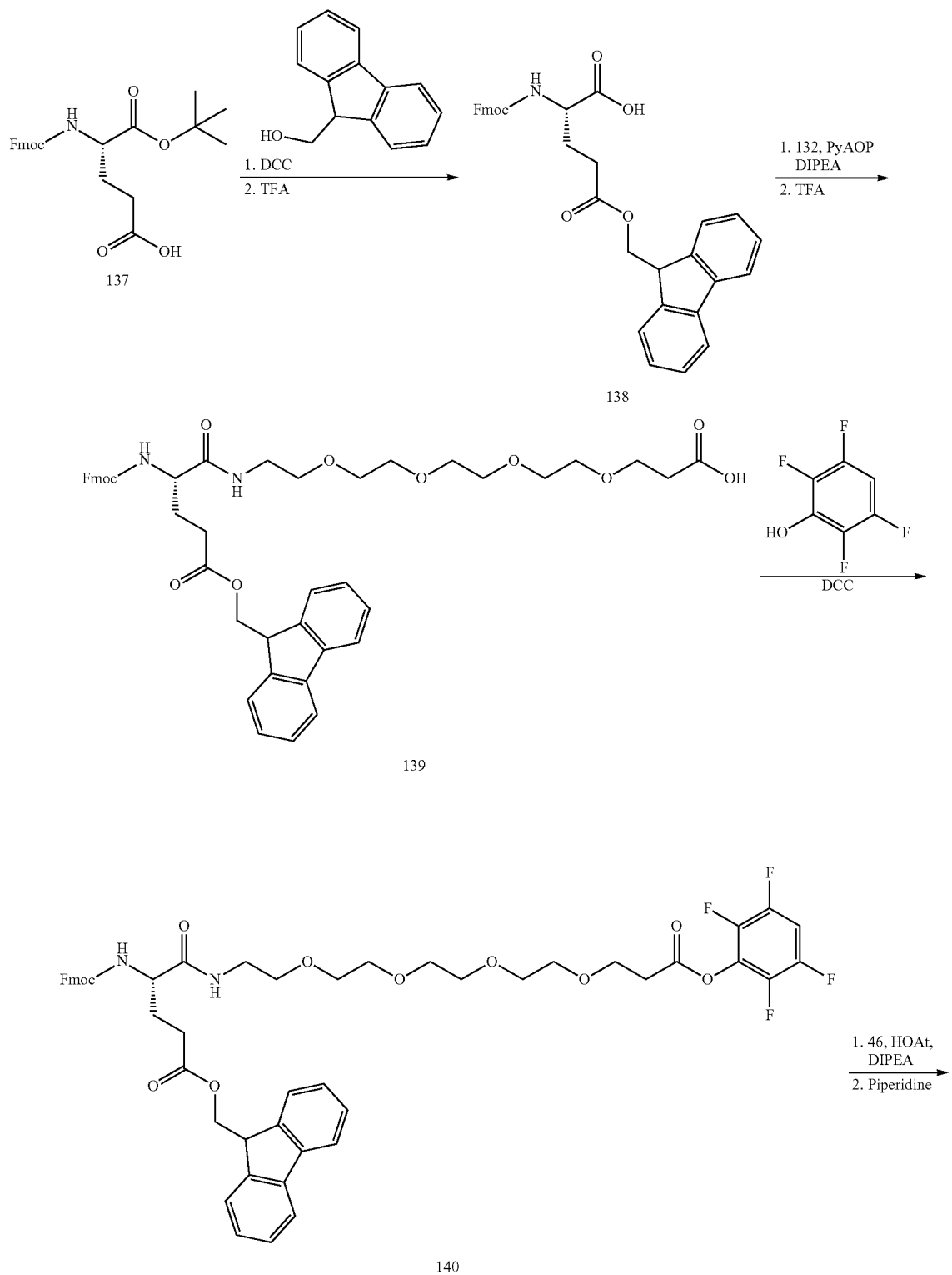

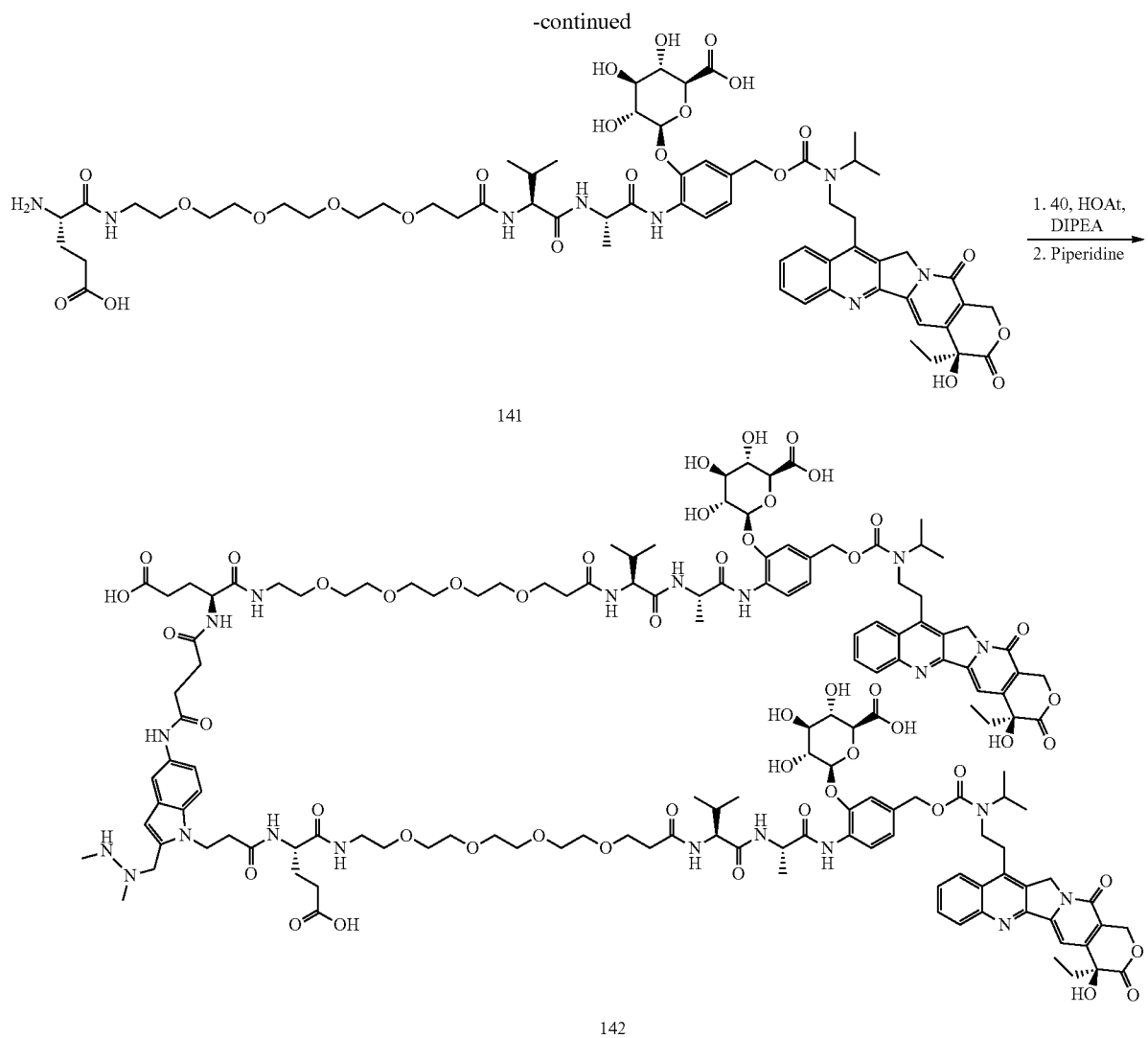

141

142

Preparation of (S)-5-((9H-fluoren-9-yl)methoxy)-2-(((((9H-fluoren-9-yl)methoxy)carbonyl)amino)-5-oxopentanoic Acid (138)

To a mixture of Fmoc-Glu-OtBu 137 (426 mg, 1 mmol) and (9H-fluoren-9-yl)methanol (216 mg, 1.1 mmol) in 5 mL of anhydrous THF were added DCC (247 mg, 1.2 mmol) in one portion at room temperature. The resulting mixture was stirred overnight, filtered, and concentrated under vacuum. The residue was dissolved in DCM-TFA mixture (1:1 v/v, 6 mL) and let stand at room temperature for 30 minutes. Solvents were removed under vacuum, the residue was dissolved in 40 mL of EtOAc, washed with sat. ammonium chloride, water, and brine, dried over sodium sulfate, and purified by silica gel chromatography (0-25% v/v EtOAc-hexane) to afford 230 mg of Fmoc-Glu(OFm)-OH 138 as a colorless solid (0.42 mmol, 42% yield). LRMS (ESI): m/z 548.2 [M+H]$^+$, Calcd for $C_{34}H_{29}NO_6$ m/z 548.2.

Preparation of (S)-5-(3-((9H-fluoren-9-yl)methoxy)-3-oxopropyl)-1-(9H-fluoren-9-yl)-3,6-dioxo-2,10,13,16,19-pentaoxa-4,7-diazadocosan-22-oic Acid (139)

To a mixture of Fmoc-Glu(OFm)-OH 138 (230 mg, 0.42 mmol) and amino-PEG4-OtBu 132 (162 mg, 0.46 mmol) in 2 mL of DMF were added DIPEA (0.22 mL, 1.26 mmol), followed by PyAOP (240 mg, 0.42 mmol) at room temperature. Reaction mixture was stirred for 30 minutes, then poured into sat. ammonium chloride solution and extracted with EtOAc. Organic layer was washed with brine, and dried over sodium sulfate. After removal of solvents in vacuum, the residue was reconstituted in DCM-TFA mixture (1:1 v/v, 4 mL) at room temperature and stirred for 15 minutes, then solvents were removed in vacuum and the residue was purified by reversed phase chromatography (C18, 0-70% v/v MeCN—H$_2$O with 0.05% TFA) to give 306 mg of compound 139 as a clear colorless oil (0.39 mmol, 92% yield). LRMS (ESI): m/z 795.3 [M+H]$^+$, Calcd for $C_{45}H_{50}N_2O_{11}$ m/z 795.3.

Preparation of 21-((9H-fluoren-9-yl)methyl) 1-(2,3,5,6-tetrafluorophenyl) (S)-18-((((9H-fluoren-9-yl)methoxy)carbonyl)amino)-17-oxo-4,7,10,13-tetraoxa-16-azahenicosanedioate (140)

To a mixture of compound 139 (145 mg, 0.18 mmol) and 2,3,5,6,-tatrafluorophenol (61 mg, 0.36 mmol) in 2 mL of THF were added DCC (45 mg, 0.36 mmol) in one portion at room temperature. The resulting mixture was stirred overnight, filtered, concentrated under vacuum and purified by reversed phase chromatography (C18, 0-80% v/v MeCN—H$_2$O with 0.05% TFA) to give 84 mg of TFP-ester 140 as a colorless oil (0.09 mmol, 50% yield). LRMS (ESI): m/z 965.3 [M+Na]$^+$, Calcd for C$_{51}$H$_{50}$F$_4$N$_2$O$_{11}$ m/z 965.3.

Preparation of (2S,5S,24S)-24-amino-1-((2-(((2S, 3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-5-isopropyl-2-methyl-1,4,7,23-tetraoxo-10,13,16,19-tetraoxa-3,6,22-triazaheptacosan-27-oic Acid (141)

To a solution of compound 46 (19 mg, 20 µmol) in 3 mL of anhydrous DMF were added DIPEA (9 µL, 60 µmol) and HOAt (2.7 mg, 20 µmol), followed by TFP ester 140 (19 mg, 20 µmol) in one portion at room temperature. Reaction mixture was stirred for 30 minutes, monitored by LCMS analysis. After reaction was judged complete, piperidine (40 µL) was added to the mixture, and stirring continued for 20 minutes. Reaction mixture was then purified by reversed-phase prep HPLC (C18, 0-50% v/v MeCN—H$_2$O with 0.05% TFA). Pure fractions were lyophilized to afford 14.6 mg of compound 141 as a yellow powder (11 µmol, 55% yield). LRMS (ESI): m/z 1321.5 [M+H]$^+$, Calcd for C$_{63}$H$_{84}$N$_8$O$_{23}$ m/z 1321.6.

Preparation of (2S,3S,4S,5R,6S)-6-(2-((2S,5S,24S)-28-(5-((2S,5S,24S)-1-((2-(((2S,3R,4S,5S,6S)-6-carboxy-3,4,5-trihydroxytetrahydro-2H-pyran-2-yl)oxy)-4-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenyl)amino)-24-(2-carboxyethyl)-5-isopropyl-2-methyl-1,4,7,23,26-pentaoxo-10,13,16,19-tetraoxa-3,6,22,25-tetraazanonacosan-29-amido)-2-((1,2-dimethylhydrazinyl)methyl)-1H-indol-1-yl)-24-(2-carboxyethyl)-5-isopropyl-2-methyl-4,7,23,26-tetraoxo-10,13,16,19-tetraoxa-3,6,22,25-tetraazaoctacosanamido)-5-((((2-((S)-4-ethyl-4-hydroxy-3,14-dioxo-3,4,12,14-tetrahydro-1H-pyrano[3',4':6,7]indolizino[1,2-b]quinolin-11-yl)ethyl)(isopropyl)carbamoyl)oxy)methyl)phenoxy)-3,4,5-trihydroxytetrahydro-2H-pyran-2-carboxylic Acid (142)

To a solution of compound 141 (14.6 mg, 11 µmol) in 2 mL of DMA were added DIPEA (6 µL, 33 µmol) and HOAt (1.5 mg, 11 µmol), followed by bis-PFP ester 40 (4.5 mg, 5 µmol) in one portion at room temperature. The resulting mixture was allowed to stand at room temperature for 30 minutes, then piperidine (10 µL) was added directly to the mixture. After 20 minutes, reaction mixture was purified by reversed-phase prep HPLC (C18, 0-50% v/v MeCN—H$_2$O with 0.05% TFA). Pure fractions were combined and lyophilized to give 6 mg (2 µmol, 40% yield) of compound 142 as a yellow solid. LRMS (ESI): m/z 1491.2 [M+2H]$^{2+}$, Calcd for C$_{144}$H$_{188}$N$_{20}$O$_{49}$ m/z 1491.6.

Scheme 27. Synthesis of branched des-Me-topotecan construct 147

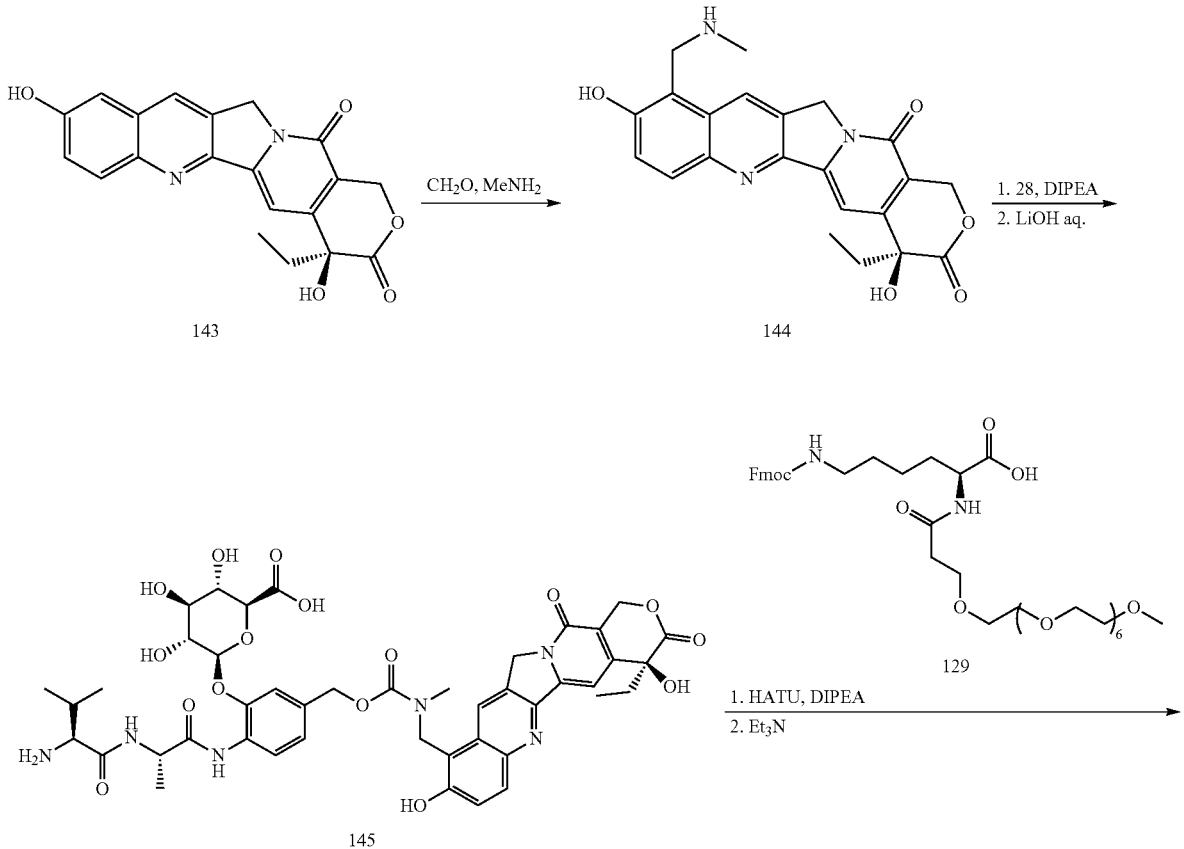

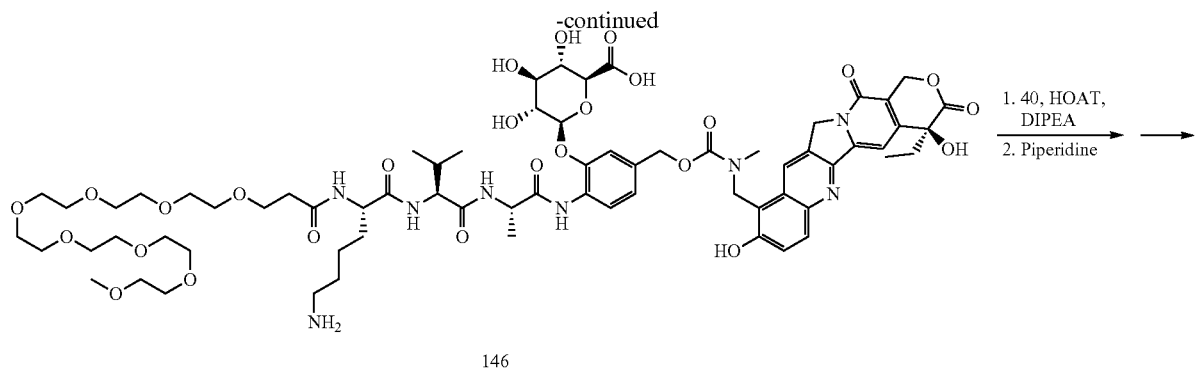

146

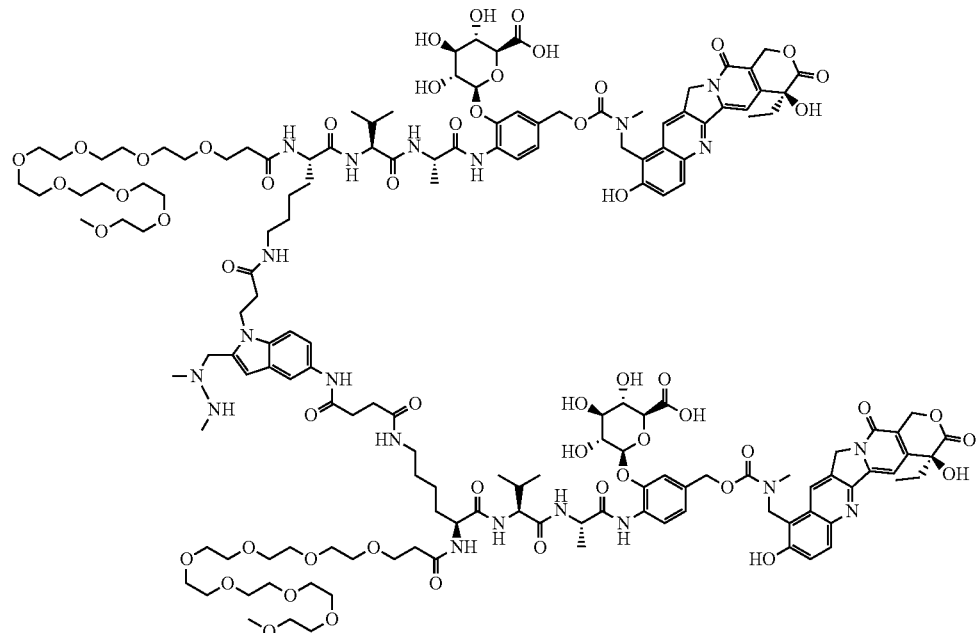

147

Preparation of (S)-4-ethyl-4,9-dihydroxy-10-((methylamino)methyl)-1,12-dihydro-14H-pyrano[3',4':6,7]indolizino[1,2-b]quinoline-3,14(4H)-dione (144)

To a solution of 10-hydroxycamtothecin 143 (500 mg, 1.37 mmol) in acetic acid (30 mL) and EtOH (15 mL) were added formaldehyde (1 mL, 37 wt % in $H_2O$) and $MeNH_2$ (1 mL, 40% w/w water solution). Reaction mixture was allowed to stir overnight at room temperature, then concentrated under reduced pressure. The residue was purified by reversed phase chromatography (C18, 0-70% v/v MeCN—$H_2O$ with 0.05% TFA). Pure fractions were collected and lyophilized to obtain des-Me-topotecan 144 as a light-yellow solid (150 mg, 0.46 mmol, 27% yield). LRMS (ESI): m/z 408.2 $[M+H]^+$, Calcd for $C_{22}H_{21}N_3O_5$ m/z 408.2.

Preparation of (2S,3S,4S,5R,6S)-6-(2-((S)-2-((S)-2-amino-3-methylbutanamido)propanamido)-5-((((((S)-4-ethyl-4,9-dihydroxy-3,14-dioxo-3,4,12,14-tetrahydro-1H-pyrano[3',4':6,7]indolizino[1,2-b]quinolin-10-yl)methyl)(methyl)carbamoyl)oxy)methyl)phenoxy)-3,4,5-trihydroxytetrahydro-2H-pyran-2-carboxylic Acid (145)

To a stirred solution of des-Me-topotecan 144 (25 mg, 61 µmol) in DMF (1.5 mL) were added HOAt (8.5 mg, 62 µmol) and DIPEA (30 µL, 184 µmol) at room temperature. The resulting mixture was then treated with PNP-carbonate 28 (58 mg, 62 µmol) in one portion at room temperature. Reaction mixture was stirred overnight until all the starting materials were consumed as judged by LCMS analysis. Reaction mixture was poured into 10 mL of water, and the resulting precipitate was collected and dissolved in THF (2 mL). The THF solution was then treated with aq. LiOH (1 mL, 1M) slowly at 0° C. and stirred for 30 min. Reaction mixture was allowed to slowly warm to room temperature and stirred for an additional hour, quenched by adding 1M aq. HCl to pH~4, filtered, and purified by reversed-phase prep HPLC (C18, 0-70% v/v MeCN—$H_2O$ with 0.05% TFA). Pure fractions were collected and lyophilized to obtain compound 145 as a yellow solid (25 mg, 27 µmol, 44% yield). LRMS (ESI): m/z 919.3 $[M+H]^+$, Calcd for $C_{44}H_{50}N_6O_{16}$ m/z 919.3.

Preparation of (2S,3S,4S,5R,6S)-6-(2-((28S,31S,34S)-28-(4-aminobutyl)-31-isopropyl-34-methyl-26,29,32-trioxo-2,5,8,11,14,17,20,23-octaoxa-27,30,33-triazapentatriacontan-35-amido)-5-((((((S)-4-ethyl-4,9-dihydroxy-3,14-dioxo-3,4,12,14-tetrahydro-1H-pyrano[3',4':6,7]indolizino[1,2-b]quinolin-10-yl)methyl)(methyl)carbamoyl)oxy)methyl)phenoxy)-3,4,5-trihydroxytetrahydro-2H-pyran-2-carboxylic Acid (146)

To a solution of compound 128 (21 mg, 27.5 µmol) in DMF (2 mL) were added HATU (10 mg, 31 µmol) and DIPEA (14 µL, 82 µmol) at room temperature. The resulting mixture was stirred for one hour, then compound 145 (25 mg, 27 µmol) was added to the mixture, and stirring continued for 1 h, until coupling was judged complete by LCMS analysis. Next, reaction mixture was treated with triethylamine (0.4 mL) and stirred at room temperature for 5 h. Reaction mixture was purified by reversed phase prep HPLC (C18, 0-70% v/v MeCN—$H_2O$ with 0.05% TFA). Pure fractions were collected and lyophilized to obtain compound 146 as a yellow solid (26 mg, 18 µmol, 67% yield). LRMS (ESI): m/z 1441.6 [M+H]$^+$, Calcd for $C_{68}H_{96}N_8O_{26}$ m/z 1441.6.

Preparation of (2S,3S,4S,5R,6S)-6-(2-((28S,31S,34S)-28-(4-(3-(5-((S)-28-(((S)-1-(((S)-1-((2-(((2S,3R,4S,5S,6S)-6-carboxy-3,4,5-trihydroxytetrahydro-2H-pyran-2-yl)oxy)-4-((((((S)-4-ethyl-4,9-dihydroxy-3,14-dioxo-3,4,12,14-tetrahydro-1H-pyrano[3',4':6,7]indolizino[1,2-b]quinolin-10-yl)methyl)(methyl)carbamoyl)oxy)methyl)phenyl)amino)-1-oxopropan-2-yl)amino)-3-methyl-1-oxobutan-2-yl)carbamoyl)-26,34-dioxo-2,5,8,11,14,17,20,23-octaoxa-27,33-diazaheptatriacontan-37-amido)-2-((1,2-dimethylhydrazinyl)methyl)-1H-indol-1-yl)propanamido)butyl)-31-isopropyl-34-methyl-26,29,32-trioxo-2,5,8,11,14,17,20,23-octaoxa-27,30,33-triazapentatriacontan-35-amido)-5-((((((S)-4-ethyl-4,9-dihydroxy-3,14-dioxo-3,4,12,14-tetrahydro-1H-pyrano[3',4':6,7]indolizino[1,2-b]quinolin-10-yl)methyl)(methyl)carbamoyl)oxy)methyl)phenoxy)-3,4,5-trihydroxytetrahydro-2H-pyran-2-carboxylic Acid (147)

To a solution of compound 146 (26 mg, 18 µmol) in DMF (1.5 mL) were added DIPEA (10 µL, 55 µmol) and HOAt (7 mg, 23 µmol), followed by bis-PFP ester 40 (8.4 mg, 9 µmol) in one portion at room temperature. Reaction mixture was stirred for 30 minutes until coupling was judged complete by LCMS analysis, then diethylamine (37 µL, 0.36 mmol) was added to the mixture and stirring continued for 2 hours. Reaction mixture was purified by reversed phase prep HPLC (C18, 0-70% v/v MeCN—$H_2O$ with 0.05% TFA). Pure fractions were collected and lyophilized to give compound 147 as a yellow solid (18 mg, 6 µmol, 67% yield). LRMS (ESI): m/z 1612.2 [M+2H]$^{2+}$, Calcd for $C_{154}H_{212}N_{20}O_{55}$ m/z 1612.2.

Scheme 28. Synthesis of branched construct 151

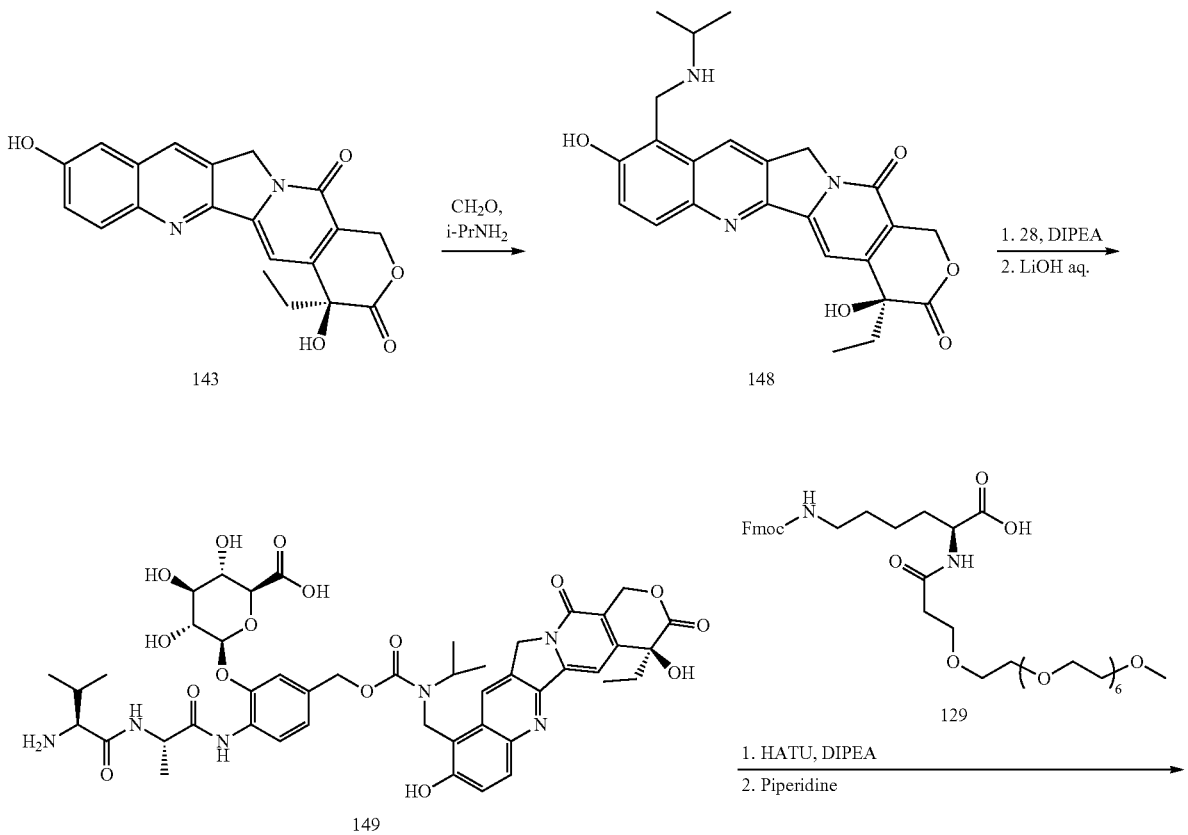

-continued

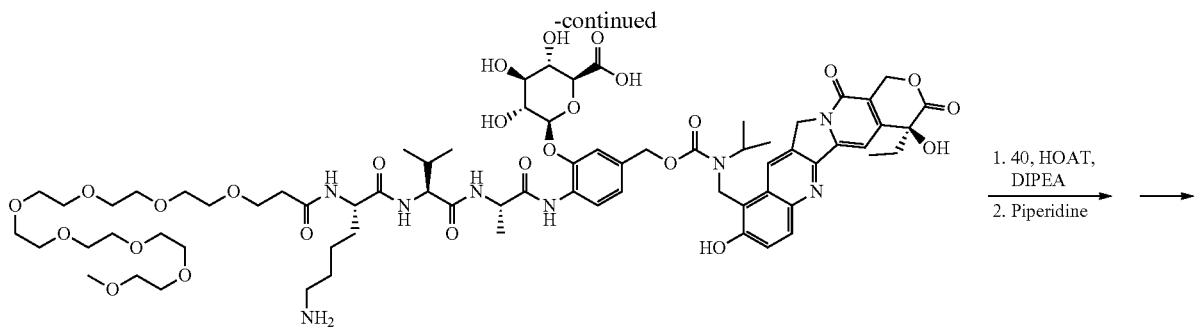

150

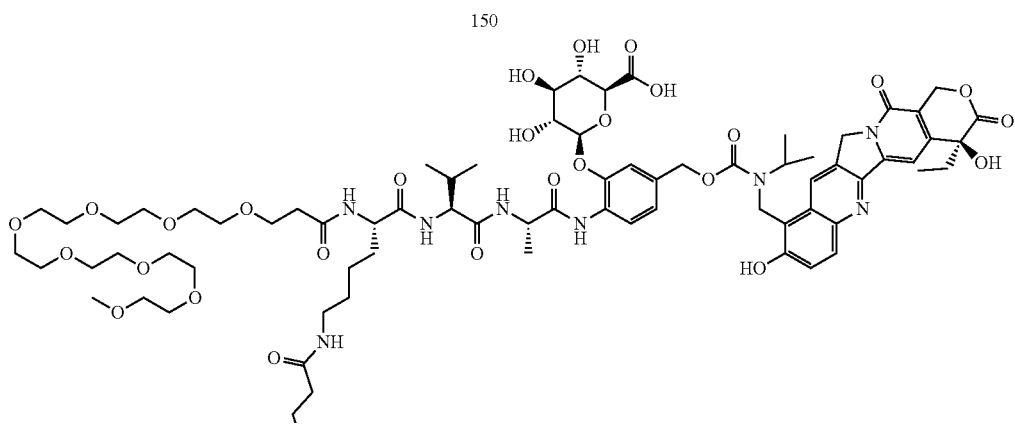

151

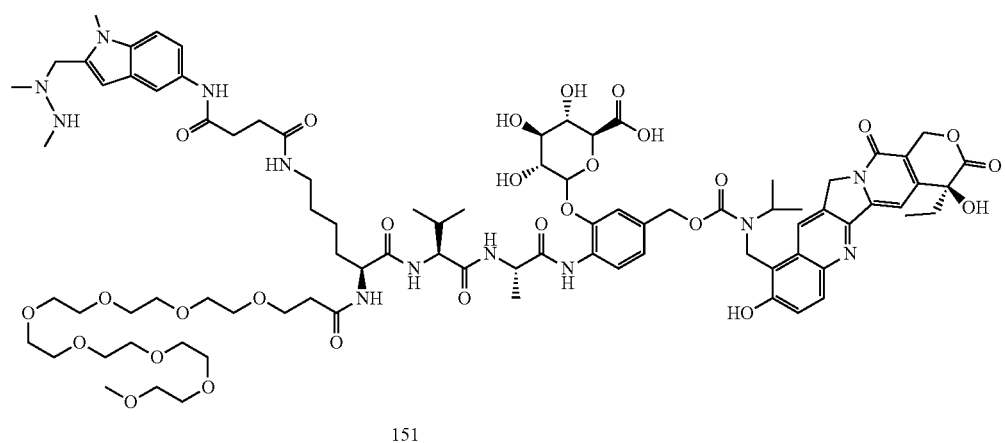

Preparation of (S)-4-ethyl-4,9-dihydroxy-10-((isopropylamino)methyl)-1,12-dihydro-14H-pyrano[3',4':6,7]indolizino[1,2-b]quinoline-3,14(4H)-dione (148)

To a solution of 10-hydroxycamptothecin (500 mg, 1.37 mmol) in HOAc (30 mL) and EtOH (15 mL) were added formaldehyde (1 mL, 37 wt % in H$_2$O) and i-PrNH$_2$ (150 μL, 1.83 mmol) at room temperature. Reaction mixture was stirred overnight and then concentrated in vacuum. The residue was purified by reversed phase chromatography (C18, 0-70% v/v MeCN—H$_2$O with 0.05% TFA). Pure fractions were collected and lyophilized to obtain compound 148 as an orange solid (200 mg, 0.46 mmol, 36% yield). LRMS (ESI): m/z 436.2 [M+H]$^+$, Calcd for C$_{24}$H$_{25}$N$_3$O$_5$ m/z 436.2.

Preparation of (2S,3S,4S,5R,6S)-6-(2-((S)-2-((S)-2-amino-3-methylbutanamido)propanamido)-5-((((((S)-4-ethyl-4,9-dihydroxy-3,14-dioxo-3,4,12,14-tetrahydro-1H-pyrano[3',4':6,7]indolizino[1,2-b]quinolin-10-yl)methyl)(isopropyl)carbamoyl)oxy)methyl)phenoxy)-3,4,5-trihydroxytetrahydro-2H-pyran-2-carboxylic Acid (149)

To a solution of compound 148 (50 mg, 115 μmol) in DMF (3 mL) were added HOAt (16 mg, 115 μmol) and DIPEA (60 μL, 344 μmol) at room temperature. The resulting mixture was treated with PNP-carbonate 28 (116 mg, 115 μmol) and stirred at room temperature overnight until all starting materials were consumed as judged by HPLC analysis. Reaction mixture was then diluted with water (10 mL), the resulting precipitate was collected and dissolved in THF (3 mL). The THF solution was then treated with aq. LiOH (1 mL, 1M) in at 0° C., stirred for 30 min, warmed up to room temperature, and stirred for 1 h. Reaction mixture was purified by reversed phase prep HPLC (C18, 0-70% v/v MeCN—H$_2$O with 0.05% TFA). Pure fractions were combined and lyophilized to give compound 149 as a yellow solid (31 mg, 33 µmol, 29% yield). LRMS (ESI): m/z 947.4 [M+H]$^+$, Calcd for C$_{46}$H$_{54}$N$_6$O$_{16}$ m/z 947.4.

Preparation of (2S,3S,4S,5R,6S)-6-(2-((28S,31S, 34S)-28-(4-aminobutyl)-31-isopropyl-34-methyl-26, 29,32-trioxo-2,5,8,11,14,17,20,23-octaoxa-27,30,33-triazapentatriacontan-35-amido)-5-((((((S)-4-ethyl-4, 9-dihydroxy-3,14-dioxo-3,4,12,14-tetrahydro-1H-pyrano[3',4':6,7]indolizino[1,2-b]quinolin-10-yl) methyl)(isopropyl)carbamoyl)oxy)methyl)phenoxy)-3,4,5-trihydroxytetrahydro-2H-pyran-2-carboxylic Acid (150)

To a stirred solution of carboxylic acid 129 (31 mg, 41 µmol) in anhydrous DMF (2 mL) were added HATU (15 mg, 36 µmol) and DIPEA (17 µL, 94 µmol) at room temperature. The resulting mixture was stirred for 1 h, then compound 149 (31 mg, 33 µmol) was added to the mixture, and stirring continued for 1 h. Next, reaction mixture was directly treated with piperidine (62 µL, 0.63 mmol) at room temperature, stirred for 20 minutes, and purified by reversed-phase prep HPLC (C18, 0-70% v/v MeCN—H$_2$O with 0.05% TFA). Pure fractions were collected and lyophilized to afford compound 150 as a yellow solid (26 mg, 18 µmol, 55% yield). LRMS (ESI): m/z 1469.7 [M+H]$^+$, Calcd for C$_{70}$H$_{100}$N$_8$O$_{26}$ m/z 1469.7.

Preparation of (2S,3S,4S,5R,6S)-6-(2-((28S,31S, 34S)-28-(4-(3-(5-((S)-28-(((S)-1-(((S)-1-((2-(((2S, 3R,4S,5S,6S)-6-carboxy-3,4,5-trihydroxytetrahydro-2H-pyran-2-yl)oxy)-4-((((((S)-4-ethyl-4,9-dihydroxy-3,14-dioxo-3,4,12,14-tetrahydro-1H-pyrano[3',4':6,7]indolizino[1,2-b]quinolin-10-yl) methyl)(isopropyl)carbamoyl)oxy)methyl)phenyl) amino)-1-oxopropan-2-yl)amino)-3-methyl-1-oxobutan-2-yl)carbamoyl)-26,34-dioxo-2,5,8,11,14, 17,20,23-octaoxa-27,33-diazaheptatriacontan-37-amido)-2-((1,2-dimethylhydrazinyl)methyl)-1H-indol-1-yl)propanamido)butyl)-31-isopropyl-34-methyl-26,29,32-trioxo-2,5,8,11,14,17,20,23-octaoxa-27,30,33-triazapentatriacontan-35-amido)-5-((((((S)-4-ethyl-4,9-dihydroxy-3,14-dioxo-3,4,12,14-tetrahydro-1H-pyrano[3',4':6,7]indolizino[1,2-b] quinolin-10-yl)methyl)(isopropyl)carbamoyl)oxy) methyl)phenoxy)-3,4,5-trihydroxytetrahydro-2H-pyran-2-carboxylic Acid (151)

To a solution of compound 150 (27 mg, 18 µmol) in DMF (1.5 mL) were added DIPEA (10 µL, 55 µmol) and HOAt (8 mg, 24 µmol) at room temperature, followed by the addition of bis-PFP ester 40 (8 mg, 9 µmol) in one portion. The resulting mixture was stirred for 30 minutes, then piperidine (36 µL, 0.36 mmol) was added to the mixture at room temperature. After 20 minutes, reaction mixture was purified by reversed-phase prep HPLC (C18, 0-70% v/v MeCN—H$_2$O with 0.05% TFA). Pure fractions were collected and lyophilized to obtain compound 151 as a yellow solid (19 mg, 5.8 µmol, 64% yield). LRMS (ESI): m/z 1640.4 [M+2H]$^{2+}$, Calcd for C$_{158}$H$_{220}$N$_{20}$O$_{55}$ m/z: 1640.3.

Scheme 29. Synthesis of SN-38 construct 154

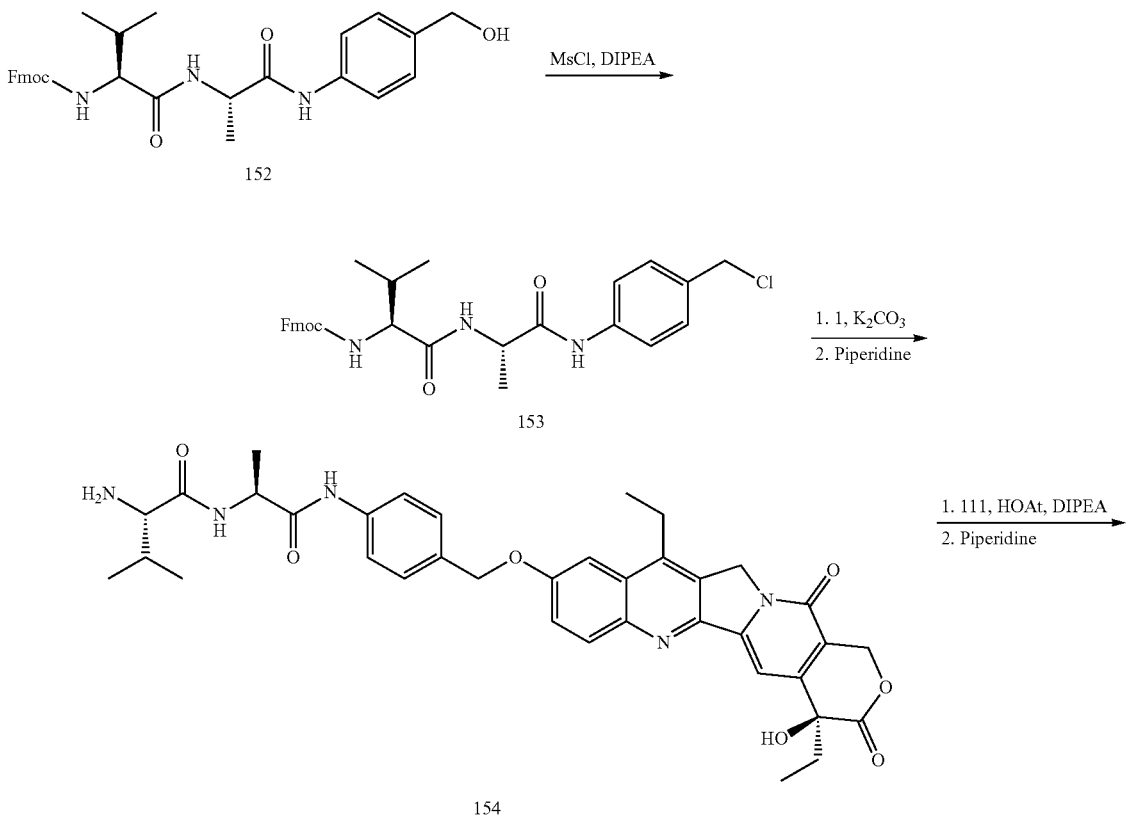

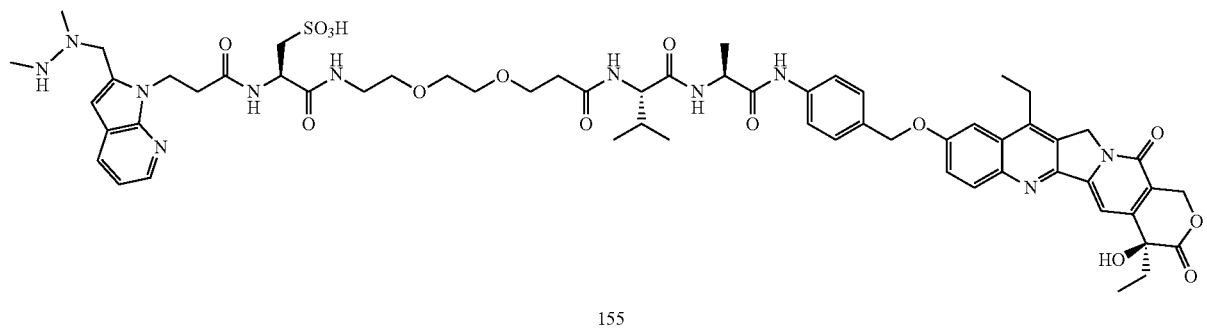

155

Preparation of (S)-2-amino-N—((S)-1-((4-(((((S)-4,11-diethyl-4-hydroxy-3,14-dioxo-3,4,12,14-tetrahydro-1H-pyrano[3',4':6,7]indolizino[1,2-b]quinolin-9-yl)oxy)methyl)phenyl)amino)-1-oxopropan-2-yl)-3-methylbutanamide (154)

To a solution of Fmoc-Val-Ala-OH 152 (30 mg, 59 μmol) in DMF (1 mL) were added MsCl (13.5 mg, 118 μmol) and DIPEA (20 μL, 118 μmol) at room temperature. After one hour, reaction mixture was concentrated and partitioned between ethyl acetate and saturated sodium bicarbonate. Organic layer was washed with brine and dried over $Na_2SO_4$. Removal of solvents under vacuum gave crude chloride 153, which was dissolved in DMF (1 mL). To this solution were added SN38 (1, 23 mg, 59 μmol) and $K_2CO_3$ (24 mg, 0.18 mmol), and the reaction mixture was stirred vigorously at 45° C. overnight. Reaction mixture was directly purified by reversed phase HPLC using C18 column ($H_2O/CH_3CN$ with 0.05% TFA, 90:10 to 45:55 v/v). Fractions containing the desired compound were pooled and lyophilized to yield compound 154 (2.7 mg, 16% yield).

LRMS (ESI): m/z 668.3 [M+H]$^+$, Calcd for $C_{37}H_{41}N_5O_7$ m/z 668.3.

Preparation of (2S,5S,18R)-1-((4-(((((S)-4,11-diethyl-4-hydroxy-3,14-dioxo-3,4,12,14-tetrahydro-1H-pyrano[3',4':6,7]indolizino[1,2-b]quinolin-9-yl)oxy)methyl)phenyl)amino)-18-(3-(2-((1,2-dimethylhydrazinyl)methyl)-1H-pyrrolo[2,3-b]pyridin-1-yl)propanamido)-5-isopropyl-2-methyl-1,4,7,17-tetraoxo-10,13-dioxa-3,6,16-triazanonadecane-19-sulfonic Acid (155)

To a mixture of amine 154 (8 mg, 9 μmol) and PFP ester 111 (12 mg, 10 μmol) in DMF (0.5 mL) were added HOAT (1.2 mg, 9 μmol) and DIPEA (5 μL, 27 μmol) at room temperature. The resulting mixture was stirred for 1 hour, then DMF (0.5 mL) and piperidine (50 μL) were added to mixture. After stirring for 15 minutes at room temperature, the reaction mixture was directly purified by reversed phase HPLC using C18 column ($H_2O/CH_3CN$ with 0.05% TFA, 90:10 to 45:55 v/v). Fractions containing the desired compound were pooled and lyophilized to yield compound 155 (3.5 mg, 2.9 μmol, 32% yield). LRMS (ESI): m/z 1222.5 [M+H]$^+$, Calcd for $C_{60}H_{75}N_{11}O_{15}S$ m/z 1222.5.

Scheme 30. Synthesis of SN-38 construct 165

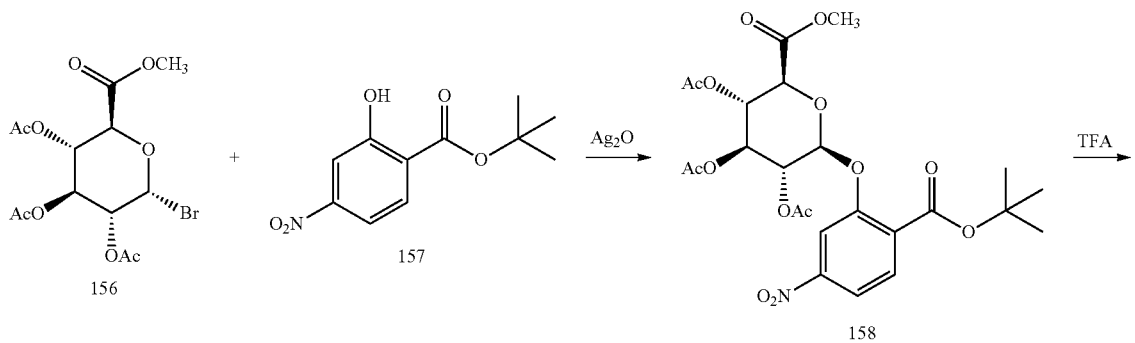

-continued
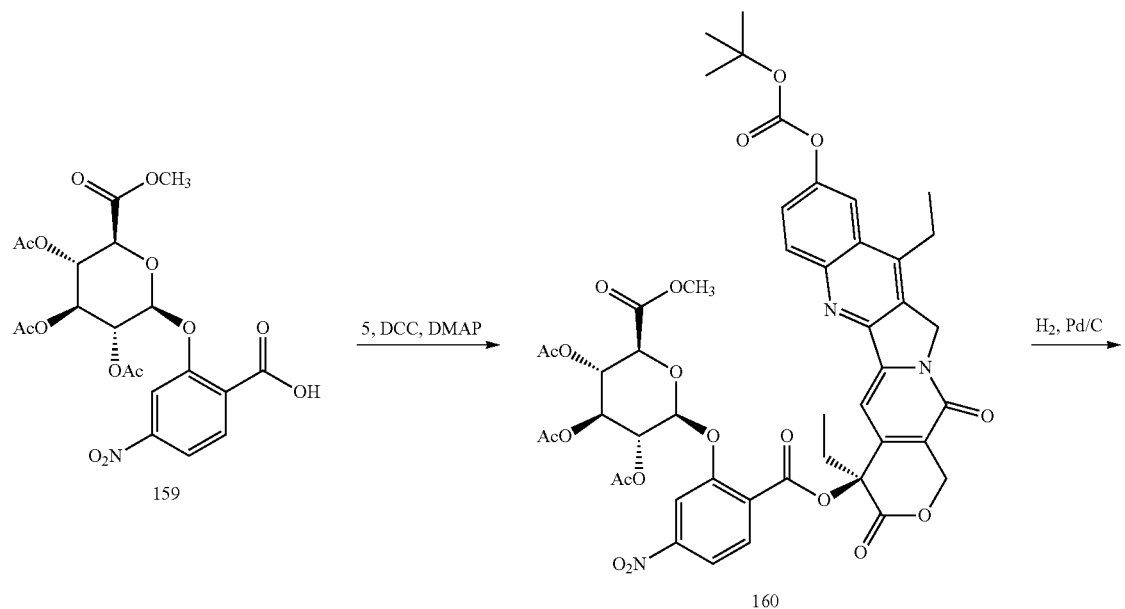
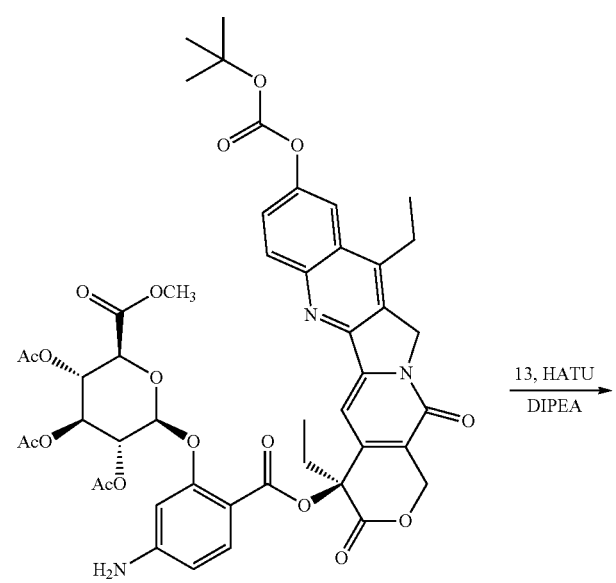

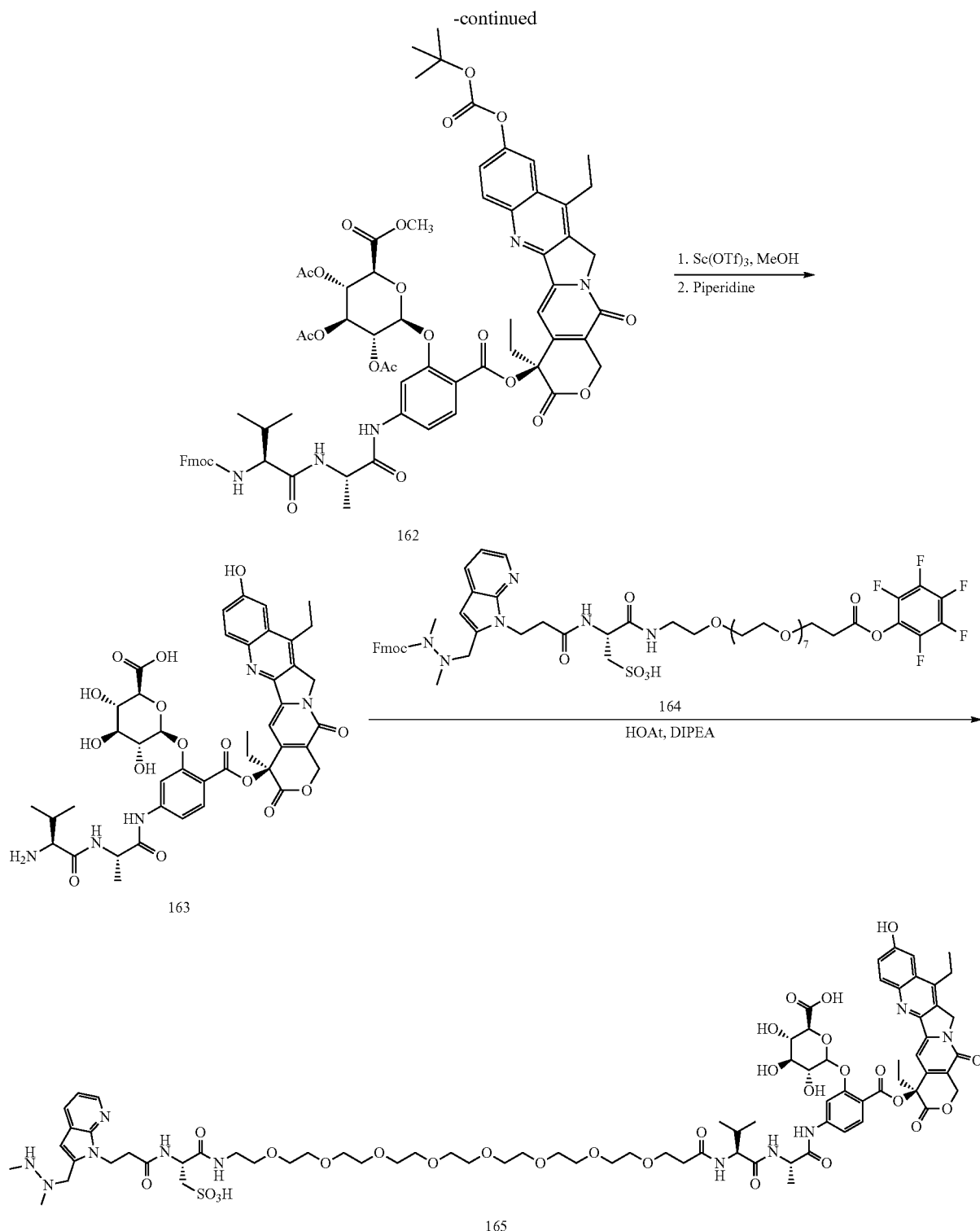

Preparation of (2S,3R,4S,5S,6S)-2-(2-(tert-butoxycarbonyl)-5-nitrophenoxy)-6-(methoxycarbonyl) tetrahydro-2H-pyran-3,4,5-triyl Triacetate (158)

To a mixture of tert-butyl 2-hydroxy-4-nitrobenzoate 157 (1.57 g, 6.6 mmol) and bromide 156 (2.37 g, 6.0 mmol) in 25 mL of acetonitrile were added silver(I) oxide (1.53 g, 6.6 mmol). The resulting mixture was stirred overnight in the dark, then filtered through a pad of silica gel, eluting with ethyl acetate, and concentrated under vacuum. The residue was purified by silica gel chromatography (0-10% EtOAc-hexane) to give 2.3 g of compound 158 as a white solid (4.1 mmol, 68% yield). LRMS (ESI): m/z 578.2 [M+Na]$^+$, Calcd for $C_{24}H_{29}NO_{14}$ m/z 578.2.

Preparation of 4-nitro-2-(((2S,3R,4S,5S,6S)-3,4,5-triacetoxy-6-(methoxycarbonyl)tetrahydro-2H-pyran-2-yl)oxy)benzoic Acid (159)

Compound 158 (180 mg, 0.32 mmol) was dissolved in 4 mL of DCM-TFA mixture (1:1 v/v) at room temperature. The resulting solution was allowed to stand for 30 minutes, then solvents were removed under vacuum, and the residue was purified by silica gel chromatography (0-5% MeOH-DCM) to give 160 mg of carboxylic acid 159 (0.32 mmol, quant. yield) as a pink foamy solid. LRMS (ESI): m/z 522.1 [M+Na]$^+$, Calcd for $C_{24}H_{29}NO_{14}$ m/z 522.1.

Preparation of (2S,3R,4S,5S,6S)-2-(2-(((((S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)-5-nitrophenoxy)-6-(methoxycarbonyl)tetrahydro-2H-pyran-3,4,5-triyl Triacetate (160)

To a solution of carboxylic acid 159 (18 mg, 36 μmol) in dichloromethane (1 mL) and DMF (0.5 mL) were added Boc-protected SN-38 5 (14 mg, 28 μmol), followed by DCC (6 mg, 29 μmol) and DMAP (3 mg, 25 μmol) at 0° C. After 1 h, reaction mixture was allowed to warm to room temperature, and stirring continued for 2 h. Reaction mixture was purified by reversed-phase chromatography using C18 column (H$_2$O/CH$_3$CN with 0.05% TFA, 100:0 to 0:100 v/v) to yield compound 160 (25 mg, 26 μmol, 93% yield) as a yellow solid. LRMS (ESI): m/z 974.3 [M+H]$^+$, Calcd for $C_{47}H_{47}N_3O_{20}$ m/z 974.3.

Preparation of (2S,3R,4S,5S,6S)-2-(5-amino-2-(((((S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)phenoxy)-6-(methoxycarbonyl)tetrahydro-2H-pyran-3,4,5-triyl Triacetate (161)

To a solution of compound 160 (35 mg, 36 μmol) in EtOAc (0.5 mL) was added Pd/C (10 wt %, 2 mg) and triethylamine (2 μL, 22 μmol)). The flask was then evacuated and filled with hydrogen gas from a balloon, in three repeating cycles. Reaction mixture was vigorously stirred for 48 h at room temperature with H$_2$ balloon attached. Solids were removed by filtration through a celite pad, the filtrate was concentrated and dried under vacuum to give 35 mg of crude compound 161, which was used in the next step without further purification. LRMS (ESI): m/z 944.3 [M+H]$^+$, Calcd for $C_{47}H_{49}N_3O_{18}$ m/z 944.3.

Preparation of (2S,3R,4S,5S,6S)-2-(5-((S)-2-((S)-2-(((((9H-fluoren-9-yl)methoxy)carbonyl)amino)-3-methylbutanamido)propanamido)-2-(((((S)-9-((tert-butoxycarbonyl)oxy)-4,11-diethyl-3,14-dioxo-3,4,12,14-tetrahydro-1H-pyrano[3',4':6,7]indolizino[1,2-b]quinolin-4-yl)oxy)carbonyl)phenoxy)-6-(methoxycarbonyl)tetrahydro-2H-pyran-3,4,5-triyl Triacetate (162)

To a mixture of crude amine 161 (35 mg) and Fmoc-Val-Ala-OH 13 (60 mg, 0.15 mmol) in DMF (0.5 mL) were added HATU (56 mg, 0.15 mmol) and DIPEA (51 μL, 0.30 mmol) at room temperature. Reaction mixture was stirred overnight and purified by reversed-phase chromatography on C18 column (H$_2$O/CH$_3$CN with 0.05% TFA, 100:0 to 0:100 v/v) to yield compound 162 (46 mg, 34 μmol, 94% yield over two steps) as a yellow solid. LRMS (ESI): m/z 1336.5 [M+H]$^+$, Calcd for $C_{70}H_{73}N_5O_{22}$ m/z 1336.5.

Preparation of (2S,3S,4S,5R,6S)-6-(5-(((S)-2-((S)-2-amino-3-methylbutanamido)propanamido)-2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)phenoxy)-3,4,5-trihydroxytetrahydro-2H-pyran-2-carboxylic Acid (163)

To a solution of compound 162 (20 mg, 15 μmol) in a MeOH—H$_2$O mixture (4:1 v/v, 1 mL) were added Sc(OTf)$_3$ (180 mg, 0.36 mmol) at room temperature. The resulting mixture was stirred for 2 days and concentrated under vacuum. The residue was reconstituted in DMF-piperidine mixture (10:1 v/v, 1.1 mL) and stirred for 1 hour at room temperature. Reaction mixture was purified by reversed-phase chromatography on C18 column (H$_2$O/CH$_3$CN with 0.05% TFA, 90:10 to 35:65 v/v) to yield compound 163 (8 mg, 9 μmol, 60% yield). LRMS (ESI): m/z 874.3 [M+H]$^+$, Calcd for $C_{43}H_{47}N_5O_{15}$ m/z 874.3.

Preparation of (R)-2-(3-(2-((2-(((9H-fluoren-9-yl)methoxy)carbonyl)-1,2-dimethylhydrazinyl)methyl)-1H-pyrrolo[2,3-b]pyridin-1-yl)propanamido)-3,31-dioxo-31-(perfluorophenoxy)-7,10,13,16,19,22,25,28-octaoxa-4-azahentriacontane-1-sulfonic Acid (164)

To a mixture of carboxylic acid 18 (180 mg, 0.17 mmol) and pentafluorophenol (125 mg, 0.68 mmol) in 4 mL of anhydrous THF were added DCC (68 mg, 0.33 mmol) at room temperature. The resulting mixture was stirred overnight, filtered through a pad of celite, concentrated under vacuum, and purified by reversed phase chromatography (C18, 0-80% acetonitrile-water/0.05% TFA) to give 100 mg of PFP ester 164 as a colorless oil (0.08 mmol, 47% yield). LRMS (ESI): m/z 1225.4 [M+H]$^+$, Calcd for $C_{56}H_{69}F_5N_6O_{17}S$ m/z 1225.4.

Preparation of (2S,3S,4S,5R,6S)-6-(2-(((((S)-4,11-diethyl-9-hydroxy-3,14-dioxo-3,4,12,14-tetrahydro-1H-pyrano[3',4':6,7]indolizino[1,2-b]quinolin-4-yl)oxy)carbonyl)-5-((2S,5S,36R)-40-(2-((1,2-dimethylhydrazinyl)methyl)-1H-pyrrolo[2,3-b]pyridin-1-yl)-5-isopropyl-2-methyl-4,7,35,38-tetraoxo-36-(sulfomethyl)-10,13,16,19,22,25,28,31-octaoxa-3,6,34,37-tetraazatetracontanamido)phenoxy)-3,4,5-trihydroxytetrahydro-2H-pyran-2-carboxylic Acid (165)

To a mixture of amine 163 (8 mg, 9 μmol) and PFP ester 164 (12 mg, 10 μmol) in DMF (0.5 mL) were added HOAt (1.2 mg, 9 μmol) and DIPEA (5 μL, 27 μmol) at ambient temperature. Reaction mixture was stirred for one hour, then DMF (0.5 mL) was added to the mixture, followed by piperidine (50 μL). After stirring for 15 minutes at room temperature, the reaction mixture was directly purified by reversed phase HPLC using C18 column (H$_2$O/CH$_3$CN with 0.05% TFA, 90:10 to 45:55 v/v). Fractions containing the desired compound were pooled lyophilized to yield compound 165 (3.5 mg, 2 μmol, 22% yield) as a yellow solid. LRMS (ESI): m/z 1692.7 [M+H]$^+$, Calcd for $C_{78}H_{105}N_{11}O_{29}S$ m/z 1692.7.

Scheme 31. Synthesis of belotecan branched construct 175
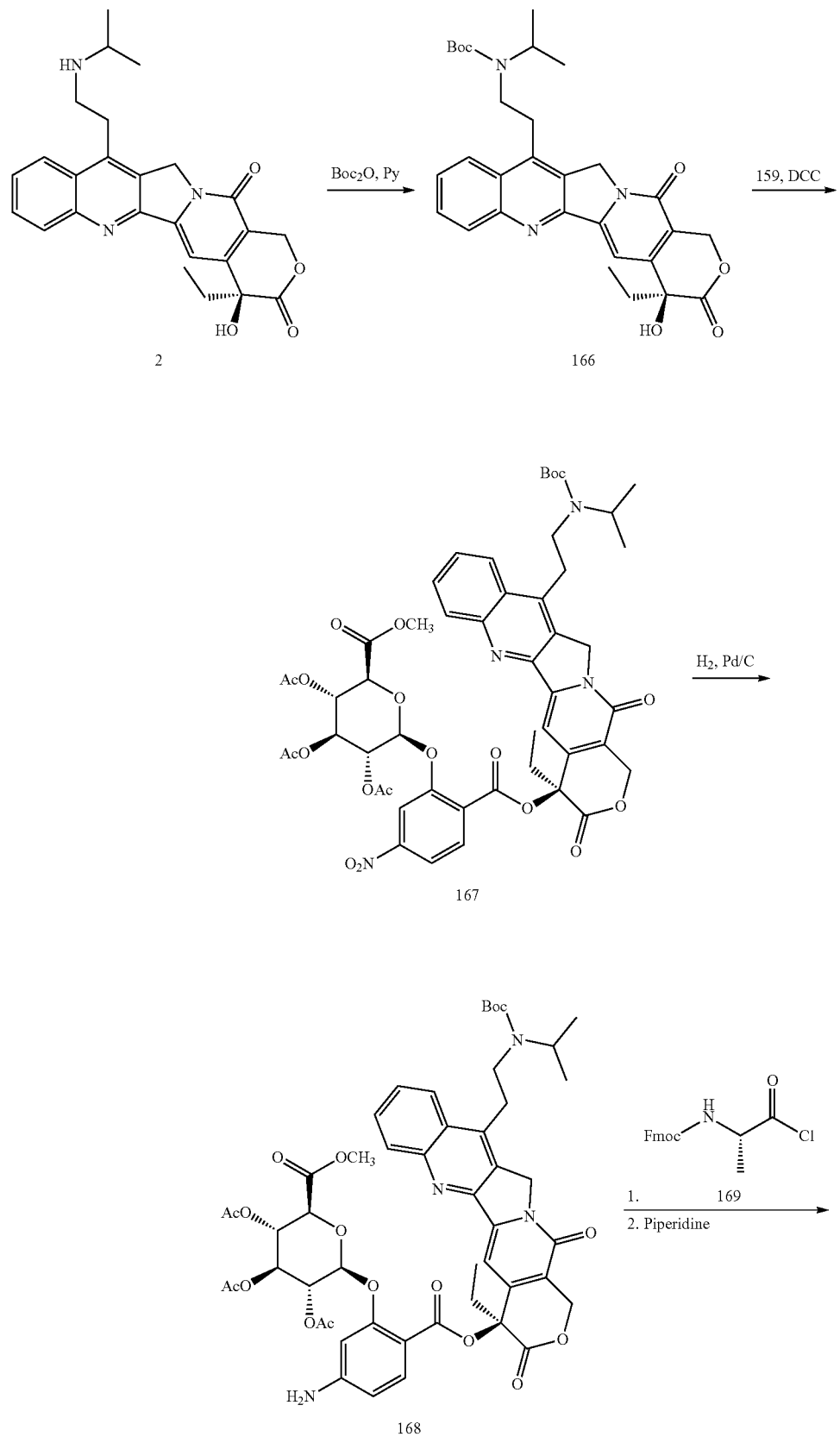

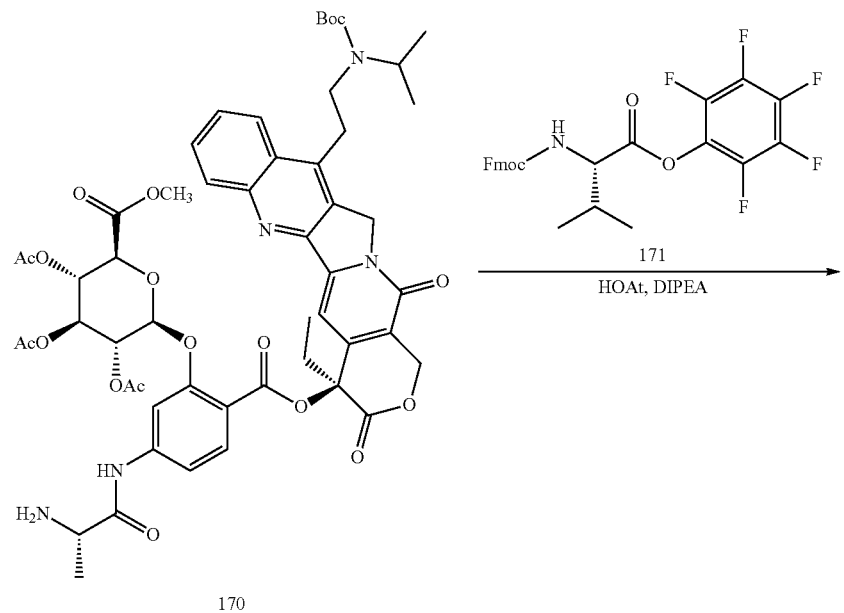
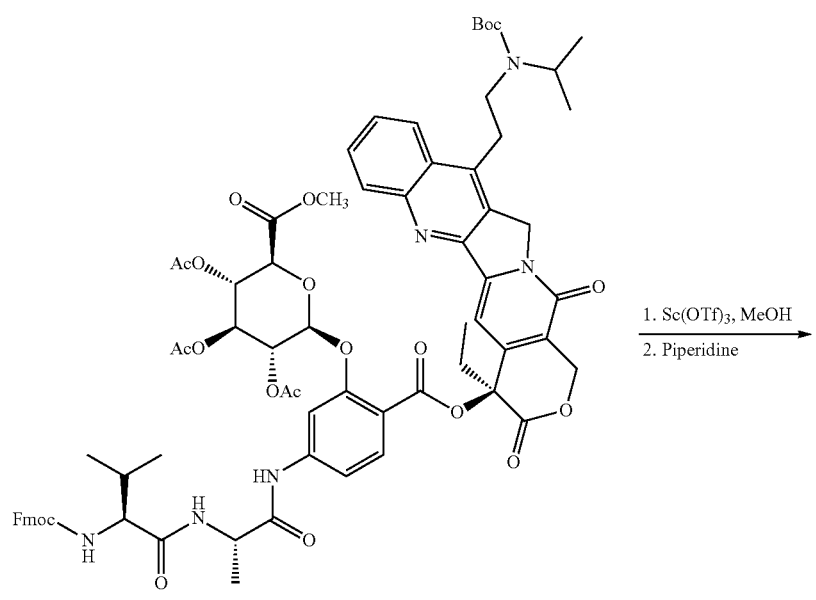

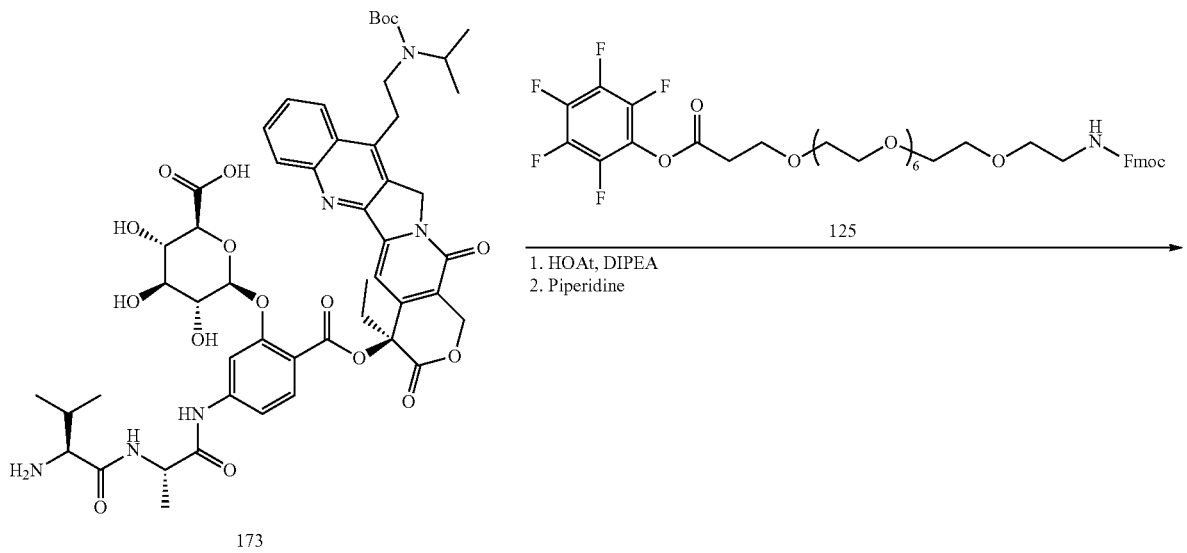
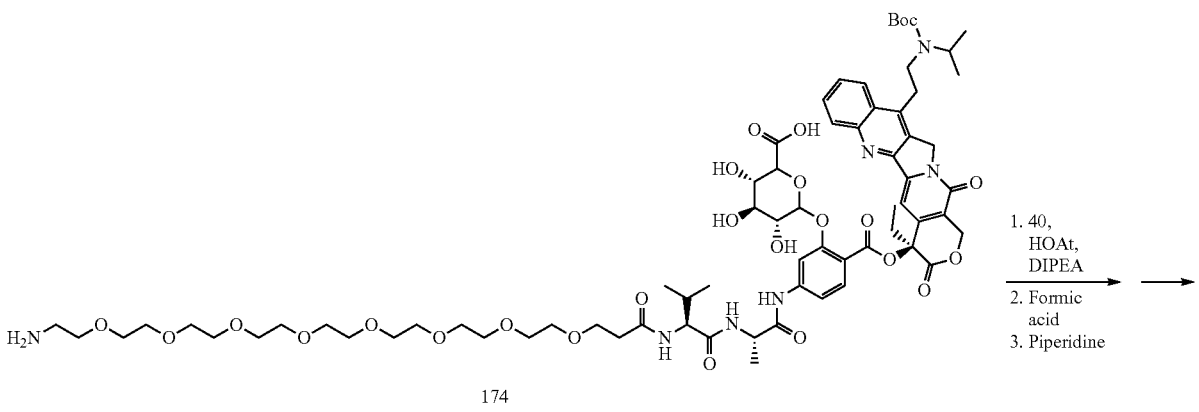
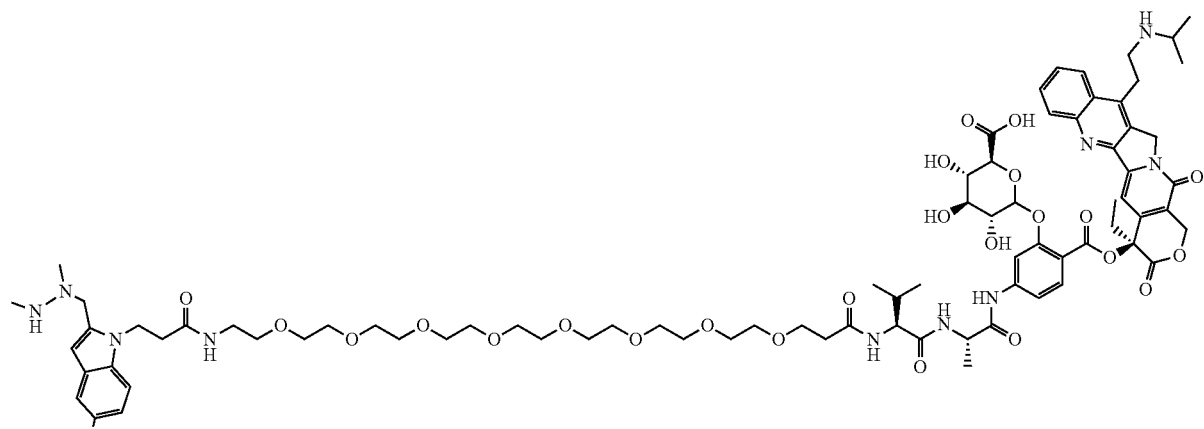

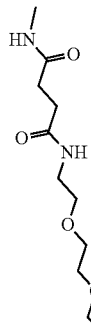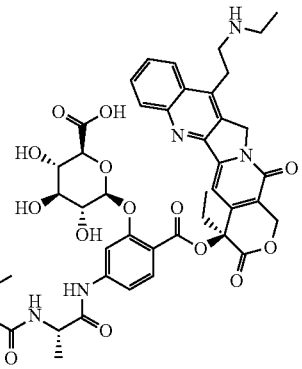

175

Preparation of tert-butyl (S)-(2-(4-ethyl-4-hydroxy-3,14-dioxo-3,4,12,14-tetrahydro-1H-pyrano[3,4':6,7]indolizino[1,2-b]quinolin-11-yl)ethyl)(isopropyl) carbamate (166)

To a mixture of belotecan 2 (50 mg, 0.11 mmol) and Boc$_2$O (12 mg, 0.23 mmol) in dichloromethane (2 mL) were added DIPEA (40 µL, 0.23 mmol) at room temperature. After stirring for 6 hours, the reaction mixture was directly purified by silica gel chromatography (DCM-MeOH, 100:0 to 95:5 v/v) to yield compound 166 (44 mg, 0.08 mmol, 73% yield) as an off-white solid. LRMS (ESI): m/z 534.3 [M+H]$^+$, Calcd for C$_{30}$H$_{35}$N$_3$O$_6$ m/z 534.3.

Preparation of (2S,3R,4S,5S,6S)-2-(5-amino-2-((((S)-11-(2-((tert-butoxycarbonyl)(isopropyl)amino)ethyl)-4-ethyl-3,14-dioxo-3,4,12,14-tetrahydro-1H-pyrano[3',4':6,7]indolizino[1,2-b]quinolin-4-yl)oxy)carbonyl)phenoxy)-6-(methoxycarbonyl)tetrahydro-2H-pyran-3,4,5-triyl Triacetate (168)

To a solution of carboxylic acid 159 (240 mg, 480 µmol) in dichloromethane (1 mL) and DMF (0.5 mL) were added Boc-protected belotecan 166 (100 mg, 190 µmol), followed by DCC (6 mg, 29 µmol) and DMAP (3 mg, 25 µmol) at 0° C. After 1 h, reaction mixture was allowed to warm to room temperature and stirred overnight. The mixture was briefly purified by passing through a silica gel pad (0-6% MeOH-DCM as an eluent) to give crude compound 167, which was dissolved in EtOAc (2 mL) and combined with Pd/C (10 wt %, 20 mg) and triethylamine (20 µL, 220 µmol). Reaction flask was then evacuated and filled with hydrogen gas from a balloon, in three repeating cycles. Reaction mixture was vigorously stirred for 48 h at room temperature with H$_2$ balloon attached, then filtered through a pad of celite. The filtrate was concentrated under vacuum and purified by silica gel chromatography (0-5% MeOH-DCM) to yield compound 168 (60 mg, 61 µmol, 33% yield) as a yellow solid. LRMS (ESI): m/z 985.4 [M+H]$^+$, Calcd for C$_{50}$H$_{56}$N$_4$O$_{17}$ m/z 985.4.

Preparation of (2S,3R,4S,5S,6S)-2-(5-((S)-2-((S)-2-(((((9H-fluoren-9-yl)methoxy)carbonyl)amino)-3-methylbutanamido)propanamido)-2-((((S)-11-(2-((tert-butoxycarbonyl)(isopropyl)amino)ethyl)-4-ethyl-3,14-dioxo-3,4,12,14-tetrahydro-1H-pyrano[3',4':6,7]indolizino[1,2-b]quinolin-4-yl)oxy)carbonyl)phenoxy)-6-(methoxycarbonyl)tetrahydro-2H-pyran-3,4,5-triyl Triacetate (172)

To a mixture of amine 168 (60 mg, 61 µmol) and Fmoc-Ala-Cl 169 (20 mg, 61 µmol) in DMF (1 mL) were added DIPEA (22 µL, 120 µmol) at room temperature. Reaction mixture was stirred for 1 h, then DMF (0.5 mL) and piperidine (50 µL) were added to the mixture. After 30 minutes, the reaction was semi-purified by silica gel chromatography with a gradient of 0 to 5% MeOH in DCM to give crude compound 170. Next, a solution of 170 in 1 mL of acetonitrile was treated with Fmoc-Val-OPfp 171 (62 mg, 120 µmol) and DIPEA (22 µL, 120 µmol) at room temperature. After stirring for 20 minutes, reaction mixture was purified by silica gel chromatography (MeOH-DCM 0-5% gradient) to yield compound 172 (70 mg, 51 µmol, 83% yield) as a yellow solid.
LRMS (ESI): m/z 1377.5 [M+H]$^+$, Calcd for C$_{73}$H$_{80}$N$_6$O$_{21}$ m/z 1377.5.

Preparation of (2S,3S,4S,5R,6S)-6-(5-((S)-2-((S)-2-amino-3-methylbutanamido)propanamido)-2-((((S)-11-(2-((tert-butoxycarbonyl)(isopropyl)amino)ethyl)-4-ethyl-3,14-dioxo-3,4,12,14-tetrahydro-1H-pyrano[3',4':6,7]indolizino[1,2-b]quinolin-4-yl)oxy)carbonyl)phenoxy)-3,4,5-trihydroxytetrahydro-2H-pyran-2-carboxylic Acid (173)

To a solution of compound 172 (70 mg, 51 µmol) in a MeOH—H$_2$O mixture (4:1 v/v, 1 mL) were added Sc(OTf)$_3$ (640 mg, 1.3 mmol) at room temperature. Reaction mixture was stirred for two days, then concentrated, and reconstituted in DMF-piperidine mixture (10:1 v/v, 1.1 mL). Reaction mixture was stirred for 1 hour and purified by reversed-phase chromatography on C18 column (H$_2$O/CH$_3$CN with 0.05% TFA, 90:10 to 20:80 v/v) to compound 173 (5 mg, 5 µmol, 10% yield). LRMS (ESI): m/z 1015.4 [M+H]$^+$, Calcd for C$_{51}$H$_{62}$N$_6$O$_{16}$ m/z 1015.4.

Preparation of (2S,3S,4S,5R,6S)-6-(5-((29S,32S)-1-amino-29-isopropyl-32-methyl-27,30-dioxo-3,6,9,12,15,18,21,24-octaoxa-28,31-diazatritriacontan-33-amido)-2-(((((S)-11-(2-((tert-butoxycarbonyl)(isopropyl)amino)ethyl)-4-ethyl-3,14-dioxo-3,4,12,14-tetrahydro-1H-pyrano[3',4':6,7]indolizino[1,2-b]quinolin-4-yl)oxy)carbonyl)phenoxy)-3,4,5-trihydroxytetrahydro-2H-pyran-2-carboxylic Acid (174)

To a mixture of amine 174 (5 mg, 5 µmol) and PFP ester 125 (12 mg, 6 µmol) in DMF (0.5 mL) were added DIPEA (5 µL, 29 µmol) at room temperature. Reaction mixture was stirred for 1 hour, then DMF (0.5 mL) and piperidine (50 µL) were added to the mixture. After stirring for 15 minutes at room temperature, the reaction mixture was directly purified by reversed phase prep HPLC using C18 column ($H_2O$/$CH_3CN$ with 0.05% TFA, 90:10 to 30:70 v/v). Fractions containing the desired compound were pooled and lyophilized to yield compound 174 (2 mg, 1.4 µmol, 28% yield). LRMS (ESI): m/z 1438.7 [M+H]$^+$, Calcd for $C_{70}H_{99}N_7O_{25}$ m/z 1438.7.

Preparation of (2S,3S,4S,5R,6S)-6-(5-((2S,5S)-38-((1-((2S,5S)-1-((3-(((2S,3R,4S,5S,6S)-6-carboxy-3,4,5-trihydroxytetrahydro-2H-pyran-2-yl)oxy)-4-((((S)-4-ethyl-11-(2-(isopropylamino)ethyl)-3,14-dioxo-3,4,12,14-tetrahydro-1H-pyrano[3',4':6,7]indolizino[1,2-b]quinolin-4-yl)oxy)carbonyl)phenyl)amino)-5-isopropyl-2-methyl-1,4,7,35-tetraoxo-10,13,16,19,22,25,28,31-octaoxa-3,6,34-triazaheptatriacontan-37-yl)-2-((1,2-dimethylhydrazineyl)methyl)-1H-indol-5-yl)amino)-5-isopropyl-2-methyl-4,7,35,38-tetraoxo-10,13,16,19,22,25,28,31-octaoxa-3,6,34-triazaoctatriacontanamido)-2-(((((S)-4-ethyl-11-(2-(isopropylamino)ethyl)-3,14-dioxo-3,4,12,14-tetrahydro-1H-pyrano[3',4':6,7]indolizino[1,2-b]quinolin-4-yl)oxy)carbonyl)phenoxy)-3,4,5-trihydroxytetrahydro-2H-pyran-2-carboxylic Acid (175)

To a stirred mixture of amine 174 (2 mg, 1.4 µmol) and bis-PFP-ester 40 (0.8 mg, 0.7 µmol) in DMF (1 mL) were added DIPEA (0.5 µL, 2.8 µmol) at room temperature. After 2 hours, reaction mixture was concentrated and then reconstituted in formic acid (1 mL) at room temperature. After 30 minutes, formic acid was removed in vacuum, and the residue was reconstituted in DMF (1 mL) and piperidine (50 µL). After stirring for 15 minutes at room temperature, the reaction mixture was directly purified by reversed phase HPLC using C18 column ($H_2O$/$CH_3CN$ with 0.05% TFA, 90:10 to 35:65 v/v). Fractions containing the desired compound were pooled and lyophilized to yield compound 175 (0.7 mg, 0.2 µmol, 33% yield) as a yellow powder. LRMS (ESI): m/z 1509.2 [M+2H]$^{2+}$, Calcd for $C_{148}H_{202}N_{18}O_{49}$ m/z 1508.7.

Example 2

Preparation of Conjugates

Figure 1:
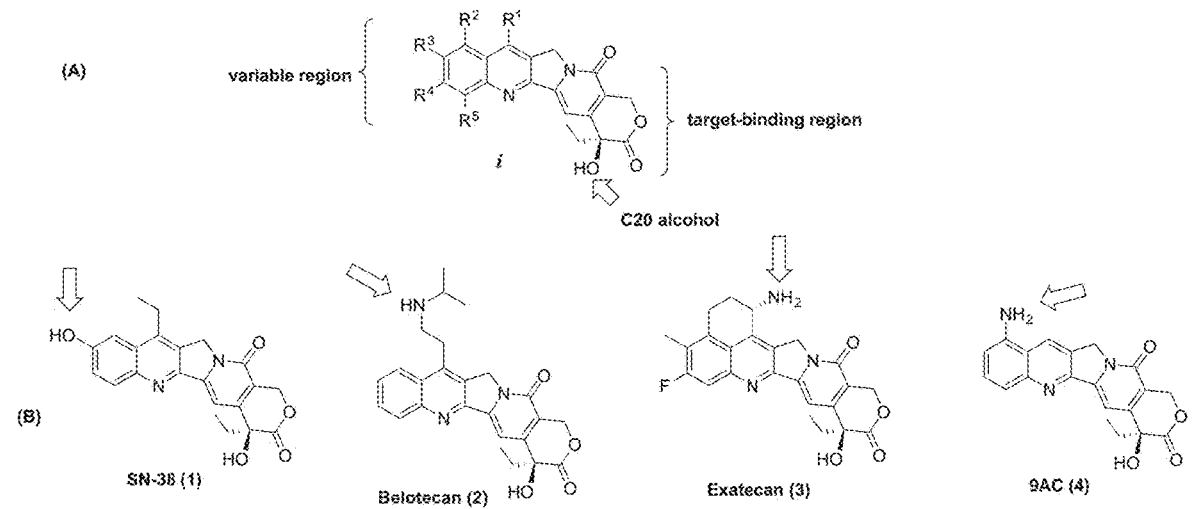
FIG. 1 shows chemical structures of the camptothecine family of topoisomerase I inhibitors.
Figure 2:
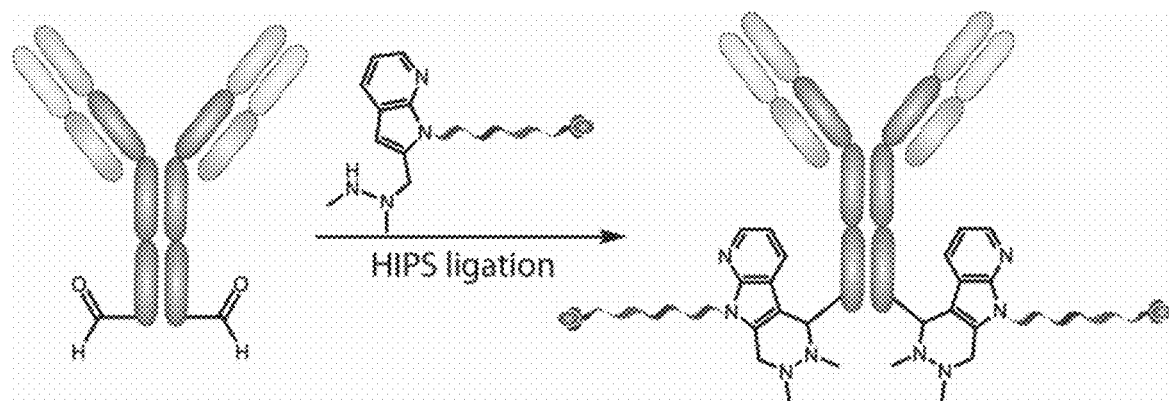
FIG. 2 shows a schematic of the HIPS ligation for the synthesis of ADCs. Antibodies carrying aldehyde moieties are reacted with a Hydrazino-iso-Pictet-Spengler (HIPS) linker and payload to generate a site-specifically conjugated ADC with a stable azacarboline linkage.
Figure 3:
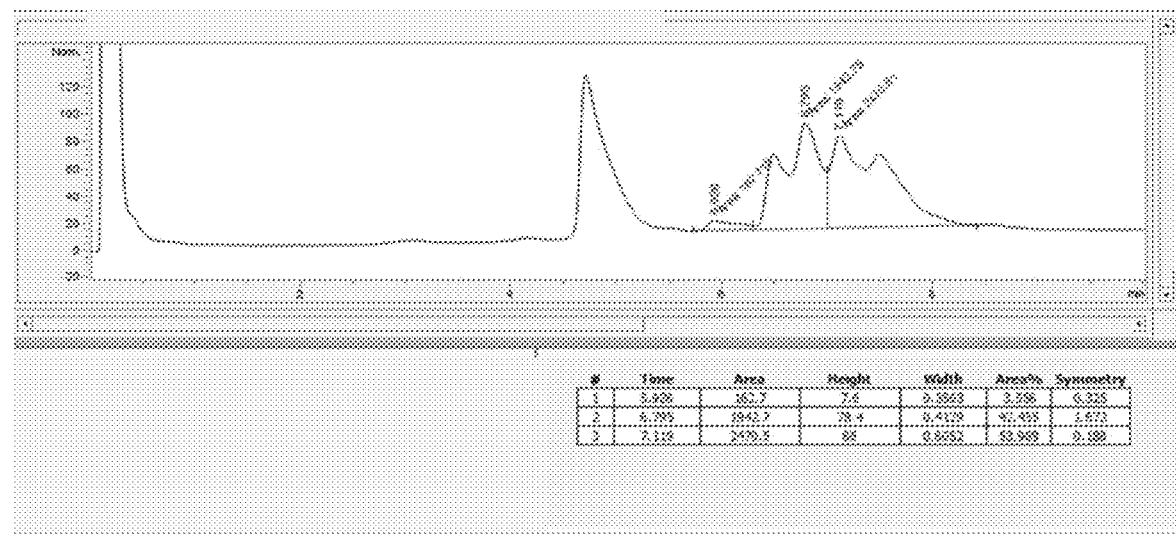
FIG. 3 shows a polymeric reversed phase column (PLRP) trace of compound 12, conjugate 2941, which included two tag sites and yielded a DAR of 2.75, 2.2% HMW.
Figure 4:
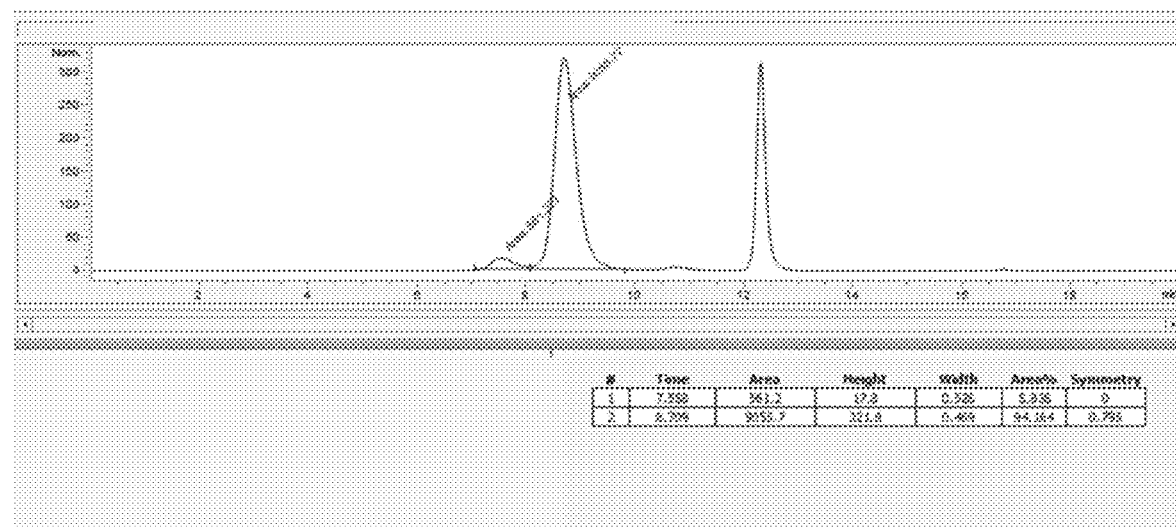
FIG. 4 shows an analytical size exclusion chromatography (SEC) trace of compound 12, conjugate 2941, which included two tag sites and yielded a DAR of 2.75, 2.2% HMW.
Figure 5:
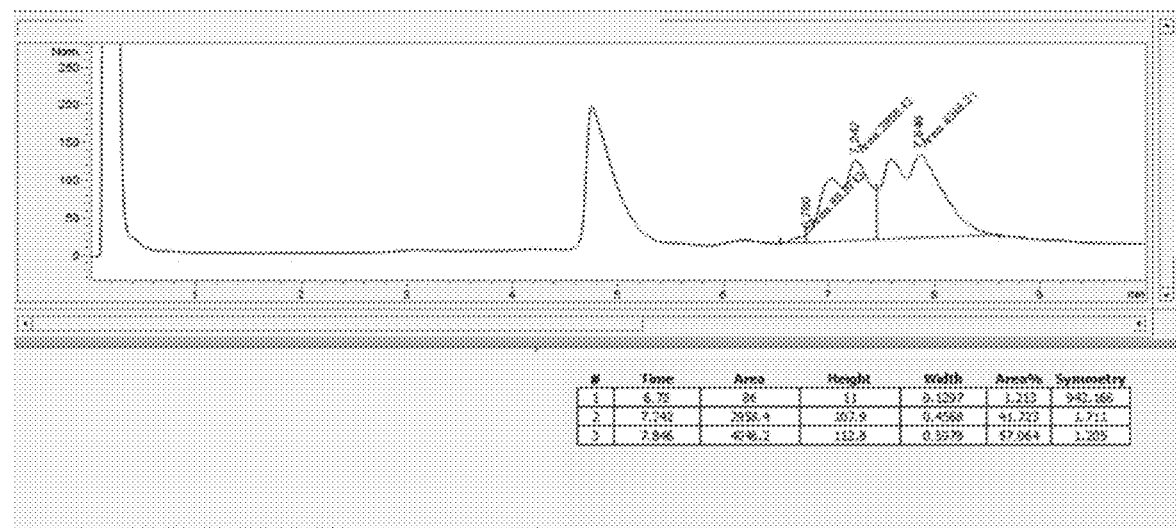
FIG. 5 shows a PLRP trace of compound 12, conjugate 2944, which included two tag sites and yielded a DAR of 3.12, 4.5% HMW.
Figure 6:
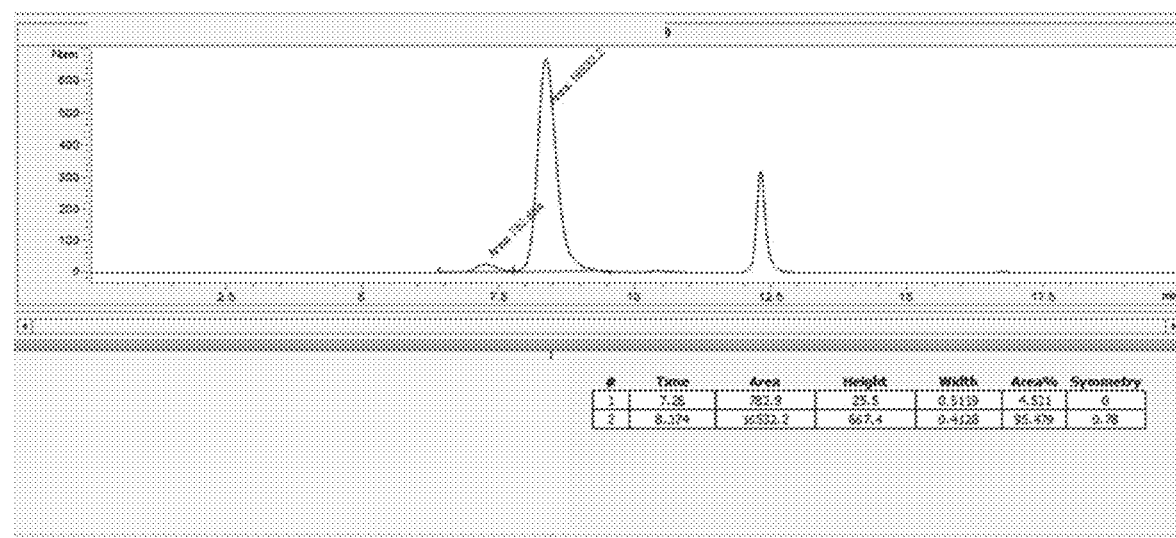
FIG. 6 shows an SEC trace of compound 12, conjugate 2944, which included two tag sites and yielded a DAR of 3.12, 4.5% HMW.
Figure 7:
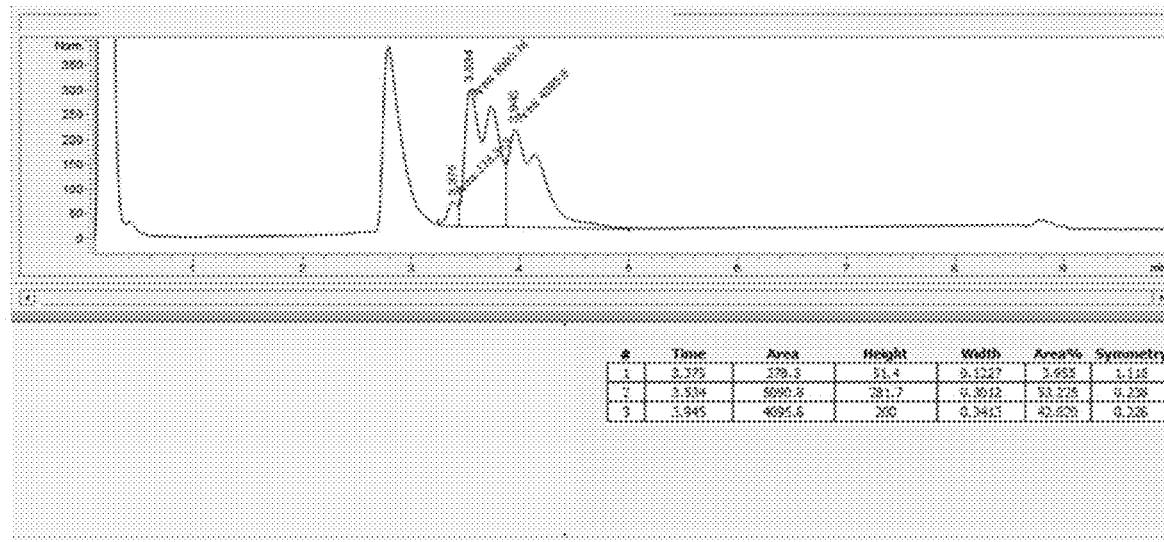
FIG. 7 shows a PLRP trace of compound 12, conjugate 2746, which included two tag sites and yielded a DAR of 2.78, 3.4% HMW.
Figure 8:
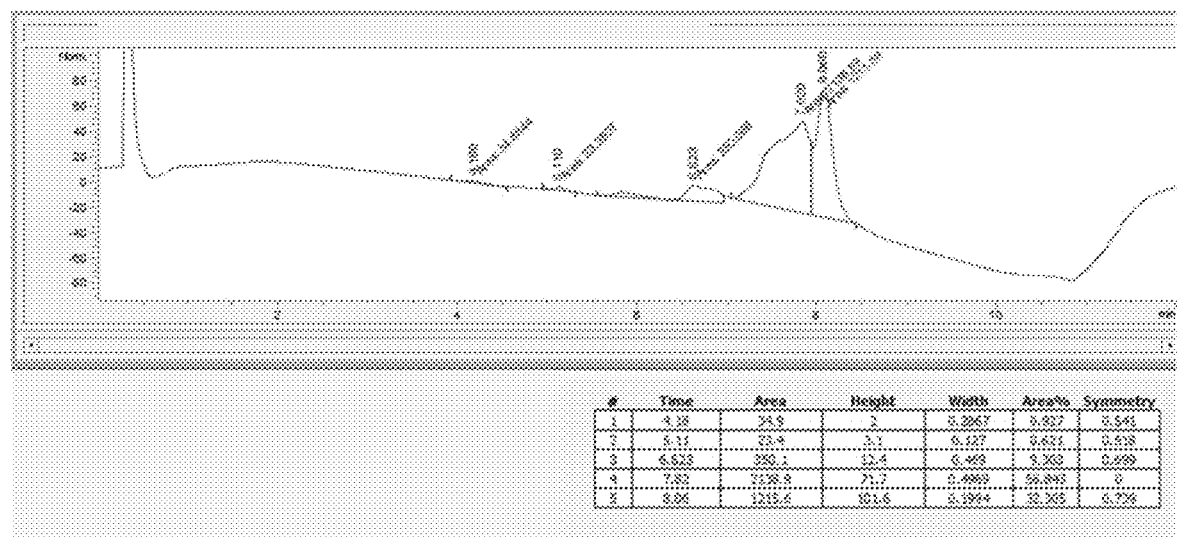
FIG. 8 shows a hydrophobic interaction column (HIC) trace of compound 12, conjugate 2746, which included two tag sites and yielded a DAR of 2.78, 3.4% HMW.
Figure 9:
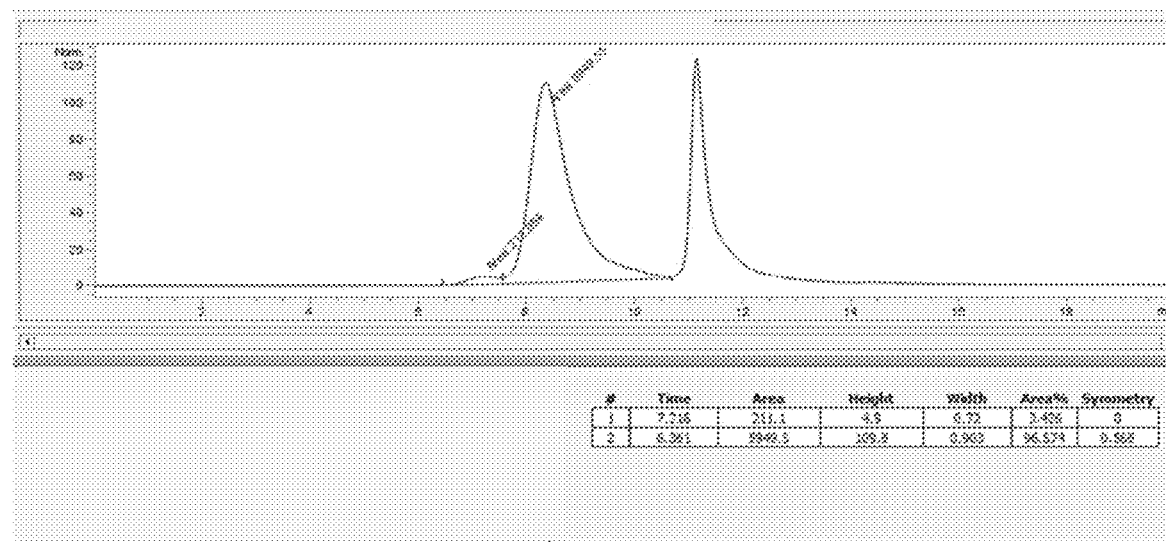
FIG. 9 shows an SEC trace of compound 12, conjugate 2746, which included two tag sites and yielded a DAR of 2.78, 3.4% HMW.
Figure 10:
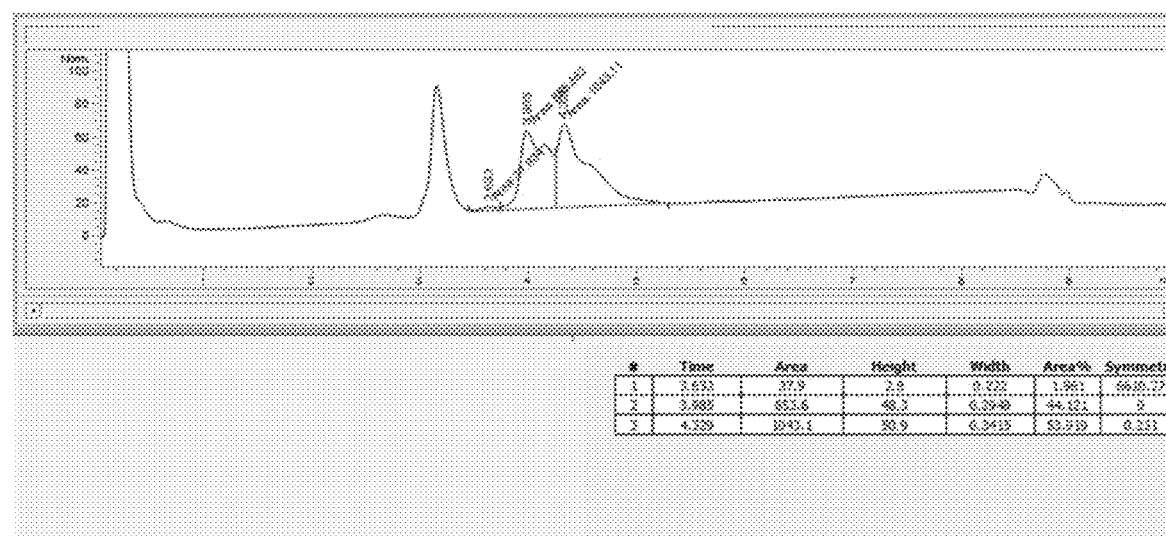
FIG. 10 shows a PLRP trace of compound 12, conjugate 2749, which included two tag sites and yielded a DAR of 3.04, 0.9% HMW.
Figure 11:
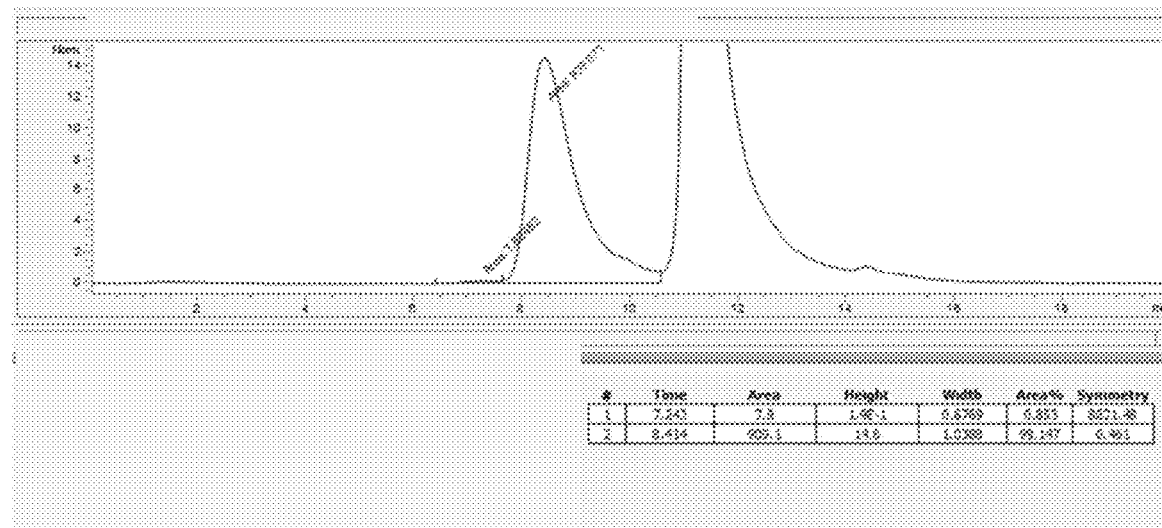
FIG. 11 shows an SEC trace of compound 12, conjugate 2749, which included two tag sites and yielded a DAR of 3.04, 0.9% HMW.
Figure 12:
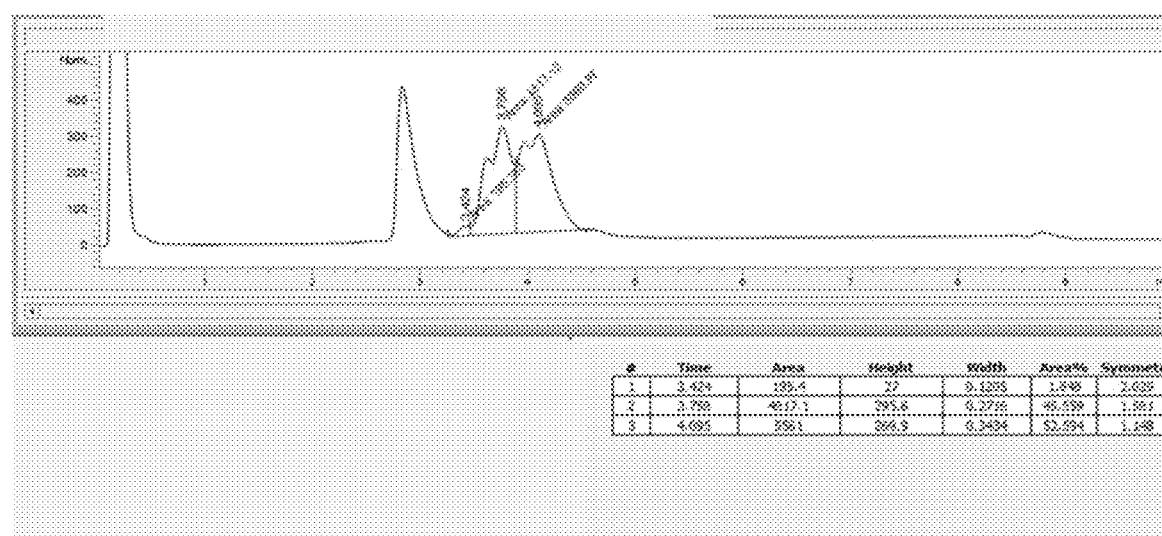
FIG. 12 shows a PLRP trace of compound 12, conjugate 2752, which included two tag sites and yielded a DAR of 3.01, 4.3% HMW.
Figure 13:
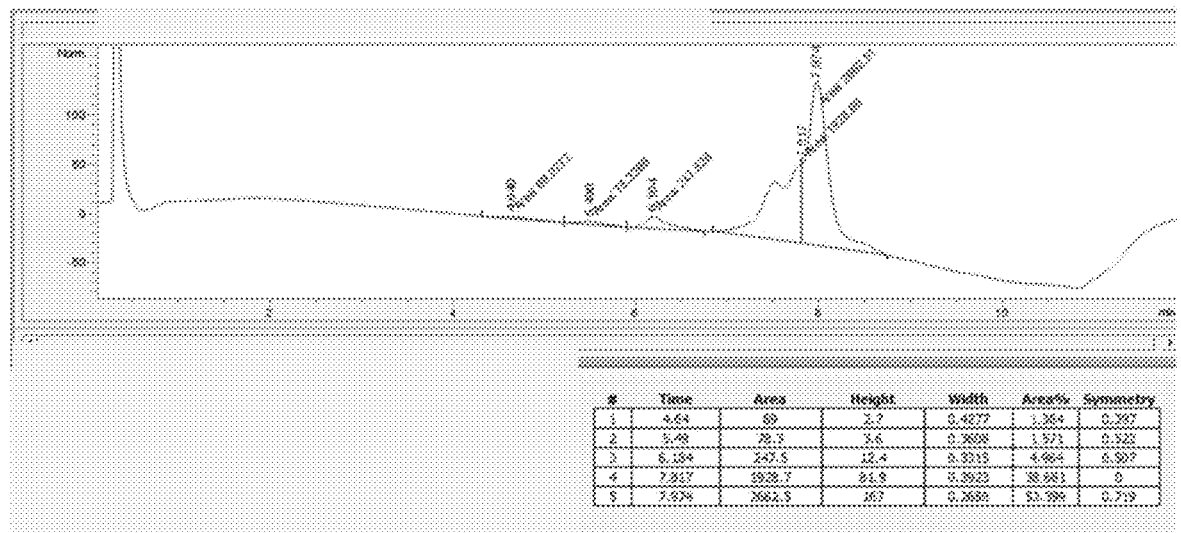
FIG. 13 shows an HIC trace of compound 12, conjugate 2752, which included two tag sites and yielded a DAR of 3.01, 4.3% HMW.
Figure 14:
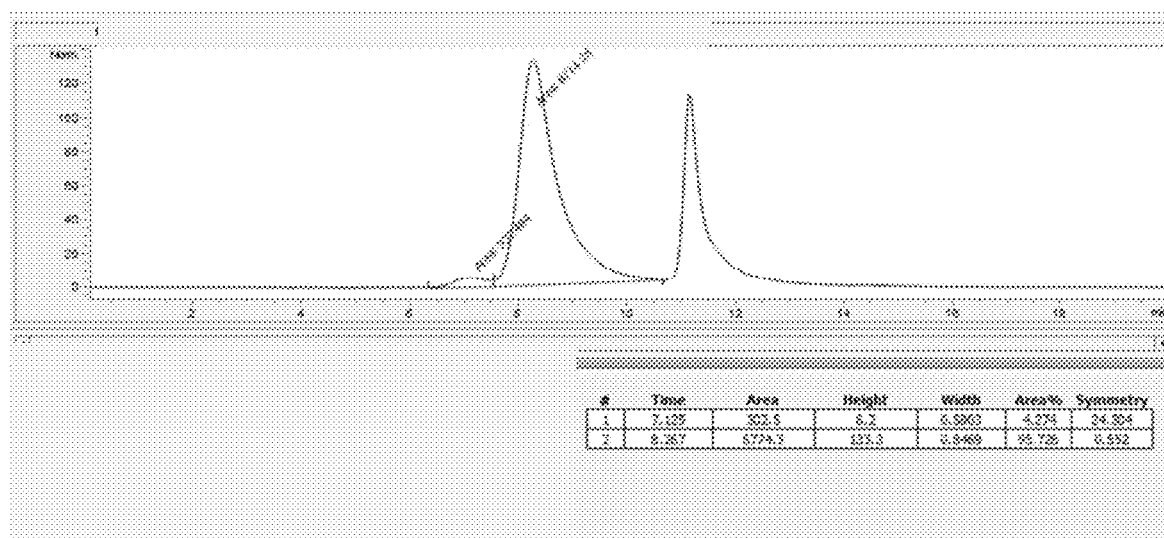
FIG. 14 shows an SEC trace of compound 12, conjugate 2752, which included two tag sites and yielded a DAR of 3.01, 4.3% HMW.
Figure 15:
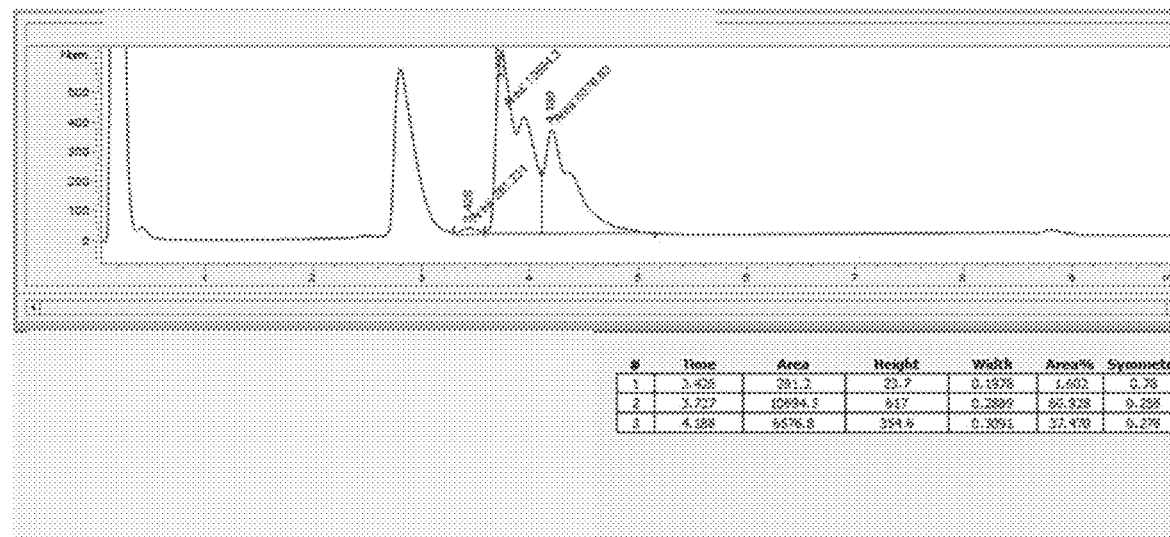
FIG. 15 shows a PLRP trace of compound 12, conjugate 2755, which included two tag sites and yielded a DAR of 2.72, 3.2% HMW.
Figure 16:
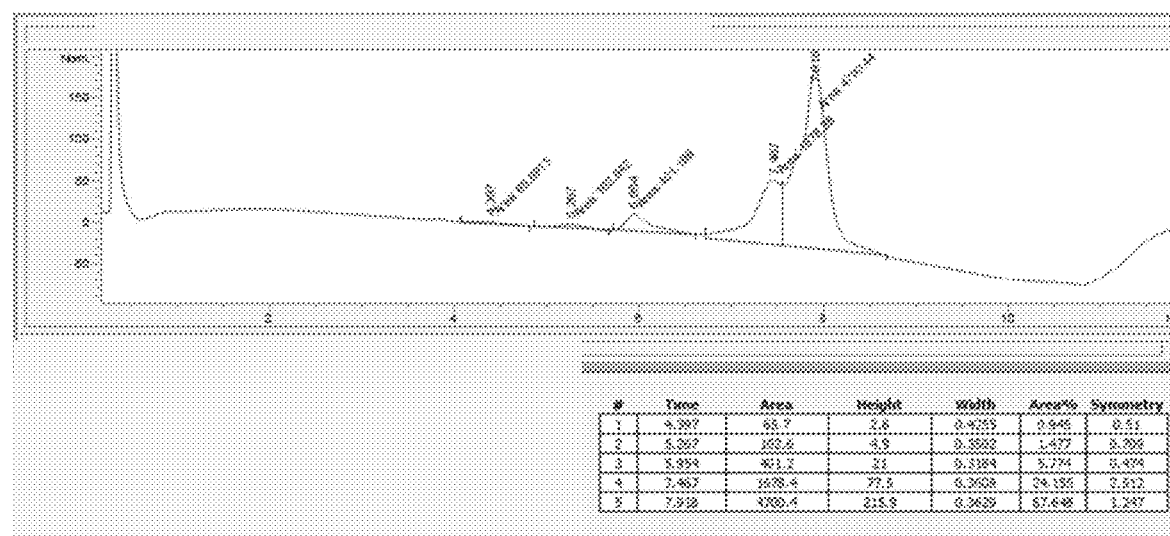
FIG. 16 shows an HIC trace of compound 12, conjugate 2755, which included two tag sites and yielded a DAR of 2.72, 3.2% HMW.
Figure 17:
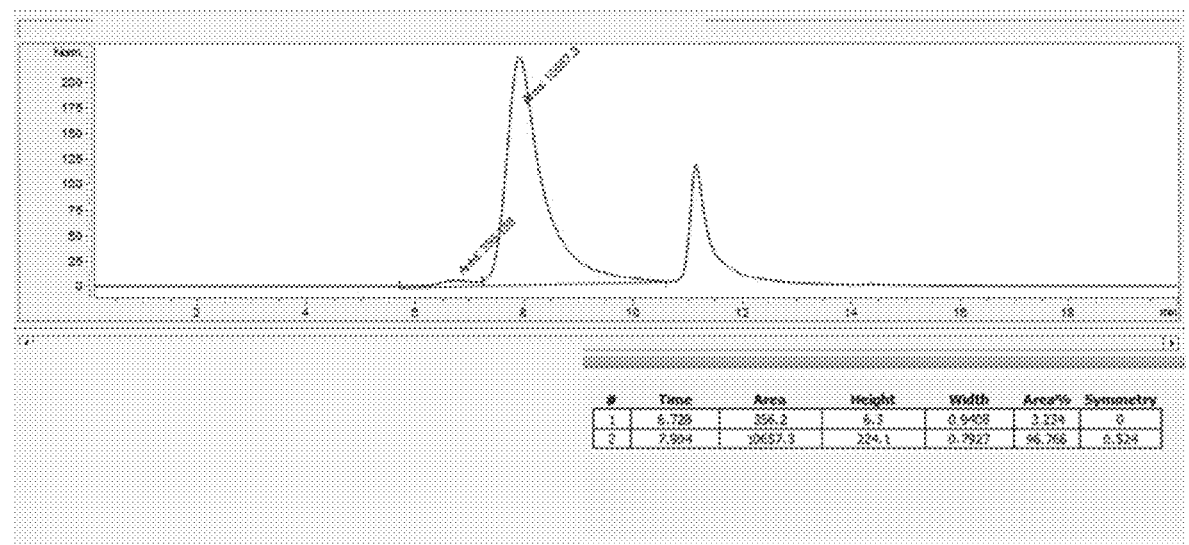
FIG. 17 shows an SEC trace of compound 12, conjugate 2755, which included two tag sites and yielded a DAR of 2.72, 3.2% HMW.
Figure 18:
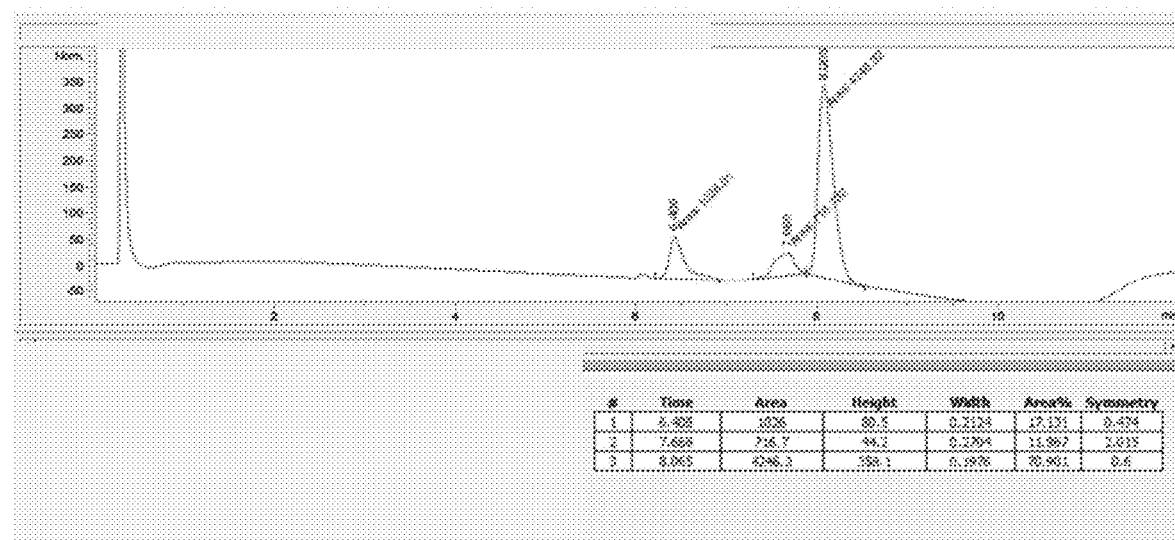
FIG. 18 shows an HIC trace of compound 12, conjugate 2758, which included one tag site and yielded a DAR of 1.54, 1.6% HMW.
Figure 19:
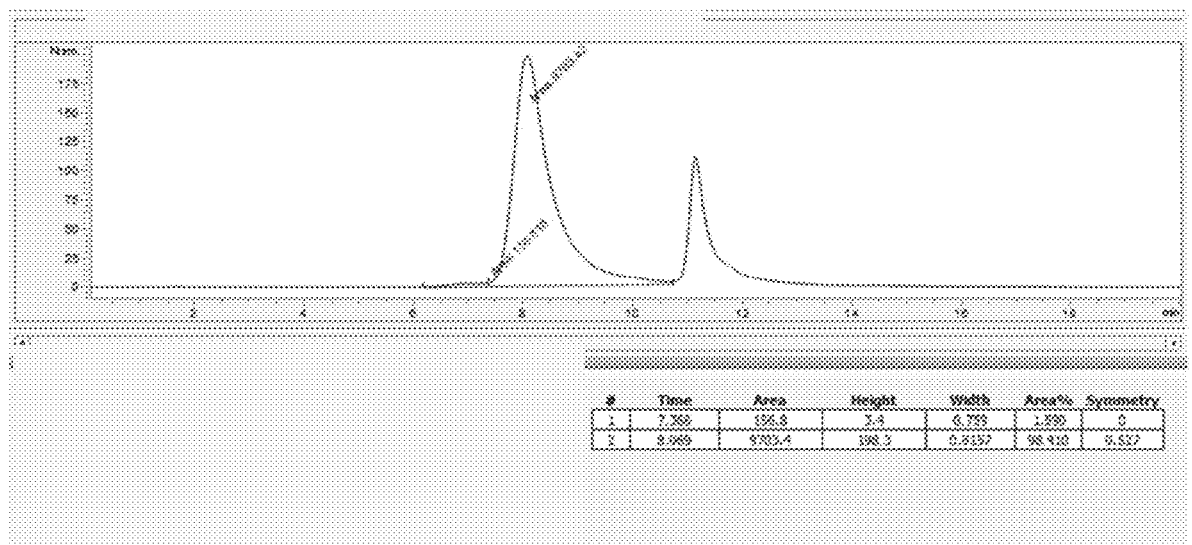
FIG. 19 shows an SEC trace of compound 12, conjugate 2758, which included one tag site and yielded a DAR of 1.54, 1.6% HMW.
Figure 20:
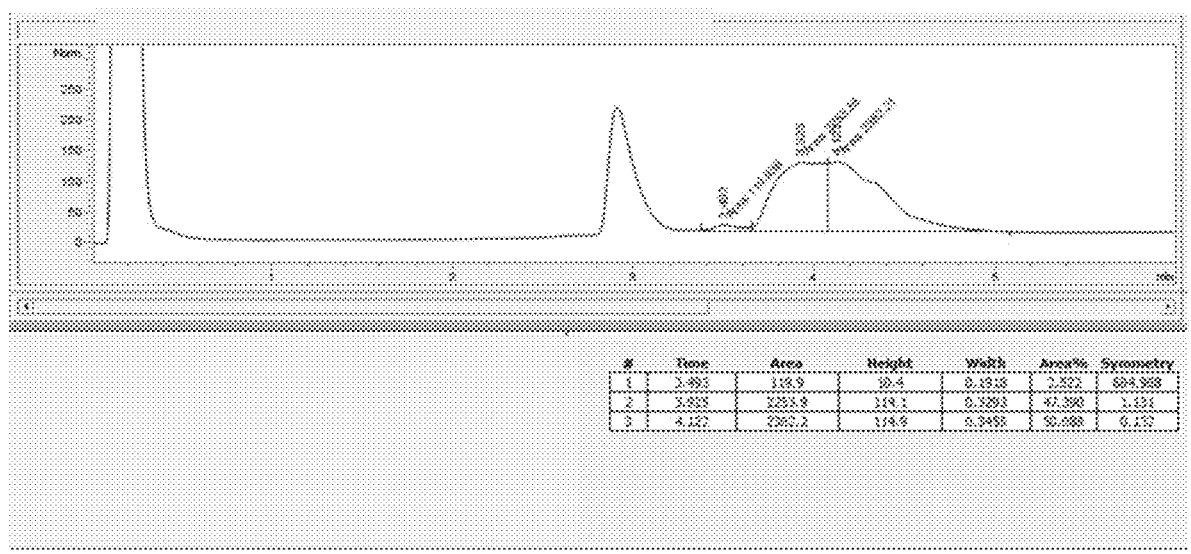
FIG. 20 shows a PLRP trace of compound 12, conjugate 2762, which included two tag sites and yielded a DAR of 2.95, 3.6% HMW.
Figure 21:
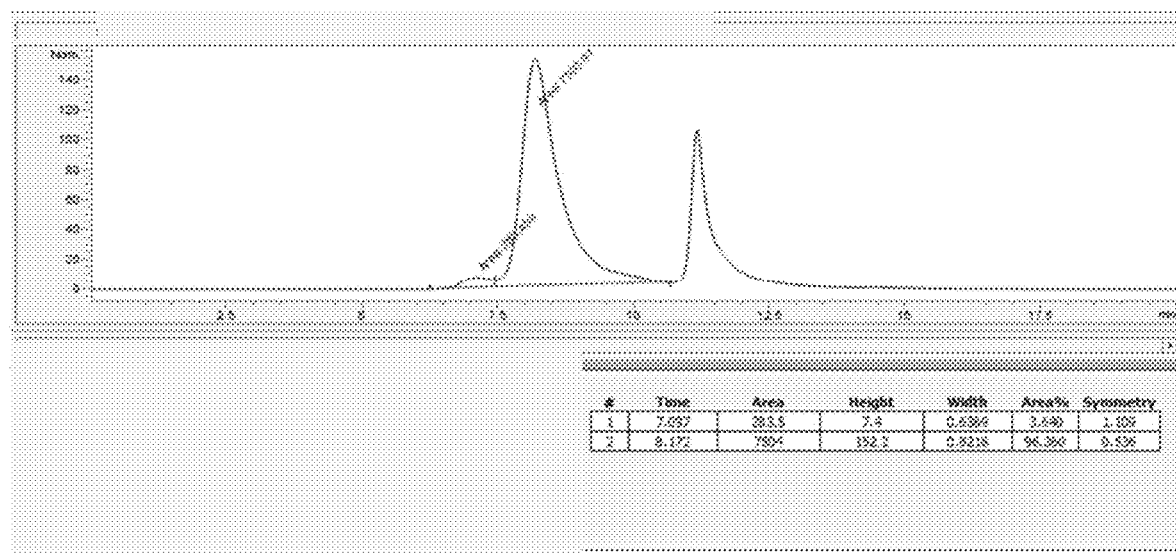
FIG. 21 shows an SEC trace of compound 20, conjugate 2762, which included two tag sites and yielded a DAR of 2.95, 3.6% HMW.
Figure 22:
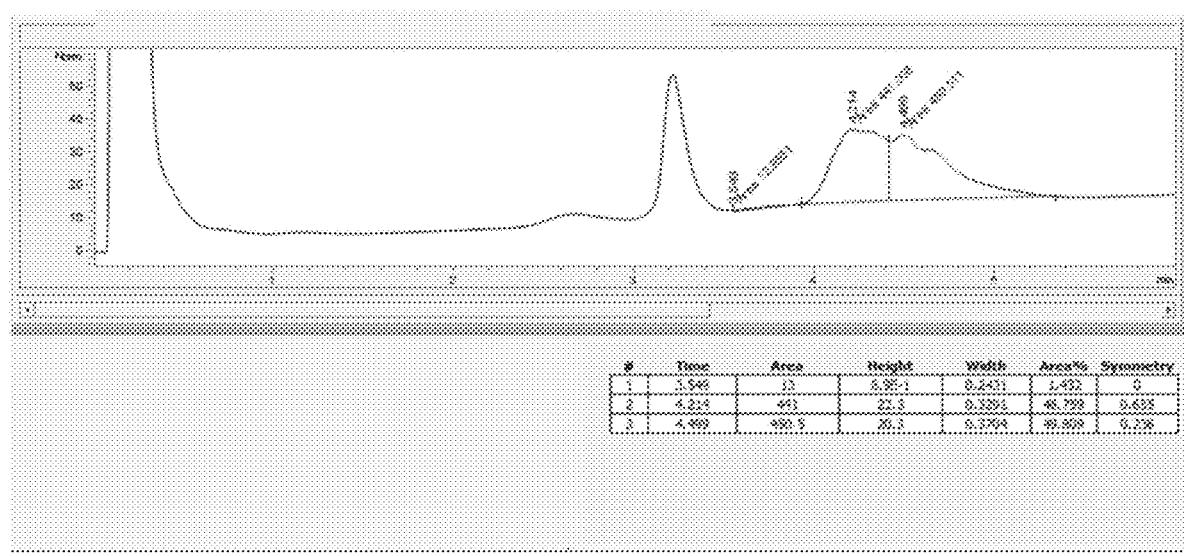
FIG. 22 shows a PLRP trace of compound 20, conjugate 2765, which included two tag sites and yielded a DAR of 2.97, 1.2% HMW.
Figure 23:
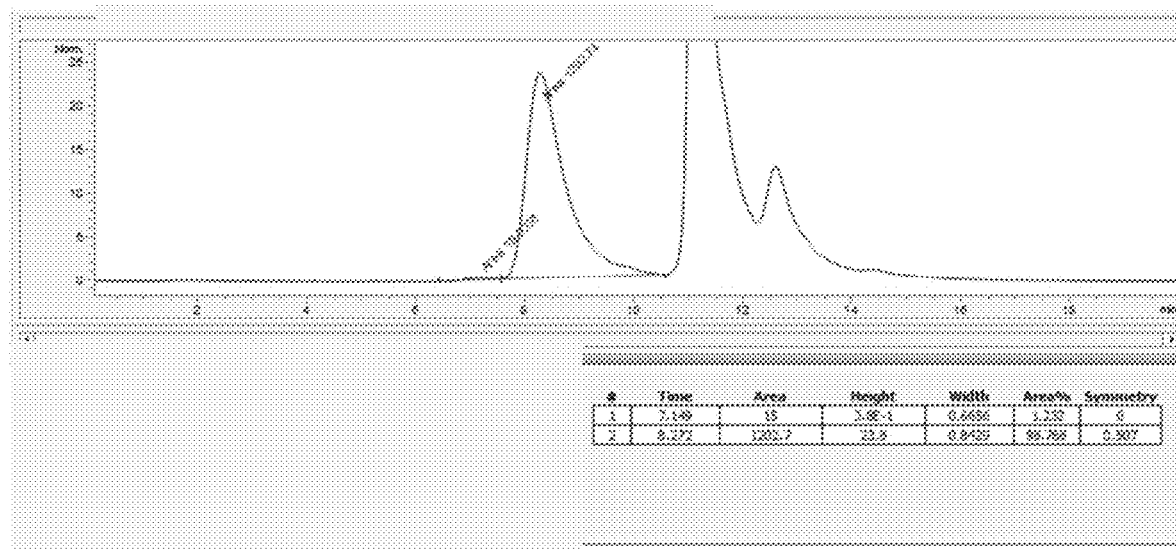
FIG. 23 shows an SEC trace of compound 20, conjugate 2765, which included two tag sites and yielded a DAR of 2.97, 1.2% HMW.
Figure 24:
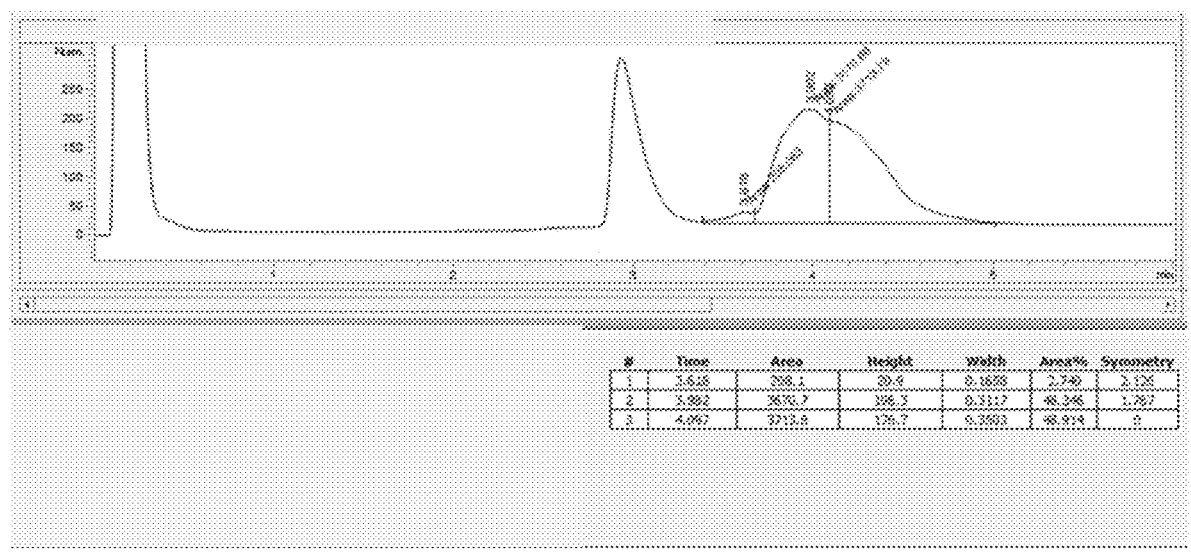
FIG. 24 shows a PLRP trace of compound 20, conjugate 2768, which included two tag sites and yielded a DAR of 2.92, 5.3% HMW.
Figure 25:
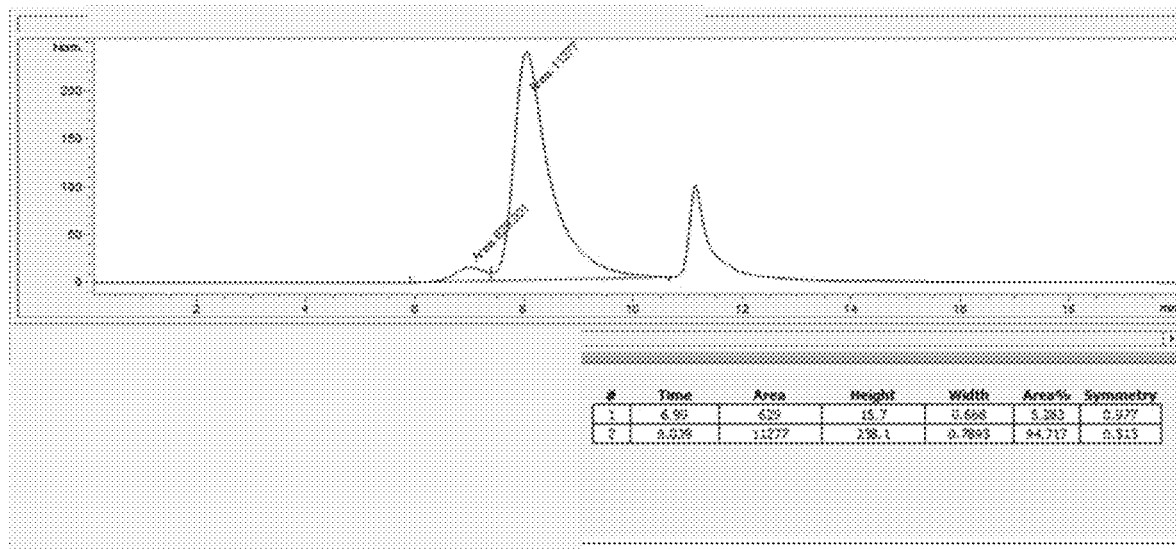
FIG. 25 shows an SEC trace of compound 20, conjugate 2768 which included two tag sites and yielded a DAR of 2.92, 5.3% HMW.
Figure 26:
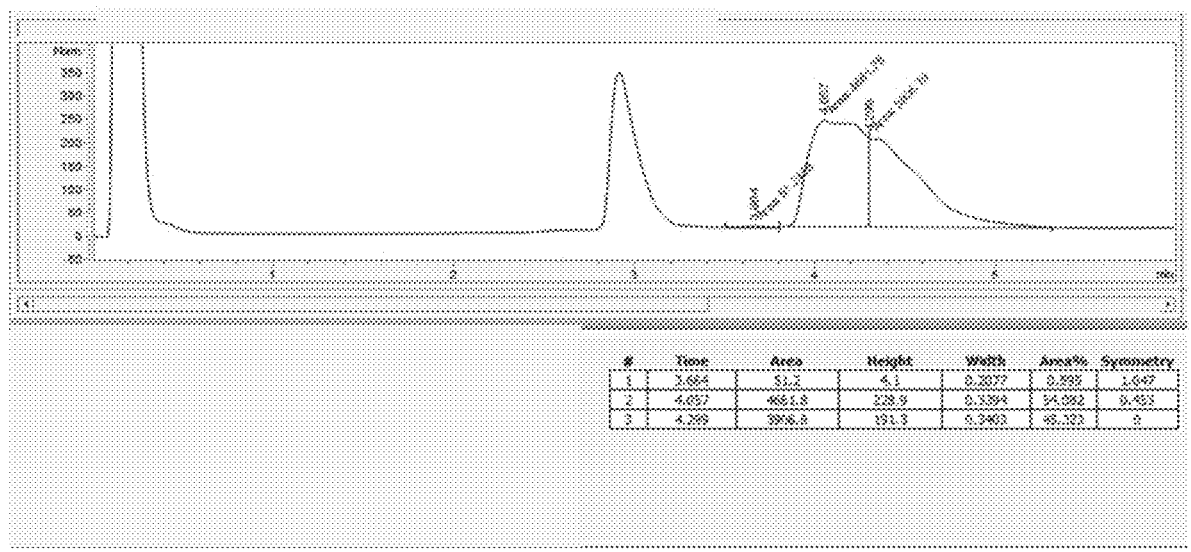
FIG. 26 shows a PLRP trace of compound 20, conjugate 2771 which included two tag sites and yielded a DAR of 2.89, 4.3% HMW.
Figure 27:
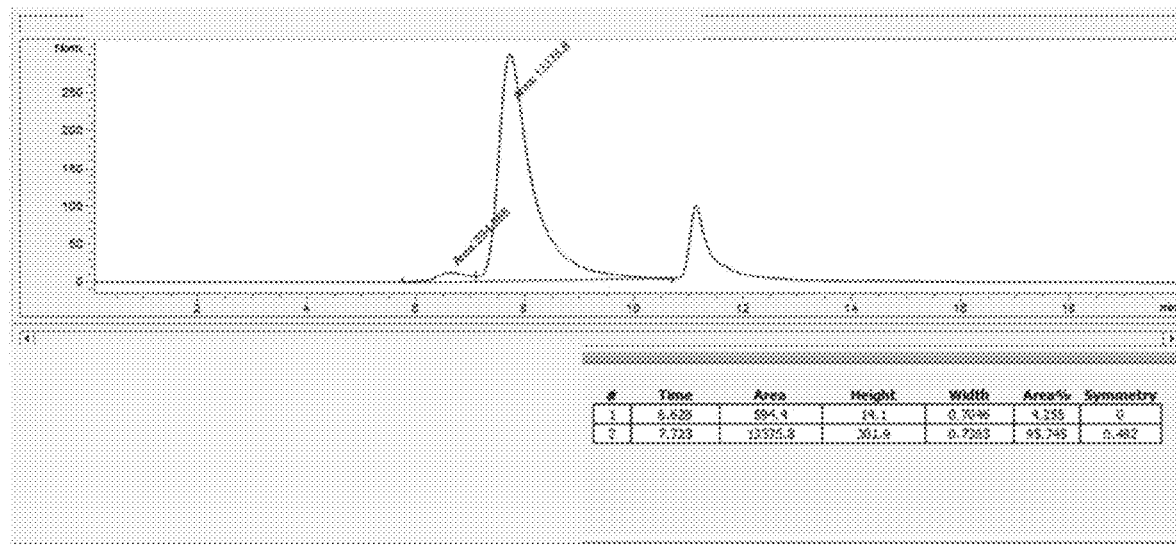
FIG. 27 shows an SEC trace of compound 20, conjugate 2771 which included two tag sites and yielded a DAR of 2.89, 4.3% HMW.
Figure 28:
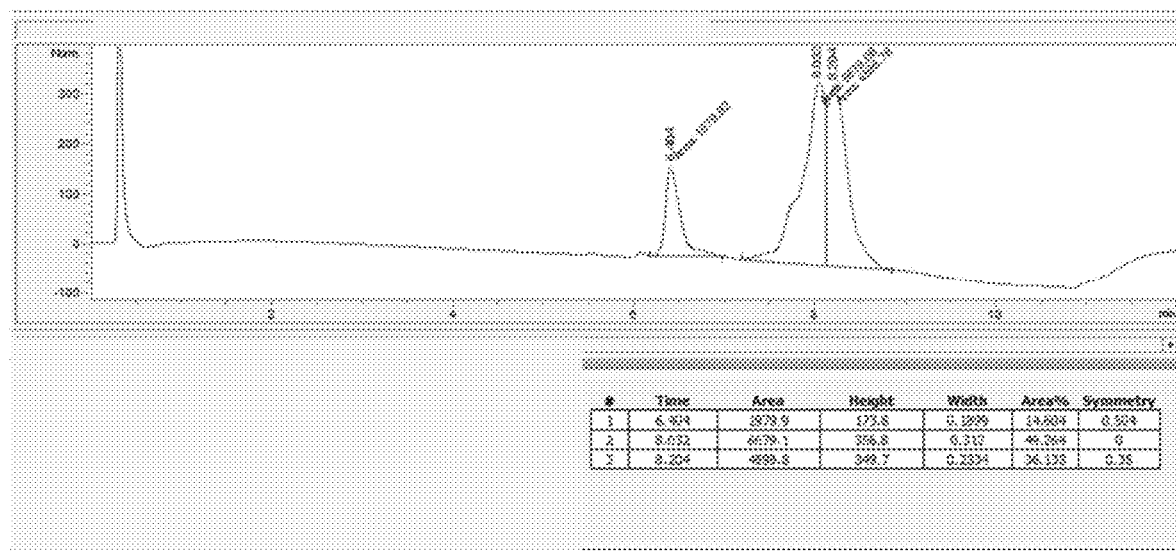
FIG. 28 shows an HIC trace of compound 20, conjugate 2774, which included one tag site and yielded a DAR of 1.22, 1.8% HMW.
Figure 29:
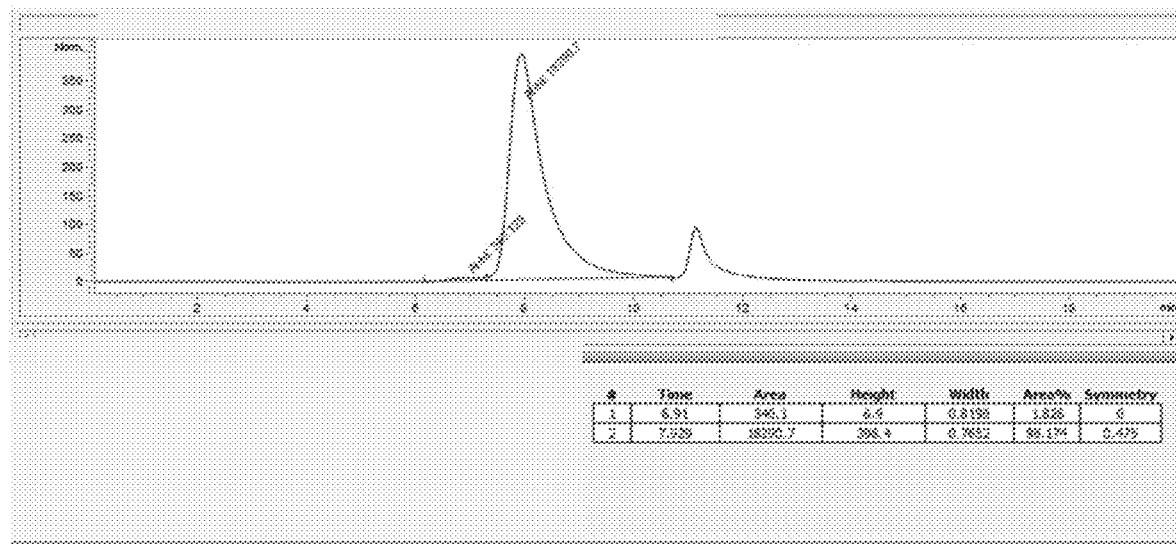
FIG. 29 shows an SEC trace of compound 20, conjugate 2774, which included one tag site and yielded a DAR of 1.22, 1.8% HMW.
Figure 30:
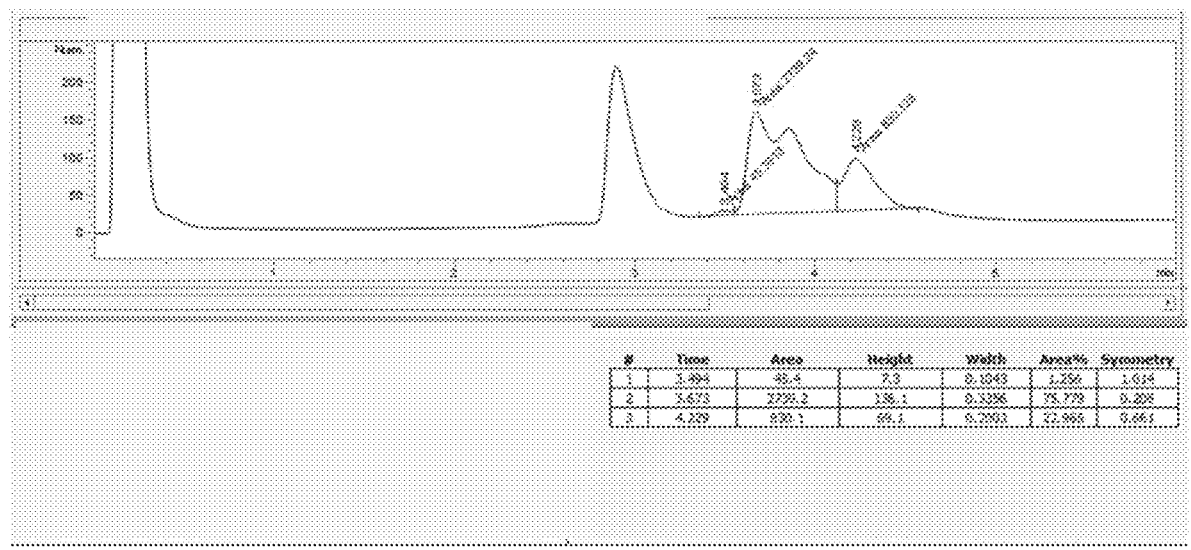
FIG. 30 shows a PLRP trace of compound 27, conjugate 2763, which included two tag sites and yielded a DAR of 2.43, 6.0% HMW.
Figure 31:
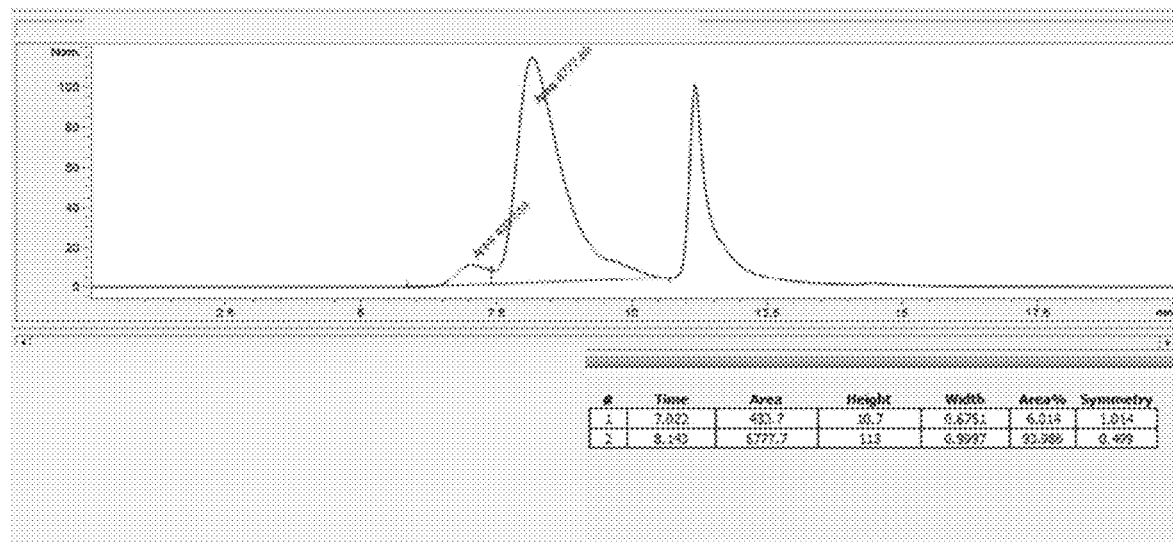
FIG. 31 shows an SEC trace of compound 27, conjugate 2763, which included two tag sites and yielded a DAR of 2.43, 6.0% HMW.
Figure 32:
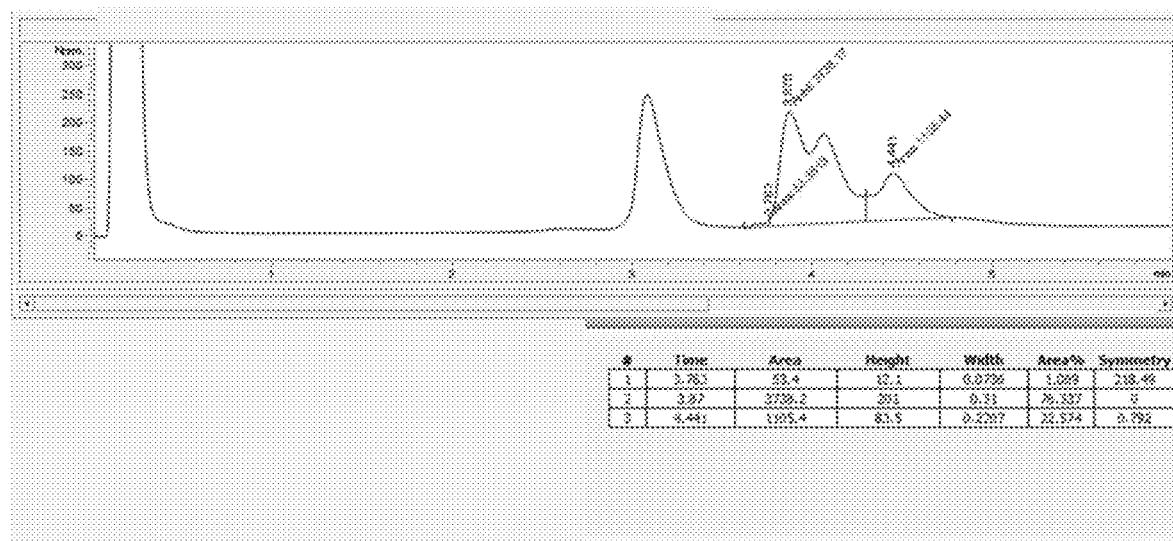
FIG. 32 shows a PLRP trace of compound 27, conjugate 2766, which included two tag sites and yielded a DAR of 2.43, 2.2% HMW.
Figure 33:
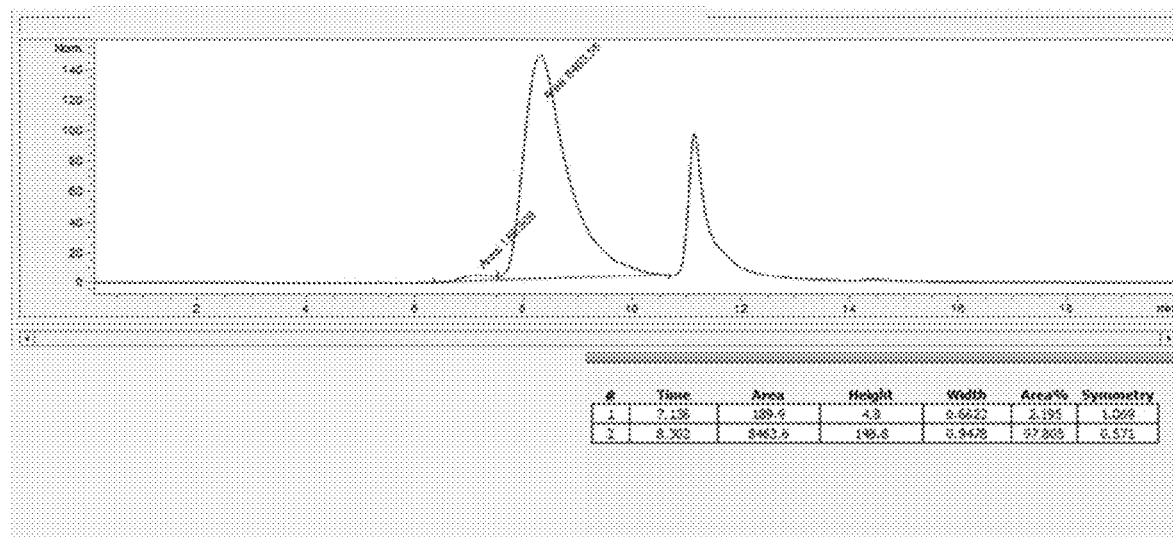
FIG. 33 shows an SEC trace of compound 27, conjugate 2766, which included two tag sites and yielded a DAR of 2.43, 2.2% HMW.
Figure 34:
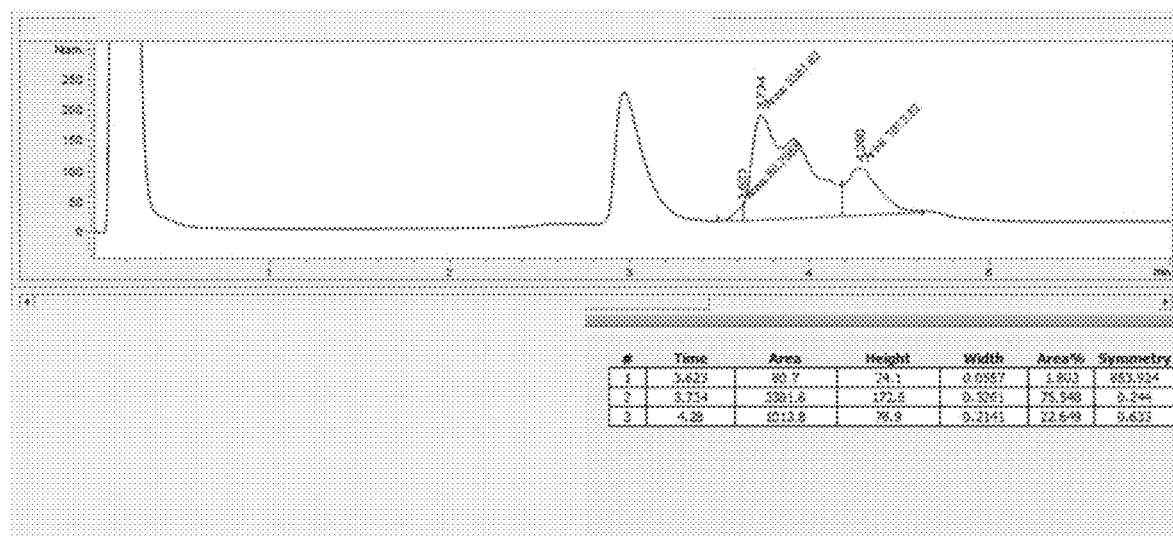
FIG. 34 shows a PLRP trace of compound 27, conjugate 2769, which included two tag sites and yielded a DAR of 2.42, 8.2% HMW.
Figure 35:
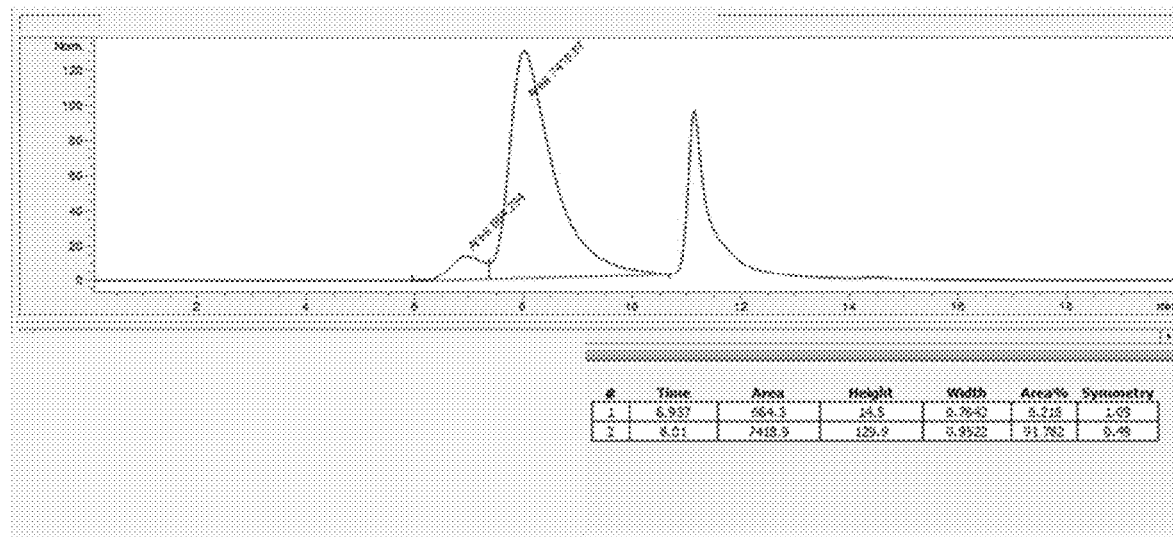
FIG. 35 shows an SEC trace of compound 27, conjugate 2769, which included two tag sites and yielded a DAR of 2.42, 8.2% HMW.
Figure 36:
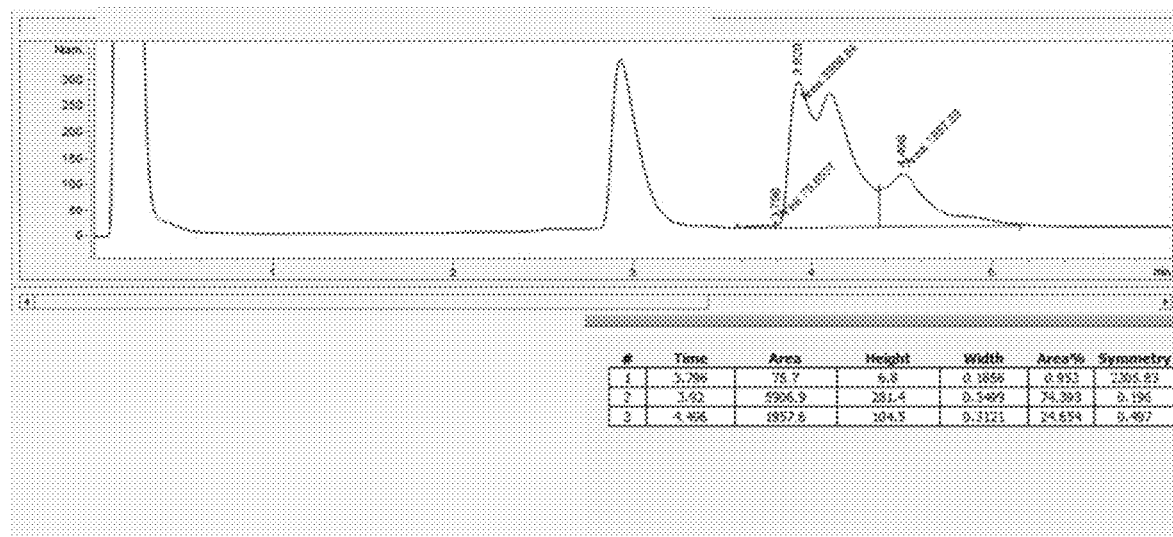
FIG. 36 shows a PLRP trace of compound 27, conjugate 2772, which included two tag sites and yielded a DAR of 2.47, 6.0% HMW.
Figure 37:
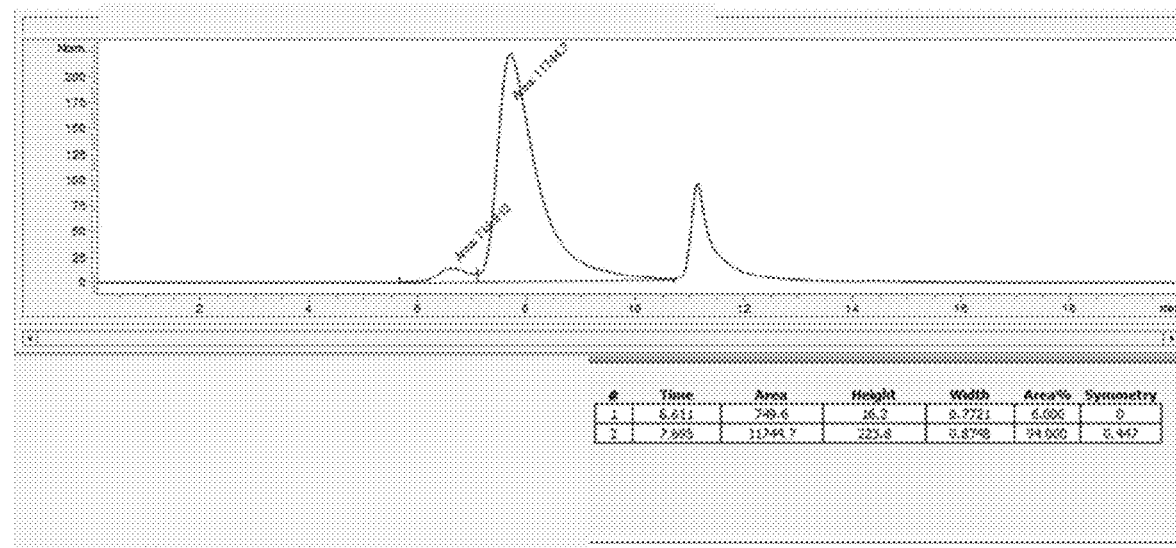
FIG. 37 shows an SEC trace of compound 27, conjugate 2772, which included two tag sites and yielded a DAR of 2.47, 6.0% HMW.
Figure 38:
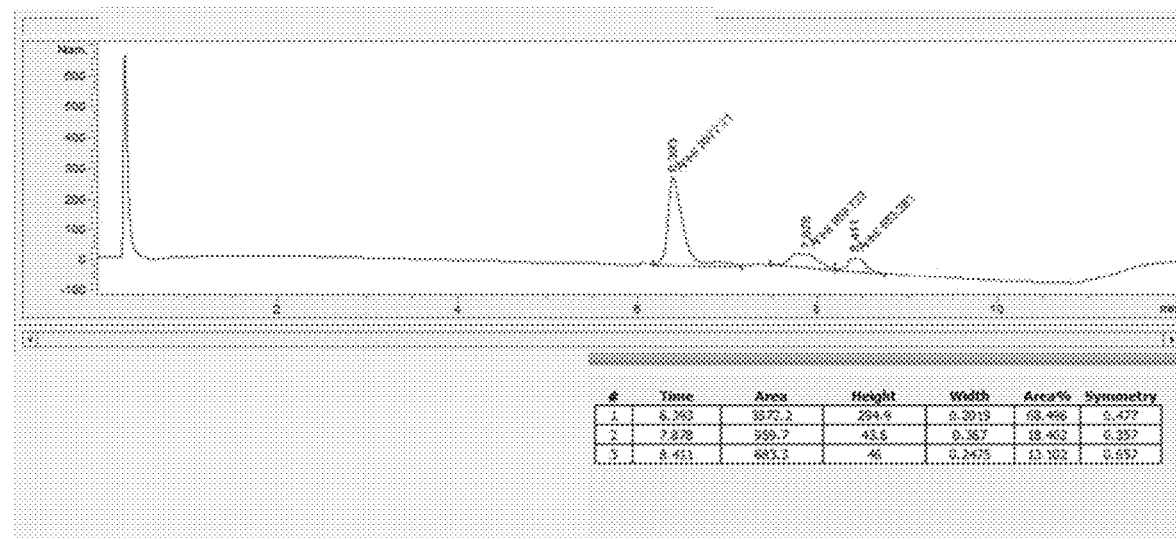
FIG. 38 shows an HIC trace of compound 27, conjugate 2775, which included one tag site and yielded a DAR of 0.45, 1.4% HMW.
Figure 39:
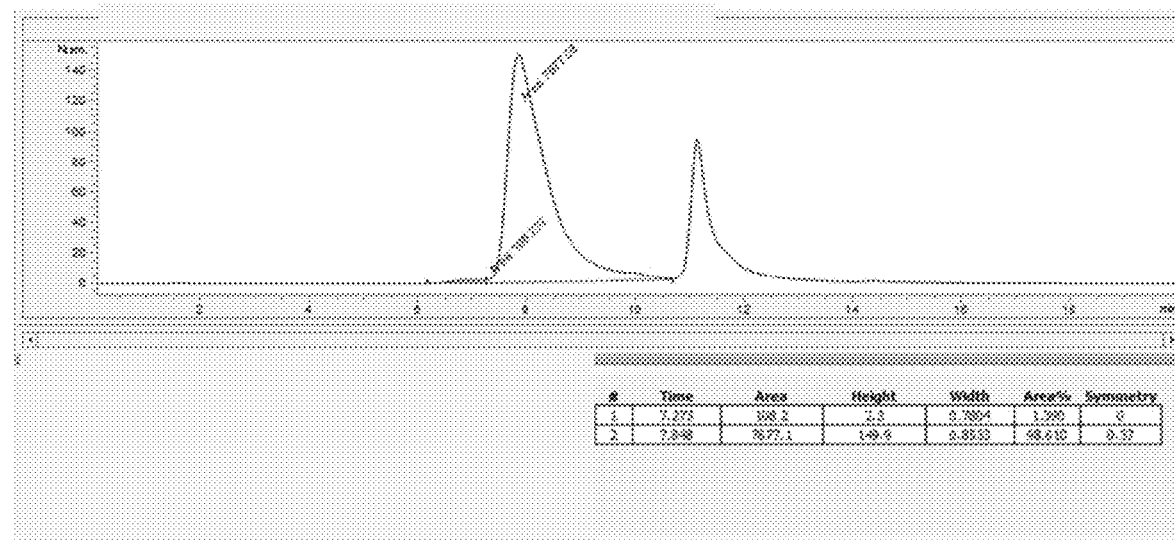
FIG. 39 shows an SEC trace of compound 27, conjugate 2775, which included one tag site and yielded a DAR of 0.45, 1.4% HMW.
Figure 40:
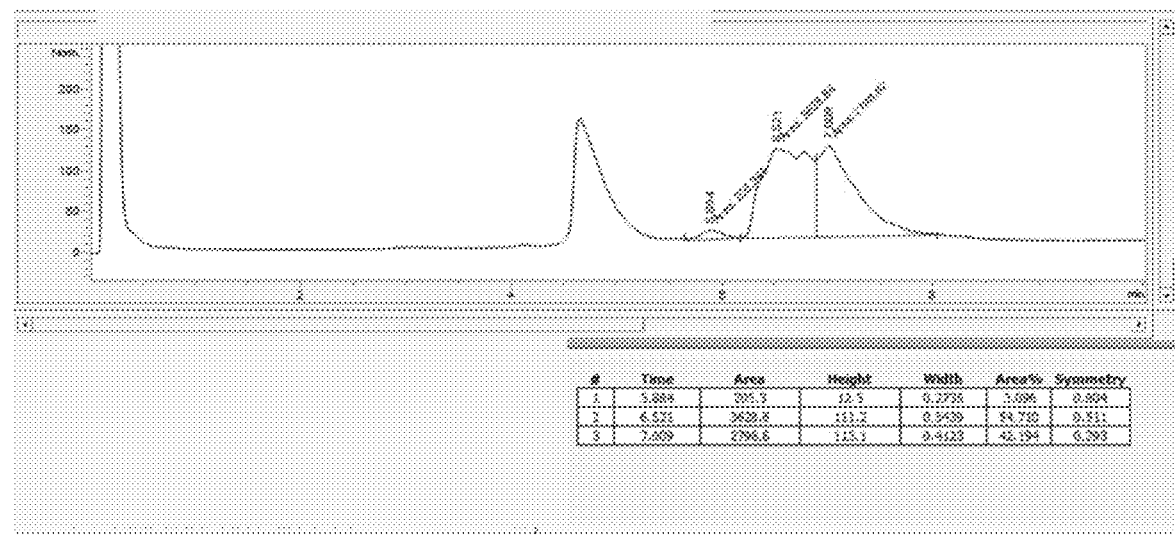
FIG. 40 shows a PLRP trace of compound 34, conjugate 2942, which included two tag sites and yielded a DAR of 2.78, 11.2% HMW.
Figure 41:
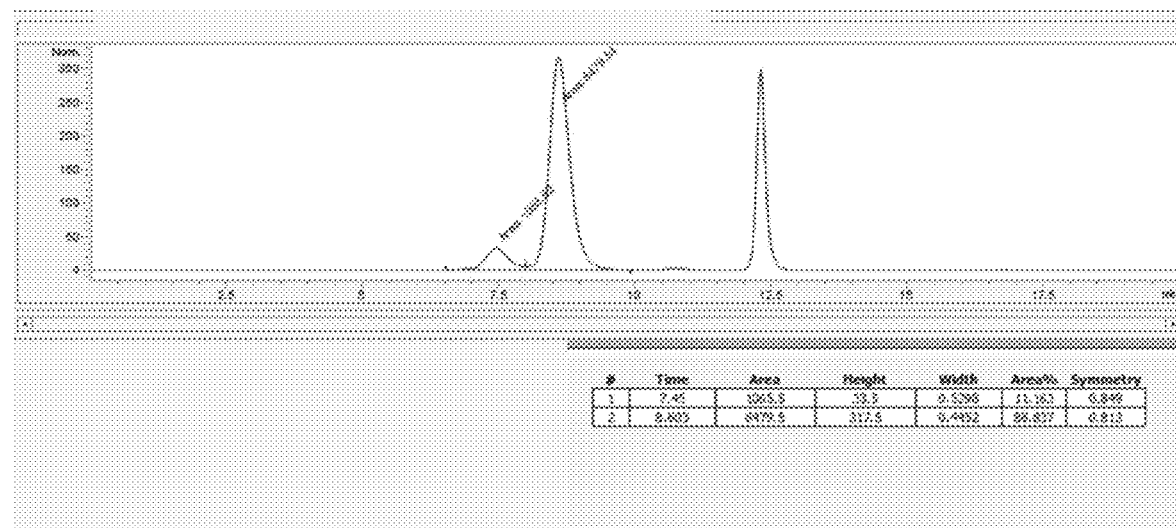
FIG. 41 shows an SEC trace of compound 34, conjugate 2942, which included two tag sites and yielded a DAR of 2.78, 11.2% HMW.
Figure 42:
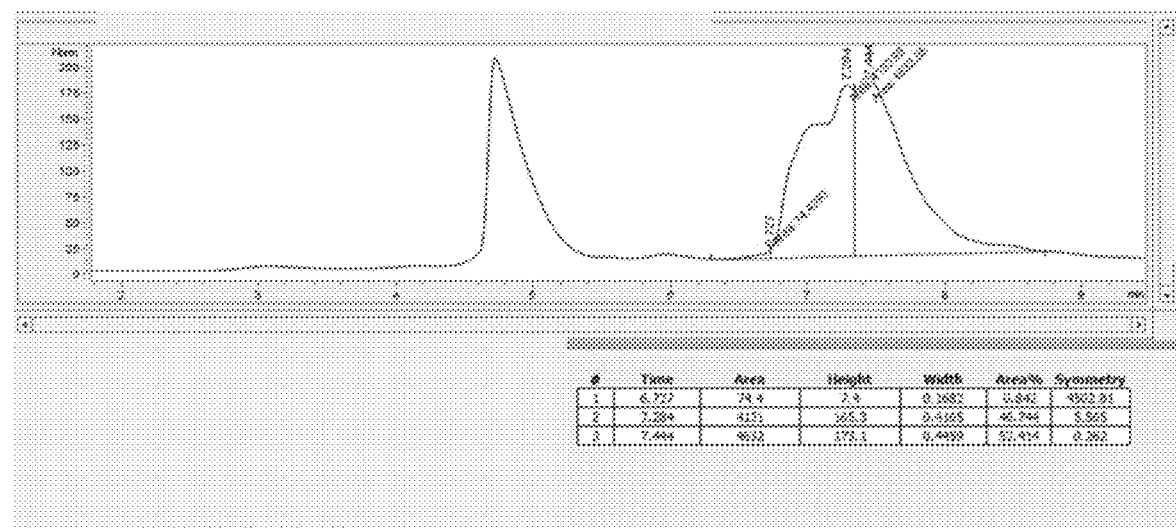
FIG. 42 shows a PLRP trace of compound 34, conjugate 2945, which included two tag sites and yielded a DAR of 3.03, 5.2% HMW.
Figure 43:
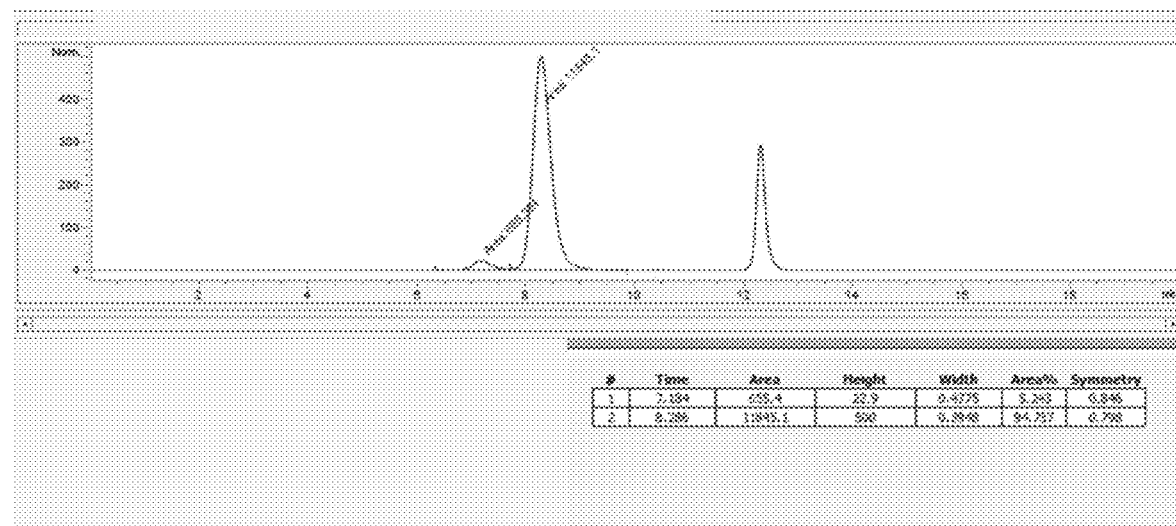
FIG. 43 shows an SEC trace of compound 34, conjugate 2945, which included two tag sites and yielded a DAR of 3.03, 5.2% HMW.
Figure 44:
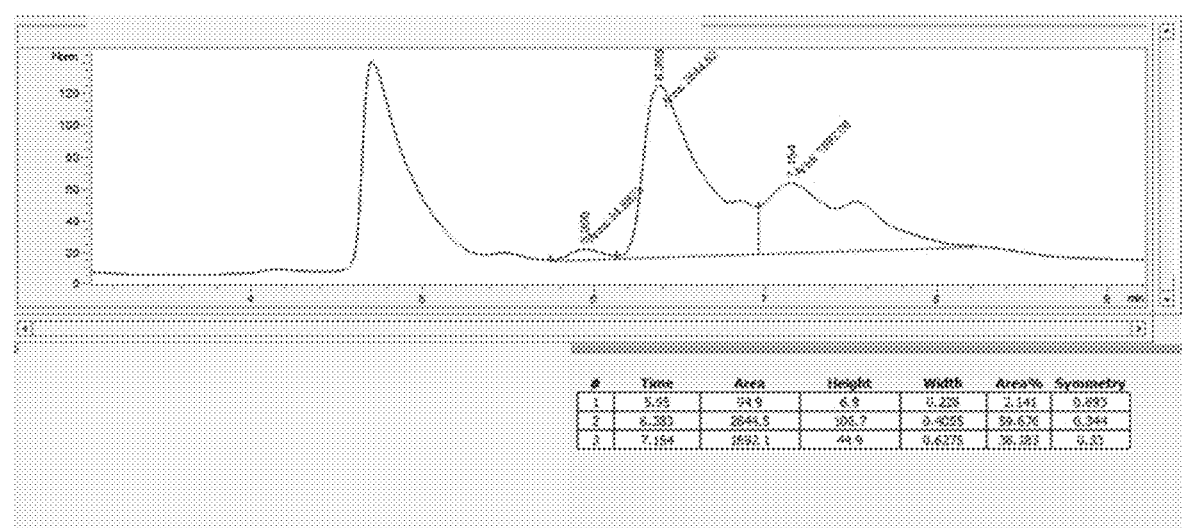
FIG. 44 shows a PLRP trace of compound 42, conjugate 2943, which included two tag sites and yielded a DAR of 5.44, 21.3% HMW.
Figure 45:
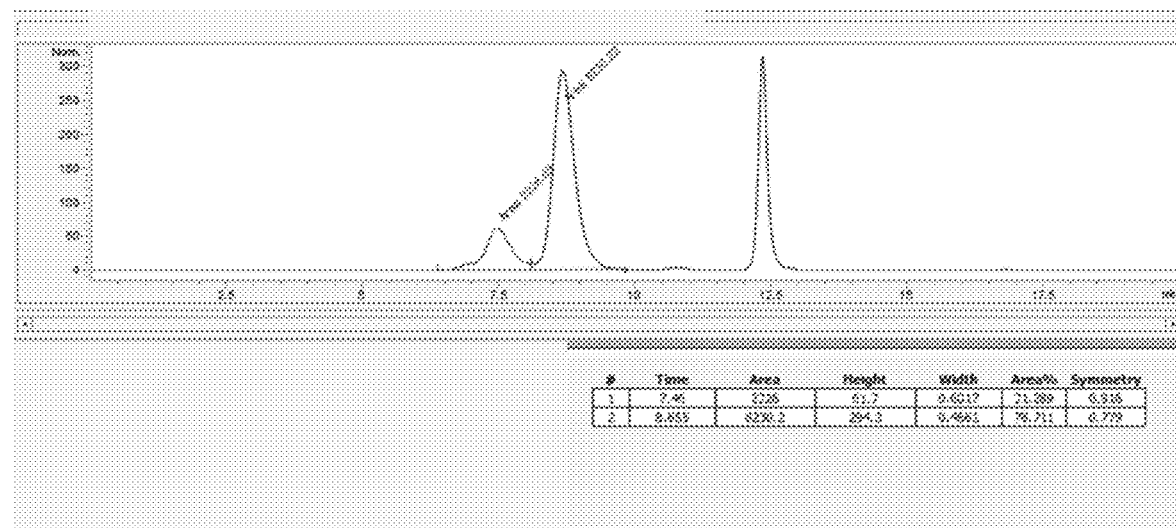
FIG. 45 shows an SEC trace of compound 42, conjugate 2943, which included two tag sites and yielded a DAR of 5.44, 21.3% HMW.
Figure 46:
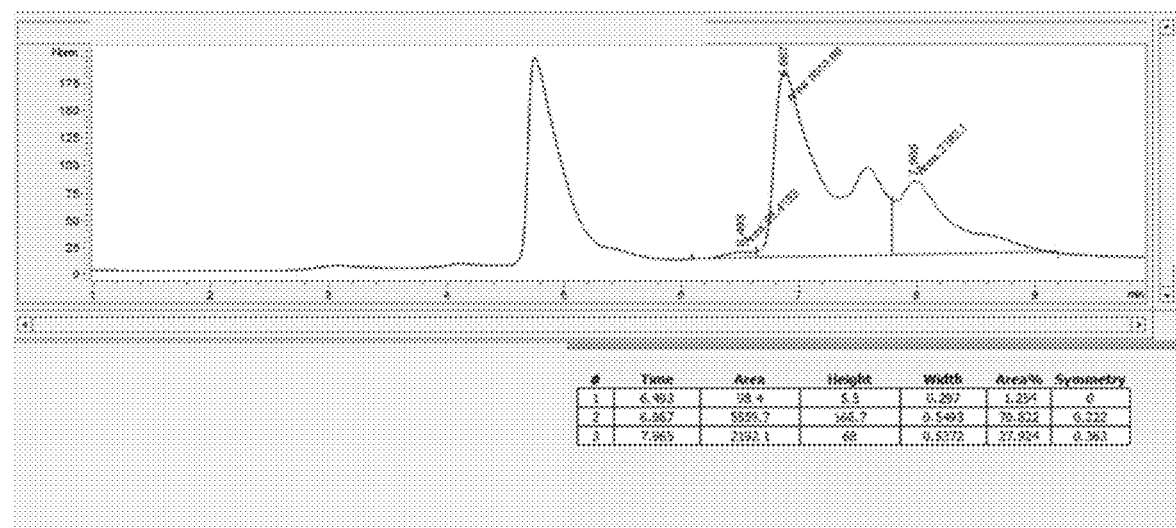
FIG. 46 shows a PLRP trace of compound 42, conjugate 2946, which included two tag sites and yielded a DAR of 5.07, 15.3% HMW.
Figure 47:
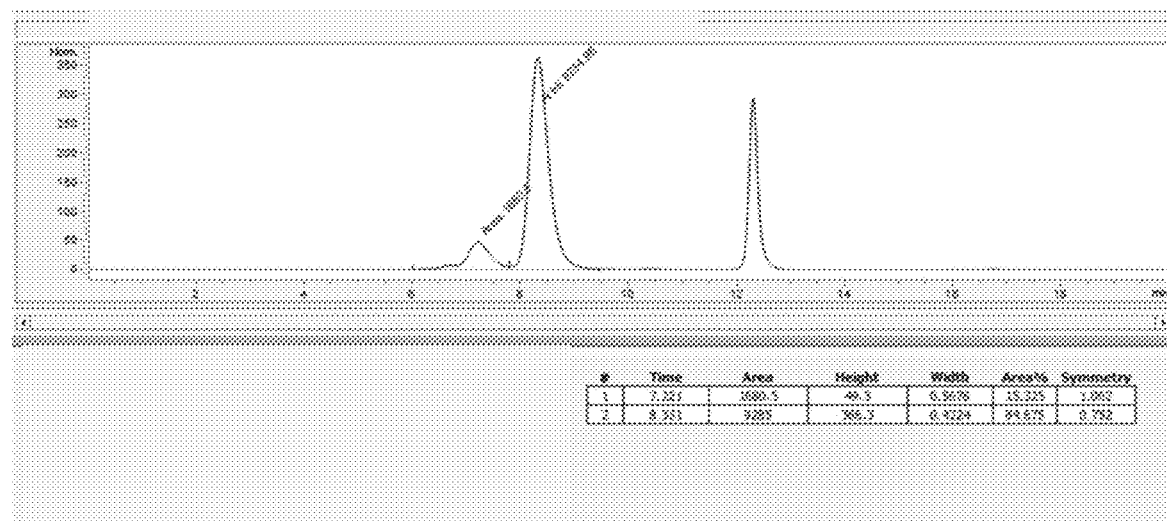
FIG. 47 shows an SEC trace of compound 42, conjugate 2946, which included two tag sites and yielded a DAR of 5.07, 15.3% HMW.
Figure 48:
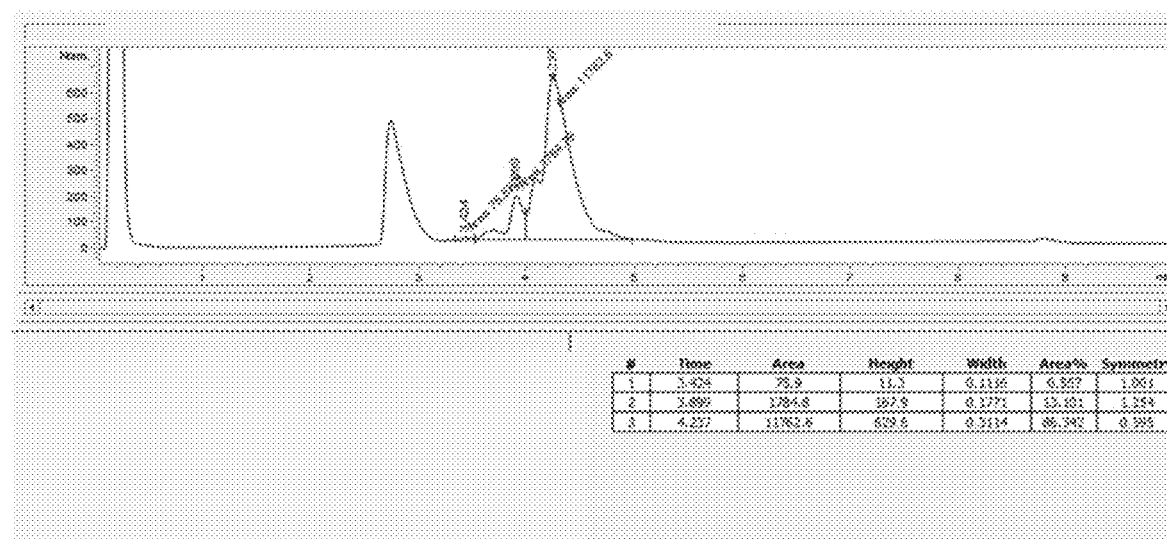
FIG. 48 shows a PLRP trace of compound 45, conjugate 2748, which included two tag sites and yielded a DAR of 3.51, 3.6% HMW.
Figure 49:
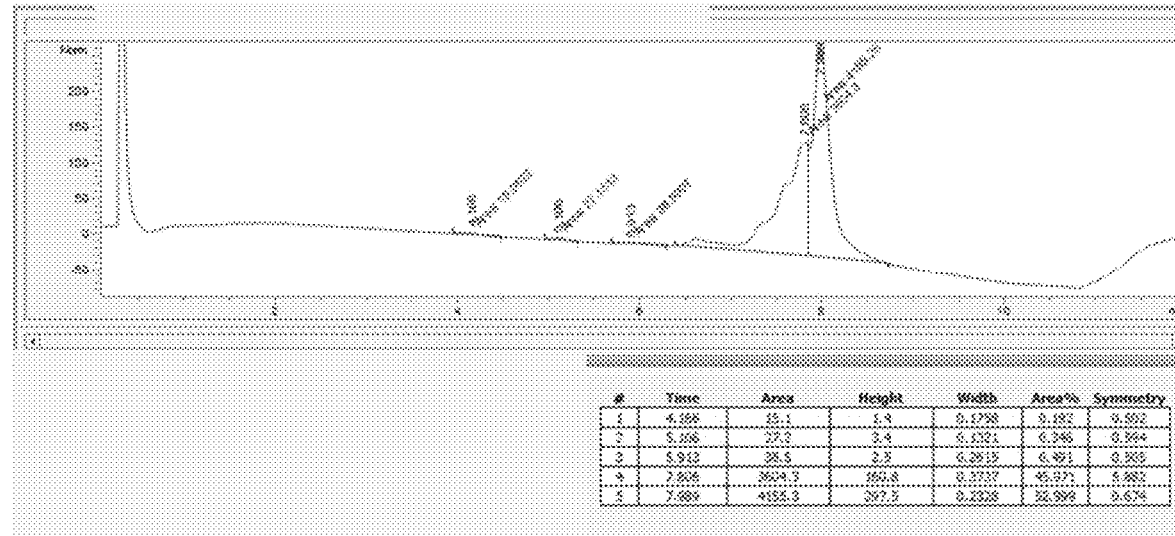
FIG. 49 shows an HIC trace of compound 45, conjugate 2748, which included two tag sites and yielded a DAR of 3.51, 3.6% HMW.
Figure 50:
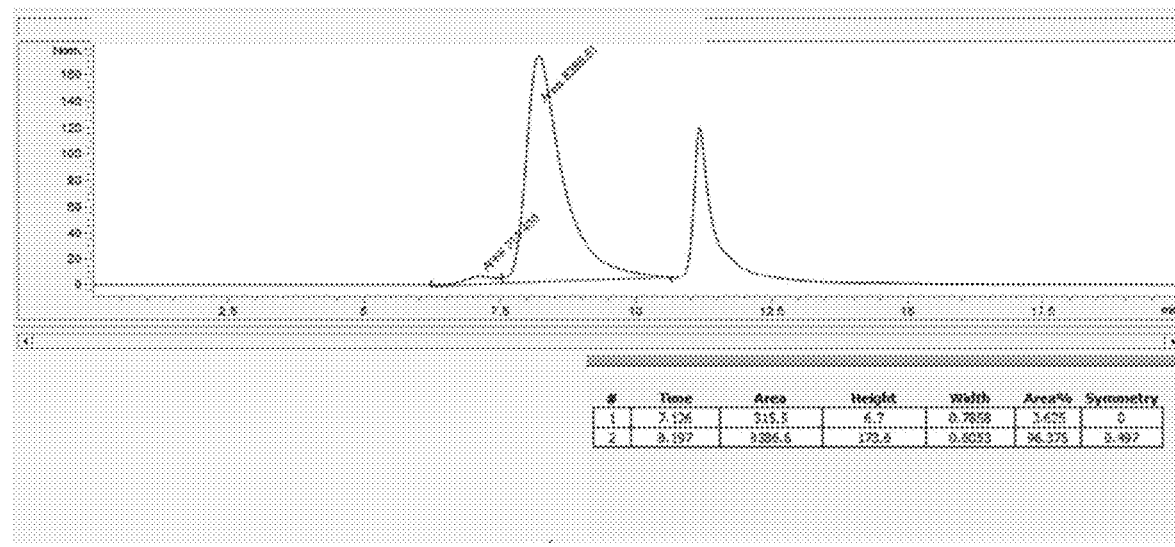
FIG. 50 shows an SEC trace of compound 45, conjugate 2748, which included two tag sites and yielded a DAR of 3.51, 3.6% HMW.
Figure 51:
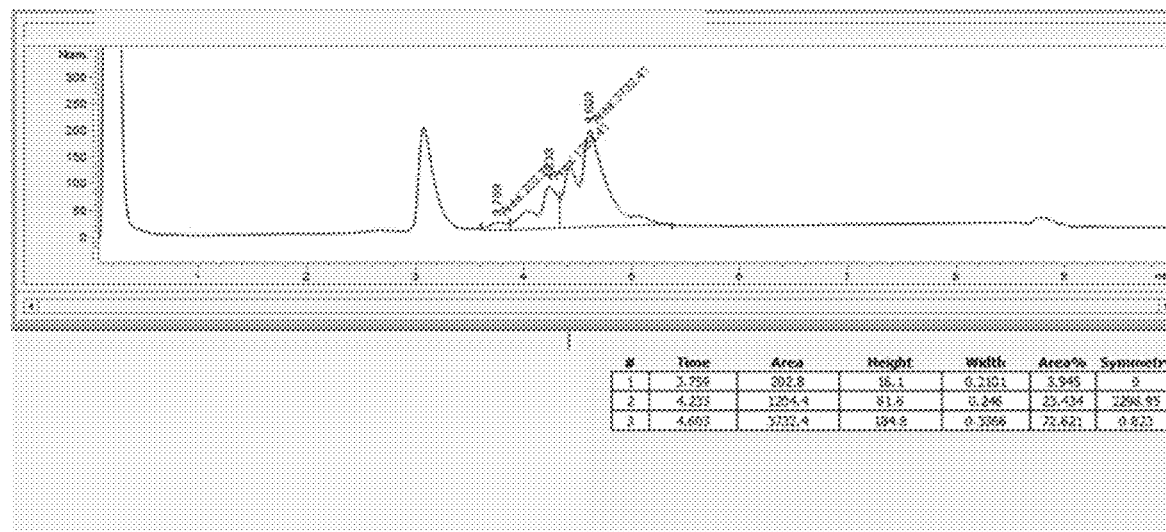
FIG. 51 shows a PLRP trace of compound 45, conjugate 2751, which included two tag sites and yielded a DAR of 2.98, 2.1% HMW.
Figure 52:
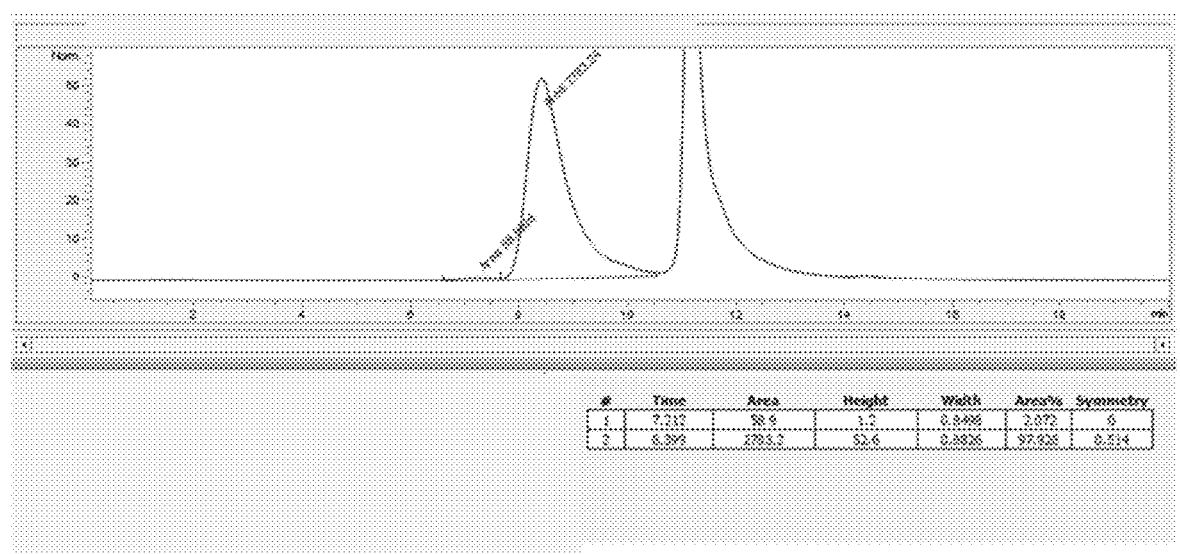
FIG. 52 shows an SEC trace of compound 45, conjugate 2751, which included two tag sites and yielded a DAR of 2.98, 2.1% HMW.
Figure 53:
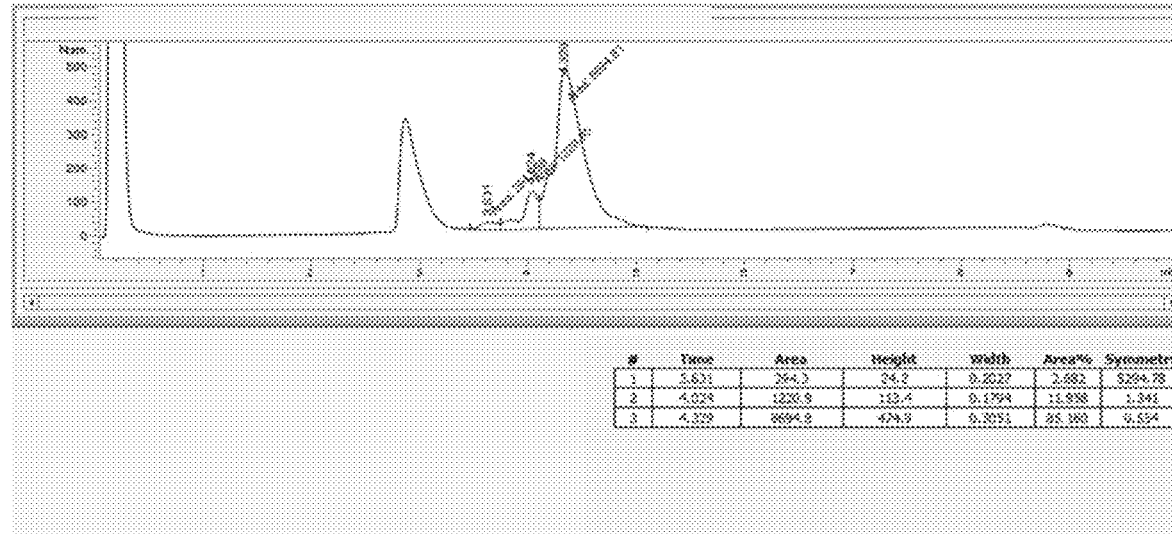
FIG. 53 shows a PLRP trace of compound 45, conjugate 2754, which included two tag sites and yielded a DAR of 3.5, 2.3% HMW.
Figure 54:
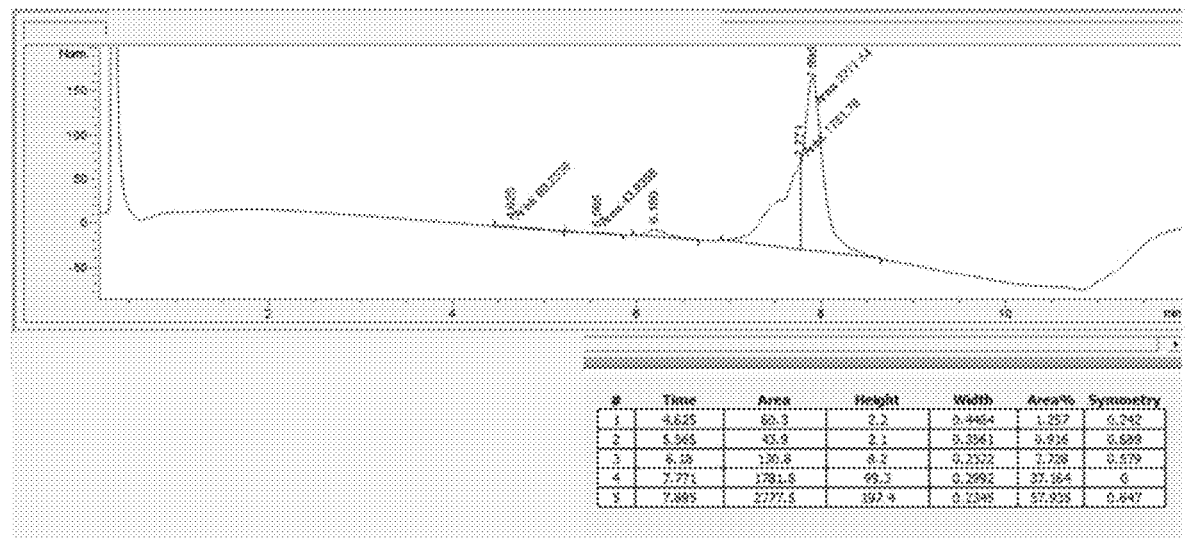
FIG. 54 shows an HIC trace of compound 45, conjugate 2754, which included two tag sites and yielded a DAR of 3.5, 2.3% HMW.
Figure 55:
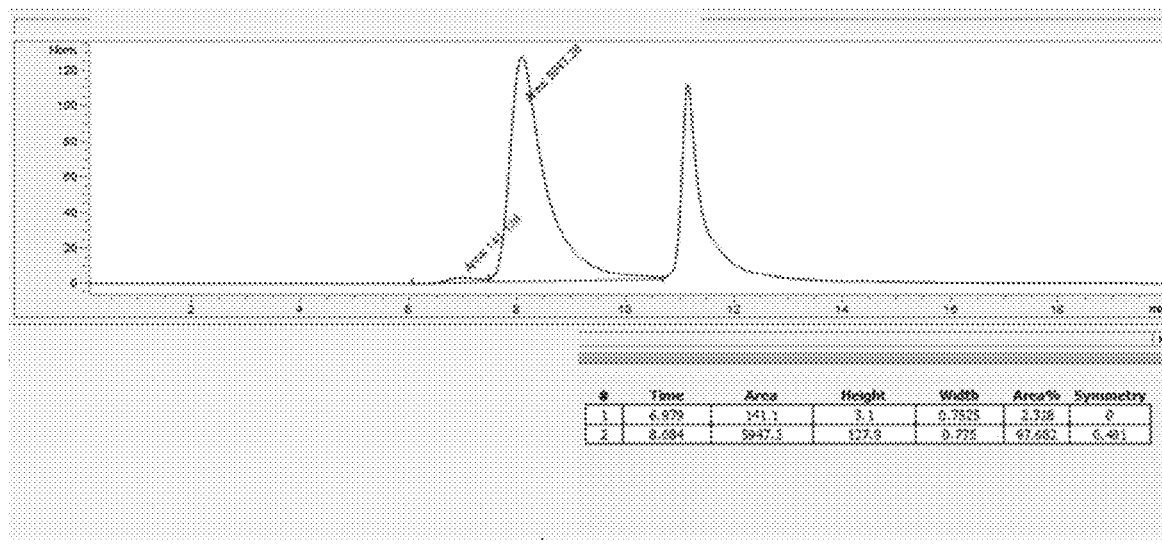
FIG. 55 shows an SEC trace of compound 45, conjugate 2754, which included two tag sites and yielded a DAR of 3.5, 2.3% HMW.
Figure 56:
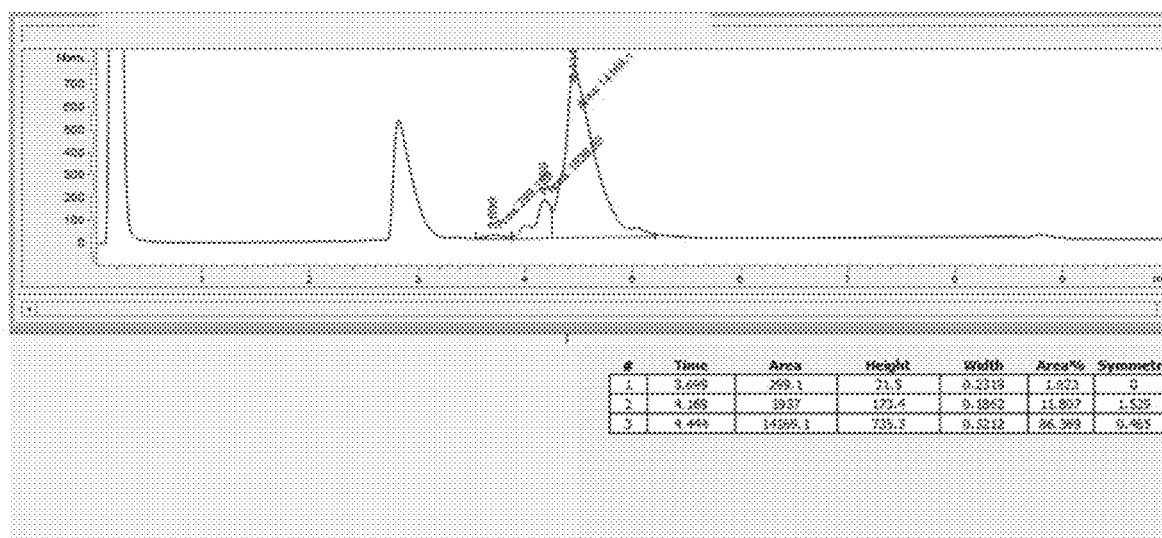
FIG. 56 shows a PLRP trace of compound 45, conjugate 2757, which included two tag sites and yielded a DAR of 3.69, 2.0% HMW.
Figure 57:
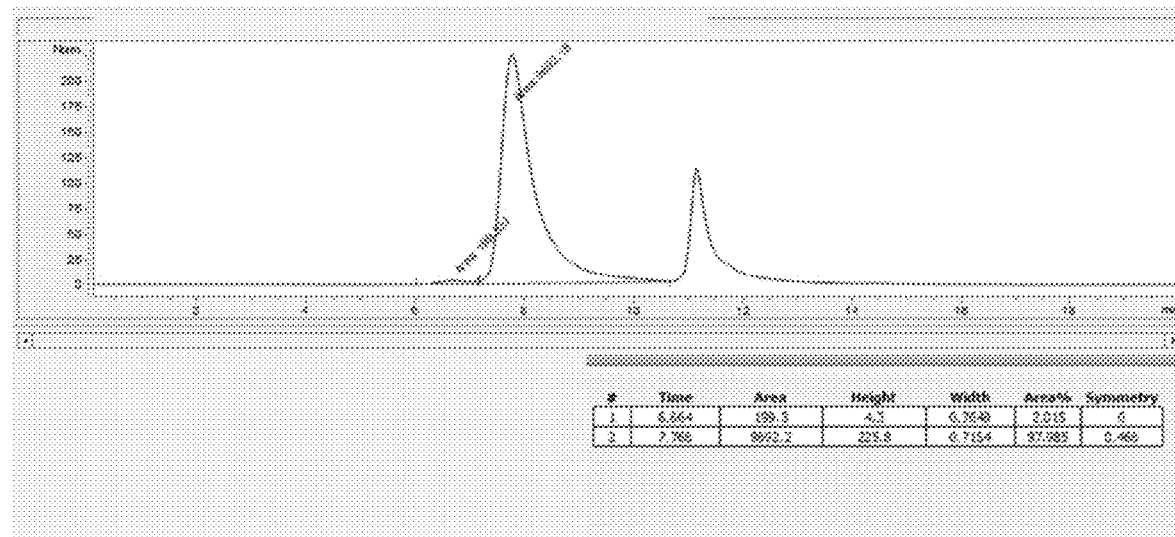
FIG. 57 shows an SEC trace of compound 45, conjugate 2757, which included two tag sites and yielded a DAR of 3.69, 2.0% HMW.
Figure 58:
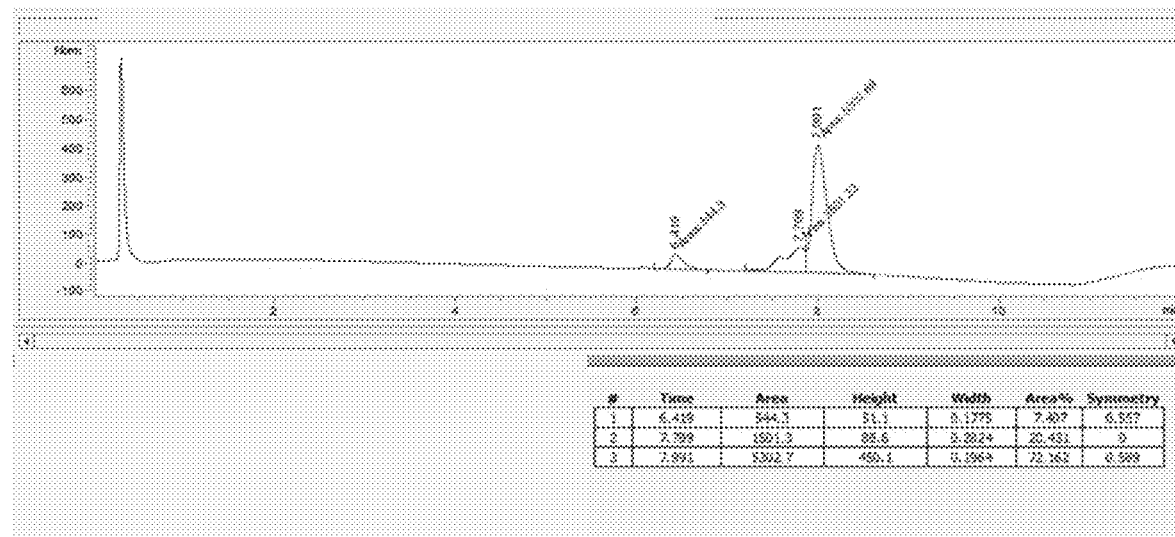
FIG. 58 shows an HIC trace of compound 45, conjugate 2760, which included one tag site and yielded a DAR of 1.65, 0.8% HMW.
Figure 59:
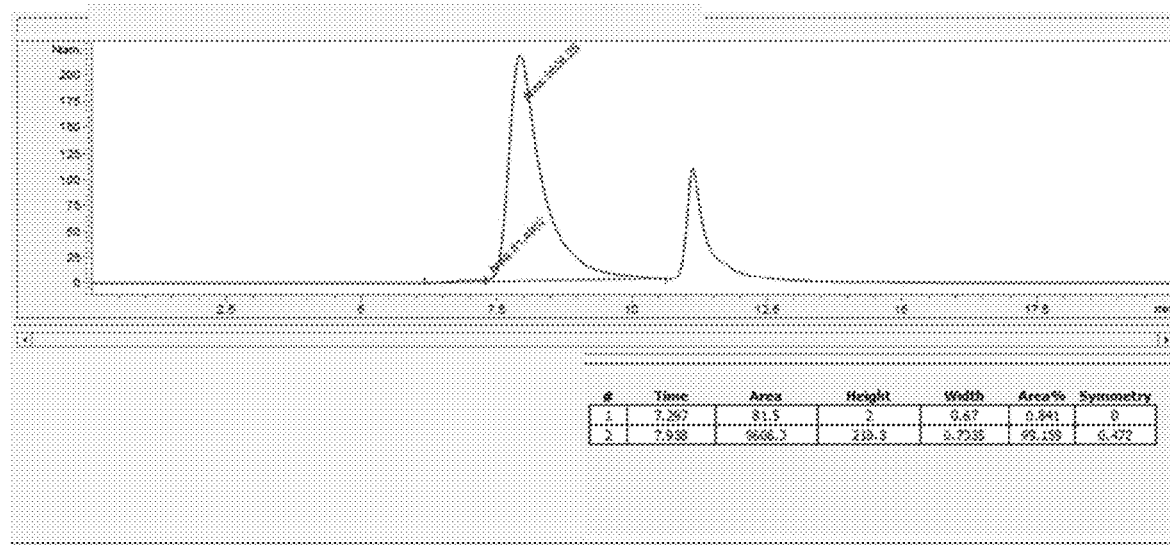
FIG. 59 shows an SEC trace of compound 45, conjugate 2760, which included one tag site and yielded a DAR of 1.65, 0.8% HMW.
Figure 60:
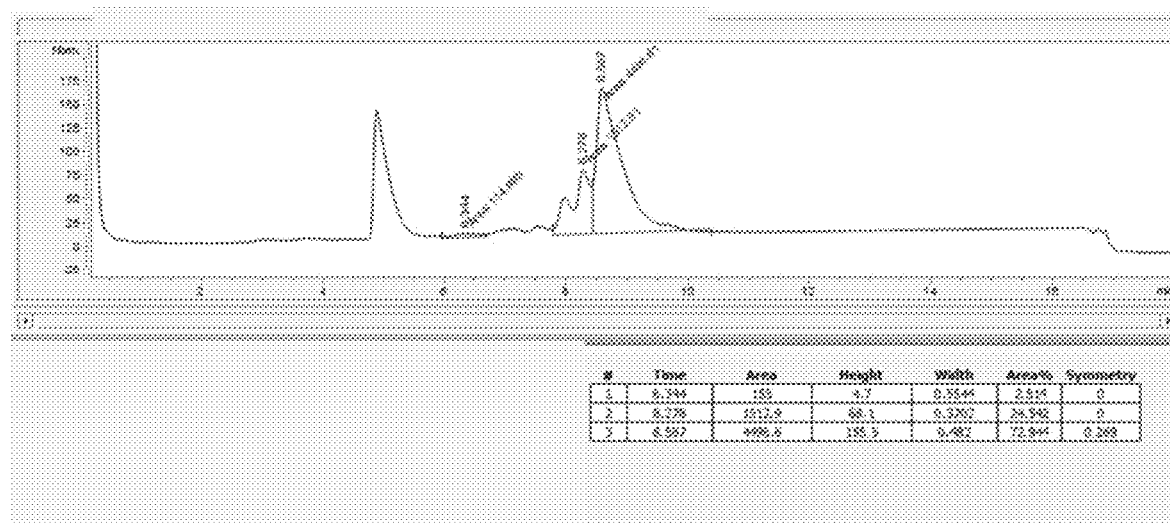
FIG. 60 shows a PLRP trace of compound 47, conjugate 3065, which included two tag sites and yielded a DAR of 6.82, 1.8% HMW.
Figure 61:
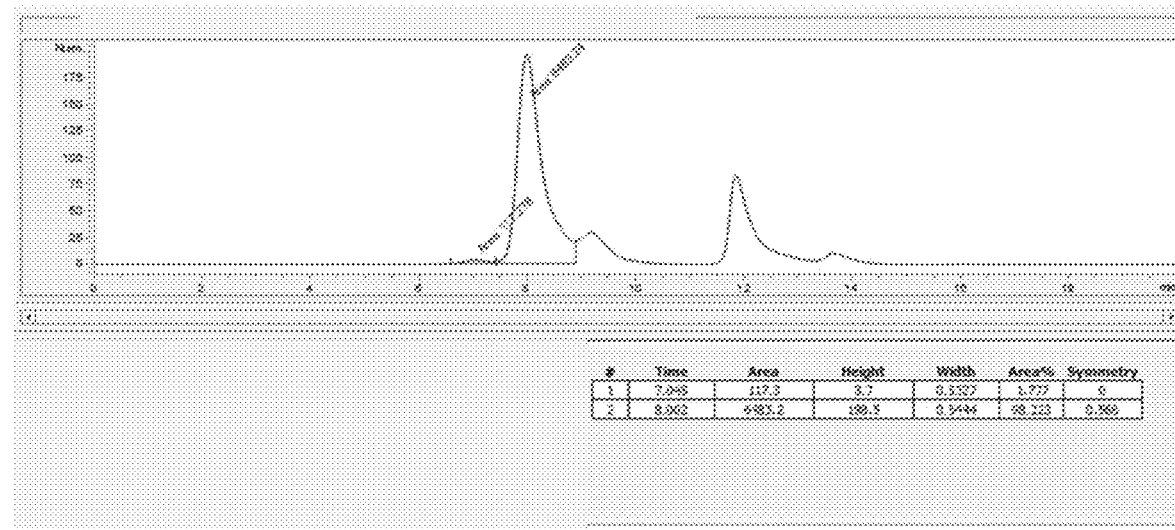
FIG. 61 shows an SEC trace of compound 47, conjugate 3065, which included two tag sites and yielded a DAR of 6.82, 1.8% HMW.
Figure 62:
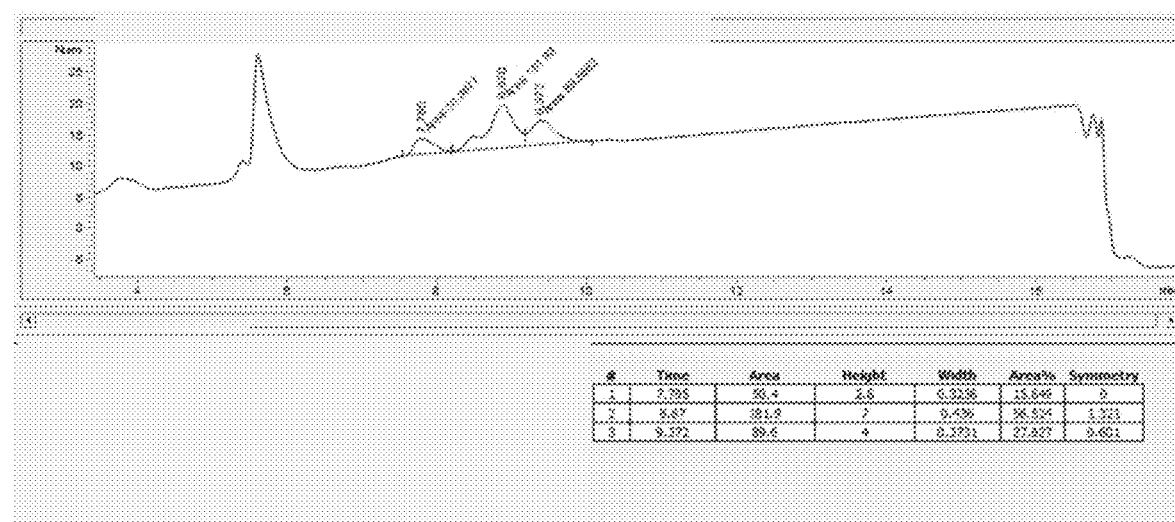
FIG. 62 shows a PLRP trace of compound 47, conjugate 3066, which included two tag sites and yielded a DAR of 4.48.
Figure 63:
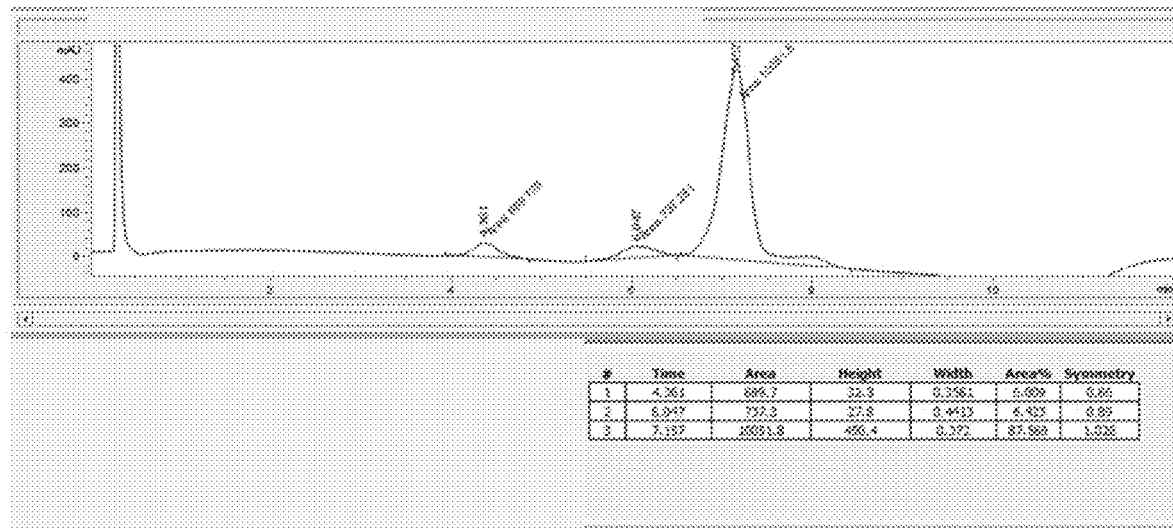
FIG. 63 shows an HIC trace of compound 47, conjugate 3067, which included one tag site and yielded a DAR of 3.63, 4.4% HMW.
Figure 64:
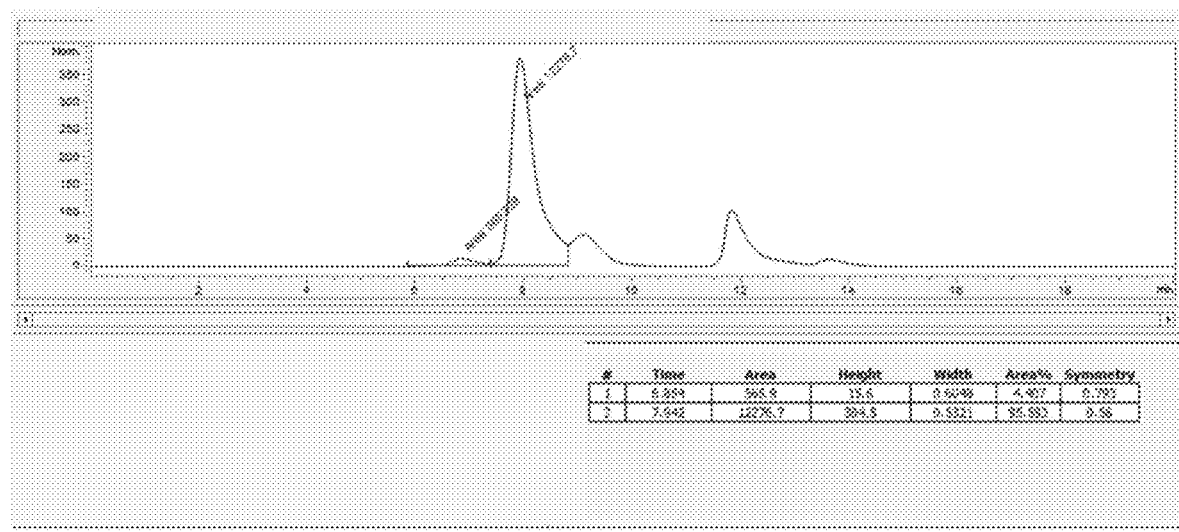
FIG. 64 shows an SEC trace of compound 47, conjugate 3067, which included one tag site and yielded a DAR of 3.63, 4.4% HMW.
Figure 65:
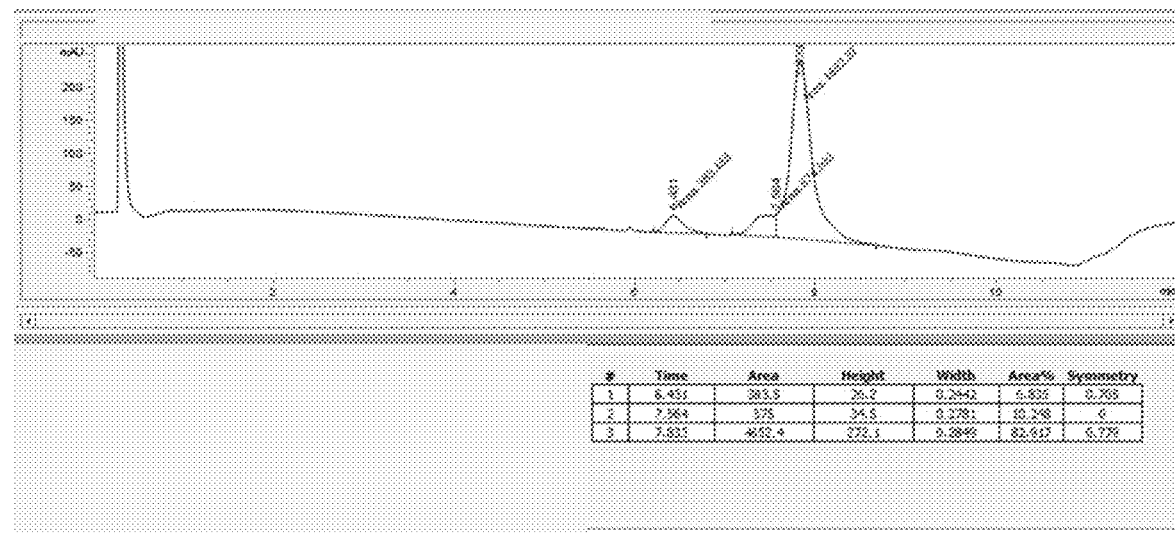
FIG. 65 shows an HIC trace of compound 47, conjugate 3068, which included one tag site and yielded a DAR of 3.52, 0.8% HMW.
Figure 66:
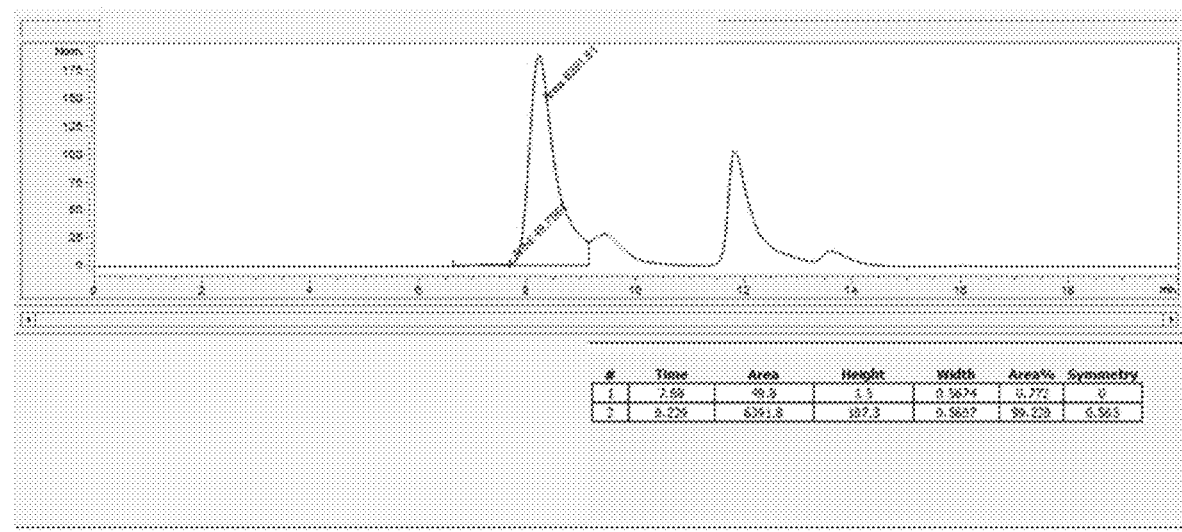
FIG. 66 shows an SEC trace of compound 47, conjugate 3068, which included one tag site and yielded a DAR of 3.52, 0.8% HMW.
Figure 67:
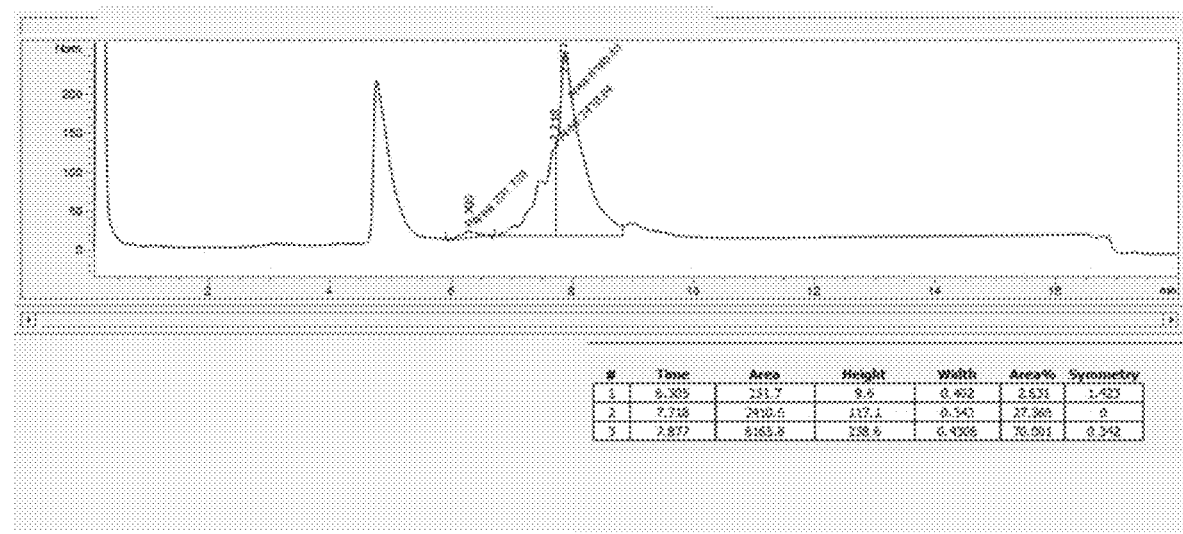
FIG. 67 shows a PLRP trace of compound 56, conjugate 3063, which included two tag sites and yielded a DAR of 3.35, 3.3% HMW.
Figure 68:
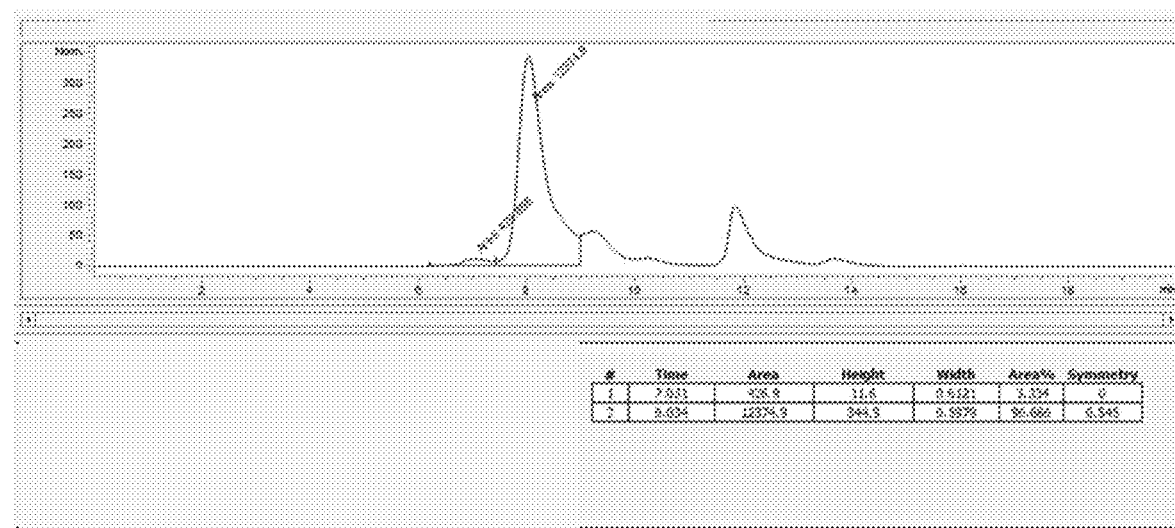
FIG. 68 shows an SEC trace of compound 56, conjugate 3063, which included two tag sites and yielded a DAR of 3.35, 3.3% HMW.
Figure 69:
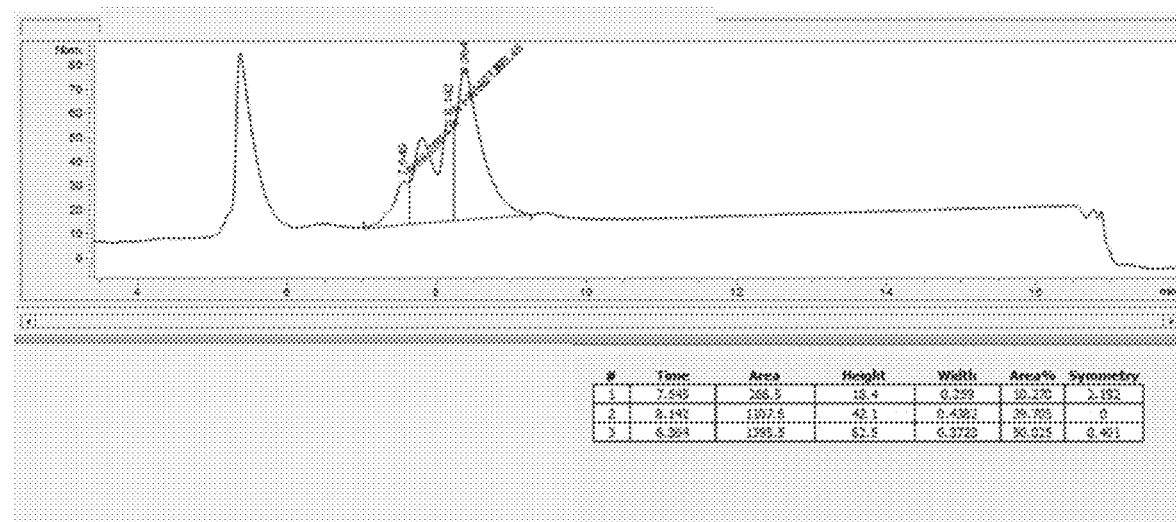
FIG. 69 shows a PLRP trace of compound 56, conjugate 3064, which included two tag sites and yielded a DAR of 2.8.
Figure 70:
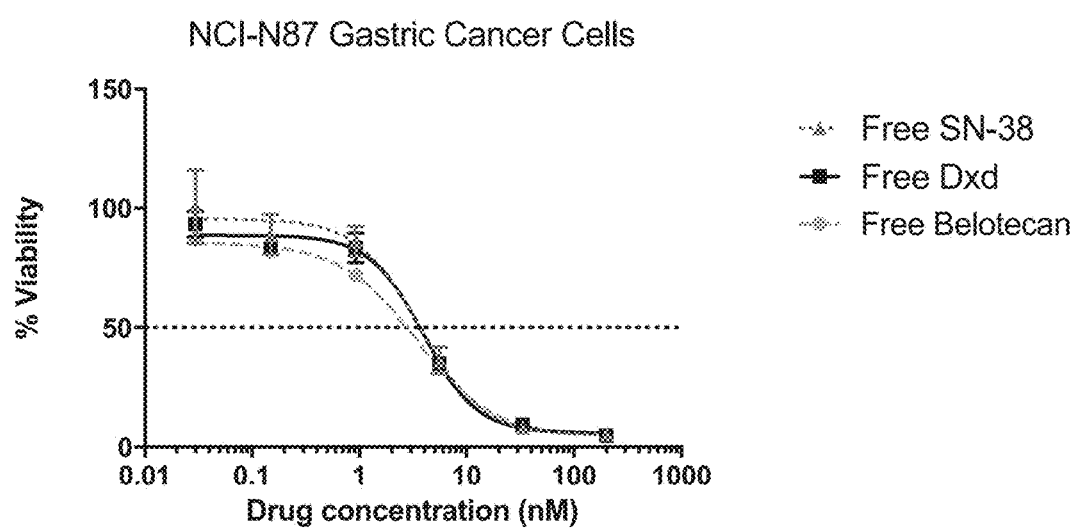
FIG. 70 shows a graph of in vitro cytotoxicity assays of free topoisomerase inhibitors in NCI-N87 gastric cancer cells.
Figure 71:
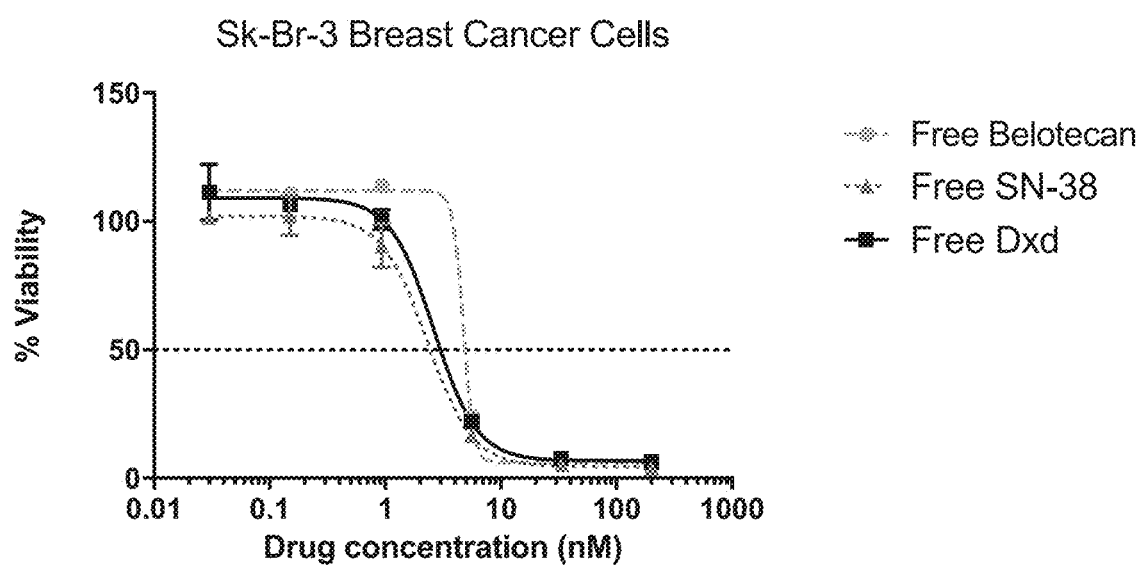
FIG. 71 shows a graph of in vitro cytotoxicity assays of free topoisomerase inhibitors in Sk-Br-3 breast cancer cells.
Figure 72:
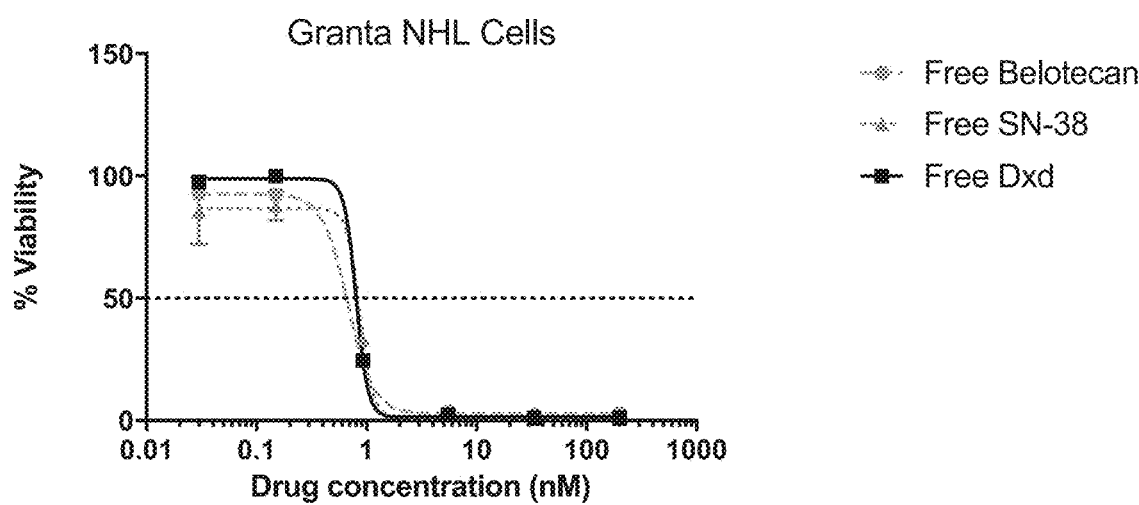
FIG. 72 shows a graph of in vitro cytotoxicity assays of free topoisomerase inhibitors in Granta NHL cells.
Figure 73:
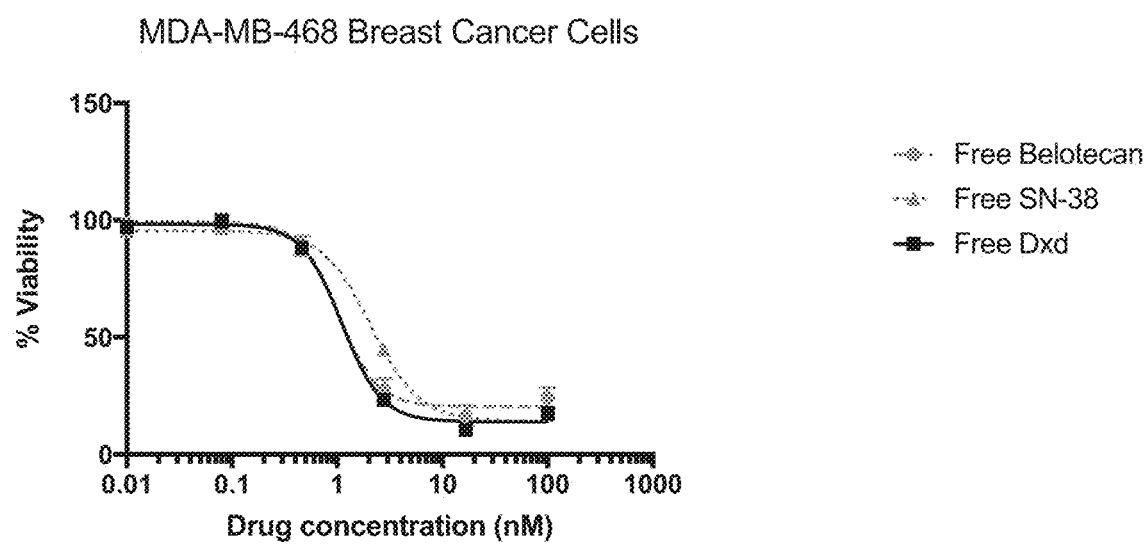
FIG. 73 shows a graph of in vitro cytotoxicity assays of free topoisomerase inhibitors in MDA-MB-468 breast cancer cells.
Figure 74:
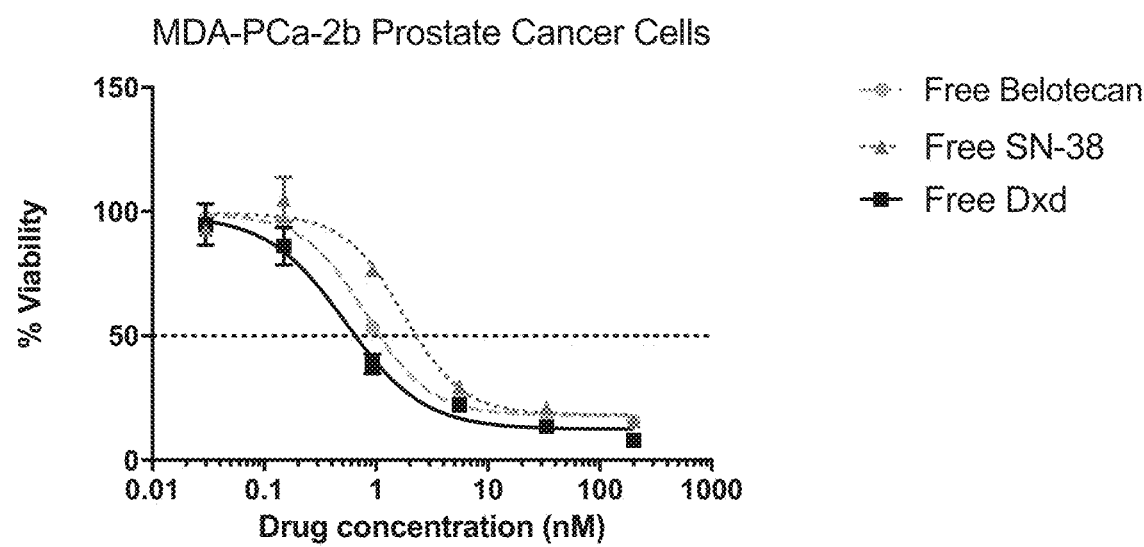
FIG. 74 shows a graph of in vitro cytotoxicity assays of free topoisomerase inhibitors in MDA-PCa-2b prostate cancer cells.
Figure 75:
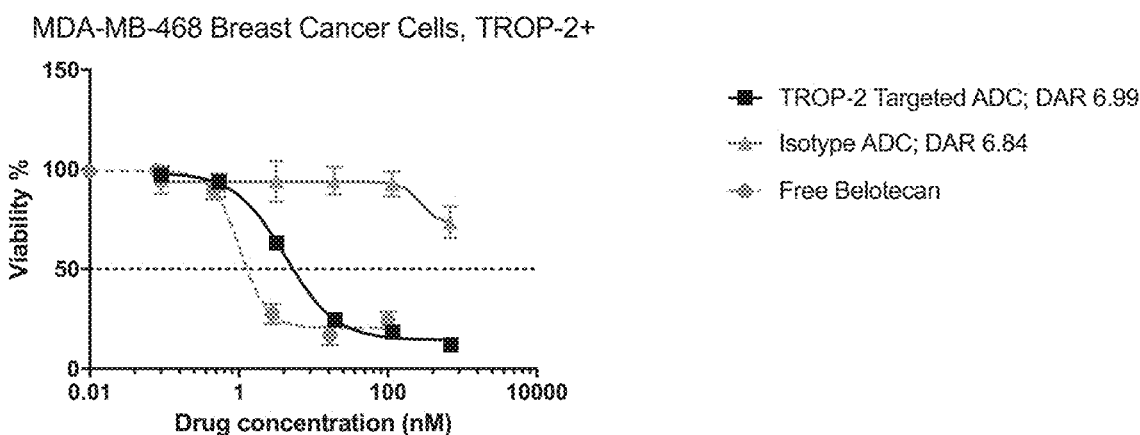
FIG. 75 shows a graph of in vitro cytotoxicity assays in MDA-MB-468 breast cancer cells of a TROP-2 targeted ADC made using Compound 61, according to embodiments of the present disclosure.
Figure 76:
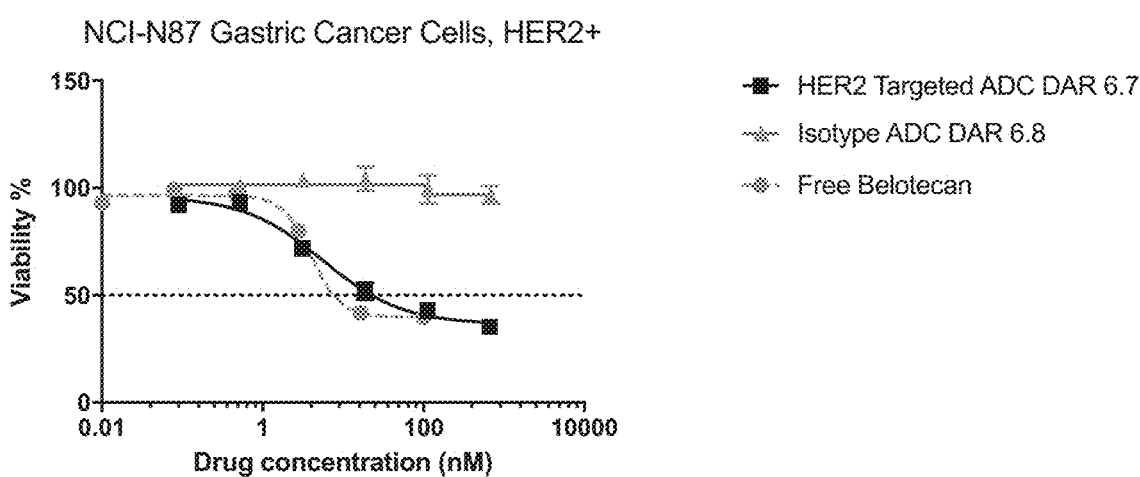
FIG. 76 shows a graph of in vitro cytotoxicity assays in NCI-N87 gastric cancer cells of a HER2 targeted ADC made using Compound 61, according to embodiments of the present disclosure.
Figure 77:
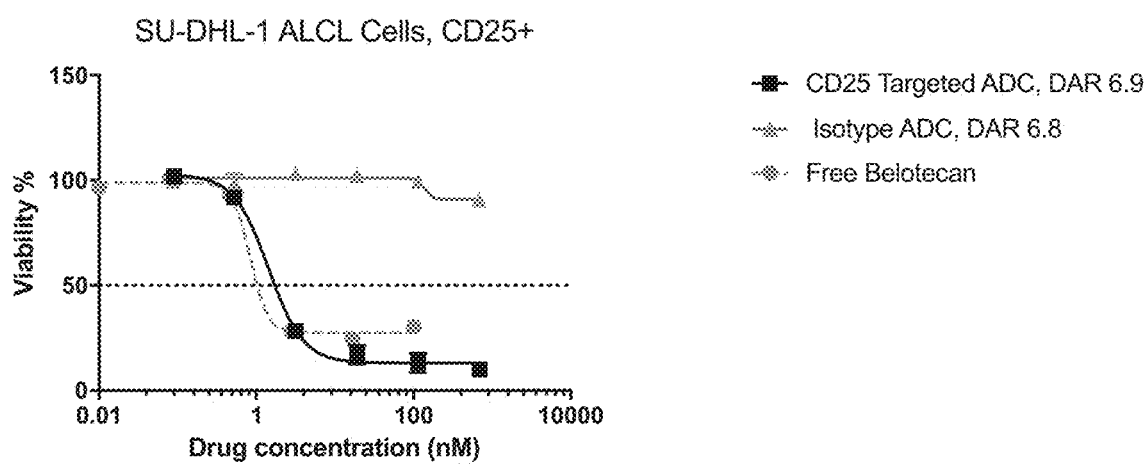
FIG. 77 shows a graph of in vitro cytotoxicity assays in SU-DHL-1 ALCL cells of a CD25 targeted ADC made using Compound 61, according to embodiments of the present disclosure.
Figure 78:
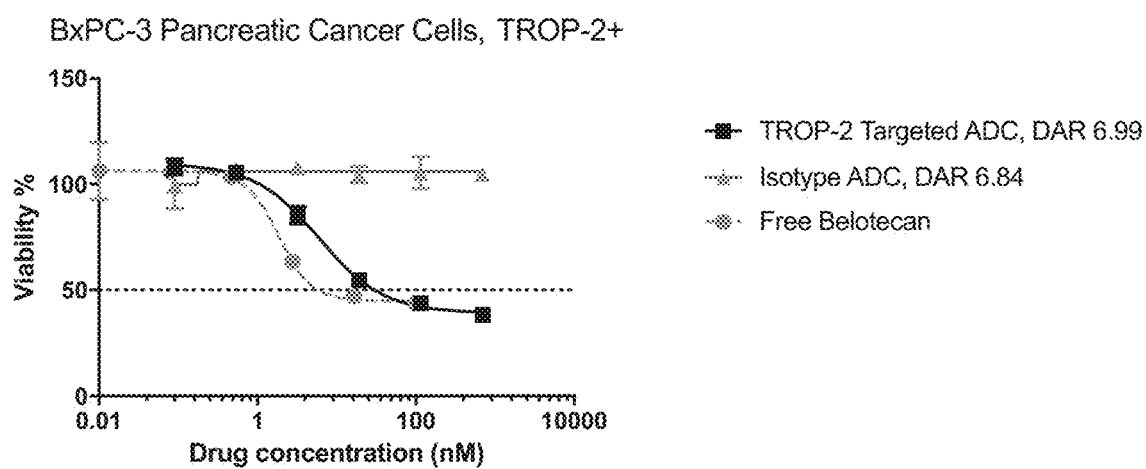
FIG. 78 shows a graph of in vitro cytotoxicity assays in BxPC-3 pancreatic cancer cells of a TROP-2 targeted ADC made using Compound 61, according to embodiments of the present disclosure.
Figure 79:
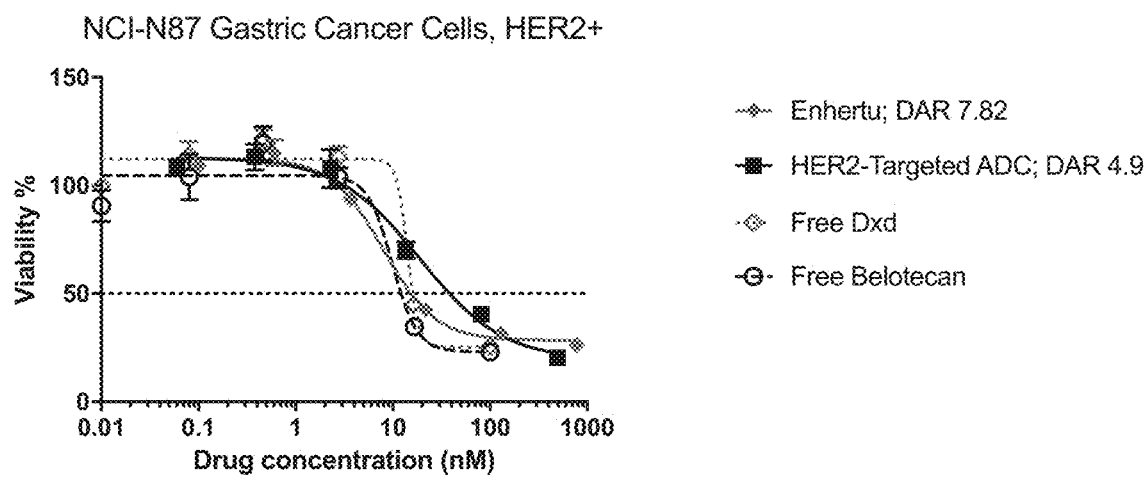
FIG. 79 shows a graph of in vitro cytotoxicity assays in NCI-N87 gastric cancer cells of a HER2 targeted ADC made using Compound 65, according to embodiments of the present disclosure.
Figure 80:
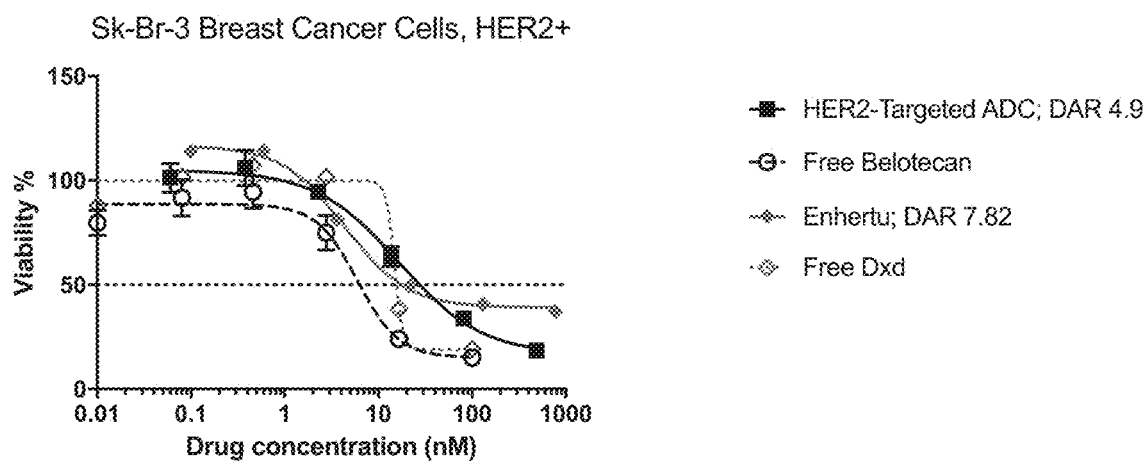
FIG. 80 shows a graph of in vitro cytotoxicity assays in Sk-Br-3 breast cancer cells of a HER2 targeted ADC made using Compound 65, according to embodiments of the present disclosure.

All synthesized constructs containing camptothecine were conjugated to a set of aldehyde-tagged monoclonal antibodies using HIPS ligation (FIG. 2). Analytical characterization of the resulting conjugates is shown in FIGS. 3-69 and FIGS. 106-144.

Bioconjugation, Purification and HPLC Analytics

Aldehyde-tagged antibodies (15 mg/mL) were conjugated to linker-payloads (8 mol. equivalents drug:antibody) for 72 h at 37° C. in 20 mM sodium citrate, 50 mM NaCl pH 5.5 containing 0.85% DMA. In some cases, to improve linker-payload solubility, additional DMA was added up to a maximum of 10% vol/vol. After conjugation, free drug was removed by using multiple rounds of dilution into 20 mM sodium citrate, 50 mM NaCl pH 5.5 and concentration using Amicon 0.5 mL 30 kD MWCO centrifugal filters (Millipore Sigma #UFC5030BK). To determine the DAR of the final product, ADCs were examined by analytical HIC or PLRP. The HIC column (Tosoh #14947) was run with mobile phase A: 1.5 M ammonium sulfate, 25 mM sodium phosphate pH 7.0, and mobile phase B: 25% isopropanol, 18.75 mM sodium phosphate pH 7.0. The PLRP column (Agilent #PL1912-1802) was run with mobile phase A: 0.1% trifluoroacetic acid in H2O, and mobile phase B: 0.1% trifluoroacetic acid in CH3CN with the column heated to 80° C. To determine aggregation, samples were analyzed using analytical size exclusion chromatography (SEC; Tosoh #08541) with a mobile phase of 300 mM NaCl, 25 mM sodium phosphate pH 6.8, 5% isopropanol.

Results of conjugation of Compounds 47, 61 and 65 to 10 different antibodies are shown in Table 1 below. Table 1 shows drug-to-antibody (DAR) ratios and % high-molecular weight species (% HMW).

TABLE 1

| Antibody Target | DAR* Compound 47 | % HMW** Compound 47 | DAR Compound 65 | % HMW Compound 65 | DAR Compound 61 | % HMW Compound 61 |
|---|---|---|---|---|---|---|
| Target 1 | 6.82 | 1.8 | n.d. | n.d. | n.d. | n.d. |
| Target 2 | 6.16 | 6.5 | 6.78 | 4.1 | 6.84 | 2.3 |
| Target 3 | 4.31 | 4.3 | 6.33 | 6.1 | 6.88 | 2.2 |
| Target 4 | 6.97 | 0.6 | n.d. | n.d. | n.d. | n.d. |
| Target 5 | 5.45 | 0.8 | 6.88 | 3.3 | 6.93 | 3.2 |
| Target 6 | 7.07 | 2.0 | n.d. | n.d. | n.d. | n.d. |
| Target 7 | 6.88 | 1.6 | n.d. | n.d. | n.d. | n.d. |
| Target 8 | 6.1 | 3.4 | 6.55 | 3.5 | 7.38 | 1.4 |
| Target 9 | 6.84 | 1.5 | 6.32 | 2.2 | 6.99 | 3.0 |
| Target 10 | 5.49 | 2.7 | 6.33 | 6.2 | 7.06 | 2.0 |

*DAR, drug-to-antibody ratio
**HMW, high-molecular weight species

Example 3

In Vitro Cytotoxicity Assays

Cell lines were plated in 96-well plates (Costar 3610) at a density of 5×104 cells/well in 100 µL of growth media. The next day, cells were treated with 20 μL of test compounds serially-diluted in media. After incubation at 37° C. with 5% $CO_2$ for 5 days, viability was measured using the Promega CellTiter Glo® reagent according to the manufacturer's recommendations. GI50 curves were calculated in GraphPad Prism normalized to the payload concentration. Graphs of the cytotoxicity assays (% viability vs. drug concentration (nM)) are shown in FIGS. 70-80 and FIGS. 89-105.

Example 4

Rat Pharmacokinetic (PK) Study

Male Sprague-Dawley rats (3 per group) were dosed intravenously with a single 0.9 mg/kg bolus of test article. K2EDTA-stabilized plasma was collected at 1 h, 8 h and 24 h, and 2, 4, 6, 8, 10, and 14 days post-dose.

PK Sample Analysis

Figure 81:
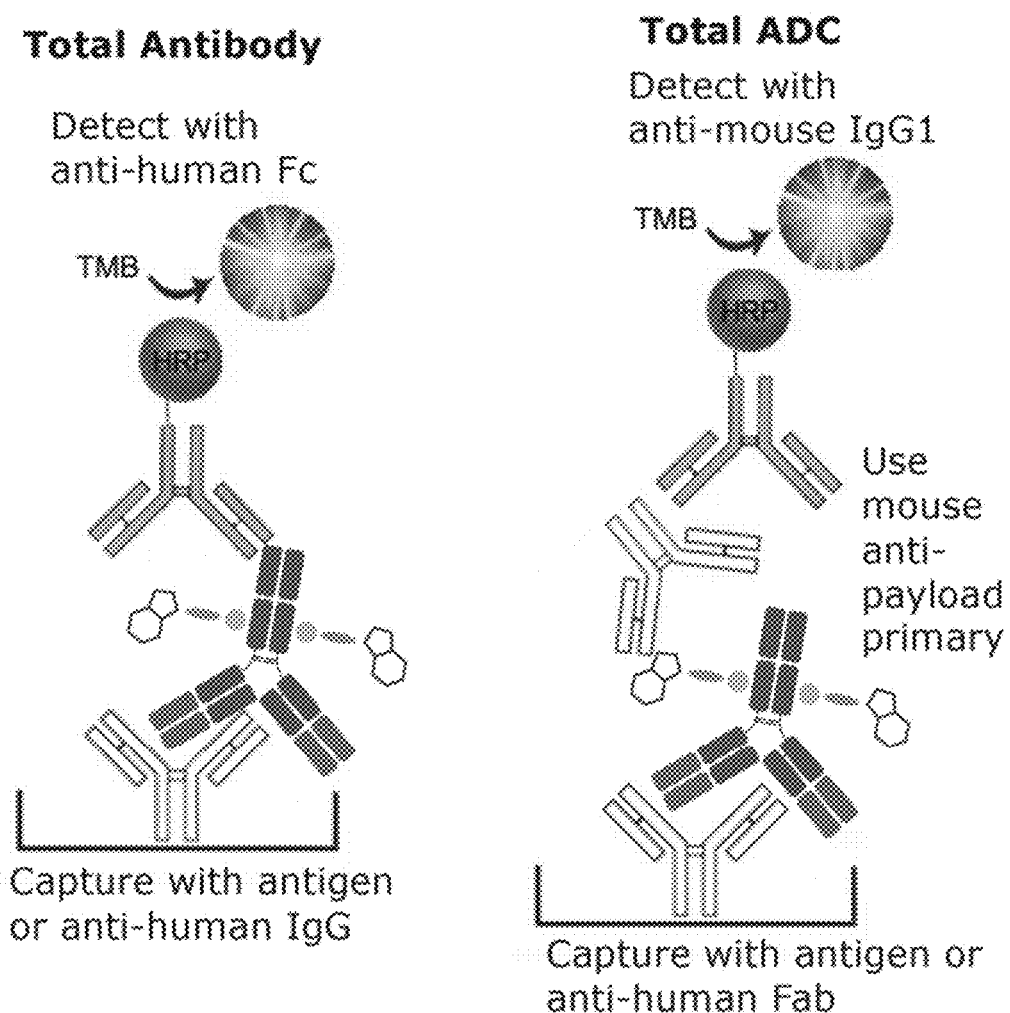
FIG. 81 shows a schematic drawing of ELISA assays used to determine total antibody and ADC concentrations for pharmacokinetic (PK) sample analysis.

Total antibody and total ADC concentrations were quantified by ELISA as diagrammed in FIG. 81. For total antibody, conjugates were captured with an anti-human IgG-specific antibody and detected with an HRP-conjugated anti-human Fc-specific antibody. For total ADC, conjugates were captured with an anti-human Fab-specific antibody and detected with a mouse anti-payload primary antibody, followed by an HRP-conjugated anti-mouse IgG-subclass 1-specific secondary antibody. Bound secondary antibody was detected using Ultra TMB One-Step ELISA substrate (Thermo Fisher). After quenching the reaction with sulfuric acid, signals were read by taking the absorbance at 450 nm on a Molecular Devices Spectra Max M5 plate reader equipped with SoftMax Pro software. Data were analyzed using GraphPad Prism and Microsoft Excel software.

Figure 82:
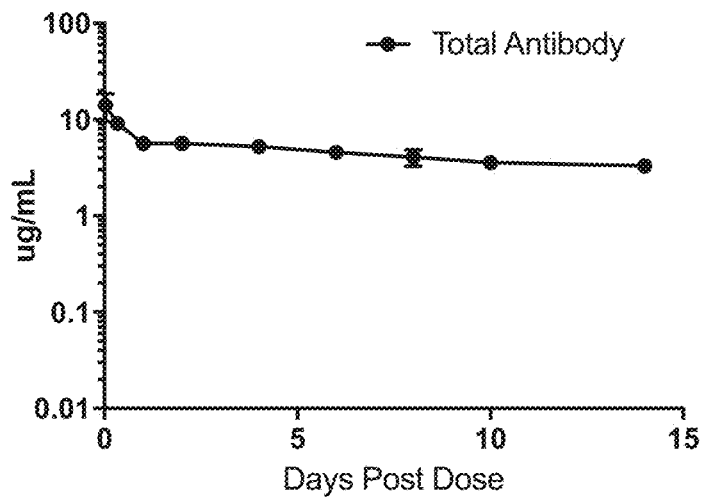
FIG. 82 shows a graph of concentration (μg/mL) vs. days post dose following a 0.9 mg/kg dose of trastuzumab antibody.
Figure 83:
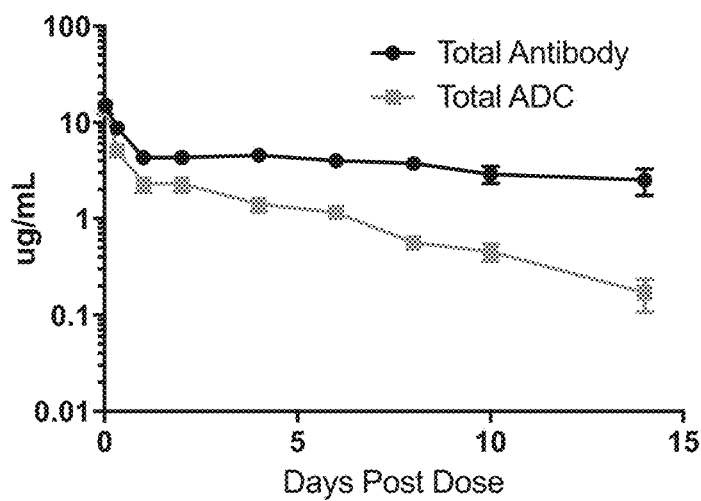
FIG. 83 shows a graph of concentration (μg/mL) vs. days post dose following a 0.9 mg/kg dose of a conventional HER2 topoisomerase inhibitor conjugated ADC bearing a protease cleavable linker.
Figure 84:
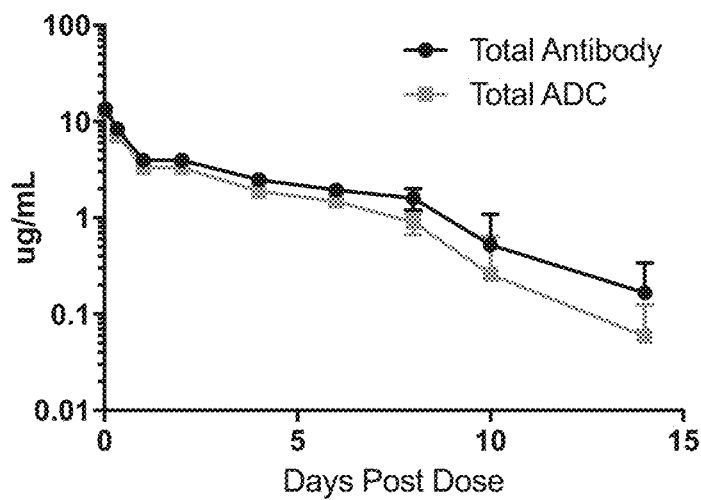
FIG. 84 shows a graph of concentration (μg/mL) vs. days post dose following a 0.9 mg/kg dose of CH1-3/CT-tagged trastuzumab conjugated to construct 61, according to embodiments of the present disclosure.
Figure 85:
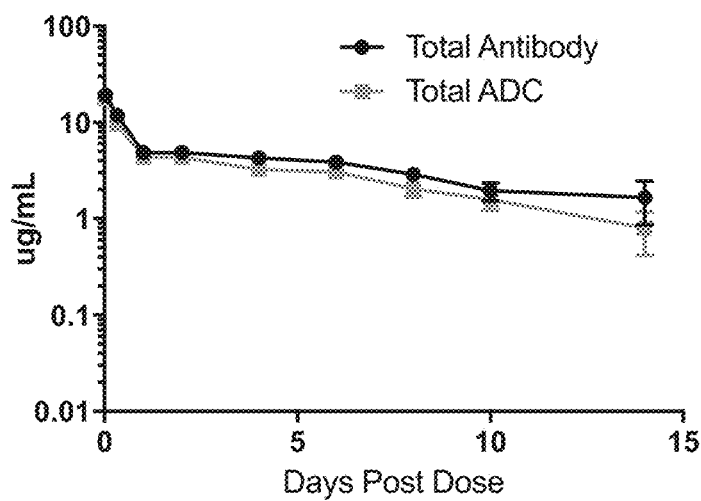
FIG. 85 shows a graph of concentration (μg/mL) vs. days post dose following a 0.9 mg/kg dose of CH1-3/CT-tagged trastuzumab conjugated to construct 65, according to embodiments of the present disclosure.

The results of the PK sample analysis are shown in FIGS. 82-85. FIG. 82 shows a graph of concentration (μg/mL) vs. days post dose following a 0.9 mg/kg dose of trastuzumab antibody. FIG. 83 shows a graph of concentration (μg/mL) vs. days post dose following a 0.9 mg/kg dose of a conventional HER2 topoisomerase inhibitor conjugated ADC bearing a protease cleavable linker. FIG. 84 shows a graph of concentration (μg/mL) vs. days post dose following a 0.9 mg/kg dose of CH1-3/CT-tagged trastuzumab conjugated to construct 61. FIG. 85 shows a graph of concentration (μg/mL) vs. days post dose following a 0.9 mg/kg dose of CH1-3/CT-tagged trastuzumab conjugated to construct 65.

Example 5

Xenograft Studies

Methods:

NCI-H292 Xenograft: Female SCID Beige mice (7 or 8/group) were inoculated subcutaneously with 5 million NCI-H292 cells in PBS. Treatment began when the tumors reached an average of 121 mm³ (Day 1). For Study 1, animals were dosed intravenously with vehicle alone, Trodelvy, DS-1062, or with conjugate 3485, a TROP-2 targeted ADC including two tag sites conjugated to compound 65 (with a DAR of 6.85). ADCs were dosed at either 10 mg/kg on Days 0, 7, and 21 (Trodelvy) or at 6 mg/kg on Days 0 and 21 (DS-1062 and conjugate 3485). For Study 2, animals were dosed intravenously with vehicle alone, DS-1062, or with conjugates 3485, 3789, or 3790, TROP-2 targeted ADCs including two tag sites conjugates to compounds 65, 127, or 131, respectively. The animals were monitored twice weekly for body weight and tumor size. Animals were euthanized when tumors reached 2000 mm³ or body weight loss exceeded 15%.

Figure 86:
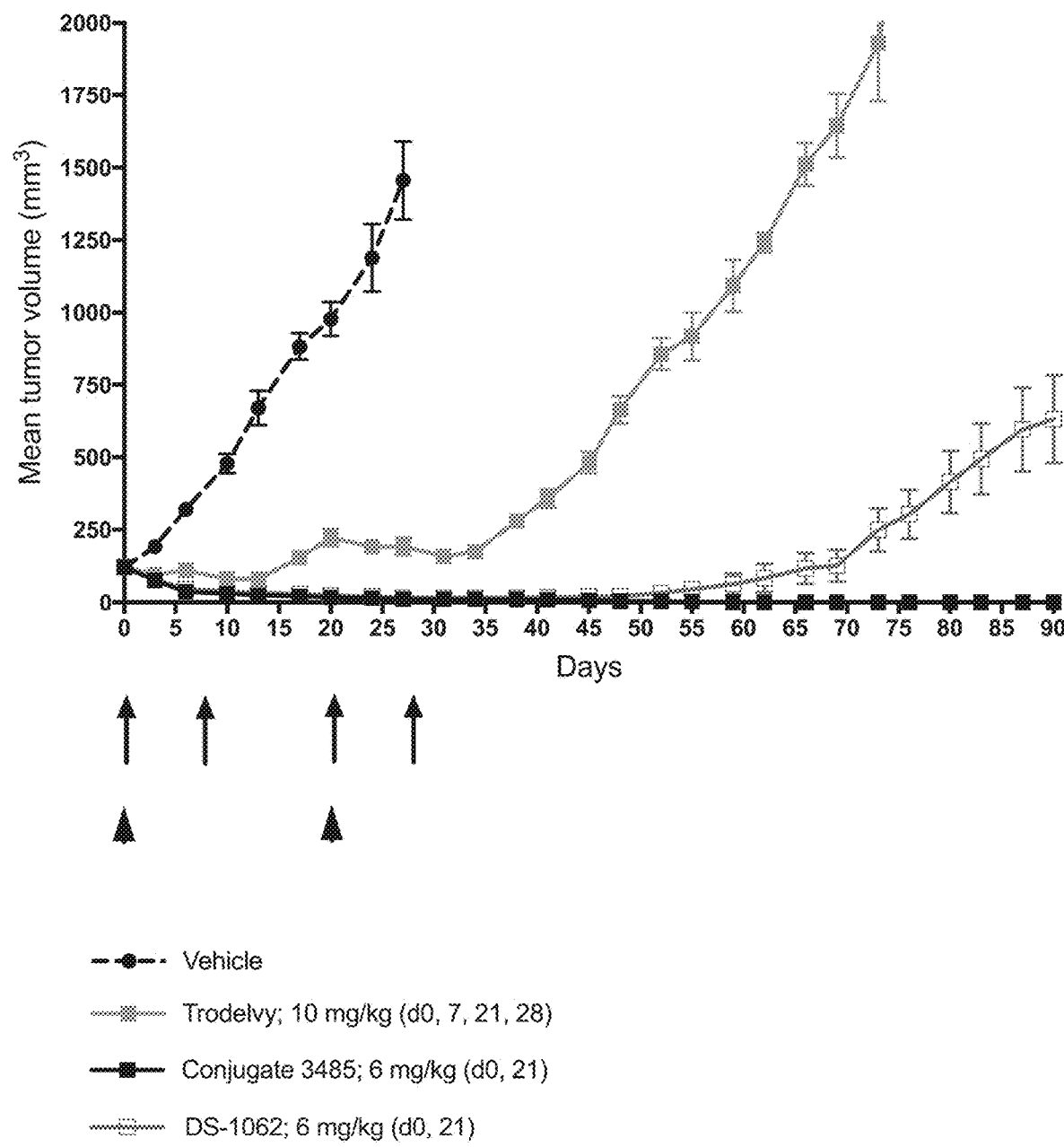
FIG. 86 shows a graph of mean tumor volume (mm$^3$) vs. days, which indicates in vivo efficacy against an NCI-H292 xenograft of TROP-2 targeted ADCs carrying topoisomerase inhibitor payloads. n=8 mice/group; dosing is indicated by arrows.

Results:

Results for Study 1 are shown in FIG. 86, which shows a graph of mean tumor volume (mm³) vs. days and indicates in vivo efficacy against the NCI-H292 xenograft of TROP-2 targeted ADCs carrying topoisomerase inhibitor payloads. n=8 mice/group; dosing is indicated by arrows.

Figure 87:
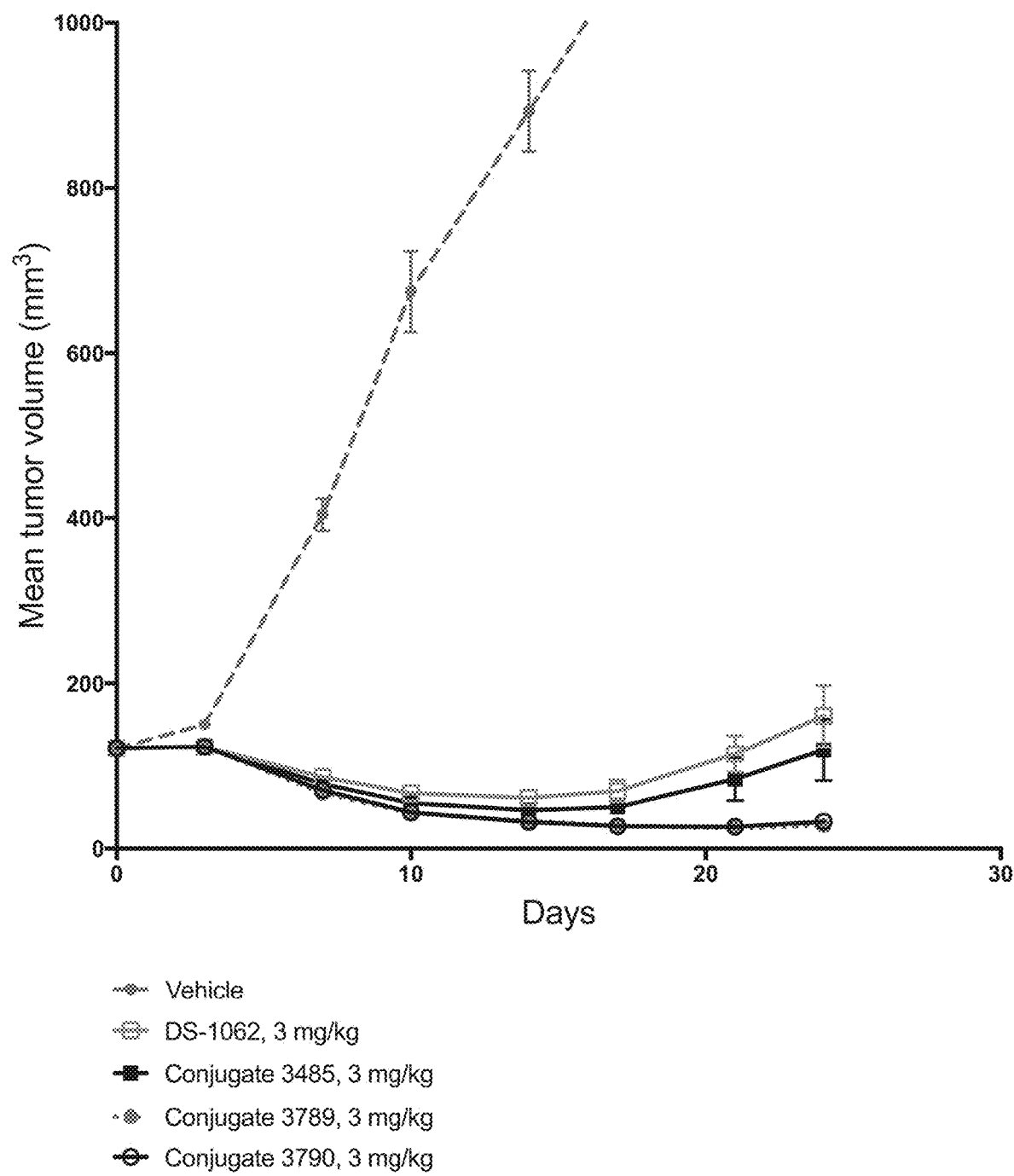
FIG. 87 shows a graph of mean tumor volume (mm$^3$) vs. days, which indicates in vivo efficacy against an NCI-H292 xenograft of TROP-2 targeted ADCs carrying topoisomerase inhibitor payloads. n=7 mice/group. A single i.v. dose was delivered on Day 0.

Results for Study 2 are shown in FIG. 87, which shows a graph of mean tumor volume (mm³) vs. days and indicates in vivo efficacy against an NCI-H292 xenograft of TROP-2 targeted ADCs carrying topoisomerase inhibitor payloads. n=7 mice/group. A single i.v. dose was delivered on Day 0.

Methods:

NCI-H1781 Xenograft: Female BALB/c nude mice (5/group) were inoculated subcutaneously with 20 million NCI-H1781 cells in PBS. Treatment began when the tumors reached an average of 222 mm³ (Day 1). Animals were dosed intravenously with vehicle alone, a nectin-4 Compound 65 conjugate with a DAR of 6.8, or a nectin-4 mc-GGFG-Dxd conjugate with a DAR of 3.7. ADCs were dosed intravenously at 5 mg/kg on Days 0 and 7. The animals were monitored twice weekly for body weight and tumor size. Animals were euthanized when tumors reached 2000 mm³ or body weight loss exceeded 15%.

Figure 88:
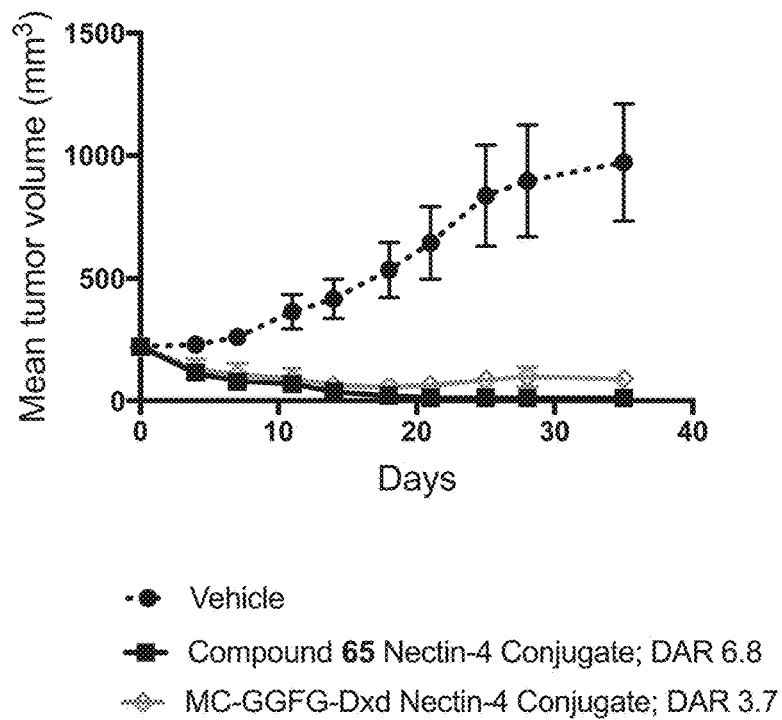
FIG. 88 shows a graph of mean tumor volume (mm$^3$) vs. days, which indicates in vivo efficacy against an NCI-H1781 xenograft of nectin-4 targeted ADCs carrying topoisomerase inhibitor payloads. n=5 mice/group. A 5 mg/kg dose was delivered i.v. on Days 0 and 7.
Figure 89:
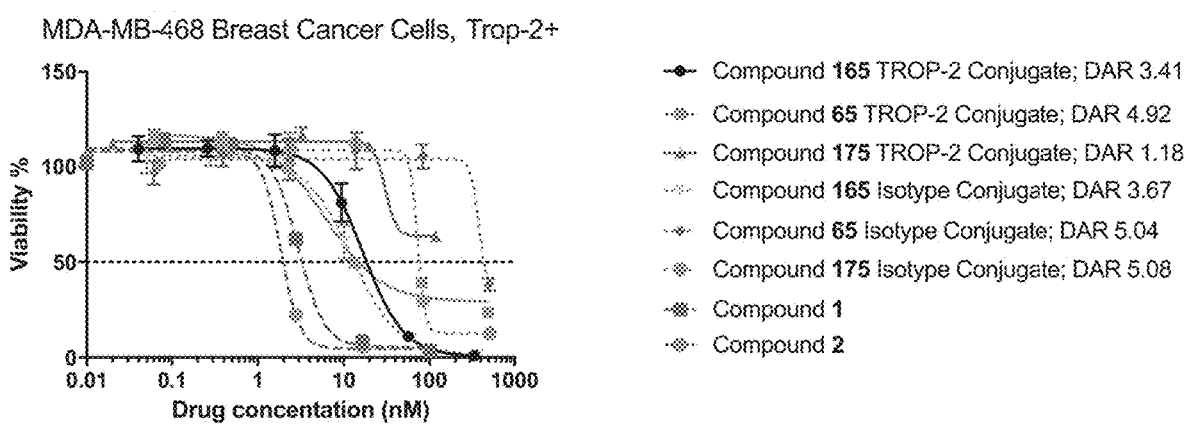
FIG. 89 shows a graph of in vitro potency of TROP-2 targeted or isotype control ADCs carrying (165), (65), (175) as compared to (1) or (2) against MBA-MB-468 cells.
Figure 90:
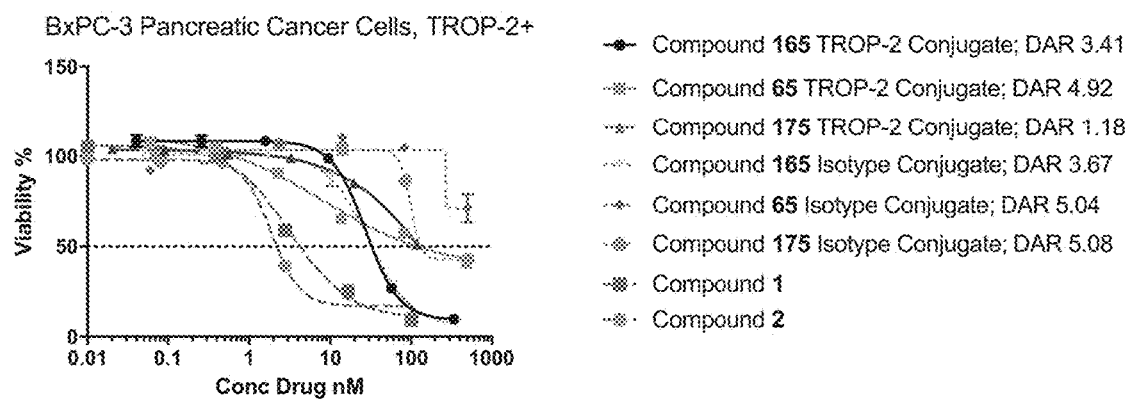
FIG. 90 shows a graph of in vitro potency of TROP-2 targeted or isotype control ADCs carrying (165), (65), (175) as compared to (1) or (2) against BxPC-3 cells.
Figure 91:
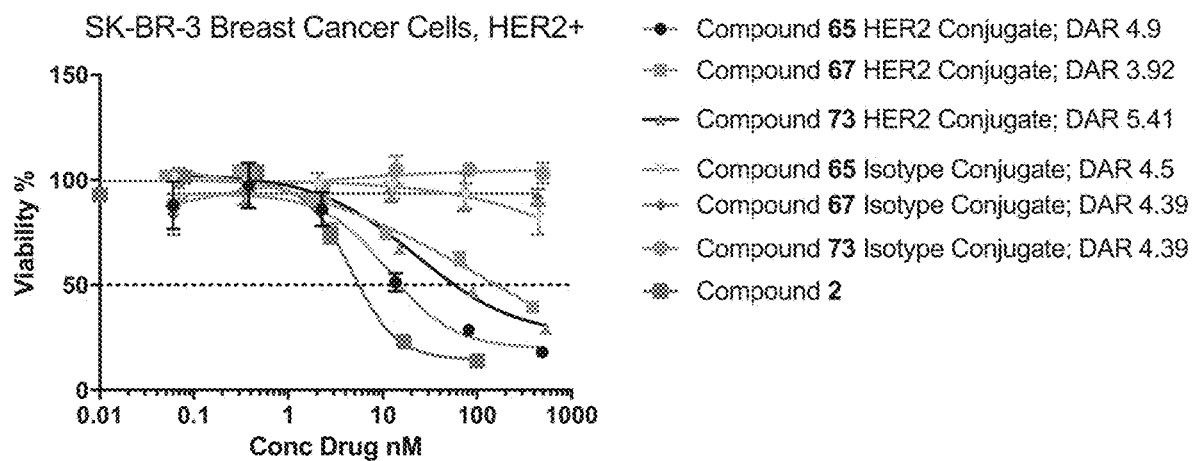
FIG. 91 shows a graph of in vitro potency of HER2 targeted or isotype control ADCs carrying (65), (67), or (73) as compared to (2) against SK-BR-3 cells.
Figure 92:
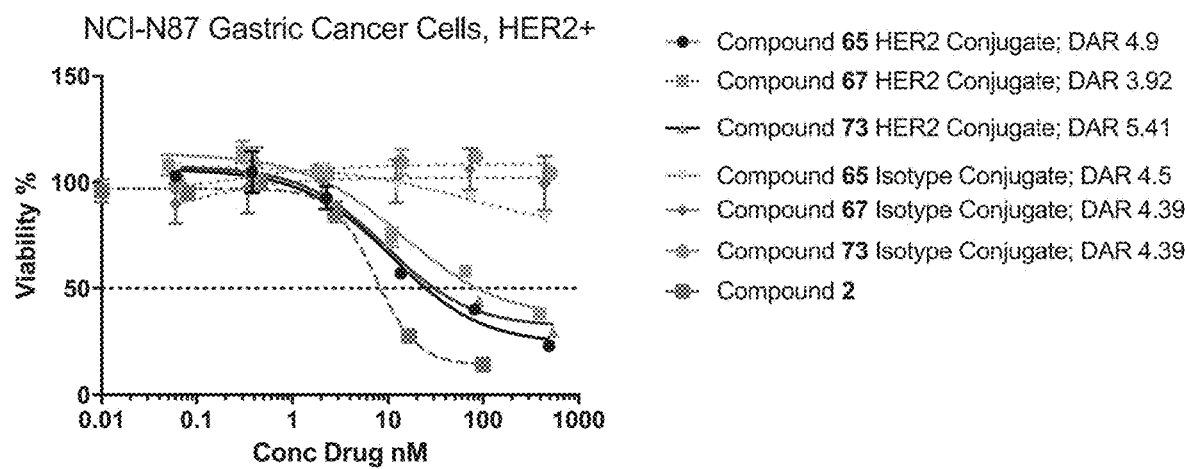
FIG. 92 shows a graph of in vitro potency of HER2 targeted or isotype control ADCs carrying (65), (67), or (73) as compared to (2) against NCI-N87 cells.
Figure 93:
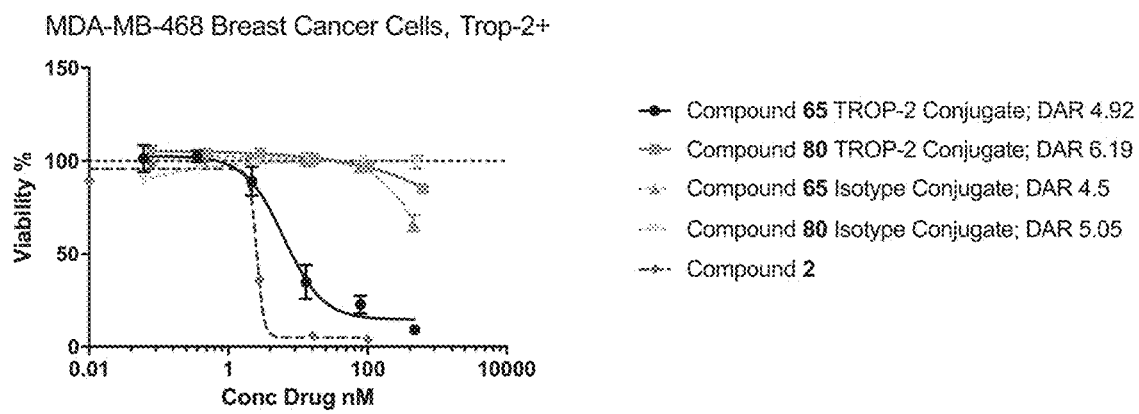
FIG. 93 shows a graph of in vitro potency of TROP-2 targeted or isotype control ADCs carrying (65) or (80) as compared to (2) against MDA-MB-468 cells.
Figure 94:
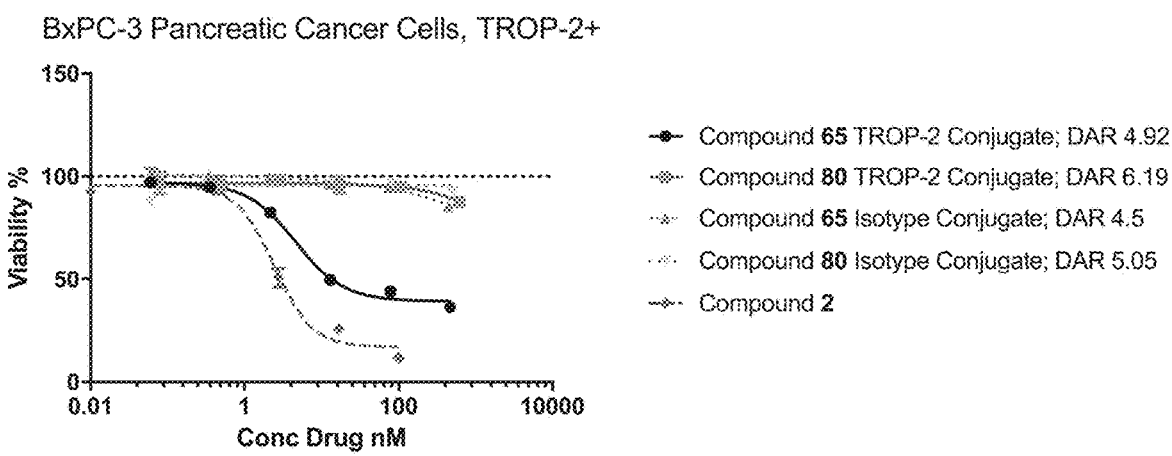
FIG. 94 shows a graph of in vitro potency of TROP-2 targeted or isotype control ADCs carrying (65) or (80) as compared to (2) against BxPC-3 cells.
Figure 95:
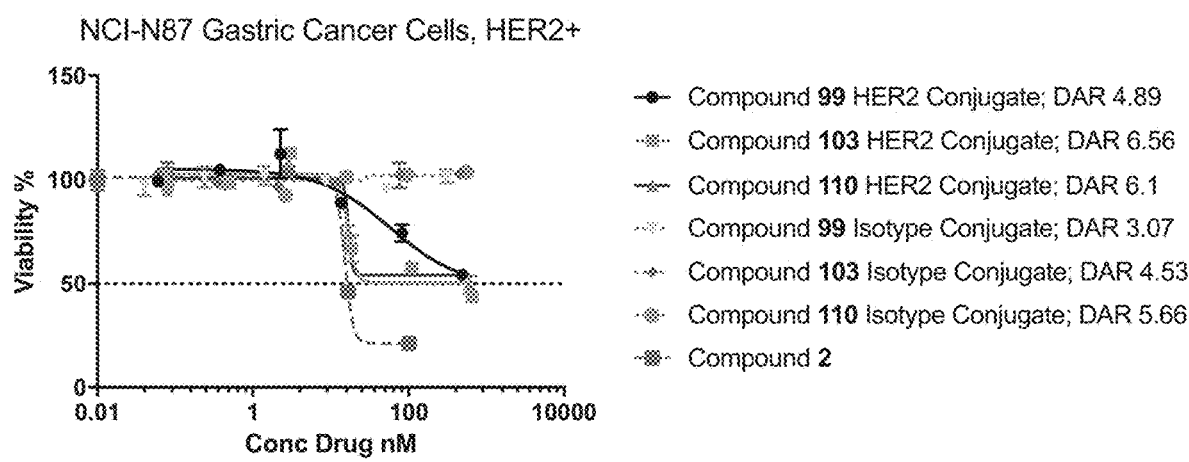
FIG. 95 shows a graph of in vitro potency of HER2 targeted or isotype control ADCs carrying (99), (103), or (110) as compared to (2) against NCI-N87 cells.
Figure 96:
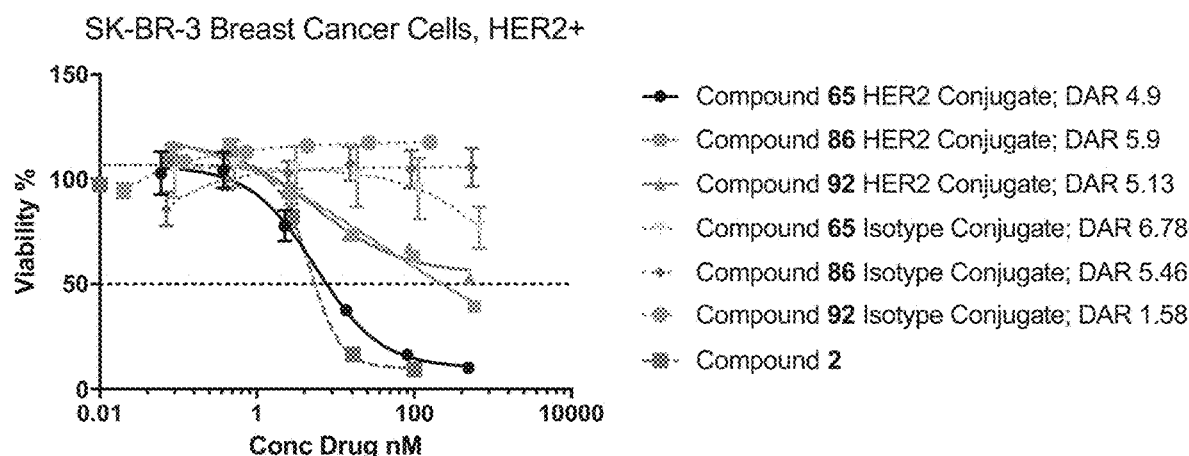
FIG. 96 shows a graph of in vitro potency of HER2 targeted or isotype control ADCs carrying (65), (86), or (92) as compared to (2) against SK-BR-3 cells.
Figure 97:
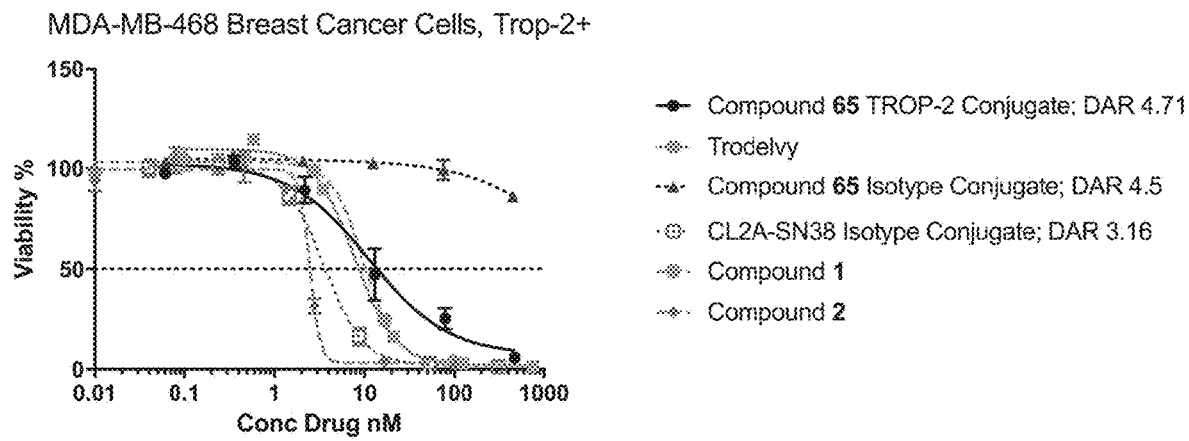
FIG. 97 shows a graph of in vitro potency of TROP-2 targeted or isotype control ADCs carrying (65), Trodelvy, or a CL2A-SN38 isotype control conjugate as compared to (1) or (2) against SK-BR-3 cells.
Figure 98:
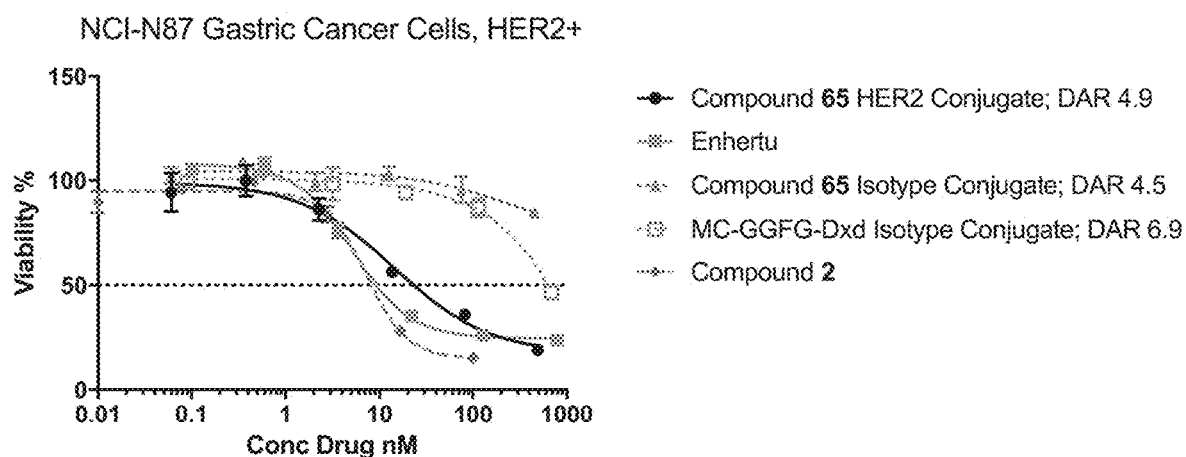
FIG. 98 shows a graph of in vitro potency of HER2 targeted or isotype control ADCs carrying (65), Enhertu, or a MC-GGFG-Dxd isotype control conjugate as compared to (2) against NCI-N87 cells.
Figure 99:
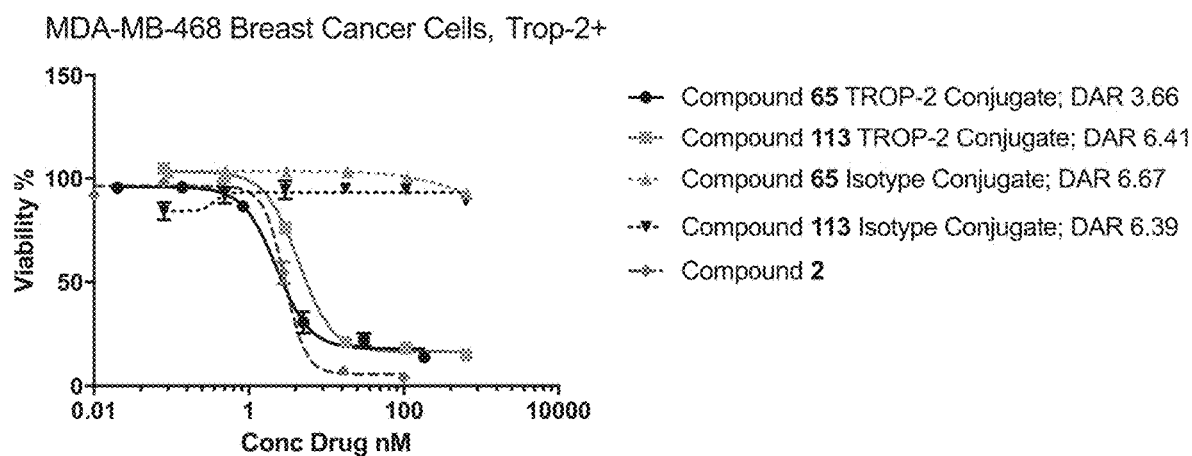
FIG. 99 shows a graph of in vitro potency of TROP-2 targeted or isotype control ADCs carrying (65) or (113) as compared to (2) against MDA-MB-468 cells.
Figure 100:
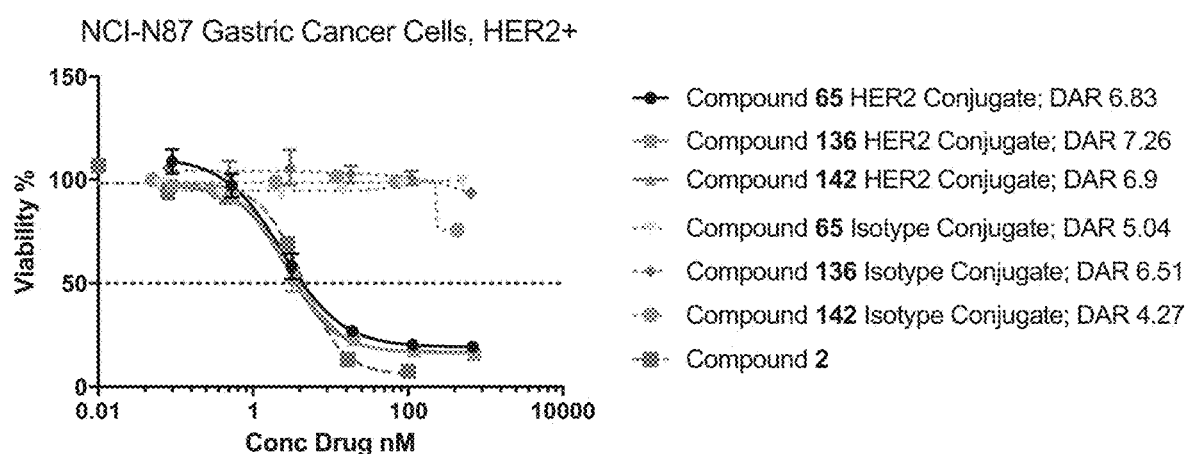
FIG. 100 shows a graph of in vitro potency of HER2 targeted or isotype control ADCs carrying (65), (136), or (142) as compared to (2) against NCI-N87 cells.
Figure 101:
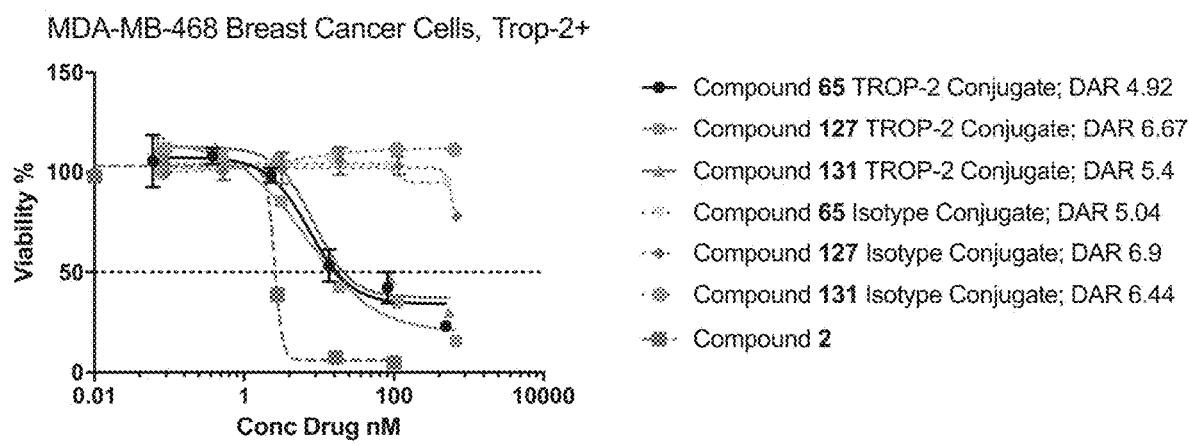
FIG. 101 shows a graph of in vitro potency of TROP-2 targeted or isotype control ADCs carrying (65), (127), or (131) as compared to (2) against MDA-MB-468 cells.
Figure 102:
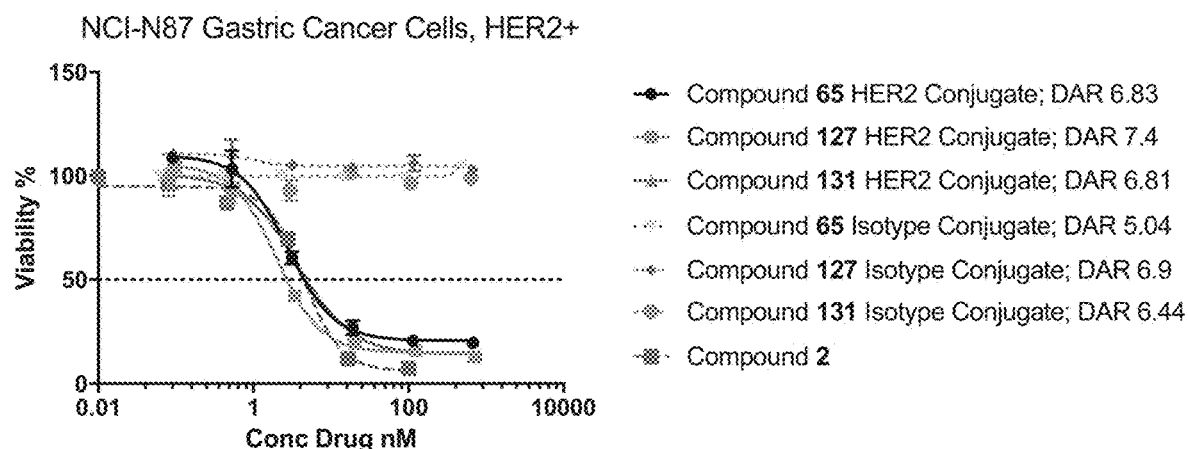
FIG. 102 shows a graph of in vitro potency of HER2 targeted or isotype control ADCs carrying (65), (127), or (131) as compared to (2) against NCI-N87 cells.
Figure 103:
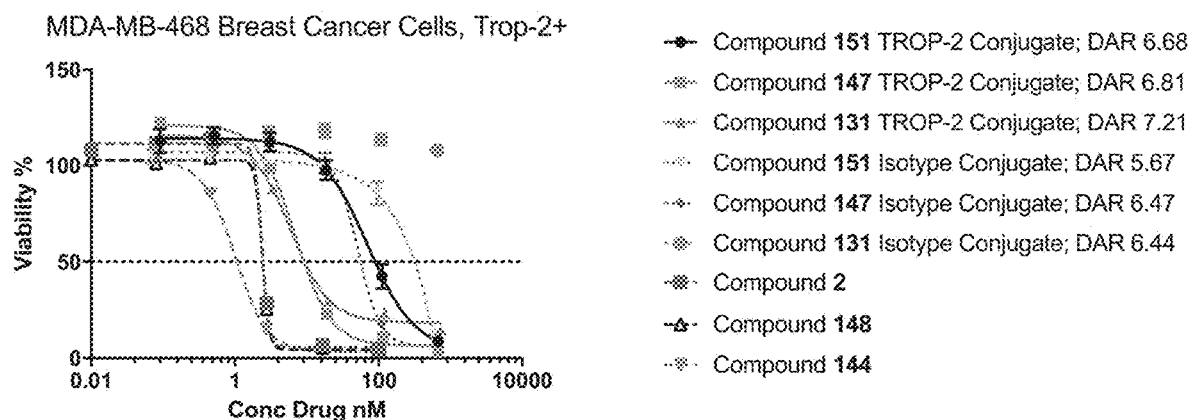
FIG. 103 shows a graph of in vitro potency of TROP-2 targeted or isotype control ADCs carrying (151), (147), or (131) as compared to (2), (148), or (144) against NCI-N87 cells.
Figure 104:
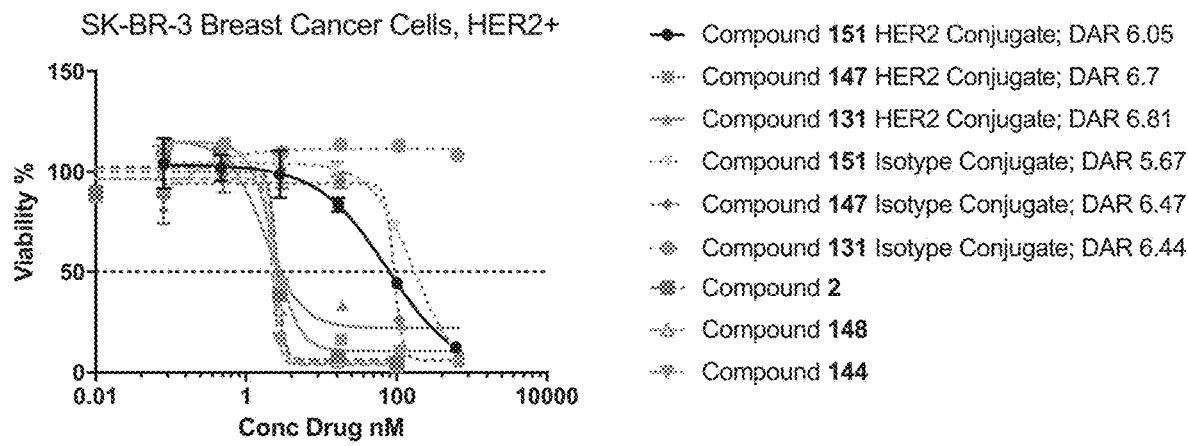
FIG. 104 shows a graph of in vitro potency of HER2 targeted or isotype control ADCs carrying (151), (147), or (131) as compared to (2), (148), or (144) against SK-BR-3 cells.
Figure 105:
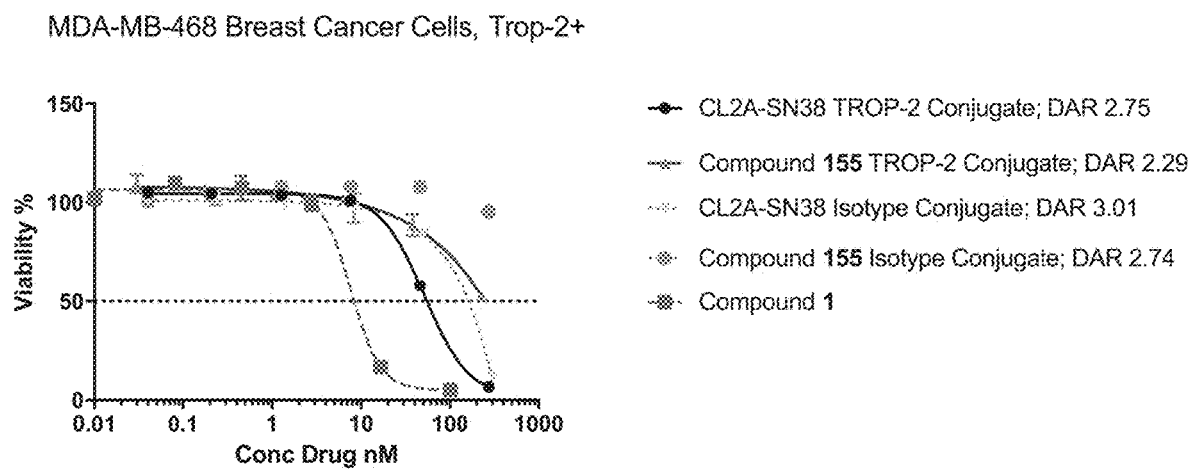
FIG. 105 shows a graph of in vitro potency of TROP-2 targeted or isotype control ADCs carrying (155) or CL2A-SN38 as compared to (1) against MDA-MB-468 cells.
Figure 106:
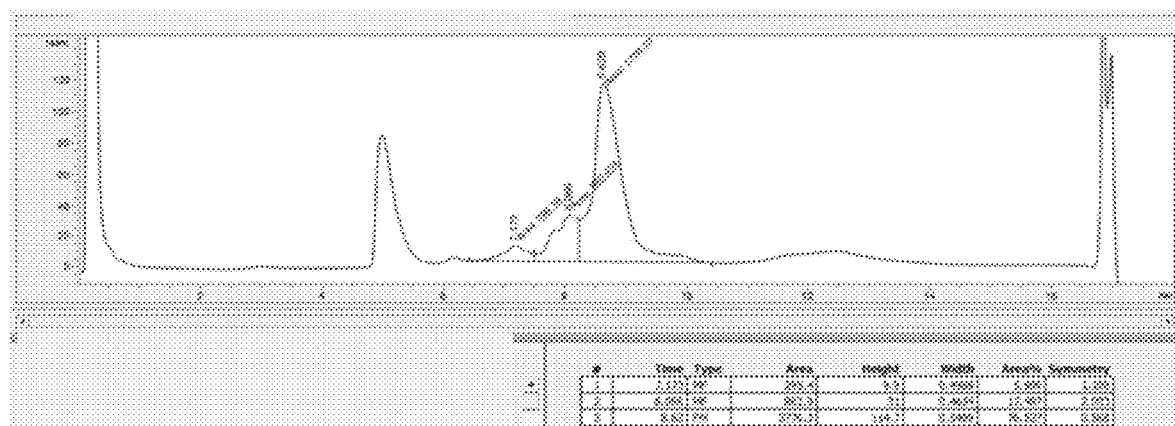
FIG. 106 shows a graph of Compound 127 CH1-3/CT-tagged trastuzumab conjugate yields a DAR of 7.15 as determined by PLRP.
Figure 107:
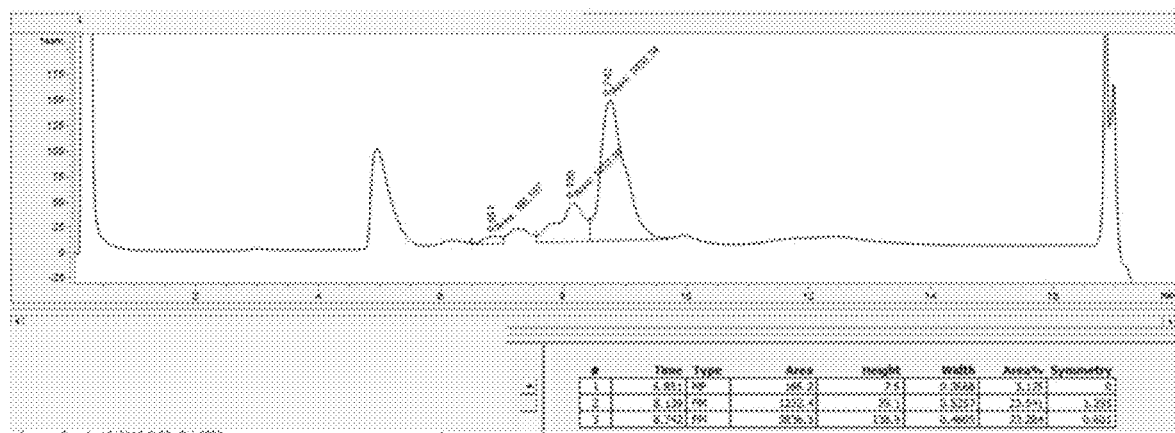
FIG. 107 shows a graph of Compound 131 CH1-3/CT-tagged trastuzumab conjugate yields a DAR of 6.80 as determined by PLRP.
Figure 108:
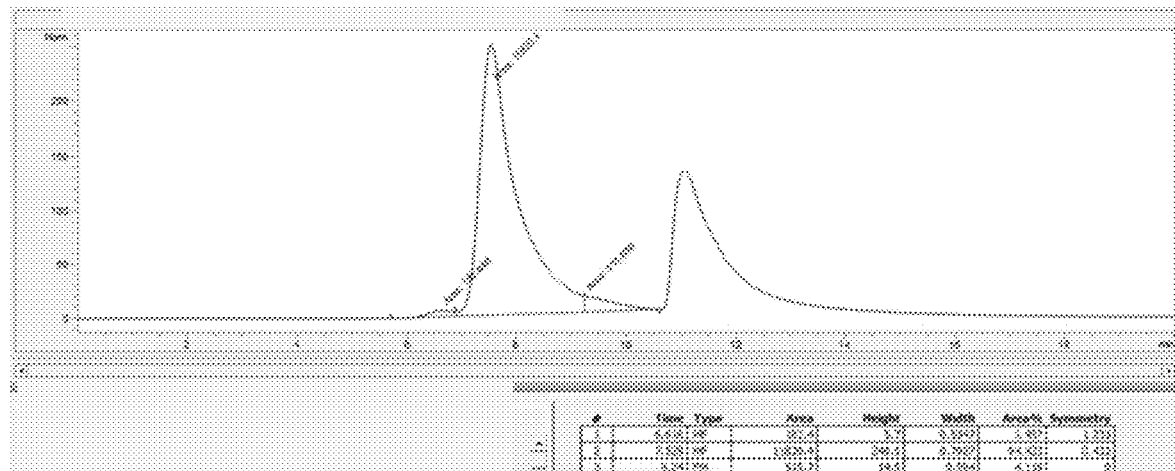
FIG. 108 shows a graph of Compound 127 CH1-3/CT-tagged trastuzumab conjugate is 94.4% monomeric as determined by analytical SEC.
Figure 109:
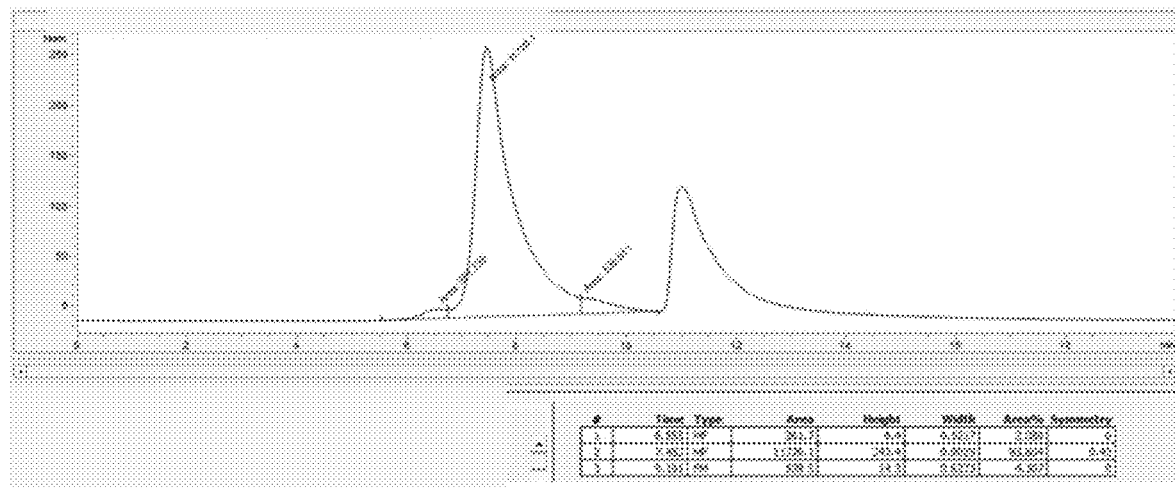
FIG. 109 shows a graph of Compound 131 CH1-3/CT-tagged trastuzumab conjugate is 93.6% monomeric as determined by analytical SEC.
Figure 110:
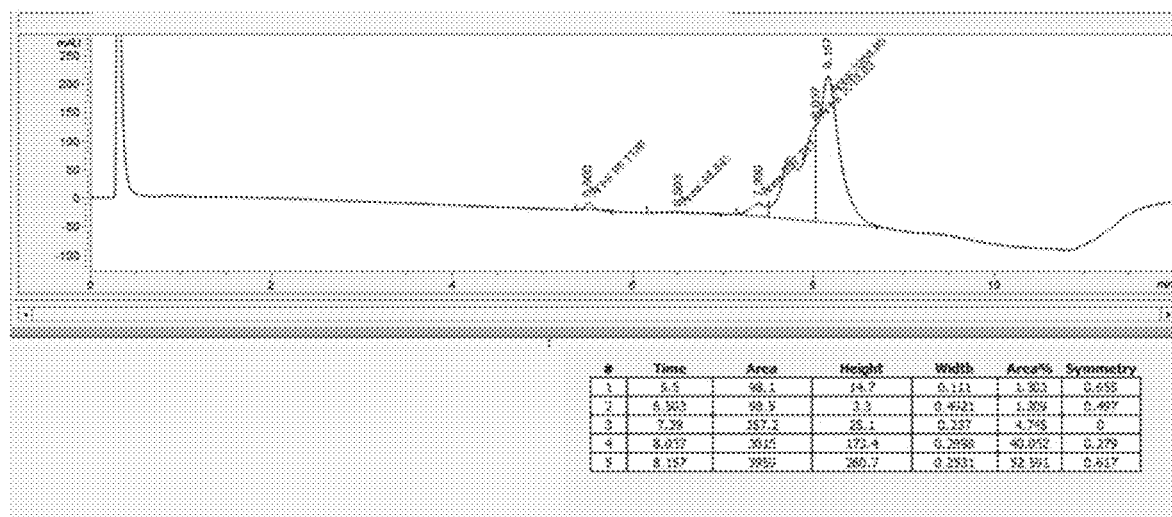
FIG. 110 shows a graph of Compound 165 CH1-3/CT-tagged sacituzumab conjugate yields a DAR of 3.41 as determined by HIC.
Figure 111:
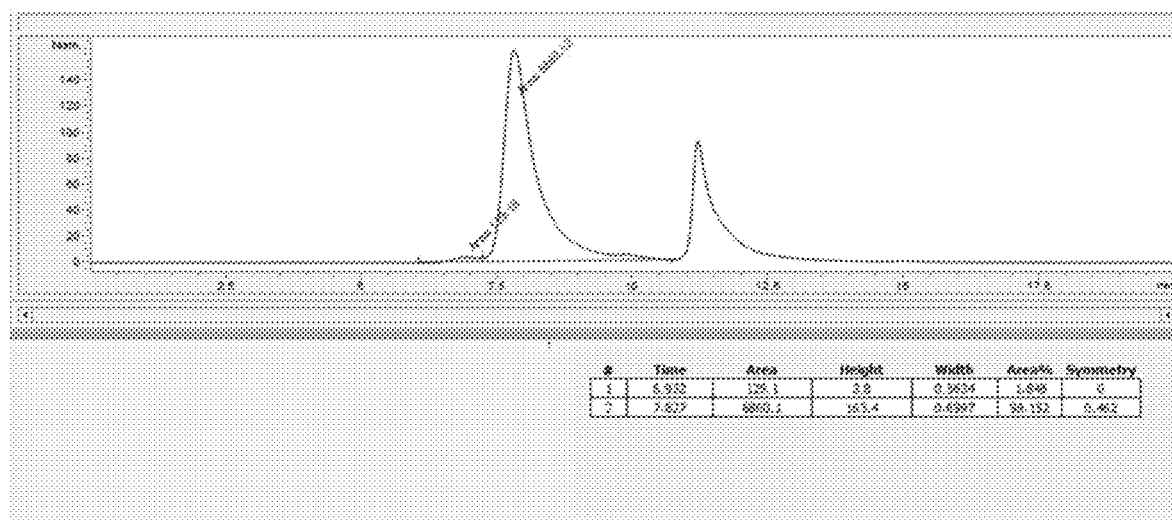
FIG. 111 shows a graph of Compound 165 CH1-3/CT-tagged sacituzumab conjugate is 98.2% monomeric as determined by analytical SEC.
Figure 112:
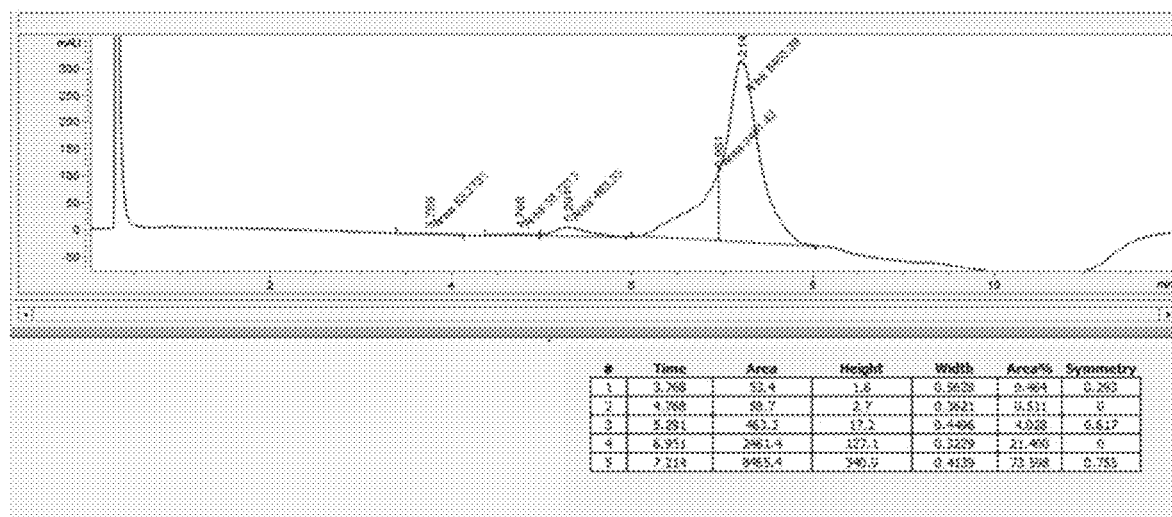
FIG. 112 shows a graph of Compound 165 CH1-3/CT-tagged polatuzumab conjugate yields a DAR of 3.67 as determined by HIC.
Figure 113:
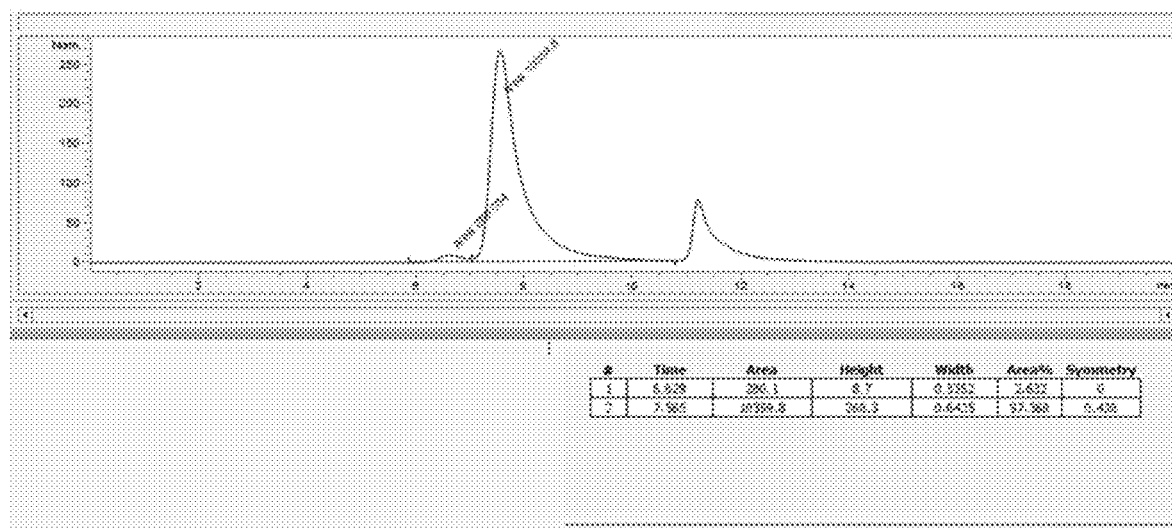
FIG. 113 shows a graph of Compound 165 CH1-3/CT-tagged polatuzumab conjugate is 97.4% monomeric as determined by analytical SEC.
Figure 114:
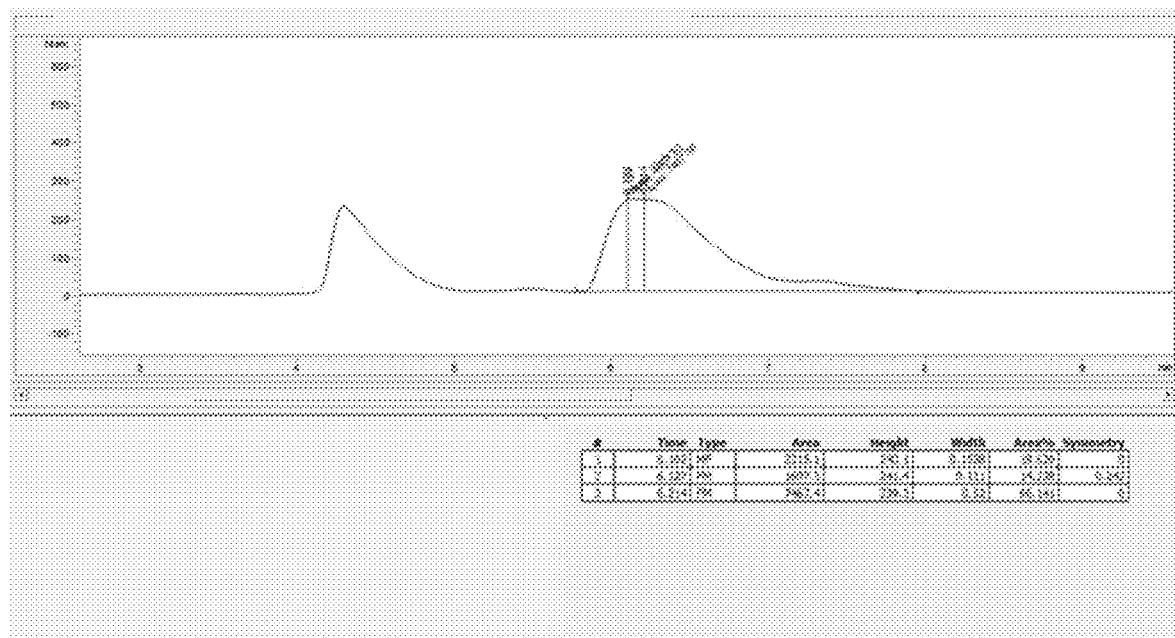
FIG. 114 shows a graph of Compound 80 CH1-3/CT-tagged trastuzumab conjugate yields a DAR of 5.86 as determined by PLRP.
Figure 115:
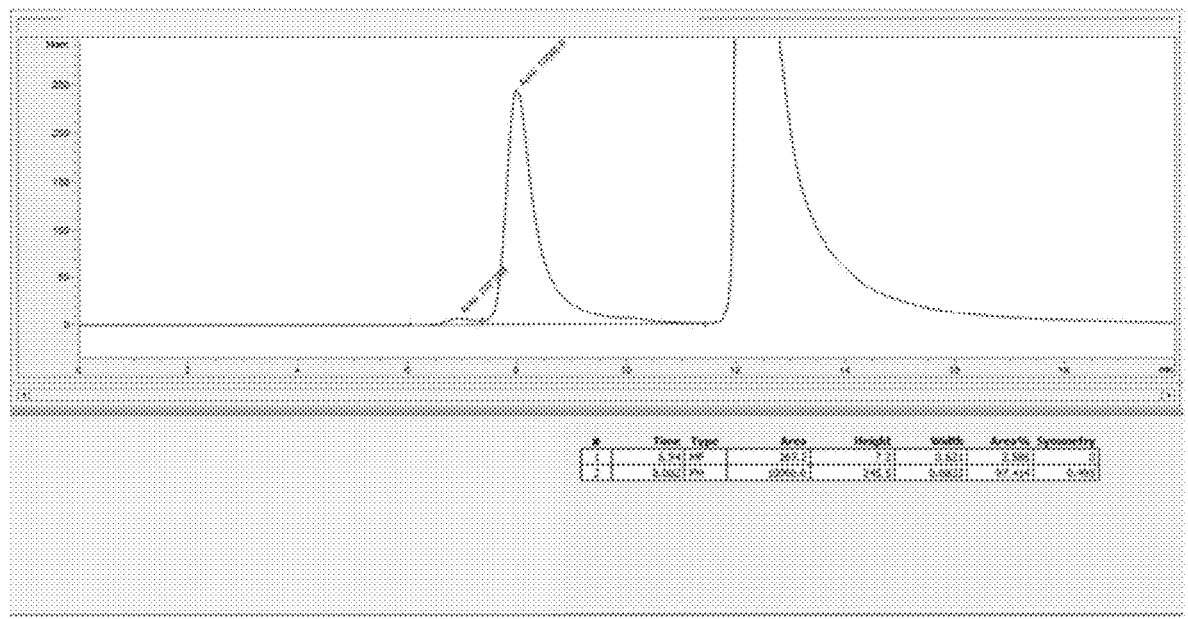
FIG. 115 shows a graph of Compound 80 CH1-3/CT-tagged trastuzumab conjugate is 97.4% monomeric as determined by analytical SEC.
Figure 116:
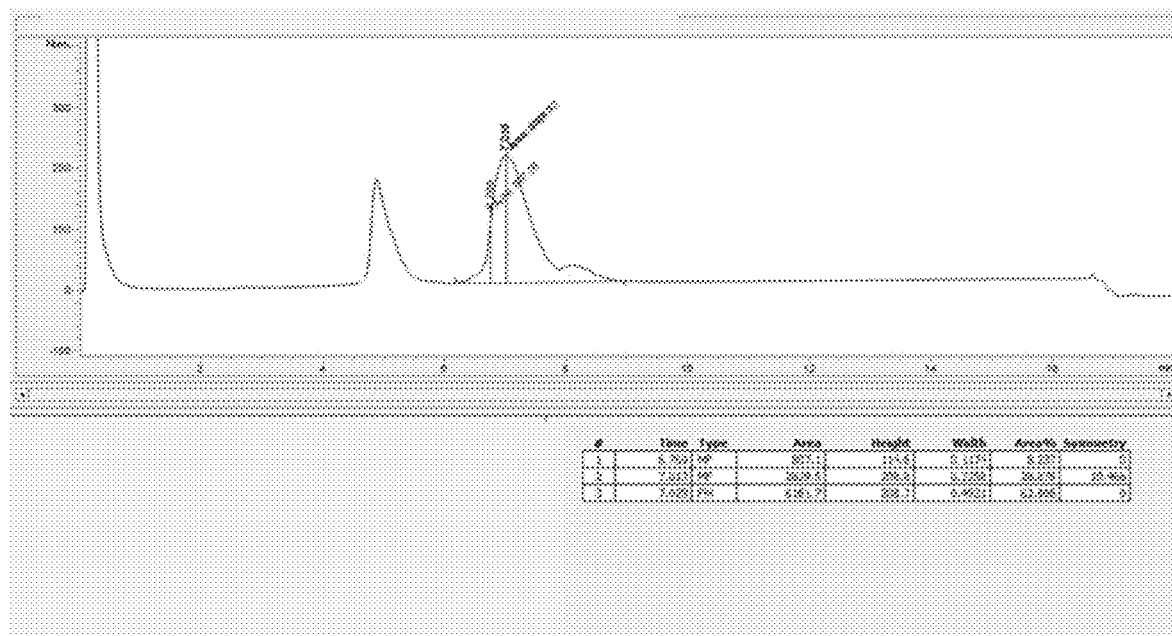
FIG. 116 shows a graph of Compound 80 CH1-3/CT-tagged sacituzumab conjugate yields a DAR of 6.19 as determined by PLRP.
Figure 117:
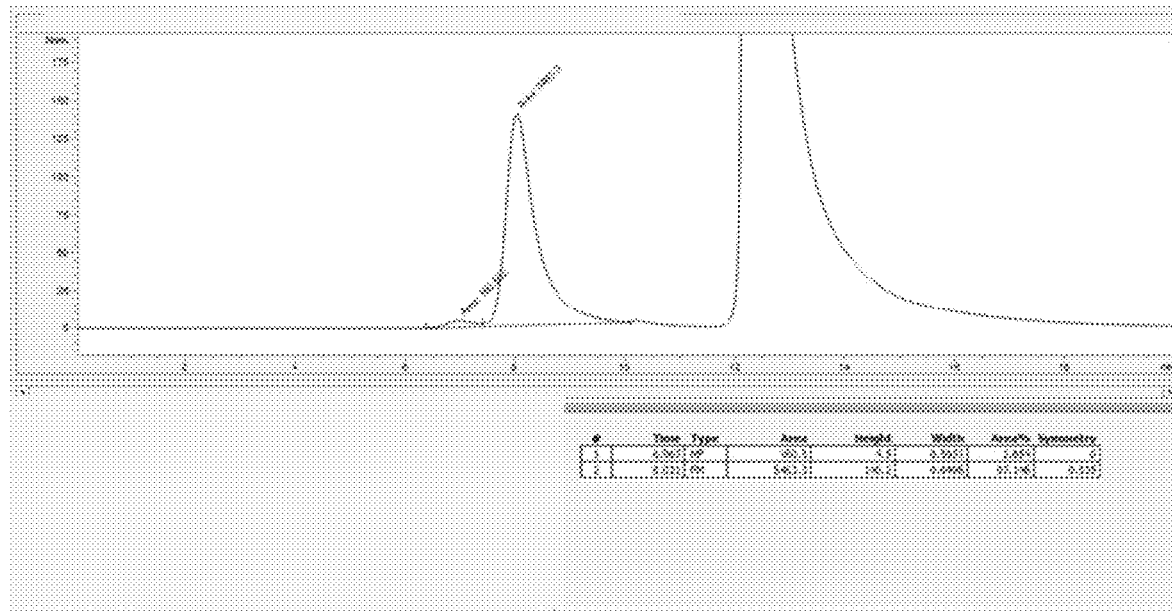
FIG. 117 shows a graph of Compound 80 CH1-3/CT-tagged sacituzumab conjugate is 97.1% monomeric as determined by analytical SEC.
Figure 118:
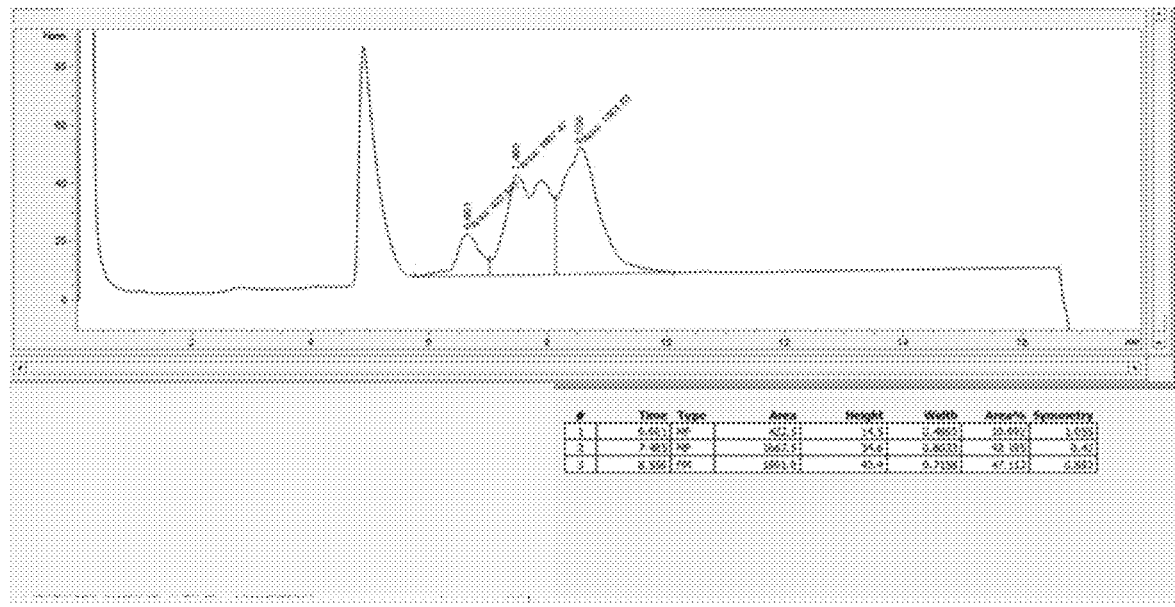
FIG. 118 shows a graph of Compound 86 CH1-3/CT-tagged anti-FITC conjugate yields a DAR of 5.46 as determined by PLRP.
Figure 119:
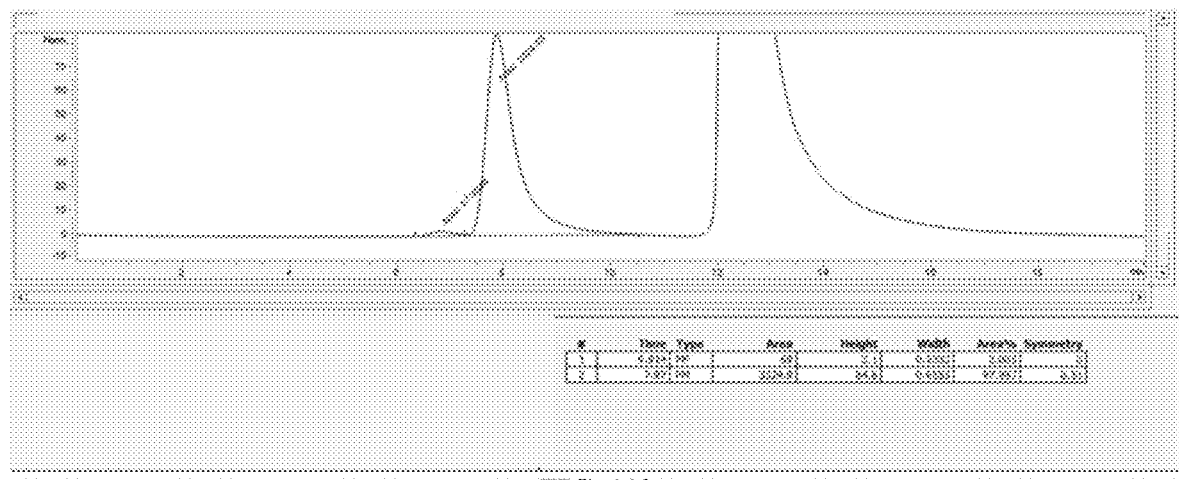
FIG. 119 shows a graph of Compound 86 CH1-3/CT-tagged anti-FITC conjugate is 98.0% monomeric as determined by analytical SEC.
Figure 120:
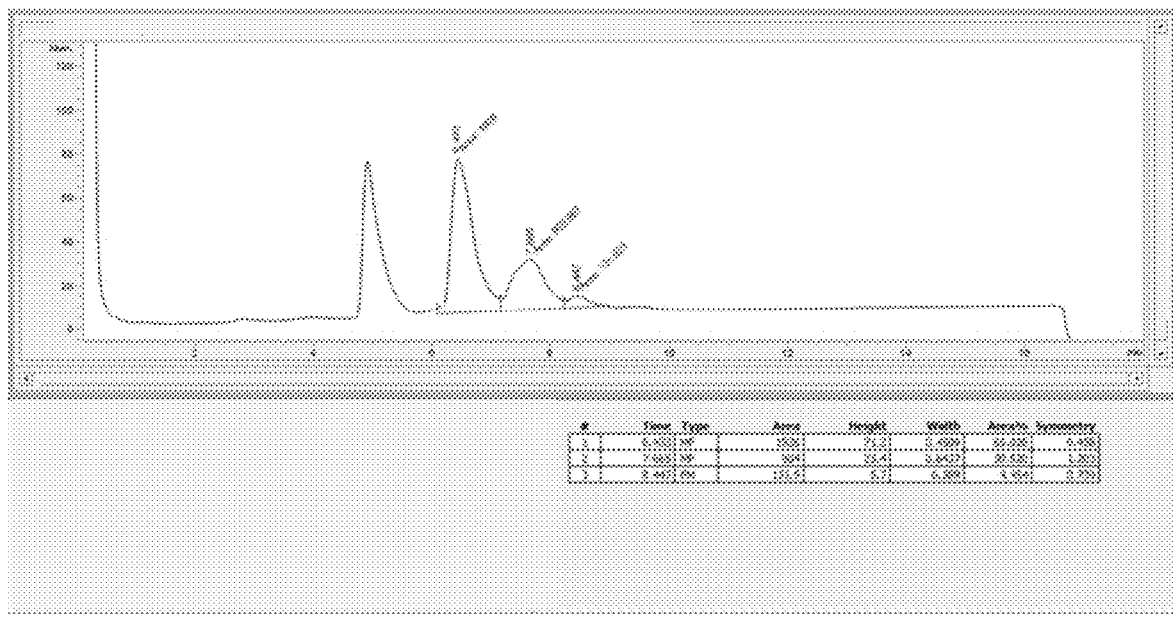
Figure 121:
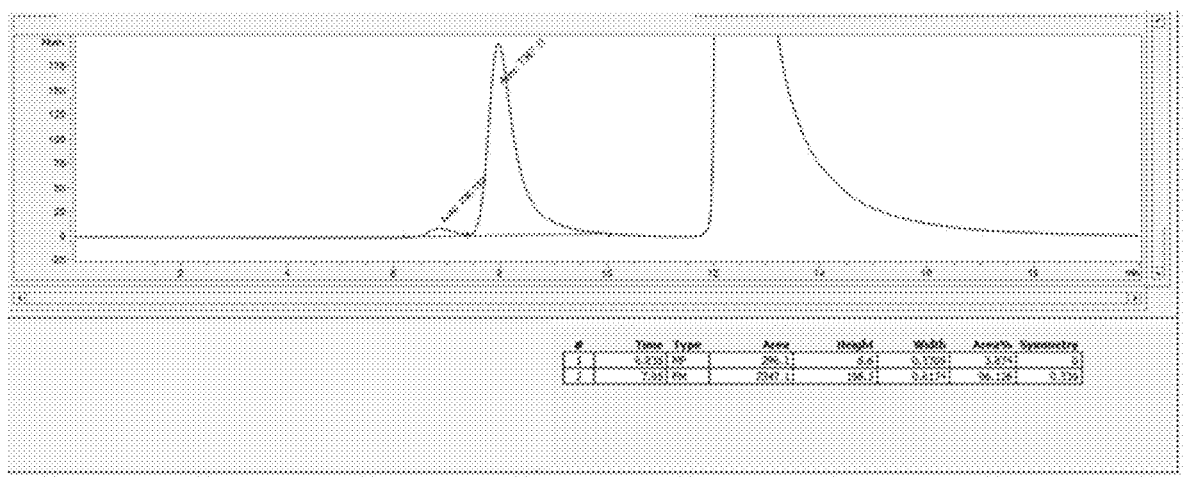
Figure 122:
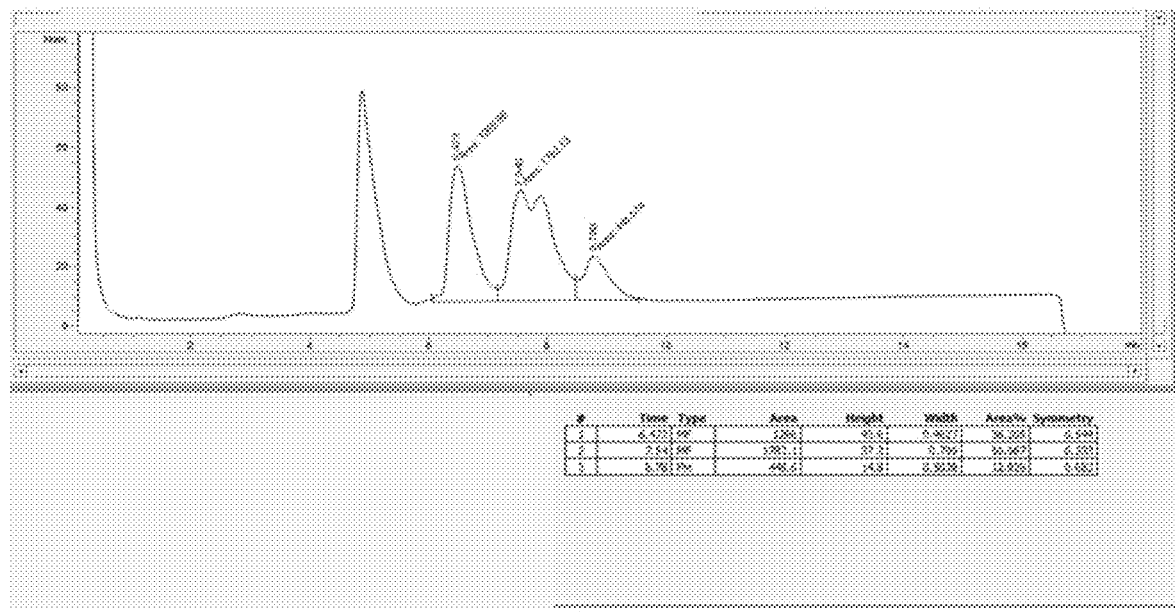
Figure 123:
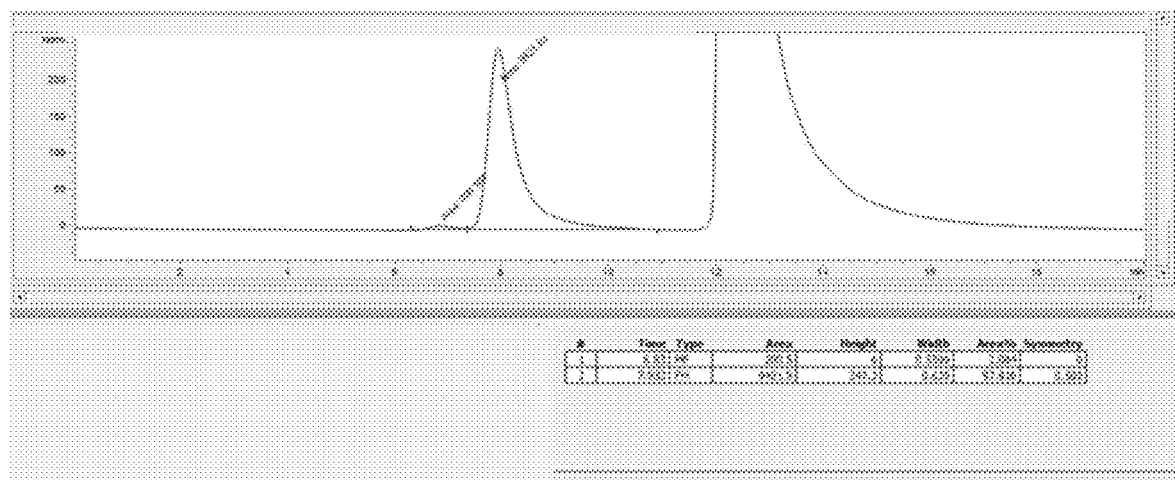
Figure 124:
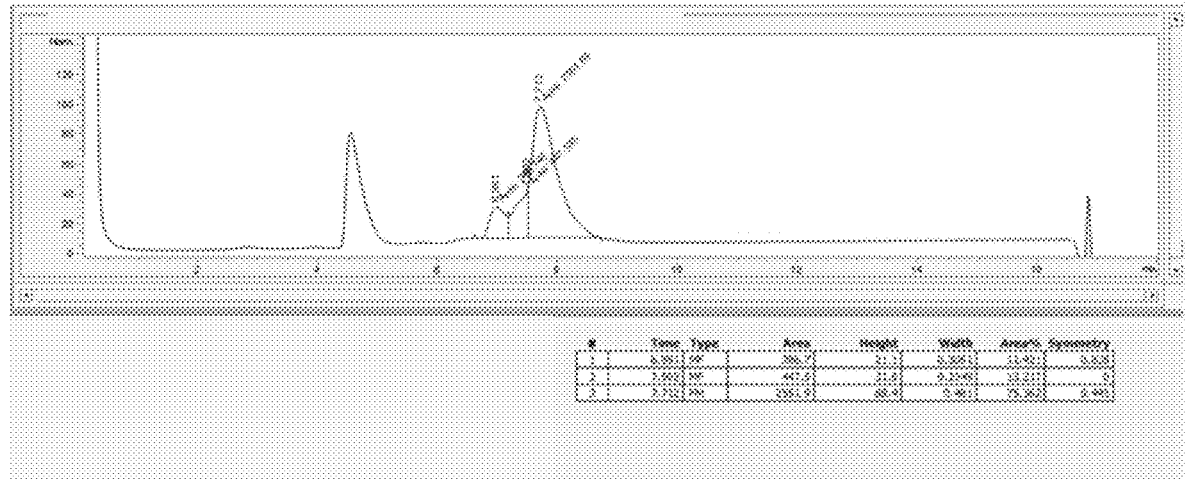
Figure 125:
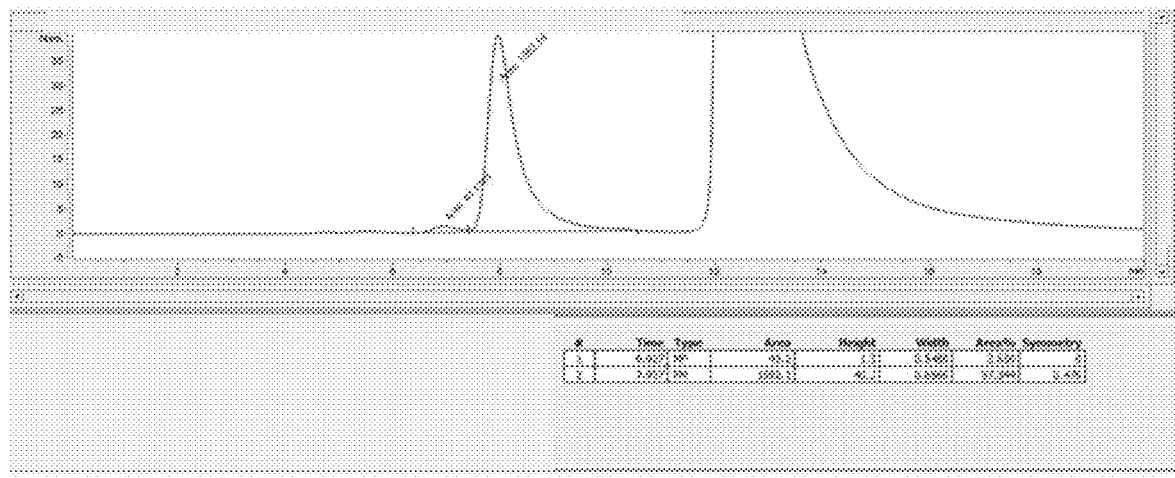
Figure 126:
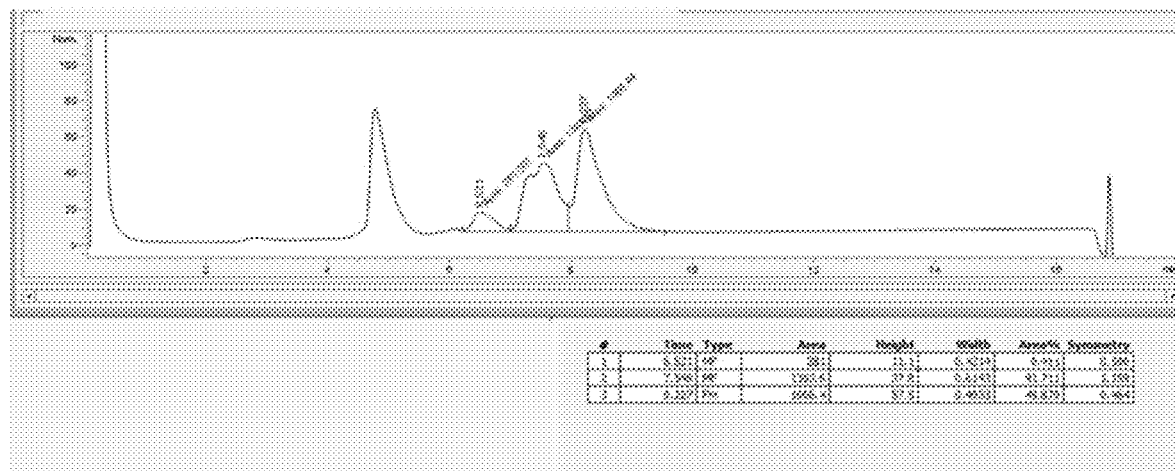
Figure 127:
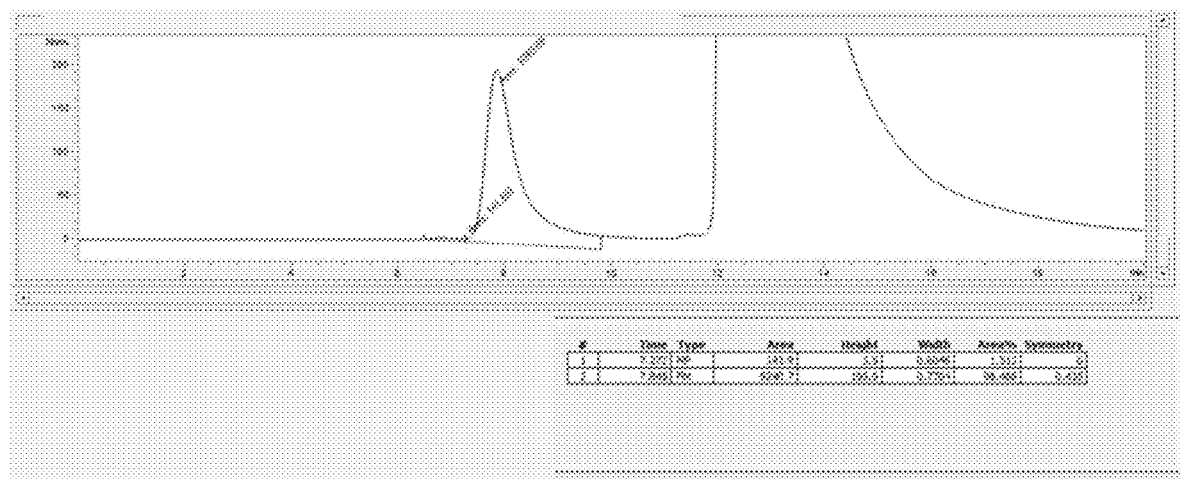
Figure 128:
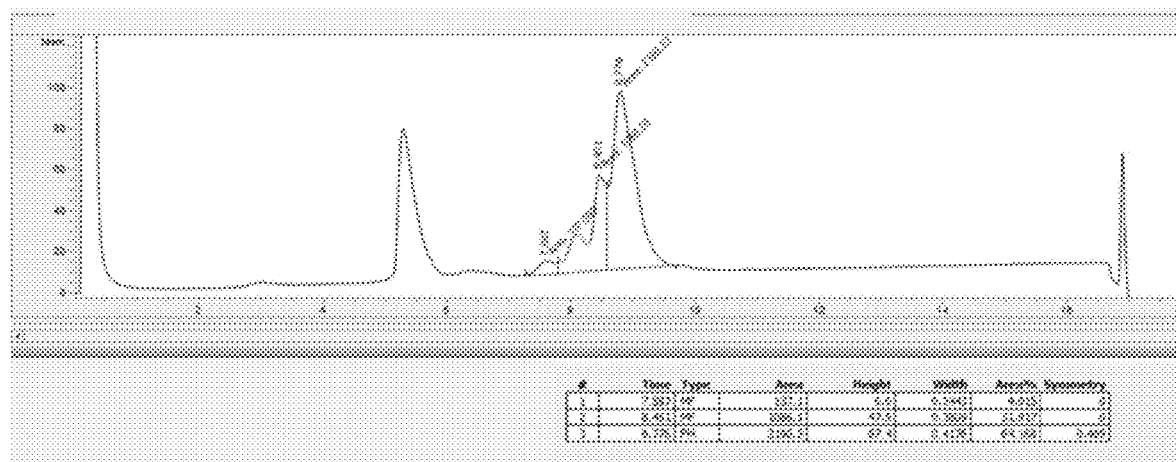
Figure 129:
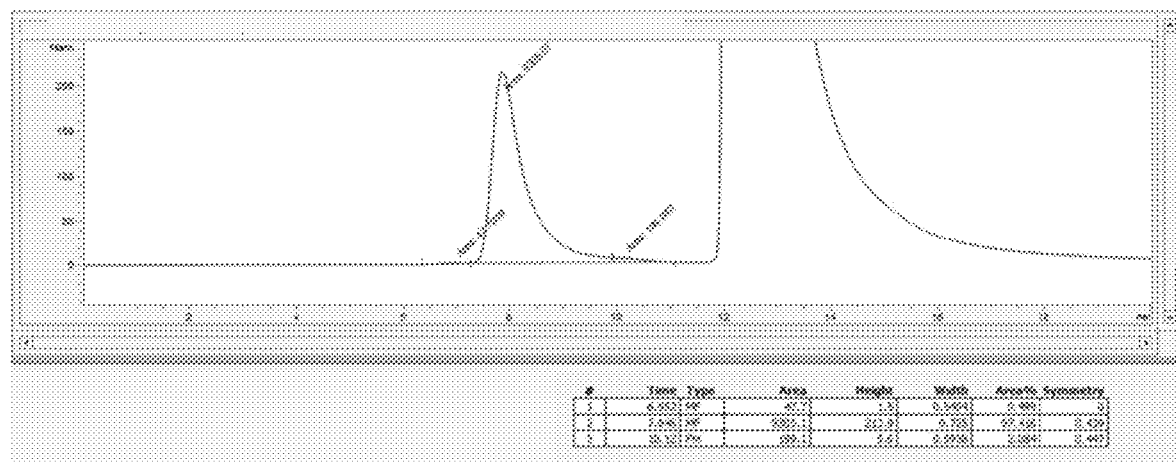
Figure 130:
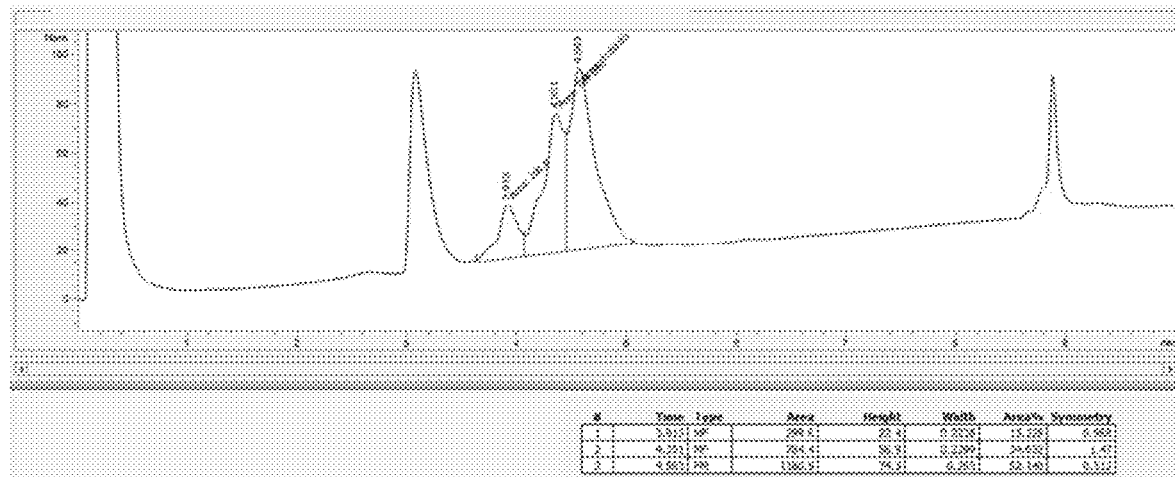
Figure 131:
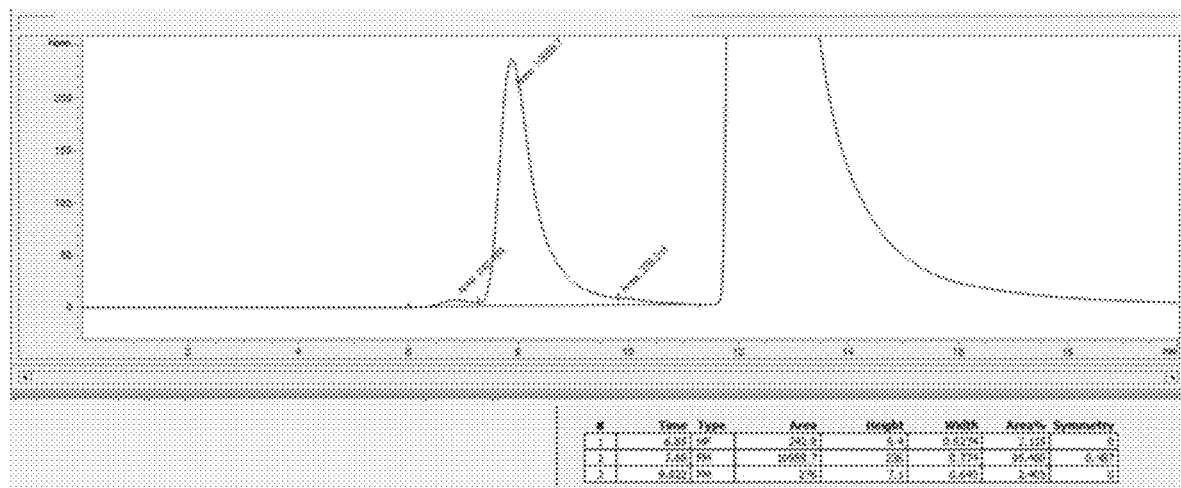

Results:

Results the NCI-H1781 study are shown in FIG. 88, which shows a graph of mean tumor volume (mm³) vs. days and indicates in vivo efficacy against an NCI-H1781 xenograft of nectin-4 targeted ADCs carrying topoisomerase inhibitor payloads. n=5 mice/group. A 5 mg/kg dose was delivered i.v. on Days 0 and 7.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:
1. A conjugate of formula (I):

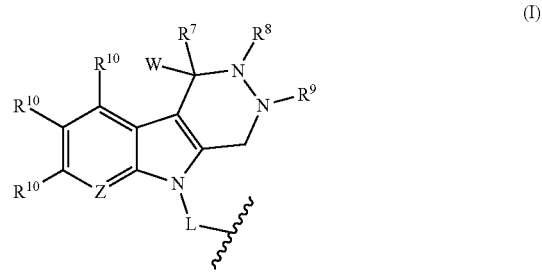

wherein:
Z is $CR^{10}$ or N,
$R^7$ is selected from hydrogen, alkyl, and substituted alkyl;
$R^8$ and $R^9$ are each independently selected from hydrogen, alkyl, and substituted alkyl;
each $R^{10}$ is independently selected from hydrogen, alkyl, and substituted alkyl;
W is a polypeptide;
L is a linker attached to a compound of formula (II) at $R^1$, $R^2$, $R^3$, $R^4$, $R^5$ or $R^6$:

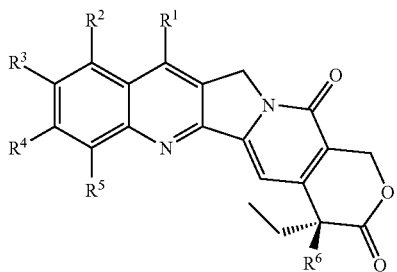

(II)

R[1] and R[2] are each independently selected from hydrogen, halogen, hydroxy, amino, substituted amino, alkyl, and substituted alkyl, or R[1] and R[2] are optionally cyclically linked to form a 5 or 6-membered cycloalkyl or heterocyclyl ring;

R[3] and R[4] are each independently selected from hydrogen, halo, hydroxy, amino, substituted amino, alkyl, and substituted alkyl;

R[5] is selected from hydrogen, halogen, hydroxy, amino, substituted amino, alkyl, and substituted alkyl;

R[6] is selected from OH and OC(O)R[11]; and

R[11] is selected from hydrogen, alkyl, and substituted alkyl, wherein at least one R[10] is optionally linked to a second compound of formula (II).

2. The conjugate of claim 1,
wherein the compound of formula (II) has the structure of formula (IIa):

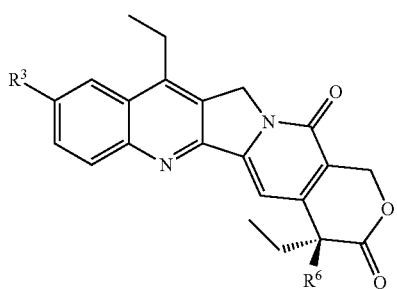

(IIa)

wherein R[3] is OH and L is attached at R[6]; or L is attached at R[3] and R[6] is OH; or wherein the compound of formula (II) has the structure of formula (IIb):

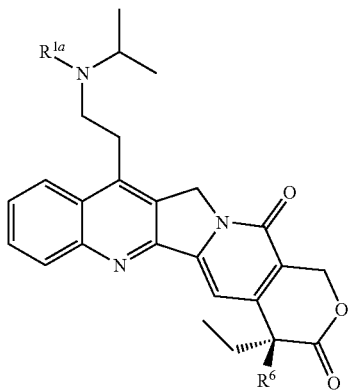

(IIb)

wherein R[1a] is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at R[6]; or L is attached at R[1a] and R[6] is OH; or wherein the compound of formula (II) has the structure of formula (IIc):

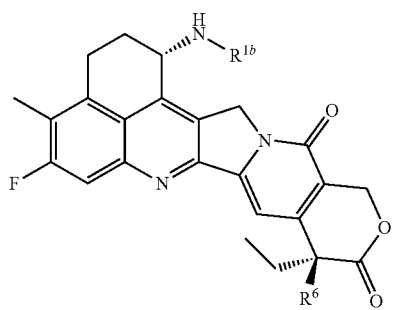

(IIc)

wherein R[1b] is selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at R[6]; or L is attached at R[1b] and R[6] is OH; or wherein the compound of formula (II) has the structure of formula (IId):

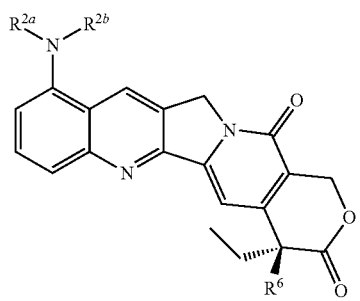

(IId)

wherein R[2a] and R[2b] are each independently selected from H, alkyl, substituted alkyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and L is attached at R[6]; or L is attached at R[2a] or R[2b] and R[6] is OH; or wherein the compound of formula (II) has the structure of formula (IIe):

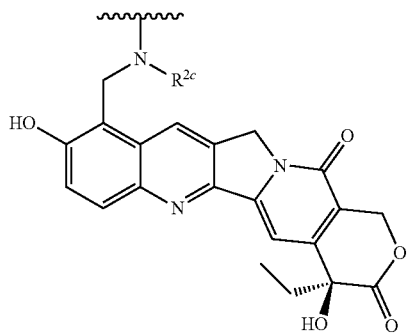

(IIe)

wherein $R^{2c}$ is selected from alkyl, substituted alkyl, alkenyl, substituted alkenyl, alkynyl, substituted alkynyl, aryl, substituted aryl, heteroaryl, substituted heteroaryl, cycloalkyl, substituted cycloalkyl, heterocyclyl, substituted heterocyclyl, carboxyl, carboxyl ester, acyl, and sulfonyl, and attachment to L is indicated by the wavy line.

3. The conjugate of claim 1, wherein L comprises:

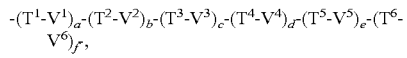

wherein a, b, c, d, e and f are each independently 0 or 1;

$T^1$, $T^2$, $T^3$, $T^4$, $T^5$ and $T^6$ are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, $-(CR^{13}OH)_m-$, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;

$V^1$, $V^2$, $V^3$, $V^4$, $V^5$ and $V^6$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$ and $-P(O)OH-$, wherein each q is an integer from 1 to 6;

each $R^{13}$ is independently selected from hydrogen, alkyl, substituted alkyl, aryl, and substituted aryl; and each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

4. The conjugate of claim 3, wherein:

$T^1$ is selected from a $(C_1-C_{12})$alkyl and a substituted $(C_1-C_{12})$alkyl;

$T^2$, $T^3$, $T^4$, $T^5$ and $T^6$ are each independently selected from a covalent bond, $(C_1-C_{12})$alkyl, substituted $(C_1-C_{12})$alkyl, aryl, substituted aryl, heteroaryl, substituted heteroaryl, cycloalkyl, substituted cycloalkyl, heterocyclyl, and substituted heterocyclyl, $(EDA)_w$, $(PEG)_n$, $(AA)_p$, $-(CR^{13}OH)_m-$, 4-amino-piperidine (4AP), MABO, MABC, PABO, PABC, PAB, PABA, PAP, PHP, an acetal group, a hydrazine, and an ester; and $V^1$, $V^2$, $V^3$, $V^4$, $V^5$ and $V^6$ are each independently selected from the group consisting of a covalent bond, $-CO-$, $-NR^{15}-$, $-NR^{15}(CH_2)_q-$, $-NR^{15}(C_6H_4)-$, $-CONR^{15}-$, $-NR^{15}CO-$, $-C(O)O-$, $-OC(O)-$, $-O-$, $-S-$, $-S(O)-$, $-SO_2-$, $-SO_2NR^{15}-$, $-NR^{15}SO_2-$, and $-P(O)OH-$;

wherein:
$(PEG)_n$ is

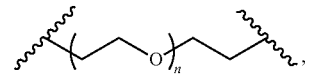

where n is an integer from 1 to 30;

EDA is an ethylene diamine moiety having the following structure:

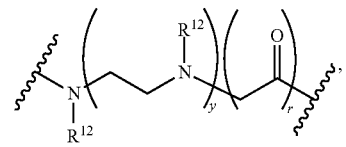

where y is an integer from 1 to 6 and r is 0 or 1;

4-amino-piperidine (4AP) is

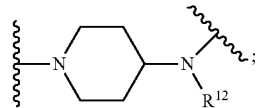

and each $R^{12}$ is independently selected from hydrogen, an alkyl, a substituted alkyl, a polyethylene glycol moiety, an aryl and a substituted aryl, wherein any two adjacent $R^{12}$ groups may be cyclically linked to form a piperazinyl ring.

5. The conjugate of claim 3, wherein $T^1$, $T^2$, $T^3$, $T^4$, $T^5$ and $T^6$ are each optionally substituted with a glycoside.

6. The conjugate of claim 3, wherein MABO, MABC, PABO, PABC, PAB, PABA, PAP and PHP are each optionally substituted with a glycoside.

7. The conjugate of claim 5, wherein the glycoside is selected from a glucuronide, a galactoside, a glucoside, a mannoside, a fucoside, O-GlcNAc, and O-GalNAc.

8. The conjugate of claim 3,
wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is PABC and $V^5$ is absent; and
$T^6$ is EDA and $V^6$ is $-CO-$; or
wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is absent and $V^5$ is $-NR^{15}(C_6H_4)-$; and
$T^6$ is absent and $V^6$ is $-CO-$; or
wherein:
$T^1$ is $(C_1-C_{12})$alkyl and $V^1$ is $-CO-$;
$T^2$ is an amino acid analog and $V^2$ is $-NH-$;
$T^3$ is $(PEG)_n$ and $V^3$ is $-CO-$;
$T^4$ is AA and $V^4$ is absent;
$T^5$ is PABC and $V^5$ is $-NR^{15}-$; and
$T^6$ is $(C_1-C_{12})$alkyl and $V^6$ is $-CO-$; or
wherein:
$T^1$ is $(C_1-C_{12})$alkyl and $V^1$ is $-CO-$;
$T^2$ is AA and $V^2$ is absent;
$T^3$ is PABC and $V^3$ is absent;

$T^4$ is EDA and $V^4$ is —CO—; and
e and f are each 0; or
wherein:
$T^1$ is ($C_1$-$C_{12}$)alkyl and $V^1$ is —CO—;
$T^2$ is an amino acid analog and $V^2$ is —NH—;
$T^3$ is (PEG)$_n$ and $V^3$ is —CO—;
$T^4$ is AA and $V^4$ is absent;
$T^5$ is PABC and $V^5$ is absent; and
f is 0; or
wherein:
$T^1$ is ($C_1$-$C_{12}$)alkyl and $V^1$ is —CO—;
$T^2$ is AA and $V^2$ is absent;
$T^3$ is PABC and $V^3$ is absent; and
d, e and f are each 0; or
wherein:
$T^1$ is ($C_1$-$C_{12}$)alkyl and $V^1$ is —CO—;
$T^2$ is an amino acid analog and $V^2$ is —NH—;
$T^3$ is (PEG)$_n$ and $V^3$ is —CO—;
$T^4$ is AA and $V^4$ is absent;
$T^5$ is PABA and $V^5$ is —CO—; and
$T^6$ is ($C_1$-$C_{12}$)alkyl and $V^6$ is —SO$_2$—; or
wherein:
$T^1$ is ($C_1$-$C_{12}$)alkyl and $V^1$ is —CONH—;
$T^2$ is (PEG)$_n$ and $V^2$ is —CO—;
$T^3$ is AA and $V^3$ is absent;
$T^4$ is PABC and $V^4$ is absent;
e and f are each 0; or
wherein:
$T^1$ is ($C_1$-$C_{12}$)alkyl and $V^1$ is —CONH—;
$T^2$ is substituted ($C_1$-$C_{12}$)alkyl and $V^2$ is —CO—;
$T^3$ is AA and $V^3$ is absent;
$T^4$ is PABC and $V^4$ is absent;
e and f are each 0; or
wherein:
$T^1$ is ($C_1$-$C_{12}$)alkyl and $V^1$ is —CONH—;
$T^2$ is (PEG)$_n$ and $V^2$ is —CO—;
$T^3$ is AA and $V^3$ is absent;
$T^4$ is PABC and $V^4$ is absent;
$T^5$ is ($C_1$-$C_{12}$)alkyl and $V^5$ is absent;
f is 0; or
wherein:
$T^1$ is ($C_1$-$C_{12}$)alkyl and $V^1$ is —CO—;
$T^2$ is 4AP and $V^2$ is —CO—;
$T^3$ is ($C_1$-$C_{12}$)alkyl and $V^3$ is —CO—;
$T^4$ is AA and $V^4$ is absent;
$T^5$ is PABC and $V^5$ is absent;
f is 0; or
wherein:
$T^1$ is ($C_1$-$C_{12}$)alkyl and $V^1$ is —CO—;
$T^2$ is 4AP and $V^2$ is —CO—;
$T^3$ is ($C_1$-$C_{12}$)alkyl and $V^3$ is —O—;
$T^4$ is ($C_1$-$C_{12}$)alkyl and $V^4$ is —CO—;
$T^5$ is AA and $V^5$ is absent;
$T^6$ is PABC and $V^6$ is absent; or
wherein:
$T^1$ is ($C_1$-$C_{12}$)alkyl and $V^1$ is —CO—;
$T^2$ is an amino acid analog and $V^2$ is absent;
$T^3$ is AA and $V^3$ is absent;
$T^4$ is PABC and $V^4$ is absent;
e and f are each 0; or
wherein:
$T^1$ is ($C_1$-$C_{12}$)alkyl and $V^1$ is —CONH—;
$T^2$ is (PEG)$_n$ and $V^2$ is —CONH—;
$T^3$ is substituted ($C_1$-$C_{12}$)alkyl and $V^3$ is —CO—;
$T^4$ is AA and $V^4$ is absent;
$T^5$ is PABC and $V^5$ is absent;
f is 0; or wherein:
$T^1$ is ($C_1$-$C_{12}$)alkyl and $V^1$ is —CO—;
$T^2$ is AA and $V^2$ is —NH—;
$T^3$ is (PEG)$_n$ and $V^3$ is —CO—;
$T^4$ is AA and $V^4$ is absent;
$T^5$ is PABC and $V^5$ is absent;
f is 0; or
wherein:
$T^1$ is ($C_1$-$C_{12}$)alkyl and $V^1$ is —CO—;
$T^2$ is an amino acid analog and $V^2$ is —NH—;
$T^3$ is (PEG)$_n$ and $V^3$ is —CO—;
$T^4$ is AA and $V^4$ is absent;
$T^5$ is PABO and $V^5$ is absent; and
f is 0; or
wherein:
$T^1$ is ($C_1$-$C_{12}$)alkyl and $V^1$ is —CO—;
$T^2$ is an amino acid analog and $V^2$ is —NH—;
$T^3$ is (PEG)$_n$ and $V^3$ is —CO—;
$T^4$ is AA and $V^4$ is absent;
$T^5$ is PAP and $V^5$ is —COO—; and
f is 0; or
wherein:
$T^1$ is ($C_1$-$C_{12}$)alkyl and $V^1$ is —CONH—;
$T^2$ is (PEG)$_n$ and $V^2$ is —CO—;
$T^3$ is AA and $V^3$ is absent;
$T^4$ is PAP and $V^4$ is —COO—; and
e and f are each 0.

9. The conjugate of claim 1, wherein one $R^{10}$ is linked via a second linker, $L^B$, to a second compound of formula (II).

10. The conjugate of claim 9, wherein $L^B$ comprises:

$$-(T^7\text{-}V^7)_g\text{-}(T^8\text{-}V^8)_h\text{-}(T^9\text{-}V^9)_i\text{-}(T^{10}\text{-}V^{10})_j\text{-}(T^{11}\text{-}V^{11})_k\text{-}(T^{12}\text{-}V^{12})_l,$$

wherein
g, h, i, j, k and l are each independently 0 or 1;
$T^7$, $T^8$, $T^9$, $T^{10}$, $T^{11}$ and $T^{12}$ are each independently selected from a covalent bond, ($C_1$-$C_{12}$)alkyl, substituted ($C_1$-$C_{12}$)alkyl, aryl, substituted aryl, heteroaryl, substituted heteroaryl, cycloalkyl, substituted cycloalkyl, heterocyclyl, and substituted heterocyclyl, (EDA)$_w$, (PEG)$_n$, (AA)$_p$, —(CR$^{13}$OH)$_m$—, 4-amino-piperidine (4AP), meta-amino-benzyloxy (MABO), meta-amino-benzyloxycarbonyl (MABC), para-amino-benzyloxy (PABO), para-amino-benzyloxycarbonyl (PABC), para-aminobenzyl (PAB), para-amino-benzylamino (PABA), para-amino-phenyl (PAP), para-hydroxy-phenyl (PHP), an acetal group, a hydrazine, a disulfide, and an ester, wherein EDA is an ethylene diamine moiety, PEG is a polyethylene glycol, and AA is an amino acid residue or an amino acid analog, wherein each w is an integer from 1 to 20, each n is an integer from 1 to 30, each p is an integer from 1 to 20, and each m is an integer from 1 to 12;
$V^7$, $V^8$, $V^9$, $V^{10}$, $V^{11}$ and $V^{12}$ are each independently selected from the group consisting of a covalent bond, —CO—, —NR$^{15}$—, —NR$^{15}$(CH$_2$)$_q$—, —NR$^{15}$(C$_6$H$_4$)—, —CONR$^{15}$—, —NR$^{15}$CO—, —C(O)O—, —OC(O)—, —O—, —S—, —S(O)—, —SO$_2$—, —SO$_2$NR$^{15}$—, —NR$^{15}$SO$_2$— and —P(O)OH—, wherein each q is an integer from 1 to 6;
each $R^{13}$ is independently selected from hydrogen, alkyl, substituted alkyl, aryl, and substituted aryl; and
each $R^{15}$ is independently selected from hydrogen, alkyl, substituted alkyl, alkenyl, substituted alkenyl, alkynyl, substituted alkynyl, carboxyl, carboxyl ester, acyl, aryl, substituted aryl, heteroaryl, substituted heteroaryl, cycloalkyl, substituted cycloalkyl, heterocyclyl, and substituted heterocyclyl.

11. The conjugate of claim 10, wherein $T^7$, $T^8$, $T^9$, $T^{10}$, $T^{11}$ and $T^{12}$ are each optionally substituted with a glycoside.

12. The conjugate of claim 10, wherein MABO, MABC, PABO, PABC, PAB, PABA, PAP and PHP are each optionally substituted with a glycoside.

13. The conjugate of claim 11, wherein the glycoside is selected from a glucuronide, a galactoside, a glucoside, a mannoside, a fucoside, O-GlcNAc, and O-GalNAc.

14. The conjugate of claim 10,
wherein:
$T^7$ is absent and $V^7$ is —NHCO—;
$T^8$ is ($C_1$-$C_{12}$)alkyl and $V^8$ is —CO—;
$T^9$ is AA and $V^9$ is absent;
$T^{10}$ is PABC and $V^{10}$ is absent;
$T^{11}$ is EDA and $V^{11}$ is —CO—; and
l is 0; or
wherein:
$T^7$ is absent and $V^7$ is —NHCO—;
$T^8$ is ($C_1$-$C_{12}$)alkyl and $V^8$ is —CO—;
$T^9$ is AA and $V^9$ is absent;
$T^{10}$ is PABC and $V^{10}$ is absent; and
k and l are each 0; or
wherein:
$T^7$ is absent and $V^7$ is —NHCO—;
$T^8$ is ($C_1$-$C_{12}$)alkyl and $V^8$ is —CO—;
$T^9$ is an amino acid analog and $V^9$ is —NH—;
$T^{10}$ is (PEG)$_n$ and $V^{10}$ is —CO—;
$T^{11}$ is AA and $V^{11}$ is absent; and
$T^{12}$ is PABC and $V^{12}$ is absent; or
wherein:
$T^7$ is absent and $V^7$ is —NHCO—;
$T^8$ is ($C_1$-$C_{12}$)alkyl and $V^8$ is —CONH—;
$T^9$ is (PEG)$_n$ and $V^9$ is —CO—;
$T^{10}$ is AA and $V^{10}$ is absent;
$T^{11}$ is PABC and $V^{11}$ is absent; and
l is 0; or
wherein:
$T^7$ is ($C_1$-$C_{12}$)alkyl and $V^7$ is —CONH—;
$T^8$ is substituted ($C_1$-$C_{12}$)alkyl and $V^8$ is —CO—;
$T^9$ is AA and $V^9$ is absent;
$T^{10}$ is PABC and $V^{10}$ is absent;
k and l are each 0; or
wherein:
$T^7$ is ($C_1$-$C_{12}$)alkyl and $V^7$ is —CONH—;
$T^8$ is (PEG)$_n$ and $V^8$ is —CO—;
$T^9$ is AA and $V^9$ is absent;
$T^{10}$ is PABC and $V^{10}$ is absent;
$T^{11}$ is ($C_1$-$C_{12}$)alkyl and $V^{11}$ is absent;
l is 0; or
wherein:
$T^7$ is ($C_1$-$C_{12}$)alkyl and $V^7$ is —CO—;
$T^8$ is 4AP and $V^8$ is —CO—;
$T^9$ is ($C_1$-$C_{12}$)alkyl and $V^9$ is —CO—;
$T^{10}$ is AA and $V^{10}$ is absent;
$T^{11}$ is PABC and $V^{11}$ is absent;
l is 0; or
wherein:
$T^7$ is ($C_1$-$C_{12}$)alkyl and $V^7$ is —CO—;
$T^8$ is 4AP and $V^8$ is —CO—;
$T^9$ is ($C_1$-$C_{12}$)alkyl and $V^9$ is —O—;
$T^{10}$ is ($C_1$-$C_{12}$)alkyl and $V^{10}$ is —CO—;
$T^{11}$ is AA and $V^{11}$ is absent;
$T^{12}$ is PABC and $V^{12}$ is absent; or
wherein:
$T^7$ is ($C_1$-$C_{12}$)alkyl and $V^7$ is —CO—;
$T^8$ is an amino acid analog and $V^8$ is absent;
$T^9$ is AA and $V^9$ is absent;
$T^{10}$ is PABC and $V^{10}$ is absent;
k and l are each 0; or
wherein:
$T^7$ is ($C_1$-$C_{12}$)alkyl and $V^7$ is —CONH—;
$T^8$ is (PEG)$_n$ and $V^8$ is —CONH—;
$T^9$ is substituted ($C_1$-$C_{12}$)alkyl and $V^9$ is —CO—;
$T^{10}$ is AA and $V^{10}$ is absent;
$T^{11}$ is PABC and $V^{11}$ is absent;
l is 0; or
wherein:
$T^7$ is ($C_1$-$C_{12}$)alkyl and $V^7$ is —CO—;
$T^8$ is AA and $V^8$ is —NH—;
$T^9$ is (PEG)$_n$ and $V^9$ is —CO—;
$T^{10}$ is AA and $V^{10}$ is absent;
$T^{11}$ is PABC and $V^{11}$ is absent;
l is 0; or
wherein:
$T^7$ is ($C_1$-$C_{12}$)alkyl and $V^7$ is —CONH—;
$T^8$ is (PEG)$_n$ and $V^8$ is —CO—;
$T^9$ is AA and $V^9$ is absent;
$T^{10}$ is PAP and $V^{10}$ is —COO—; and
k and l are each 0.

15. The conjugate of claim 1, wherein the conjugate is selected from:

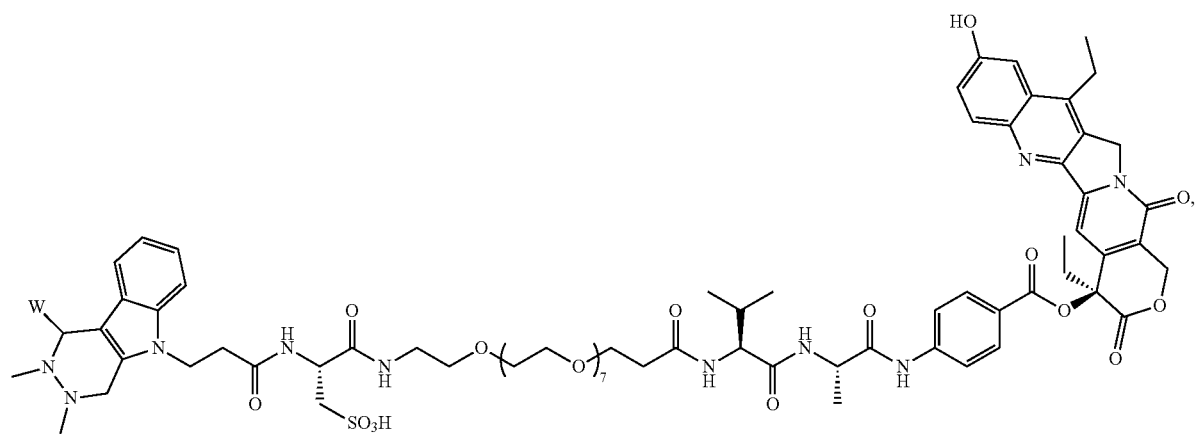
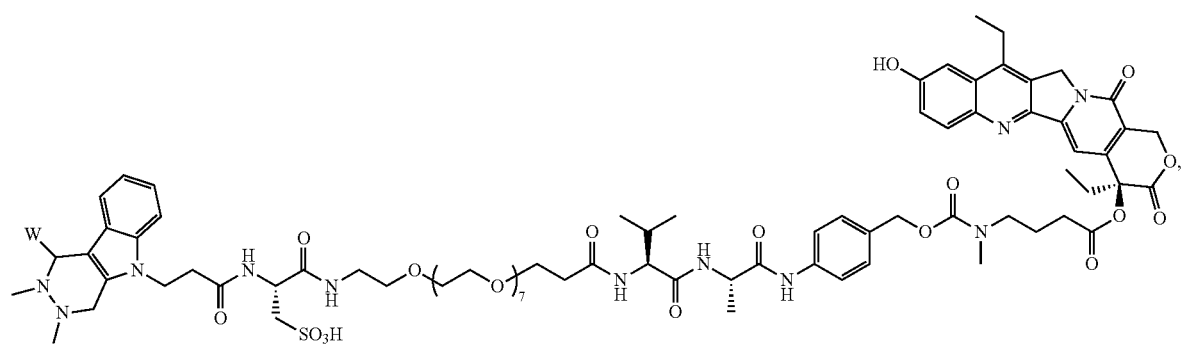
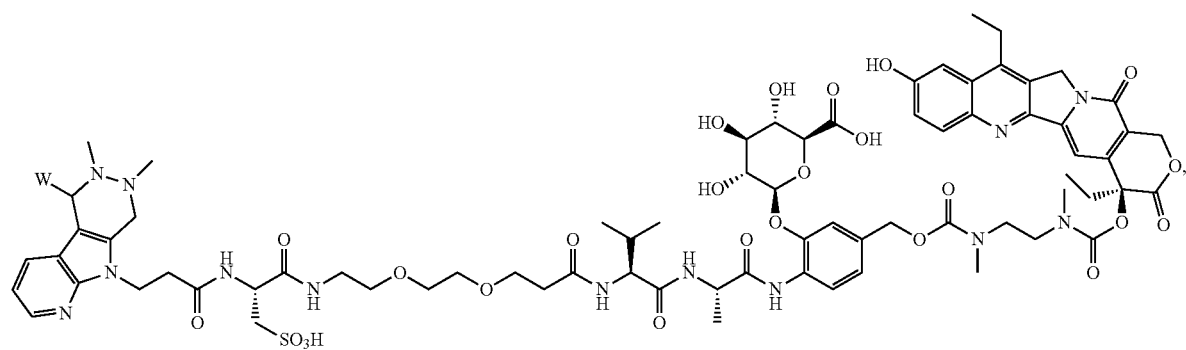

-continued
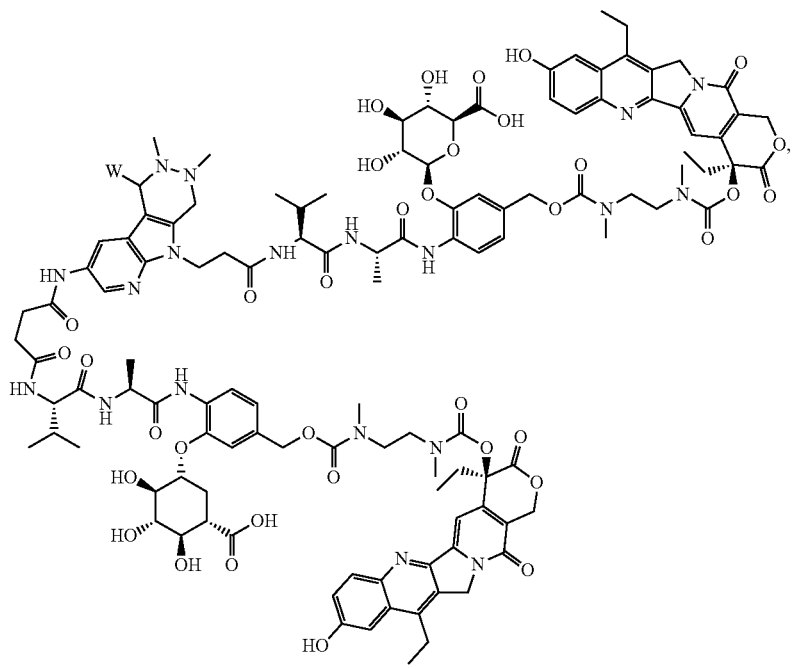
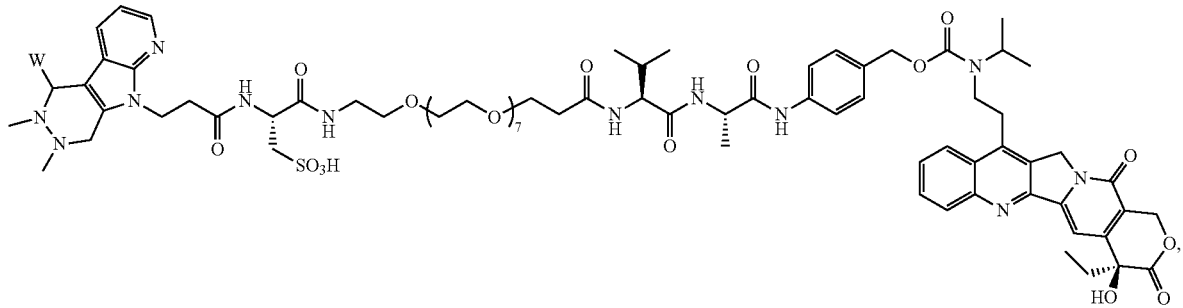
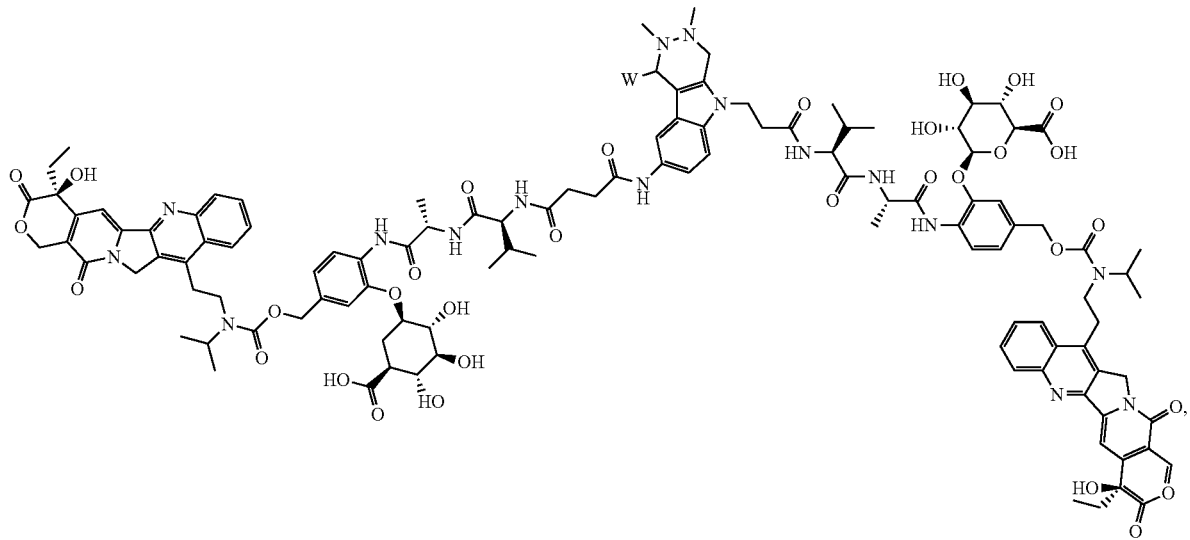

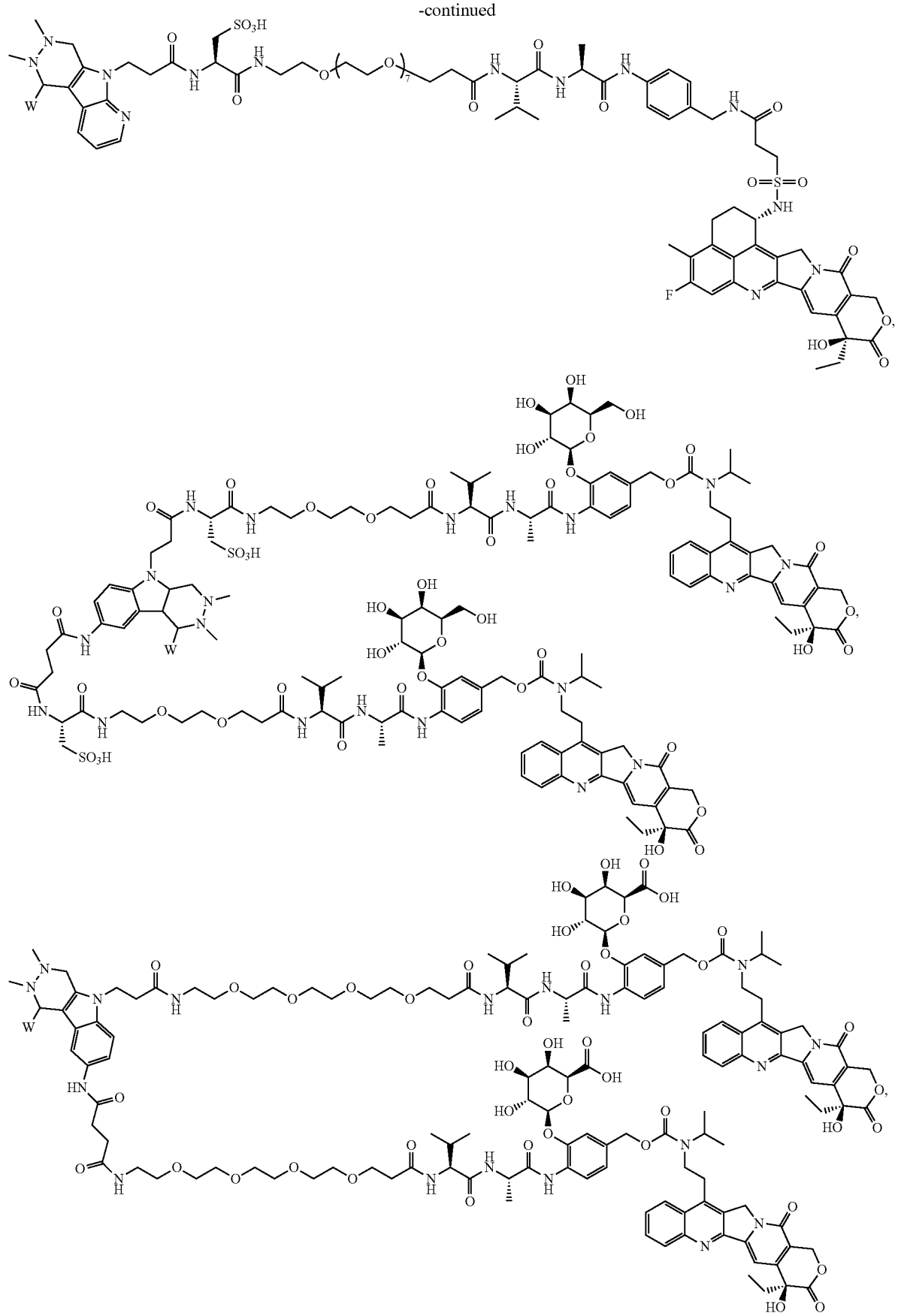

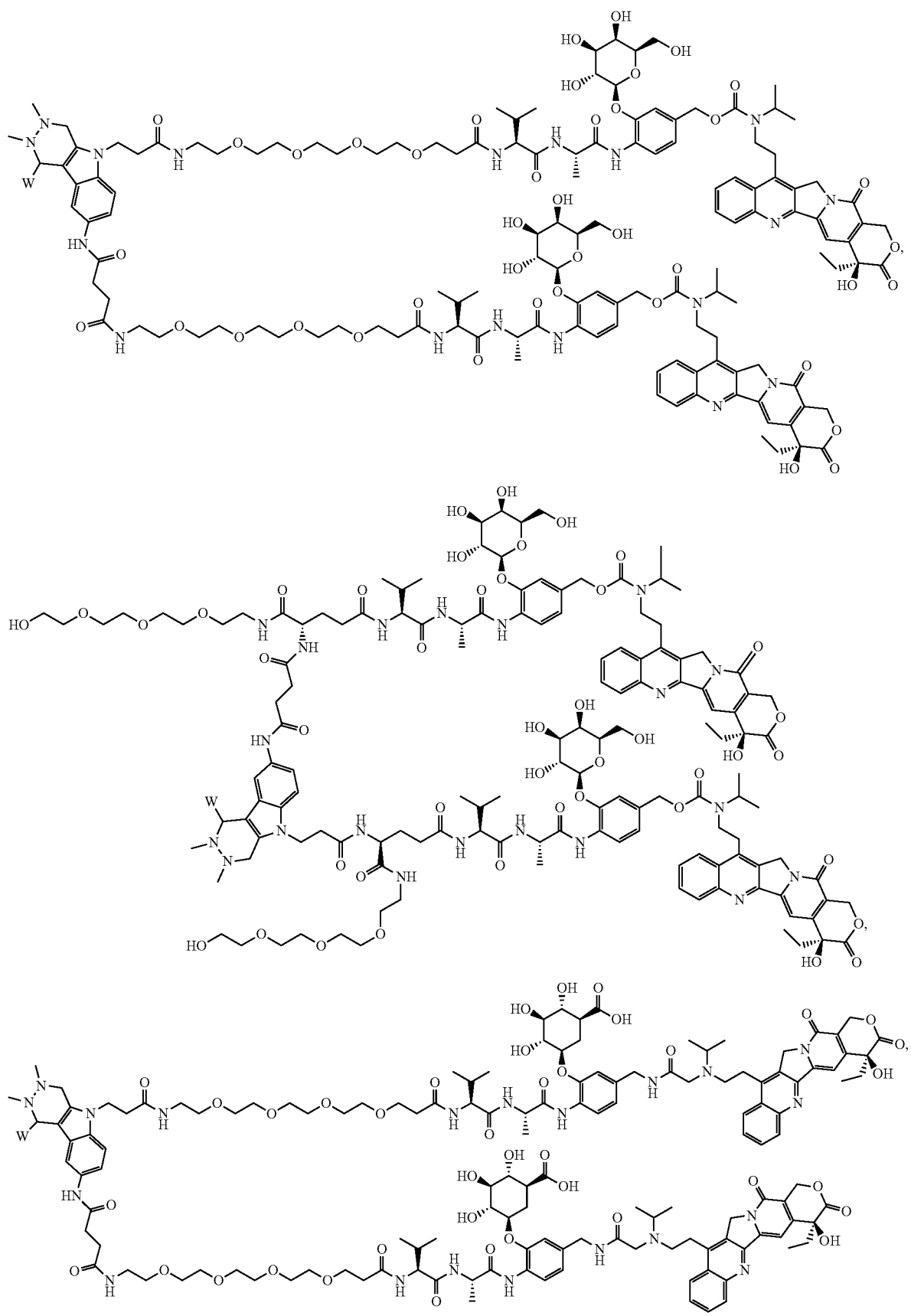

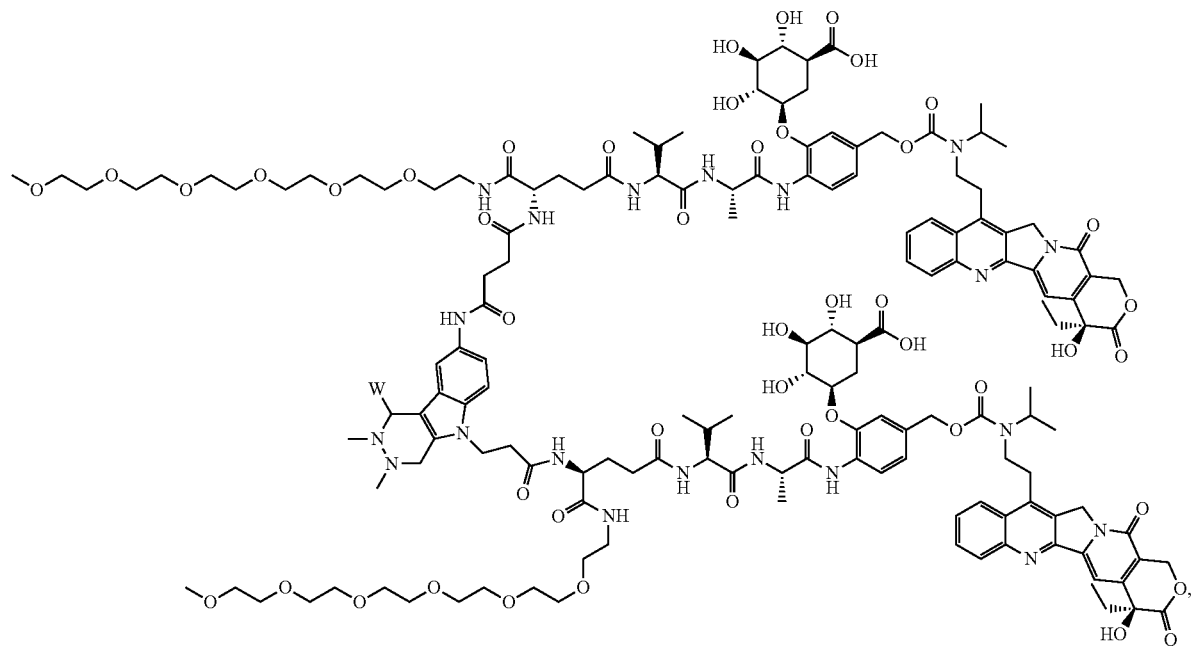
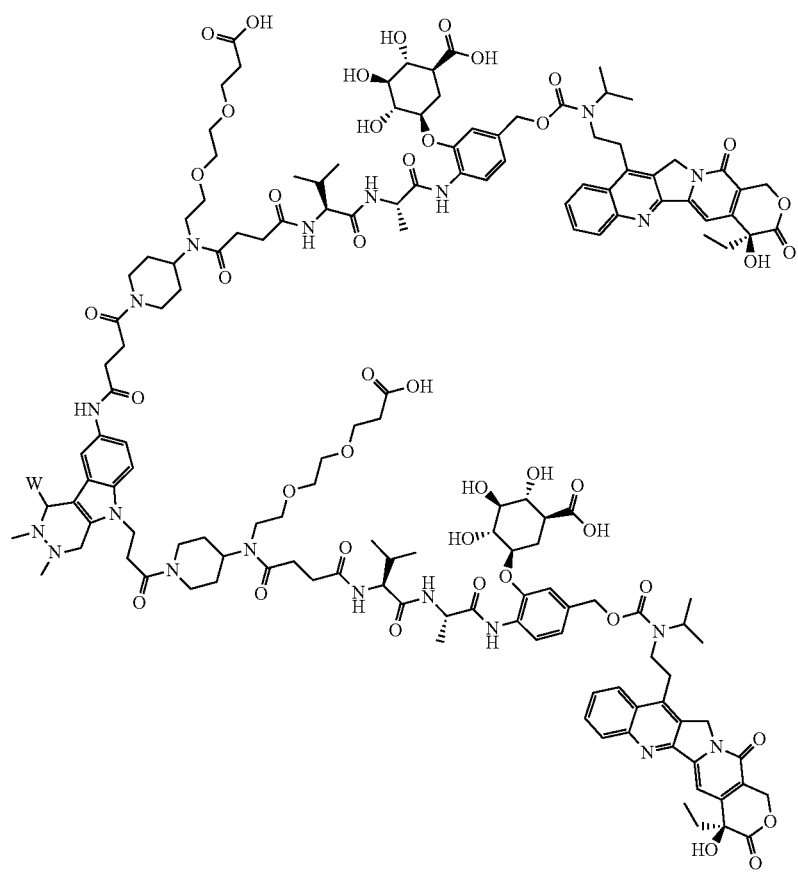

-continued
365
366
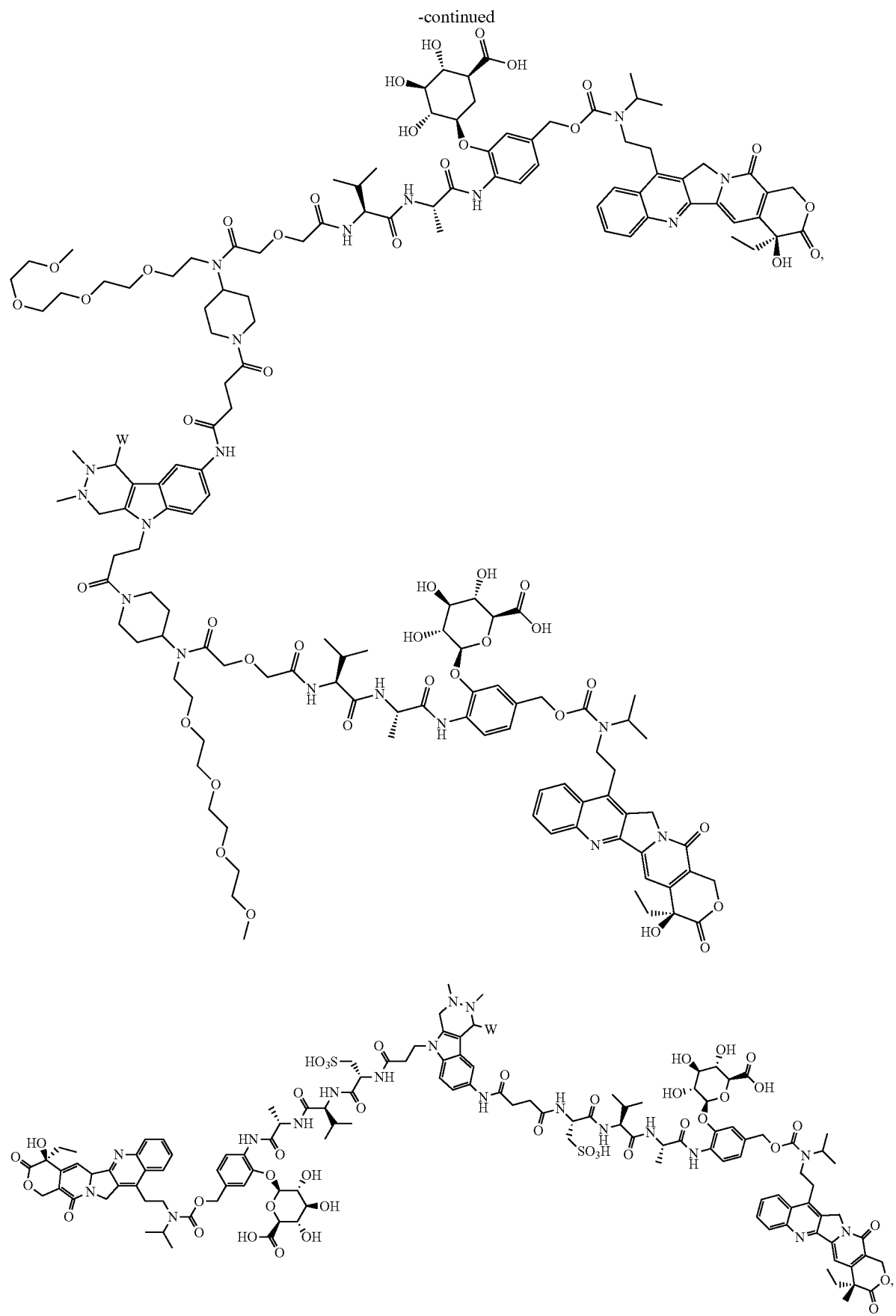

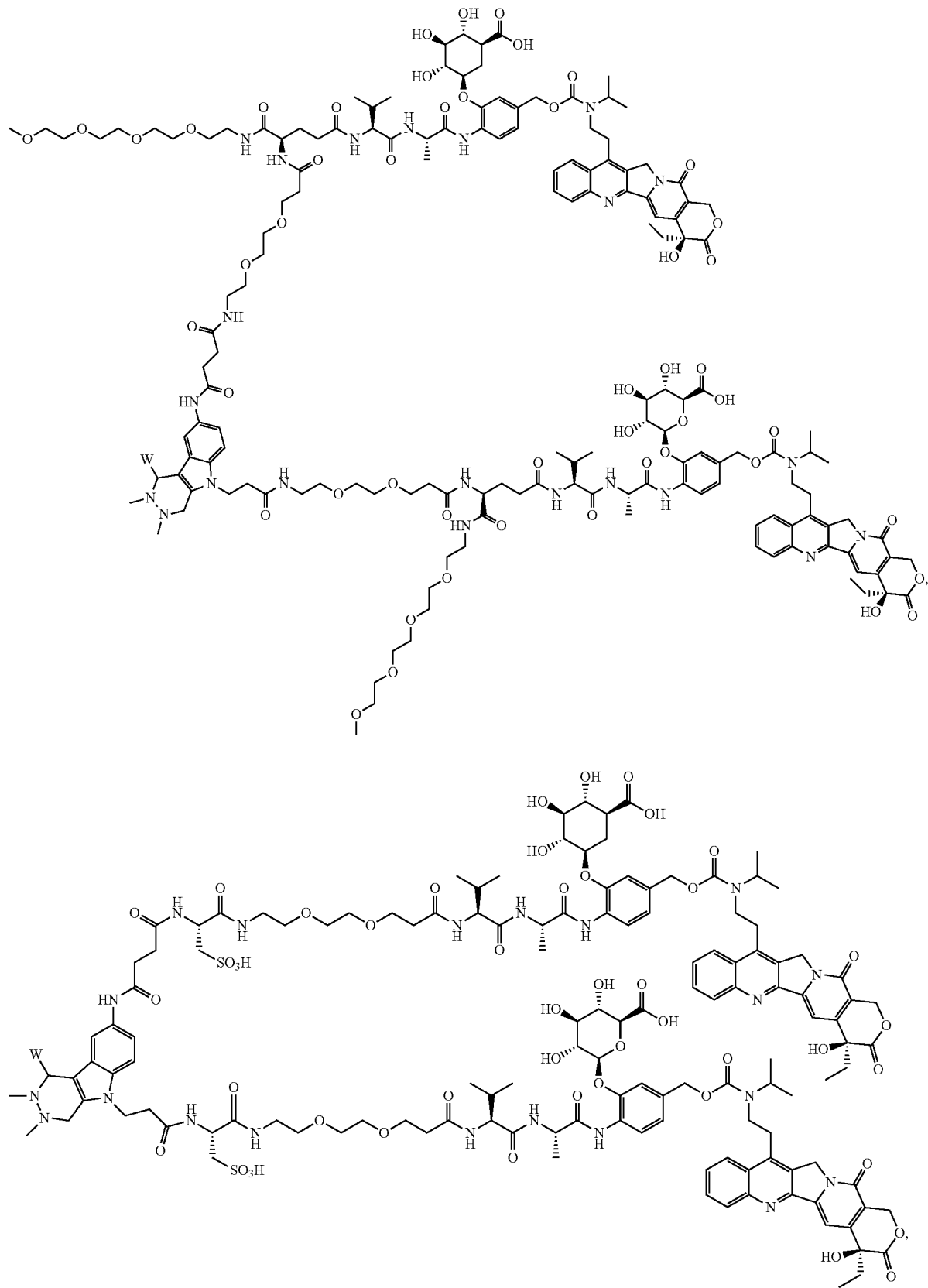

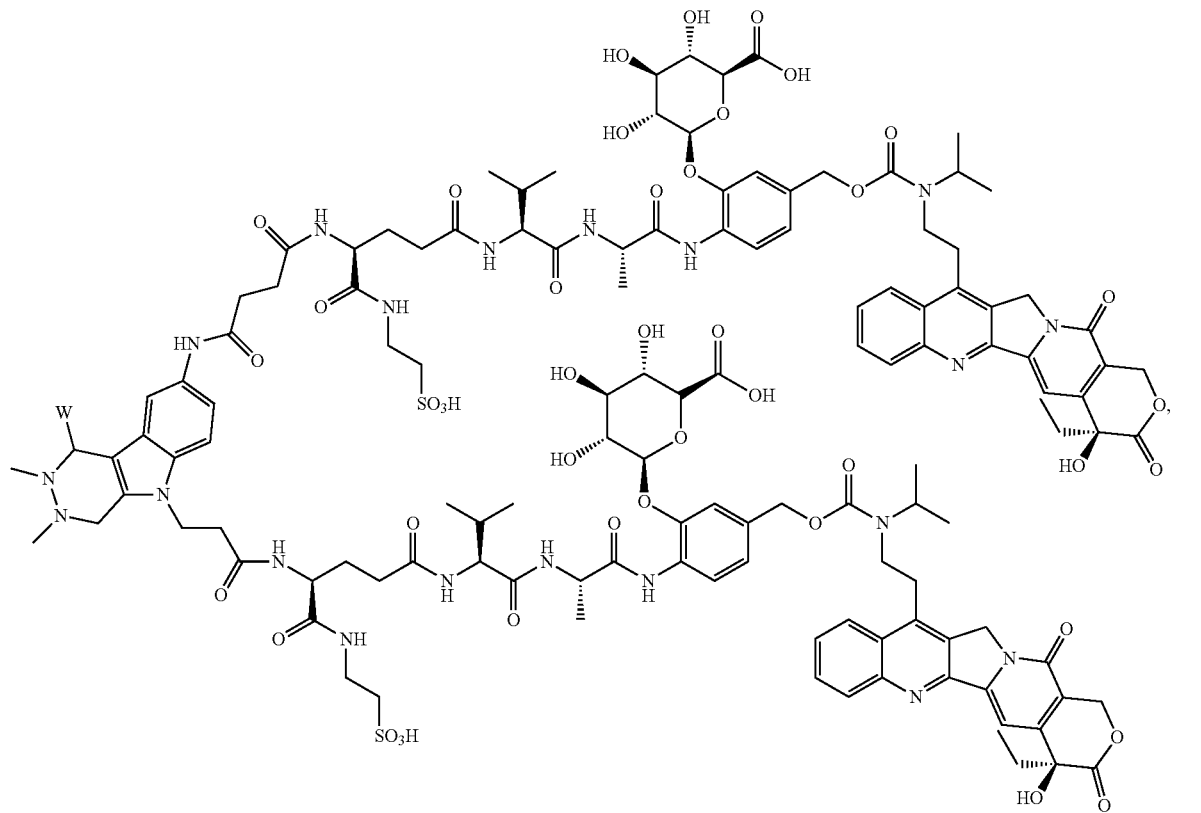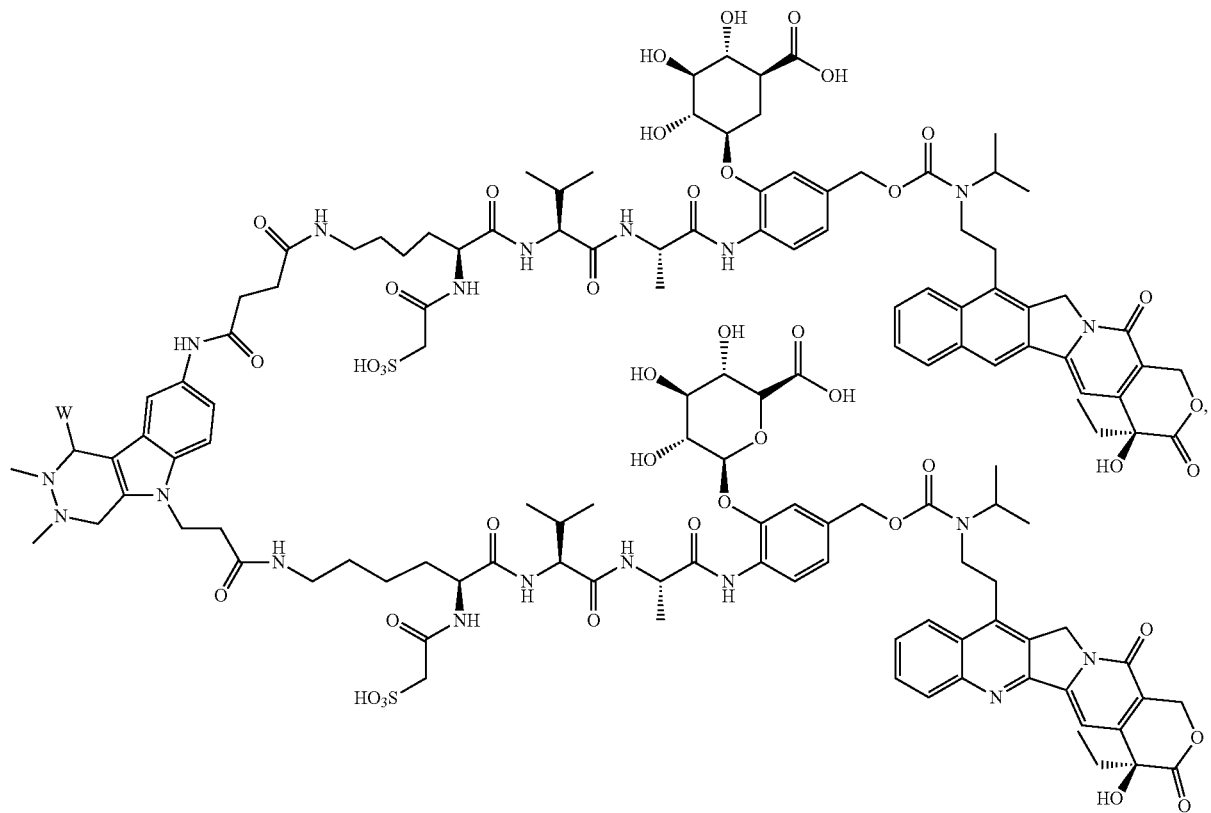

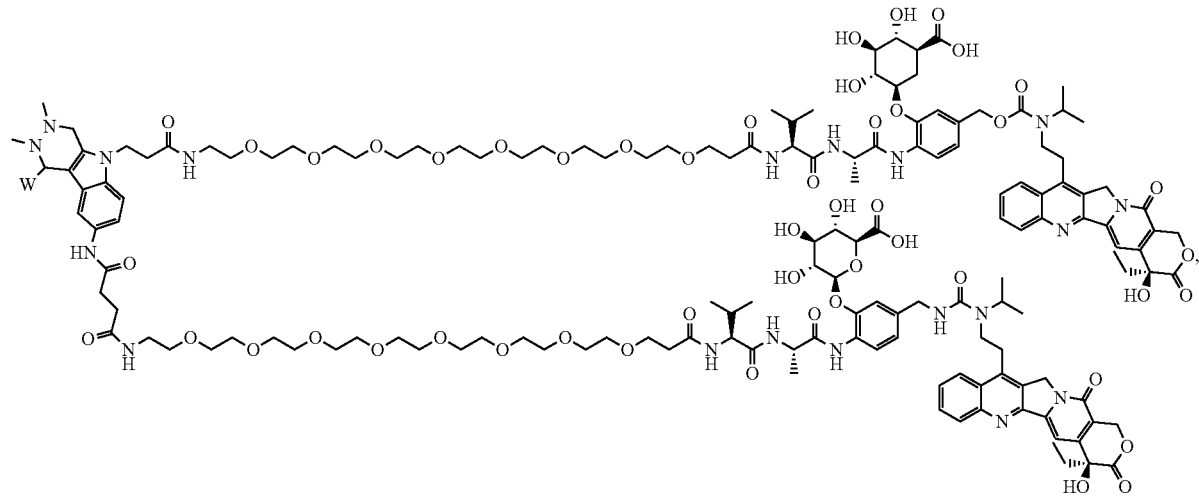
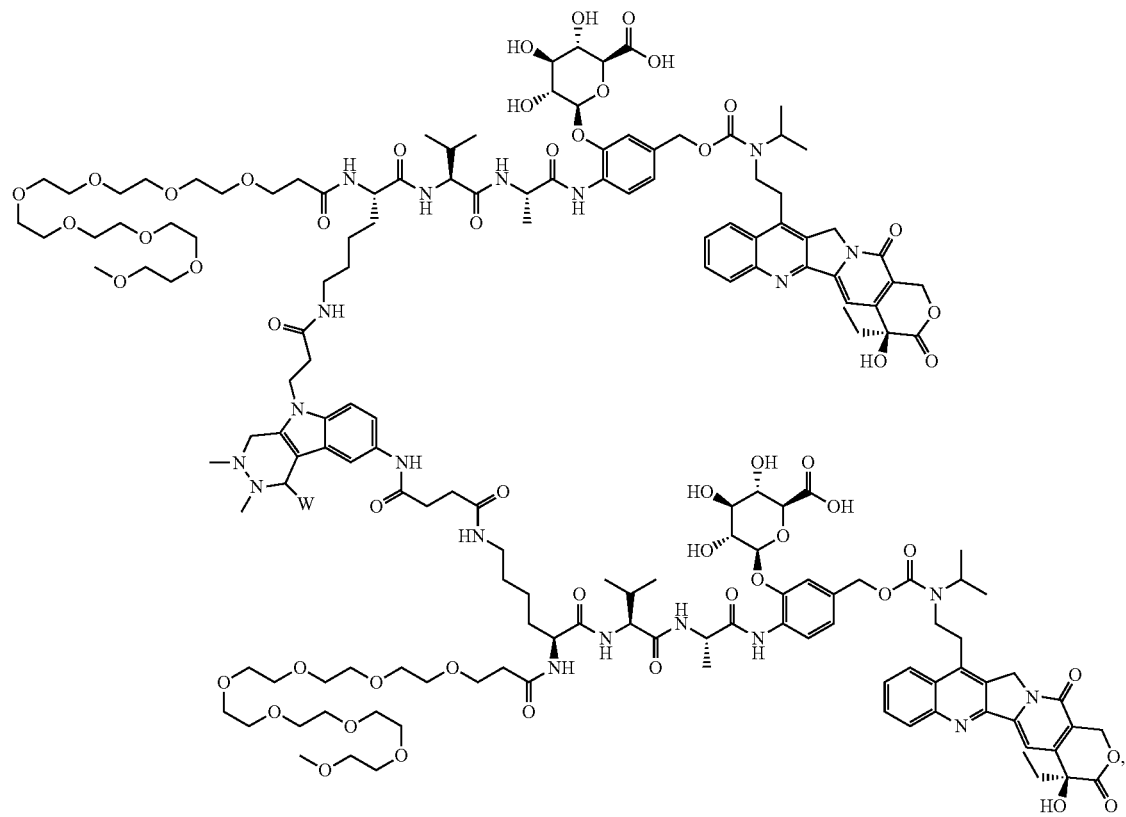

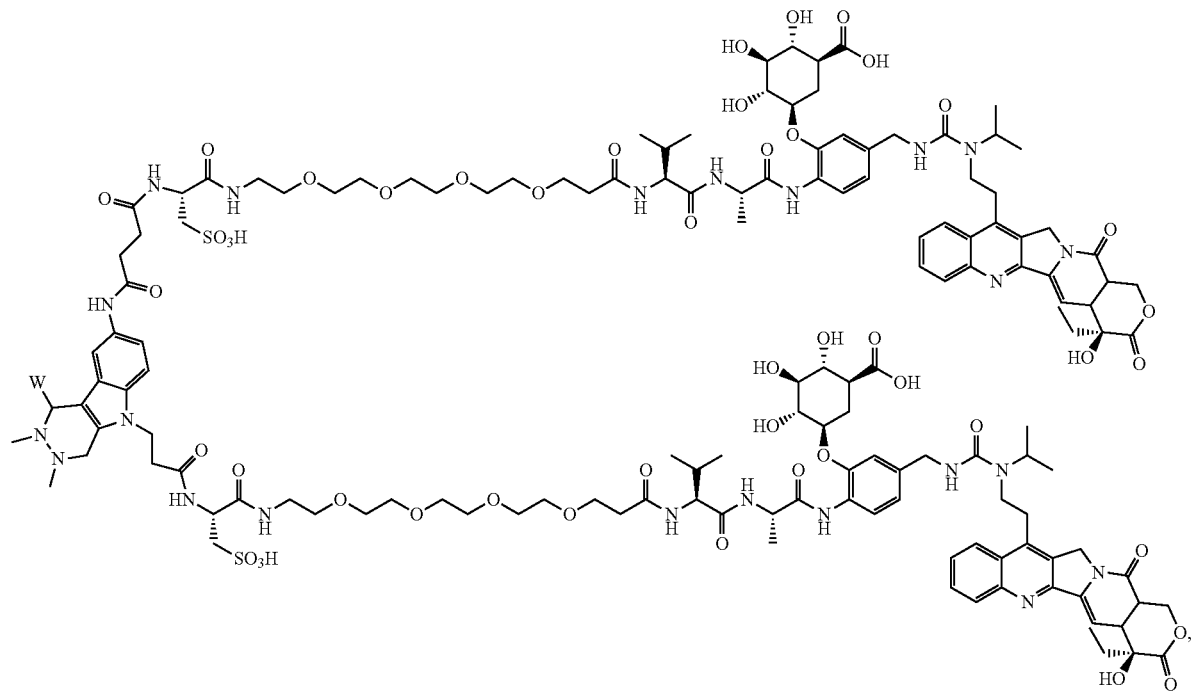
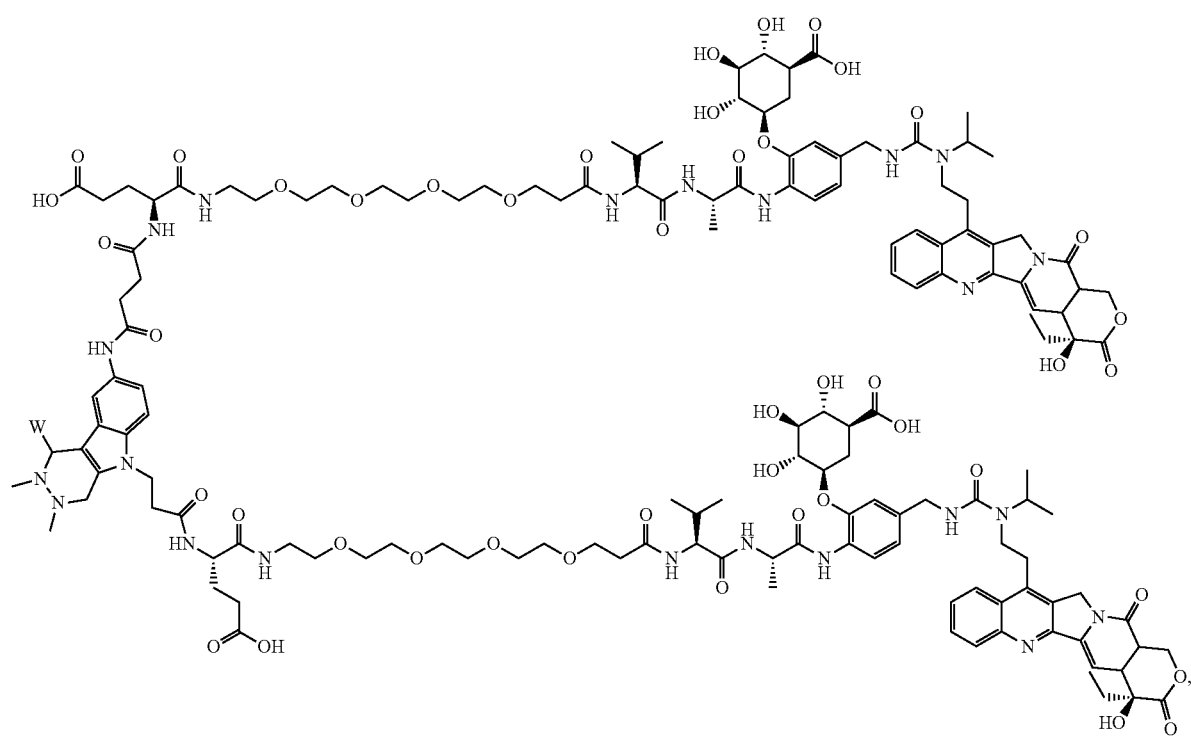

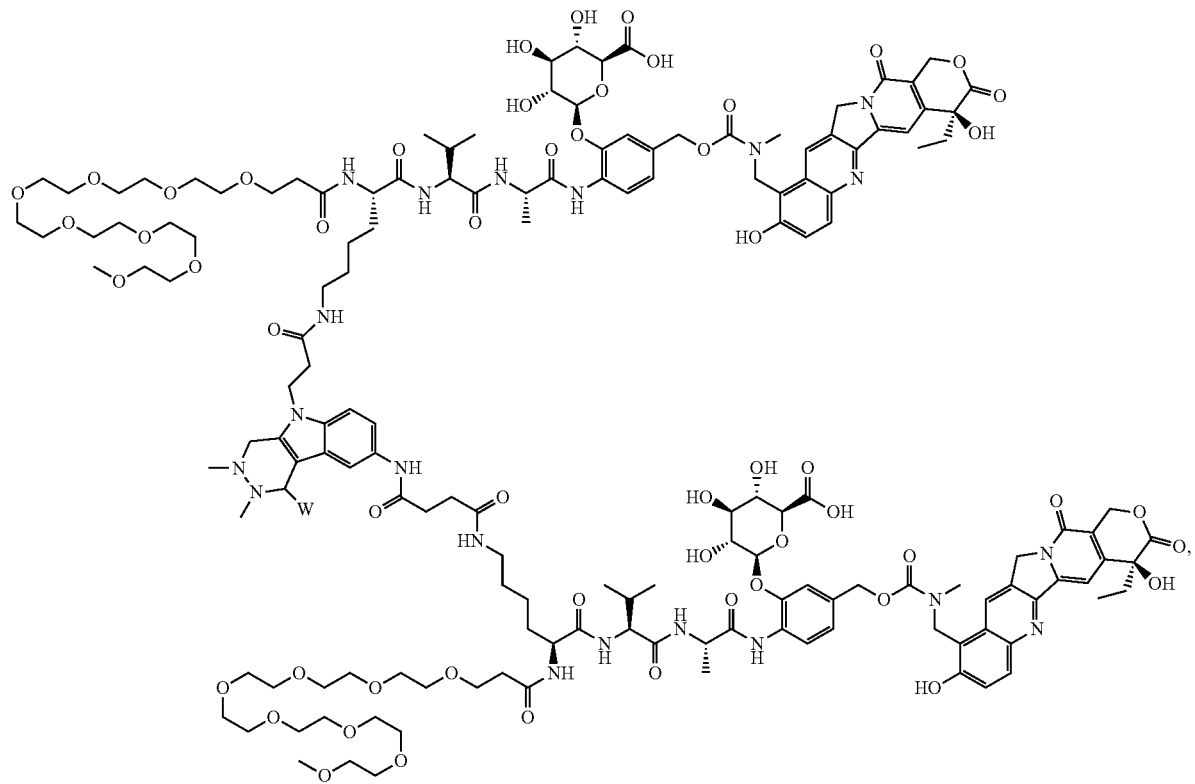
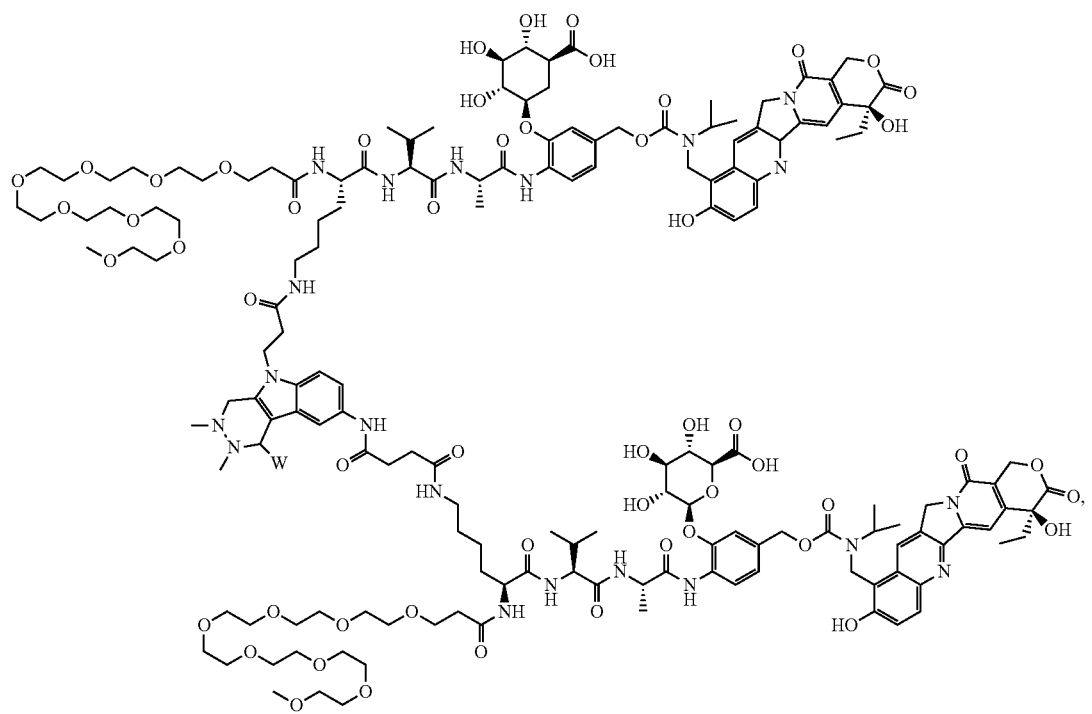

-continued
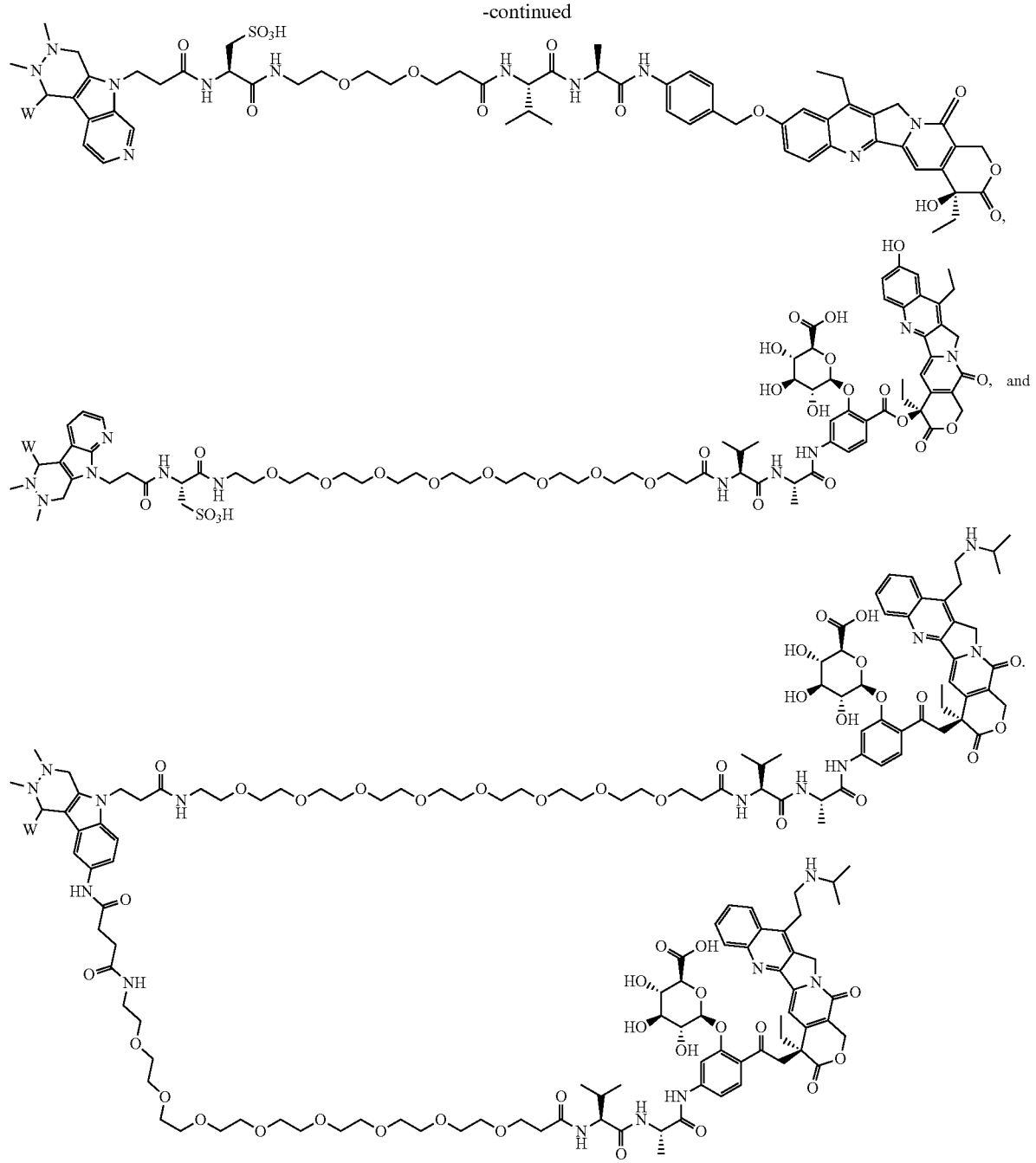
16. A pharmaceutical composition comprising:
a conjugate of claim 1; and
a pharmaceutically-acceptable excipient.
17. A method comprising:
administering to a subject an amount of a conjugate of claim 1.
* * * * *